US012545718B2

(12) United States Patent
Krammer et al.

(10) Patent No.: US 12,545,718 B2
(45) Date of Patent: Feb. 10, 2026

(54) ANTI-INFLUENZA B VIRUS NEURAMINIDASE ANTIBODIES AND USES THEREOF

(71) Applicant: ICAHN SCHOOL OF MEDICINE AT MOUNT SINAI, New York, NY (US)

(72) Inventors: Florian Krammer, New York, NY (US); Teddy John Wohlbold, New York, NY (US); Adolfo Garcia-Sastre, New York, NY (US); Peter Palese, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 1068 days.

(21) Appl. No.: 17/605,893

(22) PCT Filed: Apr. 23, 2020

(86) PCT No.: PCT/US2020/029582

§ 371 (c)(1),
(2) Date: Oct. 22, 2021

(87) PCT Pub. No.: WO2020/219719

PCT Pub. Date: Oct. 29, 2020

(65) Prior Publication Data

US 2022/0153873 A1 May 19, 2022

Related U.S. Application Data

(60) Provisional application No. 62/838,251, filed on Apr. 24, 2019.

(51) Int. Cl.

| | |
|---|---|
| ***C07K 16/10*** | (2006.01) |
| ***A61K 39/00*** | (2006.01) |
| ***A61K 39/42*** | (2006.01) |
| ***A61K 47/68*** | (2017.01) |
| ***A61P 31/16*** | (2006.01) |
| ***C07K 16/40*** | (2006.01) |

(52) U.S. Cl.

CPC .......... *C07K 16/1018* (2013.01); *A61K 39/42* (2013.01); *A61K 47/6871* (2017.08); *A61P 31/16* (2018.01); *C07K 16/40* (2013.01); *A61K 39/00* (2013.01); *C07K 2317/24* (2013.01); *C07K 2317/51* (2013.01); *C07K 2317/515* (2013.01); *C07K 2317/565* (2013.01); *C07K 2317/76* (2013.01)

(58) Field of Classification Search

CPC ................ C07K 16/1018; C07K 16/40; C07K 2317/24; C07K 2317/51; C07K 2317/515; C07K 2317/565; C07K 2317/76; C07K 2317/622; A61K 39/42; A61K 47/6871; A61K 39/00; A61K 31/215; A61P 31/16

See application file for complete search history.

(56) References Cited

U.S. PATENT DOCUMENTS

| | | | |
|---|---|---|---|
| 4,444,887 | A | 4/1984 | Hoffmann |
| 4,522,811 | A | 6/1985 | Eppstein et al. |
| 4,603,112 | A | 7/1986 | Paoletti et al. |
| 4,693,981 | A | 9/1987 | Wiesehahn et al. |
| 4,716,111 | A | 12/1987 | Osband et al. |
| 4,722,848 | A | 2/1988 | Paoletti et al. |
| 4,769,330 | A | 9/1988 | Paoletti et al. |
| 5,057,540 | A | 10/1991 | Kensil et al. |
| 5,106,619 | A | 4/1992 | Wiesehahn et al. |
| 5,110,587 | A | 5/1992 | Paoletti et al. |
| 5,166,057 | A | 11/1992 | Palese et al. |
| 5,174,993 | A | 12/1992 | Paoletti |
| 5,182,192 | A | 1/1993 | Steplewski et al. |
| 5,413,923 | A | 5/1995 | Kucherlapati et al. |
| 5,484,719 | A | 1/1996 | Lam et al. |
| 5,545,806 | A | 8/1996 | Lonberg et al. |
| 5,569,825 | A | 10/1996 | Lonberg et al. |
| 5,571,709 | A | 11/1996 | Devauchelle et al. |
| 5,573,916 | A | 11/1996 | Cheronis et al. |
| 5,589,174 | A | 12/1996 | Okuno et al. |
| 5,612,487 | A | 3/1997 | Lam et al. |
| 5,625,126 | A | 4/1997 | Lonberg et al. |
| 5,631,350 | A | 5/1997 | Okuno et al. |
| 5,633,425 | A | 5/1997 | Lonberg et al. |
| 5,643,576 | A | 7/1997 | Johnston et al. |
| 5,661,016 | A | 8/1997 | Lonberg et al. |

(Continued)

FOREIGN PATENT DOCUMENTS

| | | | |
|---|---|---|---|
| CA | 2121559 | A1 | 10/1994 |
| CA | 2718923 | A1 | 9/2009 |

(Continued)

OTHER PUBLICATIONS

Gershoni (Biodrugs (2007) 21(3): 145-156) (Year: 2007).*
Sela-Culang (Frontiers in Immunology (2013) 4: 302) (Year: 2013).*
Almagro (Frontiers in Immunology (2018) 8: 1751) (Year: 2018).*
Bouvier (Vaccines (2018) 6(3): 58) (Year: 2018).*
Yasuhara (Nature Communications (2022) 13: 6602) (Year: 2022).*
Ni (The Protein Journal (2024) 43: 683-696) (Year: 2024).*
Corder et al., 2019, "Influenza H1 Mosaic Hemagglutinin Vaccine Induces Broad Immunity and Protection in Mice," Vaccines (Basel), 7(4):195 with Supplemental Materials (19 pages).

(Continued)

*Primary Examiner* — Julie Wu
*Assistant Examiner* — Elizabeth A Shupe
(74) *Attorney, Agent, or Firm* — JONES DAY

(57) ABSTRACT

Provided herein are antibodies that bind to neuraminidase (NA) of different strains of influenza B virus, host cells for producing such antibodies, and kits comprising such antibodies. Also provided herein are compositions comprising antibodies that bind to NA of different strains of influenza B virus and methods of using such antibodies to diagnose, prevent or treat influenza virus disease.

27 Claims, 47 Drawing Sheets

Figure 1A:
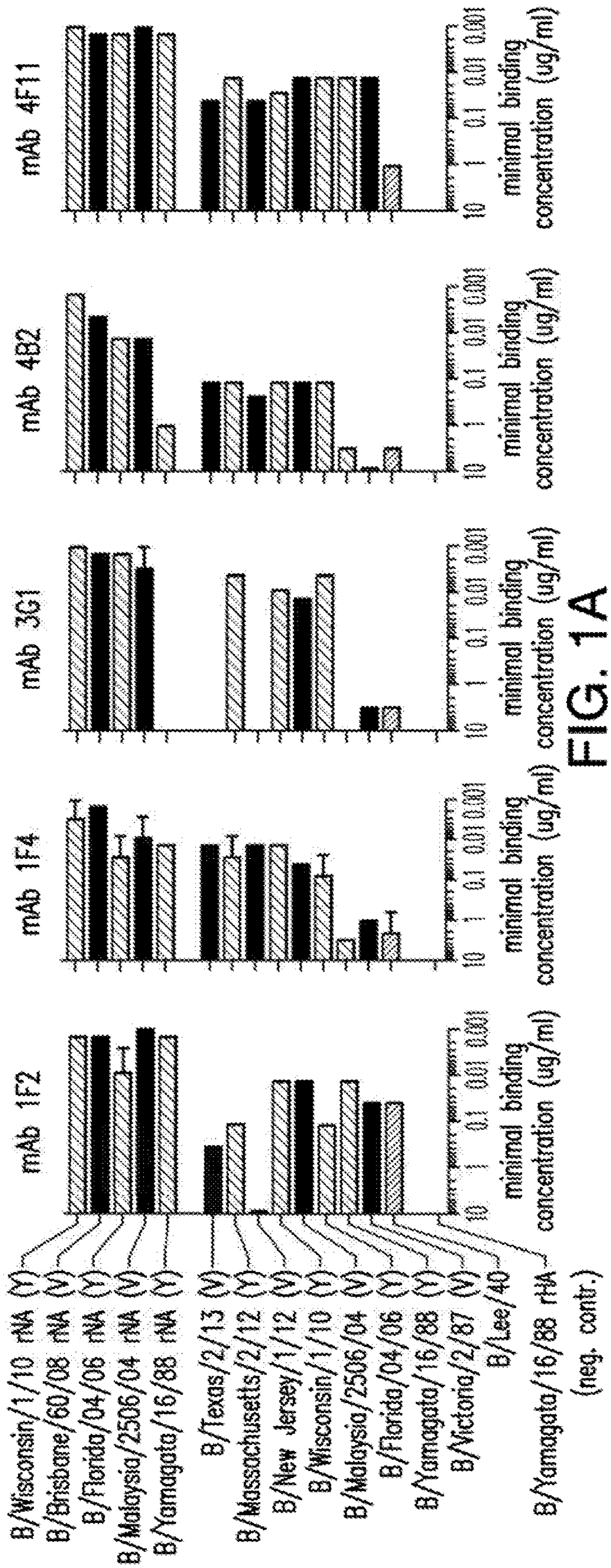

Specification includes a Sequence Listing.

(56) References Cited

U.S. PATENT DOCUMENTS

| | | | |
|---|---|---|---|
| 5,820,871 | A | 10/1998 | Palese et al. |
| 5,854,037 | A | 12/1998 | Palese et al. |
| 5,885,793 | A | 3/1999 | Griffiths et al. |
| 5,891,705 | A | 4/1999 | Budowsky et al. |
| 5,916,771 | A | 6/1999 | Hori et al. |
| 5,929,304 | A | 7/1999 | Radin et al. |
| 6,001,634 | A | 12/1999 | Palese et al. |
| 6,022,726 | A | 2/2000 | Palese et al. |
| 6,034,298 | A | 3/2000 | Lam et al. |
| 6,136,320 | A | 10/2000 | Arntzen et al. |
| 6,146,642 | A | 11/2000 | Garcia-Sastre et al. |
| 6,165,476 | A | 12/2000 | Strom et al. |
| 6,265,189 | B1 | 7/2001 | Paoletti et al. |
| 6,337,070 | B1 | 1/2002 | Okuno et al. |
| 6,468,544 | B1 | 10/2002 | Egorov et al. |
| 6,544,785 | B1 | 4/2003 | Palese et al. |
| 6,551,820 | B1 | 4/2003 | Mason et al. |
| 6,573,079 | B1 | 6/2003 | Palese et al. |
| 6,635,246 | B1 | 10/2003 | Barrett et al. |
| 6,649,372 | B1 | 11/2003 | Palese et al. |
| 6,669,943 | B1 | 12/2003 | Palese et al. |
| 6,720,409 | B2 | 4/2004 | Okuno et al. |
| 6,770,799 | B2 | 8/2004 | Mor et al. |
| 6,852,522 | B1 | 2/2005 | Palese et al. |
| 6,867,293 | B2 | 3/2005 | Andrews et al. |
| 6,887,699 | B1 | 5/2005 | Palese et al. |
| 6,942,861 | B2 | 9/2005 | McKee et al. |
| 6,951,754 | B2 | 10/2005 | Hoffmann |
| 7,312,064 | B2 | 12/2007 | Hoffmann |
| 7,316,813 | B2 | 1/2008 | Eichhorn |
| 7,384,774 | B2 | 6/2008 | Palese et al. |
| 7,442,379 | B2 | 10/2008 | Garcia-Sastre et al. |
| 7,494,808 | B2 | 2/2009 | Palese et al. |
| 7,504,560 | B2 | 3/2009 | Arntzen et al. |
| 7,566,458 | B2 | 7/2009 | Yang et al. |
| 7,968,101 | B2 | 6/2011 | Kawaoka et al. |
| 8,367,077 | B2 | 2/2013 | Zurbriggen et al. |
| 8,603,467 | B2 | 12/2013 | Chen et al. |
| 8,673,314 | B2 | 3/2014 | Garcia Sastre et al. |
| 8,828,406 | B2 | 9/2014 | Garcia-Sastre et al. |
| 9,051,359 | B2 | 6/2015 | Garcia-Sastre et al. |
| 9,175,069 | B2 | 11/2015 | Garcia-Sastre et al. |
| 9,371,366 | B2 | 6/2016 | Garcia-Sastre et al. |
| 9,452,211 | B2 | 9/2016 | Meijberg et al. |
| 9,688,965 | B2 | 6/2017 | Wu et al. |
| 9,701,723 | B2 | 7/2017 | Garcia-Sastre et al. |
| 9,707,288 | B2 | 7/2017 | Schrader |
| 9,708,373 | B2 | 7/2017 | Garcia-Sastre et al. |
| 9,849,172 | B2 | 12/2017 | Garcia-Sastre et al. |
| 9,908,930 | B2 | 3/2018 | Palese et al. |
| 9,968,670 | B2 | 5/2018 | Garcia-Sastre et al. |
| 10,131,695 | B2 | 11/2018 | Garcia-Sastre et al. |
| 10,137,189 | B2 | 11/2018 | Garcia-Sastre et al. |
| 10,179,806 | B2 | 1/2019 | Garcia-Sastre et al. |
| 10,544,207 | B2 | 1/2020 | Palese et al. |
| 10,583,188 | B2 | 3/2020 | Garcia-Sastre et al. |
| 10,736,956 | B2 | 8/2020 | Palese et al. |
| 11,254,733 | B2 | 2/2022 | Palese et al. |
| 11,266,734 | B2 | 3/2022 | Palese et al. |
| 11,865,173 | B2 | 1/2024 | Palese et al. |
| 12,030,928 | B2 | 7/2024 | Palese et al. |
| 12,233,123 | B2 | 2/2025 | Palese et al. |
| 12,364,746 | B2 | 7/2025 | Garcia-Sastre et al. |
| 2002/0054882 | A1 | 5/2002 | Okuno et al. |
| 2002/0164770 | A1 | 11/2002 | Hoffman |
| 2003/0134338 | A1 | 7/2003 | Makarocskiy |
| 2004/0002061 | A1 | 1/2004 | Kawaoka |
| 2004/0073011 | A1 | 4/2004 | Hagay et al. |
| 2005/0009008 | A1 | 1/2005 | Robinson et al. |
| 2005/0042229 | A1 | 2/2005 | Yang et al. |
| 2005/0048074 | A1 | 3/2005 | Cardineau et al. |
| 2005/0064391 | A1 | 3/2005 | Segal et al. |
| 2005/0106178 | A1 | 5/2005 | O'hagan et al. |
| 2005/0201946 | A1 | 9/2005 | Friede et al. |
| 2006/0008473 | A1 | 1/2006 | Yana et al. |
| 2006/0019350 | A1 | 1/2006 | Palese et al. |
| 2006/0204487 | A1 | 9/2006 | Shaaltiel et al. |
| 2006/0217338 | A1 | 9/2006 | Lu et al. |
| 2006/0280754 | A1 | 12/2006 | Garry et al. |
| 2007/0020238 | A1 | 1/2007 | Baltimore et al. |
| 2007/0036809 | A1 | 2/2007 | Michl et al. |
| 2007/0207171 | A1 | 9/2007 | Dubensky et al. |
| 2007/0275014 | A1 | 11/2007 | Yusibov et al. |
| 2008/0019998 | A1 | 1/2008 | Wang et al. |
| 2008/0032921 | A1 | 2/2008 | Alexander et al. |
| 2008/0038232 | A1 | 2/2008 | Shaaltiel et al. |
| 2008/0152657 | A1 | 6/2008 | Horowitz et al. |
| 2008/0176247 | A1 | 7/2008 | Chou et al. |
| 2008/0181911 | A1 | 7/2008 | Hanon et al. |
| 2008/0193455 | A1 | 8/2008 | Stassen et al. |
| 2008/0207550 | A1 | 8/2008 | Fearon et al. |
| 2008/0248066 | A1 | 10/2008 | Dubensky et al. |
| 2008/0254060 | A1 | 10/2008 | Palese et al. |
| 2009/0053762 | A1 | 2/2009 | Shaaltiel |
| 2009/0068221 | A1 | 3/2009 | Morrison |
| 2009/0081255 | A1 | 3/2009 | Bublot et al. |
| 2009/0082548 | A1 | 3/2009 | Shaaltiel et al. |
| 2009/0169547 | A1 | 7/2009 | Sahin et al. |
| 2009/0208477 | A1 | 8/2009 | Shaaltiel et al. |
| 2009/0246830 | A1 | 10/2009 | Kawaoka et al. |
| 2009/0263422 | A1 | 10/2009 | Hanon et al. |
| 2009/0291472 | A1 | 11/2009 | Lu et al. |
| 2009/0304730 | A1 | 12/2009 | Amon et al. |
| 2009/0304739 | A1 | 12/2009 | Rappouli et al. |
| 2009/0311265 | A1 | 12/2009 | Van Den Brink et al. |
| 2009/0311669 | A1 | 12/2009 | Kawaoka |
| 2010/0184192 | A1 | 7/2010 | Smith et al. |
| 2010/0247571 | A1 | 9/2010 | Wong et al. |
| 2010/0297165 | A1 | 11/2010 | Berzofsky et al. |
| 2010/0297174 | A1 | 11/2010 | Garcia-Sastre et al. |
| 2011/0027270 | A1 | 2/2011 | Garcia-Sastre et al. |
| 2011/0111494 | A1 | 5/2011 | Hill et al. |
| 2011/0182938 | A1 | 7/2011 | Weiner et al. |
| 2011/0300604 | A1 | 12/2011 | Kawaoka et al. |
| 2012/0039898 | A1 | 2/2012 | Throsby et al. |
| 2012/0058538 | A1 | 3/2012 | Palese et al. |
| 2012/0122185 | A1 | 5/2012 | Palese et al. |
| 2012/0189658 | A1 | 7/2012 | Couture et al. |
| 2012/0244183 | A1 | 9/2012 | Garcia-Sastre et al. |
| 2012/0294796 | A1 | 11/2012 | Johnson et al. |
| 2013/0022623 | A1 | 1/2013 | Karsunky et al. |
| 2013/0129747 | A1 | 5/2013 | Schrader |
| 2013/0129761 | A1 | 5/2013 | Garcia-Sastre et al. |
| 2013/0209499 | A1 | 8/2013 | Garcia-Sastre et al. |
| 2013/0224187 | A1 | 8/2013 | Rother et al. |
| 2013/0315929 | A1 | 11/2013 | Bock |
| 2014/0004149 | A1 | 1/2014 | Tobin et al. |
| 2014/0170163 | A1 | 6/2014 | Garcia Sastre et al. |
| 2014/0193484 | A1 | 7/2014 | Bertholet Girardin et al. |
| 2014/0328875 | A1 | 11/2014 | Garcia Sastre et al. |
| 2015/0132253 | A1 | 5/2015 | Sahin et al. |
| 2015/0132330 | A1 | 5/2015 | Garcia-Sastre et al. |
| 2015/0239960 | A1 | 8/2015 | Garcia-Sastre et al. |
| 2015/0252103 | A1 | 9/2015 | Sahin et al. |
| 2015/0266951 | A1 | 9/2015 | Song |
| 2015/0297712 | A1 | 10/2015 | Garcia-Sastre et al. |
| 2015/0299270 | A1 | 10/2015 | Galarza et al. |
| 2015/0335729 | A1 | 11/2015 | Garcia-Sastre et al. |
| 2015/0352202 | A1 | 12/2015 | Osorio et al. |
| 2016/0015828 | A1 | 1/2016 | Torgov et al. |
| 2016/0017025 | A1 | 1/2016 | Samira et al. |
| 2016/0022806 | A1 | 1/2016 | Weiner et al. |
| 2016/0024196 | A1 | 1/2016 | Majeti et al. |
| 2016/0038585 | A1 | 2/2016 | Dormitzer et al. |
| 2016/0067328 | A1 | 3/2016 | Wu et al. |
| 2016/0137721 | A1 | 5/2016 | Palese et al. |
| 2016/0185860 | A1 | 6/2016 | Sahin et al. |
| 2016/0311918 | A1 | 10/2016 | Wang et al. |
| 2016/0355553 | A1 | 12/2016 | Meijberg et al. |
| 2016/0355590 | A1 | 12/2016 | Epstein |
| 2016/0361408 | A1 | 12/2016 | Garcia-Sastre et al. |
| 2016/0362455 | A1 | 12/2016 | Meijberg et al. |
| 2016/0376347 | A1 | 12/2016 | Saelens et al. |
| 2017/0204177 | A1 | 7/2017 | Wang et al. |

(56) References Cited

U.S. PATENT DOCUMENTS

| | | | |
|---|---|---|---|
| 2017/0327565 | A1 | 11/2017 | Schrader |
| 2018/0002385 | A1 | 1/2018 | Garcia-Sastre et al. |
| 2018/0008696 | A1 | 1/2018 | Palese et al. |
| 2018/0022804 | A1 | 1/2018 | Peters et al. |
| 2018/0265573 | A1 | 9/2018 | Palese et al. |
| 2018/0312592 | A1 | 11/2018 | Junutula et al. |
| 2018/0333479 | A1 | 11/2018 | Garcia-Sastre et al. |
| 2019/0048324 | A1 | 2/2019 | Kawaoka et al. |
| 2019/0099484 | A1 | 4/2019 | Garcia-Sastre et al. |
| 2019/0106461 | A1 | 4/2019 | Garcia-Sastre et al. |
| 2019/0125859 | A1 | 5/2019 | Palese et al. |
| 2019/0292229 | A1 | 9/2019 | Blackledge et al. |
| 2019/0314485 | A1 | 10/2019 | Palese et al. |
| 2020/0223905 | A1 | 7/2020 | Palese et al. |
| 2021/0246432 | A1 | 8/2021 | Kawaoka et al. |
| 2021/0260179 | A1 | 8/2021 | Palese et al. |
| 2022/0249652 | A1 | 8/2022 | Palese et al. |
| 2022/0257749 | A1 | 8/2022 | Palese et al. |
| 2022/0363736 | A1 | 11/2022 | Palese et al. |
| 2022/0403358 | A1 | 12/2022 | Palese et al. |
| 2024/0335524 | A1 | 10/2024 | Palese et al. |
| 2025/0019423 | A1 | 1/2025 | Palese et al. |
| 2025/0121049 | A1 | 4/2025 | Palese et al. |
| 2025/0161430 | A1 | 5/2025 | Krammer et al. |

FOREIGN PATENT DOCUMENTS

| | | | |
|---|---|---|---|
| CN | 1196788 | C | 4/2005 |
| CN | 101076355 | A | 11/2007 |
| CN | 103665155 | A | 3/2014 |
| CN | 104185476 | A | 12/2014 |
| CN | 105263516 | A | 1/2016 |
| CN | 105400753 | A | 3/2016 |
| EP | 0621339 | A2 | 10/1994 |
| EP | 0702085 | A1 | 3/1996 |
| EP | 0780475 | A1 | 6/1997 |
| EP | 2540312 | A1 | 1/2013 |
| JP | H 789992 | A | 4/1995 |
| JP | H 10-502168 | A | 2/1998 |
| JP | 2004258814 | A | 9/2004 |
| JP | 2006347922 | A | 12/2006 |
| JP | 2008249712 | A | 10/2008 |
| JP | 2009022186 | A | 2/2009 |
| JP | 2009131237 | A | 6/2009 |
| JP | 2012521786 | A | 10/2010 |
| JP | 2011057653 | A | 3/2011 |
| JP | 2012530499 | A | 12/2012 |
| JP | 2014530003 | A | 11/2014 |
| JP | 2016508133 | A | 3/2016 |
| WO | WO 1984000687 | A1 | 3/1984 |
| WO | WO 1991010741 | A1 | 7/1991 |
| WO | WO 1992001047 | A1 | 1/1992 |
| WO | WO 1994009136 | A1 | 4/1994 |
| WO | WO 1994012629 | A1 | 6/1994 |
| WO | WO 1994016109 | A1 | 7/1994 |
| WO | WO 1994017826 | A1 | 8/1994 |
| WO | WO 1995034324 | A1 | 12/1995 |
| WO | WO 1996011279 | A2 | 4/1996 |
| WO | WO 1996033735 | A1 | 10/1996 |
| WO | WO 1996034096 | A1 | 10/1996 |
| WO | WO 1996034625 | A1 | 11/1996 |
| WO | WO 1997006270 | A1 | 2/1997 |
| WO | WO 1997012032 | A1 | 4/1997 |
| WO | WO 1997040161 | A1 | 10/1997 |
| WO | WO 1997040177 | A1 | 10/1997 |
| WO | WO 1998002530 | A1 | 1/1998 |
| WO | WO 1998013501 | A2 | 4/1998 |
| WO | WO 1998016654 | A1 | 4/1998 |
| WO | WO 1998024893 | A2 | 6/1998 |
| WO | WO 1998046645 | A2 | 10/1998 |
| WO | WO 1998050433 | A2 | 11/1998 |
| WO | WO 1998053078 | A1 | 11/1998 |
| WO | WO 1999002657 | A1 | 1/1999 |
| WO | WO 1999015672 | A1 | 4/1999 |
| WO | WO 2001004333 | A1 | 1/2001 |
| WO | WO 2002000885 | A2 | 1/2002 |
| WO | WO 2002097072 | A2 | 12/2002 |
| WO | WO 2002097072 | A3 | 12/2002 |
| WO | WO 2003068923 | A3 | 8/2003 |
| WO | WO 2004018698 | A2 | 3/2004 |
| WO | WO 2004018698 | A3 | 3/2004 |
| WO | WO 2005000901 | A2 | 1/2005 |
| WO | WO 2006062637 | A2 | 6/2006 |
| WO | WO 2006062637 | A3 | 6/2006 |
| WO | WO 2006100109 | A1 | 9/2006 |
| WO | WO 2007045674 | A1 | 4/2007 |
| WO | WO 2007064802 | A1 | 6/2007 |
| WO | WO 2007103322 | A2 | 9/2007 |
| WO | WO 2007109812 | A2 | 9/2007 |
| WO | WO 2007109813 | A1 | 9/2007 |
| WO | WO 2007110776 | A1 | 10/2007 |
| WO | WO 2007134237 | A2 | 11/2007 |
| WO | WO 2007134327 | A2 | 11/2007 |
| WO | WO 2008005777 | A2 | 1/2008 |
| WO | WO 2008009309 | A1 | 1/2008 |
| WO | WO 2008028946 | A2 | 3/2008 |
| WO | WO 2008032219 | A2 | 3/2008 |
| WO | WO 2009001217 | A2 | 12/2008 |
| WO | WO 2009009876 | A1 | 1/2009 |
| WO | WO 2009012489 | A1 | 1/2009 |
| WO | WO 2009025770 | A2 | 2/2009 |
| WO | WO 2009036157 | A1 | 3/2009 |
| WO | WO 2009068992 | A1 | 6/2009 |
| WO | WO 2009076778 | A1 | 6/2009 |
| WO | WO 2009079259 | A2 | 6/2009 |
| WO | WO 2009092038 | A1 | 7/2009 |
| WO | WO 2009121004 | A2 | 10/2009 |
| WO | WO 2009150532 | A1 | 12/2009 |
| WO | WO 2009156405 | A1 | 12/2009 |
| WO | WO 2010003235 | A1 | 1/2010 |
| WO | WO 2010036170 | A1 | 4/2010 |
| WO | WO 2010036948 | A2 | 4/2010 |
| WO | WO 2010117786 | A1 | 10/2010 |
| WO | WO 2010130636 | A1 | 11/2010 |
| WO | WO 2010138564 | A1 | 12/2010 |
| WO | WO 2010148511 | A1 | 12/2010 |
| WO | WO 2011014645 | A1 | 2/2011 |
| WO | WO 2011044152 | A1 | 4/2011 |
| WO | WO 2011087092 | A1 | 7/2011 |
| WO | WO 2011103453 | A2 | 8/2011 |
| WO | WO 2011111966 | A2 | 9/2011 |
| WO | WO 2011123495 | A1 | 10/2011 |
| WO | WO 2011126370 | A1 | 10/2011 |
| WO | WO 2012009790 | A1 | 1/2012 |
| WO | WO 2013043729 | A1 | 3/2013 |
| WO | WO 2013079473 | A1 | 6/2013 |
| WO | WO 2014159960 | A1 | 1/2014 |
| WO | WO 2014099931 | A1 | 6/2014 |
| WO | WO 2014152841 | A1 | 9/2014 |
| WO | WO 2015199564 | A1 | 12/2015 |
| WO | WO 2016005480 | A1 | 1/2016 |
| WO | WO 2016005482 | A1 | 1/2016 |
| WO | WO 2016118937 | A1 | 7/2016 |
| WO | WO 2016205347 | A1 | 12/2016 |
| WO | WO 2017021893 | A1 | 2/2017 |
| WO | WO 2017035479 | A1 | 3/2017 |
| WO | WO 2017053413 | A1 | 3/2017 |
| WO | WO 2017136575 | A1 | 8/2017 |
| WO | WO 2017136575 | A8 | 8/2017 |
| WO | WO 2017148889 | A1 | 9/2017 |
| WO | WO 2017210445 | A1 | 12/2017 |
| WO | WO 2017218624 | A1 | 12/2017 |
| WO | WO 2018089407 | A1 | 5/2018 |
| WO | WO 2018148383 | A1 | 8/2018 |
| WO | WO 2018187706 | A2 | 10/2018 |
| WO | WO 2019032463 | A1 | 2/2019 |
| WO | WO 2019246363 | A1 | 12/2019 |
| WO | WO 2020264141 | A1 | 12/2020 |
| WO | WO 2021081120 | A1 | 4/2021 |
| WO | WO 2003068923 | A2 | 8/2023 |
| WO | WO 2023167868 | A2 | 9/2023 |

(56) References Cited

FOREIGN PATENT DOCUMENTS

WO WO 2023167868 A3 9/2023
WO WO 2025019631 A1 1/2025

OTHER PUBLICATIONS

Dai et al., 2016, "Identification of Residues That Affect Oligomerization and/or Enzymatic Activity of Influenza Virus H5N1 Neuraminidase Proteins," J. Virol., 90(20): 9457-9470.
Florek et al., 2017, "A modified vaccinia Ankara vaccine vector expressing a mosaic H5 hemagglutinin reduces viral shedding in rhesus macaques," PLoS One, 12(8):e0181738 (19 pages).
Gao et al., 2021, "Balancing the influenza neuraminidase and hemagglutinin responses by exchanging the vaccine virus backbone," PLoS Pathog., 17(4):e1009171 (22 pages).
International Searching Authority, International Preliminary Report on Patentability for International Patent Application No. PCT/US2010/043697 (Pub No. WO 2011014645) issued Jan. 31, 2012 (10 pages).
International Searching Authority, International Search Report and Written Opinion for International Patent Application No. PCT/US2010/043697 (Pub No. WO 2011014645) mailed Nov. 17, 2010 (16 pages).
International Searching Authority, International Search Report and Written Opinion for International Patent Application No. PCT/US2023/014150 (Pub No. WO 2023167868) mailed Aug. 11, 2023 (14 pages).
Job et al., 2018, "Antibodies Directed toward Neuraminidase N1 Control Disease in a Mouse Model of Influenza," J. Virol., 92(4):e01584-17 (17 pages).
Kamlangdee et al., 2014, "Broad protection against avian influenza virus by using a modified vaccinia Ankara virus expressing a mosaic hemagglutinin gene," J. Virol., 88(22):13300-13309.
Liao et al., 2020, "Chimeric hemagglutinin vaccine elicits broadly protective CD4 and CD8 T cell responses against multiple influenza strains and subtypes," Proc. Natl. Acad. Sci. USA, 117(30):17757-17763.
Liu et al., 2018, "Antigenic sites in influenza H1 hemagglutinin display species-specific immunodominance," J. Clin. Invest., 128(11):4992-4996.
Liu et al., 2021, "Mosaic Hemagglutinin-Based Whole Inactivated Virus Vaccines Induce Broad Protection Against Influenza B Virus Challenge in Mice," Front. Immunol., 12:746447 (13 pages).
Lugovtsev et al., 2007, "Generation of the influenza B viruses with improved growth phenotype by substitution of specific amino acids of hemagglutinin," Virology, 365(2):315-323.
Madsen et al., 2020, "Human Antibodies Targeting Influenza B Virus Neuraminidase Active Site Are Broadly Protective," Immunity, 53(4):852-863.e7 (20 pages).
Martinet et al., 1997, "Protection of mice against a lethal influenza challenge by immunization with yeast-derived recombinant influenza neuraminidase," Eur. J. Biochem., 247(1):332-338.
Myers et al., 2013, "Compensatory hemagglutinin mutations alter antigenic properties of influenza viruses," J. Virol., 87(20):11168-11172.
Nachbagauer et al., 2020, "Is a Universal Influenza Virus Vaccine Possible?" Annu. Rev. Med., 71:315-327.
Nakagawa et al., 2002, "Emergence of an influenza B virus with antigenic change," J. Clin. Microbiol., 40(8):3068-3070.
Nakagawa et al., 2003, "Neutralizing epitopes specific for influenza B virus Yamagata group strains are in the loop," J. Gen. Virol., 84(Pt 4):769-773.
Sriwilaijaroen et al., 2012, "Molecular basis of the structure and function of H1 hemagglutinin of influenza virus," Proc. Jpn. Acad. Ser. B Phys. Biol. Sci. 88(6):226-249.
Strohmeier et al., 2022, "A CpG 1018 adjuvanted neuraminidase vaccine provides robust protection from influenza virus challenge in mice," NPJ Vaccines, 7(1):81 (13 pages).
Sun et al., 2019, "Antibody responses toward the major antigenic sites of influenza B virus hemagglutinin in mice, ferrets, and humans," J. Virol., 93(2):e01673-18 (11 pages).
Suntronwong et al., 2017, "Genetic and antigenic divergence in the influenza A(H3N2) virus circulating between 2016 and 2017 in Thailand," PLoS One, 12(12):e0189511 (12 pages).
Tan et al., 2022, "Murine Broadly Reactive Antineuraminidase Monoclonal Antibodies Protect Mice from Recent Influenza B Virus Isolates and Partially Inhibit Virus Transmission in the Guinea Pig Model," mSphere, 7(5):e0092721 (13 pages).
Abe et al., 2004, "Effect of the addition of oligosaccharides on the biological activities and antigenicity of influenza A/H3N2 virus hemagglutinin," J Virol., 78(18):9605-9611.
Abed et al., 2002, "Divergent evolution of hemagglutinin and neuraminidase genes in recent influenza A:H3N2 viruses isolated in Canada," J. Med. Virol., 67(4):589-595.
Air et al., 1985, "Location of antigenic sites on the three-dimensional structure of the influenza N2 virus neuraminidase," Virology, 145(2):237-248.
Air et al., 1990, "Antigenic, sequence, and crystal variation in influenza B neuraminidase," Virology, 177(2):578-587.
Air et al., 2012, "Influenza neuraminidase," Influenza Other Respir Viruses, 6(4):245-256 (Epub 2011).
Air, 2015, "Influenza virus antigenicity and broadly neutralizing epitopes," Curr. Opin. Virol. 11:113-121.
Altman et al., 2018, "Antibody Immunodominance: The Key to Understanding Influenza Virus Antigenic Drift," Viral. Immunol., 31(2):142-149.
Altschul et al., 1997, "Gapped BLAST and PSI-BLAST: a new generation of protein database search programs," Nucleic Acids Res., 25(17):3389-3402.
Amanat et al., 2019, "Cross-reactive antibodies binding to H4 hemagglutinin protect against a lethal H4N6 influenza virus challenge in the mouse model," Emerg. Microbes. Infect., 8(1):155-168.
Angeletti et al., 2017, "Defining B cell immunodominance to viruses," Nat Immunol., 18(4):456-463.
Angeletti et al., 2018, "Is It Possible to Develop a "Universal" Influenza Virus Vaccine? Outflanking Antibody Immunodominance on the Road to Universal Influenza Vaccination, " Cold Spring Harb Perspect Biol., 10(7):a028852 (9 pages).
Anonymous, "alignment" IBIS—Integrated Biotechnological Information, European Patent Office, retrieved from ibis.internal.epo.org/exam/jobResult?id=285344, on Sep. 26, 2014 (1 page).
Anonymous, "Amino Acids Reference Chart—Sigma-Aldrich" retrieved from www.sigmaaldrich.com/life-science/metabolomics/learning-center/amino-acid-reference-chart.html, on Jul. 17, 2015 (3 pages).
Anthony et al., 2012, "Emergence of fatal avian influenza in New England harbor seals," MBio., 3(4):e00166-12.
Antoine et al., 1998, "The complete genomic sequence of the modified vaccinia Ankara strain: comparison with other orthopoxviruses," Virology, 244(2):365-396.
Arzey et al., 2012, "Influenza virus A (H10N7) in chickens and poultry abattoir workers, Australia," Emerg Infect Dis., 18(5):814-816.
Babai et al., 2001, "A novel liposomal influenza vaccine (Influsome-Vac) containing hemagglutinin-neuraminidase and IL-2 or GM-CSF induces protective anti-neuraminidase antibodies cross-reacting with a wide spectrum of influenza A viral strains," Vaccine 20(3-4):505-515.
Babu et al., 2014, "Live attenuated H7N7 influenza vaccine primes for a vigorous antibody response to inactivated H7N7 influenza vaccine," Vaccine 32:6798-6804.
Bailey et al., 2018, "A Method to Assess Fc-mediated Effector Functions Induced by Influenza Hemagglutinin Specific Antibodies," J. Vis. Exp., (132):e56256 (5 pages).
Baker et al., 1976, "Effect of Ca++ on the stability of influenza virus neuraminidase," Arch Virol., 52(1-2):7-18.
Baker et al., 2013, "Protection against lethal influenza with a viral mimic," J Virol., 87(15):8591-8605.
Basler et al., 1999, "Mutation of neuraminidase cysteine residues yields temperature-sensitive influenza viruses," J Virol., 73(10):8095-8103.

(56) References Cited

OTHER PUBLICATIONS

Baz et al., 2013, "Replication and immunogenicity of swine, equine, and avian h3 subtype influenza viruses in mice and ferrets," J Virol., 87(12):6901-6910.
Beare et al., 1975, "Trials in man with live recombinants made from A/PR/8/34 (H0 N1) and wild H3 N2 influenza viruses," Lancet, 2(7938):729-732.
Belongia et al., 2016, "Variable influenza vaccine effectiveness by subtype: a systematic review and meta-analysis of test-negative design studies," Lancet Infect. Dis., 16(8):942-951.
Belshe, 2007, "Translational research on vaccines: influenza as an example," Clin Pharmacol Ther., 82(6):745-749.
Benjamin et al., 2014, "A broadly neutralizing human monoclonal antibody directed against a novel conserved epitope on the influenza virus H3 hemagglutinin globular head," J. Virol., 88(12):6743-6750.
Benne et al., 1998, "Comparison of neutralizing and hemagglutination-inhibiting antibody responses to influenza A virus vaccination of human immunodeficiency virus-infected individuals," Clin. Diagn. Lab Immunol., 5(1):114-117.
Benoit et al., 2015, "Hemagglutination Inhibition Antibody Titers as a Correlate of Protection Against Seasonal A/H3N2 Influenza Disease," Open Forum Infect. Dis., 2(2):ofv067 (8 pages).
Berry, 2007, "Cross-reactive MAb to the binding domain of botulinum neurotoxin A, B, and E developed using a sequential immunization strategy: anti-botulinum neurotoxin," Hybridoma 26(6):435-436.
Bett et al., 1993, "Packaging capacity and stability of human adenovirus type 5 vectors," J Virol., 67(10):5911-5921.
Beyer et al., 2013, "Cochrane re-arranged: support for policies to vaccinate elderly people against influenza," Vaccine, 31(50):6030-6033.
Bhatt et al., 2011, "The genomic rate of molecular adaptation of the human influenza A virus," Mol. Biol. Evol., 28(9):2443-2451.
Bianchi et al., 2005, "Universal influenza B vaccine based on the maturational cleavage site of the hemagglutinin precursor," J. Virol. 79(12):7380-7388.
Bommakanti et al., 2010, "Design of an HA2-based *Escherichia coli* expressed influenza immunogen that protects mice from pathogenic challenge," Proc. Natl. Acad. Sci. USA 107:13701-13706.
Bommakanti et al., 2012, "Design of *Eschericia coli*-Expressed Stalk Domain Immunogens of H1N1 Hemagglutinin That Protect Mice from Lethal Challenge," J. Virol. 86(24):13434-13444.
Boni et al., 2010, "Guidelines for identifying homologous recombination events in influenza A virus," PLoS One 5(5):e10434.
Boni et al., 2012, "No evidence for intra-segment recombination of 2009 H1N1 influenza virus in swine," Gene 494(2):242-245.
Bouvier et al., 2008, "Oseltamivir-resistant influenza A viruses are transmitted efficiently among guinea pigs by direct contact but not by aerosol," J Virol., 82(20):10052-10058.
Bouvier et al., 2010, "Animal Models for Influenza Virus Pathogenesis and Transmission," Viruses, 2(8):1530-1563.
Bowie et al., 1990, "Deciphering the Message in Protein Sequences: Tolerance to Amino Acid Substitutions," Science 247:1306-1310.
Bright et al., 2007, "Influenza virus-like particles elicit broader immune responses than whole virion inactivated influenza virus or recombinant hemagglutinin," Vaccine, 25(19):3871-3878.
Broecker et al., 2018, "Immunodominance of Antigenic Site B in the Hemagglutinin of the Current H3N2 Influenza Virus in Humans and Mice," J Virol., 92(20):e01100-18.
Broecker et al., 2019, "A Mosaic Hemagglutinin-Based Influenza Virus Vaccine Candidate Protects Mice From Challenge With Divergent H3N2 Strains," NPJ Vaccines, 4:31 (9 pages).
Broecker et al., 2019, "Extending the Stalk Enhances Immunogenicity of the Influenza Virus Neuraminidase," J. Virol., 93(18):e00840-19 (12 pages).
Brottet et al., 2014, "Influenza season in Réunion dominated by influenza B virus circulation associated with numerous cases of severe disease, France, 2014," Eurosurveillance (4 pages).
Bruhn et al., 2014, "Crystal structure of the nipah virus phosphoprotein tetramerization domain," J Virol., 88(1):758-762 (Epub 2013).
Budd et al., 2018, "Update: Influenza Activity—United States, Oct. 1, 2017-Feb. 3, 2018," MMWR Morb Mortal Wkly Rep., 67(6):169-179.
Bullough et al., 1994, "Structure of influenza haemagglutinin at the pH of membrane fusion," Nature 371:37-43.
Carter et al., 2016, "Design and Characterization of a Computationally Optimized Broadly Reactive Hemagglutinin Vaccine for H1N1 Influenza Viruses," J Virol., 90(9):4720-4734.
Casali et al., 2008, "Site-directed mutagenesis of the hinge peptide from the hemagglutinin protein: enhancement of the pH-responsive conformational change," Protein Eng. Des. Sel. 21(6):395-404.
Castrucci et al., 1993, "Biologic importance of neuraminidase stalk length in influenza A virus," J. Virol., 67(2):759-764.
Caton et al., 1982, "The antigenic structure of the influenza virus A/PR/8/34 hemagglutinin (H1 subtype)," Cell, 31(2 Pt 1):417-427.
Centers for Disease Control and Prevention Metropolitan Atlanta Congenital Defects Program (CDC MACDP) guidelines. Birth defects and genetic diseases branch 6-digit code for reportable congenital anomalies; http://www.cdc.gov/ncbddd/birthdefects/documents/MACDPcode0807.pdf, pp. A32-A108 (2007).
Centers for Disease Control and Prevention (CDC), 2009, "Swine influenza A (H1N1) infection in two children—Southern California, Mar.-Apr. 2009," MMWR Morb Mortal Wkly Rep., 58(15):400-402.
Centers for Disease Control and Prevention (CDC), 2009, "Update on influenza A (H1N1) 2009 monovalent vaccines," MMWR Morb Mortal Wkly Rep., 58(39):1100-1101.
Centers for Disease Control and Prevention (CDC), 2010, "Estimates of deaths associated with seasonal influenza—United States, 1976-2007," MMWR Morb Mortal Wkly Rep., 59(33):1057-1062.
Centers for Disease Control and Prevention (CDC), 2011, "Influenza-Associated Pediatric Deaths—United States, Sep. 2010-Aug. 2011," MMWR Morb Mortal Wkly Rep., 60(36):1233-1267.
Centers for Disease Control and Prevention (CDC), 2012, "Notes from the field: Highly pathogenic avian influenza A (H7N3) virus infection in two poultry workers—Jalisco, Mexico, Jul. 2012," MMWR Morb Mortal Wkly Rep., 61(36):726-727.
Centers for Disease Control and Prevention (CDC), 2012, "Notes from the field: Outbreak of influenza A (H3N2) virus among persons and swine at a county fair—Indiana, Jul. 2012," MMWR Morb Mortal Wkly Rep., 61(29):561.
Centers for Disease Control and Prevention (CDC), 2018, "Interim Estimates of 2017-18 Seasonal Influenza Vaccine Effectiveness—United States, Feb. 2018," MMWR Morb Mortal Wkly Rep., 67(6);180-185.
Chen et al., 1999, "N- and C-terminal residues combine in the fusion-pH influenza hemagglutinin $HA_2$ subunit to form an N cap that terminates the triple-stranded coiled coil," Proc. Natl. Acad. Sci. 96(16):8967-8972.
Chen et al., 2000, "Cross-protection against a lethal influenza virus infection by DNA vaccine to neuraminidase," Vaccine, 18(28):3214-3222.
Chen et al., 2007, "Exploration of the emergence of the Victoria lineage of influenza B virus," Arch Virol., 152(2):415-422 (Epub 2006).
Chen et al., 2007, "Influenza Virus Hemagglutinin and Neuraminidase, but Not the Matrix Protein, Are Required for Assembly and Budding of Plasmid-Derived Virus-Like Particles," J. Virol. 81(13):7111-7123.
Chen et al., 2009, "Evaluation of live attenuated influenza a virus h6 vaccines in mice and ferrets," J Virol., 83(1):65-72.
Chen et al., 2010, "Generation of Live Attenuated Novel Influenza Virus A/California/7/09 (H1N1) Vaccines with High Yield in Embryonated Chicken Eggs," J. Virol. 84(1):44-51.
Chen et al., 2011, "Vaccine design of hemagglutinin glycoprotein against influenza," Trends Biotechnol. 29(9):426-434.
Chen et al., 2012, "The 2009 pandemic H1N1 virus induces anti-neuraminidase (NA) antibodies that cross-react with the NA of H5N1 viruses in ferrets," Vaccine, 30(15):2516-2522.

(56) References Cited

OTHER PUBLICATIONS

Chen et al., 2014, "Clinical and epidemiological characteristics of a fatal case of avian influenza A H10N8 virus infection: a descriptive study," Lancet, 383(9918):714-721.
Chen et al., 2016, "Influenza A viruses expressing intra- or intergroup chimeric hemagglutinins," 90:3789-3793, doi:10.1128/JVI.03060-15.
Chen et al., 2018, "Influenza Infection in Humans Induces Broadly Cross-Reactive and Protective Neuraminidase-Reactive Antibodies," Cell, 173(2):417-429.
Chromikova et al., 2017, "Generation of a serum free CHO DG44 cell line stably producing a broadly protective anti-influenza virus monoclonal antibody," PLoS One, 12(9):e0183315 (11 pages).
Claas et al., 1998, "Human influenza A H5N1 virus related to a highly pathogenic avian influenza virus," Lancet, 351(9101):472-477.
Clementi et al., 2011, "A Human Monoclonal Antibody with Neutralizing Activity against Highly Divergent Influenza Subtypes," PLoS ONE 6(12):e28001.
Clements et al., 1986, "Serum and nasal wash antibodies associated with resistance to experimental challenge with influenza A wild-type virus," J. Clin. Microbiol., 24(1):157-160.
Cobey et al., 2017, "Immune history and influenza virus susceptibility," Curr. Opin. Virol., 22:105-111.
Cohen et al., 2013, "Influenza A penetrates host mucus by cleaving sialic acids with neuraminidase," Virol J., 10:321 (13 pages).
Communie et al., 2013, "Structure of the tetramerization domain of measles virus phosphoprotein," J Virol., 87(12):7166-7169.
Copeland et al., 2005, "Functional chimeras of human immunodeficiency virus type 1 Gp120 and influenza A virus (H3) hemagglutinin," J. Virol. 79:6459-6471.
Corti et al., 2010, "Heterosubtypic neutralizing antibodies are produced by individuals immunized with a seasonal influenza vaccine," J Clin Invest., 120(5):1663-1673.
Corti et al., 2011, "A neutralizing antibody selected from plasma cells that binds to group 1 and group 2 influenza A hemagglutinins," Science 333(6044):850-856.
Cotter et al., 2014, "A Single Amino Acid in the Stalk Region of the H1N1pdm Influenza Virus HA Protein Affects Viral Fusion, Stability and Infectivity," PLoS Pathogens 10(1):e1003831.
Couch et al., 1974, "Induction of partial immunity to influenza by a neuraminidase-specific vaccine," J Infect Dis., 129(4):411-420.
Couch et al., 2012, "A randomized clinical trial of an inactivated avian influenza A (H7N7) vaccine," PLoS One, 7(12):e49704 (6 pages).
Couch et al., 2012, "Randomized comparative study of the serum antihemagglutinin and antineuraminidase antibody responses to six licensed trivalent influenza vaccines," Vaccine, 31(1):190-195.
Couch et al., 2013, "Antibody correlates and predictors of immunity to naturally occurring influenza in humans and the importance of antibody to the neuraminidase," J Infect Dis., 207(6):974-981.
Coudeville et al., 2010, "Relationship between haemagglutination-inhibiting antibody titres and clinical protection against influenza: development and application of a bayesian random-effects model," BMC Med. Res. Methodol., 10:18 (11 pages).
Cox et al., 1998, "Influenza," Infect. Dis. Clin. North Am. 12(1):27-38.
Cox, 2013, "Correlates of protection to influenza virus, where do we go from here?," Hum. Vaccin. Immunother., 9(2):405-408.
Crotty et al., 2004, "Tracking human antigen-specific memory B cells: a sensitive and generalized ELISPOT system," J. Immunol. Methods 286 (1-2):111-122.
D'Aoust et al., 2008, "Influenza virus-like particles produced by transient expression in Nicotiana benthaminana induce a protective immune response against a lethal viral challenge in mice," J. Plant Biotechnol. 6(9):930-940.
D'Aoust et al., 2010, "The production of hemagglutinin-based virus-like particles in plants: a rapid, efficient and safe response to pandemic influenza," Plant Biotechnol. 8(5):607-619.
Da Silva et al., 2013, "Assembly of subtype 1 influenza neuraminidase is driven by both the transmembrane and head domains," J Biol Chem., 288(1):644-653 (Epub 2012).
Dalakouras et al., 2006, "Development of recombinant protein-based influenza vaccine. Expression and affinity purification of H1N1 influenza virus neuraminidase," J Chromatogr A., 1136(1):48-56.
Das et al., 2010, "Glycosylation Focuses Sequence Variation in the Influenza A Virus H1 Hemagglutinin Globular Domain," PLoS Pathogens 6(11):e1001211.
Das et al., 2013, "Defining influenza A virus hemagglutinin antigenic drift by sequential monoclonal antibody selection," Cell Host Microbe, 13(3):314-323.
Database Geneseq "Influenza A virus hemagglutinin protein, H1PR8", Accession No. AJG95109, dated Nov. 15, 2007.
Database GenPept "Hemagglutinin precursor [Contains: Hemagglutinin HA1 chain; Hemagglutinin HA2 chain]", Accession No. P03437, dated Jul. 21, 1986.
De Jong et al., 2000, "Mismatch between the 1997/1998 influenza vaccine and the major epidemic A(H3N2) virus strain as the cause of an inadequate vaccine-induced antibody response to this strain in the elderly," J Med Virol., 61(1):94-99.
Deroo et al., 1996, "Recombinant neuraminidase vaccine protects against lethal influenza," Vaccine, 14(6):561-569.
Desselberger et al., 1978, "Biochemical evidence that "new" influenza virus strains in nature may arise by recombination (reassortment)," Proc Natl Acad Sci USA, 75(7):3341-3345.
Dijkstra et al., 2009, "Long time trends in influenza-like illness and associated determinants in the Netherlands," Epidemiol Infect., 137(4):473-479.
Dilillo et al., 2014, "Broadly neutralizing hemagglutinin stalk-specific antibodies require FcγR interactions for protection against influenza virus in vivo," Nat Med., 20(2):143-151.
Dilillo et al., 2016, "Broadly neutralizing anti-influenza antibodies require Fc receptor engagement for in vivo protection," J Clin Invest., 126(2):605-610.
Dillon et al., 1992, "Induction of protective class I MHC-restricted CTL in mice by a recombinant influenza vaccine in aluminum hydroxide adjuvant," Vaccine 10(5):309-318.
Domnich et al., 2017, "Effectiveness of MF59-adjuvanted seasonal influenza vaccine in the elderly: A systematic review and meta-analysis," Vaccine, 35(4):513-520.
Doms et al., 2000, "HIV-1 Membrane Fusion: Targets of Opportunity," JCB, 151(2): F9-F13.
Dowdle et al., 1973, "Inactivated influenza vaccines. 2. Laboratory indices of protection," Postgrad Med J., 49(569):159-163.
Doyle et al., 1986, "Analysis of Progressive Deletions of the Transmembrane and Cytoplasmic Domains of Influenza Hemagglutinin," JCB 103:1193-1204.
Doyle et al., 2013, "A monoclonal antibody targeting a highly conserved epitope in influenza B neuraminidase provides protection against drug resistant strains," Biochem. Biophys. Res. Commun. 441(1):226-229.
Doyle et al., 2013, "Universal anti-neuraminidase antibody inhibiting all influenza A subtypes," Antiviral Res., 100(2):567-574.
Dreyfus et al., 2012, "Highly conserved protective epitopes on influenza B viruses," Science, 337(6100):1343-1348.
Dubensky et al., 1996, "Sindbis virus DNA-based expression vectors: utility for in vitro and in vivo gene transfer," J Virol., 70(1):508-519.
Dunand et al., 2016, "Both Neutralizing and Non-Neutralizing Human H7N9 Influenza Vaccine-Induced Monoclonal Antibodies Confer Protection," Cell Host Microbe., 19(6):800-813.
Durrant et al., 2016, "Microsecond Molecular Dynamics Simulations of Influenza Neuraminidase Suggest a Mechanism for the Increased Virulence of Stalk-Deletion Mutants," J. Phys. Chem. B., 120(33):8590-8599.
Easterbrook et al., 2012, "Protection against a lethal H5N1 influenza challenge by intranasal immunization with virus-like particles containing 2009 pandemic H1N1 neuraminidase in mice," Virology, 432(1):39-44.
Eda et al., 2006, "Sequential immunization with V3 peptides from primary human immunodeficiency virus type 1 produces cross-

(56) References Cited

OTHER PUBLICATIONS neutralizing antibodies against primary isolates with a matching narrow-neutralization sequence motif," J. Virol. 80(11):5552-5562.
Edwards et al., 2003, "The remarkable flexibility of the human antibody repertoire; isolation of over one thousand different antibodies to a single protein, BLyS," J. Mol. Biol., 334(1):103-118.
Ekiert et al., 2009, "Antibody recognition of a highly conserved influenza virus epitope", Science; 324(5924):246-251.
Ekiert et al., 2011, "A highly conserved neutralizing epitope on group 2 influenza A viruses", Science 333:843-850.
Ekiert et al., 2012, ,"Broadly neutralizing antibodies against influenza virus and prospects for universal therapies," Curr Opin Virol., 2(2):134-141.
Ekiert et al., 2012, "Cross-neutralization of influenza A viruses mediated by a single antibody loop," Nature 489:526-532.
Ellebedy et al., 2014, "Induction of broadly cross-reactive antibody responses to the influenza HA stem region following H5N1 vaccination in humans," Proc Natl Acad Sci USA, 111(36):13133-13138.
EMA Guideline on the exposure to medicinal products during pregnancy: need for post-authorization data (Doc. Ref. EMEA/CHMP/313666/2005), adopted at Community level in May 2006; http://www.ema.europa.eu/docs/en_GB/document_library/Regulatory_and_procedural_guideline/2009/11/WC500011303.pdf (21 pages).
Eriksson et al., 2007, "Local and systemic cytokine and chemokine responses after parenteral influenza vaccination," Influenza Other Respir Viruses, 1(4):139-146.
Ermler et al., 2017, "Chimeric Hemagglutinin Constructs Induce Broad Protection against Influenza B Virus Challenge in the Mouse Model," J. Virol. 91(12): e00286-17.
Extended European Search Report for European Application No. 11763347.9, dated Feb. 2, 2015.
Fields et al., 1981, "Structure of the neuraminidase gene in human influenza virus A/PR/8/34," Nature, 290(5803):213-217.
Fiore et al., 2010, "Prevention and control of influenza with vaccines: recommendations of the Advisory Committee on Immunization Practices (ACIP), 2010," MMWR Recomm. Rep., 59(RR-8):1-62.
Fiore et al., 2011, "Antiviral agents for the treatment and chemoprophylaxis of influenza—recommendations of the Advisory Committee on Immunization Practices (ACIP)," MMWR Recomm Rep., 60(1):1-24.
Fitch et al., 1997, "Long term trends in the evolution of H(3) HA1 human influenza type A," Proc. Natl. Acad. Sci. USA, 94(15):7712-7718.
Flandorfer et al., 2003, "Chimeric Influenza A Viruses with a Functional Influenza B Virus Neuraminidase or Hemagglutinin," J. Virol. 77(17):9116-9123.
Fleury, et al., 2007, GenBank Acc. No. P03437, Updated Apr. 3, 2007.
Fluzone®, 2009-2010 Fluzone Seasonal influenza vaccine package insert, 2009.
Fodor et al., 1999, "Rescue of influenza A virus from recombinant DNA," J. Virol. 73:9679-9682 (1999).
Fouchier et al., 2004, "Avian influenza A virus (H7N7) associated with human conjunctivitis and a fatal case of acute respiratory distress syndrome," Proc Natl Acad Sci USA, 101(5):1356-1361.
Fox et al., 1982, "Influenzavirus infections in Seattle families, 1975-1979. II. Pattern of infection in invaded households and relation of age and prior antibody to occurrence of infection and related illness," Am J Epidemiol., 116(2):228-242.
Friesen et al., 2014, "A common solution to group 2 influenza virus neutralization," Proc. Natl. Acad. Sci. USA, 111(1):445-450 (Epub 2013).
Fujii et al., 2002, "Selective incorporation of influenza virus RNA segments into virions," Proc. Natl. Acad. Sci. USA 100:2002-2007.
Fulton et al., 2018, "The Influenza B Virus Hemagglutinin Head Domain Is Less Tolerant to Transposon Mutagenesis than That of the Influenza A Virus," J Virol., 92(16):e00754-18 (13 pages).
Gamblin et al., 2004, "The structure and receptor binding properties of the 1918 influenza hemagglutinin," Science, 303(5665):1838-1842.
Gao et al., 2009, "Rewiring the RNAs of influenza virus to prevent reassortment," Proc. Natl. Acad. Sci. USA 106:15891-15896.
Gao et al., 2013, "Human infection with a novel avian-origin influenza A(H7N9) virus," N. Engl. J. Med. 368:1888-1897.
Gao et al., 2016, "Measuring Influenza Neuraminidase Inhibition Antibody Titers by Enzyme-linked Lectin Assay," J. Vis. Exp., (115):e54573 (9 pages).
Gao et al., 2019, "Antigenic Drift of the Influenza A(H1N1)pdm09 Virus Neuraminidase Results in Reduced Effectiveness of A/California/7/2009 (H1N1pdm09)-Specific Antibodies," mBio, 10(2):e00307-19 (17 pages).
García-Sastre et al., 1994, "Introduction of foreign sequences into the genome of influenza A virus," Dev. Biol. Stand 82:237-246.
García-Sastre et al., 1994, "Use of a mammalian internal ribosomal entry site element for expression of a foreign protein by a transfectant influenza virus," J. Virol. 68:6254-6261.
Garcon et al., 2012, "Development and evaluation of AS03, an Adjuvant System containing α-tocopherol and squalene in an oil-in-water emulsion," Expert Rev Vaccines, 11(3):349-366.
Gauger et al., 2011, "Enhanced pneumonia and disease in pigs vaccinated with an inactivated human-like (δ-cluster) H1N2 vaccine and challenged with pandemic 2009 H1N1 influenza virus," Vaccine 29(15):2712-2719.
Gavigan et al., 2019, "Influenza: annual seasonal severity," Curr. Opin. Pediatr., 31(1):112-118.
Gaymard et al., 2016, "Functional balance between neuraminidase and haemagglutinin in influenza viruses," Clin. Microbiol. Infect., 22(12):975-983.
GenBan Accession No. AAA43397.1, neuraminidase [Influenza A virus (A/WSN/1933(H1N1))], 1982.
GenBan Accession No. ABG23658.1, neuraminidase, partial [Influenza A virus (A/Zhejiang/16/2006(H5N1))], 2007.
GenBank Accession No. AAA43412.1, neuraminidase [Influenza A virus (A/Puerto Rico/8/1934(H1N1))], 1981.
GenBank Accession No. AAQ90293.1, neuraminidase [Influenza A virus (A/equine/Santiago/77(H7N7))], 2003.
GenBank Accession No. AAS89005.1, neuraminidase [Influenza A virus (A/Thailand/3(SP-83)/2004(H5N1))], 2005.
GenBank Accession No. ABE97718.1, neuraminidase [Influenza A virus (A/Vietnam/CL100/2004(H5N1))], 2006.
GenBank Accession No. ABE97719.1, neuraminidase [Influenza A virus (A/Vietnam/CL105/2005(H5N1))], 2006.
GenBank Accession No. ABE97720.1, neuraminidase [Influenza A virus (A/Vietnam/CL115/2005(H5N1))], 2006.
GenBank Accession No. ACQ76318, hemagglutinin [Influenza A virus (A/California/04/2009(H1N1))], 2009.
GenBank Accession No. ACS71642, haemagglutinin [Influenza A virus (A/Perth/16/2009(H3N2))], 2009.
GenBank Accession No. AEX30531.1, neuraminidase [Influenza A virus (A/chicken/N101/Iran/2011(H9N2))], 2011.
GenBank Accession No. AEX30532.1, neuraminidase [Influenza A virus (A/chicken/N102/Iran/2011(H9N2))], 2011.
GenBank Accession No. AG018161.1, *Homo sapiens* genomic DNA, 21q region, clone: B396A17A4a015, genomic survey sequence, 1999.
GenBank Accession No. AIA62041.1, neuraminidase [Influenza A virus (A/goose/Guangxi/020G/2009(H3N8))], 2014.
GenBank Accession No. AII30325.1, neuraminidase [Influenza A virus (A/pigeon/Guangxi/020P/2009(H3N6))], 2015.
GenBank Accession No. BAF48478-2007, haemagglutinin [Influenza A virus (A/duck/Czech/1956(H4N6))], 2007.
GenBank Accession No. CRI06477.1, neuraminidase [Influenza A virus (A/England/10740685/2010(H1N1))], 2015.
GenBank Accession No. CY209719.1, Influenza B virus (B/Arizona/36/2016) NB protein (NB) and neuraminidase (NA) genes, complete cds, last modified Dec. 21, 2016.
GenBank Accession No. DQ017504.1, Influenza A virus (A/mallard/Alberta/24/01(H7N3)) from Canada segment 4, complete sequence, 2005.

(56) References Cited

OTHER PUBLICATIONS

GenBank Accession No. KY090574.1, Influenza B virus (B/Pennsylvania/34/2015) segment 6 NB protein (NB) and neuraminidase (NA) genes, complete cds, last modified Aug. 24, 2017.
GenBank Accession No. NP_040981.1, neuraminidase [Influenza A virus (A/Puerto Rico/8/1934(H1N1))], 1981.
GenBank, NCBI Reference Sequence: YP_163736.1, HA2 [Influenza A virus (A/Puerto Rico/8/1934(H1N1))].
Georgiev et al., 2018, "Two-Component Ferritin Nanoparticles for Multimerization of Diverse Trimeric Antigens," ACS Infect Dis., 4(5):788-796.
Gerdil, 2003, "The annual production cycle for influenza vaccine," Vaccine, 21(16):1776-1779.
Gerhard et al., 1981, "Antigenic structure of influenza virus haemagglutinin defined by hybridoma antibodies," Nature, 290(5808):713-717.
Gerhard et al., 2006, "Prospects for universal influenza virus vaccine," Emerging Infectious Diseases; 12(4):569-574.
Gibbs et al., 2001, "Recombination in the hemagglutinin gene of the 1918 Spanish Flu," Science 293(5536):1842-1845.
Giddings et al., 2000, "Transgenic plants as factories for biopharmaceuticals," Nat. Biotechnol. 18:1151-1155.
Giles et al., 2012, "Computationally optimized antigens to overcome influenza viral diversity," Expert Rev Vaccines, 11(3):267-269.
Glezen et al., 1978, "Interpandemic influenza in the Houston area, 1974-76," N Engl J Med., 298(11):587-592.
Gocnik et al., 2008, "Antibodies Induced by the HA2 Glycopolypeptide of Influenza Virus Haemagglutinin Improve Recovery from Influenza A Virus Infection," J Gen Virol., 89:958-967.
Goel et al., 2004, "Plasticity within the antigen-combining site may manifest as molecular mimicry in the humoral immune response," J. Immunol., 173(12):7358-7367.
Goff et al., 2013, "Induction of cross-reactive antibodies to novel H7N9 influenza virus by recombinant Newcastle disease virus expressing a North American lineage H7 subtype hemagglutinin," *J. Virol.*, 87 (14): 8235-40.
Goff et al., 2013, "Adjuvants and immunization strategies to induce influenza virus hemagglutinin stalk antibodies", PLoS One 8:e79194.
Gomord et al., 2005, "Biopharmaceutical production in plants: problems, solutions and opportunities." Trends in Biotechnology, 23(11):559-565.
Goto et al., 2013, "The genome-packaging signal of the influenza A virus genome comprises a genome incorporation signal and a genome-bundling signal," J. Virol., 87(21):11316-11322.
Gould et al., 1987, "Mouse H-2k-Restricted Cytotoxic T Cells Recognize Antigenic Determinants in Both the HA1 and HA2 Subunits of the Influenza A/PR/8/34 Hemagglutinin," J. Exp. Med., 166:693-701.
Graham et al., 2013, "DNA Vaccine Delivered by a Needle-Free Injection Device Improves Potency of Priming for Antibody and CD8+ TCell Responses after rAd5 Boost in a Randomized Clinical Trial," PLoS ONE, 8(4): 1-11, e59340.
Gravel et al., 2010, "Qualitative and quantitative analyses of virtually all subtypes of influenza A and B viral neuraminidases using antibodies targeting the universally conserved sequences," Vaccine 28(36):5774-5784.
Graves et al., 1983, "Preparation of influenza virus subviral particles lacking the HAI subunit of hemagglutinin: unmasking of cross-reactive HA2 determinants," Virology 126(1):106-116.
Grohskopf et al., 2017, "Prevention and Control of Seasonal Influenza with Vaccines: Recommendations of the Advisory Committee on Immunization Practices—United States, 2017-18 Influenza Season," MMWR Recomm. Rep., 66(2):1-20.
Gross et al., 1995, "The efficacy of influenza vaccine in elderly persons. A meta-analysis and review of the literature," Ann Intern Med., 123(7):518-527.
Gubareva et al., 2000, "Influenza virus neuraminidase inhibitors," Lancet, 355(9206):827-835.
Gulati et al., 2002, "Antibody epitopes on the neuraminidase of a recent H3N2 influenza virus (A/Memphis/31/98)," J Virol., 76(23):12274-12280.
Haffer et al., 1990, "Human immunodeficiency virus-like, nonreplicating, gag-env particles assemble in a recombinant vaccinia virus expression system," J Virol., 64(6):2653-2659.
Hagnesee et al., 1991, "Self-assembly of human papillomavirus type 1 capsids by expression of the L1 protein alone or by coexpression of the L1 and L2 capsid proteins," J Virol., 67(1):315-322.
Hai et al., 2008, "Influenza B virus NS1-truncated mutants: live-attenuated vaccine approach", J Virol 82:10580-10590.
Hai et al., 2011, "A reassortment-incompetent live attenuated influenza virus vaccine for protection against pandemic virus strains", Journal of virology 85:6832-6843.
Hai et al., 2012, "Influenza viruses expressing chimeric hemagglutinins: globular head and stalk domains derived from different subtypes", J. Virol. 86:5774-5781.
Hai et al., 2013, "Influenza A(H7N9) virus gains neuraminidase inhibitor resistance without loss of in vivo virulence or transmissibility," Nat Commun., 4:2854 (9 pages).
Halbherr et al., 2015, "Biological and protective properties of immune sera directed to the influenza virus neuraminidase," J Virol., 89(3):1550-1563 (Epub Nov. 12, 2014).
Hallily et al., 2015, "High-Affinity H7 Head and Stalk Domain-Specific Antibody Response to an Inactivated Influenza H7N7 Vaccine After Priming With Live Attenuated Influenza Vaccine," Journal of Infectious Diseases, 212: 1270-1278.
Hamilton et al., 2016, "Club cells surviving influenza A virus infection induce temporary nonspecific antiviral immunity," Proc Natl Acad Sci USA, 113(14):3861-3866.
Hanks et al., 2005, "Re-engineered CD40 receptor enables potent pharmacological activation of dendritic-cell cancer vaccines in vivo," Nat Med., 11(2):130-137 and supplemental materials.
Harris et al., 2006, "Influenza virus pleiomorphy characterized by cryoelectron tomography," Proc Natl Acad Sci USA, 103(50):19123-19127.
Harvey et al., 2011, "Improved antigen yield in pandemic H1N1 (2009) candidate vaccine viruses with chimeric hemagglutinin molecules," J Virol., 85(12):6086-6090.
Haynes, 2009, "Influenza virus-like particle vaccines", Expert Rev. Vaccines, 8(4): 435-445.
He et al., 2014, "Infection of influenza virus neuraminidase-vaccinated mice with homologous influenza virus leads to strong protection against heterologous influenza viruses," J Gen Virol., 95(Pt 12):2627-2637.
He et al., 2017, "Alveolar macrophages are critical for broadly-reactive antibody-mediated protection against influenza A virus in mice," Nat. Commun., 8(1):846 (14 pages).
Heaton et al., 2013, "Genome-wide mutagenesis of influenza virus reveals unique plasticity of the hemagglutinin and NS1 proteins," Proc Natl Acad Sci USA, 110(50):20248-20253.
Heaton et al., 2013, "In Vivo Bioluminescent Imaging of Influenza A Virus Infection and Characterization of Novel Cross-Protective Monoclonal Antibodies," J. Virol. 87(15):8272-8281.
Heikkinen et al., 2014, ",Impact of influenza B lineage-level mismatch between trivalent seasonal influenza vaccines and circulating viruses, 1999-2012" Clin Infect Dis., 59(11):1519-1524.
Heinonen et al., 2010, "Early oseltamivir treatment of influenza in children 1-3 years of age: a randomized controlled trial," Clin Infect Dis., 51(8):887-894.
Hobson et al., 1972, "The role of serum haemagglutination-inhibiting antibody in protection against challenge infection with influenza A2 and B viruses," J Hyg (Lond), 70(4):767-777.
Hoffmann et al., 2000, "A DNA transfection system for generation of influenza A virus from eight plasmids," Proc Natl Acad Sci USA, 97(11):6108-6113.
Hong et al., 2013, "Antibody recognition of the pandemic H1N1 Influenza virus hemagglutinin receptor binding site," J. Virol. 87(22):12471-12480.
Horimoto et al., 2003, "Generation of influenza A viruses with chimeric (type A/B) hemagglutinins." J Virol. 77(14):8031-8038.

(56) References Cited

OTHER PUBLICATIONS

Horimoto et al., 2004, "Influenza A viruses possessing type B hemagglutinin and neuraminidase: potential as vaccine components," Microbes and Infection, 6(6):579-583.
Horvath et al., 1998, "Hemagglutinin-based multipeptide construct elicits enhanced protective immune response in mice against influenza A virus infection", Immunology Letters; 60(2/03):127-136.
Hu et al., 2013, "Fully human broadly neutralizing monoclonal antibodies against influenza A viruses generated from the memory B cells of a 2009 pandemic H1N1 influenza vaccine recipient," Virology 435(2):320-328.
Huang et al., 2004, "The Reverse Genetics Systems for Human and Animal RNA Viruses," Chinese Journal of Biotechnology, vol. 20, Issue 3, which is also published in Lian Yu, "Molecular Biology of Infectious Bursal Disease Virus and Research on New Vaccines," Zhejiang University Press, pp. 254-266, published on Dec. 31, 2007 (in Chinese with English abstract).
Hutchinson et al., 2010, "Genome packaging in influenza A virus," J. Gen. Virol., 91(Pt 2):313-328 (Epub 2009).
Iba et al., 2014, "Conserved neutralizing epitope at globular head of hemagglutinin in H3N2 influenza viruses" J. Virol., 88(13):7130-7144.
Igarashi et al.: 2008, "Genetically destined potentials for N-linked glycosylation of influenza virus hemagglutinin" Virology, 376:323-329.
Impagliazzo et al., 2015, "A stable trimeric influenza hemagglutinin stem as a broadly protective immunogen." Science, 349(6254):1301-1306 and supplemental materials.
Influenza Research Database, strain name: A/Anhui/1/2005, Collection Date: 2005 (2 pages).
Influenza Research Database, strain name: A/Bar-headed Goose/Qinghai/59/05, Collection Date: 2005 (2 pages).
Influenza Research Database, strain name: A/California/07/2009, Collection Date: Apr. 9, 2009 (3 pages).
Influenza Research Database, strain name: A/Indonesia/5/2005, Collection Date: 2005 (3 pages).
Influenza Research Database, strain name: A/turkey/Turkey/1/2005, Collection Date: 2005 (2 pages).
Influenza Research Database, strain name: A/Viet Nam/1203/2004, Collection Date: 2004 (3 pages).
Influenza Research Database, strain name: A/whooper swan/Mongolia/244/2005, Collection Date: 2005 (2 pages).
Influenza Research Database, strain name: B/Brisbane/60/2008, Collection Date: 2008 (2 pages).
Influenza Research Database, strain name: B/Florida/04/2006, Collection Date: Nov. 1, 2006 (1 page).
Influenza Research Database, strain name: B/Florida/4/2006, Collection Date: Nov. 1, 2006 (1 page).
Influenza Research Database, strain name: B/lee/40, Collection Date: 1940 (1 page).
Influenza Research Database, strain name: B/Malaysia/2506/2004, Collection Date: May 12, 2004 (2 pages).
Influenza Research Database, strain name: B/Massachusetts/02/2012, Collection Date: Mar. 13, 2012 (1 page).
Influenza Research Database, strain name: B/New Jersey/01/2012, Collection Date: Apr. 26, 2012 (1 page).
Influenza Research Database, strain name: B/Texas/02/2013, Collection Date: Jan. 9, 2013 (1 page).
Influenza Research Database, strain name: B/Victoria/2/87, Collection Date: 1987 (1 page).
Influenza Research Database, strain name: B/Wisconsin/01/2010, Collection Date: 2010 (1 page).
Influenza Research Database, strain name: B/Yamagata/16/88, Collection Date: 1988 (2 pages).
International Preliminary Report on Patentability of International application No. PCT/US2011/030441, dated Oct. 2, 2012.
International Search Report and Corrected Written Opinion for International Patent Application No. PCT/US2020/029582 (Pub No. WO 2020219719) mailed Sep. 28, 2020 (30 pages).
International Search Report and Written Opinion for International Patent Application No. PCT/US2020/039588 (Pub No. WO 2020264141) mailed Nov. 9, 2020 (18 pages).
International Search Report and Written Opinion for International Patent Application No. PCT/US2020/056703 (Pub No. WO 2021081120) mailed Feb. 9, 2021 (13 pages).
International Search Report and Written Opinion mailed Oct. 29, 2019 of International Patent Application No. PCT/US2019/038178 (16 pages).
International Search Report issued on Feb. 19, 2013 or PCT Application No. PCT/US2012/056122, Published as WO 2013/043729.
International Search Report issued on Apr. 28, 2014 of PCT Application No. PCT/US2013/075697, Published as WO 2014/099931.
International Search Report issued on Jun. 26, 2014 for PCT Application No. PCT/US2014/025526, Published as WO 2014/159960.
International Search Report issued on Jul. 13, 2011 of PCT Application No. PCT/US2011/030441, Published as WO 2011/123495.
International Search Report issued on Aug. 24, 2010 or PCT Application No. PCT/US2010/029202, Published as WO 2010/117786.
International Search Report of International Application No. PCT/US2010/036170, dated Aug. 17, 2010.
International Search Report of International Application No. PCT/US2011/025467, dated Oct. 19, 2011.
International Search Report of International Application No. PCT/US2016/014640, mailed Jun. 3, 2016.
International Search Report of International Application No. PCT/US2016/037595, mailed Sep. 15, 2016.
International Search Report of International Application No. PCT/US2017/035479, mailed Oct. 25, 2017.
International Search Report of International Application No. PCT/US2017/037384, mailed Nov. 3, 2017.
International Search Report of International Application No. PCT/US2018/026489, mailed Aug. 27, 2018.
International Search Report of International Application No. PCT/US2018/045399, mailed Nov. 29, 2018.
Isakova-Sivak et al., 2011, "Genetic bases of the temperature-sensitive phenotype of a master donor virus used in live attenuated influenza vaccines: A/Leningrad/134/17/57 (H2N2)," Virology, 412(2):297-305.
Isakova-Sivak et al., 2015, "Safety, immunogenicity and infectivity of new live attenuated influenza vaccines," Expert Rev Vaccines, 14(10):1313-1329.
Izurieta et al., 2000, "Influenza and the rates of hospitalization for respiratory disease among infants and young children," *NEJM* 342(4):232-239.
Jacobsen et al., 2017, "Influenza Virus Hemagglutinin Stalk-Specific Antibodies in Human Serum are a Surrogate Marker for In Vivo Protection in a Serum Transfer Mouse Challenge Model," mBio, 8(5):e01463-17 (13 pages).
Jayasundara et al., 2014, "Natural attack rate of influenza in unvaccinated children and adults: a meta-regression analysis," BMC Infect Dis., 14:670 (9 pages).
Jefferson et al., 2005, "Assessment of the efficacy and effectiveness of influenza vaccines in healthy children: systematic review," Lancet, 365(9461):773-780.
Jefferson et al., 2005, "Efficacy and effectiveness of influenza vaccines in elderly people: a systematic review," Lancet, 366(9492):1165-1174.
Jeoung et al., 1995, "Effects of tumor necrosis factor-alpha on antimitogenicity and cell cycle-related proteins in MCF-7 cells." J Biol Chem., 270(31):18367-18373.
Jerne et al., 1982, "Recurrent idiotopes and internal images," EMBO J., 1(2):243-247.
Jin et al., 2003, "Multiple amino acid residues confer temperature sensitivity to human influenza virus vaccine strains (FluMist) derived from cold-adapted A/Ann Arbor/6/60," Virology, 306(1):18-24.
Job et al., 2018, "Broadened immunity against influenza by vaccination with computationally designed influenza virus N1 neuraminidase constructs," NPJ Vaccines, 3:55 (11 pages).

(56) References Cited

OTHER PUBLICATIONS

Joh Hira et al., 2004, "Production of monoclonal antibodies against a conserved region of Hemagglutinin of Influenza A virus and enzymatic activity of the light chain," Lectures in the Chemical Society of Japan, 84(2):1156, 2 J6-15 in Japanese with English translation of Abstract (4 pages).
Johansson et al., 1987, "Antigen-presenting B cells and helper T cells cooperatively mediate intravirionic antigenic competition between influenza A virus surface glycoproteins," Proc Natl Acad Sci USA, 84(19):6869-6873.
Johansson et al., 1987, "Immunologic response to influenza virus neuraminidase is influenced by prior experience with the associated viral hemagglutinin. II. Sequential infection of mice simulates human experience," J. Immunol., 139(6):2010-2014.
Johansson et al., 1989, "Purified influenza virus hemagglutinin and neuraminidase are equivalent in stimulation of antibody response but induce contrasting types of immunity to infection," J. Virol., 63(3):1239-1246.
Johansson et al., 1993, "Dissociation of influenza virus hemagglutinin and neuraminidase eliminates their intravirionic antigenic competition," J Virol., 67(10):5721-5723.
Johansson et al., 1994, "Immunization with purified N1 and N2 influenza virus neuraminidases demonstrates cross-reactivity without antigenic competition," Proc Natl Acad Sci USA, 91(6):2358-2361.
Johansson et al., 1998, "Supplementation of conventional influenza A vaccine with purified viral neuraminidase results in a balanced and broadened immune response," Vaccine, 16(9-10):1009-1015.
Johansson et al., 2011, "Influenza viral neuraminidase: the forgotten antigen," Expert Rev. Vaccines, 10(12):1683-1695.
Johnson et al., 2002, "Updating the accounts: global mortality of the 1918-1920 "Spanish" influenza pandemic," Bull Hist Med., 76(1):105-115.
Joseph et al., 2007, "Evaluation of replication and pathogenicity of avian influenza a H7 subtype viruses in a mouse model," J Virol., 81(19):10558-10566.
Kabat et al., 1971, "Attempts to locate complementarity-determining residues in the variable positions of light and heavy chains," Ann N Y Acad Sci., 190:382-393.
Kamlangdee et al., 2016, "Mosaic H5 Hemagglutinin Provides Broad Humoral and Cellular Immune Responses Against Influenza Viruses," J Virol., 90(15):6771-6783.
Kanekiyo et al., 2013, "Self-assembling influenza nanoparticle vaccines elicit broadly neutralizing H1N1 antibodies." Nature, 499(7456):102-6.
Karlin et al., 1990, "Methods for assessing the statistical significance of molecular sequence features by using general scoring schemes," Proc Natl Acad Sci USA, 87(6):2264-2268.
Karlin et al., 1993, "Applications and statistics for multiple high-scoring segments in molecular sequences," Proc Natl Acad Sci USA, 90(12):5873-5877.
Kashyap et al., 2008, "Combinatorial antibody libraries from survivors of the Turkish H5N1 avian influenza outbreak reveal virus neutralization strategies", Proc Natl Acad Sci USA; 105:5986-5991.
Kaverin et al., 2004, "Structural Differences Among Hemagglutinins of Influenza A Virus Subtypes Are Reflected in Their Antigenic Architecture: Analysis of H9 Escape Mutants", Journal of Virology, 78(1):240-249.
Kawai et al., 2006, "A comparison of the effectiveness of oseltamivir for the treatment of influenza A and influenza B: a Japanese multicenter study of the 2003-2004 and 2004-2005 influenza seasons," Clin Infect Dis., 43(4):439-444.
Kawai et al., 2007, "Longer virus shedding in influenza B than in influenza A among outpatients treated with oseltamivir," J Infect., 55(3):267-272.
Kayali et al., 2011, "Evidence of infection with H4 and H11 avian influenza viruses among Lebanese chicken growers," PLoS One, 6(10):e26818.
Khanna et al., 2014, "Protective Immunity Based on the Conserved Hemagglutinin Stalk Domain and Its Prospects for Universal Influenza Vaccine Development," Biomed Res Int., 2014:546274 (7 pages).
Khiabanian et al., 2009, "Differences in patient age distribution between influenza A subtypes," PLoS One, 4(8):e6832 (5 pages).
Khurana et al., 2011, "MF59 adjuvant enhances diversity and affinity of antibody-mediated immune response to pandemic influenza vaccines," Sci. Transl. Med., 3(85):85ra48 (10 pages).
Khurana et al., 2013, "Vaccine-induced anti-HA2 antibodies promote virus fusion and enhance influenza virus respiratory disease," Sci Transl Med., 5(200):200ra114.
Khurana et al., 2013, "DNA Priming Prior to Inactivated Influenza A(H5N1) Vaccination Expands the Antibody Epitope Repertoire and Increases Affinity Maturation in a Boost-Interval-Dependent Manner in Adults," Journal of Infectious Disease, 208:413-417.
Kilbourne et al., 1976, "Comparative efficacy of neuraminidase-specific and conventional influenza virus vaccines in induction of antibody to neuraminidase in humans," J Infect Dis., 134(4):384-394.
Kilbourne et al., 1987, "Immunologic response to the influenza virus neuraminidase is influenced by prior experience with the associated viral hemagglutinin. I. Studies in human vaccinees," J Immunol., 138(9):3010-3013.
Kilbourne et al., 1990, "Independent and disparate evolution in nature of influenza A virus hemagglutinin and neuraminidase glycoproteins," Proc Natl Acad Sci USA, 87(2):786-790.
Kilbourne et al., 1995, "Purified influenza A virus N2 neuraminidase vaccine is immunogenic and non-toxic in humans," Vaccine, 13(18):1799-1803.
Kirnbauer et al., 1992, "Papillomavirus L1 major capsid protein self-assembles into virus-like particles that are highly immunogenic," Proc Natl Acad Sci USA, 89(24):12180-12184.
Kistner et al., 2007, "Cell culture (Vero) derived whole virus (H5N1) vaccine based on wild-type virus strain induces cross-protective immune responses," Vaccine 25(32):6028-6036.
Klausberger et al., 2014, "One-shot vaccination with an insect cell-derived low-dose influenza A H7 virus-like particle preparation protects mice against H7N9 challenge," Vaccine, 32(3):355-362 (Epub 2013).
Koel et al., 2013, "Substitutions near the receptor binding site determine major antigenic change during influenza virus evolution," Science, 342(6161):976-979.
Kon et al., 2016, "Influenza Vaccine Manufacturing: Effect of Inactivation, Splitting and Site of Manufacturing. Comparison of Influenza Vaccine Production Processes," PLoS One, 11(3):e0150700 (19 pages).
Kosik et al., 2019, "Neuraminidase inhibition contributes to influenza A virus neutralization by anti-hemagglutinin stem antibodies," J. Exp. Med., 216(2):304-316.
Krammer et al., 2010. "Trichoplusia ni cells (High Five) are highly efficient for the production of influenza A virus-like particles: a comparison of two insect cell lines as production platforms for influenza vaccines," Mol Biotechnol., 45(3):226-234.
Krammer et al., 2012, "A carboxy-terminal trimerization domain stabilizes conformational epitopes on the stalk domain of soluble recombinant hemagglutinin substrates," PLoS One. 7:e43603.
Krammer et al., 2012, "Hemagglutinin stalk-reactive antibodies are boosted following sequential infection with seasonal and pandemic H1N1 influenza virus in mice", J Virol, 86:10302-10307.
Krammer et al., 2013, "Influenza virus hemagglutinin stalk-based antibodies and vaccines," Curr. Opin. Virol., 3(5):521-530.
Krammer et al., 2013, "Chimeric hemagglutinin influenza virus vaccine constructs elicit broadly protective stalk-specific antibodies", J Virol. 87:6542-6550.
Krammer et al., 2014, "An H7N1 influenza virus vaccine induces broadly reactive antibody responses against H7N9 in humans," Clin Vaccine Immunol., 21(8):1153-1163.
Krammer et al., 2014, "Divergent H7 immunogens offer protection from H7N9 virus challenge," J Virol., 88(8):3976-3985.
Krammer et al., 2014, "Assessment of influenza virus hemagglutinin stalk-based immunity in ferrets," J. Virol., 88:3432-3442.

(56) References Cited

OTHER PUBLICATIONS

Krammer et al., 2014, "H3 stalk-based chimeric hemagglutinin influenza virus constructs protect mice from H7N9 challenge", J Virol, 88:2340-2343.
Krammer et al., 2015, "Advances in the development of influenza virus vaccines," Nat Rev Drug Discov., 14(3):167-182.
Krammer et al., 2018, "Influenza," Nat. Rev. Dis. Primers, 4(1):3 (21 pages).
Krammer et al., 2018, "NAction! How Can Neuraminidase-Based Immunity Contribute to Better Influenza Virus Vaccines?," mBio, 9(2):e02332-17 (12 pages).
Krammer et al., 2019, "Emerging from the Shadow of Hemagglutinin: Neuraminidase Is an Important Target for Influenza Vaccination," Cell Host Microbe., 26(6):712-713.
Krammer et al., 2019, "Universal Influenza Virus Vaccines That Target the Conserved Hemagglutinin Stalk and Conserved Sites in the Head Domain," J. Infect. Dis., 219(Suppl_1):S62-S67.
Krammer, 2015, "Emerging influenza viruses and the prospect of a universal influenza virus vaccine," Biotechnol. J., 10(5):690-701.
Krammer, 2015, "The quest for a universal flu vaccine: headless HA 2.0", Cell Host Microbe, 18:395-397.
Krammer, 2016, "Novel universal influenza virus vaccine approaches", Current Opinion in Virology, 17:95-103.
Krammer, 2017, "Annex I: Sequence comparison of the J&J, VRC and MSSM headless HA constructs (tentative H3 numbering included)" (3 pages).
Krammer, 2017, "Strategies to induce broadly protective antibody responses to viral glycoproteins," Expert Rev. Vaccines, 16(5):503-513.
Krammer, 2019, "The human antibody response to influenza A virus infection and vaccination," Nat. Rev. Immunol., 19(6):383-397.
Krause et al., 2011, "A broadly neutralizing human monoclonal antibody that recognizes a conserved, novel epitope on the globular head of the influenza H1N1 virus hemagglutinin", J. Virol., 85(20):10905-10908.
Krause et al., 2012, "Human monoclonal antibodies to pandemic 1957 H2N2 and pandemic 1968 H3N2 influenza viruses", J. Virol. 86:6334-6340.
Laguio-Vila et al., 2015, "Comparison of serum hemagglutinin and neuraminidase inhibition antibodies after 2010-2011 trivalent inactivated influenza vaccination in healthcare personnel," Open Forum Infect. Dis., 2(1):oful15 (9 pages).
Lambe et al., 2013, "Immunity against heterosubtypic influenza virus induced by adenovirus and MVA expressing nucleoprotein and matrix protein-1," Sci Rep., 3:1443 (8 pages).
Landry et al., 2008, "Three-dimensional structure determines the pattern of CD4+ T-cell epitope dominance in influenza virus hemagglutinin", Journal of Virology; 82(3):1238-1248.
Landry et al., 2010, "Preclinical and Clinical Development of Plant-Made Virus-Like Particle Vaccine against Avian H5N1 Influenza", PLoS One, 5(12): e15559. (12 pages).
Larkin et al., 2007, "Clustal W and Clustal X version 2.0," Bioinformatics, 23(21):2947-2948.
Laver et al., 1981, "Mechanism of antigenic drift in influenza virus. Amino acid sequence changes in an antigenically active region of Hong Kong (H3N2) influenza virus hemagglutinin," J Mol Biol., 145(2):339-361.
Laver et al., 1988, "Crystallization and preliminary X-ray analysis of type B influenza virus neuraminidase complexed with antibody Fab fragments," Virology, 167(2):621-624.
Lebendiker, 2006, "Purification Protocols." The Wolfson Centre for Applied Structural Biology, http://wolfson.huji.ac.il/purification/Purification_Protocols.html. Apr. 5, 2006 (30 pages).
Ledgerwood et al., 2011, "DNA priming and influenza vaccine immunogenicity: two phase 1 open label randomised clinical trials," Lancet Infect Dis., 11(12):916-924.
Ledgerwood, et al., 2013, "Prime-Boost Interval Matters: A Randomized Phase 1 Study to Identify the Minimum Interval Necessary to Observe the H5 DNA Influenza Vaccine Priming Effect," Journal of Infectious Diseases, 208:418-422.
Lee et al., 2012, "Heterosubtypic antibody recognition of the influenza virus hemagglutinin receptor binding site enhanced by avidity", Proc. Natl. Acad. Sci. USA 109:17040-17045.
Lee et al., 2014, "Receptor mimicry by antibody F045-092 facilitates universal binding to the H3 subtype of influenza virus," Nat. Commun., 5:3614 (9 pages).
Leon et al., 2016, "Optimal activation of Fc-mediated effector functions by influenza virus hemagglutinin antibodies requires two points of contact," Proc. Natl. Acad. Sci. USA, 113(40):E5944-E5951.
Leroux-Roels, et al. 2008. "Broad Glade 2 cross-reactive immunity induced by an adjuvanted Glade 1 rH5N1 pandemic influenza vaccine", PLOS One; 3(2):e1665 (5 pages).
Li et al., 1992, "Influenza A virus transfectants with chimaeric haemagglutinins containing epitopes from different subytpes", Journal of Virology, 67:399-404.
Li et al., 1999, "Recombinant influenza A virus vaccines for the pathogenic human A/Hong Kong/97 (H5N1) viruses," J Infect Dis., 179(5):1132-1138.
Li et al., 2011, "A novel tetrameric PilZ domain structure from xanthomonads," PLoS One, 6(7):e22036 (13 pages).
Li et al., 2011, "Emergence and genetic variation of neuraminidase stalk deletions in avian influenza viruses," PLoS One, 6(2):e14722 (11 pages).
Li et al., 2012, "Pandemic H1N1 influenza vaccine induces a recall response in humans that favors broadly cross-reactive memory B cells," Proc Natl Acad Sci USA, 109(23):9047-9052.
Liang et al., 1994, "Heterosubtypic immunity to influenza type A virus in mice. Effector mechanisms and their longevity," J Immunol., 152(4):1653-1661.
Liang et al., 2005, "cis-Acting packaging signals in the influenza virus PB1, PB2, and PA genomic RNA segments," J. Virol., 79(16):10348-10355.
Liu et al., 2015, "Cross-Reactive Neuraminidase-Inhibiting Antibodies Elicited by Immunization with Recombinant Neuraminidase Proteins of H5N1 and Pandemic H1N1 Influenza A Viruses," J. Virol., 89(14):7224-7234.
Liu et al., 2019, "Sequential Immunization With Live-Attenuated Chimeric Hemagglutinin-Based Vaccines Confers Heterosubtypic Immunity Against Influenza A Viruses in a Preclinical Ferret Model," Front. Immunol., 10:756 and Supplemental Figs. S1 to S7 (25 pages).
Lloyd et al., 2009, "Modelling the human immune response: performance of a 1011 human antibody repertoire against a broad panel of therapeutically relevant antigens," Protein Eng. Des. Sel., 22(3):159-168 (Epub 2008).
Lorieau et al., 2010, "The complete influenza hemagglutinin fusion domain adopts a tight helical hairpin arrangement at the lipid:water interface," PNAS, 107(25):11341-11346.
Lowen et al., 2006, "The guinea pig as a transmission model for human influenza viruses," Proc Natl Acad Sci USA, 103(26):9988-9992.
Lowen et al., 2009, "Blocking interhost transmission of influenza virus by vaccination in the guinea pig model," J. Virol. 83(7):2803-2818.
Lu et al., 2013, "Production and stabilization of the trimeric influenza hemagglutinin stem domain for potentially broadly protective influenza vaccines." PNAS, 111(1):125-130.
Luke et al., 2014, "Improving pandemic H5N1 influenza vaccines by combining different vaccine platforms," Expert Review of Vaccines 13(7):873-883.
Luo et al., 1993, "Alterations of the stalk of the influenza virus neuraminidase: deletions and insertions," Virus Res., 29(2):141-153.
Maier et al., 2020, "Pre-existing Antineuraminidase Antibodies Are Associated With Shortened Duration of Influenza A(H1N1)pdm Virus Shedding and Illness in Naturally Infected Adults," Clin Infect Dis., 70(11):2290-2297.
Mallajosyula et al., 2014, "Influenza hemagglutinin stem-fragment immunogen elicits broadly neutralizing antibodies and confers heterologous protection." PNAS, 111(25):E2514-23.
Manini et al., 2015, "Flucelvax (Optaflu) for seasonal influenza," Expert Rev. Vaccines, 14(6):789-804.

(56) References Cited

OTHER PUBLICATIONS

Marasco et al.. 2007, "The growth and potential of human antiviral monoclonal antibody therapeutics", Nat. Biotechnol: 25(12):1421-1434.
Marathe et al., 2016, "Combinations of Oseltamivir and T-705 Extend the Treatment Window for Highly Pathogenic Influenza A(H5N1) Virus Infection in Mice," Sci Rep., 6:26742 (14 pages).
Marcelin et al., 2012, "Contribution of antibody production against neuraminidase to the protection afforded by influenza vaccines," Rev Med Virol., 22(4):267-279.
Margine et al., 2013, "Expression of functional recombinant hemagglutinin and neuraminidase proteins from the novel H7N9 influenza virus using the baculovirus expression system," J Vis Exp., (81):e51112 (10 pages).
Margine et al., 2013, "H3N2 influenza virus infection induces broadly reactive hemagglutinin stalk antibodies in humans and mice", J. Virol. 87(8):4728-4737.
Margine et al., 2013, "Hemagglutinin stalk-based universal vaccine constructs protect against group 2 influenza A viruses", J Virol, 10435-10446.
Marsh et al., 2007, "Specific residues of the influenza A virus hemagglutinin viral RNA are important for efficient packaging into budding virions," J. Virol., 81(18):9727-9736.
Martinez-Romero et al., 2013, "Substitutions T200A and E227A in the hemagglutinin of pandemic 2009 influenza A virus increase lethality but decrease transmission," J Virol., 87(11):6507-6511.
Martinez-Sobrido et al., 2010, "Generation of recombinant influenza virus from plasmid DNA," J Vis Exp., 3(42):e2057 (5 pages).
Matias et al., 2016, "Model estimates of the burden of outpatient visits attributable to influenza in the United States," BMC Infect. Dis., 16(1):641 (11 pages).
Matrosovich et al., 2004, "Neuraminidase is important for the initiation of influenza virus infection in human airway epithelium," J Virol., 78(22):12665-12667.
Matsuzaki et al., 2014, "Epitope mapping of the hemagglutinin molecule of A/(H1N1)pdm09 influenza virus by using monoclonal antibody escape mutants," J. Virol., 88(21):12364-12373.
Matthews et al., 2006, "A tryptophan amphiphilic tetramerization domain-containing acetylcholinesterase from the bovine lungworm, *Dictyocaulus viviparus*," Parasitology, 133(Pt 3):381-387.
Mbawuike et al., 1994, "Influenza A subtype cross-protection after immunization of outbred mice with purified chimeric NS1/HA2 influenza virus protein", Vaccine, 1994: 12(14):1340-1348.
McAuley et al., 2019, "Influenza Virus Neuraminidase Structure and Functions, " Front Microbiol., 10:39 (13 pages).
McMahon et al., 2019, "Mucosal Immunity against Neuraminidase Prevents Influenza B Virus Transmission in Guinea Pigs," mBio, 10(3):e00560-19 (12 pages).
Memoli et al., 2016, "Evaluation of Antihemagglutinin and Antineuraminidase Antibodies as Correlates of Protection in an Influenza A/H1N1 Virus Healthy Human Challenge Model," mBio, 7(2):e00417-16 (12 pages).
Mendez-Legaza et al., 2019, "Heterotypic Neuraminidase Antibodies Against Different A(H1N1) Strains are Elicited after Seasonal Influenza Vaccination," Vaccines (Basel), 7(1):30 (15 pages).
Meseda et al., 2018, "Immunogenicity and Protection Against Influenza H7N3 in Mice by Modified Vaccinia Virus Ankara Vectors Expressing Influenza Virus Hemagglutinin or Neuraminidase," Sci. Rep., 8(1):5364 (14 pages).
Mett et al., 2008, "A plant-produced influenza subunit vaccine protects ferrets against virus challenge", Influenza and Other Respiratory Viruses, 2(1):33-40.
Miller et al., 2013, "1976 and 2009 H1N1 influenza virus vaccines boost anti-hemagglutinin stalk antibodies in humans", J. Infect. Dis. 207:98-105.
Mo et al., 2003. "Coexpression of complementary fragments of CIC-5 and restoration of chloride channel function in a Dent's disease mutation", Am J Physiol Cell Physiol; 286:C79-C89.
Mok et al., 2008, "Enhancement of the CD8<+> T cell response to a subdominant epitope respiratory syncytial virus by deletion of an immunodominant epitope", Vaccine: 26(37):4775-4782.
Molinari et al., 2007, "The annual impact of seasonal influenza in the US: measuring disease burden and costs," Vaccine, 25(27):5086-5096.
Montgomery et al., 1993, "Heterologous and homologous protection against influenza A by DNA vaccination: optimization of DNA vectors," DNA Cell Biol. 12(9):777-783.
Monto et al., 2015, "Antibody to Influenza Virus Neuraminidase: An Independent Correlate of Protection," J Infect Dis., 212(8):1191-1199.
Montplaisir et al., 2009, "Risk of narcolepsy associated with inactivated adjuvanted (AS03) A/H1N1 (2009) pandemic influenza vaccine in Quebec," *PLoS One* 9 (9): e108489 (9 pages).
Moody et al., 2011, "H3N2 influenza infection elicits more cross-reactive and less clonally expanded anti-hemagglutinin antibodies than influenza vaccination," PLoS One, 6(10):e25797 (14 pages).
Morel et al., 2011, "Adjuvant System AS03 containing α-tocopherol modulates innate immune response and leads to improved adaptive immunity," Vaccine, 29(13):2461-2473.
Moscona, 2005, "Neuraminidase inhibitors for influenza," N Engl J Med., 353(13):1363-1373.
Mullarkey et al., 2016, "Broadly Neutralizing Hemagglutinin Stalk-Specific Antibodies Induce Potent Phagocytosis of Immune Complexes by Neutrophils in an Fc-Dependent Manner," mBio, 7(5):e01624-16 (12 pages).
Muramoto et al., 2006, "Hierarchy among viral RNA (vRNA) segments in their role in vRNA incorporation into influenza A virions," J. Virol., 80(5):2318-2325.
Murphy et al., 1972, "Association of serum anti-neuraminidase antibody with resistance to influenza in man," N. Engl. J. Med., 286(25):1329-1332.
Nachbagauer et al., 2014, "Induction of broadly reactive anti-hemagglutinin stalk antibodies by an H5N1 vaccine in humans," *J. Virol.* 88 (22): 13260-13268.
Nachbagauer et al., 2015, "Hemagglutinin stalk immunity reduces influenza virus replication and transmission in ferrets," J Virol., 90(6):3268-3273.
Nachbagauer et al., 2016, "A chimeric haemagglutinin-based influenza split virion vaccine adjuvanted with AS03 induces protective stalk-reactive antibodies in mice," Npj Vaccines 1:16015 (10 pages).
Nachbagauer et al., 2016, "Age Dependence and Isotype Specificity of Influenza Virus Hemagglutinin Stalk-Reactive Antibodies in Humans," MBio., 7(1):e01996-15 (10 pages).
Nachbagauer et al., 2017, "A universal influenza virus vaccine candidate confers protection against pandemic H1N1 infection in preclinical ferret studies," NPJ Vaccines, 2:26 (13 pages).
Nakajima et al., 2000, "Variation in response among individuals to antigenic sites on the HA protein of human influenza virus may be responsible for the emergence of drift strains in the human population," Virology, 274(1):220-231.
Nakaya et al., 2001, "Recombinant Newcastle disease virus as a vaccine vector," J Virol., 75(23):11868-11873.
National Insitutes of Health Pubchem, "Zanamivir," found at https://pubchem.ncbi.nim.nih.gov/zompound/Zanamivir (Year: 2021).
NCT01676402, Clinical Trial, "Seasonal Influenza HA DNA With Trivalent Inactivated Vaccine (TIV) Administered ID or IM in Healthy Adults 18-70 Years," last updated Jul. 17, 2014 (6 pages).
Nelson et al., 2008, "Lehninger Principles of Biochemistry—Fifth Edition," Chapter 4.3, p. 123, W.H. Freeman and Company.
Neumann et al., 1999, "Generation of influenza A viruses entirely from cloned cDNAs", PNAS 96:9345-9350.
Ni et al., 2013, "Structural basis for the divergent evolution of influenza B virus hemagglutinin," Virology 446(1-2):112-122.
Nichol et al., 1995, "The effectiveness of vaccination against influenza in healthy, working adults," N Engl J Med., 333(14):889-893.
Nicholson et al., 2000, "Efficacy and safety of oseltamivir in treatment of acute influenza: a randomised controlled trial," Lancet, 355(9218):1845-1850.

(56) References Cited

OTHER PUBLICATIONS

O'Brien et al. 2004, "Incidence of outpatient visits and hospitalizations related to influenza in infants and young children," Pediatrics, 113:585-593.
Ogburn et al., 2007, "Impact of clinic interventions on the rate of influenza vaccination in pregnant women," J Reprod Med., 52(9):753-756.
Ohkura et al., 2012, "Epitope mapping of neutralizing monoclonal antibody in avian influenza A H5N1 virus hemagglutinin," Biochem. Biophys. Res. Commun. 418(1):38-43 (Epub 2011).
Ohmit et al., 2011, "Influenza hemagglutination-inhibition antibody titer as a correlate of vaccine-induced protection," J Infect Dis., 204(12):1879-1885.
Okuno et al., 1993, "A common neutralizing epitope conserved between the hemagglutinins of influenza A virus H1 and H2 strains," J. Virol., 67(5):2552-2558.
Okuno et al., 1994, "Protection against the mouse-adapted A/FM/1/47 strain of influenza A virus in mice by a monoclonal antibody with cross-neutralizing activity among E11 and H2 strains," J. Virol., 68(1):517-520.
Olson et al., 2007, "Monitoring the impact of influenza by age: emergency department fever and respiratory complaint surveillance in New York City," PLoS Med., 4(8):e247 (13 pages).
Oshima et al., 2011, "Naturally Occurring Antibodies in Humans Can Neutralize a Variety of Influenza Virus Strains, Including H3, H1, H2, and H5". Journal of Virology, 85(21):11048-11057.
Ott et al., 2000. The Adjuvant MF59: A 10-Year Perspective, p. 211-228. In O'Hagan DT (ed.), Vaccine Adjuvants, vol. 42. Springer.
Oxford, 2013, "Towards a universal influenza vaccine: volunteer virus challenge studies in quarantine to speed the development and subsequent licensing," Br J Clin Pharmacol., 76(2):210-216.
Ozawa et al., 2007, "Contributions of two nuclear localization signals of influenza A virus nucleoprotein to viral replication," J. Virol., 81(1):30-41 (Epub 2006).
Ozawa et al., 2009, "Nucleotide sequence requirements at the 5' end of the influenza A virus M RNA segment for efficient virus replication," J. Virol., 83(7):3384-3388.
Palese et al., 1974, "Characterization of temperature sensitive influenza virus mutants defective in neuraminidase," Virology, 61(2):397-410.
Palese et al., 2007, "Orthomyxoviridae: The Viruses and Their Replication," in Fields Virology, D.M. Knipe, & P.M. Howley (Eds.), Philadelphia, PA: Wolters Kluwer Lippincott Williams & Wilkins, pp. 1647-1689.
Palese, 2004, "Influenza: old and new threats," Nat Med., 10(12 Suppl):S82-87.
Pan et al., 2011, "Selective pressure to increase charge in immunodominant epitopes of the H3 hemagglutinin influenza protein," J Mol Evol., 72(1):90-103.
Pantua et al., 2006, "Requirements for the assembly and release of Newcastle disease virus-like particles," J Virol, 80(22):11062-11073.
Papanikolopoulou et al., 2004, "Formation of highly stable chimeric trimers by fusion of an adenovirus fiber shaft fragment with the foldon domain of bacteriophage t4 fibritin", J. Biol. Chem. 279(10):8991-8998.
Park et al., 2006, "Engineered viral vaccine constructs with dual specificity: avian influenza and Newcastle disease," Proc Natl Acad Sci USA, 103(21):8203-8208.
Pearson et al., 1988, "Improved tools for biological sequence comparison," Proc Natl Acad Sci USA, 85(8):2444-2448.
Perricone et al., 2013, "Autoimmune/inflammatory syndrome induced by adjuvants (ASIA) 2013: Unveiling the pathogenic, clinical and diagnostic aspects," *J Autoimmun.*, 47:1-16.
Pettersen et al., 2004, "UCSF Chimera—a visualization system for exploratory research and analysis," J Comput Chem., 25(13):1605-1612.
Pica et al., 2012, "Hemagglutinin stalk antibodies elicited by the 2009 pandemic influenza virus as a mechanism for the extinction or seasonal H1N1 viruses." Proc Nat Acad Sci USA, 109(7):2573-2578.
Piepenbrink et al., 2019, "Broad and Protective Influenza B Virus Neuraminidase Antibodies in Humans after Vaccination and their Clonal Persistence as Plasma Cells," mBio, 10(2):e00066-19 (17 pages).
Ping et al., 2015, "Development of high-yield influenza A virus vaccine viruses," Nat. Commun., 6:8148 (15 pages).
Pleschka et al., 1996, "A plasmid-based reverse genetics system for influenza A virus", J Virol 70:4188-4192.
Ponomarenko et al., 2009, "B-Cell Epitope Prediction" Ch. 35 in Structural Bioinformatics, 2nd Edition, Gu and Bourne Editors, John Wiley & Sons. Inc., pp. 849-879.
Popova et al., 2012, "Immunodominance of antigenic site B over site A of hemagglutinin of recent H3N2 influenza viruses," PLoS One, 7(7):e41895 (11 pages).
Potter et al., 1979, "Determinants of immunity to influenza infection in man," Br. Med. Bull, 35(1):69-75.
Powers et al., 1996, "Neuraminidase-specific antibody responses to inactivated influenza virus vaccine in young and elderly adults," Clin. Diagn. Lab. Immunol., 3(5):511-516.
Q0PZR5, UniProtKB Accession No. Q0PZR5, Oct. 29, 2014 [online]. [Retrieved on Sep. 2, 2016]. Retrieved from the internet <URL:http://www.uniprot.org/uniprot/Q0PZR5.txt?version=53> (2 pages).
Quinlivan et al., 2005, "Attenuation of equine influenza viruses through truncations of the NS1 protein," J Virol., 79(13):8431-8439.
Rajendran et al., 2017, "Analysis of Anti-Influenza Virus Neuraminidase Antibodies in Children, Adults, and the Elderly by ELISA and Enzyme Inhibition: Evidence for Original Antigenic Sin" mBio, 8(2):e02281-16 (12 pages).
Rambaut et al., 2008, "The genomic and epidemiological dynamics of human influenza A virus," Nature, 453(7195):615-619.
Rasala et al., 2010, "Production of therapeutic proteins in algae, analysis of expression of seven human proteins in the chloroplast of Chlamydomonas reinhardtii," Plant Biotechnol J., 8(6):719-733.
Reid et al., Hemagglutinin [Influenza A virus (A/South Carolina/1/1918(H1N1))]. GenBank Acc. No .AAD17229.1. Dep. Oct. 11, 2000.
Retamal et al., 2014, "Epitope mapping of the 2009 pandemic and the A/Brisbane/59/2007 seasonal (H1N1) influenza virus haemagglutinins using mAbs and escape mutants," J. Gen. Virol., 95(Pt 11):2377-2389.
Ridenour et al., 2015, "Development of influenza A(H7N9) candidate vaccine viruses with improved hemagglutinin antigen yield in eggs," Influenza Other Respir Viruses, 9(5):263-270.
Rivera et al., 1995, "Probing the structure of influenza B hemagglutinin using site-directed mutagenesis," Virology 206(2):787-795.
Roberts el al., 1993, "Role of conserved glycosylation sites in maturation and transport of influenza A virus hemagglutinin." J Virol, 67(6):3048-3060.
Robertson, 1987, "Sequence Analysis of the Haemagglutinin of A/Taiwan/1/86, a New Variant of Human Influenza A(H1/N1) Virus," J. Gen. Virol., 68(4):1205-1208.
Rockman et al., 2013, "Neuraminidase-inhibiting antibody is a correlate of cross-protection against lethal H5N1 influenza virus in ferrets immunized with seasonal influenza vaccine," J Virol., 87(6):3053-3061.
Rolfes et al., 2014, "Update: influenza activity—United States, Sep. 28-Dec. 6, 2014," MMWR Morb Mortal Wkly Rep., 63(50):1189-1194.
Rolfes et al., 2018, "Annual estimates of the burden of seasonal influenza in the United States: A tool for strengthening influenza surveillance and preparedness," Influenza Other Respir Viruses, 12(1):132-137.
Rudenko et al., 2015, "Assessment of immune responses to H5N1 inactivated influenza vaccine among individuals previously primed with H5N2 live attenuated influenza vaccine," Human Vaccines & Immunotherapeutics, 11(12):2839-2848.
Rudikoff et al., 1982, "Single amino acid substitution altering antigen-binding specificity." Proc Nat Acad Sci U S A., 79(6):1979-1983.

(56) References Cited

OTHER PUBLICATIONS

Rumpler et al., 2018, "A conserved leucine zipper-like motif accounts for strong tetramerization capabilities of SEPALLATA-like MADS-domain transcription factors," J Exp Bot., 69(8):1943-1954.
Runstadler et al., 2013, "Connecting the study of wild influenza with the potential for pandemic disease," Infect Genet Evol., 17:162-187.
Ryder et al., 2016, "Vaccination with VSV-vectored chimeric hemagglutinins protects mice against divergent influenza virus challenge strains", J. Virol., 90(5):2544-2550.
Sagawa et al., 1996, "The immunological activity of a deletion mutant of influenza virus haemagglutinin lacking the globular region", J Gen Virol; 77:1483-1487.
Salem, 2000, "In vivo acute depletion of CD8(+) T cells before murine cytomegalovirus infection upregulated innate antiviral activity of natural killer cells", Int. J. Immunopharmacol. 22:707-718.
Sandbulte et al., 2007, "Cross-reactive neuraminidase antibodies afford partial protection against H5N1 in mice and are present in unexposed humans," PLoS Med., 4(2):e59 (8 pages).
Sandbulte et al., 2011, "Discordant antigenic drift of neuraminidase and hemagglutinin in H1N1 and H3N2 influenza viruses," Proc. Natl. Acad. Sci. USA, 108(51):20748-20753.
Santak, 2012, "Old and new ways to combat human influenza virus." Periodicus Biologorum, 114(2):221-234.
Sautto et al., 2018, "Towards a Universal Influenza Vaccine: Different Approaches for One Goal," Virol J., 15(1):17 (12 pages).
Scheiffele et al., 1997, "Interaction of influenza virus haemagglutinin with sphingolipid-cholesterol membrane domains via its transmembrane domain," EMBO J., 16(18):5501-5508.
Scheres, 2012, "RELION: implementation of a Bayesian approach to cryo-EM structure determination," J Struct Biol., 180(3):519-530.
Schneeman et al., 2012, "A Virus-Like Particle That Elicits Cross-Reactive Antibodies to the Conserved Stem of Influenza Virus Hemagglutinin," J. Virol., 86(21): 11686-22697.
Schuind et al., 2015, "Immunogenicity and Safety of an EB66 Cell-Culture-Derived Influenza A/Indonesia/5/2005(H5N1) AS03-Adjuvanted Vaccine: A Phase 1 Randomized Trial," J Infect Dis., 212(4):531-541.
Schulman et al., 1968, "Protective effects of specific immunity to viral neuraminidase on influenza virus infection of mice," J Virol., 2(8):778-786.
Schulman, 1969, "The role of antineuraminidase antibody in immunity to influenza virus infection," Bull World Health Organ., 41(3):647-650.
Schulze, 1997, "Effects of Glycosylation on the Properites and Functions of Influenza Virus Hemagglutinin", The Journal of Infectious Diseases, 176(S1):S24-S28.
Seibert et al., 2010, "Oseltamivir-resistant variants of the 2009 pandemic H1N1 influenza A virus are not attenuated in the guinea pig and ferret transmission models," J Virol., 84(21):11219-11226.
Seibert et al., 2013, "Recombinant IgA is sufficient to prevent influenza virus transmission in guinea pigs," J Virol., 87(14):7793-7804.
Shaw et al., 2013, "Chapter 40: Orthomyxoviridae," in Fields Virology, 6th Ed., Lippincott Williams & Wilkins, a Wolters Kluwer, Philadelphia, PA, pp. 1151-1181 and references (107 pages).
Shoji et al., 2008, "Plant-expressed HA as a seasonal influenza vaccine candidate", Vaccine, 26(23):2930-2934.
Shoji et al., 2011, "An influenza N1 neuraminidase-specific monoclonal antibody with broad neuraminidase inhibition activity against H5N1 HPAI viruses," Hum Vaccin., 7 Suppl:199-204.
Simmons et al., 2007. "Prophylactic and therapeutic efficacy of human monoclonal antibodies against H5N1 Influenza", PLOS Medicine; 4(5):928-936.
Singleton et al., 1995, "Dictionary of Microbiology and Molecular Biology—Second Edition." A Wiley-Interscience Publication (3 pages).
Skehel et al., 1984, "A carbohydrate side chain on hemagglutinins of Hong Kong influenza viruses inhibits recognition by a monoclonal antibody," Proc. Natl. Acad. Sci. USA, 81(6):1779-1783.
Skowronski et al., 2013, "Virus-host interactions and the unusual age and sex distribution of human cases of influenza A(H7N9) in China, Apr. 2013," Euro Surveill., 18(17):20465 (4 pages).
Smith et al., 1981, "Comparison of biosequences," Advances in Applied Mathematics, 2(4):482-489.
Smith et al., 2004, "Mapping the antigenic and genetic evolution of influenza virus," Science, 305(5682):371-376.
Smith et al., 2017, "Neuraminidase-based recombinant virus-like particles protect against lethal avian influenza A(H5N1) virus infection in ferrets," Virology, 509:90-97.
Song et al., 2007, "Influenza A Virus Hemagglutinin Protein, H1PR8," GENESEQ, XP002595511.
Sparrow et al., 2016, "Passive immunization for influenza through antibody therapies, a review of the pipeline, challenges, and potential applications." Vaccine, 34: 5442-5448.
Stadlbauer et al., 2018, "Cross-reactive mouse monoclonal antibodies raised against the hemagglutinin of A/Shanghai/1/2013 (H7N9) protect against novel H7 virus isolates in the mouse model," Emerg. Microbes. Infect., 7(1):110 (12 pages).
Stadlbauer et al., 2019, "Broadly Protective Human Antibodies That Target the Active Site of Influenza Virus Neuraminidase," Science, 366(6464):499-504.
Stech et al., 2005, "A new approach to an influenza live vaccine: modification of the cleavage site of hemagglutinin", Nat. Med. 11(6):683-689.
Steel et al., 2009, "Live attenuated influenza viruses containing NS1 truncations as vaccine candidates against H5N1 highly pathogenic avian influenza," J Virol., 83(4):1742-1753.
Steel et al., 2010, "Influenza Virus Vaccine Based on the Conserved Hemagglutinin Stalk Domain," mBIO 1(1). pii: e00018-10 (9 pages).
Stephenson et al., 2005, "Cross-reactivity to highly pathogenic avian influenza H5N1 viruses alter vaccination with nonadjuvantcd and MF59-adjuvanted influenza A/Duck/Singapore/97 (H5N3) vaccine: a potential priming strategy." J Infect Dis., 191(8):1210-1215.
Steuler et al., 1984, "Sequence of the neuraminidase gene of an avian influenza A virus (A/parrot/ulster/73, H7N1)," Virology, 135(1):118-124.
Stevens et al., 2006, "Structure and Receptor Specificity of the Hemagglutinin from an H5N1 Influenza Virus" Science, 312:404-409.
Stoute et al., 1997, "A preliminary evaluation of a recombinant circumsporozoite protein vaccine against Plasmodium falciparum malaria. RTS,S Malaria Vaccine Evaluation Group," N Engl J Med., 336(2):86-91.
Strobel et al., 2000, "Efficient Expression of the Tumor-Associated Antigen MAGE-3 in Human Dendritic Cells, Using an Avian Influenza Virus Vector", Human Gene Therapy 11:2207-2218.
Su et al., 2014, "Comparing clinical characteristics between hospitalized adults with laboratory-confirmed influenza A and B virus infection," Clin Infect Dis., 59(2):252-255.
Subbarao et al., 2013, "The prospects and challenges of universal vaccines for influenza," Trends Microbiol., 21(7):350-358.
Sugaya et al., 2007, "Lower clinical effectiveness of oseltamivir against influenza B contrasted with influenza A infection in children," Clin Infect Dis., 44(2):197-202 (Epub 2006).
Sui et al., 2011, "Wide prevalence of heterosubtypic broadly neutralizing human anti-influenza A antibodies," Clin Infect Dis., 52(8):1003-1009.
Sui et al.. 2009, "Structural and functional bases for broad-spectrum neutralization of avian and human influenza A viruses", Nat Struct Mol Biol; 16(3):265-273 with Supplementary Information (31 pages).
Sultana et al., 2014, "Stability of neuraminidase in inactivated influenza vaccines," Vaccine, 32(19):2225-2230.
Sun et al., 2011, "Glycosylation Site Alteration in the Evolution of Influenza A (H1N1) Viruses." PLoS Pathogens, 6(7):e22844 (9 pages).
Sun et al., 2019, "Development of Influenza B Universal Vaccine Candidates Using the "Mosaic" Hemagglutinin Approach," J Virol., 93(12):e00333-19 (17 pages).

(56) References Cited

OTHER PUBLICATIONS

Sutter et al., 1992, "Nonreplicating vaccinia vector efficiently expresses recombinant genes," Proc Natl Acad Sci USA, 89(22):10847-10851.
Swayne et al., 2003, "Recombinant paramyxovirus type 1-avian influenza-H7 virus as a vaccine for protection of chickens against influenza and Newcastle disease," Avian Dis., 47(3 Suppl):1047-1050.
Sylte et al., 2007, "Influenza neuraminidase antibodies provide partial protection for chickens against high pathogenic avian influenza infection," Vaccine, 25(19):3763-3772.
Talaat et al., 2014, "A Live Attenuated Influenza A(H5N1) Vaccine Induces Long-Term Immunity in the Absence of a Primary Antibody Response," Journal of Infectious Disease; 208:1860-1869.
Tamura et al., 1998, "Definition of amino acid residues on the epitope responsible for recognition by influenza A virus H1-specific, H2-specific, and H1- and H2-cross-reactive murine cytotoxic T-lymphocyte clones", J. Virol. 72:9404-9406.
Tan et al., 2012, "A pan-H1 anti-hemagglutinin monoclonal antibody with potent broad-spectrum efficacy in vivo", J. Virol. 86:6179-6188.
Tan et al., 2014, "Characterization of a broadly neutralizing monoclonal antibody that targets the fusion domain of group 2 influenza A virus hemagglutinin," J. Virol., 88(23):13580-13592.
Tan et al., 2018, "Universal influenza virus vaccines and therapeutics: where do we stand with influenza B virus?," Curr Opin Immunol., 53:45-50.
Tao et al., 2009, "Enhanced protective immunity against H5N1 influenza virus challenge by vaccination with DNA expressing a chimeric hemagglutinin in combination with an MHC class I-restricted epitope of nucleoprotein in mice", Antiviral research. 2009; 81(3); 253-260.
Tarbouriech et al., 2000, "Tetrameric coiled coil domain of Sendai virus phosphoprotein, " Nat Struct Biol., 7(9):777-781.
Tate et al., 2001, "Specific Sites of N-Linked Glycosylation on the Hemagglutinin of H1N1 Subtype Influenza A Virus Determine Sensitivity to Inhibitors of the Innate Immune Systema nd Virulence in Mice." Journal of Immunology, 187(4):1884-1894.
Tete et al., 2016, "Dissecting the hemagglutinin head and stalk-specific IgG antibody response in healthcare workers following pandemic H1N1 vaccination," *Nature Partner Journals* (*NPJ*) *Vaccine*, Article No. 16001 doi:10.1038/npjvaccines.2016.1 (9 pages).
Thoennes et al., 2008, "Analysis of residues near the fusion peptide in the influenza hemagglutinin structure for roles in triggering membrane fusion", Virology; 370(2):403-414.
Thompson et al., 2003, "Mortality associated with influenza and respiratory syncytial virus in the United States," JAMA, 289(2):179-186.
Thomson et al., 2012, "Pandemic H1N1 Influenza Infection and Vaccination in Humans Induces Cross-Protective Antibodies that Target the Hemagglutinin Stem", Front. Immunol. 3:87 (19 pages).
Throsby et al., 2008, "Heterosubtypic neutralizing monoclonal antibodies cross-protective against H5N1 and H1N1 recovered from human IgM+ memory B cells", PLoS ONE; 3(12):e3942 (15 pages).
Tong et al., 2013. "New world bats harbor diverse influenza A viruses," PLoS Pathog. 9: e1003657 (12 pages).
Tran et al., 2016, "Cryo-electron microscopy structures of chimeric hemagglutinin displayed on a universal influenza vaccine candidate", MBio, 7(2): e00257-16 (9 pages).
Treanor et al., 2007, "Safety and immunogenicity of a baculovirus-expressed hemagglutinin influenza vaccine: a randomized controlled trial," JAMA, 297(14):1577-1582.
Tricco et al., 2013, "Comparing influenza vaccine efficacy against mismatched and matched strains: a systematic review and meta-analysis," BMC Med., 11:153 (19 pages).
Truelove et al., 2016, "A comparison of hemagglutination inhibition and neutralization assays for characterizing immunity to seasonal influenza A," Influenza Other Respir Viruses, 10(6):518-524.
Tscherne et al., 2010, "An enzymatic virus-like particle assay for sensitive detection of virus entry," J Virol Methods, 163(2):336-343.
Tsibane et al., 2012, "Influenza human monoclonal antibody 1F1 interacts with three major antigenic sites and residues mediating human receptor specificity in H1N1 viruses," PLoS Pathog., 8(12):e1003067 (9 pages).
Turbelin et al., 2013, "Age distribution of influenza like illness cases during post-pandemic A(H3N2): comparison with the twelve previous seasons, in France," PLoS One, 8(6):e65919 (9 pages).
Tweed et al., 2004, "Human illness from avian influenza H7N3, British Columbia," Emerg Infect Dis., 10(12):2196-2199.
UniProtKB: P16199.1, Influenza B virus (B/Memphis/3/89), last modified Dec. 11, 2019.
UniProtKB: P16203.1, Influenza B virus (B/Singapore/222/79), last modified Apr. 22, 2020.
UniProtKB: P16205.1, Influenza B virus (B/USSR/100/83), last modified Dec. 11, 2019.
UniProtKB: P16207.1, Influenza B virus (Strain B/Victoria/3/85), last modified Dec. 11, 2019.
UniProtKB: P27907, Influenza B virus (strain B/Beijing/1/1987), last modified Dec. 11, 2019.
UniProtKB: Q90021.1, Influenza B virus (B/Yamagata/16/1988), last modified Dec. 11, 2019.
Vahey et al., 2019, "Low-Fidelity Assembly of Influenza A Virus Promotes Escape from Host Cells," Cell, 176(1-2):281-294.e19 (Epub 2018).
Vajdos et al., 2002, "Comprehensive Functional Maps of the Antigenbinding Site of an Anti-ErbB2 Antibody Obtained with Shotgun Scanning Mutagenesis," Journal of Molecular Biology, 320:415-428.
Van Der Brand et al., 2011, "Efficacy of vaccination with different combinations of MF59-adjuvanted and nonadjuvanted seasonal and pandemic influenza vaccines against pandemic H1N1 (2009) influenza virus infection in ferrets," J Virol., 85(6):2851-2858.
Van Der Lubbe, 2018, "Mini-HA Is Superior to Full Length Hemagglutinin Immunization in Inducing Stem-Specific Antibodies and Protection Against Group 1 Influenza Virus Challenges in Mice," Front Immunol., 9:2350 (13 pages).
Van Der Most et al., 2014, "Seeking help: B cells adapting to flu variability," Sci Transl Med., 6(246):246ps8 (7 pages).
Van Reeth et al., 2009, "Prior infection with an H1N1 swine influenza virus partially protects pigs against a low pathogenic H5N1 avian influenza virus," Vaccine, 27(45):6330-6339.
Vanlandschoot et al., 1995. "A fairly conserved epitope on the hemagglutinin of influenza A (H3N2) virus with variable accessibility to neutralizing antibody." Virology, 212(2)526-534.
Vanlandschoot et al., 1998. "An antibody which binds to the membrane-proximal end of influenza virus haemagglutinin (1-13 subtype) inhibits the low-pH-induced conformational change and cell-cell fusion but does not neutralize virus", Journal of General Virology; 79:1781-1791.
Vareckova et al., 2008, "HA2-specific monoclonal antibodies as tools for differential recognition of influenza A virus antigenic subtypes," Virus Research, 132:181-186.
Vaughn et al., 2014, "Safety of AS03-adjuvanted inactivated split virion A(H1N1)pdm09 and H5N1 influenza virus vaccines administered to adults: pooled analysis of 28 clinical trials," Hum Vaccin Immunother, 10(10):2942-2957.
Vavricka et al., 2011, "Structural and functional analysis of laninamivir and its octanoate prodrug reveals group specific mechanisms for influenza NA inhibition," PLoS Pathog., 7(10):e1002249 (10 pages).
Vigerust et al., 2007, "N-Linked Glycosylation Attenuates H3N2 Influenza Viruses", Journal of Virology, 81(16): 8593-8600.
Vincent et al., 2008, "Failure of protection and enhanced pneumonia with a US H1N2 swine influenza virus in pigs vaccinated with an inactivated classical swine H1N1 vaccine," *Vet Microbiol.*, 126(4):310-323.
Wagner et al., 2002, "Functional balance between haemagglutinin and neuraminidase in influenza virus infections," Rev. Med. Virol., 12(3):159-166.
Walz et al., 2018, "Neuraminidase-Inhibiting Antibody Titers Correlate with Protection from Heterologous Influenza Virus Strains of the Same Neuraminidase Subtype," J Virol., 92(17):e01006-18 (15 pages).

(56) References Cited

OTHER PUBLICATIONS

Wan et al., 2013, "Molecular basis for broad neuraminidase immunity: conserved epitopes in seasonal and pandemic H1N1 as well as H5N1 influenza viruses," J Virol., 87(16):9290-9300.
Wan et al., 2015, "Structural characterization of a protective epitope spanning A(H1N1)pdm09 influenza virus neuraminidase monomers," Nat Commun., 6:6114 (10 pages).
Wang et al., 1992, "High-affinity laminin receptor is a receptor for Sindbis virus in mammalian cells," J Virol., 66(8):4992-5001.
Wang et al., 2006, "Hemagglutinin (HA) proteins from H1 and H3 serotypes of influenza A viruses require different antigen designs for the induction of optimal protective antibody responses as studied by codon-optimized HA DNA vaccines," J Virol., 80(23):11628-11637.
Wang et al., 2007, "Incorporation of High Levels of Chimeric Human Immunodeficiency Virus Envelope Glycoproteins into Virus-Like Particles", J. Virol., 81(20):10869-10878.
Wang et al., 2008, "Crystal structure of unliganded influenza B virus hemagglutinin," J. Virol. 82(6):3011-3020.
Wang et al., 2008, "Simplified recombinational approach for influenza A virus reverse genetics", J. Virol. Methods 151:74-78.
Wang et al., 2009, "Characterization of cross-reactive antibodies against the influenza virus hemagglutinin", American Society for Virology 28th Annual Meeting, University of British Columbia, Vancouver, BC, Canada dated Jul. 11-15, 2009; Abstract W30-6.
Wang et al., 2009, "Glycans on influenza hemagglutinin affect receptor binding and immune response." PNAS, 106(43): 18137-18142.
Wang et al., 2009, "Universal epitopes of influenza virus hemagglutinins? ", Nature Structural and Molecular Biology; 16(3):233-234.
Wang et al., 2010, "Broadly protective monoclonal antibodies against H3 influenza viruses following sequential immunization with different hemagglutinins", PLOS Pathogens; 6(2):e1000796 (9 pages).
Wang et al., 2010, "Vaccination with a synthetic peptide from the influenza virus hemagglutinin provides protection against distinct viral subtypes". PNAS. 107(44):18979-18984.
Wang et al., 2011, "Biochemistry. Catching a moving target," Science, 333(6044):834-835.
Wang et al., 2012, "Generation of recombinant pandemic H1N1 influenza virus with the HA cleavable by bromelain and identification of the residues influencing HA bromelain cleavage." Vaccine, 30(4):872-878.
Ward et al., 1982, "Amino acid sequence of the Pronase-released heads of neuraminidase subtype N2 from the Asian strain A/Tokyo/3/67 of influenza virus," Biochem J., 207(1):91-95.
Webby et al., 2010, Hemagglutinin [Influenza A virus (A/Brisbane/59/2007(H1N1))]. GenBank Acc. No. ADE28750.1. Dep. Mar. 29, 2010.
Webster et al., 1968, "Reactions of antibodies with surface antigens of influenza virus," J Gen Virol., 3(3):315-326.
Webster et al., 1980, "Determination of the number of nonoverlapping antigenic areas on Hong Kong (H3N2) influenza virus hemagglutinin with monoclonal antibodies and the selection of variants with potential epidemiological significance," Virology, 104(1):139-148.
Webster et al., 1984, "Antigenic and biological characterization of influenza virus neuraminidase (N2) with monoclonal antibodies," Virology, 135(1):30-42.
Wei et al., 2010, "Induction of Broadly Neutralizing H1N1 Influenza Antibodies by Vaccination," Science; 329:1060-1064.
Wei et al., 2020, "Next-generation influenza vaccines: opportunities and challenges," Nat. Rev. Drug Discov., 19(4):239-252.
Weir et al., 2016, "An overview of the regulation of influenza vaccines in the United States," Influenza Other Respir Viruses, 10(5):354-360.
Weis et al., 1988, "Structure of the influenza virus haemagglutinin complexed with its receptor, sialic acid." Nature, 333:426-431.
Weis et al., 1990, "Refinement of the Influenza Virus Hemagglutinin by Simulated Annealing." J. Mol. Biol. 212:737-761.
Weldon et al., 2010, "Enhanced immunogenicity of stabilized trimeric soluble influenza hemagglutinin", PLoSONE 5(9):e12466 (8 pages).
Whittle et al., 2011, "Broadly neutralizing human antibody that recognizes the receptor-binding pocket of influenza virus hemagglutinin," Proc. Natl. Acad. Sci. USA, 108(34):14216-14221.
WHO World Health Organization Factsheet No. 211. Influenza Nov. 2016. https://www.who.int/mediacentre/factsheets/fs211/en.
Wiley et al., 1981, "Structural identification of the antibody-binding sites of Hong Kong influenza haemagglutinin and their involvement in antigenic variation," Nature, 289(5796):373-378.
Wiley et al., 1983, "The three-dimensional structure and antigenic variation of the influenza virus haemagglutinin." Division of Virology, 107-111.
Wiley, 1987, "The Structure and Function of the Hemagglutinin Membrane Glycoprotein of Influenza Virus." Ann. Rev. Biochem., 56:365-394.
Wilson et al., 1981, "Structure of the haemagglutinin membrane glycoprotein of influenza virus at 3 A resolution." Nature, 289:366-373.
Wilson et al., 1990, "Structural basis of immune recognition of influenza virus hemagglutinin," Annu. Rev. Immunol., 8:737-771.
Winokur et al., 1991, "The hepatitis A virus polyprotein expressed by a recombinant vaccinia virus undergoes proteolytic processing and assembly into viruslike particles," J Virol., 65(9):5029-5036.
Winter et al., 1981, "Nucleotide Sequence of the Haemagglutinin Gene of a Human Influenza Virus H1 Subtype" Nature, 292:72-75.
Wohlbold et al., 2014, "In the Shadow of Hemagglutinin: A Growing Interest in Influenza Viral Neuraminidase and Its Role as a Vaccine Antigen," Viruses 6(6):2465-2494.
Wohlbold et al., 2015, "An H10N8 influenza virus vaccine strain and mouse challenge model based on the human isolate A/Jiangxi-Donghu/346/13," Vaccine, 33(9):1102-1106.
Wohlbold et al., 2015, "Vaccination with soluble headless hemagglutinin protects mice from challenge with divergent influenza viruses." Vaccine, 33(29):3314-3321.
Wohlbold et al., 2015, "Vaccination with adjuvanted recombinant neuraminidase induces broad heterologous, but not heterosubtypic, cross-protection against influenza virus infection in mice." MBio, 6(2):e02556.
Wohlbold et al., 2016, "Hemagglutinin Stalk- and Neuraminidase-Specific Monoclonal Antibodies Protect against Lethal H10N8 Influenza Virus Infection in Mice," J Virol., 90(2):851-861.
Wohlbold et al., 2017, "Broadly protective murine monoclonal antibodies against influenza B virus target highly conserved neuraminidase epitopes," Nat. Microbiol. 2(10):1415-1424 with supplemental materials.
Wohlbold, 2017, "The influenza virus neuraminidase as a vaccine antigen and the potential of neuraminidase antibodies to protect against infection," dissertation submitted to the Graduate Faculty of the Graduate School of Biomedical Sciences, Biomedical Sciences Doctoral Program, in partial fulfillment of the requirements for the degree of Doctor of Philosophy, Icahn School of Medicine at Mount Sinai (236 pages).
Worobey et al., 2002, "Questioning the Evidence for Genetic Recombination in the 1918 "Spanish Flu" Virus", Science, 296(5566):211a (3 pages).
Wrammert et al., 2008, "Rapid cloning of high-affinity human monoclonal antibodies against influenza virus," Nature, 453(7195):667-671.
Wrammert et al., 2011, "Broadly cross-reactive antibodies dominate the human B cell response against 2009 pandemic H1N1 influenza virus infection", J. Exp. Med. 208:181-193.
Written Opinion dated Feb. 19, 2013 for PCT Application No. PCT/US2012/056122, Published as WO 2013/043729.
Written Opinion dated Apr. 28, 2014 for PCT Application No. PCT/US2013/075697, Published as WO 2014/099931.
Written Opinion dated Jun. 26, 2014 for PCT Application No. PCT/US2014/025526, Published as WO 2014/159960.
Written Opinion dated Jul. 13, 2011 for PCT Application No. PCT/US2011/030441, Published as WO 2011/123495.
Written Opinion dated Sep. 30, 2011 for PCT Application No. PCT/US2010/029202, Published as WO 2010/117786.

(56) References Cited

OTHER PUBLICATIONS

Written Opinion of International application No. PCT/US2010/036170, dated Aug. 17, 2010.
Written Opinion of International application No. PCT/US2011/025467, dated Oct. 19, 2011.
Written Opinion of the International Searching Authority for International Application No. PCT/US2016/014640, mailed Jun. 3, 2016.
Written Opinion of the International Searching Authority for International Application No. PCT/US2016/037595, mailed Sep. 15, 2016.
Written Opinion of the International Searching Authority for International Application No. PCT/US2017/035479, mailed Oct. 25, 2017.
Written Opinion of the International Searching Authority for International Application No. PCT/US2017/037384, mailed Nov. 3, 2017.
Written Opinion of the International Searching Authority for International Application No. PCT/US2018/026489, mailed Aug. 27, 2018.
Written Opinion of the International Searching Authority for International Application No. PCT/US2018/045399, mailed Nov. 29, 2018.
Wu et al., 2018, "Structural insights into the design of novel anti-influenza therapies," Nat. Struct. Mol. Biol., 25(2):115-121.
Xiao et al., 1996, "High efficiency, long-term clinical expression of cottontail rabbit papillomavirus (CRPV) DNA in rabbit skin following particle-mediated DNA transfer," Nucleic Acids Res., 24(13):2620-2622.
Xie et al., 2011, "Revisiting the 1976 "swine flu" vaccine clinical trials: cross-reactive hemagglutinin and neuraminidase antibodies and their role in protection against the 2009 H1N1 pandemic virus in mice," Clin. Infect. Dis., 53(12):1179-1187.
Xu et al., 2008, "Structural characterization of the 1918 influenza virus H1N1 neuraminidase," J Virol., 82(21):10493-10501.
Xu et al., 2012, "Structural characterization of the hemagglutinin receptor specificity from the 2009 H1N1 influenza pandemic," J. Virol., 86(2):982-990 (Epub 2011).
Yan et al., 2012, "Microbial Resources and Utilization," Harbin Engineering University Press, pp. 100-101, in Chinese with machine English translation of Section 4 (11 pages).
Yang et al., 2006, "Targeting lentiviral vectors to specific cell types in vivo", PNAS 103: 11479-11484.
Yang et al., 2007, "Immunization by Avian H5 Influenza Hemagglutinin Mutants with Altered Receptor Binding Specificity", Science, 317(5839):825-828.
Yang et al., 2014, "A beneficiary role for neuraminidase in influenza virus penetration through the respiratory mucus," PLoS One, 9(10):e110026 (11 pages).
Yang et al., 2014, "Structural stability of influenza A(H1N1)pdm09 virus hemagglutinins." J. Virol., 88(9):4828-4838.
Yang, 2013, "Recombinant trivalent influenza vaccine (flublok(®)): a review of its use in the prevention of seasonal influenza in adults," Drugs, 73(12):1357-1366.
Yassine et al., 2015, "Hemagglutinin-stem nanoparticles generate heterosubtypic influenza protection." Nat. Med. 21(9):1065-1070.
Yasugi et al., 2013, "Human monoclonal antibodies broadly neutralizing against influenza B virus", PLoS Pathog. 9(2):e1003150 (12 pages).
Yasuhara et al., 2019, "Antigenic drift originating from changes to the lateral surface of the neuraminidase head of influenza A virus" Nat. Microbiol., 4(6):1024-1034.
Yen et al., 2011, "Hemagglutinin-neuraminidase balance confers respiratory-droplet transmissibility of the pandemic H1N1 influenza virus in ferrets," Proc. Natl. Acad. Sci. USA, 108(34):14264-14269.
Yewdell., 2013, "To dream the impossible dream: universal influenza vaccination," Curr Opin Virol., 3(3):316-321.
Yoshida et al., 2007, "Preparation of monoclonal antibodies against common region of influenza A virus hemagglutinin (HA)," Lectures in the Chemical Society of Japan, 87(2):1307, 2 J3-02 in Japanese with English translation of Abstract (4 pages).
Yoshida et al., 2009, "Cross-protective potential of a novel monoclonal antibody directed against antigenic site B of the hemagglutinin of influenza A viruses." PLoS Pathog., 5(3):e1000350 (9 pages).
Zamarin et al., 2006, "Influenza A virus PB1-F2 protein contributes to viral pathogenesis in mice," J Virol. 80(16):7976-7983.
Zerangue et al., 2000, "An artificial tetramerization domain restores efficient assembly of functional Shaker channels lacking T1," Proc Natl Acad Sci USA, 97(7):3591-3595.
Zhang et al., 2010, "Crystal structure of the swine-origin A (H1N1)-2009 influenza A virus hemagglutinin (HA) reveals similar antigenicity to that of the 1918 pandemic virus," Protein Cell 1(5):459-467.
Zhang et al., 2011, "Determination of serum neutralization antibodies against seasonal influenza A strain H3N2 and the emerging strains 2009 H1N1 and avian H5N1," Scand. J. Infect. Dis. 43(3):216-220.
Zhang et al., 2015, "A human-infecting H10N8 influenza virus retains a strong preference for avian-type receptors," Cell Host Microbe, 17(3):377-384.
Zhao et al., 2011, "Identification of a highly conserved H1 subtype-specific epitope with diagnostic potential in the hemagglutinin protein of influenza A virus," PLoS One, 6(8):e23374 (10 pages).
Zheng et al., 2020, "Enhancing Neuraminidase Immunogenicity of Influenza A Viruses by Rewiring RNA Packaging Signals," J. Virol., 94(16):e00742-20 (12 pages).
Zheng, et al., 1996, "Nonconserved nucleotides at the 3' and 5' ends of an influenza A virus RNA play an important role in viral RNA replication", Virology 217:242-251.
Zhou et al., 1994, "Adeno-associated virus 2-mediated high efficiency gene transfer into immature and mature subsets of hematopoietic progenitor cells in human umbilical cord blood," J Exp Med., 179(6):1867-1875.
Ziegler et al., 1995, "Type- and subtype-specific detection of influenza viruses in clinical specimens by rapid culture assay," J Clin Microbiol., 33(2):318-321.
Zost et al., 2017, "Contemporary H3N2 influenza viruses have a glycosylation site that alters binding of antibodies elicited by egg-adapted vaccine strains," Proc. Natl. Acad. Sci. USA, 114(47):12578-12583.
Lehninger et al., 1993, "Chapter 7: The Three-Dimensional Structure of Proteins," Principles of Biochemistry with an Extended Desicussion of Oxygen-Binding Proteins, Second Edition, Worth Publishers, pp. 160, 161 and 175-185.
Strohmeier et al., 2021, "A Novel Recombinant Influenza Virus Neuraminidase Vaccine Candidate Stabilized by a Measles Virus Phosphoprotein Tetramerization Domain Provides Robust Protection from Virus Challenge in the Mouse Model," mBio., 12(6):e02241-21 (17 pages).
Chen et al., 2024, "COVID-19 pandemic interventions reshaped the global dispersal of seasonal influenza viruses," Science, 386(6722):eadq3003 (12 pages).
Ghate et al., 1999, "Influenza type B neuraminidase can replace the function of type A neuraminidase," Virology, 264(2):265-277.
Gonzalez-Dominguez et al., 2024, "Preclinical evaluation of a universal inactivated influenza B vaccine based on the mosaic hemagglutinin-approach," NPJ Vaccines, 9(1):222 and Supplementary Materials (27 pages).
Hoxie et al., 2024, "A recombinant N2 neuraminidase-based CpG 1018® adjuvanted vaccine provides protection against challenge with heterologous influenza viruses in mice and hamsters," Vaccine, 42(24):126269 (16 pages).
Kanekiyo et al., 2021, "Next-Generation Influenza Vaccines," Cold Spring Harb. Perspect Med., 11(8):a038448 (17 pages).
Kilbourne et al., 2004, "Protection of mice with recombinant influenza virus neuraminidase," J. Infect. Dis., 189(3):459-461.
Kirkpatrick Roubidoux et al., 2021, "Identification and Characterization of Novel Antibody Epitopes on the N2 Neuraminidase," mSphere, 6(1):e00958-20 (11 pages).
Lai et al., 2019, "Neuraminidase activity and specificity of influenza A virus are influenced by haemagglutinin-receptor binding," Emerg Microbes Infect., 8(1):327-338.

(56) References Cited

OTHER PUBLICATIONS

Marcelin et al., 2011, "A contributing role for anti-neuraminidase antibodies on immunity to pandemic H1N1 2009 influenza A virus," PLoS One, 6(10):e26335 (10 pages).
McMahon et al., 2020, "Correctly folded—but not necessarily functional—influenza virus neuraminidase is required to induce protective antibody responses in mice," Vaccine, 38(45):7129-7137.
McMahon et al., 2023, "Immunity induced by vaccination with recombinant influenza B virus neuraminidase protein breaks viral transmission chains in guinea pigs in an exposure intensity-dependent manner," J. Virol., 97(10):e0105723 (12 pages).
Puente-Massaguer et al., 2025, "Combination of recombinant neuraminidase with cHA-based inactivated split vaccines improves the breadth of cross-reactivity and protection against influenza viruses in mice," Vaccine, 61:127388 (5 pages).

* cited by examiner

| | Position | Amino Acid Residue | % Conservation |
|---|---|---|---|
| 4F11 escape mutant | 385 | G | 100 |
| 1F2 escape mutant | 338 | E | 99.36 |
| 3G1 escape mutant | 346 | G | 99.89 |
| 1F4 escape mutant | 453 | Q | 99.89 |
| 4B2 escape mutant | 344 | G | 99.89 |

FIG. 8

IF2 VARIABLE REGION HEAVY CHAIN POLYNUCLEOTIDE SEQUENCE caggttcacctgcagcagtctggacctgaggtggcgaggcccggggcttcagtga
agctgtcctgcaaggcttctggctacaccttcactgactactatcttaactgggt
gaagcagaggcctagacagggccttgagtggattggacagattcatcctggaagt
actaatacttactacaatgagaagttcaagggcaaggccacactgactgcagaca
aatcctccagcacagcctacatgcagctcagcagcctgacatctgaggactctgc
agtctatttctgtgcaagatcgcttggtgatggttactacgtctatgctatggac
tactggggtcagggaaccgcagtcaccgtctcctca (SEQ ID NO: 81)

IF2 VARIABLE REGION LIGHT CHAIN POLYNUCLEOTIDE SEQUENCE gacattgtgatgacccagtctcaaaaattcatgtccacatcagtaggagacaggg
tcagcgtcacctgcaaggccagtcagaatgtggttactaatgtagtctggtatca
acagaaaccaggtcagtctcctaaaccactgatttactcggcatcctaccggtac
agtggagtccctgatcgcttcacaggcagtggatctgggacagatttcactctca
ccatcagcaatgtgcagtctgaagacttggcagagtactgctgtcagcaatatca
cagctatccattcacgttcggctcggggacaaagttggaagtaaaa (SEQ ID
NO: 82)

FIG. 9

IF2 VARIABLE REGION HEAVY CHAIN AMINO ACID SEQUENCE

QVHLQQSGPEVARPGASVKLSCKASGYTFTDYYLNWVKQRPRQGLEWIGQIHPGS
TNTYYNEKFKGKATLTADKSSSTAYMQLSSLTSEDSAVYFCARSLGDGYYVYAMD
YWGQGTAVTVSS (SEQ ID NO: 1)

IF2 VARIABLE REGION LIGHT CHAIN AMINO ACID SEQUENCE

DIVMTQSQKFMSTSVGDRVSVTCKASQNVVTNVVWYQQKPGQSPKPLIYSASYRY
SGVPDRFTGSGSGTDFTLTISNVQSEDLAEYCCQQYHSYPFTFGSGTKLEVK
(SEQ ID NO: 2)

FIG. 10

IF4 VARIABLE REGION HEAVY CHAIN POLYNUCLEOTIDE SEQUENCE caggttcacctacaacagtctggttctgaactgaggagtcctgggtcttcagtaa
agctttcatgcaaggattttgattcagaagtcttccctattgtttatatgagatg
gattaggcagaagcctggccatggatttgaatggattggagacatactcccaagt
tttggtagaacaatctatggagagaagtttgaggacaaagccacactagatgcag
acacagtgtccaacacagcctacttggagctcaacagtctgacatctgaggactc
tgctatctactactgtgcaagggggaccatggtaactggcttgcttactggggc
caagggactctggtcactgtctctgca (SEQ ID NO: 83)

IF4 VARIABLE REGION LIGHT CHAIN POLYNUCLEOTIDE SEQUENCE gacattgtgatgacccagtctcacaaattcatgtccacatcagttggagacaggg
tcaccatcacctgcaaggccagtcaggatgtgagtactgctgtagcctggtatca
acaaaaaccaggccaatctcctaaactactgatttactgggcatccacccggcac
actggagtccctaatcgcttcacaggcattatatctgggacagattacactctca
ctatcagcagtgtgcaggctgaagacctggcactttattactgtcagcaacatta
tagcgctccgtggacgttcggtggaggcaccaagctggaaatcaaa (SEQ ID
NO: 84)

FIG. 11

IF4 VARIABLE REGION HEAVY CHAIN AMINO ACID SEQUENCE

QVHLQQSGSELRSPGSSVKLSCKDFDSEVFPIVYMRWIRQKPGHGFEWIGDILPS
FGRTIYGEKFEDKATLDADTVSNTAYLELNSLTSEDSAIYYCARGDHGNWLAYWG
QGTLVTVSA (SEQ ID NO: 17)

IF4 VARIABLE REGION LIGHT CHAIN AMINO ACID SEQUENCE

DIVMTQSHKFMSTSVGDRVTITCKASQDVSTAVAWYQQKPGQSPKLLIYWASTRH
TGVPNRFTGIISGTDYTLTISSVQAEDLALYYCQQHYSAPWTFGGGTKLEIK
(SEQ ID NO: 18)

3G1 VARIABLE REGION HEAVY CHAIN POLYNUCLEOTIDE SEQUENCE

CAGGTTCAGCTGCAGCAGTCTGGAGCTGAATTGATGAAGCCTGGGGCCTCAGTGAAGATTTC
CTGCAAGGCTACTGGGTACAAATTCACTAGTTATTGGATAGGGTGGGTAAAGCAGAGGCCGG
GACATGGCCTTGAGTGGTGTGGAGAGATTTTTCCTGGAAGTGGCAGTATTAACTATAATGAG
AAATTTAAGGGCAAGGCCACATTCACTGCAGATACATCCTCCAACACAGCCTACTTGCAACT
GACCAGCCTGACATCTGAGGACTCTGCCGTCTATTACTGTGCAAGAGGGGAGGATTATTACG
GTAGTAGTTACGGTGCTATGGACTACTGGGGTCAAGGAACCTCACTCACCGTCTCCTCA
(SEQ I D NO: 85)

3G1 VARIABLE REGION LIGHT POLYNUCLEOTIDE SEQUENCE

GATGTCCAGATAACCCAGTCTCCATCTTATCTTGCTGCATCTCCTGGAGAAACCATTACTAT
TAATTGCAGGGCAAGTAAGAGCATCAGCAAATATGTAGCCTGGTATCAAGAGAAACCTGGGA
GAACTAACAAGGTTCTTATATATTCTGGATCAATCTTGTCATTTGGAAATCCATCAAGGTTC
AGTGGCAGTGGATCTGGTACAGATTTCACTCTCACCATCAGTAGCCTGGAGCCTGAAGATTT
TGCAATGTATTACTGTCAACAGCATAATGAATACCCGTGGACGTTCGGTGGAGGCACCAAGC
TGGAAATCAAA (SEQ ID NO: 86)

FIG. 12

3G1 VARIABLE REGION HEAVY CHAIN AMINO ACID SEQUENCE

QVQLQQSGAELMKPGASVKISCKATGYKFTSYWIGWVKQRPGHGLEWCGEIFPGSGSINYNE
KFKGKATFTADTSSNTAYLQLTSLTSEDSAVYYCARGEDYYGSSYGAMDYWGQGTSLTVSS
(SEQ ID NO: 33)

3G1 VARIABLE REGION LIGHT CHAIN AMINO ACID SEQUENCE

DVQITQSPSYLAASPGETITINCRASKSISKYVAWYQEKPGRTNKVLIYSGSILSFGNPSRF
SGSGSGTDFTLTISSLEPEDFAMYYCQQHNEYPWTFGGGTKLEIK (SEQ ID NO: 34)

FIG. 13

FIG. 14

4B2 VARIABLE REGION HEAVY CHAIN POLYNUCLEOTIDE SEQUENCE

Cagatccagttggtgcagtctggacctgagctgaagaagcctggagagacagtca
agatctcctgcaaggcttctggttttaccttcacagactatccaatgcactgggt
gaagcaggctccaggaaagagtttaaagtggatgggttggataaacactgagact
gaagagccaacatattcagatgacttcaagggacggtttgccttgtctttggaaa
cctctgccagcacaacctatttgcagatcaacaatctcaaaaatgaggacacggc
tacatatttctgtgctagatcaggttattactatggtagtacctacgcctggttt
ggttactggggccaagggactctggtcactgtctctgca (SEQ ID NO: 87)

4B2 VARIABLE REGION LIGHT CHAIN POLYNUCLEOTIDE SEQUENCE

Gatgttgtgatgacccaaattccactctccctgcctgtcagtctcggagatcagg
cctccatctcttgcagatctagtcagagccttatacacactaatggagacacctt
tttacattggtacctgcagaagccaggccagtctccaaagctcctgatctacaaa
gtttccaaccgattttctggggtcccagacaggttcactggcggtggatcaggga
cagatttcacactcaagatcagcagagtggaggctgaggatctgggaatttattt
ctgctctcaaagtgcacttttccgtacacgttcggaggggggaccaacctggaa
ataaaa (SEQ ID NO: 88)

FIG. 15

4B2 VARIABLE REGION HEAVY CHAIN AMINO ACID SEQUENCE

QIQLVQSGPELKKPGETVKISCKASGFTFTDYPMHWVKQAPGKSLKWMGWINTET
EEPTYSDDFKGRFALSLETSASTTYLQINNLKNEDTATYFCARSGYYYGSTYAWF
GYWGQGTLVTVSA (SEQ ID NO: 49)

4B2 VARIABLE REGION LIGHT CHAIN AMINO ACID SEQUENCE

DVVMTQIPLSLPVSLGDQASISCRSSQSLIHTNGDTFLHWYLQKPGQSPKLLIYK
VSNRFSGVPDRFTGGGSGTDFTLKISRVEAEDLGIYFCSQSALFPYTFGGGTNLE
IK (SEQ ID NO: 50)

FIG. 16

4F11 VARIABLE REGION HEAVY CHAIN POLYNUCLEOTIDE SEQUENCE

Gacgtgaaactggtggaatctgggggagacttagtgaagcctggagggtccctga
aactctcctgtgcagcctctggattcactttcagtgcctattccatgtcttgggt
tcgccagactccggagaggaggctggagtgggtcgcaaccattaatactggtggt
agtttcacctactatccagacagtgtgaagggccgattcaccatctccagagaca
atgccaagaacaccctgtacctgcaaatgagcagtctgaagtctgaggacacagc
catgtatttctgtacaagagtttccgactacggtaatagcgcctactttccttac
tggggccaagggactctggtcattgtctctgca (SEQ ID NO: 89)

4F11 VARIABLE REGION LIGHT CHAIN POLYNUCLEOTIDE SEQUENCE

Caagttgttctcacccagtctccagcactcatatctgcgtctccaggggagaagg
tcaccatgacctgcagtgccagctcaaatgtaaattacatgtcctggtaccagca
gaggccaagatcctcccccaaaccctggatttatctcacatccaaactggcttct
ggagtccctcctcgtttcagtggcagtgggtctgggacctcttactctctcacaa
tcagcagcatggaggctgaagatgttgccacttattactgccagcagtggagcag
tgacccccagacgttcggagggggggaccaaggtggaaataaaa (SEQ ID NO: 90)

FIG. 17

4F11 VARIABLE REGION HEAVY CHAIN AMINO ACID SEQUENCE

DVKLVESGGDLVKPGGSLKLSCAASGFTFSAYSMSWVRQTPERRLEWVATINTGG
SFTYYPDSVKGRFTISRDNAKNTLYLQMSSLKSEDTAMYFCTRVSDYGNSAYFPY
WGQGTLVIVSA (SEQ ID NO: 65)

4F11 VARIABLE REGION LIGHT CHAIN AMINO ACID SEQUENCE

QVVLTQSPALISASPGEKVTMTCSASSNVNYMSWYQQRPRSSPKPWIYLTSKLAS
GVPPRFSGSGSGTSYSLTISSMEAEDVATYYCQQWSSDPQTFGGGTKVEIK
(SEQ ID NO: 66)

Figure 27:
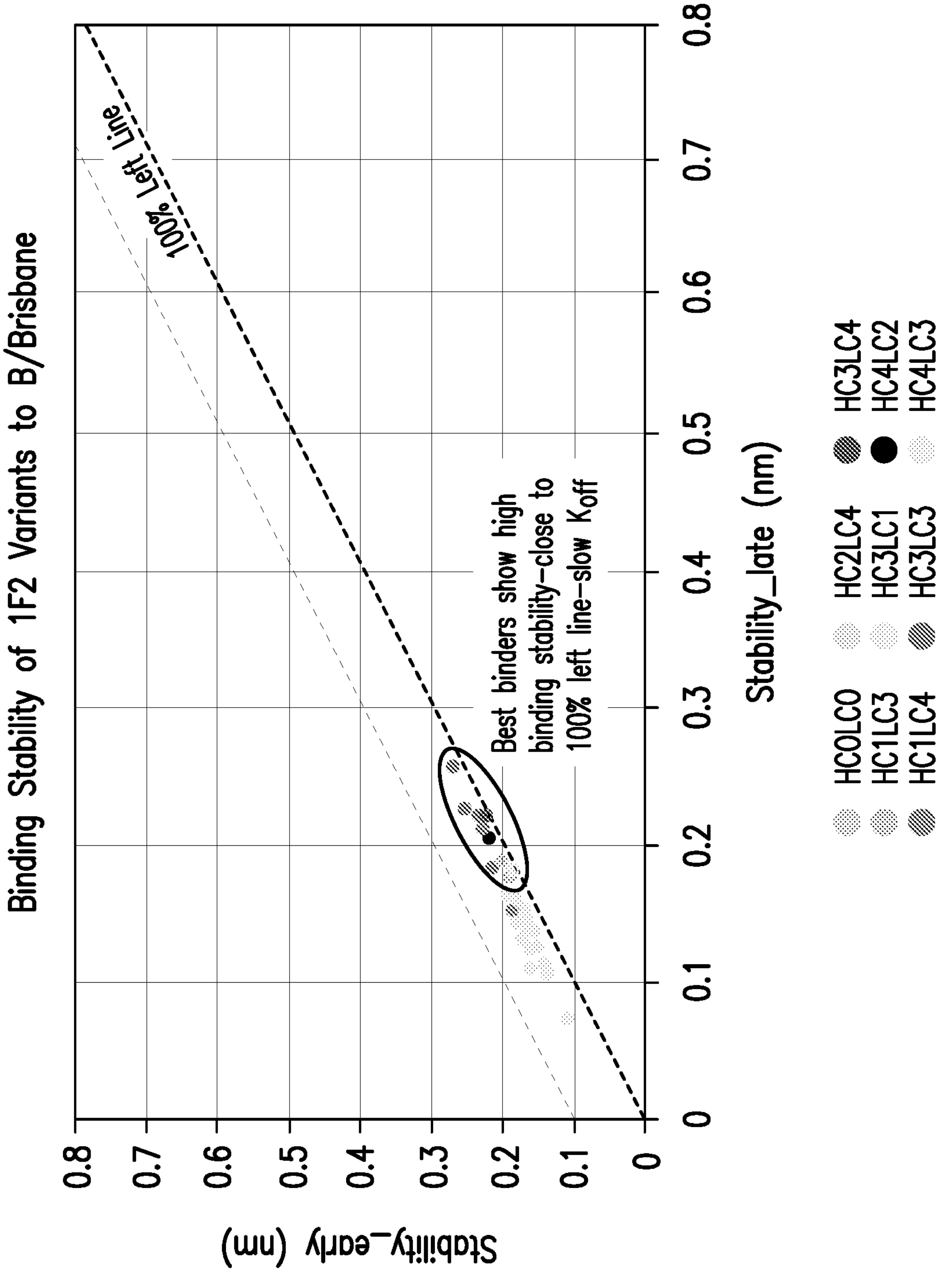

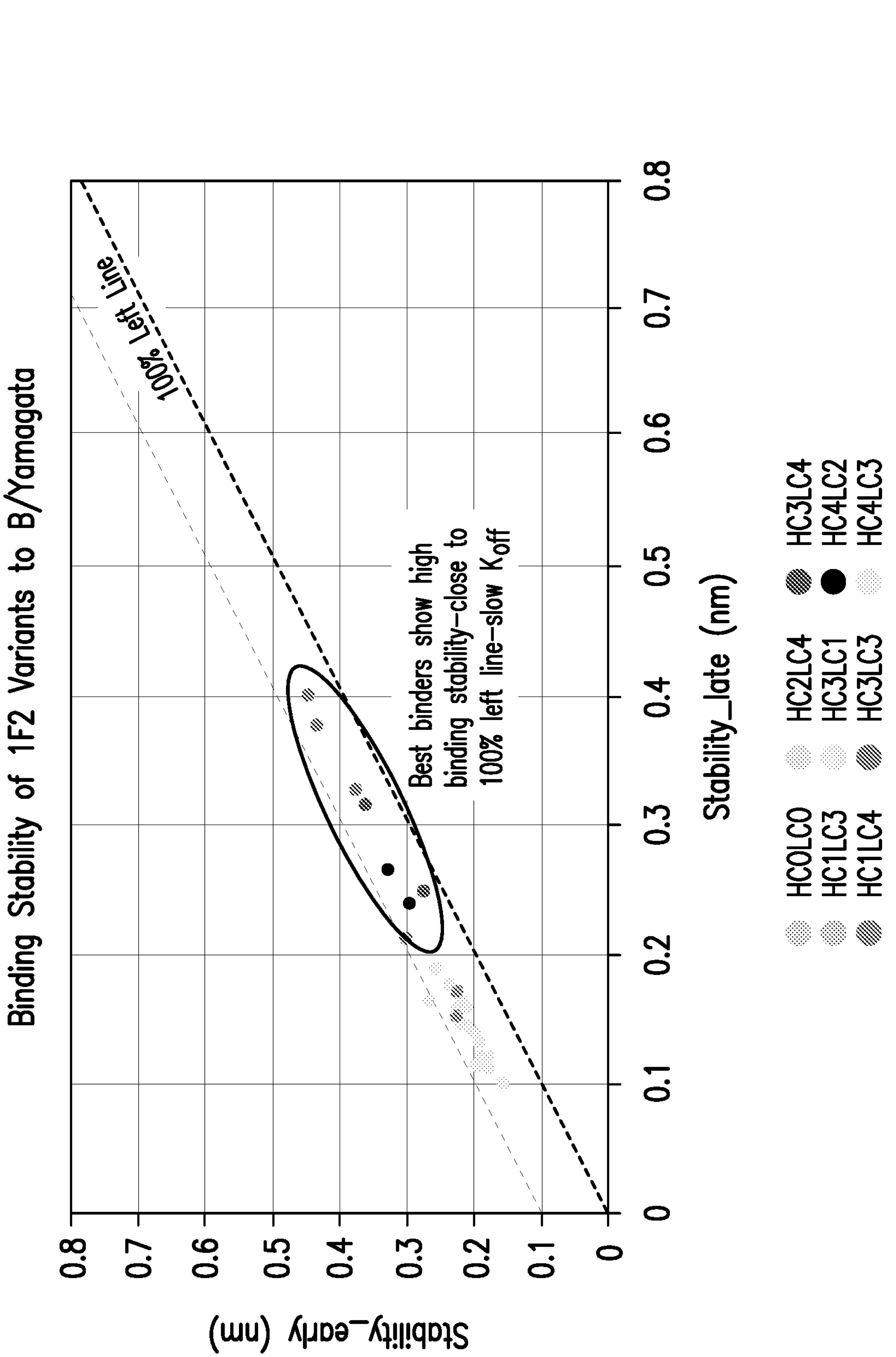
FIG. 27 Continuation

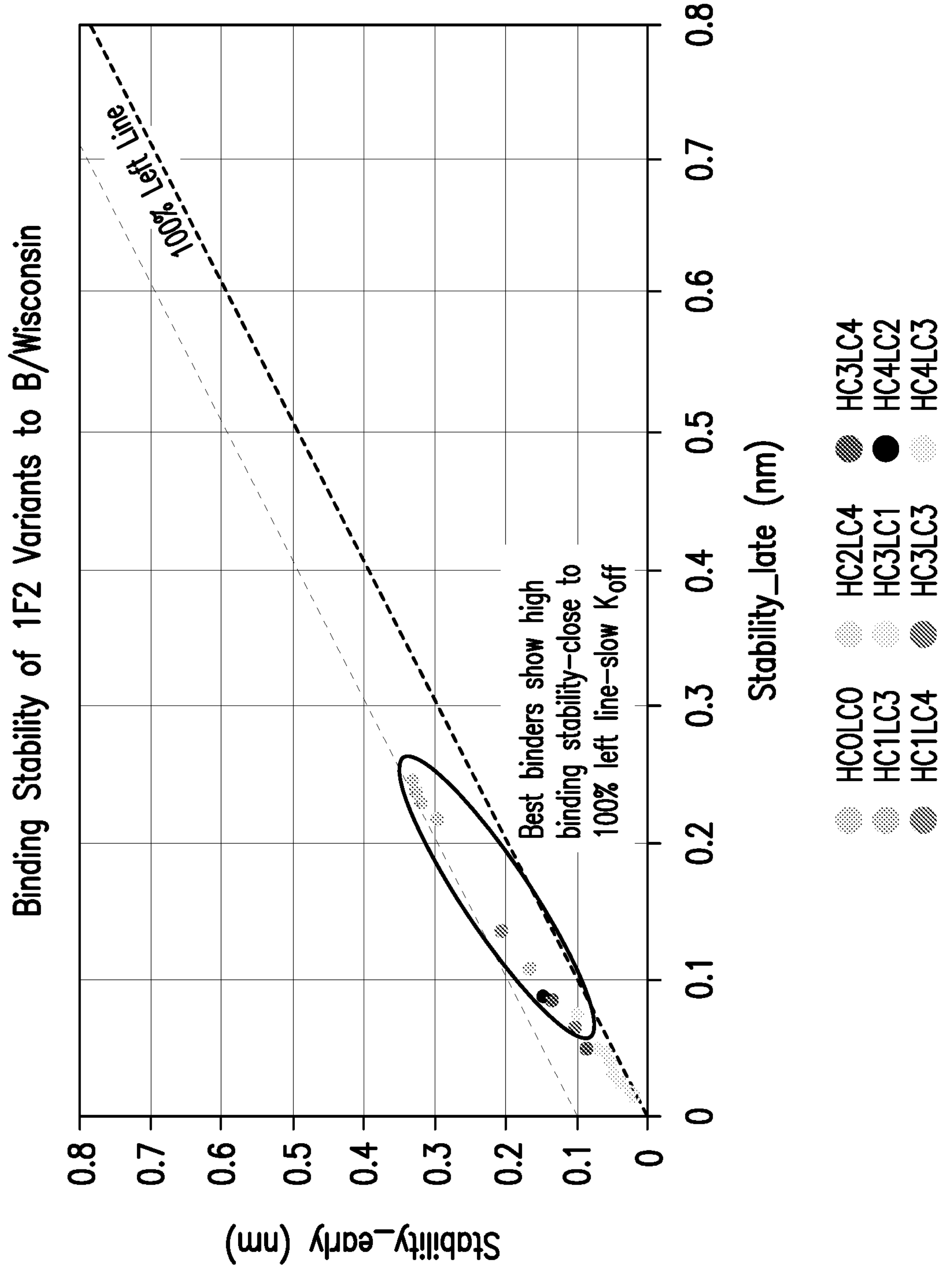
FIG. 27 Continuation

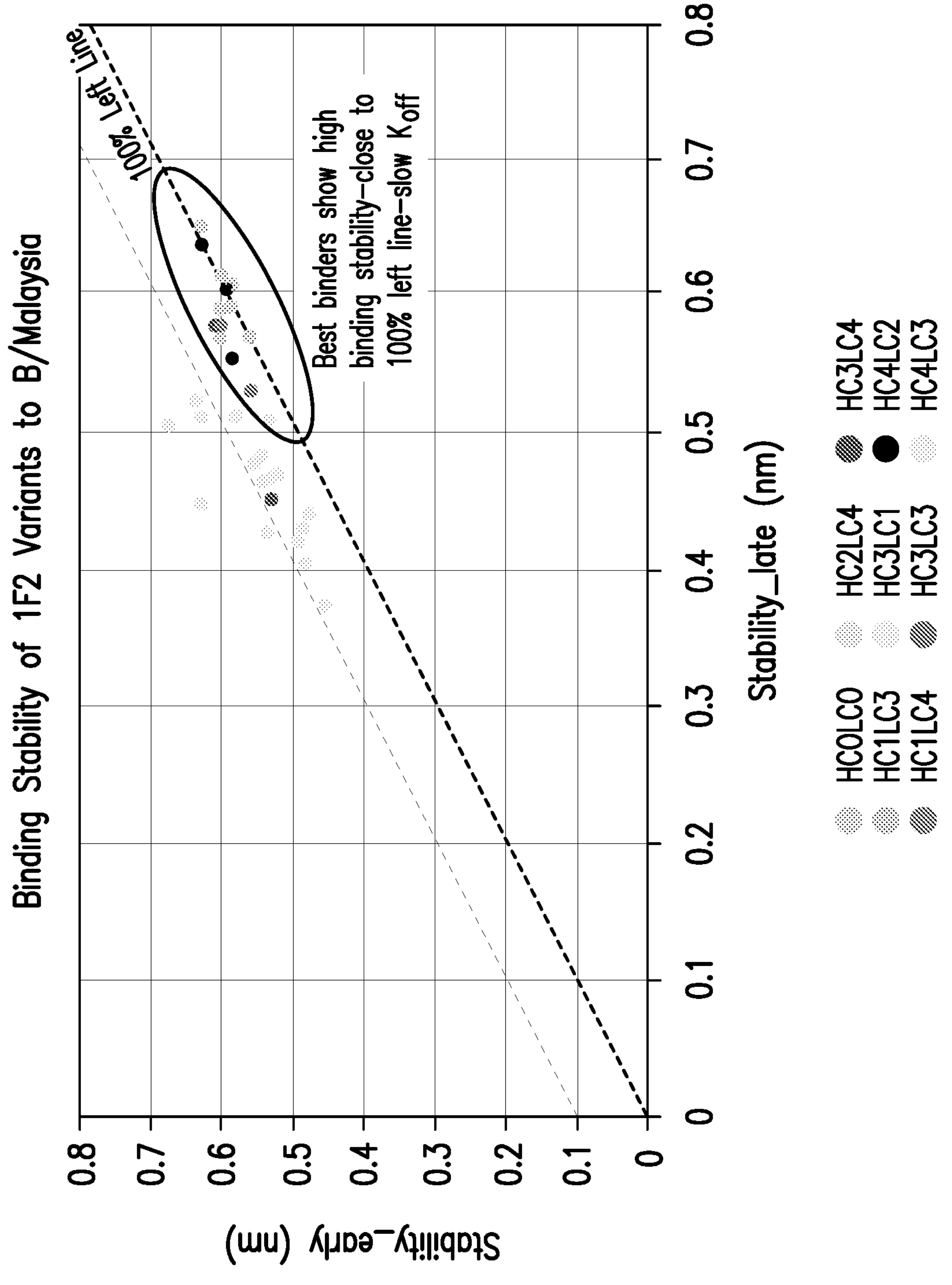
FIG. 27 Continuation

Table 2: Off-rate ranking results obtained for the binding of 1F2 variants binding to either B/Brisbane, B/Yamagata, B/Wisconsin or the B/Malaysia antigen.

| | B/Brisbane | | | |
|---|---|---|---|---|
| Antibody | Capture level (nm) | Early Stability X=902 | Late Stability X=2098 | % Dissociation |
| HC0LC0 | 0.44 | 0.19 | 0.18 | 5.37 |
| HC1LC1 | 0.52 | 0.18 | 0.16 | 13.99 |
| HC1LC2 | 0.51 | 0.18 | 0.14 | 19.41 |
| HC1LC3 | 0.52 | 0.19 | 0.15 | 17.93 |
| HC1LC4 | 0.53 | 0.22 | 0.21 | 5.50 |
| HC1LC5 | 0.56 | 0.18 | 0.16 | 15.25 |
| HC2LC1 | 0.53 | 0.17 | 0.14 | 14.35 |
| HC0LC0 | 0.42 | 0.20 | 0.19 | 6.13 |
| HC2LC2 | 0.55 | 0.17 | 0.13 | 21.25 |
| HC2LC3 | 0.54 | 0.16 | 0.11 | 31.06 |
| HC2LC4 | 0.49 | 0.18 | 0.17 | 10.55 |
| HC2LC5 | 0.59 | 0.17 | 0.15 | 11.90 |
| HC3LC1 | 0.50 | 0.17 | 0.14 | 14.31 |
| HC3LC2 | 0.45 | 0.15 | 0.13 | 16.60 |
| HC0LC0 | 0.50 | 0.27 | 0.26 | 4.68 |
| HC3LC3 | 0.55 | 0.21 | 0.19 | 13.01 |
| HC3LC4 | 0.54 | 0.22 | 0.22 | 0.63 |
| HC3LC5 | 0.52 | 0.18 | 0.16 | 11.62 |
| HC4LC1 | 0.51 | 0.16 | 0.14 | 11.04 |
| HC4LC2 | 0.51 | 0.22 | 0.21 | 5.25 |
| HC4LC3 | 0.50 | 0.19 | 0.16 | 14.67 |
| HC0LC0 | 0.48 | 0.23 | 0.22 | 3.62 |
| HC4LC4 | 0.46 | 0.14 | 0.11 | 17.65 |
| HC4LC5 | 0.48 | 0.17 | 0.15 | 11.95 |
| HC5LC1 | 0.53 | 0.17 | 0.15 | 13.21 |
| HC5LC2 | 0.45 | 0.11 | 0.08 | 29.36 |
| HC5LC3 | 0.48 | 0.14 | 0.11 | 22.13 |
| HC5LC4 | 0.50 | 0.19 | 0.18 | 2.11 |
| HC0LC0 | 0.50 | 0.25 | 0.23 | 8.95 |
| HC5LC5 | 0.59 | 0.16 | 0.13 | 20.19 |

FIG. 28

Table 2: Off-rate ranking results obtained for the binding of 1F2 variants binding to either B/Brisbane, B/Yamagata, B/Wisconsin or the B/Malaysia antigen.

| | B/Yamagata | | | |
|---|---|---|---|---|
| Antibody | Capture level (nm) | Early Stability X=902 | Late Stability X=2098 | % Dissociation |
| HC0LC0 | 0.51 | 0.36 | 0.32 | 11.95 |
| HC1LC1 | 0.51 | 0.23 | 0.18 | 24.30 |
| HC1LC2 | 0.51 | 0.21 | 0.14 | 31.70 |
| HC1LC3 | 0.50 | 0.22 | 0.15 | 31.41 |
| HC1LC4 | 0.54 | 0.32 | 0.27 | 17.57 |
| HC1LC5 | 0.55 | 0.21 | 0.15 | 30.26 |
| HC2LC1 | 0.52 | 0.19 | 0.13 | 28.79 |
| HC0LC0 | 0.53 | 0.37 | 0.33 | 12.09 |
| HC2LC2 | 0.56 | 0.18 | 0.12 | 32.90 |
| HC2LC3 | 0.55 | 0.18 | 0.12 | 34.93 |
| HC2LC4 | 0.51 | 0.22 | 0.17 | 23.49 |
| HC2LC5 | 0.60 | 0.18 | 0.12 | 32.63 |
| HC3LC1 | 0.51 | 0.21 | 0.16 | 23.46 |
| HC3LC2 | 0.46 | 0.19 | 0.14 | 27.15 |
| HC0LC0 | 0.56 | 0.37 | 0.33 | 11.54 |
| HC3LC3 | 0.57 | 0.23 | 0.17 | 23.74 |
| HC3LC4 | 0.67 | 0.27 | 0.25 | 8.64 |
| HC3LC5 | 0.54 | 0.18 | 0.12 | 30.13 |
| HC4LC1 | 0.52 | 0.16 | 0.10 | 34.81 |
| HC4LC2 | 0.52 | 0.29 | 0.24 | 17.56 |
| HC4LC3 | 0.50 | 0.22 | 0.16 | 28.90 |
| HC0LC0 | 0.36 | 0.43 | 0.38 | 11.93 |
| HC4LC4 | 0.31 | 0.22 | 0.15 | 32.33 |
| HC4LC5 | 0.33 | 0.26 | 0.19 | 25.12 |
| HC5LC1 | 0.36 | 0.22 | 0.15 | 31.97 |
| HC5LC2 | 0.34 | 0.19 | 0.12 | 38.42 |
| HC5LC3 | 0.38 | 0.26 | 0.17 | 36.37 |
| HC5LC4 | 0.35 | 0.30 | 0.21 | 28.61 |
| HC0LC0 | 0.37 | 0.45 | 0.40 | 10.05 |
| HC5LC5 | 0.38 | 0.18 | 0.11 | 35.25 |

FIG. 28 Continuation

Table 2: Off-rate ranking results obtained for the binding of 1F2 variants binding to either B/Brisbane, B/Yamagata, B/Wisconsin or the B/Malaysia antigen.

| | B/Wisconsin | | | |
|---|---|---|---|---|
| Antibody | Capture level (nm) | Early Stability X=902 | Late Stability X=2098 | % Dissociation |
| HC0LC0 | 0.48 | 0.32 | 0.23 | 27.00 |
| HC1LC1 | 0.49 | 0.10 | 0.07 | 34.07 |
| HC1LC2 | 0.45 | 0.08 | 0.05 | 31.17 |
| HC1LC3 | 0.54 | 0.16 | 0.11 | 34.15 |
| HC1LC4 | 0.52 | 0.20 | 0.14 | 32.72 |
| HC1LC5 | 0.49 | 0.04 | 0.03 | 27.98 |
| HC2LC1 | 0.52 | 0.03 | 0.02 | 15.81 |
| HC0LC0 | 0.50 | 0.32 | 0.24 | 26.22 |
| HC2LC2 | 0.49 | 0.03 | 0.02 | 21.90 |
| HC2LC3 | 0.62 | 0.05 | 0.04 | 20.89 |
| HC2LC4 | 0.54 | 0.07 | 0.05 | 33.78 |
| HC2LC5 | 0.63 | 0.03 | 0.03 | 2.72 |
| HC3LC1 | 0.52 | 0.05 | 0.03 | 29.68 |
| HC3LC2 | 0.46 | 0.07 | 0.05 | 31.01 |
| HC0LC0 | 0.50 | 0.30 | 0.22 | 26.03 |
| HC3LC3 | 0.53 | 0.08 | 0.05 | 40.14 |
| HC3LC4 | 0.56 | 0.14 | 0.09 | 37.26 |
| HC3LC5 | 0.52 | 0.03 | 0.03 | 17.35 |
| HC4LC1 | 0.55 | 0.02 | 0.02 | 0.00 |
| HC4LC2 | 0.57 | 0.15 | 0.09 | 39.65 |
| HC4LC3 | 0.54 | 0.08 | 0.05 | 37.74 |
| HC0LC0 | 0.49 | 0.33 | 0.25 | 24.97 |
| HC4LC4 | 0.47 | 0.07 | 0.05 | 25.60 |
| HC4LC5 | 0.47 | 0.06 | 0.05 | 15.62 |
| HC5LC1 | 0.53 | 0.03 | 0.03 | 5.41 |
| HC5LC2 | 0.51 | 0.03 | 0.03 | 18.79 |
| HC5LC3 | 0.46 | 0.05 | 0.04 | 17.93 |
| HC5LC4 | 0.52 | 0.10 | 0.08 | 23.01 |
| HC0LC0 | 0.50 | 0.32 | 0.24 | 26.69 |
| HC5LC5 | 0.60 | 0.02 | 0.02 | 4.05 |

FIG. 28 Continuation

Table 2: Off-rate ranking results obtained for the binding of 1F2 variants binding to either B/Brisbane, B/Yamagata, B/Wisconsin or the B/Malaysia antigen.

| | B/Malaysia | | | |
|---|---|---|---|---|
| Antibody | Capture level (nm) | Early Stability X=902 | Late Stability X=2098 | % Dissociation |
| HC0LC0 | 0.49 | 0.59 | 0.59 | 0.52 |
| HC1LC1 | 0.50 | 0.53 | 0.47 | 12.66 |
| HC1LC2 | 0.46 | 0.49 | 0.40 | 17.51 |
| HC1LC3 | 0.48 | 0.53 | 0.45 | 15.65 |
| HC1LC4 | 0.54 | 0.61 | 0.57 | 6.18 |
| HC1LC5 | 0.55 | 0.64 | 0.45 | 29.73 |
| HC2LC1 | 0.56 | 0.56 | 0.47 | 14.92 |
| HC0LC0 | 0.49 | 0.61 | 0.61 | 0.00 |
| HC2LC2 | 0.54 | 0.55 | 0.48 | 12.79 |
| HC2LC3 | 0.55 | 0.58 | 0.51 | 13.04 |
| HC2LC4 | 0.55 | 0.61 | 0.56 | 6.78 |
| HC2LC5 | 0.63 | 0.68 | 0.50 | 26.22 |
| HC3LC1 | 0.53 | 0.56 | 0.53 | 6.30 |
| HC3LC2 | 0.47 | 0.52 | 0.47 | 11.12 |
| HC0LC0 | 0.52 | 0.63 | 0.65 | 0.00 |
| HC3LC3 | 0.54 | 0.59 | 0.55 | 6.86 |
| HC3LC4 | 0.54 | 0.61 | 0.59 | 3.09 |
| HC3LC5 | 0.58 | 0.64 | 0.52 | 18.75 |
| HC4LC1 | 0.59 | 0.63 | 0.51 | 19.67 |
| HC4LC2 | 0.58 | 0.63 | 0.63 | 0.08 |
| HC4LC3 | 0.59 | 0.61 | 0.57 | 6.83 |
| HC0LC0 | 0.50 | 0.56 | 0.57 | 0.00 |
| HC4LC4 | 0.49 | 0.49 | 0.43 | 12.79 |
| HC4LC5 | 0.48 | 0.48 | 0.44 | 8.99 |
| HC5LC1 | 0.53 | 0.50 | 0.42 | 15.47 |
| HC5LC2 | 0.49 | 0.46 | 0.37 | 19.15 |
| HC5LC3 | 0.53 | 0.55 | 0.46 | 15.54 |
| HC5LC4 | 0.52 | 0.54 | 0.50 | 6.22 |
| HC0LC0 | 0.51 | 0.59 | 0.60 | 0.00 |
| HC5LC5 | 0.58 | 0.54 | 0.42 | 21.44 |

FIG. 28 Continuation

| # | Name | Sequence |
|---|---|---|
| 1 | VH0 | QVHLQQSGPEVARPGASVKLSCKASGYTFTDYYLNWVKQRPRQGLEWIGQIHPGSTNTYYNEKFKGKATLTADKSSSTAYMQLSSLTSEDSAVYFCARSLGDGYYVYAMDYWGQGTAVTVSS |
| 2 | IGHV1-46 | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCAR |
| 3 | IGHV1-2 | QVQLVQSGAEVKKPGASVKVSCKASGYTFTGYYMHWVRQAPGQGLEWMGRINPNSGGTNYAQKFQGRVTMTRDTSISTAYMELSRLRSDDTAVYYCAR |
| 4 | VH1 | QVQLQESGAEVKKPGASVKVSCKASGYTFTDYYLNWVRQAPGQGLEWMGQIHPGSTNTYYNEKFKGRVTMTRDTSTSTVYMELSSLRSEDTAVYYCARSLGDGYYVYAMDYWGQGTTVTVSS |
| 5 | VH2 | QVQLVQSGAEVKKPGASVKVSCKASGYTFTDYYLNWVRQAPGQGLEWMGQIHPGSTNTYYNEKFKGRVTMTRDTSISTAYMELSRLRSDDTAVYFCARSLGDGYYVYAMDYWGQGTTVTVSS |
| 6 | VH3 | EVQLVESGPEVKKPGATVKISCKVSGYTFTDYYLNWVQQAPGRGLEWMGQIHPGSTNTYYNEKFKGRVTMTADTSTGTAYMQLSSLTSEDTAVYFCARSLGDGYYVYAMDYWGQGTTVTVAS |
| 7 | VH4 | QVQLVQSGAEVKKPGSSVKVSCKASGYTFTDYYLNWVRQAPGQGLEWMGQIHPGSTNTYYNEKFKGRVTITADKSTSTAYMELSSLRSEDTAVYYCARSLGDGYYVYAMDYWGQGTTVTVSS |
| 8 | VH5 | QVQLVQSGAEVKKPGASVKVSCKASGYTFTDYYLNWVRQAPGQGLEWMGQIHPGSTNTYYNEKFKGRVTMTRDTSTSTVYMELSSLRSEDTAVYYCARSLGDGYYVYAMDYWGQGTLVTVSS |
| 9 | VH6 | QVHLQESGAEVKKPGASVKVSCKASGYTFTDYYLNWVRQRPRQGLEWMGQIHPGSTNTYYNEKFKGRVTMTRDTSTSTVYMQLSSLTSEDTAVYFCARSLGDGYYVYAMDYWGQGTAVTVSS |
| 10 | VH7 | QVQLQQSGPEVAKPGASVKLSCKASGYTFTDYYLNWVRQAPGQGLEWLGQIHPGSTNTYYNEKFKGRVTMTRDTSTSTVYMELSSLTSEDTAVYYCARSLGDGYYVYAMDYWGQGTAVTVSS |
| 11 | VH8 | QVHLQQSGPEVAKPGASVKVSCKASGYTFTDYYLNWVRQAPGQGLEWLGQIHPGSTNTYYNEKFKGRVTMTADKSTSTVYMELSSLRSEDTAVYFCARSLGDGYYVYAMDYWGQGTAVTVSS |

FIG. 30

| # | Name | Sequence |
|---|---|---|
| 1 | VL0 | DIVMTQSQKFMSTSVGDRVSVTCKASQNVVTNVVWYQQKPGQSPKPLIYSASYRYSGVPDRFTGSGSGTDFTLTISNVQSEDLAEYCCQQYHSYPFTFGSGTKLEVK |
| 2 | IGKV1-8 | AIRMTQSPSSFSASTGDRVTITCRASQGISSYLAWYQQKPGKAPKLLIYAASTLQSGVPSRFSGSGSGTDFTLTISCLQSEDFATYYCQQYYSYP |
| 3 | VL1 | DIQMTQSPSFLSASVGDRVTITCKASQNVVTNVVWYQQKPGKAPKLLIYSASYRYSGVPSRFSGSGSGTEFTLTISSLQPEDFATYSCQQYHSYPFTFGQGTRLEIK |
| 4 | VL2 | DVVMTQSPDSLAVSLGERVTINCKASQNVVTNVVWYQQKPGQSPKLLIYSASYRYSGVPDRFSGSGSGTDFTLTISSLQAEDVAVYYCQQYHSYPFTFGQGTKLEIK |
| 5 | VL3 | DVVMTQSPSSLSASVGDRVSITCKASQNVVTNVVWYQQKPGKAPKLLVYSASYRYSGVPSRFSGSGSGTDFTLTISSLQPEDFATYCCQQYHSYPFTFGQGTKLDIK |
| 6 | VL4 | DIQMTQSPSSLSASVGDRVTITCKASQNVVTNVVWYQQKPGQAPKLLIYSASYRYSGVPSRFSGSGSGTEFTFTISSLQPEDLATYSCQQYHSYPFTFGQGTKLEIK |
| 7 | VL5 | AIRMTQSPSSFSASTGDRVTITCKASQNVVTNVVWYQQKPGKAPKLLIYSASYRYSGVPSRFSGSGSGTDFTLTISCLQSEDFATYYCQQYHSYPFTFGQGTKLEIK |
| 8 | VL6 | DIQLTQSPKFLSASVGDRVTITCKASQNVVTNVVWYQQKPGKAPKLLIYSASYRYSGVPDRFSGSGSGTEFTLTISSLQPEDFAEYSCQQYHSYPFTFGSGTKLEVK |
| 9 | VL7 | DIVMTQSPSFLSASVGDRVTITCKASQNVVTNVVWYQQKPGKAPKPLIYSASYRYSGVPSRFSGSGSGTEFTLTISSLQPEDLAEYYCQQYHSYPFTFGSGTKLEVK |
| 10 | VL8 | DIQMTQSPSTLSASVGDRVTITCKASQNVVTNVVWYQQKPGQAPKLLIYSASYRYSGVPSRFSGSGSGTEFTFTISSLQSEDLAEYYCQQYHSYPFTFGSGTKLEVK |

FIG. 31

SEQUENCE LISTING

```
<160> NUMBER OF SEQ ID NOS: 204

<210> SEQ ID NO 1
<211> LENGTH: 122
<212> TYPE: PRT
<213> ORGANISM: Artificial Sequence
<220> FEATURE:
<223> OTHER INFORMATION: 1F2 VH

<400> SEQUENCE: 1

Gln Val His Leu Gln Gln Ser Gly Pro Glu Val Ala Arg Pro Gly Ala
1               5                   10                  15

Ser Val Lys Leu Ser Cys Lys Ala Ser Gly Tyr Thr Phe Thr Asp Tyr
            20                  25                  30

Tyr Leu Asn Trp Val Lys Gln Arg Pro Arg Gln Gly Leu Glu Trp Ile
        35                  40                  45

Gly Gln Ile His Pro Gly Ser Thr Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Leu Gly Asp Gly Tyr Tyr Val Tyr Ala Met Asp Tyr Trp
            100                 105                 110

Gly Gln Gly Thr Ala Val Thr Val Ser Ser
        115                 120


<210> SEQ ID NO 2
<211> LENGTH: 107
<212> TYPE: PRT
<213> ORGANISM: Artificial Sequence
<220> FEATURE:
<223> OTHER INFORMATION: 1F2 VL

<400> SEQUENCE: 2

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Val Thr Asn
```

```
            20                  25                  30

Val Val Trp Tyr Gln Gln Lys Pro Gly Gln Ser Pro Lys Pro Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Cys Cys Gln Gln Tyr His Ser Tyr Pro Phe
                85                  90                  95

Thr Phe Gly Ser Gly Thr Lys Leu Glu Val Lys
            100                 105


<210> SEQ ID NO 3
<211> LENGTH: 8
<212> TYPE: PRT
<213> ORGANISM: Artificial Sequence
<220> FEATURE:
<223> OTHER INFORMATION: 1F2 HCDR1 (IMGT)

<400> SEQUENCE: 3

Gly Tyr Thr Phe Thr Asp Tyr Tyr
1               5


<210> SEQ ID NO 4
<211> LENGTH: 8
<212> TYPE: PRT
<213> ORGANISM: Artificial Sequence
<220> FEATURE:
<223> OTHER INFORMATION: 1F2 HCDR2 (IMGT)

<400> SEQUENCE: 4

Ile His Pro Gly Ser Thr Asn Thr
1               5


<210> SEQ ID NO 5
<211> LENGTH: 15
<212> TYPE: PRT
<213> ORGANISM: Artificial Sequence
<220> FEATURE:
<223> OTHER INFORMATION: 1F2 HCDR3 (IMGT)

<400> SEQUENCE: 5

Ala Arg Ser Leu Gly Asp Gly Tyr Tyr Val Tyr Ala Met Asp Tyr
1               5                   10                  15


<210> SEQ ID NO 6
<211> LENGTH: 6
<212> TYPE: PRT
<213> ORGANISM: Artificial Sequence
<220> FEATURE:
<223> OTHER INFORMATION: 1F2 LCDR1 (IMGT)

<400> SEQUENCE: 6

Gln Asn Val Val Thr Asn
1               5


<210> SEQ ID NO 7
<211> LENGTH: 3
<212> TYPE: PRT
<213> ORGANISM: Artificial Sequence
<220> FEATURE:
<223> OTHER INFORMATION: 1F2 LCDR2 (IMGT)

<400> SEQUENCE: 7
```

Ser Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: 1F2 LCDR3 (IMGT)

<400> SEQUENCE: 8

Gln Gln Tyr His Ser Tyr Pro Phe Thr
1               5

<210> SEQ ID NO 9
<211> LENGTH: 25
<212> TYPE: PRT
<213> ORGANISM: Artificial Sequence
<220> FEATURE:
<223> OTHER INFORMATION: 1F2 VH FR1 (IMGT)

<400> SEQUENCE: 9

Gln Val His Leu Gln Gln Ser Gly Pro Glu Val Ala Arg Pro Gly Ala
1               5                   10                  15

Ser Val Lys Leu Ser Cys Lys Ala Ser
            20                  25

<210> SEQ ID NO 10
<211> LENGTH: 17
<212> TYPE: PRT
<213> ORGANISM: Artificial Sequence
<220> FEATURE:
<223> OTHER INFORMATION: 1F2 VH FR2 (IMGT)

<400> SEQUENCE: 10

Leu Asn Trp Val Lys Gln Arg Pro Arg Gln Gly Leu Glu Trp Ile Gly
1               5                   10                  15

Gln

<210> SEQ ID NO 11
<211> LENGTH: 38
<212> TYPE: PRT
<213> ORGANISM: Artificial Sequence
<220> FEATURE:
<223> OTHER INFORMATION: 1F2 VH FR3 (IMGT)

<400> SEQUENCE: 11

Tyr Tyr Asn Glu Lys Phe Lys Gly Lys Ala Thr Leu Thr Ala Asp Lys
1               5                   10                  15

Ser Ser Ser Thr Ala Tyr Met Gln Leu Ser Ser Leu Thr Ser Glu Asp
            20                  25                  30

Ser Ala Val Tyr Phe Cys
        35

<210> SEQ ID NO 12
<211> LENGTH: 11
<212> TYPE: PRT
<213> ORGANISM: Artificial Sequence
<220> FEATURE:
<223> OTHER INFORMATION: 1F2 VH FR4 (IMGT)

<400> SEQUENCE: 12

Trp Gly Gln Gly Thr Ala Val Thr Val Ser Ser
1               5                   10

<210> SEQ ID NO 13
<211> LENGTH: 26
<212> TYPE: PRT
<213> ORGANISM: Artificial Sequence
<220> FEATURE:
<223> OTHER INFORMATION: 1F2 VL FR1 (IMGT)

<400> SEQUENCE: 13

Asp Ile Val Met Thr Gln Ser Gln Lys Phe Met Ser Thr Ser Val Gly
1 5 10 15

Asp Arg Val Ser Val Thr Cys Lys Ala Ser
20 25

<210> SEQ ID NO 14
<211> LENGTH: 17
<212> TYPE: PRT
<213> ORGANISM: Artificial Sequence
<220> FEATURE:
<223> OTHER INFORMATION: 1F2 VL FR2 (IMGT)

<400> SEQUENCE: 14

Val Val Trp Tyr Gln Gln Lys Pro Gly Gln Ser Pro Lys Pro Leu Ile
1 5 10 15

Tyr

<210> SEQ ID NO 15
<211> LENGTH: 36
<212> TYPE: PRT
<213> ORGANISM: Artificial Sequence
<220> FEATURE:
<223> OTHER INFORMATION: 1F2 VL FR3 (IMGT)

<400> SEQUENCE: 15

Tyr Arg Tyr Ser Gly Val Pro Asp Arg Phe Thr Gly Ser Gly Ser Gly
1 5 10 15

Thr Asp Phe Thr Leu Thr Ile Ser Asn Val Gln Ser Glu Asp Leu Ala
20 25 30

Glu Tyr Cys Cys
35

<210> SEQ ID NO 16
<211> LENGTH: 10
<212> TYPE: PRT
<213> ORGANISM: Artificial Sequence
<220> FEATURE:
<223> OTHER INFORMATION: 1F2 VL FR4 (IMGT)

<400> SEQUENCE: 16

Phe Gly Ser Gly Thr Lys Leu Glu Val Lys
1 5 10

<210> SEQ ID NO 17
<211> LENGTH: 119
<212> TYPE: PRT
<213> ORGANISM: Artificial Sequence
<220> FEATURE:
<223> OTHER INFORMATION: 1F4 VH

<400> SEQUENCE: 17

Gln Val His Leu Gln Gln Ser Gly Ser Glu Leu Arg Ser Pro Gly Ser
1 5 10 15

Ser Val Lys Leu Ser Cys Lys Asp Phe Asp Ser Glu Val Phe Pro Ile
20 25 30

Val Tyr Met Arg Trp Ile Arg Gln Lys Pro Gly His Gly Phe Glu Trp
35 40 45

Ile Gly Asp Ile Leu Pro Ser Phe Gly Arg Thr Ile Tyr Gly Glu Lys
50 55 60

Phe Glu Asp Lys Ala Thr Leu Asp Ala Asp Thr Val Ser Asn Thr Ala
65 70 75 80

Tyr Leu Glu Leu Asn Ser Leu Thr Ser Glu Asp Ser Ala Ile Tyr Tyr
85 90 95

Cys Ala Arg Gly Asp His Gly Asn Trp Leu Ala Tyr Trp Gly Gln Gly
100 105 110

Thr Leu Val Thr Val Ser Ala
115

<210> SEQ ID NO 18
<211> LENGTH: 107
<212> TYPE: PRT
<213> ORGANISM: Artificial Sequence
<220> FEATURE:
<223> OTHER INFORMATION: 1F4 VL

<400> SEQUENCE: 18

Asp Ile Val Met Thr Gln Ser His Lys Phe Met Ser Thr Ser Val Gly
1 5 10 15

Asp Arg Val Thr Ile Thr Cys Lys Ala Ser Gln Asp Val Ser Thr Ala
20 25 30

Val Ala Trp Tyr Gln Gln Lys Pro Gly Gln Ser Pro Lys Leu Leu Ile
35 40 45

Tyr Trp Ala Ser Thr Arg His Thr Gly Val Pro Asn Arg Phe Thr Gly
50 55 60

Ile Ile Ser Gly Thr Asp Tyr Thr Leu Thr Ile Ser Ser Val Gln Ala
65 70 75 80

Glu Asp Leu Ala Leu Tyr Tyr Cys Gln Gln His Tyr Ser Ala Pro Trp
85 90 95

Thr Phe Gly Gly Gly Thr Lys Leu Glu Ile Lys
100 105

<210> SEQ ID NO 19
<211> LENGTH: 9
<212> TYPE: PRT
<213> ORGANISM: Artificial Sequence
<220> FEATURE:
<223> OTHER INFORMATION: 1F4 HCDR1 (IMGT)

<400> SEQUENCE: 19

Asp Ser Glu Val Phe Pro Ile Val Tyr
1 5

<210> SEQ ID NO 20
<211> LENGTH: 8
<212> TYPE: PRT
<213> ORGANISM: Artificial Sequence
<220> FEATURE:
<223> OTHER INFORMATION: 1F4 HCDR2 (IMGT)

<400> SEQUENCE: 20

Ile Leu Pro Ser Phe Gly Arg Thr
1 5

<210> SEQ ID NO 21
<211> LENGTH: 11
<212> TYPE: PRT

<213> ORGANISM: Artificial Sequence
<220> FEATURE:
<223> OTHER INFORMATION: 1F4 HCDR3 (IMGT)

<400> SEQUENCE: 21

Ala Arg Gly Asp His Gly Asn Trp Leu Ala Tyr
1 5 10

<210> SEQ ID NO 22
<211> LENGTH: 6
<212> TYPE: PRT
<213> ORGANISM: Artificial Sequence
<220> FEATURE:
<223> OTHER INFORMATION: 1F4 LCDR1 (IMGT)

<400> SEQUENCE: 22

Gln Asp Val Ser Thr Ala
1 5

<210> SEQ ID NO 23
<211> LENGTH: 3
<212> TYPE: PRT
<213> ORGANISM: Artificial Sequence
<220> FEATURE:
<223> OTHER INFORMATION: 1F4 LCDR2 (IMGT)

<400> SEQUENCE: 23

Trp Ala Ser
1

<210> SEQ ID NO 24
<211> LENGTH: 9
<212> TYPE: PRT
<213> ORGANISM: Artificial Sequence
<220> FEATURE:
<223> OTHER INFORMATION: 1F4 LCDR3 (IMGT)

<400> SEQUENCE: 24

Gln Gln His Tyr Ser Ala Pro Trp Thr
1 5

<210> SEQ ID NO 25
<211> LENGTH: 25
<212> TYPE: PRT
<213> ORGANISM: Artificial Sequence
<220> FEATURE:
<223> OTHER INFORMATION: 1F4 VH FR1 (IMGT)

<400> SEQUENCE: 25

Gln Val His Leu Gln Gln Ser Gly Ser Glu Leu Arg Ser Pro Gly Ser
1 5 10 15

Ser Val Lys Leu Ser Cys Lys Asp Phe
20 25

<210> SEQ ID NO 26
<211> LENGTH: 17
<212> TYPE: PRT
<213> ORGANISM: Artificial Sequence
<220> FEATURE:
<223> OTHER INFORMATION: 1F4 VH FR2 (IMGT)

<400> SEQUENCE: 26

Met Arg Trp Ile Arg Gln Lys Pro Gly His Gly Phe Glu Trp Ile Gly
1 5 10 15

Asp

<210> SEQ ID NO 27
<211> LENGTH: 38
<212> TYPE: PRT
<213> ORGANISM: Artificial Sequence
<220> FEATURE:
<223> OTHER INFORMATION: 1F4 VH FR3 (IMGT)

<400> SEQUENCE: 27

```
Ile Tyr Gly Glu Lys Phe Glu Asp Lys Ala Thr Leu Asp Ala Asp Thr
1               5                   10                  15

Val Ser Asn Thr Ala Tyr Leu Glu Leu Asn Ser Leu Thr Ser Glu Asp
            20                  25                  30

Ser Ala Ile Tyr Tyr Cys
        35
```

<210> SEQ ID NO 28
<211> LENGTH: 11
<212> TYPE: PRT
<213> ORGANISM: Artificial Sequence
<220> FEATURE:
<223> OTHER INFORMATION: 1F4 VH FR4 (IMGT)

<400> SEQUENCE: 28

```
Trp Gly Gln Gly Thr Leu Val Thr Val Ser Ala
1               5                   10
```

<210> SEQ ID NO 29
<211> LENGTH: 26
<212> TYPE: PRT
<213> ORGANISM: Artificial Sequence
<220> FEATURE:
<223> OTHER INFORMATION: 1F4 VL FR1 (IMGT)

<400> SEQUENCE: 29

```
Asp Ile Val Met Thr Gln Ser His Lys Phe Met Ser Thr Ser Val Gly
1               5                   10                  15

Asp Arg Val Thr Ile Thr Cys Lys Ala Ser
            20                  25
```

<210> SEQ ID NO 30
<211> LENGTH: 17
<212> TYPE: PRT
<213> ORGANISM: Artificial Sequence
<220> FEATURE:
<223> OTHER INFORMATION: 1F4 VL FR2 (IMGT)

<400> SEQUENCE: 30

```
Val Ala Trp Tyr Gln Gln Lys Pro Gly Gln Ser Pro Lys Leu Leu Ile
1               5                   10                  15

Tyr
```

<210> SEQ ID NO 31
<211> LENGTH: 36
<212> TYPE: PRT
<213> ORGANISM: Artificial Sequence
<220> FEATURE:
<223> OTHER INFORMATION: 1F4 VL FR3 (IMGT)

<400> SEQUENCE: 31

```
Thr Arg His Thr Gly Val Pro Asn Arg Phe Thr Gly Ile Ile Ser Gly
1               5                   10                  15

Thr Asp Tyr Thr Leu Thr Ile Ser Ser Val Gln Ala Glu Asp Leu Ala
            20                  25                  30
```

Leu Tyr Tyr Cys
35

<210> SEQ ID NO 32
<211> LENGTH: 10
<212> TYPE: PRT
<213> ORGANISM: Artificial Sequence
<220> FEATURE:
<223> OTHER INFORMATION: 1F4 VL FR4 (IMGT)

<400> SEQUENCE: 32

Phe Gly Gly Gly Thr Lys Leu Glu Ile Lys
1 5 10

<210> SEQ ID NO 33
<211> LENGTH: 123
<212> TYPE: PRT
<213> ORGANISM: Artificial Sequence
<220> FEATURE:
<223> OTHER INFORMATION: 3G1 VH

<400> SEQUENCE: 33

Gln Val Gln Leu Gln Gln Ser Gly Ala Glu Leu Met Lys Pro Gly Ala
1 5 10 15

Ser Val Lys Ile Ser Cys Lys Ala Thr Gly Tyr Lys Phe Thr Ser Tyr
20 25 30

Trp Ile Gly Trp Val Lys Gln Arg Pro Gly His Gly Leu Glu Trp Cys
35 40 45

Gly Glu Ile Phe Pro Gly Ser Gly Ser Ile Asn Tyr Asn Glu Lys Phe
50 55 60

Lys Gly Lys Ala Thr Phe Thr Ala Asp Thr Ser Ser Asn Thr Ala Tyr
65 70 75 80

Leu Gln Leu Thr Ser Leu Thr Ser Glu Asp Ser Ala Val Tyr Tyr Cys
85 90 95

Ala Arg Gly Glu Asp Tyr Tyr Gly Ser Ser Tyr Gly Ala Met Asp Tyr
100 105 110

Trp Gly Gln Gly Thr Ser Leu Thr Val Ser Ser
115 120

<210> SEQ ID NO 34
<211> LENGTH: 107
<212> TYPE: PRT
<213> ORGANISM: Artificial Sequence
<220> FEATURE:
<223> OTHER INFORMATION: 3G1 VL

<400> SEQUENCE: 34

Asp Val Gln Ile Thr Gln Ser Pro Ser Tyr Leu Ala Ala Ser Pro Gly
1 5 10 15

Glu Thr Ile Thr Ile Asn Cys Arg Ala Ser Lys Ser Ile Ser Lys Tyr
20 25 30

Val Ala Trp Tyr Gln Glu Lys Pro Gly Arg Thr Asn Lys Val Leu Ile
35 40 45

Tyr Ser Gly Ser Ile Leu Ser Phe Gly Asn Pro Ser Arg Phe Ser Gly
50 55 60

Ser Gly Ser Gly Thr Asp Phe Thr Leu Thr Ile Ser Ser Leu Glu Pro
65 70 75 80

Glu Asp Phe Ala Met Tyr Tyr Cys Gln Gln His Asn Glu Tyr Pro Trp
85 90 95

Thr Phe Gly Gly Gly Thr Lys Leu Glu Ile Lys 100 105

<210> SEQ ID NO 35
<211> LENGTH: 8
<212> TYPE: PRT
<213> ORGANISM: Artificial Sequence
<220> FEATURE:
<223> OTHER INFORMATION: 3G1 HCDR1 (IMGT)

<400> SEQUENCE: 35

Gly Tyr Lys Phe Thr Ser Tyr Trp
1 5

<210> SEQ ID NO 36
<211> LENGTH: 8
<212> TYPE: PRT
<213> ORGANISM: Artificial Sequence
<220> FEATURE:
<223> OTHER INFORMATION: 3G1 HCDR2 (IMGT)

<400> SEQUENCE: 36

Ile Phe Pro Gly Ser Gly Ser Ile
1 5

<210> SEQ ID NO 37
<211> LENGTH: 16
<212> TYPE: PRT
<213> ORGANISM: Artificial Sequence
<220> FEATURE:
<223> OTHER INFORMATION: 3G1 HCDR3 (IMGT)

<400> SEQUENCE: 37

Ala Arg Gly Glu Asp Tyr Tyr Gly Ser Ser Tyr Gly Ala Met Asp Tyr
1 5 10 15

<210> SEQ ID NO 38
<211> LENGTH: 6
<212> TYPE: PRT
<213> ORGANISM: Artificial Sequence
<220> FEATURE:
<223> OTHER INFORMATION: 3G1 LCDR1 (IMGT)

<400> SEQUENCE: 38

Lys Ser Ile Ser Lys Tyr
1 5

<210> SEQ ID NO 39
<211> LENGTH: 3
<212> TYPE: PRT
<213> ORGANISM: Artificial Sequence
<220> FEATURE:
<223> OTHER INFORMATION: 3G1 LCDR2 (IMGT)

<400> SEQUENCE: 39

Ser Gly Ser
1

<210> SEQ ID NO 40
<211> LENGTH: 9
<212> TYPE: PRT
<213> ORGANISM: Artificial Sequence
<220> FEATURE:
<223> OTHER INFORMATION: 3G1 LCDR3 (IMGT)

<400> SEQUENCE: 40

Gln Gln His Asn Glu Tyr Pro Trp Thr
1 5

<210> SEQ ID NO 41
<211> LENGTH: 25
<212> TYPE: PRT
<213> ORGANISM: Artificial Sequence
<220> FEATURE:
<223> OTHER INFORMATION: 3G1 VH FR1 (IMGT)

<400> SEQUENCE: 41

Gln Val Gln Leu Gln Gln Ser Gly Ala Glu Leu Met Lys Pro Gly Ala
1 5 10 15

Ser Val Lys Ile Ser Cys Lys Ala Thr
20 25

<210> SEQ ID NO 42
<211> LENGTH: 17
<212> TYPE: PRT
<213> ORGANISM: Artificial Sequence
<220> FEATURE:
<223> OTHER INFORMATION: 3G1 VH FR2 (IMGT)

<400> SEQUENCE: 42

Ile Gly Trp Val Lys Gln Arg Pro Gly His Gly Leu Glu Trp Cys Gly
1 5 10 15

Glu

<210> SEQ ID NO 43
<211> LENGTH: 38
<212> TYPE: PRT
<213> ORGANISM: Artificial Sequence
<220> FEATURE:
<223> OTHER INFORMATION: 3G1 VH FR3 (IMGT)

<400> SEQUENCE: 43

Asn Tyr Asn Glu Lys Phe Lys Gly Lys Ala Thr Phe Thr Ala Asp Thr
1 5 10 15

Ser Ser Asn Thr Ala Tyr Leu Gln Leu Thr Ser Leu Thr Ser Glu Asp
20 25 30

Ser Ala Val Tyr Tyr Cys
35

<210> SEQ ID NO 44
<211> LENGTH: 11
<212> TYPE: PRT
<213> ORGANISM: Artificial Sequence
<220> FEATURE:
<223> OTHER INFORMATION: 3G1 VH FR4 (IMGT)

<400> SEQUENCE: 44

Trp Gly Gln Gly Thr Ser Leu Thr Val Ser Ser
1 5 10

<210> SEQ ID NO 45
<211> LENGTH: 26
<212> TYPE: PRT
<213> ORGANISM: Artificial Sequence
<220> FEATURE:
<223> OTHER INFORMATION: 3G1 VL FR1 (IMGT)

<400> SEQUENCE: 45

Asp Val Gln Ile Thr Gln Ser Pro Ser Tyr Leu Ala Ala Ser Pro Gly
1 5 10 15

Glu Thr Ile Thr Ile Asn Cys Arg Ala Ser
20 25

<210> SEQ ID NO 46
<211> LENGTH: 17
<212> TYPE: PRT
<213> ORGANISM: Artificial Sequence
<220> FEATURE:
<223> OTHER INFORMATION: 3G1 VL FR2 (IMGT)

<400> SEQUENCE: 46

Val Ala Trp Tyr Gln Glu Lys Pro Gly Arg Thr Asn Lys Val Leu Ile
1 5 10 15

Tyr

<210> SEQ ID NO 47
<211> LENGTH: 36
<212> TYPE: PRT
<213> ORGANISM: Artificial Sequence
<220> FEATURE:
<223> OTHER INFORMATION: 3G1 VL FR3 (IMGT)

<400> SEQUENCE: 47

Ile Leu Ser Phe Gly Asn Pro Ser Arg Phe Ser Gly Ser Gly Ser Gly
1 5 10 15

Thr Asp Phe Thr Leu Thr Ile Ser Ser Leu Glu Pro Glu Asp Phe Ala
20 25 30

Met Tyr Tyr Cys
35

<210> SEQ ID NO 48
<211> LENGTH: 10
<212> TYPE: PRT
<213> ORGANISM: Artificial Sequence
<220> FEATURE:
<223> OTHER INFORMATION: 3G1 VL FR4 (IMGT)

<400> SEQUENCE: 48

Phe Gly Gly Gly Thr Lys Leu Glu Ile Lys
1 5 10

<210> SEQ ID NO 49
<211> LENGTH: 123
<212> TYPE: PRT
<213> ORGANISM: Artificial Sequence
<220> FEATURE:
<223> OTHER INFORMATION: 4B2 VH

<400> SEQUENCE: 49

Gln Ile Gln Leu Val Gln Ser Gly Pro Glu Leu Lys Lys Pro Gly Glu
1 5 10 15

Thr Val Lys Ile Ser Cys Lys Ala Ser Gly Phe Thr Phe Thr Asp Tyr
20 25 30

Pro Met His Trp Val Lys Gln Ala Pro Gly Lys Ser Leu Lys Trp Met
35 40 45

Gly Trp Ile Asn Thr Glu Thr Glu Glu Pro Thr Tyr Ser Asp Asp Phe
50 55 60

Lys Gly Arg Phe Ala Leu Ser Leu Glu Thr Ser Ala Ser Thr Thr Tyr
65 70 75 80

Leu Gln Ile Asn Asn Leu Lys Asn Glu Asp Thr Ala Thr Tyr Phe Cys
85 90 95

Ala Arg Ser Gly Tyr Tyr Tyr Gly Ser Thr Tyr Ala Trp Phe Gly Tyr
100 105 110

```
Trp Gly Gln Gly Thr Leu Val Thr Val Ser Ala
        115                 120


<210> SEQ ID NO 50
<211> LENGTH: 112
<212> TYPE: PRT
<213> ORGANISM: Artificial Sequence
<220> FEATURE:
<223> OTHER INFORMATION: 4B2 VL

<400> SEQUENCE: 50

Asp Val Val Met Thr Gln Ile Pro Leu Ser Leu Pro Val Ser Leu Gly
1               5                   10                  15

Asp Gln Ala Ser Ile Ser Cys Arg Ser Ser Gln Ser Leu Ile His Thr
            20                  25                  30

Asn Gly Asp Thr Phe Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Thr Gly Gly Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Ala Leu Phe Pro Tyr Thr Phe Gly Gly Gly Thr Asn Leu Glu Ile Lys
            100                 105                 110


<210> SEQ ID NO 51
<211> LENGTH: 8
<212> TYPE: PRT
<213> ORGANISM: Artificial Sequence
<220> FEATURE:
<223> OTHER INFORMATION: 4B2 HCDR1 (IMGT)

<400> SEQUENCE: 51

Gly Phe Thr Phe Thr Asp Tyr Pro
1               5


<210> SEQ ID NO 52
<211> LENGTH: 8
<212> TYPE: PRT
<213> ORGANISM: Artificial Sequence
<220> FEATURE:
<223> OTHER INFORMATION: 4B2 HCDR2 (IMGT)

<400> SEQUENCE: 52

Ile Asn Thr Glu Thr Glu Glu Pro
1               5


<210> SEQ ID NO 53
<211> LENGTH: 16
<212> TYPE: PRT
<213> ORGANISM: Artificial Sequence
<220> FEATURE:
<223> OTHER INFORMATION: 4B2 HCDR3 (IMGT)

<400> SEQUENCE: 53

Ala Arg Ser Gly Tyr Tyr Tyr Gly Ser Thr Tyr Ala Trp Phe Gly Tyr
1               5                   10                  15


<210> SEQ ID NO 54
<211> LENGTH: 11
<212> TYPE: PRT
<213> ORGANISM: Artificial Sequence
<220> FEATURE:
```

<223> OTHER INFORMATION: 4B2 LCDR1 (IMGT)

<400> SEQUENCE: 54

Gln Ser Leu Ile His Thr Asn Gly Asp Thr Phe
1 5 10

<210> SEQ ID NO 55
<211> LENGTH: 3
<212> TYPE: PRT
<213> ORGANISM: Artificial Sequence
<220> FEATURE:
<223> OTHER INFORMATION: 4B2 LCDR2 (IMGT)

<400> SEQUENCE: 55

Lys Val Ser
1

<210> SEQ ID NO 56
<211> LENGTH: 9
<212> TYPE: PRT
<213> ORGANISM: Artificial Sequence
<220> FEATURE:
<223> OTHER INFORMATION: 4B2 LCDR3 (IMGT)

<400> SEQUENCE: 56

Ser Gln Ser Ala Leu Phe Pro Tyr Thr
1 5

<210> SEQ ID NO 57
<211> LENGTH: 25
<212> TYPE: PRT
<213> ORGANISM: Artificial Sequence
<220> FEATURE:
<223> OTHER INFORMATION: 4B2 VH FR1 (IMGT)

<400> SEQUENCE: 57

Gln Ile Gln Leu Val Gln Ser Gly Pro Glu Leu Lys Lys Pro Gly Glu
1 5 10 15

Thr Val Lys Ile Ser Cys Lys Ala Ser
20 25

<210> SEQ ID NO 58
<211> LENGTH: 17
<212> TYPE: PRT
<213> ORGANISM: Artificial Sequence
<220> FEATURE:
<223> OTHER INFORMATION: 4B2 VH FR2 (IMGT)

<400> SEQUENCE: 58

Met His Trp Val Lys Gln Ala Pro Gly Lys Ser Leu Lys Trp Met Gly
1 5 10 15

Trp

<210> SEQ ID NO 59
<211> LENGTH: 38
<212> TYPE: PRT
<213> ORGANISM: Artificial Sequence
<220> FEATURE:
<223> OTHER INFORMATION: 4B2 VH FR3 (IMGT)

<400> SEQUENCE: 59

Thr Tyr Ser Asp Asp Phe Lys Gly Arg Phe Ala Leu Ser Leu Glu Thr
1 5 10 15

Ser Ala Ser Thr Thr Tyr Leu Gln Ile Asn Asn Leu Lys Asn Glu Asp
20 25 30

```
Thr Ala Thr Tyr Phe Cys
        35


<210> SEQ ID NO 60
<211> LENGTH: 11
<212> TYPE: PRT
<213> ORGANISM: Artificial Sequence
<220> FEATURE:
<223> OTHER INFORMATION: 4B2 VH FR4 (IMGT)

<400> SEQUENCE: 60

Trp Gly Gln Gly Thr Leu Val Thr Val Ser Ala
1               5                   10


<210> SEQ ID NO 61
<211> LENGTH: 26
<212> TYPE: PRT
<213> ORGANISM: Artificial Sequence
<220> FEATURE:
<223> OTHER INFORMATION: 4B2 VL FR1 (IMGT)

<400> SEQUENCE: 61

Asp Val Val Met Thr Gln Ile Pro Leu Ser Leu Pro Val Ser Leu Gly
1               5                   10                  15

Asp Gln Ala Ser Ile Ser Cys Arg Ser Ser
            20                  25


<210> SEQ ID NO 62
<211> LENGTH: 17
<212> TYPE: PRT
<213> ORGANISM: Artificial Sequence
<220> FEATURE:
<223> OTHER INFORMATION: 4B2 VL FR2 (IMGT)

<400> SEQUENCE: 62

Leu His Trp Tyr Leu Gln Lys Pro Gly Gln Ser Pro Lys Leu Leu Ile
1               5                   10                  15

Tyr


<210> SEQ ID NO 63
<211> LENGTH: 36
<212> TYPE: PRT
<213> ORGANISM: Artificial Sequence
<220> FEATURE:
<223> OTHER INFORMATION: 4B2 VL FR3 (IMGT)

<400> SEQUENCE: 63

Asn Arg Phe Ser Gly Val Pro Asp Arg Phe Thr Gly Gly Gly Ser Gly
1               5                   10                  15

Thr Asp Phe Thr Leu Lys Ile Ser Arg Val Glu Ala Glu Asp Leu Gly
            20                  25                  30

Ile Tyr Phe Cys
        35


<210> SEQ ID NO 64
<211> LENGTH: 10
<212> TYPE: PRT
<213> ORGANISM: Artificial Sequence
<220> FEATURE:
<223> OTHER INFORMATION: 4B2 VL FR4 (IMGT)

<400> SEQUENCE: 64

Phe Gly Gly Gly Thr Asn Leu Glu Ile Lys
1               5                   10
```

```
<210> SEQ ID NO 65
<211> LENGTH: 121
<212> TYPE: PRT
<213> ORGANISM: Artificial Sequence
<220> FEATURE:
<223> OTHER INFORMATION: 4F11 VH

<400> SEQUENCE: 65

Asp Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ala Tyr
            20                  25                  30

Ser Met Ser Trp Val Arg Gln Thr Pro Glu Arg Arg Leu Glu Trp Val
        35                  40                  45

Ala Thr Ile Asn Thr Gly Gly Ser Phe Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Phe Cys
                85                  90                  95

Thr Arg Val Ser Asp Tyr Gly Asn Ser Ala Tyr Phe Pro Tyr Trp Gly
            100                 105                 110

Gln Gly Thr Leu Val Ile Val Ser Ala
        115                 120


<210> SEQ ID NO 66
<211> LENGTH: 106
<212> TYPE: PRT
<213> ORGANISM: Artificial Sequence
<220> FEATURE:
<223> OTHER INFORMATION: 4F11 VL

<400> SEQUENCE: 66

Gln Val Val Leu Thr Gln Ser Pro Ala Leu Ile Ser Ala Ser Pro Gly
1               5                   10                  15

Glu Lys Val Thr Met Thr Cys Ser Ala Ser Ser Asn Val Asn Tyr Met
            20                  25                  30

Ser Trp Tyr Gln Gln Arg Pro Arg Ser Ser Pro Lys Pro Trp Ile Tyr
        35                  40                  45

Leu Thr Ser Lys Leu Ala Ser Gly Val Pro Pro Arg Phe Ser Gly Ser
    50                  55                  60

Gly Ser Gly Thr Ser Tyr Ser Leu Thr Ile Ser Ser Met Glu Ala Glu
65                  70                  75                  80

Asp Val Ala Thr Tyr Tyr Cys Gln Gln Trp Ser Ser Asp Pro Gln Thr
                85                  90                  95

Phe Gly Gly Gly Thr Lys Val Glu Ile Lys
            100                 105


<210> SEQ ID NO 67
<211> LENGTH: 8
<212> TYPE: PRT
<213> ORGANISM: Artificial Sequence
<220> FEATURE:
<223> OTHER INFORMATION: 4F11 HCDR1 (IMGT)

<400> SEQUENCE: 67

Gly Phe Thr Phe Ser Ala Tyr Ser
1               5
```

<210> SEQ ID NO 68
<211> LENGTH: 8
<212> TYPE: PRT
<213> ORGANISM: Artificial Sequence
<220> FEATURE:
<223> OTHER INFORMATION: 4F11 HCDR2 (IMGT)

<400> SEQUENCE: 68

Ile Asn Thr Gly Gly Ser Phe Thr
1               5

<210> SEQ ID NO 69
<211> LENGTH: 14
<212> TYPE: PRT
<213> ORGANISM: Artificial Sequence
<220> FEATURE:
<223> OTHER INFORMATION: 4F11 HCDR3 (IMGT)

<400> SEQUENCE: 69

Thr Arg Val Ser Asp Tyr Gly Asn Ser Ala Tyr Phe Pro Tyr
1               5                   10

<210> SEQ ID NO 70
<211> LENGTH: 5
<212> TYPE: PRT
<213> ORGANISM: Artificial Sequence
<220> FEATURE:
<223> OTHER INFORMATION: 4F11 LCDR1 (IMGT)

<400> SEQUENCE: 70

Ser Asn Val Asn Tyr
1               5

<210> SEQ ID NO 71
<211> LENGTH: 3
<212> TYPE: PRT
<213> ORGANISM: Artificial Sequence
<220> FEATURE:
<223> OTHER INFORMATION: 4F11 LCDR2 (IMGT)

<400> SEQUENCE: 71

Leu Thr Ser
1

<210> SEQ ID NO 72
<211> LENGTH: 9
<212> TYPE: PRT
<213> ORGANISM: Artificial Sequence
<220> FEATURE:
<223> OTHER INFORMATION: 4F11 LCDR3 (IMGT)

<400> SEQUENCE: 72

Gln Gln Trp Ser Ser Asp Pro Gln Thr
1               5

<210> SEQ ID NO 73
<211> LENGTH: 25
<212> TYPE: PRT
<213> ORGANISM: Artificial Sequence
<220> FEATURE:
<223> OTHER INFORMATION: 4F11 VH FR1 (IMGT)

<400> SEQUENCE: 73

Asp Val Lys Leu Val Glu Ser Gly Gly Asp Leu Val Lys Pro Gly Gly
1               5                   10                  15

Ser Leu Lys Leu Ser Cys Ala Ala Ser 20 25

<210> SEQ ID NO 74
<211> LENGTH: 17
<212> TYPE: PRT
<213> ORGANISM: Artificial Sequence
<220> FEATURE:
<223> OTHER INFORMATION: 4F11 VH FR2 (IMGT)

<400> SEQUENCE: 74

Met Ser Trp Val Arg Gln Thr Pro Glu Arg Arg Leu Glu Trp Val Ala
1 5 10 15

Thr

<210> SEQ ID NO 75
<211> LENGTH: 38
<212> TYPE: PRT
<213> ORGANISM: Artificial Sequence
<220> FEATURE:
<223> OTHER INFORMATION: 4F11 VH FR3 (IMGT)

<400> SEQUENCE: 75

Tyr Tyr Pro Asp Ser Val Lys Gly Arg Phe Thr Ile Ser Arg Asp Asn
1 5 10 15

Ala Lys Asn Thr Leu Tyr Leu Gln Met Ser Ser Leu Lys Ser Glu Asp
20 25 30

Thr Ala Met Tyr Phe Cys
35

<210> SEQ ID NO 76
<211> LENGTH: 11
<212> TYPE: PRT
<213> ORGANISM: Artificial Sequence
<220> FEATURE:
<223> OTHER INFORMATION: 4F11 VH FR4 (IMGT)

<400> SEQUENCE: 76

Trp Gly Gln Gly Thr Leu Val Ile Val Ser Ala
1 5 10

<210> SEQ ID NO 77
<211> LENGTH: 26
<212> TYPE: PRT
<213> ORGANISM: Artificial Sequence
<220> FEATURE:
<223> OTHER INFORMATION: 4F11 VL FR1 (IMGT)

<400> SEQUENCE: 77

Gln Val Val Leu Thr Gln Ser Pro Ala Leu Ile Ser Ala Ser Pro Gly
1 5 10 15

Glu Lys Val Thr Met Thr Cys Ser Ala Ser
20 25

<210> SEQ ID NO 78
<211> LENGTH: 17
<212> TYPE: PRT
<213> ORGANISM: Artificial Sequence
<220> FEATURE:
<223> OTHER INFORMATION: 4F11 VL FR2 (IMGT)

<400> SEQUENCE: 78

Met Ser Trp Tyr Gln Gln Arg Pro Arg Ser Ser Pro Lys Pro Trp Ile
1 5 10 15

Tyr

<210> SEQ ID NO 79
<211> LENGTH: 36
<212> TYPE: PRT
<213> ORGANISM: Artificial Sequence
<220> FEATURE:
<223> OTHER INFORMATION: 4F11 VL FR3 (IMGT)

<400> SEQUENCE: 79

Lys Leu Ala Ser Gly Val Pro Pro Arg Phe Ser Gly Ser Gly Ser Gly
1 5 10 15

Thr Ser Tyr Ser Leu Thr Ile Ser Ser Met Glu Ala Glu Asp Val Ala
20 25 30

Thr Tyr Tyr Cys
35

<210> SEQ ID NO 80
<211> LENGTH: 10
<212> TYPE: PRT
<213> ORGANISM: Artificial Sequence
<220> FEATURE:
<223> OTHER INFORMATION: 4F11 VL FR4 (IMGT)

<400> SEQUENCE: 80

Phe Gly Gly Gly Thr Lys Val Glu Ile Lys
1 5 10

<210> SEQ ID NO 81
<211> LENGTH: 366
<212> TYPE: DNA
<213> ORGANISM: Artificial Sequence
<220> FEATURE:
<223> OTHER INFORMATION: 1F2 VH

<400> SEQUENCE: 81
caggttcacc tgcagcagtc tggacctgag gtggcgaggc ccggggcttc agtgaagctg 60
tcctgcaagg cttctggcta caccttcact gactactatc ttaactgggt gaagcagagg 120
cctagacagg gccttgagtg gattggacag attcatcctg gaagtactaa tacttactac 180
aatgagaagt tcaagggcaa ggccacactg actgcagaca aatcctccag cacagcctac 240
atgcagctca gcagcctgac atctgaggac tctgcagtct atttctgtgc aagatcgctt 300
ggtgatggtt actacgtcta tgctatggac tactggggtc agggaaccgc agtcaccgtc 360
tcctca 366

<210> SEQ ID NO 82
<211> LENGTH: 321
<212> TYPE: DNA
<213> ORGANISM: Artificial Sequence
<220> FEATURE:
<223> OTHER INFORMATION: 1F2 VL

<400> SEQUENCE: 82
gacattgtga tgacccagtc tcaaaaattc atgtccacat cagtaggaga cagggtcagc 60
gtcacctgca aggccagtca gaatgtggtt actaatgtag tctggtatca acagaaacca 120
ggtcagtctc ctaaaccact gatttactcg gcatcctacc ggtacagtgg agtccctgat 180
cgcttcacag gcagtggatc tgggacagat ttcactctca ccatcagcaa tgtgcagtct 240
gaagacttgg cagagtactg ctgtcagcaa tatcacagct atccattcac gttcggctcg 300
gggacaaagt tggaagtaaa a 321

<210> SEQ ID NO 83
<211> LENGTH: 357
<212> TYPE: DNA
<213> ORGANISM: Artificial Sequence
<220> FEATURE:
<223> OTHER INFORMATION: 1F4 VH

<400> SEQUENCE: 83
caggttcacc tacaacagtc tggttctgaa ctgaggagtc ctgggtcttc agtaaagctt 60
tcatgcaagg attttgattc agaagtcttc cctattgttt atatgagatg gattaggcag 120
aagcctggcc atggatttga atggattgga gacatactcc caagttttgg tagaacaatc 180
tatggagaga agtttgagga caaagccaca ctagatgcag acacagtgtc caacacagcc 240
tacttggagc tcaacagtct gacatctgag gactctgcta tctactactg tgcaaggggg 300
gaccatggta actggcttgc ttactggggc caagggactc tggtcactgt ctctgca 357

<210> SEQ ID NO 84
<211> LENGTH: 321
<212> TYPE: DNA
<213> ORGANISM: Artificial Sequence
<220> FEATURE:
<223> OTHER INFORMATION: 1F4 VL

<400> SEQUENCE: 84
gacattgtga tgacccagtc tcacaaattc atgtccacat cagttggaga cagggtcacc 60
atcacctgca aggccagtca ggatgtgagt actgctgtag cctggtatca acaaaaacca 120
ggccaatctc ctaaactact gatttactgg gcatccaccc ggcacactgg agtccctaat 180
cgcttcacag gcattatatc tgggacagat tacactctca ctatcagcag tgtgcaggct 240
gaagacctgg cactttatta ctgtcagcaa cattatagcg ctccgtggac gttcggtgga 300
ggcaccaagc tggaaatcaa a 321

<210> SEQ ID NO 85
<211> LENGTH: 369
<212> TYPE: DNA
<213> ORGANISM: Artificial Sequence
<220> FEATURE:
<223> OTHER INFORMATION: 3G1 VH

<400> SEQUENCE: 85
caggttcagc tgcagcagtc tggagctgaa ttgatgaagc ctggggcctc agtgaagatt 60
tcctgcaagg ctactgggta caaattcact agttattgga tagggtgggt aaagcagagg 120
ccgggacatg gccttgagtg gtgtggagag atttttcctg gaagtggcag tattaactat 180
aatgagaaat ttaagggcaa ggccacattc actgcagata catcctccaa cacagcctac 240
ttgcaactga ccagcctgac atctgaggac tctgccgtct attactgtgc aagaggggag 300
gattattacg gtagtagtta cggtgctatg gactactggg gtcaaggaac ctcactcacc 360
gtctcctca 369

<210> SEQ ID NO 86
<211> LENGTH: 321
<212> TYPE: DNA
<213> ORGANISM: Artificial Sequence
<220> FEATURE:
<223> OTHER INFORMATION: 3G1 VL

<400> SEQUENCE: 86
gatgtccaga taacccagtc tccatcttat cttgctgcat ctcctggaga aaccattact 60
attaattgca gggcaagtaa gagcatcagc aaatatgtag cctggtatca agagaaacct 120
gggagaacta acaaggttct tatatattct ggatcaatct tgtcatttgg aaatccatca 180
aggttcagtg gcagtggatc tggtacagat ttcactctca ccatcagtag cctggagcct 240
gaagattttg caatgtatta ctgtcaacag cataatgaat acccgtggac gttcggtgga 300
ggcaccaagc tggaaatcaa a 321

<210> SEQ ID NO 87
<211> LENGTH: 369
<212> TYPE: DNA
<213> ORGANISM: Artificial Sequence
<220> FEATURE:
<223> OTHER INFORMATION: 4B2 VH

<400> SEQUENCE: 87
cagatccagt tggtgcagtc tggacctgag ctgaagaagc ctggagagac agtcaagatc 60
tcctgcaagg cttctggttt taccttcaca gactatccaa tgcactgggt gaagcaggct 120
ccaggaaaga gtttaaagtg gatgggttgg ataaacactg agactgaaga gccaacatat 180
tcagatgact tcaagggacg gtttgccttg tctttggaaa cctctgccag cacaacctat 240
ttgcagatca acaatctcaa aaatgaggac acggctacat atttctgtgc tagatcaggt 300
tattactatg gtagtaccta cgcctggttt ggttactggg gccaagggac tctggtcact 360
gtctctgca 369

<210> SEQ ID NO 88
<211> LENGTH: 336
<212> TYPE: DNA
<213> ORGANISM: Artificial Sequence
<220> FEATURE:
<223> OTHER INFORMATION: 4B2 VL

<400> SEQUENCE: 88
gatgttgtga tgacccaaat tccactctcc ctgcctgtca gtctcggaga tcaggcctcc 60
atctcttgca gatctagtca gagccttata cacactaatg gagacacctt tttacattgg 120
tacctgcaga agccaggcca gtctccaaag ctcctgatct acaaagtttc caaccgattt 180
tctggggtcc cagacaggtt cactggcggt ggatcaggga cagatttcac actcaagatc 240
agcagagtgg aggctgagga tctgggaatt tatttctgct ctcaaagtgc actttttccg 300
tacacgttcg gaggggggac caacctggaa ataaaa 336

<210> SEQ ID NO 89
<211> LENGTH: 363
<212> TYPE: DNA
<213> ORGANISM: Artificial Sequence
<220> FEATURE:
<223> OTHER INFORMATION: 4F11 VH

<400> SEQUENCE: 89
gacgtgaaac tggtggaatc tgggggagac ttagtgaagc ctggagggtc cctgaaactc 60
tcctgtgcag cctctggatt cactttcagt gcctattcca tgtcttgggt tcgccagact 120
ccggagagga ggctggagtg ggtcgcaacc attaatactg gtggtagttt cacctactat 180
ccagacagtg tgaagggccg attcaccatc tccagagaca atgccaagaa caccctgtac 240
ctgcaaatga gcagtctgaa gtctgaggac acagccatgt atttctgtac aagagtttcc 300
gactacggta atagcgccta ctttccttac tggggccaag ggactctggt cattgtctct 360
gca 363

<210> SEQ ID NO 90
<211> LENGTH: 318
<212> TYPE: DNA
<213> ORGANISM: Artificial Sequence
<220> FEATURE:
<223> OTHER INFORMATION: 4F11 VL

<400> SEQUENCE: 90
caagttgttc tcacccagtc tccagcactc atatctgcgt ctccagggga gaaggtcacc 60
atgacctgca gtgccagctc aaatgtaaat tacatgtcct ggtaccagca gaggccaaga 120
tcctccccca aaccctggat ttatctcaca tccaaactgg cttctggagt ccctcctcgt 180
ttcagtggca gtgggtctgg gacctcttac tctctcacaa tcagcagcat ggaggctgaa 240
gatgttgcca cttattactg ccagcagtgg agcagtgacc cccagacgtt cggagggggg 300
accaaggtgg aaataaaa 318

<210> SEQ ID NO 91
<211> LENGTH: 36
<212> TYPE: DNA
<213> ORGANISM: Artificial Sequence
<220> FEATURE:
<223> OTHER INFORMATION: 5' consensus anchor primer
<220> FEATURE:
<221> NAME/KEY: misc_feature
<222> LOCATION: (24)..(25)
<223> OTHER INFORMATION: where n is c, u or a
<220> FEATURE:
<221> NAME/KEY: misc_feature
<222> LOCATION: (29)..(30)
<223> OTHER INFORMATION: where n is c, u or a
<220> FEATURE:
<221> NAME/KEY: misc_feature
<222> LOCATION: (34)..(35)
<223> OTHER INFORMATION: where n is c, u or a

<400> SEQUENCE: 91
ggccacgcgt cgactagtac gggnngggnn gggnng 36

<210> SEQ ID NO 92
<211> LENGTH: 23
<212> TYPE: DNA
<213> ORGANISM: Artificial Sequence
<220> FEATURE:
<223> OTHER INFORMATION: Constant region specific reverse primer IgG2a

<400> SEQUENCE: 92
ccttgaccag gcatcctaga gtc 23

<210> SEQ ID NO 93
<211> LENGTH: 24
<212> TYPE: DNA
<213> ORGANISM: Artificial Sequence
<220> FEATURE:
<223> OTHER INFORMATION: Constant region specific reverse primer IgG2b

<400> SEQUENCE: 93
ggaggtgtgc acactgctgg acag 24

<210> SEQ ID NO 94
<211> LENGTH: 7
<212> TYPE: PRT
<213> ORGANISM: Artificial Sequence
<220> FEATURE:
<223> OTHER INFORMATION: IF2 VHCDR1 (Chothia)

<400> SEQUENCE: 94

Gly Tyr Thr Phe Thr Asp Tyr
1 5

<210> SEQ ID NO 95
<211> LENGTH: 6
<212> TYPE: PRT
<213> ORGANISM: Artificial Sequence
<220> FEATURE:
<223> OTHER INFORMATION: IF2 VHCDR2 (Chothia)

<400> SEQUENCE: 95

His Pro Gly Ser Thr Asn
1 5

<210> SEQ ID NO 96
<211> LENGTH: 13
<212> TYPE: PRT
<213> ORGANISM: Artificial Sequence
<220> FEATURE:
<223> OTHER INFORMATION: IF2 VHCDR3 (Chothia)

<400> SEQUENCE: 96

Ser Leu Gly Asp Gly Tyr Tyr Val Tyr Ala Met Asp Tyr
1 5 10

<210> SEQ ID NO 97
<211> LENGTH: 11
<212> TYPE: PRT
<213> ORGANISM: Artificial Sequence
<220> FEATURE:
<223> OTHER INFORMATION: IF2 VLCDR1 (Chothia)

<400> SEQUENCE: 97

Lys Ala Ser Gln Asn Val Val Thr Asn Val Val
1 5 10

<210> SEQ ID NO 98
<211> LENGTH: 7
<212> TYPE: PRT
<213> ORGANISM: Artificial Sequence
<220> FEATURE:
<223> OTHER INFORMATION: IF2 VLCDR2 (Chothia)

<400> SEQUENCE: 98

Ser Ala Ser Tyr Arg Tyr Ser
1 5

<210> SEQ ID NO 99
<211> LENGTH: 9
<212> TYPE: PRT
<213> ORGANISM: Artificial Sequence
<220> FEATURE:
<223> OTHER INFORMATION: IF2 VLCDR3 (Chothia)

<400> SEQUENCE: 99

Gln Gln Tyr His Ser Tyr Pro Phe Thr
1 5

<210> SEQ ID NO 100
<211> LENGTH: 10
<212> TYPE: PRT
<213> ORGANISM: Artificial Sequence
<220> FEATURE:
<223> OTHER INFORMATION: IF2 VHCDR1 (ABM)

<400> SEQUENCE: 100

Gly Tyr Thr Phe Thr Asp Tyr Tyr Leu Asn
1 5 10

<210> SEQ ID NO 101
<211> LENGTH: 10
<212> TYPE: PRT
<213> ORGANISM: Artificial Sequence
<220> FEATURE:
<223> OTHER INFORMATION: IF2 VHCDR2 (ABM)

<400> SEQUENCE: 101

Gln Ile His Pro Gly Ser Thr Asn Thr Tyr
1 5 10

<210> SEQ ID NO 102
<211> LENGTH: 13
<212> TYPE: PRT
<213> ORGANISM: Artificial Sequence
<220> FEATURE:
<223> OTHER INFORMATION: IF2 VLCDR3 (ABM)

<400> SEQUENCE: 102

Ser Leu Gly Asp Gly Tyr Tyr Val Tyr Ala Met Asp Tyr
1 5 10

<210> SEQ ID NO 103
<211> LENGTH: 11
<212> TYPE: PRT
<213> ORGANISM: Artificial Sequence
<220> FEATURE:
<223> OTHER INFORMATION: IF2 VLCDR1 (ABM)

<400> SEQUENCE: 103

Lys Ala Ser Gln Asn Val Val Thr Asn Val Val
1 5 10

<210> SEQ ID NO 104
<211> LENGTH: 7
<212> TYPE: PRT
<213> ORGANISM: Artificial Sequence
<220> FEATURE:
<223> OTHER INFORMATION: IF2 VLCDR2 (ABM)

<400> SEQUENCE: 104

Ser Ala Ser Tyr Arg Tyr Ser
1 5

<210> SEQ ID NO 105
<211> LENGTH: 9
<212> TYPE: PRT
<213> ORGANISM: Artificial Sequence
<220> FEATURE:
<223> OTHER INFORMATION: IF2 VLCDR3 (ABM)

<400> SEQUENCE: 105

Gln Gln Tyr His Ser Tyr Pro Phe Thr
1 5

<210> SEQ ID NO 106
<211> LENGTH: 5
<212> TYPE: PRT
<213> ORGANISM: Artificial Sequence
<220> FEATURE:
<223> OTHER INFORMATION: IF2 VHCDR1 (Kabat)

<400> SEQUENCE: 106

Asp Tyr Tyr Leu Asn
1 5

<210> SEQ ID NO 107
<211> LENGTH: 17
<212> TYPE: PRT
<213> ORGANISM: Artificial Sequence
<220> FEATURE:
<223> OTHER INFORMATION: IF2 VHCDR2 (Kabat)

<400> SEQUENCE: 107

Gln Ile His Pro Gly Ser Thr Asn Thr Tyr Tyr Asn Glu Lys Phe Lys
1 5 10 15

Gly

<210> SEQ ID NO 108
<211> LENGTH: 13
<212> TYPE: PRT
<213> ORGANISM: Artificial Sequence
<220> FEATURE:
<223> OTHER INFORMATION: IF2 VHCDR3 (Kabat)

<400> SEQUENCE: 108

Ser Leu Gly Asp Gly Tyr Tyr Val Tyr Ala Met Asp Tyr
1 5 10

<210> SEQ ID NO 109
<211> LENGTH: 11
<212> TYPE: PRT
<213> ORGANISM: Artificial Sequence
<220> FEATURE:
<223> OTHER INFORMATION: IF2 VLCDR1 (Kabat)

<400> SEQUENCE: 109

Lys Ala Ser Gln Asn Val Val Thr Asn Val Val
1 5 10

<210> SEQ ID NO 110
<211> LENGTH: 7
<212> TYPE: PRT
<213> ORGANISM: Artificial Sequence
<220> FEATURE:
<223> OTHER INFORMATION: IF2 VLCDR2 (Kabat)

<400> SEQUENCE: 110

Ser Ala Ser Tyr Arg Tyr Ser
1 5

<210> SEQ ID NO 111
<211> LENGTH: 9
<212> TYPE: PRT
<213> ORGANISM: Artificial Sequence
<220> FEATURE:
<223> OTHER INFORMATION: IF2 VLCDR3 (Kabat)

<400> SEQUENCE: 111

Gln Gln Tyr His Ser Tyr Pro Phe Thr
1 5

<210> SEQ ID NO 112
<211> LENGTH: 8
<212> TYPE: PRT
<213> ORGANISM: Artificial Sequence
<220> FEATURE:
<223> OTHER INFORMATION: IF4 VHCDR1 (Chothia)

<400> SEQUENCE: 112

Asp Ser Glu Val Phe Pro Ile Val
1 5

<210> SEQ ID NO 113
<211> LENGTH: 6
<212> TYPE: PRT
<213> ORGANISM: Artificial Sequence
<220> FEATURE:
<223> OTHER INFORMATION: IF4 VHCDR2 (Chothia)

<400> SEQUENCE: 113

Leu Pro Ser Phe Gly Arg
1 5

<210> SEQ ID NO 114
<211> LENGTH: 9
<212> TYPE: PRT
<213> ORGANISM: Artificial Sequence
<220> FEATURE:
<223> OTHER INFORMATION: IF4 VHCDR3 (Chothia)

<400> SEQUENCE: 114

Gly Asp His Gly Asn Trp Leu Ala Tyr
1 5

<210> SEQ ID NO 115
<211> LENGTH: 11
<212> TYPE: PRT
<213> ORGANISM: Artificial Sequence
<220> FEATURE:
<223> OTHER INFORMATION: IF4 VLCDR1 (Chothia)

<400> SEQUENCE: 115

Lys Ala Ser Gln Asp Val Ser Thr Ala Val Ala
1 5 10

<210> SEQ ID NO 116
<211> LENGTH: 7
<212> TYPE: PRT
<213> ORGANISM: Artificial Sequence
<220> FEATURE:
<223> OTHER INFORMATION: IF4 VLCDR2 (Chothia)

<400> SEQUENCE: 116

Trp Ala Ser Thr Arg His Thr
1 5

<210> SEQ ID NO 117
<211> LENGTH: 9
<212> TYPE: PRT
<213> ORGANISM: Artificial Sequence
<220> FEATURE:
<223> OTHER INFORMATION: IF4 VLCDR3 (Chothia)

<400> SEQUENCE: 117

Gln Gln His Tyr Ser Ala Pro Trp Thr
1 5

<210> SEQ ID NO 118
<211> LENGTH: 11
<212> TYPE: PRT
<213> ORGANISM: Artificial Sequence
<220> FEATURE:
<223> OTHER INFORMATION: IF4 VHCDR1 (ABM)

<400> SEQUENCE: 118

Asp Ser Glu Val Phe Pro Ile Val Tyr Met Arg
1 5 10

<210> SEQ ID NO 119
<211> LENGTH: 9
<212> TYPE: PRT
<213> ORGANISM: Artificial Sequence
<220> FEATURE:
<223> OTHER INFORMATION: IF4 VHCDR2 (ABM)

<400> SEQUENCE: 119

Asp Ile Leu Pro Ser Phe Gly Arg Thr
1 5

<210> SEQ ID NO 120
<211> LENGTH: 9
<212> TYPE: PRT
<213> ORGANISM: Artificial Sequence
<220> FEATURE:
<223> OTHER INFORMATION: IF4 VHCDR3 (ABM)

<400> SEQUENCE: 120

Gly Asp His Gly Asn Trp Leu Ala Tyr
1 5

<210> SEQ ID NO 121
<211> LENGTH: 11
<212> TYPE: PRT
<213> ORGANISM: Artificial Sequence
<220> FEATURE:
<223> OTHER INFORMATION: IF4 VLCDR1 (ABM)

<400> SEQUENCE: 121

Lys Ala Ser Gln Asp Val Ser Thr Ala Val Ala
1 5 10

<210> SEQ ID NO 122
<211> LENGTH: 7
<212> TYPE: PRT
<213> ORGANISM: Artificial Sequence
<220> FEATURE:
<223> OTHER INFORMATION: IF4 VLCDR2 (ABM)

<400> SEQUENCE: 122

Trp Ala Ser Thr Arg His Thr
1 5

<210> SEQ ID NO 123
<211> LENGTH: 9
<212> TYPE: PRT
<213> ORGANISM: Artificial Sequence
<220> FEATURE:
<223> OTHER INFORMATION: IF4 VLCDR3 (ABM)

<400> SEQUENCE: 123

Gln Gln His Tyr Ser Ala Pro Trp Thr
1 5

<210> SEQ ID NO 124
<211> LENGTH: 6
<212> TYPE: PRT
<213> ORGANISM: Artificial Sequence
<220> FEATURE:
<223> OTHER INFORMATION: IF4 VHCDR1 (Kabat)

<400> SEQUENCE: 124

Pro Ile Val Tyr Met Arg
1 5

<210> SEQ ID NO 125
<211> LENGTH: 17
<212> TYPE: PRT
<213> ORGANISM: Artificial Sequence
<220> FEATURE:
<223> OTHER INFORMATION: IF4 VHCDR2 (Kabat)

<400> SEQUENCE: 125

Asp Ile Leu Pro Ser Phe Gly Arg Thr Ile Tyr Gly Glu Lys Phe Glu
1 5 10 15

Asp

<210> SEQ ID NO 126
<211> LENGTH: 9
<212> TYPE: PRT
<213> ORGANISM: Artificial Sequence
<220> FEATURE:
<223> OTHER INFORMATION: IF4 VHCDR3 (Kabat)

<400> SEQUENCE: 126

Gly Asp His Gly Asn Trp Leu Ala Tyr
1 5

<210> SEQ ID NO 127
<211> LENGTH: 11
<212> TYPE: PRT
<213> ORGANISM: Artificial Sequence
<220> FEATURE:
<223> OTHER INFORMATION: IF4 VLCDR1 (Kabat)

<400> SEQUENCE: 127

Lys Ala Ser Gln Asp Val Ser Thr Ala Val Ala
1 5 10

<210> SEQ ID NO 128
<211> LENGTH: 7
<212> TYPE: PRT
<213> ORGANISM: Artificial Sequence
<220> FEATURE:
<223> OTHER INFORMATION: IF4 VLCDR2 (Kabat)

<400> SEQUENCE: 128

Trp Ala Ser Thr Arg His Thr
1 5

<210> SEQ ID NO 129
<211> LENGTH: 9
<212> TYPE: PRT
<213> ORGANISM: Artificial Sequence
<220> FEATURE:
<223> OTHER INFORMATION: IF4 VLCDR3 (Kabat)

<400> SEQUENCE: 129

Gln Gln His Tyr Ser Ala Pro Trp Thr
1 5

<210> SEQ ID NO 130
<211> LENGTH: 7
<212> TYPE: PRT
<213> ORGANISM: Artificial Sequence
<220> FEATURE:
<223> OTHER INFORMATION: 4B2 VHCDR1 (Chothia)

<400> SEQUENCE: 130

Gly Phe Thr Phe Thr Asp Tyr
1 5

<210> SEQ ID NO 131
<211> LENGTH: 6
<212> TYPE: PRT
<213> ORGANISM: Artificial Sequence
<220> FEATURE:
<223> OTHER INFORMATION: 4B2 VHCDR2 (Chothia)

<400> SEQUENCE: 131

Asn Thr Glu Thr Glu Glu
1 5

<210> SEQ ID NO 132
<211> LENGTH: 14
<212> TYPE: PRT
<213> ORGANISM: Artificial Sequence
<220> FEATURE:
<223> OTHER INFORMATION: 4B2 VHCDR3 (Chothia)

<400> SEQUENCE: 132

Ser Gly Tyr Tyr Tyr Gly Ser Thr Tyr Ala Trp Phe Gly Tyr
1 5 10

<210> SEQ ID NO 133
<211> LENGTH: 16
<212> TYPE: PRT
<213> ORGANISM: Artificial Sequence
<220> FEATURE:
<223> OTHER INFORMATION: 4B2 VLCDR1 (Chothia)

<400> SEQUENCE: 133

Arg Ser Ser Gln Ser Leu Ile His Thr Asn Gly Asp Thr Phe Leu His
1 5 10 15

<210> SEQ ID NO 134
<211> LENGTH: 7
<212> TYPE: PRT
<213> ORGANISM: Artificial Sequence
<220> FEATURE:
<223> OTHER INFORMATION: 4B2 VLCDR2 (Chothia)

<400> SEQUENCE: 134

Lys Val Ser Asn Arg Phe Ser
1 5

<210> SEQ ID NO 135
<211> LENGTH: 9
<212> TYPE: PRT
<213> ORGANISM: Artificial Sequence
<220> FEATURE:
<223> OTHER INFORMATION: 4B2 VLCDR3 (Chothia)

<400> SEQUENCE: 135

Ser Gln Ser Ala Leu Phe Pro Tyr Thr
1 5

<210> SEQ ID NO 136
<211> LENGTH: 10
<212> TYPE: PRT
<213> ORGANISM: Artificial Sequence
<220> FEATURE:
<223> OTHER INFORMATION: 4B2 VHCDR1 (ABM)

<400> SEQUENCE: 136

Gly Phe Thr Phe Thr Asp Tyr Pro Met His
1 5 10

<210> SEQ ID NO 137
<211> LENGTH: 10
<212> TYPE: PRT
<213> ORGANISM: Artificial Sequence
<220> FEATURE:
<223> OTHER INFORMATION: 4B2 VHCDR2 (ABM)

<400> SEQUENCE: 137

Trp Ile Asn Thr Glu Thr Glu Glu Pro Thr
1 5 10

<210> SEQ ID NO 138
<211> LENGTH: 14
<212> TYPE: PRT
<213> ORGANISM: Artificial Sequence
<220> FEATURE:
<223> OTHER INFORMATION: 4B2 VHCDR3 (ABM)

<400> SEQUENCE: 138

Ser Gly Tyr Tyr Tyr Gly Ser Thr Tyr Ala Trp Phe Gly Tyr
1 5 10

<210> SEQ ID NO 139
<211> LENGTH: 16
<212> TYPE: PRT
<213> ORGANISM: Artificial Sequence
<220> FEATURE:
<223> OTHER INFORMATION: 4B2 VLCDR1 (ABM)

<400> SEQUENCE: 139

Arg Ser Ser Gln Ser Leu Ile His Thr Asn Gly Asp Thr Phe Leu His
1 5 10 15

<210> SEQ ID NO 140
<211> LENGTH: 7
<212> TYPE: PRT
<213> ORGANISM: Artificial Sequence
<220> FEATURE:
<223> OTHER INFORMATION: 4B2 VLCDR2 (Kabat)

<400> SEQUENCE: 140

Lys Val Ser Asn Arg Phe Ser
1 5

<210> SEQ ID NO 141
<211> LENGTH: 9
<212> TYPE: PRT
<213> ORGANISM: Artificial Sequence
<220> FEATURE:
<223> OTHER INFORMATION: 4B2 VLCDR3 (ABM)

<400> SEQUENCE: 141

Ser Gln Ser Ala Leu Phe Pro Tyr Thr
1 5

<210> SEQ ID NO 142
<211> LENGTH: 5
<212> TYPE: PRT
<213> ORGANISM: Artificial Sequence
<220> FEATURE:
<223> OTHER INFORMATION: 4B2 VHCDR1 (Kabat)

<400> SEQUENCE: 142

Asp Tyr Pro Met His 1 5

<210> SEQ ID NO 143
<211> LENGTH: 17
<212> TYPE: PRT
<213> ORGANISM: Artificial Sequence
<220> FEATURE:
<223> OTHER INFORMATION: 4B2 VHCDR2 (Kabat)

<400> SEQUENCE: 143

Trp Ile Asn Thr Glu Thr Glu Glu Pro Thr Tyr Ser Asp Asp Phe Lys
1 5 10 15

Gly

<210> SEQ ID NO 144
<211> LENGTH: 14
<212> TYPE: PRT
<213> ORGANISM: Artificial Sequence
<220> FEATURE:
<223> OTHER INFORMATION: 4B2 VHCDR3 (Kabat)

<400> SEQUENCE: 144

Ser Gly Tyr Tyr Tyr Gly Ser Thr Tyr Ala Trp Phe Gly Tyr
1 5 10

<210> SEQ ID NO 145
<211> LENGTH: 16
<212> TYPE: PRT
<213> ORGANISM: Artificial Sequence
<220> FEATURE:
<223> OTHER INFORMATION: 4B2 VLCDR1 (Kabat)

<400> SEQUENCE: 145

Arg Ser Ser Gln Ser Leu Ile His Thr Asn Gly Asp Thr Phe Leu His
1 5 10 15

<210> SEQ ID NO 146
<211> LENGTH: 7
<212> TYPE: PRT
<213> ORGANISM: Artificial Sequence
<220> FEATURE:
<223> OTHER INFORMATION: 4B2 VLCDR2 (Kabat)

<400> SEQUENCE: 146

Lys Val Ser Asn Arg Phe Ser
1 5

<210> SEQ ID NO 147
<211> LENGTH: 9
<212> TYPE: PRT
<213> ORGANISM: Artificial Sequence
<220> FEATURE:
<223> OTHER INFORMATION: 4B2 VLCDR3 (Kabat)

<400> SEQUENCE: 147

Ser Gln Ser Ala Leu Phe Pro Tyr Thr
1 5

<210> SEQ ID NO 148
<211> LENGTH: 7
<212> TYPE: PRT
<213> ORGANISM: Artificial Sequence
<220> FEATURE:
<223> OTHER INFORMATION: 4F11 VHCDR1 (Chothia)

<400> SEQUENCE: 148

Gly Phe Thr Phe Ser Ala Tyr
1 5

<210> SEQ ID NO 149
<211> LENGTH: 6
<212> TYPE: PRT
<213> ORGANISM: Artificial Sequence
<220> FEATURE:
<223> OTHER INFORMATION: 4F11 VHCDR2 (Chothia)

<400> SEQUENCE: 149

Asn Thr Gly Gly Ser Phe
1 5

<210> SEQ ID NO 150
<211> LENGTH: 12
<212> TYPE: PRT
<213> ORGANISM: Artificial Sequence
<220> FEATURE:
<223> OTHER INFORMATION: 4F11 VHCDR3 (Chothia)

<400> SEQUENCE: 150

Val Ser Asp Tyr Gly Asn Ser Ala Tyr Phe Pro Tyr
1 5 10

<210> SEQ ID NO 151
<211> LENGTH: 10
<212> TYPE: PRT
<213> ORGANISM: Artificial Sequence
<220> FEATURE:
<223> OTHER INFORMATION: 4F11 VLCDR1 (Chothia)

<400> SEQUENCE: 151

Ser Ala Ser Ser Asn Val Asn Tyr Met Ser
1 5 10

<210> SEQ ID NO 152
<211> LENGTH: 7
<212> TYPE: PRT
<213> ORGANISM: Artificial Sequence
<220> FEATURE:
<223> OTHER INFORMATION: 4F11 VLCDR2 (Chothia)

<400> SEQUENCE: 152

Leu Thr Ser Lys Leu Ala Ser
1 5

<210> SEQ ID NO 153
<211> LENGTH: 9
<212> TYPE: PRT
<213> ORGANISM: Artificial Sequence
<220> FEATURE:
<223> OTHER INFORMATION: 4F11 VLCDR3 (Chothia)

<400> SEQUENCE: 153

Gln Gln Trp Ser Ser Asp Pro Gln Thr
1 5

<210> SEQ ID NO 154
<211> LENGTH: 10
<212> TYPE: PRT
<213> ORGANISM: Artificial Sequence
<220> FEATURE:
<223> OTHER INFORMATION: 4F11 VHCDR1 (ABM)

<400> SEQUENCE: 154

Gly Phe Thr Phe Ser Ala Tyr Ser Met Ser 1 5 10

<210> SEQ ID NO 155
<211> LENGTH: 10
<212> TYPE: PRT
<213> ORGANISM: Artificial Sequence
<220> FEATURE:
<223> OTHER INFORMATION: 4F11 VHCDR2 (ABM)

<400> SEQUENCE: 155

Thr Ile Asn Thr Gly Gly Ser Phe Thr Tyr
1 5 10

<210> SEQ ID NO 156
<211> LENGTH: 12
<212> TYPE: PRT
<213> ORGANISM: Artificial Sequence
<220> FEATURE:
<223> OTHER INFORMATION: 4F11 VHCDR3 (ABM)

<400> SEQUENCE: 156

Val Ser Asp Tyr Gly Asn Ser Ala Tyr Phe Pro Tyr
1 5 10

<210> SEQ ID NO 157
<211> LENGTH: 10
<212> TYPE: PRT
<213> ORGANISM: Artificial Sequence
<220> FEATURE:
<223> OTHER INFORMATION: 4F11 VLCDR2 (ABM)

<400> SEQUENCE: 157

Ser Ala Ser Ser Asn Val Asn Tyr Met Ser
1 5 10

<210> SEQ ID NO 158
<211> LENGTH: 7
<212> TYPE: PRT
<213> ORGANISM: Artificial Sequence
<220> FEATURE:
<223> OTHER INFORMATION: 4F11 VLCDR2 (ABM)

<400> SEQUENCE: 158

Leu Thr Ser Lys Leu Ala Ser
1 5

<210> SEQ ID NO 159
<211> LENGTH: 9
<212> TYPE: PRT
<213> ORGANISM: Artificial Sequence
<220> FEATURE:
<223> OTHER INFORMATION: 4F11 VLCDR3 (ABM)

<400> SEQUENCE: 159

Gln Gln Trp Ser Ser Asp Pro Gln Thr
1 5

<210> SEQ ID NO 160
<211> LENGTH: 6
<212> TYPE: PRT
<213> ORGANISM: Artificial Sequence
<220> FEATURE:
<223> OTHER INFORMATION: 4F11 VHCDR1 (Kabat)

<400> SEQUENCE: 160

Ser Ala Tyr Ser Met Ser
1 5

<210> SEQ ID NO 161
<211> LENGTH: 17
<212> TYPE: PRT
<213> ORGANISM: Artificial Sequence
<220> FEATURE:
<223> OTHER INFORMATION: 4F11 VHCDR2 (Kabat)

<400> SEQUENCE: 161

Thr Ile Asn Thr Gly Gly Ser Phe Thr Tyr Tyr Pro Asp Ser Val Lys
1 5 10 15

Gly

<210> SEQ ID NO 162
<211> LENGTH: 12
<212> TYPE: PRT
<213> ORGANISM: Artificial Sequence
<220> FEATURE:
<223> OTHER INFORMATION: 4F11 VHCDR3 (Kabat)

<400> SEQUENCE: 162

Val Ser Asp Tyr Gly Asn Ser Ala Tyr Phe Pro Tyr
1 5 10

<210> SEQ ID NO 163
<211> LENGTH: 10
<212> TYPE: PRT
<213> ORGANISM: Artificial Sequence
<220> FEATURE:
<223> OTHER INFORMATION: 4F11 VLCDR1 (Kabat)

<400> SEQUENCE: 163

Ser Ala Ser Ser Asn Val Asn Tyr Met Ser
1 5 10

<210> SEQ ID NO 164
<211> LENGTH: 7
<212> TYPE: PRT
<213> ORGANISM: Artificial Sequence
<220> FEATURE:
<223> OTHER INFORMATION: 4F11 VLCDR2 (Kabat)

<400> SEQUENCE: 164

Leu Thr Ser Lys Leu Ala Ser
1 5

<210> SEQ ID NO 165
<211> LENGTH: 9
<212> TYPE: PRT
<213> ORGANISM: Artificial Sequence
<220> FEATURE:
<223> OTHER INFORMATION: 4F11 VLCDR3 (Kabat)

<400> SEQUENCE: 165

Gln Gln Trp Ser Ser Asp Pro Gln Thr
1 5

<210> SEQ ID NO 166
<211> LENGTH: 98
<212> TYPE: PRT
<213> ORGANISM: Artificial Sequence
<220> FEATURE:
<223> OTHER INFORMATION: IGHV1-46

<400> SEQUENCE: 166

Gln Val Gln Leu Val Gln Ser Gly Ala Glu Val Lys Lys Pro Gly Ala

```
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg


<210> SEQ ID NO 167
<211> LENGTH: 98
<212> TYPE: PRT
<213> ORGANISM: Artificial Sequence
<220> FEATURE:
<223> OTHER INFORMATION: IGHV1-2

<400> SEQUENCE: 167

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg


<210> SEQ ID NO 168
<211> LENGTH: 122
<212> TYPE: PRT
<213> ORGANISM: Artificial Sequence
<220> FEATURE:
<223> OTHER INFORMATION: 1F2 VH1

<400> SEQUENCE: 168

Gln Val Gln Leu Gln Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu Asn Trp Val Arg Gln Ala Pro Gly Gln Gly Leu Glu Trp Met
        35                  40                  45

Gly Gln Ile His Pro Gly Ser Thr Asn Thr Tyr Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Leu Gly Asp Gly Tyr Tyr Val Tyr Ala Met Asp Tyr Trp
            100                 105                 110
```

Gly Gln Gly Thr Thr Val Thr Val Ser Ser
115 120

<210> SEQ ID NO 169
<211> LENGTH: 122
<212> TYPE: PRT
<213> ORGANISM: Artificial Sequence
<220> FEATURE:
<223> OTHER INFORMATION: 1F2 VH2

<400> SEQUENCE: 169

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Tyr Leu Asn Trp Val Arg Gln Ala Pro Gly Gln Gly Leu Glu Trp Met
35 40 45

Gly Gln Ile His Pro Gly Ser Thr Asn Thr Tyr Tyr Asn Glu Lys Phe
50 55 60

Lys Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Phe Cys
85 90 95

Ala Arg Ser Leu Gly Asp Gly Tyr Tyr Val Tyr Ala Met Asp Tyr Trp
100 105 110

Gly Gln Gly Thr Thr Val Thr Val Ser Ser
115 120

<210> SEQ ID NO 170
<211> LENGTH: 122
<212> TYPE: PRT
<213> ORGANISM: Artificial Sequence
<220> FEATURE:
<223> OTHER INFORMATION: 1F2 VH3

<400> SEQUENCE: 170

Glu Val Gln Leu Val Glu Ser Gly Pro Glu Val Lys Lys Pro Gly Ala
1 5 10 15

Thr Val Lys Ile Ser Cys Lys Val Ser Gly Tyr Thr Phe Thr Asp Tyr
20 25 30

Tyr Leu Asn Trp Val Gln Gln Ala Pro Gly Arg Gly Leu Glu Trp Met
35 40 45

Gly Gln Ile His Pro Gly Ser Thr Asn Thr Tyr Tyr Asn Glu Lys Phe
50 55 60

Lys Gly Arg Val Thr Met Thr Ala Asp Thr Ser Thr Gly Thr Ala Tyr
65 70 75 80

Met Gln Leu Ser Ser Leu Thr Ser Glu Asp Thr Ala Val Tyr Phe Cys
85 90 95

Ala Arg Ser Leu Gly Asp Gly Tyr Tyr Val Tyr Ala Met Asp Tyr Trp
100 105 110

Gly Gln Gly Thr Thr Val Thr Val Ala Ser
115 120

<210> SEQ ID NO 171
<211> LENGTH: 122
<212> TYPE: PRT
<213> ORGANISM: Artificial Sequence
<220> FEATURE:
<223> OTHER INFORMATION: 1F2 VH4

<400> SEQUENCE: 171

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Leu Asn Trp Val Arg Gln Ala Pro Gly Gln Gly Leu Glu Trp Met
        35                  40                  45

Gly Gln Ile His Pro Gly Ser Thr Asn Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Leu Gly Asp Gly Tyr Tyr Val Tyr Ala Met Asp Tyr Trp
            100                 105                 110

Gly Gln Gly Thr Thr Val Thr Val Ser Ser
        115                 120

<210> SEQ ID NO 172
<211> LENGTH: 122
<212> TYPE: PRT
<213> ORGANISM: Artificial Sequence
<220> FEATURE:
<223> OTHER INFORMATION: 1F2 VH5

<400> SEQUENCE: 172

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu Asn Trp Val Arg Gln Ala Pro Gly Gln Gly Leu Glu Trp Met
        35                  40                  45

Gly Gln Ile His Pro Gly Ser Thr Asn Thr Tyr Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Leu Gly Asp Gly Tyr Tyr Val Tyr Ala Met Asp Tyr Trp
            100                 105                 110

Gly Gln Gly Thr Leu Val Thr Val Ser Ser
        115                 120

<210> SEQ ID NO 173
<211> LENGTH: 122
<212> TYPE: PRT
<213> ORGANISM: Artificial Sequence
<220> FEATURE:
<223> OTHER INFORMATION: 1F2 VH6

<400> SEQUENCE: 173

Gln Val His Leu Gln Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu Asn Trp Val Arg Gln Arg Pro Arg Gln Gly Leu Glu Trp Met
        35                  40                  45

```
Gly Gln Ile His Pro Gly Ser Thr Asn Thr Tyr Tyr Asn Glu Lys Phe
    50                  55                  60

Lys Gly Arg Val Thr Met Thr Arg Asp Thr Ser Thr Ser Thr Val Tyr
65                  70                  75                  80

Met Gln Leu Ser Ser Leu Thr Ser Glu Asp Thr Ala Val Tyr Phe Cys
                85                  90                  95

Ala Arg Ser Leu Gly Asp Gly Tyr Tyr Val Tyr Ala Met Asp Tyr Trp
            100                 105                 110

Gly Gln Gly Thr Ala Val Thr Val Ser Ser
        115                 120


<210> SEQ ID NO 174
<211> LENGTH: 122
<212> TYPE: PRT
<213> ORGANISM: Artificial Sequence
<220> FEATURE:
<223> OTHER INFORMATION: 1F2 VH7

<400> SEQUENCE: 174

Gln Val Gln Leu Gln Gln Ser Gly Pro Glu Val Ala Lys Pro Gly Ala
1               5                   10                  15

Ser Val Lys Leu Ser Cys Lys Ala Ser Gly Tyr Thr Phe Thr Asp Tyr
            20                  25                  30

Tyr Leu Asn Trp Val Arg Gln Ala Pro Gly Gln Gly Leu Glu Trp Leu
        35                  40                  45

Gly Gln Ile His Pro Gly Ser Thr Asn Thr Tyr Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Ser Leu Gly Asp Gly Tyr Tyr Val Tyr Ala Met Asp Tyr Trp
            100                 105                 110

Gly Gln Gly Thr Ala Val Thr Val Ser Ser
        115                 120


<210> SEQ ID NO 175
<211> LENGTH: 122
<212> TYPE: PRT
<213> ORGANISM: Artificial Sequence
<220> FEATURE:
<223> OTHER INFORMATION: 1F2 VH8

<400> SEQUENCE: 175

Gln Val His Leu Gln Gln Ser Gly Pro Glu Val Ala Lys Pro Gly Ala
1               5                   10                  15

Ser Val Lys Val Ser Cys Lys Ala Ser Gly Tyr Thr Phe Thr Asp Tyr
            20                  25                  30

Tyr Leu Asn Trp Val Arg Gln Ala Pro Gly Gln Gly Leu Glu Trp Leu
        35                  40                  45

Gly Gln Ile His Pro Gly Ser Thr Asn Thr Tyr Tyr Asn Glu Lys Phe
    50                  55                  60

Lys Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Arg Ser Leu Gly Asp Gly Tyr Tyr Val Tyr Ala Met Asp Tyr Trp
```

```
            100                 105                 110

Gly Gln Gly Thr Ala Val Thr Val Ser Ser
        115                 120


<210> SEQ ID NO 176
<211> LENGTH: 95
<212> TYPE: PRT
<213> ORGANISM: Artificial Sequence
<220> FEATURE:
<223> OTHER INFORMATION: IGKV1-8

<400> SEQUENCE: 176

Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Tyr Pro
                85                  90                  95


<210> SEQ ID NO 177
<211> LENGTH: 107
<212> TYPE: PRT
<213> ORGANISM: Artificial Sequence
<220> FEATURE:
<223> OTHER INFORMATION: 1F2 VL1

<400> SEQUENCE: 177

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Val Thr Asn
            20                  25                  30

Val Val Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Ser Cys Gln Gln Tyr His Ser Tyr Pro Phe
                85                  90                  95

Thr Phe Gly Gln Gly Thr Arg Leu Glu Ile Lys
            100                 105


<210> SEQ ID NO 178
<211> LENGTH: 107
<212> TYPE: PRT
<213> ORGANISM: Artificial Sequence
<220> FEATURE:
<223> OTHER INFORMATION: 1F2 VL2

<400> SEQUENCE: 178

Asp Val Val Met Thr Gln Ser Pro Asp Ser Leu Ala Val Ser Leu Gly
1               5                   10                  15

Glu Arg Val Thr Ile Asn Cys Lys Ala Ser Gln Asn Val Val Thr Asn
            20                  25                  30
```

```
Val Val Trp Tyr Gln Gln Lys Pro Gly Gln Ser Pro Lys Leu Leu Ile
        35                  40                  45

Tyr Ser Ala Ser Tyr Arg Tyr Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr His Ser Tyr Pro Phe
                85                  90                  95

Thr Phe Gly Gln Gly Thr Lys Leu Glu Ile Lys
            100                 105


<210> SEQ ID NO 179
<211> LENGTH: 107
<212> TYPE: PRT
<213> ORGANISM: Artificial Sequence
<220> FEATURE:
<223> OTHER INFORMATION: 1F2 VL3

<400> SEQUENCE: 179

Asp Val Val Met Thr Gln Ser Pro Ser Ser Leu Ser Ala Ser Val Gly
1               5                   10                  15

Asp Arg Val Ser Ile Thr Cys Lys Ala Ser Gln Asn Val Val Thr Asn
            20                  25                  30

Val Val Trp Tyr Gln Gln Lys Pro Gly Lys Ala Pro Lys Leu Leu Val
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Cys Cys Gln Gln Tyr His Ser Tyr Pro Phe
                85                  90                  95

Thr Phe Gly Gln Gly Thr Lys Leu Asp Ile Lys
            100                 105


<210> SEQ ID NO 180
<211> LENGTH: 107
<212> TYPE: PRT
<213> ORGANISM: Artificial Sequence
<220> FEATURE:
<223> OTHER INFORMATION: 1F2 VL4

<400> SEQUENCE: 180

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Val Thr Asn
            20                  25                  30

Val Val Trp Tyr Gln Gln Lys Pro Gly Gln Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Glu Phe Thr Phe Thr Ile Ser Ser Leu Gln Pro
65                  70                  75                  80

Glu Asp Leu Ala Thr Tyr Ser Cys Gln Gln Tyr His Ser Tyr Pro Phe
                85                  90                  95

Thr Phe Gly Gln Gly Thr Lys Leu Glu Ile Lys
            100                 105
```

<210> SEQ ID NO 181
<211> LENGTH: 107
<212> TYPE: PRT
<213> ORGANISM: Artificial Sequence
<220> FEATURE:
<223> OTHER INFORMATION: 1F2 VL5

<400> SEQUENCE: 181

```
Ala Ile Arg Met Thr Gln Ser Pro Ser Ser Phe Ser Ala Ser Thr Gly
1               5                   10                  15

Asp Arg Val Thr Ile Thr Cys Lys Ala Ser Gln Asn Val Val Thr Asn
            20                  25                  30

Val Val Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr His Ser Tyr Pro Phe
                85                  90                  95

Thr Phe Gly Gln Gly Thr Lys Leu Glu Ile Lys
            100                 105
```

<210> SEQ ID NO 182
<211> LENGTH: 107
<212> TYPE: PRT
<213> ORGANISM: Artificial Sequence
<220> FEATURE:
<223> OTHER INFORMATION: 1F2 VL6

<400> SEQUENCE: 182

```
Asp Ile Gln Leu Thr Gln Ser Pro Lys Phe Leu Ser Ala Ser Val Gly
1               5                   10                  15

Asp Arg Val Thr Ile Thr Cys Lys Ala Ser Gln Asn Val Val Thr Asn
            20                  25                  30

Val Val Trp Tyr Gln Gln Lys Pro Gly Lys Ala Pro Lys Leu Leu Ile
        35                  40                  45

Tyr Ser Ala Ser Tyr Arg Tyr Ser Gly Val Pro Asp Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Glu Tyr Ser Cys Gln Gln Tyr His Ser Tyr Pro Phe
                85                  90                  95

Thr Phe Gly Ser Gly Thr Lys Leu Glu Val Lys
            100                 105
```

<210> SEQ ID NO 183
<211> LENGTH: 107
<212> TYPE: PRT
<213> ORGANISM: Artificial Sequence
<220> FEATURE:
<223> OTHER INFORMATION: 1F2 VL7

<400> SEQUENCE: 183

```
Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asn Val Val Thr Asn
            20                  25                  30

Val Val Trp Tyr Gln Gln Lys Pro Gly Lys Ala Pro Lys Pro Leu Ile
        35                  40                  45
```

Tyr Ser Ala Ser Tyr Arg Tyr Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Leu Ala Glu Tyr Tyr Cys Gln Gln Tyr His Ser Tyr Pro Phe
85 90 95

Thr Phe Gly Ser Gly Thr Lys Leu Glu Val Lys
100 105

<210> SEQ ID NO 184
<211> LENGTH: 107
<212> TYPE: PRT
<213> ORGANISM: Artificial Sequence
<220> FEATURE:
<223> OTHER INFORMATION: 1F2 VL8

<400> SEQUENCE: 184

Asp Ile Gln Met Thr Gln Ser Pro Ser Thr Leu Ser Ala Ser Val Gly
1 5 10 15

Asp Arg Val Thr Ile Thr Cys Lys Ala Ser Gln Asn Val Val Thr Asn
20 25 30

Val Val Trp Tyr Gln Gln Lys Pro Gly Gln Ala Pro Lys Leu Leu Ile
35 40 45

Tyr Ser Ala Ser Tyr Arg Tyr Ser Gly Val Pro Ser Arg Phe Ser Gly
50 55 60

Ser Gly Ser Gly Thr Glu Phe Thr Phe Thr Ile Ser Ser Leu Gln Ser
65 70 75 80

Glu Asp Leu Ala Glu Tyr Tyr Cys Gln Gln Tyr His Ser Tyr Pro Phe
85 90 95

Thr Phe Gly Ser Gly Thr Lys Leu Glu Val Lys
100 105

<210> SEQ ID NO 185
<211> LENGTH: 471
<212> TYPE: PRT
<213> ORGANISM: Artificial Sequence
<220> FEATURE:
<223> OTHER INFORMATION: 1F2 HC0

<400> SEQUENCE: 185

Met Gly Trp Thr Leu Val Phe Leu Phe Leu Leu Ser Val Thr Ala Gly
1 5 10 15

Val His Ser Gln Val His Leu Gln Gln Ser Gly Pro Glu Val Ala Arg
20 25 30

Pro Gly Ala Ser Val Lys Leu Ser Cys Lys Ala Ser Gly Tyr Thr Phe
35 40 45

Thr Asp Tyr Tyr Leu Asn Trp Val Lys Gln Arg Pro Arg Gln Gly Leu
50 55 60

Glu Trp Ile Gly Gln Ile His Pro Gly Ser Thr Asn Thr Tyr Tyr Asn
65 70 75 80

Glu Lys Phe Lys Gly Lys Ala Thr Leu Thr Ala Asp Lys Ser Ser Ser
85 90 95

Thr Ala Tyr Met Gln Leu Ser Ser Leu Thr Ser Glu Asp Ser Ala Val
100 105 110

Tyr Phe Cys Ala Arg Ser Leu Gly Asp Gly Tyr Tyr Val Tyr Ala Met
115 120 125

Asp Tyr Trp Gly Gln Gly Thr Ala Val Thr Val Ser Ser Ala Ser Thr

```
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470
```

<210> SEQ ID NO 186
<211> LENGTH: 471
<212> TYPE: PRT
<213> ORGANISM: Artificial Sequence
<220> FEATURE:
<223> OTHER INFORMATION: 1F2 HC1

<400> SEQUENCE: 186

```
Met Gly Trp Thr Leu Val Phe Leu Phe Leu Leu Ser Val Thr Ala Gly
1               5                   10                  15

Val His Ser Gln Val Gln Leu Gln Glu Ser Gly Ala Glu Val Lys Lys
```

```
            20                  25                  30

Pro Gly Ala Ser Val Lys Val Ser Cys Lys Ala Ser Gly Tyr Thr Phe
        35                  40                  45

Thr Asp Tyr Tyr Leu Asn Trp Val Arg Gln Ala Pro Gly Gln Gly Leu
    50                  55                  60

Glu Trp Met Gly Gln Ile His Pro Gly Ser Thr Asn Thr Tyr Tyr Asn
65                  70                  75                  80

Glu Lys Phe Lys Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Ser Leu Gly Asp Gly Tyr Tyr Val Tyr Ala Met
        115                 120                 125

Asp Tyr Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445
```

```
Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 187
<211> LENGTH: 471
<212> TYPE: PRT
<213> ORGANISM: Artificial Sequence
<220> FEATURE:
<223> OTHER INFORMATION: 1F2 HC2

<400> SEQUENCE: 187

Met Gly Trp Thr Leu Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Tyr Leu Asn Trp Val Arg Gln Ala Pro Gly Gln Gly Leu
    50                  55                  60

Glu Trp Met Gly Gln Ile His Pro Gly Ser Thr Asn Thr Tyr Tyr Asn
65                  70                  75                  80

Glu Lys Phe Lys Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Phe Cys Ala Arg Ser Leu Gly Asp Gly Tyr Tyr Val Tyr Ala Met
        115                 120                 125

Asp Tyr Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335
```

```
Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470
```

<210> SEQ ID NO 188
<211> LENGTH: 471
<212> TYPE: PRT
<213> ORGANISM: Artificial Sequence
<220> FEATURE:
<223> OTHER INFORMATION: 1F2 HC3

<400> SEQUENCE: 188

```
Met Gly Trp Thr Leu Val Phe Leu Phe Leu Leu Ser Val Thr Ala Gly
1               5                   10                  15

Val His Ser Glu Val Gln Leu Val Glu Ser Gly Pro Glu Val Lys Lys
            20                  25                  30

Pro Gly Ala Thr Val Lys Ile Ser Cys Lys Val Ser Gly Tyr Thr Phe
        35                  40                  45

Thr Asp Tyr Tyr Leu Asn Trp Val Gln Gln Ala Pro Gly Arg Gly Leu
    50                  55                  60

Glu Trp Met Gly Gln Ile His Pro Gly Ser Thr Asn Thr Tyr Tyr Asn
65                  70                  75                  80

Glu Lys Phe Lys Gly Arg Val Thr Met Thr Ala Asp Thr Ser Thr Gly
                85                  90                  95

Thr Ala Tyr Met Gln Leu Ser Ser Leu Thr Ser Glu Asp Thr Ala Val
            100                 105                 110

Tyr Phe Cys Ala Arg Ser Leu Gly Asp Gly Tyr Tyr Val Tyr Ala Met
        115                 120                 125

Asp Tyr Trp Gly Gln Gly Thr Thr Val Thr Val Ala Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220
```

Asn Val Asn His Lys Pro Ser Asn Thr Lys Val Asp Lys Lys Val Glu
225 230 235 240

Pro Lys Ser Cys Asp Lys Thr His Thr Cys Pro Pro Cys Pro Ala Pro
245 250 255

Glu Leu Leu Gly Gly Pro Ser Val Phe Leu Phe Pro Pro Lys Pro Lys
260 265 270

Asp Thr Leu Met Ile Ser Arg Thr Pro Glu Val Thr Cys Val Val Val
275 280 285

Asp Val Ser His Glu Asp Pro Glu Val Lys Phe Asn Trp Tyr Val Asp
290 295 300

Gly Val Glu Val His Asn Ala Lys Thr Lys Pro Arg Glu Glu Gln Tyr
305 310 315 320

Asn Ser Thr Tyr Arg Val Val Ser Val Leu Thr Val Leu His Gln Asp
325 330 335

Trp Leu Asn Gly Lys Glu Tyr Lys Cys Lys Val Ser Asn Lys Ala Leu
340 345 350

Pro Ala Pro Ile Glu Lys Thr Ile Ser Lys Ala Lys Gly Gln Pro Arg
355 360 365

Glu Pro Gln Val Tyr Thr Leu Pro Pro Ser Arg Asp Glu Leu Thr Lys
370 375 380

Asn Gln Val Ser Leu Thr Cys Leu Val Lys Gly Phe Tyr Pro Ser Asp
385 390 395 400

Ile Ala Val Glu Trp Glu Ser Asn Gly Gln Pro Glu Asn Asn Tyr Lys
405 410 415

Thr Thr Pro Pro Val Leu Asp Ser Asp Gly Ser Phe Phe Leu Tyr Ser
420 425 430

Lys Leu Thr Val Asp Lys Ser Arg Trp Gln Gln Gly Asn Val Phe Ser
435 440 445

Cys Ser Val Met His Glu Ala Leu His Asn His Tyr Thr Gln Lys Ser
450 455 460

Leu Ser Leu Ser Pro Gly Lys
465 470

<210> SEQ ID NO 189
<211> LENGTH: 471
<212> TYPE: PRT
<213> ORGANISM: Artificial Sequence
<220> FEATURE:
<223> OTHER INFORMATION: 1F2 HC4

<400> SEQUENCE: 189

Met Gly Trp Thr Leu Val Phe Leu Phe Leu Leu Ser Val Thr Ala Gly
1 5 10 15

Val His Ser Gln Val Gln Leu Val Gln Ser Gly Ala Glu Val Lys Lys
20 25 30

Pro Gly Ser Ser Val Lys Val Ser Cys Lys Ala Ser Gly Tyr Thr Phe
35 40 45

Thr Asp Tyr Tyr Leu Asn Trp Val Arg Gln Ala Pro Gly Gln Gly Leu
50 55 60

Glu Trp Met Gly Gln Ile His Pro Gly Ser Thr Asn Thr Tyr Tyr Asn
65 70 75 80

Glu Lys Phe Lys Gly Arg Val Thr Ile Thr Ala Asp Lys Ser Thr Ser
85 90 95

Thr Ala Tyr Met Glu Leu Ser Ser Leu Arg Ser Glu Asp Thr Ala Val
100 105 110

```
Tyr Tyr Cys Ala Arg Ser Leu Gly Asp Gly Tyr Tyr Val Tyr Ala Met
        115                 120                 125

Asp Tyr Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470
```

<210> SEQ ID NO 190
<211> LENGTH: 471
<212> TYPE: PRT
<213> ORGANISM: Artificial Sequence
<220> FEATURE:
<223> OTHER INFORMATION: 1F2 HC5

<400> SEQUENCE: 190

```
Met Gly Trp Thr Leu Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Tyr Leu Asn Trp Val Arg Gln Ala Pro Gly Gln Gly Leu
    50                  55                  60

Glu Trp Met Gly Gln Ile His Pro Gly Ser Thr Asn Thr Tyr Tyr Asn
65                  70                  75                  80

Glu Lys Phe Lys Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Ser Leu Gly Asp Gly Tyr Tyr Val Tyr Ala Met
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415
```

```
Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 191
<211> LENGTH: 471
<212> TYPE: PRT
<213> ORGANISM: Artificial Sequence
<220> FEATURE:
<223> OTHER INFORMATION: 1F2 HC6

<400> SEQUENCE: 191

Met Gly Trp Thr Leu Val Phe Leu Phe Leu Leu Ser Val Thr Ala Gly
1               5                   10                  15

Val His Ser Gln Val His Leu Gln Glu Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Tyr Leu Asn Trp Val Arg Gln Arg Pro Arg Gln Gly Leu
    50                  55                  60

Glu Trp Met Gly Gln Ile His Pro Gly Ser Thr Asn Thr Tyr Tyr Asn
65                  70                  75                  80

Glu Lys Phe Lys Gly Arg Val Thr Met Thr Arg Asp Thr Ser Thr Ser
                85                  90                  95

Thr Val Tyr Met Gln Leu Ser Ser Leu Thr Ser Glu Asp Thr Ala Val
            100                 105                 110

Tyr Phe Cys Ala Arg Ser Leu Gly Asp Gly Tyr Tyr Val Tyr Ala Met
        115                 120                 125

Asp Tyr Trp Gly Gln Gly Thr Ala Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300
```

```
Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 192
<211> LENGTH: 471
<212> TYPE: PRT
<213> ORGANISM: Artificial Sequence
<220> FEATURE:
<223> OTHER INFORMATION: 1F2 HC7

<400> SEQUENCE: 192

Met Gly Trp Thr Leu Val Phe Leu Phe Leu Leu Ser Val Thr Ala Gly
1               5                   10                  15

Val His Ser Gln Val Gln Leu Gln Gln Ser Gly Pro Glu Val Ala Lys
            20                  25                  30

Pro Gly Ala Ser Val Lys Leu Ser Cys Lys Ala Ser Gly Tyr Thr Phe
        35                  40                  45

Thr Asp Tyr Tyr Leu Asn Trp Val Arg Gln Ala Pro Gly Gln Gly Leu
    50                  55                  60

Glu Trp Leu Gly Gln Ile His Pro Gly Ser Thr Asn Thr Tyr Tyr Asn
65                  70                  75                  80

Glu Lys Phe Lys Gly Arg Val Thr Met Thr Arg Asp Thr Ser Thr Ser
                85                  90                  95

Thr Val Tyr Met Glu Leu Ser Ser Leu Thr Ser Glu Asp Thr Ala Val
            100                 105                 110

Tyr Tyr Cys Ala Arg Ser Leu Gly Asp Gly Tyr Tyr Val Tyr Ala Met
        115                 120                 125

Asp Tyr Trp Gly Gln Gly Thr Ala Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190
```

```
Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 193
<211> LENGTH: 471
<212> TYPE: PRT
<213> ORGANISM: Artificial Sequence
<220> FEATURE:
<223> OTHER INFORMATION: 1F2 HC8

<400> SEQUENCE: 193

Met Gly Trp Thr Leu Val Phe Leu Phe Leu Leu Ser Val Thr Ala Gly
1               5                   10                  15

Val His Ser Gln Val His Leu Gln Gln Ser Gly Pro Glu Val Ala Lys
            20                  25                  30

Pro Gly Ala Ser Val Lys Val Ser Cys Lys Ala Ser Gly Tyr Thr Phe
        35                  40                  45

Thr Asp Tyr Tyr Leu Asn Trp Val Arg Gln Ala Pro Gly Gln Gly Leu
    50                  55                  60

Glu Trp Leu Gly Gln Ile His Pro Gly Ser Thr Asn Thr Tyr Tyr Asn
65                  70                  75                  80
```

```
Glu Lys Phe Lys Gly Arg Val Thr Met Thr Ala Asp Lys Ser Thr Ser
                85                  90                  95

Thr Val Tyr Met Glu Leu Ser Ser Leu Arg Ser Glu Asp Thr Ala Val
            100                 105                 110

Tyr Phe Cys Ala Arg Ser Leu Gly Asp Gly Tyr Tyr Val Tyr Ala Met
        115                 120                 125

Asp Tyr Trp Gly Gln Gly Thr Ala Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470
```

<210> SEQ ID NO 194
<211> LENGTH: 234
<212> TYPE: PRT

<213> ORGANISM: Artificial Sequence
<220> FEATURE:
<223> OTHER INFORMATION: 1F2 LC0

<400> SEQUENCE: 194

Met Val Ser Ser Ala Gln Phe Leu Gly Leu Leu Leu Leu Cys Phe Gln
1 5 10 15

Gly Thr Arg Cys Asp Ile Val Met Thr Gln Ser Gln Lys Phe Met Ser
20 25 30

Thr Ser Val Gly Asp Arg Val Ser Val Thr Cys Lys Ala Ser Gln Asn
35 40 45

Val Val Thr Asn Val Val Trp Tyr Gln Gln Lys Pro Gly Gln Ser Pro
50 55 60

Lys Pro Leu Ile Tyr Ser Ala Ser Tyr Arg Tyr Ser Gly Val Pro Asp
65 70 75 80

Arg Phe Thr Gly Ser Gly Ser Gly Thr Asp Phe Thr Leu Thr Ile Ser
85 90 95

Asn Val Gln Ser Glu Asp Leu Ala Glu Tyr Cys Cys Gln Gln Tyr His
100 105 110

Ser Tyr Pro Phe Thr Phe Gly Ser Gly Thr Lys Leu Glu Val Lys Arg
115 120 125

Thr Val Ala Ala Pro Ser Val Phe Ile Phe Pro Pro Ser Asp Glu Gln
130 135 140

Leu Lys Ser Gly Thr Ala Ser Val Val Cys Leu Leu Asn Asn Phe Tyr
145 150 155 160

Pro Arg Glu Ala Lys Val Gln Trp Lys Val Asp Asn Ala Leu Gln Ser
165 170 175

Gly Asn Ser Gln Glu Ser Val Thr Glu Gln Asp Ser Lys Asp Ser Thr
180 185 190

Tyr Ser Leu Ser Ser Thr Leu Thr Leu Ser Lys Ala Asp Tyr Glu Lys
195 200 205

His Lys Val Tyr Ala Cys Glu Val Thr His Gln Gly Leu Ser Ser Pro
210 215 220

Val Thr Lys Ser Phe Asn Arg Gly Glu Cys
225 230

<210> SEQ ID NO 195
<211> LENGTH: 234
<212> TYPE: PRT
<213> ORGANISM: Artificial Sequence
<220> FEATURE:
<223> OTHER INFORMATION: 1F2 LC1

<400> SEQUENCE: 195

Met Val Ser Ser Ala Gln Phe Leu Gly Leu Leu Leu Leu Cys Phe Gln
1 5 10 15

Gly Thr Arg Cys Asp Ile Gln Met Thr Gln Ser Pro Ser Phe Leu Ser
20 25 30

Ala Ser Val Gly Asp Arg Val Thr Ile Thr Cys Lys Ala Ser Gln Asn
35 40 45

Val Val Thr Asn Val Val Trp Tyr Gln Gln Lys Pro Gly Lys Ala Pro
50 55 60

Lys Leu Leu Ile Tyr Ser Ala Ser Tyr Arg Tyr Ser Gly Val Pro Ser
65 70 75 80

Arg Phe Ser Gly Ser Gly Ser Gly Thr Glu Phe Thr Leu Thr Ile Ser
85 90 95

```
Ser Leu Gln Pro Glu Asp Phe Ala Thr Tyr Ser Cys Gln Gln Tyr His
            100                 105                 110

Ser Tyr Pro Phe Thr Phe Gly Gln Gly Thr Arg Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 196
<211> LENGTH: 234
<212> TYPE: PRT
<213> ORGANISM: Artificial Sequence
<220> FEATURE:
<223> OTHER INFORMATION: 1F2 LC2

<400> SEQUENCE: 196

Met Val Ser Ser Ala Gln Phe Leu Gly Leu Leu Leu Leu Cys Phe Gln
1               5                   10                  15

Gly Thr Arg Cys Asp Val Val Met Thr Gln Ser Pro Asp Ser Leu Ala
            20                  25                  30

Val Ser Leu Gly Glu Arg Val Thr Ile Asn Cys Lys Ala Ser Gln Asn
        35                  40                  45

Val Val Thr Asn Val Val Trp Tyr Gln Gln Lys Pro Gly Gln Ser Pro
    50                  55                  60

Lys Leu Leu Ile Tyr Ser Ala Ser Tyr Arg Tyr Ser Gly Val Pro Asp
65                  70                  75                  80

Arg Phe Ser Gly Ser Gly Ser Gly Thr Asp Phe Thr Leu Thr Ile Ser
                85                  90                  95

Ser Leu Gln Ala Glu Asp Val Ala Val Tyr Tyr Cys Gln Gln Tyr His
            100                 105                 110

Ser Tyr Pro Phe Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220
```

```
Val Thr Lys Ser Phe Asn Arg Gly Glu Cys
225                 230


<210> SEQ ID NO 197
<211> LENGTH: 234
<212> TYPE: PRT
<213> ORGANISM: Artificial Sequence
<220> FEATURE:
<223> OTHER INFORMATION: 1F2 LC3

<400> SEQUENCE: 197

Met Val Ser Ser Ala Gln Phe Leu Gly Leu Leu Leu Leu Cys Phe Gln
1               5                   10                  15

Gly Thr Arg Cys Asp Val Val Met Thr Gln Ser Pro Ser Ser Leu Ser
            20                  25                  30

Ala Ser Val Gly Asp Arg Val Ser Ile Thr Cys Lys Ala Ser Gln Asn
        35                  40                  45

Val Val Thr Asn Val Val Trp Tyr Gln Gln Lys Pro Gly Lys Ala Pro
    50                  55                  60

Lys Leu Leu Val Tyr Ser Ala Ser Tyr Arg Tyr Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Cys Cys Gln Gln Tyr His
            100                 105                 110

Ser Tyr Pro Phe Thr Phe Gly Gln Gly Thr Lys Leu Asp Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 198
<211> LENGTH: 234
<212> TYPE: PRT
<213> ORGANISM: Artificial Sequence
<220> FEATURE:
<223> OTHER INFORMATION: 1F2 LC4

<400> SEQUENCE: 198

Met Val Ser Ser Ala Gln Phe Leu Gly Leu Leu Leu Leu Cys Phe Gln
1               5                   10                  15

Gly Thr Arg Cys Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asn
        35                  40                  45

Val Val Thr Asn Val Val Trp Tyr Gln Gln Lys Pro Gly Gln Ala Pro
    50                  55                  60
```

Lys Leu Leu Ile Tyr Ser Ala Ser Tyr Arg Tyr Ser Gly Val Pro Ser
65 70 75 80

Arg Phe Ser Gly Ser Gly Ser Gly Thr Glu Phe Thr Phe Thr Ile Ser
85 90 95

Ser Leu Gln Pro Glu Asp Leu Ala Thr Tyr Ser Cys Gln Gln Tyr His
100 105 110

Ser Tyr Pro Phe Thr Phe Gly Gln Gly Thr Lys Leu Glu Ile Lys Arg
115 120 125

Thr Val Ala Ala Pro Ser Val Phe Ile Phe Pro Pro Ser Asp Glu Gln
130 135 140

Leu Lys Ser Gly Thr Ala Ser Val Val Cys Leu Leu Asn Asn Phe Tyr
145 150 155 160

Pro Arg Glu Ala Lys Val Gln Trp Lys Val Asp Asn Ala Leu Gln Ser
165 170 175

Gly Asn Ser Gln Glu Ser Val Thr Glu Gln Asp Ser Lys Asp Ser Thr
180 185 190

Tyr Ser Leu Ser Ser Thr Leu Thr Leu Ser Lys Ala Asp Tyr Glu Lys
195 200 205

His Lys Val Tyr Ala Cys Glu Val Thr His Gln Gly Leu Ser Ser Pro
210 215 220

Val Thr Lys Ser Phe Asn Arg Gly Glu Cys
225 230

<210> SEQ ID NO 199
<211> LENGTH: 234
<212> TYPE: PRT
<213> ORGANISM: Artificial Sequence
<220> FEATURE:
<223> OTHER INFORMATION: 1F2 LC5

<400> SEQUENCE: 199

Met Val Ser Ser Ala Gln Phe Leu Gly Leu Leu Leu Leu Cys Phe Gln
1 5 10 15

Gly Thr Arg Cys Ala Ile Arg Met Thr Gln Ser Pro Ser Ser Phe Ser
20 25 30

Ala Ser Thr Gly Asp Arg Val Thr Ile Thr Cys Lys Ala Ser Gln Asn
35 40 45

Val Val Thr Asn Val Val Trp Tyr Gln Gln Lys Pro Gly Lys Ala Pro
50 55 60

Lys Leu Leu Ile Tyr Ser Ala Ser Tyr Arg Tyr Ser Gly Val Pro Ser
65 70 75 80

Arg Phe Ser Gly Ser Gly Ser Gly Thr Asp Phe Thr Leu Thr Ile Ser
85 90 95

Cys Leu Gln Ser Glu Asp Phe Ala Thr Tyr Tyr Cys Gln Gln Tyr His
100 105 110

Ser Tyr Pro Phe Thr Phe Gly Gln Gly Thr Lys Leu Glu Ile Lys Arg
115 120 125

Thr Val Ala Ala Pro Ser Val Phe Ile Phe Pro Pro Ser Asp Glu Gln
130 135 140

Leu Lys Ser Gly Thr Ala Ser Val Val Cys Leu Leu Asn Asn Phe Tyr
145 150 155 160

Pro Arg Glu Ala Lys Val Gln Trp Lys Val Asp Asn Ala Leu Gln Ser
165 170 175

Gly Asn Ser Gln Glu Ser Val Thr Glu Gln Asp Ser Lys Asp Ser Thr
180 185 190

```
Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 200
<211> LENGTH: 234
<212> TYPE: PRT
<213> ORGANISM: Artificial Sequence
<220> FEATURE:
<223> OTHER INFORMATION: 1F2 LC6

<400> SEQUENCE: 200

Met Val Ser Ser Ala Gln Phe Leu Gly Leu Leu Leu Leu Cys Phe Gln
1               5                   10                  15

Gly Thr Arg Cys Asp Ile Gln Leu Thr Gln Ser Pro Lys Phe Leu Ser
            20                  25                  30

Ala Ser Val Gly Asp Arg Val Thr Ile Thr Cys Lys Ala Ser Gln Asn
        35                  40                  45

Val Val Thr Asn Val Val Trp Tyr Gln Gln Lys Pro Gly Lys Ala Pro
    50                  55                  60

Lys Leu Leu Ile Tyr Ser Ala Ser Tyr Arg Tyr Ser Gly Val Pro Asp
65                  70                  75                  80

Arg Phe Ser Gly Ser Gly Ser Gly Thr Glu Phe Thr Leu Thr Ile Ser
                85                  90                  95

Ser Leu Gln Pro Glu Asp Phe Ala Glu Tyr Ser Cys Gln Gln Tyr His
            100                 105                 110

Ser Tyr Pro Phe Thr Phe Gly Ser Gly Thr Lys Leu Glu Val Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 201
<211> LENGTH: 234
<212> TYPE: PRT
<213> ORGANISM: Artificial Sequence
<220> FEATURE:
<223> OTHER INFORMATION: 1F2 LC7

<400> SEQUENCE: 201

Met Val Ser Ser Ala Gln Phe Leu Gly Leu Leu Leu Leu Cys Phe Gln
1               5                   10                  15

Gly Thr Arg Cys Asp Ile Val Met Thr Gln Ser Pro Ser Phe Leu Ser
```

```
            20                  25                  30

Ala Ser Val Gly Asp Arg Val Thr Ile Thr Cys Lys Ala Ser Gln Asn
        35                  40                  45

Val Val Thr Asn Val Val Trp Tyr Gln Gln Lys Pro Gly Lys Ala Pro
    50                  55                  60

Lys Pro Leu Ile Tyr Ser Ala Ser Tyr Arg Tyr Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Glu Asp Leu Ala Glu Tyr Tyr Cys Gln Gln Tyr His
            100                 105                 110

Ser Tyr Pro Phe Thr Phe Gly Ser Gly Thr Lys Leu Glu Val Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 202
<211> LENGTH: 234
<212> TYPE: PRT
<213> ORGANISM: Artificial Sequence
<220> FEATURE:
<223> OTHER INFORMATION: 1F2 LC8

<400> SEQUENCE: 202

Met Val Ser Ser Ala Gln Phe Leu Gly Leu Leu Leu Leu Cys Phe Gln
1               5                   10                  15

Gly Thr Arg Cys Asp Ile Gln Met Thr Gln Ser Pro Ser Thr Leu Ser
            20                  25                  30

Ala Ser Val Gly Asp Arg Val Thr Ile Thr Cys Lys Ala Ser Gln Asn
        35                  40                  45

Val Val Thr Asn Val Val Trp Tyr Gln Gln Lys Pro Gly Gln Ala Pro
    50                  55                  60

Lys Leu Leu Ile Tyr Ser Ala Ser Tyr Arg Tyr Ser Gly Val Pro Ser
65                  70                  75                  80

Arg Phe Ser Gly Ser Gly Ser Gly Thr Glu Phe Thr Phe Thr Ile Ser
                85                  90                  95

Ser Leu Gln Ser Glu Asp Leu Ala Glu Tyr Tyr Cys Gln Gln Tyr His
            100                 105                 110

Ser Tyr Pro Phe Thr Phe Gly Ser Gly Thr Lys Leu Glu Val Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
```

-continued

```
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 203
<211> LENGTH: 19
<212> TYPE: PRT
<213> ORGANISM: Artificial Sequence
<220> FEATURE:
<223> OTHER INFORMATION: 1F2 Heavy Chain Signal Peptide

<400> SEQUENCE: 203

Met Gly Trp Thr Leu Val Phe Leu Phe Leu Leu Ser Val Thr Ala Gly
1               5                   10                  15

Val His Ser


<210> SEQ ID NO 204
<211> LENGTH: 20
<212> TYPE: PRT
<213> ORGANISM: Artificial Sequence
<220> FEATURE:
<223> OTHER INFORMATION: 1F2 Light Chain Signal Peptide

<400> SEQUENCE: 204

Met Val Ser Ser Ala Gln Phe Leu Gly Leu Leu Leu Leu Cys Phe Gln
1               5                   10                  15

Gly Thr Arg Cys
            20
```

ANTI-INFLUENZA B VIRUS NEURAMINIDASE ANTIBODIES AND USES THEREOF

This application is a U.S. National Stage Application under 35 U.S.C. § 371 of International Patent Application No. PCT/US2020/029582, filed on Apr. 23, 2020, which claims the benefit of U.S. Provisional Application No. 62/838,251, filed on Apr. 24, 2019, the disclosure of each of which is incorporated by reference herein in its entirety.

This invention was made with Government support under award AI117287 and AI109946 awarded by the National Institutes of Health. The Government has certain rights in this invention.

This application incorporates by reference a Sequence Listing submitted with this application as text file entitled "06923-297-228_SEQ_LISTING.txt" created on Apr. 22, 2020 and having a size of 126,882 bytes.

1. INTRODUCTION

Provided herein are antibodies that bind to neuraminidase (NA) of different strains of influenza B virus, host cells for producing such antibodies, and kits comprising such antibodies. Also provided herein are compositions comprising antibodies that bind to NA of different strains of influenza B virus and methods of using such antibodies to diagnose, prevent or treat influenza virus disease.

2. BACKGROUND

Influenza B viruses (IBVs) co-circulate in humans as two lineages based on the genetic and antigenic differences of the hemagglutinin (HA) glycoprotein. The two lineages—Yamagata (named after the B/Yamagata/16/88 strain) and Victoria (named after the B/Victoria/2/87 strain)—are thought to have diverged from a common ancestor strain in the 1970s (Shaw and Palese, *Fields Virol.* 2, 1648-1689 (2013) and Chen et al., *Arch. Virol.* 152, 415-422 (2007)). While IBVs are responsible for 20-30% of influenza cases per year on average, IBV is the predominant cause of influenza disease in some years (Molinari et al., *Vaccine* 25, 5086-5096 (2007), Djkstra et al., *Epidemiol. Infect.* 137, 473-9 (2009), Heikkinen et al., *Clin. Infect. Dis.* 59, 1519-24 (2014), Brottet et al., *Eurosurveillance* 19, 1-4 (2014)), and Tan et al., "*Universal influenza virus vaccines and therapeutics: where do we stand with influenza B virus?" Curr Opin Immunol.* August 2018; 53:45-50. Current studies challenge the notion that influenza B cases are clinically milder than those of influenza A, with the finding of no difference between influenza B and influenza A in terms of the length of hospital stay, intensive care unit admission frequency, or rate of death among hospitalized influenza patients (Su et al., *Clin. Infect. Dis.* 59, 252-5 (2014)). Additionally, epidemiologic data suggest IBVs disproportionally afflict children. During the 2010-2011 influenza season in the United States, IBVs accounted for 25% of all influenza infections but caused 38% of influenza-related pediatric deaths, and nearly half of these children had no pre-existing health conditions (Centers for Disease Control, Influenza-Associated Pediatric Deaths—United States, September 2010-August 2011, *MMWR. Morb. Mortal. Wkly. Rep.* 60 (2011)).

Neuraminidase (NA) inhibitors are the only antivirals officially recommended by the Advisory Committee on Immunization Practices (ACIP) for the treatment of influenza virus infection (Fiore et al., *MMWR. Recomm. Rep.* 60, 1-24 (2011)). This is particularly problematic for IBV infections since oseltamivir has been shown to be less effective when treating influenza B than when treating influenza A in both pediatric and adult outpatient populations (Kawai et al., *Clin. Infect. Dis.* 43, 439-444 (2006), Kawai et al., *J. Infect.* 55, 267-272 (2007), and Sugaya et al., *Clin. Infect. Dis.* 44, 197-202 (2007)); furthermore, zanamivir (an alternative NA inhibitor) is not approved for children under the age of seven (Fiore et al., *MMWR. Recomm. Rep.* 60, 1-24 (2011)). Given the substantial disease burden attributable to IBV despite the availability of vaccines and antivirals, development of novel therapeutics, such as the monoclonal antibodies (mAbs) described below, is crucial.

There have been reports of murine and human mAbs against the IBV HA (Wang et al., *J. Virol.* 82, 3011-20 (2008), Dreyfus et al., *Science* 337, 1343-1348 (2012), and Yasugi et al., *PLoS Pathog.* 9, 1-12 (2013)), but no broadly cross-reactive, protective mAbs binding the IBV NA have been reported thus far. The potential of the IBV NA globular head domain to harbor highly conserved epitopes has been recognized for some time (Air et al., *Virology* 177, 578-587 (1990)). MAbs against the IBV NA were previously isolated, yet the antibodies were not assessed for in vivo protection, and structures of antibody bound to NA were not solved (Air et al., *Virology* 177, 578-587 (1990), Laver, et al., *Virology* 167, 621-624 (1988) and Doyle et al., *Biochem. Biophys. Res. Commun.* 441, 226-229 (2013)). Although the importance of anti-NA immunity in protection from viral infection has been extensively demonstrated (Schulman et al., *J Virol.* 2, 778-776 (1968), Dowdle et al., *Postgrad. Med. J* 49, 159-63 (1973), Couch et al., *J. Infect. Dis.* 129 (1974), Johansson and Kilbourne, *Proc. Natl. Acad. Sci. U.S.A* 91, 2358-2361 (1994), Rockman et al., *J Virol* 87, 3053-3061 (2013), Easterbrook et al., *Virology* 432, 39-44 (2012), Wan et al., *J Virol* 87, 9290-9300 (2013), Wohlbold et al., *MBio* 6, 1-13 (2015), Wohlbold et al., *J Virol* 90, 851-861 (2015), and Memoli et al., *MBio* 7, e00417-16 (2016)), far less is known about NA epitopes compared to HA epitopes. While NA does not serve as the receptor binding protein, it is critically responsible for freeing nascent virus from host cells and virus in the airway from mucins (Palese et al., *Virology* 61, 397-410 (1974), Matrosovich et al., *J. Virol.* 78, 12665-12667 (2004), and Cohen, et al., *Virol. J.* 10, 321 (2013)); thus, antibodies that bind to the NA and interfere with its activity may confer protection through several mechanisms.

Thus, there is a need for therapies to prevent and treat influenza virus (in particular, influenza B virus) infections and influenza virus diseases.

3. SUMMARY

In one aspect, provided herein are antibodies (see, e.g., Sections 5.1 and 5.2, infra) that bind to NA of influenza B virus strains and compositions comprising such antibodies (see, e.g., Section 5.4, infra). In one embodiment, provided herein is an antibody that binds to a neuraminidase (NA) of an influenza B virus strain of the Victoria lineage and an NA of an influenza B virus strain of the Yamagata lineage, wherein said antibody inhibits the enzymatic activity of the NA of the influenza B virus strains of the Victoria and Yamagata lineages. In certain embodiments, the influenza B virus strain of the Victoria lineage is B/Brisbane/60/08, B/Malaysia/2506/04, B/Texas/2/13, B/New Jersey/1/12, or B/Victoria/2/81. In some embodiments, the influenza B virus strain of the Yamagata lineage is B/Wisconsin/1/10, B/Florida/04/06, B/Yamagata/16/88, or B/Massachusetts/2/12.

In another embodiment, provided herein is an antibody that cross-reacts with an NA of two or more influenza B virus strains of the Victoria lineage and two or more influenza B virus strains of the Yamagata lineage, wherein said antibody inhibits the enzymatic activity of the NA of the influenza B virus strains of the Victoria and Yamagata lineages. In certain embodiments, the two or more influenza B virus strains of the Victoria lineage span over a decade, over 25 years, over 50 years or over 70 years. In some embodiments, the two or more influenza B virus strains of the Yamagata lineage span over a decade, over 25 years, over 50 years or over 70 years. In some embodiments, the two or more influenza B virus strains of the Victoria lineage are selected from the group consisting of B/Brisbane/60/08, B/Malaysia/2506/04, B/Texas/2/13, B/New Jersey/1/12, and B/Victoria/2/81. In certain embodiments, the two or more influenza B virus strains of the Yamagata lineage are selected from the group consisting of B/Wisconsin/1/10, B/Florida/04/06, B/Yamagata/16/88, and B/Massachusetts/2/12.

In a specific embodiment, an antibody that binds to an influenza B virus NA comprises: (a) a variable heavy chain region comprising: (i) a variable heavy chain region complementarity determining region (CDR) 1 comprising the amino acid sequence of SEQ ID NO: 3, (ii) a variable heavy chain region CDR2 comprising the amino acid sequence of SEQ ID NO: 4, and (iii) a variable heavy chain region CDR3 comprising the amino acid sequence of SEQ ID NO: 5; or (b) a variable light chain region comprising: (i) a variable light chain region complementarity determining region (CDR) 1 comprising the amino acid sequence of SEQ ID NO: 6, (ii) a variable light chain region CDR2 comprising the amino acid sequence of SEQ ID NO: 7, and (iii) a variable light chain region CDR3 comprising the amino acid sequence of SEQ ID NO: 8.

In a specific embodiment, an antibody that binds to an influenza B virus NA comprises: (a) a variable heavy chain region comprising: (i) a variable heavy chain region complementarity determining region (CDR) 1 comprising the amino acid sequence of SEQ ID NO: 3, (ii) a variable heavy chain region CDR2 comprising the amino acid sequence of SEQ ID NO: 4, and (iii) a variable heavy chain region CDR3 comprising the amino acid sequence of SEQ ID NO: 5; and (b) a variable light chain region comprising: (i) a variable light chain region complementarity determining region (CDR) 1 comprising the amino acid sequence of SEQ ID NO: 6, (ii) a variable light chain region CDR2 comprising the amino acid sequence of SEQ ID NO: 7, and (iii) a variable light chain region CDR3 comprising the amino acid sequence of SEQ ID NO: 8.

In a specific embodiment, an antibody that binds to an influenza B virus NA comprises: (a) a variable heavy chain region comprising the variable heavy chain region CDRs of the antibody 1F2; or (b) a variable light chain region comprising the variable light chain region CDRs of the antibody 1F2; or (c) a variable heavy chain region comprising the variable heavy chain region CDRs of the antibody 1F2 and a variable light chain region comprising the variable light chain region CDRs of the antibody 1F2.

In a specific embodiment, an antibody that binds to an influenza B virus NA comprises: (i) a variable heavy chain region complementarity determining region (CDR) 1 comprising the amino acid sequence of SEQ ID NO: 3, (ii) a variable heavy chain region CDR2 comprising the amino acid sequence of SEQ ID NO: 4, (iii) a variable heavy chain region CDR3 comprising the amino acid sequence of SEQ ID NO: 5, (iv) a variable light chain region complementarity determining region (CDR) 1 comprising the amino acid sequence of SEQ ID NO: 6, (v) a variable light chain region CDR2 comprising the amino acid sequence of SEQ ID NO: 7, and (vi) a variable light chain region CDR3 comprising the amino acid sequence of SEQ ID NO: 8.

In a specific embodiment, an antibody that binds to an influenza B virus NA comprises: (a) a variable heavy chain region comprising: (i) a variable heavy chain region complementarity determining region (CDR) 1 comprising the amino acid sequence of SEQ ID NO: 19, (ii) a variable heavy chain region CDR2 comprising the amino acid sequence of SEQ ID NO: 20, and (iii) a variable heavy chain region CDR3 comprising the amino acid sequence of SEQ ID NO: 21; or (b) a variable light chain region comprising: (i) a variable light chain region complementarity determining region (CDR) 1 comprising the amino acid sequence of SEQ ID NO: 22, (ii) a variable light chain region CDR2 comprising the amino acid sequence of SEQ ID NO: 23, and (iii) a variable light chain region CDR3 comprising the amino acid sequence of SEQ ID NO: 24.

In a specific embodiment, an antibody that binds to an influenza B virus NA comprises: (a) a variable heavy chain region comprising: (i) a variable heavy chain region complementarity determining region (CDR) 1 comprising the amino acid sequence of SEQ ID NO: 19, (ii) a variable heavy chain region CDR2 comprising the amino acid sequence of SEQ ID NO: 20, and (iii) a variable heavy chain region CDR3 comprising the amino acid sequence of SEQ ID NO: 21; and (b) a variable light chain region comprising: (i) a variable light chain region complementarity determining region (CDR) 1 comprising the amino acid sequence of SEQ ID NO: 22, (ii) a variable light chain region CDR2 comprising the amino acid sequence of SEQ ID NO: 23, and (iii) a variable light chain region CDR3 comprising the amino acid sequence of SEQ ID NO: 24.

In a specific embodiment, an antibody that binds to an influenza B virus NA comprises: (a) a variable heavy chain region comprising the variable heavy chain region CDRs of the antibody 1F4; or (b) a variable light chain region comprising the variable light chain region CDRs of the antibody 1F4; or (c) a variable heavy chain region comprising the variable heavy chain region CDRs of the antibody 1F4 and a variable light chain region comprising the variable light chain region CDRs of the antibody 1F4.

In a specific embodiment, an antibody that binds to an influenza B virus NA comprises: (i) a variable heavy chain region complementarity determining region (CDR) 1 comprising the amino acid sequence of SEQ ID NO: 19, (ii) a variable heavy chain region CDR2 comprising the amino acid sequence of SEQ ID NO: 20, (iii) a variable heavy chain region CDR3 comprising the amino acid sequence of SEQ ID NO: 21, (iv) a variable light chain region complementarity determining region (CDR) 1 comprising the amino acid sequence of SEQ ID NO: 22, (v) a variable light chain region CDR2 comprising the amino acid sequence of SEQ ID NO: 23, and (vi) a variable light chain region CDR3 comprising the amino acid sequence of SEQ ID NO: 24.

In a specific embodiment, an antibody that binds to an influenza B virus NA comprises: (a) a variable heavy chain region comprising: (i) a variable heavy chain region complementarity determining region (CDR) 1 comprising the amino acid sequence of SEQ ID NO: 51, (ii) a variable heavy chain region CDR2 comprising the amino acid sequence of SEQ ID NO: 52, and (iii) a variable heavy chain region CDR3 comprising the amino acid sequence of SEQ ID NO: 53; or (b) a variable light chain region comprising: (i) a variable light chain region complementarity determining region (CDR) 1 comprising the amino acid sequence of SEQ ID NO: 54, (ii) a variable light chain region CDR2 comprising the amino acid sequence of SEQ ID NO: 55, and (iii) a variable light chain region CDR3 comprising the amino acid sequence of SEQ ID NO: 56.

In a specific embodiment, an antibody that binds to an influenza B virus NA comprises: (a) a variable heavy chain region comprising: (i) a variable heavy chain region complementarity determining region (CDR) 1 comprising the amino acid sequence of SEQ ID NO: 51, (ii) a variable heavy chain region CDR2 comprising the amino acid sequence of SEQ ID NO: 52, and (iii) a variable heavy chain region CDR3 comprising the amino acid sequence of SEQ ID NO: 53; and (b) a variable light chain region comprising: (i) a variable light chain region complementarity determining region (CDR) 1 comprising the amino acid sequence of SEQ ID NO: 54, (ii) a variable light chain region CDR2 comprising the amino acid sequence of SEQ ID NO: 55, and (iii) a variable light chain region CDR3 comprising the amino acid sequence of SEQ ID NO: 56.

In a specific embodiment, an antibody that binds to an influenza B virus NA comprises: (a) a variable heavy chain region comprising the variable heavy chain region CDRs of the antibody 4B2; or (b) a variable light chain region comprising the variable light chain region CDRs of the antibody 4B2; or (c) a variable heavy chain region comprising the variable heavy chain region CDRs of the antibody 4B2 and a variable light chain region comprising the variable light chain region CDRs of the antibody 4B2.

In a specific embodiment, an antibody that binds to an influenza B virus NA comprises: (i) a variable heavy chain region complementarity determining region (CDR) 1 comprising the amino acid sequence of SEQ ID NO: 51, (ii) a variable heavy chain region CDR2 comprising the amino acid sequence of SEQ ID NO: 52, (iii) a variable heavy chain region CDR3 comprising the amino acid sequence of SEQ ID NO: 53, (iv) a variable light chain region complementarity determining region (CDR) 1 comprising the amino acid sequence of SEQ ID NO: 54, (v) a variable light chain region CDR2 comprising the amino acid sequence of SEQ ID NO: 55, and (vi) a variable light chain region CDR3 comprising the amino acid sequence of SEQ ID NO: 56.

In another embodiment, provided herein is an antibody that binds to an influenza B virus NA, wherein the antibody comprises: (a) a variable heavy chain region comprising the variable heavy chain region CDRs of the antibody 1F2; or (b) a variable light chain region comprising the variable light chain region CDRs of the antibody 1F2; or (c) a variable heavy chain region comprising the variable heavy chain region CDRs of the antibody 1F2 and a variable light chain region comprising the variable light chain region CDRs of the antibody 1F2.

In another embodiment, provided herein is an antibody that binds to an influenza B virus NA, wherein the antibody comprises: (i) a variable heavy chain region complementarity determining region (CDR) 1 comprising the amino acid sequence of SEQ ID NO: 3, (ii) a variable heavy chain region CDR2 comprising the amino acid sequence of SEQ ID NO: 4, (iii) a variable heavy chain region CDR3 comprising the amino acid sequence of SEQ ID NO: 5, (iv) a variable light chain region complementarity determining region (CDR) 1 comprising the amino acid sequence of SEQ ID NO: 6, (v) a variable light chain region CDR2 comprising the amino acid sequence of SEQ ID NO: 7, and (vi) a variable light chain region CDR3 comprising the amino acid sequence of SEQ ID NO: 8.

In another embodiment, provided herein is an antibody that binds to an influenza B virus NA, wherein the antibody comprises: (a) a variable heavy chain region that is at least 95% identical to the amino acid sequence of SEQ ID NO: 1; (b) a variable light chain region that is at least 95% identical to the amino acid sequence of SEQ ID NO: 2; (c) a variable heavy chain region that is at least 95% identical to the amino acid sequences of SEQ ID NO: 1 and a variable light chain region that is at least 95% identical to the amino acid sequence of SEQ ID NO: 2; (d) a variable heavy chain region that is at least 95% identical to the amino acid sequence of SEQ ID NO: 1, wherein the variable heavy chain region comprises a variable heavy chain region CDR1 comprising the amino acid sequence of SEQ ID NO: 3, a variable heavy chain region CDR2 comprising the amino acid sequence of SEQ ID NO: 4, and a variable heavy chain region CDR3 comprising the amino acid sequence of SEQ ID NO: 5; (e) a variable light chain region that is at least 95% identical to the amino acid sequence of SEQ ID NO: 2, wherein the variable light chain region comprises a variable light chain region CDR1 comprising the amino acid sequence of SEQ ID NO: 6, a variable light chain region CDR2 comprising the amino acid sequence of SEQ ID NO: 7, and a variable light chain region CDR3 comprising the amino acid sequence of SEQ ID NO: 8; or (f) (I) a variable heavy chain region that is at least 95% identical to the amino acid sequences of SEQ ID NO: 1, wherein the variable heavy chain region comprises a variable heavy chain region CDR1 comprising the amino acid sequence of SEQ ID NO: 3, a variable heavy chain region CDR2 comprising the amino acid sequence of SEQ ID NO: 4: and a variable heavy chain region CDR3 comprising the amino acid sequence of SEQ ID NO: 5; and (II) a variable light chain region that is at least 95% identical to the amino acid sequence of SEQ ID NO: 2, wherein the variable light chain region comprises a variable light chain region CDR1 comprising the amino acid sequence of SEQ ID NO: 6, a variable light chain region CDR2 comprising the amino acid sequence of SEQ ID NO: 7, and a variable light chain region CDR3 comprising the amino acid sequence of SEQ ID NO: 8.

In another embodiment, provided herein is an antibody that binds to an influenza B virus NA, wherein the antibody comprises: (a) a variable heavy chain region that is at least 78% identical to the amino acid sequences of SEQ ID NO: 1, wherein the variable heavy chain region comprises a variable heavy chain region CDR1 comprising the amino acid sequence of SEQ ID NO: 3, a variable heavy chain region CDR2 comprising the amino acid sequence of SEQ ID NO: 4: and a variable heavy chain region CDR3 comprising the amino acid sequence of SEQ ID NO: 5; and (b) a variable light chain region that is at least 78% identical to the amino acid sequence of SEQ ID NO: 2, wherein the variable light chain region comprises a variable light chain region CDR1 comprising the amino acid sequence of SEQ ID NO: 6, a variable light chain region CDR2 comprising the amino acid sequence of SEQ ID NO: 7, and a variable light chain region CDR3 comprising the amino acid sequence of SEQ ID NO: 8.

In another embodiment, provided herein is an antibody that binds to an influenza B virus NA, wherein the antibody comprises: (a) a variable heavy chain region that is at least 80% identical to the amino acid sequences of SEQ ID NO: 1, wherein the variable heavy chain region comprises a variable heavy chain region CDR1 comprising the amino acid sequence of SEQ ID NO: 3, a variable heavy chain region CDR2 comprising the amino acid sequence of SEQ ID NO: 4: and a variable heavy chain region CDR3 comprising the amino acid sequence of SEQ ID NO: 5; and (b) a variable light chain region that is at least 78% or at least 80% identical to the amino acid sequence of SEQ ID NO: 2, wherein the variable light chain region comprises a variable light chain region CDR1 comprising the amino acid sequence of SEQ ID NO: 6, a variable light chain region CDR2 comprising the amino acid sequence of SEQ ID NO: 7, and a variable light chain region CDR3 comprising the amino acid sequence of SEQ ID NO: 8.

In another embodiment, provided herein is an antibody that binds to an influenza B virus NA, wherein the antibody comprises: (a) a variable heavy chain region that is at least 80% or at least 85% identical to the amino acid sequences of SEQ ID NO: 1, wherein the variable heavy chain region comprises a variable heavy chain region CDR1 comprising the amino acid sequence of SEQ ID NO: 3, a variable heavy chain region CDR2 comprising the amino acid sequence of SEQ ID NO: 4: and a variable heavy chain region CDR3 comprising the amino acid sequence of SEQ ID NO: 5; and (b) a variable light chain region that is at least 80% or at least 85% identical to the amino acid sequence of SEQ ID NO: 2, wherein the variable light chain region comprises a variable light chain region CDR1 comprising the amino acid sequence of SEQ ID NO: 6, a variable light chain region CDR2 comprising the amino acid sequence of SEQ ID NO: 7, and a variable light chain region CDR3 comprising the amino acid sequence of SEQ ID NO: 8.

In another embodiment, provided herein is an antibody that binds to an influenza B virus NA, wherein the antibody comprises: (a) a variable heavy chain region that is at least 90% identical to the amino acid sequences of SEQ ID NO: 1, wherein the variable heavy chain region comprises a variable heavy chain region CDR1 comprising the amino acid sequence of SEQ ID NO: 3, a variable heavy chain region CDR2 comprising the amino acid sequence of SEQ ID NO: 4: and a variable heavy chain region CDR3 comprising the amino acid sequence of SEQ ID NO: 5; and (b) a variable light chain region that is at least 90% identical to the amino acid sequence of SEQ ID NO: 2, wherein the variable light chain region comprises a variable light chain region CDR1 comprising the amino acid sequence of SEQ ID NO: 6, a variable light chain region CDR2 comprising the amino acid sequence of SEQ ID NO: 7, and a variable light chain region CDR3 comprising the amino acid sequence of SEQ ID NO: 8.

In another embodiment, variable heavy chain region variants of the 1F2 murine antibody have been produced and the sequences of those variable region variants may be found in FIG. 30 and in Section 4.1 under VH1 to VH8. In another embodiment, variable light chain region variants of the 1F2 murine antibody have been produced and the sequences of those variable region variants are provided in FIG. 31 and in Section 4.1 under VL1 to VL8. In another embodiment, humanized heavy chains of the 1F2 murine antibody have been produced and the sequences of those heavy chains are in Section 4.1 under HC1 to HC8. In another embodiment, humanized light chains of the 1F2 murine antibody have been produced and the sequences of those light chains are in Section 4.1 under LC1 to LC8. In another embodiment, a chimeric heavy chain and a chimeric light chain have been produced and are provided in Section 4.1 under HC0 and LC0, respectively.

In another embodiment, provided herein is an antibody, which binds to an influenza B virus NA, comprising a variable heavy chain region, wherein the variable heavy chain region comprises the amino acid sequence of VH1, VH2, VH3, VH4, VH5, VH6, VH7 or VH8 set forth in FIG. 30 or in Section 4.1. In another embodiment, provided herein is an antibody, which binds to an influenza B virus NA, comprising a variable light chain region, wherein the variable light chain region comprises the amino acid sequence of VL1, VL2, VL3, VL4, VL5, VL6, VL7 or VL8 set forth in FIG. 31 or in Section 4.1. In another embodiment, provided herein is an antibody, which binds to an influenza B virus NA, comprising a variable heavy chain region and a variable light chain region, wherein the variable heavy chain region comprises the amino acid sequence of VH1, VH2, VH3, VH4, VH5, VH6, VH7 or VH8 set forth in FIG. 30 or in Section 4.1, and wherein the variable light chain region comprises the amino acid sequence of VL1, VL2, VL3, VL4, VL5, VL6, VL7 or VL8 set forth in FIG. 31 or in Section 4.1.

In another embodiment, provided herein is an antibody, which binds to an influenza B virus NA, comprising a heavy chain, wherein the heavy chain comprises the amino acid sequence of HC1, HC2, HC3, HC4, HC5, HC6, HC7 or HC8 set forth in Section 4.1. In another embodiment, provided herein is an antibody, which binds to an influenza B virus NA, comprising a light chain, wherein the light chain comprises the amino acid sequence of LC1, LC2, LC3, LC4, LC5, LC6, LC7 or LC8 set forth in Section 4.1. In another embodiment, provided herein is an antibody, which binds to an influenza B virus NA, comprising a heavy chain and a light chain, wherein the heavy chain comprises the amino acid sequence of HC1, HC2, HC3, HC4, HC5, HC6, HC7 or HC8 set forth in Section 4.1, and wherein the light chain comprises the amino acid sequence of LC1, LC2, LC3, LC4, LC5, LC6, LC7 or LC8 set forth in Section 4.1. In another embodiment, provided herein is an antibody, which binds to an influenza B virus NA, comprising a chimeric heavy chain and a chimeric light chain, wherein the chimeric heavy chain comprises the amino acid sequence of HC0 set forth in Section 4.1, and wherein the chimeric light chain comprises the amino acid sequence of LC0 set forth in Section 4.1.

In another specific embodiment, an antibody, which binds to an influenza B virus NA, comprises the specific combination of a variable heavy chain region (VH) and a variable light chain region (VL) set forth in the following table, wherein the amino acid sequences for the VH and VL are provided in Section 4.1 or in FIGS. 30 and 31, respectively:

| | | | | | | | |
|---|---|---|---|---|---|---|---|
| VH1:VL1 | VH1:VL2 | VH1:VL3 | VH1:VL4 | VH1:VL5 | VH1:VL6 | VH1:VL7 | VH1:VL8 |
| VH2:VL1 | VH2:VL2 | VH2:VL3 | VH2:VL4 | VH2:VL5 | VH2:VL6 | VH2:VL7 | VH2:VL8 |
| VH3:VL1 | VH3:VL2 | VH3:VL3 | VH3:VL4 | VH3:VL5 | VH3:VL6 | VH3:VL7 | VH3:VL8 |
| VH4:VL1 | VH4:VL2 | VH4:VL3 | VH4:VL4 | VH4:VL5 | VH4:VL6 | VH4:VL7 | VH4:VL8 |
| VH5:VL1 | VH5:VL2 | VH5:VL3 | VH5:VL4 | VH5:VL5 | VH5:VL6 | VH5:VL7 | VH5:VL8 |
| VH6:VL1 | VH6:VL2 | VH6:VL3 | VH6:VL4 | VH6:VL5 | VH6:VL6 | VH6:VL7 | VH6:VL8 |
| VH7:VL1 | VH7:VL2 | VH7:VL3 | VH7:VL4 | VH7:VL5 | VH7:VL6 | VH7:VL7 | VH7:VL8 |
| VH8:VL1 | VH8:VL2 | VH8:VL3 | VH8:VL4 | VH8:VL5 | VH8:VL6 | VH8:VL7 | HC8:VL8 |

In another specific embodiment, an antibody, which binds to an influenza B virus NA, comprises the specific combination of a heavy chain (HC) and a light chain (LC) set forth in the following table, wherein the amino acid sequences for the HC and LC are provided in Section 4.1:

| | | | | | | | |
|---|---|---|---|---|---|---|---|
| HC1:LC1 | HC1:LC2 | HC1:LC3 | HC1:LC4 | HC1:LC5 | HC1:LC6 | HC1:LC7 | HC1:LC8 |
| HC2:LC1 | HC2:LC2 | HC2:LC3 | HC2:LC4 | HC2:LC5 | HC2:LC6 | HC2:LC7 | HC2:LC8 |
| HC3:LC1 | HC3:LC2 | HC3:LC3 | HC3:LC4 | HC3:LC5 | HC3:LC6 | HC3:LC7 | HC3:LC8 |
| HC4:LC1 | HC4:LC2 | HC4:LC3 | HC4:LC4 | HC4:LC5 | HC4:LC6 | HC4:LC7 | HC4:LC8 |
| HC5:LC1 | HC5:LC2 | HC5:LC3 | HC5:LC4 | HC5:LC5 | HC5:LC6 | HC5:LC7 | HC5:LC8 |
| HC6:LC1 | HC6:LC2 | HC6:LC3 | HC6:LC4 | HC6:LC5 | HC6:LC6 | HC6:LC7 | HC6:LC8 |
| HC7:LC1 | HC7:LC2 | HC7:LC3 | HC7:LC4 | HC7:LC5 | HC7:LC6 | HC7:LC7 | HC7:LC8 |
| HC8:LC1 | HC8:LC2 | HC8:LC3 | HC8:LC4 | HC8:LC5 | HC8:LC6 | HC8:LC7 | HC8:LC8 |

In another embodiment, provided herein is an antibody that binds to an influenza B virus NA, wherein the antibody comprises a variable heavy chain region comprising the amino acid sequence of SEQ ID NO:168, 169, 170, 171, 172, 173, 174 or 175.

In another embodiment, provided herein is an antibody that binds to an influenza B virus NA, wherein the antibody comprises a variable light chain region comprising the amino acid sequence of SEQ ID NO:177, 178, 179, 180, 181, 182, 183, or 184.

In another embodiment, provided herein is an antibody that binds to an influenza B virus NA, wherein the antibody comprises: (a) a variable heavy chain region comprising the amino acid sequence of SEQ ID NO: 168, 169, 170, 171, 172, 173, 174 or 175; and (b) a variable light chain region comprising the amino acid sequence of SEQ ID NO: 177, 178, 179, 180, 181, 182, 183, or 184.

In another embodiment, provided herein is an antibody that binds to an influenza B virus NA, wherein the antibody comprises: (a) a variable heavy chain region comprising the amino acid sequence of SEQ ID NO: 168; and (b) a variable light chain region comprising the amino acid sequence of SEQ ID NO: 177.

In another embodiment, provided herein is an antibody that binds to an influenza B virus NA, wherein the antibody comprises: (a) a variable heavy chain region comprising the amino acid sequence of SEQ ID NO: 168; and (b) a variable light chain region comprising the amino acid sequence of SEQ ID NO: 178.

In another embodiment, provided herein is an antibody that binds to an influenza B virus NA, wherein the antibody comprises: (a) a variable heavy chain region comprising the amino acid sequence of SEQ ID NO: 168; and (b) a variable light chain region comprising the amino acid sequence of SEQ ID NO: 179.

In another embodiment, provided herein is an antibody that binds to an influenza B virus NA, wherein the antibody comprises: (a) a variable heavy chain region comprising the amino acid sequence of SEQ ID NO: 168; and (b) a variable light chain region comprising the amino acid sequence of SEQ ID NO: 180.

In another embodiment, provided herein is an antibody that binds to an influenza B virus NA, wherein the antibody comprises: (a) a variable heavy chain region comprising the amino acid sequence of SEQ ID NO: 168; and (b) a variable light chain region comprising the amino acid sequence of SEQ ID NO:181.

In another embodiment, provided herein is an antibody that binds to an influenza B virus NA, wherein the antibody comprises: (a) a variable heavy chain region comprising the amino acid sequence of SEQ ID NO: 169; and (b) a variable light chain region comprising the amino acid sequence of SEQ ID NO: 177.

In another embodiment, provided herein is an antibody that binds to an influenza B virus NA, wherein the antibody comprises: (a) a variable heavy chain region comprising the amino acid sequence of SEQ ID NO: 169; and (b) a variable light chain region comprising the amino acid sequence of SEQ ID NO: 178.

In another embodiment, provided herein is an antibody that binds to an influenza B virus NA, wherein the antibody comprises: (a) a variable heavy chain region comprising the amino acid sequence of SEQ ID NO: 169; and (b) a variable light chain region comprising the amino acid sequence of SEQ ID NO:179.

In another embodiment, provided herein is an antibody that binds to an influenza B virus NA, wherein the antibody comprises: (a) a variable heavy chain region comprising the amino acid sequence of SEQ ID NO: 169; and (b) a variable light chain region comprising the amino acid sequence of SEQ ID NO: 180.

In another embodiment, provided herein is an antibody that binds to an influenza B virus NA, wherein the antibody comprises: (a) a variable heavy chain region comprising the amino acid sequence of SEQ ID NO: 169; and (b) a variable light chain region comprising the amino acid sequence of SEQ ID NO: 181.

In another embodiment, provided herein is an antibody that binds to an influenza B virus NA, wherein the antibody comprises: (a) a variable heavy chain region comprising the amino acid sequence of SEQ ID NO: 170; and (b) a variable light chain region comprising the amino acid sequence of SEQ ID NO: 177.

In another embodiment, provided herein is an antibody that binds to an influenza B virus NA, wherein the antibody comprises: (a) a variable heavy chain region comprising the amino acid sequence of SEQ ID NO: 170; and (b) a variable light chain region comprising the amino acid sequence of SEQ ID NO: 178.

In another embodiment, provided herein is an antibody that binds to an influenza B virus NA, wherein the antibody comprises: (a) a variable heavy chain region comprising the amino acid sequence of SEQ ID NO: 170; and (b) a variable light chain region comprising the amino acid sequence of SEQ ID NO: 179.

In another embodiment, provided herein is an antibody that binds to an influenza B virus NA, wherein the antibody comprises: (a) a variable heavy chain region comprising the amino acid sequence of SEQ ID NO: 170; and (b) a variable light chain region comprising the amino acid sequence of SEQ ID NO: 180.

In another embodiment, provided herein is an antibody that binds to an influenza B virus NA, wherein the antibody comprises: (a) a variable heavy chain region comprising the amino acid sequence of SEQ ID NO: 170; and (b) a variable light chain region comprising the amino acid sequence of SEQ ID NO: 181.

In another embodiment, provided herein is an antibody that binds to an influenza B virus NA, wherein the antibody comprises: (a) a variable heavy chain region comprising the amino acid sequence of SEQ ID NO: 171; and (b) a variable light chain region comprising the amino acid sequence of SEQ ID NO: 177.

In another embodiment, provided herein is an antibody that binds to an influenza B virus NA, wherein the antibody comprises: (a) a variable heavy chain region comprising the amino acid sequence of SEQ ID NO: 171; and (b) a variable light chain region comprising the amino acid sequence of SEQ ID NO: 178.

In another embodiment, provided herein is an antibody that binds to an influenza B virus NA, wherein the antibody comprises: (a) a variable heavy chain region comprising the amino acid sequence of SEQ ID NO: 171; and (b) a variable light chain region comprising the amino acid sequence of SEQ ID NO: 179.

In another embodiment, provided herein is an antibody that binds to an influenza B virus NA, wherein the antibody comprises: (a) a variable heavy chain region comprising the amino acid sequence of SEQ ID NO: 171; and (b) a variable light chain region comprising the amino acid sequence of SEQ ID NO: 180.

In another embodiment, provided herein is an antibody that binds to an influenza B virus NA, wherein the antibody comprises: (a) a variable heavy chain region comprising the amino acid sequence of SEQ ID NO: 171; and (b) a variable light chain region comprising the amino acid sequence of SEQ ID NO: 181.

In another embodiment, provided herein is an antibody that binds to an influenza B virus NA, wherein the antibody comprises: (a) a variable heavy chain region comprising the amino acid sequence of SEQ ID NO: 172; and (b) a variable light chain region comprising the amino acid sequence of SEQ ID NO: 177.

In another embodiment, provided herein is an antibody that binds to an influenza B virus NA, wherein the antibody comprises: (a) a variable heavy chain region comprising the amino acid sequence of SEQ ID NO: 172; and (b) a variable light chain region comprising the amino acid sequence of SEQ ID NO: 178.

In another embodiment, provided herein is an antibody that binds to an influenza B virus NA, wherein the antibody comprises: (a) a variable heavy chain region comprising the amino acid sequence of SEQ ID NO: 172; and (b) a variable light chain region comprising the amino acid sequence of SEQ ID NO: 179.

In another embodiment, provided herein is an antibody that binds to an influenza B virus NA, wherein the antibody comprises: (a) a variable heavy chain region comprising the amino acid sequence of SEQ ID NO: 172; and (b) a variable light chain region comprising the amino acid sequence of SEQ ID NO: 180.

In another embodiment, provided herein is an antibody that binds to an influenza B virus NA, wherein the antibody comprises: (a) a variable heavy chain region comprising the amino acid sequence of SEQ ID NO: 172; and (b) a variable light chain region comprising the amino acid sequence of SEQ ID NO: 181.

In another embodiment, provided herein is an antibody that binds to an influenza B virus NA, wherein the antibody comprises: (a) a variable heavy chain region comprising the amino acid sequence of SEQ ID NO: 173, 174 or 175; and (b) a variable light chain region comprising the amino acid sequence of SEQ ID NO: 182, 183, or 184.

In another embodiment, provided herein is an antibody that binds to an influenza B virus NA, wherein the antibody comprises: (a) a variable heavy chain region comprising the amino acid sequence of SEQ ID NO: 173; and (b) a variable light chain region comprising the amino acid sequence of SEQ ID NO: 177.

In another embodiment, provided herein is an antibody that binds to an influenza B virus NA, wherein the antibody comprises: (a) a variable heavy chain region comprising the amino acid sequence of SEQ ID NO: 173; and (b) a variable light chain region comprising the amino acid sequence of SEQ ID NO: 178.

In another embodiment, provided herein is an antibody that binds to an influenza B virus NA, wherein the antibody comprises: (a) a variable heavy chain region comprising the amino acid sequence of SEQ ID NO: 173; and (b) a variable light chain region comprising the amino acid sequence of SEQ ID NO: 179.

In another embodiment, provided herein is an antibody that binds to an influenza B virus NA, wherein the antibody comprises: (a) a variable heavy chain region comprising the amino acid sequence of SEQ ID NO: 173; and (b) a variable light chain region comprising the amino acid sequence of SEQ ID NO: 180.

In another embodiment, provided herein is an antibody that binds to an influenza B virus NA, wherein the antibody comprises: (a) a variable heavy chain region comprising the amino acid sequence of SEQ ID NO: 173; and (b) a variable light chain region comprising the amino acid sequence of SEQ ID NO: 181.

In another embodiment, provided herein is an antibody that binds to an influenza B virus NA, wherein the antibody comprises: (a) a variable heavy chain region comprising the amino acid sequence of SEQ ID NO: 173; and (b) a variable light chain region comprising the amino acid sequence of SEQ ID NO: 182.

In another embodiment, provided herein is an antibody that binds to an influenza B virus NA, wherein the antibody comprises: (a) a variable heavy chain region comprising the amino acid sequence of SEQ ID NO: 173; and (b) a variable light chain region comprising the amino acid sequence of SEQ ID NO: 183.

In another embodiment, provided herein is an antibody that binds to an influenza B virus NA, wherein the antibody comprises: (a) a variable heavy chain region comprising the amino acid sequence of SEQ ID NO: 173; and (b) a variable light chain region comprising the amino acid sequence of SEQ ID NO: 184.

In another embodiment, provided herein is an antibody that binds to an influenza B virus NA, wherein the antibody comprises: (a) a variable heavy chain region comprising the amino acid sequence of SEQ ID NO: 174; and (b) a variable light chain region comprising the amino acid sequence of SEQ ID NO: 177.

In another embodiment, provided herein is an antibody that binds to an influenza B virus NA, wherein the antibody comprises: (a) a variable heavy chain region comprising the amino acid sequence of SEQ ID NO: 174; and (b) a variable light chain region comprising the amino acid sequence of SEQ ID NO: 178.

In another embodiment, provided herein is an antibody that binds to an influenza B virus NA, wherein the antibody comprises: (a) a variable heavy chain region comprising the amino acid sequence of SEQ ID NO: 174; and (b) a variable light chain region comprising the amino acid sequence of SEQ ID NO: 179.

In another embodiment, provided herein is an antibody that binds to an influenza B virus NA, wherein the antibody comprises: (a) a variable heavy chain region comprising the amino acid sequence of SEQ ID NO: 174; and (b) a variable light chain region comprising the amino acid sequence of SEQ ID NO: 180.

In another embodiment, provided herein is an antibody that binds to an influenza B virus NA, wherein the antibody comprises: (a) a variable heavy chain region comprising the amino acid sequence of SEQ ID NO: 174; and (b) a variable light chain region comprising the amino acid sequence of SEQ ID NO: 181.

In another embodiment, provided herein is an antibody that binds to an influenza B virus NA, wherein the antibody comprises: (a) a variable heavy chain region comprising the amino acid sequence of SEQ ID NO: 174; and (b) a variable light chain region comprising the amino acid sequence of SEQ ID NO: 182.

In another embodiment, provided herein is an antibody that binds to an influenza B virus NA, wherein the antibody comprises: (a) a variable heavy chain region comprising the amino acid sequence of SEQ ID NO: 174; and (b) a variable light chain region comprising the amino acid sequence of SEQ ID NO: 183.

In another embodiment, provided herein is an antibody that binds to an influenza B virus NA, wherein the antibody comprises: (a) a variable heavy chain region comprising the amino acid sequence of SEQ ID NO: 174; and (b) a variable light chain region comprising the amino acid sequence of SEQ ID NO: 184.

In another embodiment, provided herein is an antibody that binds to an influenza B virus NA, wherein the antibody comprises: (a) a variable heavy chain region comprising the amino acid sequence of SEQ ID NO: 175; and (b) a variable light chain region comprising the amino acid sequence of SEQ ID NO: 177.

In another embodiment, provided herein is an antibody that binds to an influenza B virus NA, wherein the antibody comprises: (a) a variable heavy chain region comprising the amino acid sequence of SEQ ID NO: 175; and (b) a variable light chain region comprising the amino acid sequence of SEQ ID NO: 178.

In another embodiment, provided herein is an antibody that binds to an influenza B virus NA, wherein the antibody comprises: (a) a variable heavy chain region comprising the amino acid sequence of SEQ ID NO: 175; and (b) a variable light chain region comprising the amino acid sequence of SEQ ID NO: 179.

In another embodiment, provided herein is an antibody that binds to an influenza B virus NA, wherein the antibody comprises: (a) a variable heavy chain region comprising the amino acid sequence of SEQ ID NO: 175; and (b) a variable light chain region comprising the amino acid sequence of SEQ ID NO: 180.

In another embodiment, provided herein is an antibody that binds to an influenza B virus NA, wherein the antibody comprises: (a) a variable heavy chain region comprising the amino acid sequence of SEQ ID NO: 175; and (b) a variable light chain region comprising the amino acid sequence of SEQ ID NO: 181.

In another embodiment, provided herein is an antibody that binds to an influenza B virus NA, wherein the antibody comprises: (a) a variable heavy chain region comprising the amino acid sequence of SEQ ID NO: 175; and (b) a variable light chain region comprising the amino acid sequence of SEQ ID NO: 182.

In another embodiment, provided herein is an antibody that binds to an influenza B virus NA, wherein the antibody comprises: (a) a variable heavy chain region comprising the amino acid sequence of SEQ ID NO: 175; and (b) a variable light chain region comprising the amino acid sequence of SEQ ID NO: 183.

In another embodiment, provided herein is an antibody that binds to an influenza B virus NA, wherein the antibody comprises: (a) a variable heavy chain region comprising the amino acid sequence of SEQ ID NO: 175; and (b) a variable light chain region comprising the amino acid sequence of SEQ ID NO: 184.

In another embodiment, provided herein is an antibody that binds to an influenza B virus NA, wherein the antibody comprises: (a) a variable heavy chain region comprising the variable heavy chain region CDRs of the antibody 1F4; (b) a variable light chain region comprising the variable light chain region CDRs of the antibody 1F4; or (c) a variable heavy chain region comprising the variable heavy chain region CDRs of the antibody 1F4 and a variable light chain region comprising the variable light chain region CDRs of the antibody 1F4.

In another embodiment, provided herein is an antibody that binds to an influenza B virus NA, wherein the antibody comprises: (i) a variable heavy chain region complementarity determining region (CDR) 1 comprising the amino acid sequence of SEQ ID NO: 19, (ii) a variable heavy chain region CDR2 comprising the amino acid sequence of SEQ ID NO: 20, (iii) a variable heavy chain region CDR3 comprising the amino acid sequence of SEQ ID NO: 21, (iv) a variable light chain region complementarity determining region (CDR) 1 comprising the amino acid sequence of SEQ ID NO: 22, (v) a variable light chain region CDR2 comprising the amino acid sequence of SEQ ID NO: 23, and (vi) a variable light chain region CDR3 comprising the amino acid sequence of SEQ ID NO: 24.

In another embodiment, provided herein is an antibody that binds to an influenza B virus NA, wherein the antibody comprises: (a) a variable heavy chain region that is at least 95% identical to the amino acid sequence of SEQ ID NO: 17; (b) a variable light chain region that is at least 95% identical to the amino acid sequence of SEQ ID NO: 18; (c) a variable heavy chain region that is at least 95% identical to the amino acid sequences of SEQ ID NO: 17 and a variable light chain region that is at least 95% identical to the amino acid sequence of SEQ ID NO: 18; (d) a variable heavy chain region that is at least 95% identical to the amino acid sequence of SEQ ID NO: 17, wherein the variable heavy chain region comprises a variable heavy chain region CDR1 comprising the amino acid sequence of SEQ ID NO: 19, a variable heavy chain region CDR2 comprising the amino acid sequence of SEQ ID NO: 20, and a variable heavy chain region CDR3 comprising the amino acid sequence of SEQ ID NO: 21; (e) a variable light chain region that is least 95% identical to the amino acid sequence of SEQ ID NO: 18, wherein the variable light chain comprises a variable light chain region CDR1 comprising the amino acid sequence of SEQ ID NO: 22, a variable light chain region CDR2 comprising the amino acid sequence of SEQ ID NO: 23, and a variable light chain region CDR3 comprising the amino acid sequence of SEQ ID NO: 24; or (f) (I) a variable heavy chain region that is at least 95% identical to the amino acid sequences of SEQ ID NO: 17, wherein the variable heavy chain region comprises a variable heavy chain region CDR1 comprising the amino acid sequence of SEQ ID NO: 19, a variable heavy chain region CDR2 comprising the amino acid sequence of SEQ ID NO: 20: and a variable heavy chain region CDR3 comprising the amino acid sequence of SEQ ID NO: 21; and (II) a variable light chain region that is at least 95% identical to the amino acid sequence of SEQ ID NO: 18, wherein the variable light chain region comprises a variable light chain region CDR1 comprising the amino acid sequence of SEQ ID NO: 22, a variable light chain region CDR2 comprising the amino acid sequence of SEQ ID NO: 23, and a variable light chain region CDR3 comprising the amino acid sequence of SEQ ID NO: 24.

In another embodiment, provided herein is an antibody that binds to an influenza B virus NA, wherein the antibody comprises: (a) a variable heavy chain region comprising the variable heavy chain region CDRs of the antibody 4B2; (b) a variable light chain region comprising the variable light chain region CDRs of the antibody 4B2; or (c) a variable heavy chain region comprising the variable heavy chain region CDRs of the antibody 4B2 and a variable light chain region comprising the variable light chain region CDRs of the antibody 4B2.

In another embodiment, provided herein is an antibody that binds to an influenza B virus NA, wherein the antibody comprises: (i) a variable heavy chain region complementarity determining region (CDR) 1 comprising the amino acid sequence of SEQ ID NO: 51, (ii) a variable heavy chain region CDR2 comprising the amino acid sequence of SEQ ID NO: 52, (iii) a variable heavy chain region CDR3 comprising the amino acid sequence of SEQ ID NO: 53, (iv) a variable light chain region complementarity determining region (CDR) 1 comprising the amino acid sequence of SEQ ID NO: 54, (v) a variable light chain region CDR2 comprising the amino acid sequence of SEQ ID NO: 55, and (vi) a variable light chain region CDR3 comprising the amino acid sequence of SEQ ID NO: 56.

In another embodiment, provided herein is an antibody that binds to an influenza B virus NA, wherein the antibody comprises: (a) a variable heavy chain region comprising (i) a variable heavy chain region complementarity determining region (CDR) 1 comprising the amino acid sequence of SEQ ID NO: 51, (ii) a variable heavy chain region CDR2 comprising the amino acid sequence of SEQ ID NO: 52, (iii) a variable heavy chain region CDR3 comprising the amino acid sequence of SEQ ID NO: 53, and (b) a variable light chain region comprising (i) a variable light chain region complementarity determining region (CDR) 1 comprising the amino acid sequence of SEQ ID NO: 54, (ii) a variable light chain region CDR2 comprising the amino acid sequence of SEQ ID NO: 55, and (iii) a variable light chain region CDR3 comprising the amino acid sequence of SEQ ID NO: 56.

In another embodiment, provided herein is an antibody that binds to an influenza B virus NA, wherein the antibody comprises: (a) a variable heavy chain region that is at least 95% identical to the amino acid sequence of SEQ ID NO: 49; (b) a variable light chain region that is at least 95% identical to the amino acid sequence of SEQ ID NO: 50; (c) a variable heavy chain region that is at least 95% identical to the amino acid sequences of SEQ ID NO: 49 and a variable light chain region that is at least 95% identical to the amino acid sequence of SEQ ID NO: 50; (d) a variable heavy chain region that is at least 95% identical to the amino acid sequence of SEQ ID NO: 49, wherein the variable heavy chain region comprises a variable heavy chain region CDR1 comprising the amino acid sequence of SEQ ID NO: 51, a variable heavy chain region CDR2 comprising the amino acid sequence of SEQ ID NO: 52, and a variable heavy chain region CDR3 comprising the amino acid sequence of SEQ ID NO: 53; (e) a variable light chain region that is least 95% identical to the amino acid sequence of SEQ ID NO:50, wherein the variable light chain region comprises a variable light chain region CDR1 comprising the amino acid sequence of SEQ ID NO: 54, a variable light chain region CDR2 comprising the amino acid sequence of SEQ ID NO: 55, and a variable light chain region CDR3 comprising the amino acid sequence of SEQ ID NO: 56; or (f) (I) a variable heavy chain region that is at least 95% identical to the amino acid sequence of SEQ ID NO: 49, wherein the variable heavy chain region comprises a variable heavy chain region CDR1 comprising the amino acid sequence of SEQ ID NO: 51, a variable heavy chain region CDR2 comprising the amino acid sequence of SEQ ID NO: 52, and a variable heavy chain region CDR3 comprising the amino acid sequence of SEQ ID NO: 53; and (II) a variable light chain region that is at least 95% identical to the amino acid sequence of SEQ ID NO: 50, wherein the variable light chain region comprises a variable light chain region CDR1 comprising the amino acid sequence of SEQ ID NO: 54, a variable light chain region CDR2 comprising the amino acid sequence of SEQ ID NO: 55, and a variable light chain region CDR3 comprising the amino acid sequence of SEQ ID NO: 56.

In another embodiment, provided herein is an antibody that binds to an influenza B virus NA, wherein the antibody comprises: (a) a variable heavy chain region comprising the amino acid sequence of SEQ ID NO: 1 and a variable light chain region comprising the amino acid sequence of SEQ ID NO: 2; (b) a variable heavy chain region comprising the amino acid sequence of SEQ ID NO: 17 and a variable light chain region comprising the amino acid sequence of SEQ ID NO: 18; (c) a variable heavy chain region comprising the amino acid sequence of SEQ ID NO: 49 and a variable light chain region comprising the amino acid sequence of SEQ ID NO: 50; or (d) a variable heavy chain region comprising the amino acid sequence of SEQ ID NO: 65 and a variable light chain region comprising the amino acid sequence of SEQ ID NO: 66.

In a specific embodiment, an antibody provided herein comprises human-derived heavy and light chain constant regions. In a specific embodiment, the heavy chain constant region has an isotype selected from the group consisting of gamma1, gamma2, gamma3, and gamma4. In a specific embodiment, the light chain constant region has an isotype selected from the group consisting of kappa and lambda.

In a specific embodiment, an antibody provided herein is an immunoglobulin comprising two identical heavy chains and two identical light chains.

In a specific embodiment, an antibody provided herein comprises a heavy chain comprising the amino acid sequence of SEQ ID NO:185, 186, 187, 188, 189, 190, 191, 192, or 193.

In a specific embodiment, an antibody provided herein comprises a light chain comprising the amino acid sequence of SEQ ID NO:194, 195, 196, 197, 198, 199, 200, 201, or 202.

In a specific embodiment, an antibody provided herein comprises: (a) a heavy chain comprising the amino acid sequence of SEQ ID NO: 185, 186, 187, 188, 189, 190, 191, 192, or 193; and (b) a light chain comprising the amino acid sequence of SEQ ID NO:195, 196, 197, 198, 199, 200, 201, or 202.

In a specific embodiment, an antibody provided herein comprises: (a) a heavy chain comprising the amino acid sequence of SEQ ID NO:185; and (b) a light chain comprising the amino acid sequence of SEQ ID NO:194.

In a specific embodiment, an antibody provided herein is an IgG2a. In another specific embodiment, an antibody provided herein is an IgG1.

In a specific embodiment, an antibody provided herein is a monoclonal antibody. In a specific embodiment, an antibody provided herein is a chimeric antibody. In a specific embodiment, an antibody provided herein is a humanized antibody. In a specific embodiment, an antibody provided herein is an antigen-binding fragment. In a specific embodiment, an antibody provided herein is a single-chain variable fragment (scFv).

In a specific embodiment, an antibody provided herein is conjugated to a detectable agent or a therapeutic agent.

In another aspect, provided herein are polynucleotide sequences encoding antibodies described herein (see, e.g., 5.2, infra). In a specific embodiment, the polynucleotide sequences are isolated.

In a specific embodiment, provided herein is a polynucleotide encoding an antibody that binds to an NA of an influenza B virus strain, wherein the polynucleotide comprises: (a) a nucleotide sequence encoding a heavy chain variable region comprising the amino acid sequence of SEQ ID NO: 1 and a nucleotide sequence encoding a light chain variable region comprising the amino acid sequence of SEQ ID NO: 2; (b) a nucleotide sequence encoding a heavy chain variable region comprising the amino acid sequence of SEQ ID NO: 17 and a nucleotide sequence encoding a light chain variable region comprising the amino acid sequence of SEQ ID NO: 18; (c) a nucleotide sequence encoding a heavy chain variable region comprising the amino acid sequence of SEQ ID NO: 49 and a nucleotide sequence encoding a light chain variable region comprising the amino acid sequence of SEQ ID NO: 50; or (d) a nucleotide sequence encoding a heavy chain variable region comprising the amino acid sequence of SEQ ID NO: 65 and a nucleotide sequence encoding a light chain variable region comprising the amino acid sequence of SEQ ID NO: 66. In a specific embodiment, the polynucleotide sequences are isolated. In a specific embodiment, the polynucleotide sequence encodes a monoclonal antibody.

In a specific embodiment, provided herein is a polynucleotide encoding an antibody that binds to an NA of an influenza B virus strain, wherein the polynucleotide comprises: (a) a nucleotide sequence comprising the sequence of SEQ ID NO: 81 and a nucleotide sequence comprising the sequence of SEQ ID NO: 82; (b) a nucleotide sequence comprising the sequence of SEQ ID NO: 83 and a nucleotide sequence comprising the sequence of SEQ ID NO: 84; (c) a nucleotide sequence comprising the sequence of SEQ ID NO: 87 and a nucleotide sequence comprising the sequence of SEQ ID NO: 88; or (d) a nucleotide sequence comprising the sequence of SEQ ID NO: 89 and a nucleotide sequence comprising the sequence of SEQ ID NO: 90. In a specific embodiment, the polynucleotide sequences are isolated. In a specific embodiment, the polynucleotide sequence encodes a monoclonal antibody.

In a specific embodiment, provided herein is a polynucleotide encoding an antibody that binds to an NA of an influenza B virus strain, wherein the polynucleotide comprises a nucleotide sequence encoding a heavy chain variable region comprising the amino acid sequence of SEQ ID NO:168, 169, 170, 171, 172, 173, 174 or 175.

In a specific embodiment, provided herein is a polynucleotide encoding an antibody that binds to an NA of an influenza B virus strain, wherein the polynucleotide comprises a nucleotide sequence encoding a light chain variable region comprising the amino acid sequence of SEQ ID NO: 177, 178, 179, 180, 181, 182, 183, or 184.

In a specific embodiment, provided herein is a polynucleotide encoding an antibody that binds to an NA of an influenza B virus strain, wherein the polynucleotide comprises: (a) a nucleotide sequence encoding a heavy chain variable region comprising the amino acid sequence of SEQ ID NO: 168, 169, 170, 171, 172, 173, 174 or 175; and (b) a nucleotide sequence encoding a light chain variable region comprising the amino acid sequence of SEQ ID NO: 177, 178, 179, 180, 181, 182, 183, or 184.

In a specific embodiment, provided herein is a polynucleotide encoding an antibody that binds to an NA of an influenza B virus strain, wherein the polynucleotide comprises a nucleotide sequence encoding a heavy chain comprising the amino acid sequence of SEQ ID NO: 185, 186, 187, 188, 189, 190, 191, 192, or 193.

In a specific embodiment, provided herein is a polynucleotide encoding an antibody that binds to an NA of an influenza B virus strain, wherein the polynucleotide comprises a nucleotide sequence encoding a light chain comprising the amino acid sequence of SEQ ID NO: 194, 195, 196, 197, 198, 199, 200, 201, or 202.

In a specific embodiment, provided herein is a polynucleotide encoding an antibody that binds to an NA of an influenza B virus strain, wherein the polynucleotide comprises: (a) a nucleotide sequence encoding a heavy chain comprising the amino acid sequence of SEQ ID NO: 186, 187, 188, 189, 190, 191, 192, or 193; and (b) a nucleotide sequence encoding a light chain comprising the amino acid sequence of SEQ ID NO: 195, 196, 197, 198, 199, 200, 201, or 202.

In a specific embodiment, provided herein is a polynucleotide encoding an antibody that binds to an NA of an influenza B virus strain, wherein the polynucleotide comprises: (a) a nucleotide sequence encoding a heavy chain comprising the amino acid sequence of SEQ ID NO:185; and (b) a nucleotide sequence encoding a light chain comprising the amino acid sequence of SEQ ID NO:194.

In another aspect, provided herein are expression vectors comprising a polynucleotide encoding an antibody described herein (see, e.g., Section 5.2, infra). In a specific embodiment, an expression vector provided herein is operably linked to one or more regulatory regions.

In another aspect, provided herein are host cells comprising a polynucleotide encoding an antibody described herein (see, e.g., Section 5.3, infra). In a specific embodiment, provided herein are host cells engineered to express an antibody described herein (e.g., Section 5.3, infra). The host cells may be used to produce the antibody using techniques known to one of skill in the art or described herein (see, e.g., Section 5.3, infra).

In a specific embodiment, the host cell comprises: (a) (I) a polynucleotide comprising a nucleotide sequence encoding a variable heavy chain region comprising a variable heavy chain region complementarity determining region (CDR) 1 comprising the amino acid sequence of SEQ ID NO: 3, a variable heavy chain region CDR2 comprising the amino acid sequence of SEQ ID NO: 4, and a variable heavy chain region CDR3 comprising the amino acid sequence of SEQ ID NO: 5; and (II) a polynucleotide encoding a variable light chain region comprising a variable light chain region complementarity determining region (CDR) 1 comprising the amino acid sequence of SEQ ID NO: 6, a variable light chain region CDR2 comprising the amino acid sequence of SEQ ID NO: 7, and a variable light chain region CDR3 comprising the amino acid sequence of SEQ ID NO: 8; or (b) (I) a polynucleotide encoding a variable heavy chain region that is at least 95% identical to the amino acid sequence of SEQ ID NO: 1, wherein the variable heavy chain region comprises a variable heavy chain region CDR1 comprising the amino acid sequence of SEQ ID NO: 3, a variable heavy chain region CDR2 comprising the amino acid sequence of SEQ ID NO: 4, and a variable heavy chain region CDR3 comprising the amino acid sequence of SEQ ID NO: 5; and (II) a polynucleotide encoding a variable light chain region that is at least 95% identical to the amino acid sequence of SEQ ID NO: 2, wherein the variable light chain region comprises a variable light chain region CDR1 comprising the amino acid sequence of SEQ ID NO: 6, a variable light chain region CDR2 comprising the amino acid sequence of SEQ ID NO: 7, and a variable light chain region CDR3 comprising the amino acid sequence of SEQ ID NO: 8.

In a specific embodiment, the host cell comprises: (a) a polynucleotide encoding a variable heavy chain region that is at least 78% identical to the amino acid sequence of SEQ ID NO: 1, wherein the variable heavy chain region comprises a variable heavy chain region CDR1 comprising the amino acid sequence of SEQ ID NO: 3, a variable heavy chain region CDR2 comprising the amino acid sequence of SEQ ID NO: 4, and a variable heavy chain region CDR3 comprising the amino acid sequence of SEQ ID NO: 5; and (b) a polynucleotide encoding a variable light chain region that is at least 78% identical to the amino acid sequence of SEQ ID NO: 2, wherein the variable light chain region comprises a variable light chain region CDR1 comprising the amino acid sequence of SEQ ID NO: 6, a variable light chain region CDR2 comprising the amino acid sequence of SEQ ID NO: 7, and a variable light chain region CDR3 comprising the amino acid sequence of SEQ ID NO: 8.

In a specific embodiment, the host cell comprises: (a) a polynucleotide encoding a variable heavy chain region that is at least 78% identical to the amino acid sequence of SEQ ID NO: 1, wherein the variable heavy chain region comprises a variable heavy chain region CDR1 comprising the amino acid sequence of SEQ ID NO: 3, a variable heavy chain region CDR2 comprising the amino acid sequence of SEQ ID NO: 4, and a variable heavy chain region CDR3 comprising the amino acid sequence of SEQ ID NO: 5; and (b) a polynucleotide encoding a variable light chain region that is at least 78% identical to the amino acid sequence of SEQ ID NO: 2, wherein the variable light chain region comprises a variable light chain region CDR1 comprising the amino acid sequence of SEQ ID NO: 6, a variable light chain region CDR2 comprising the amino acid sequence of SEQ ID NO: 7, and a variable light chain region CDR3 comprising the amino acid sequence of SEQ ID NO: 8.

In a specific embodiment, the host cell comprises: (a) a polynucleotide encoding a variable heavy chain region that is at least 78% or at least 80% identical to the amino acid sequence of SEQ ID NO: 1, wherein the variable heavy chain region comprises a variable heavy chain region CDR1 comprising the amino acid sequence of SEQ ID NO: 3, a variable heavy chain region CDR2 comprising the amino acid sequence of SEQ ID NO: 4, and a variable heavy chain region CDR3 comprising the amino acid sequence of SEQ ID NO: 5; and (b) a polynucleotide encoding a variable light chain region that is at least 78% or at least 80% identical to the amino acid sequence of SEQ ID NO: 2, wherein the variable light chain region comprises a variable light chain region CDR1 comprising the amino acid sequence of SEQ ID NO: 6, a variable light chain region CDR2 comprising the amino acid sequence of SEQ ID NO: 7, and a variable light chain region CDR3 comprising the amino acid sequence of SEQ ID NO: 8.

In a specific embodiment, the host cell comprises: (a) a polynucleotide encoding a variable heavy chain region that is at least 78% or at least 85% identical to the amino acid sequence of SEQ ID NO: 1, wherein the variable heavy chain region comprises a variable heavy chain region CDR1 comprising the amino acid sequence of SEQ ID NO: 3, a variable heavy chain region CDR2 comprising the amino acid sequence of SEQ ID NO: 4, and a variable heavy chain region CDR3 comprising the amino acid sequence of SEQ ID NO: 5; and (b) a polynucleotide encoding a variable light chain region that is at least 78% or at least 80% identical to the amino acid sequence of SEQ ID NO: 2, wherein the variable light chain region comprises a variable light chain region CDR1 comprising the amino acid sequence of SEQ ID NO: 6, a variable light chain region CDR2 comprising the amino acid sequence of SEQ ID NO: 7, and a variable light chain region CDR3 comprising the amino acid sequence of SEQ ID NO: 8.

In a specific embodiment, the host cell comprises: (a) a polynucleotide encoding a variable heavy chain region that is at least 78% or at least 90% identical to the amino acid sequence of SEQ ID NO: 1, wherein the variable heavy chain region comprises a variable heavy chain region CDR1 comprising the amino acid sequence of SEQ ID NO: 3, a variable heavy chain region CDR2 comprising the amino acid sequence of SEQ ID NO: 4, and a variable heavy chain region CDR3 comprising the amino acid sequence of SEQ ID NO: 5; and (b) a polynucleotide encoding a variable light chain region that is at least 90% identical to the amino acid sequence of SEQ ID NO: 2, wherein the variable light chain region comprises a variable light chain region CDR1 comprising the amino acid sequence of SEQ ID NO: 6, a variable light chain region CDR2 comprising the amino acid sequence of SEQ ID NO: 7, and a variable light chain region CDR3 comprising the amino acid sequence of SEQ ID NO: 8.

In a specific embodiment, the host cell comprises: (a) (I) a polynucleotide comprising a nucleotide sequence encoding a variable heavy chain region comprising a variable heavy chain region complementarity determining region (CDR) 1 comprising the amino acid sequence of SEQ ID NO: 19, a variable heavy chain region CDR2 comprising the amino acid sequence of SEQ ID NO: 20, and a variable heavy chain region CDR3 comprising the amino acid sequence of SEQ ID NO: 21; and (II) a polynucleotide comprising a nucleotide sequence encoding a variable light chain region comprising a variable light chain region complementarity determining region (CDR) 1 comprising the amino acid sequence of SEQ ID NO: 22, a variable light chain region CDR2 comprising the amino acid sequence of SEQ ID NO: 23, and a variable light chain region CDR3 comprising the amino acid sequence of SEQ ID NO: 24; or (b) (I) a polynucleotide encoding a variable heavy chain region that is at least 95% identical to the amino acid sequence of SEQ ID NO: 17, wherein the variable heavy chain region comprises a variable heavy chain region CDR1 comprising the amino acid sequence of SEQ ID NO: 19, a variable heavy chain region CDR2 comprising the amino acid sequence of SEQ ID NO: 20, and a variable heavy chain region CDR3 comprising the amino acid sequence of SEQ ID NO: 21; and (II) a polynucleotide encoding a variable light chain region that is at least 95% identical to the amino acid sequence of SEQ ID NO: 18, wherein the variable light chain region comprises a variable light chain region CDR1 comprising the amino acid sequence of SEQ ID NO: 22, a variable light chain region CDR2 comprising the amino acid sequence of SEQ ID NO: 23, and a variable light chain region CDR3 comprising the amino acid sequence of SEQ ID NO: 24.

In a specific embodiment, the host cell comprises: (a) (I) a polynucleotide comprising a nucleotide sequence encoding a variable heavy chain region comprising a variable heavy chain region complementarity determining region (CDR) 1 comprising the amino acid sequence of SEQ ID NO: 51, a variable heavy chain region CDR2 comprising the amino acid sequence of SEQ ID NO: 52, and a variable heavy chain region CDR3 comprising the amino acid sequence of SEQ ID NO: 53; and (II) a polynucleotide comprising a nucleotide sequence encoding a variable light chain region comprising a variable light chain region complementarity determining region (CDR) 1 comprising the amino acid sequence of SEQ ID NO: 54, a variable light chain region CDR2 comprising the amino acid sequence of SEQ ID NO: 55, and a variable light chain region CDR3 comprising the amino acid sequence of SEQ ID NO: 56; or (b) (I) a polynucleotide encoding a variable heavy chain region that is at least 95% identical to the amino acid sequence of SEQ ID NO: 49, wherein the variable heavy chain region comprises a variable heavy chain region CDR1 comprising the amino acid sequence of SEQ ID NO: 51, a variable heavy chain region CDR2 comprising the amino acid sequence of SEQ ID NO: 52, and a variable heavy chain region CDR3 comprising the amino acid sequence of SEQ ID NO: 53; and (II) a polynucleotide encoding a variable light chain region that is at least 95% identical to the amino acid sequence of SEQ ID NO: 50, wherein the variable light chain region comprises a variable light chain region CDR1 comprising the amino acid sequence of SEQ ID NO: 54, a variable light chain region CDR2 comprising the amino acid sequence of SEQ ID NO: 55, and a variable light chain region CDR3 comprising the amino acid sequence of SEQ ID NO: 56.

In a specific embodiment, the host cell comprises: (a) (I) a first expression vector comprising polynucleotide encoding a variable heavy chain region comprising a variable heavy chain region complementarity determining region (CDR) 1 comprising the amino acid sequence of SEQ ID NO: 3, a variable heavy chain region CDR2 comprising the amino acid sequence of SEQ ID NO: 4, and a variable heavy chain region CDR3 comprising the amino acid sequence of SEQ ID NO: 5; and (II) a second expression vector comprising a polynucleotide encoding a variable light chain region comprising a variable light chain region complementarity determining region (CDR) 1 comprising the amino acid sequence of SEQ ID NO: 6, a variable light chain region CDR2 comprising the amino acid sequence of SEQ ID NO: 7, (vi) a variable light chain region CDR3 comprising the amino acid sequence of SEQ ID NO: 8; or (b) (I) a first expression vector comprising a polynucleotide encoding a variable heavy chain region that is at least 95% identical to the amino acid sequence of SEQ ID NO: 1, wherein the variable heavy chain region comprises a variable heavy chain region CDR1 comprising the amino acid sequence of SEQ ID NO: 3, a variable heavy chain region CDR2 comprising the amino acid sequence of SEQ ID NO: 4, and a variable heavy chain region CDR3 comprising the amino acid sequence of SEQ ID NO: 5; and (II) a second expression vector comprising a polynucleotide encoding a variable light chain region that is at least 95% identical to the amino acid sequence of SEQ ID NO: 2, wherein the variable light chain region comprises a variable light chain region CDR1 comprising the amino acid sequence of SEQ ID NO: 6, a variable light chain region CDR2 comprising the amino acid sequence of SEQ ID NO: 7, and a variable light chain region CDR3 comprising the amino acid sequence of SEQ ID NO: 8. In a specific embodiment, the first and second expression vectors each comprise one or more regulatory regions operably linked to the polynucleotide.

In a specific embodiment, a host cell(s) comprises: (a) a first expression vector comprising a polynucleotide encoding a variable heavy chain region that is at least 78% identical to the amino acid sequence of SEQ ID NO: 1, wherein the variable heavy chain region comprises a variable heavy chain region CDR1 comprising the amino acid sequence of SEQ ID NO: 3, a variable heavy chain region CDR2 comprising the amino acid sequence of SEQ ID NO: 4, and a variable heavy chain region CDR3 comprising the amino acid sequence of SEQ ID NO: 5; and (b) a second expression vector comprising a polynucleotide encoding a variable light chain region that is at least 78% identical to the amino acid sequence of SEQ ID NO: 2, wherein the variable light chain region comprises a variable light chain region CDR1 comprising the amino acid sequence of SEQ ID NO: 6, a variable light chain region CDR2 comprising the amino acid sequence of SEQ ID NO: 7, and a variable light chain region CDR3 comprising the amino acid sequence of SEQ ID NO: 8. In a specific embodiment, the first and second expression vectors each comprise one or more regulatory regions operably linked to the polynucleotide.

In a specific embodiment, a host cell(s) comprises: (a) a first expression vector comprising a polynucleotide encoding a variable heavy chain region that is at least 80% or at least 85% identical to the amino acid sequence of SEQ ID NO: 1, wherein the variable heavy chain region comprises a variable heavy chain region CDR1 comprising the amino acid sequence of SEQ ID NO: 3, a variable heavy chain region CDR2 comprising the amino acid sequence of SEQ ID NO: 4, and a variable heavy chain region CDR3 comprising the amino acid sequence of SEQ ID NO: 5; and (b) a second expression vector comprising a polynucleotide encoding a variable light chain region that is at least 78% or at least 80% identical to the amino acid sequence of SEQ ID NO: 2, wherein the variable light chain region comprises a variable light chain region CDR1 comprising the amino acid sequence of SEQ ID NO: 6, a variable light chain region CDR2 comprising the amino acid sequence of SEQ ID NO: 7, and a variable light chain region CDR3 comprising the amino acid sequence of SEQ ID NO: 8. In a specific embodiment, the first and second expression vectors each comprise one or more regulatory regions operably linked to the polynucleotide.

In a specific embodiment, the host cell comprises: (a) a first expression vector comprising a polynucleotide encoding a variable heavy chain region that is at least 80% or at least 90% identical to the amino acid sequence of SEQ ID NO: 1, wherein the variable heavy chain region comprises a variable heavy chain region CDR1 comprising the amino acid sequence of SEQ ID NO: 3, a variable heavy chain region CDR2 comprising the amino acid sequence of SEQ ID NO: 4, and a variable heavy chain region CDR3 comprising the amino acid sequence of SEQ ID NO: 5; and (b) a second expression vector comprising a polynucleotide encoding a variable light chain region that is at least 90% identical to the amino acid sequence of SEQ ID NO: 2, wherein the variable light chain region comprises a variable light chain region CDR1 comprising the amino acid sequence of SEQ ID NO: 6, a variable light chain region CDR2 comprising the amino acid sequence of SEQ ID NO:

7, and a variable light chain region CDR3 comprising the amino acid sequence of SEQ ID NO: 8. In a specific embodiment, the first and second expression vectors each comprise one or more regulatory regions operably linked to the polynucleotide.

In a specific embodiment, the host cell comprises: (a) (I) a first expression vector comprising a polynucleotide encoding a variable heavy chain region comprising a variable heavy chain region complementarity determining region (CDR) 1 comprising the amino acid sequence of SEQ ID NO: 19, a variable heavy chain region CDR2 comprising the amino acid sequence of SEQ ID NO: 20, and a variable heavy chain region CDR3 comprising the amino acid sequence of SEQ ID NO: 21; and (II) a second expression vector comprising a polynucleotide encoding a variable light chain region comprising a variable light chain region complementarity determining region (CDR) 1 comprising the amino acid sequence of SEQ ID NO: 22, a variable light chain region CDR2 comprising the amino acid sequence of SEQ ID NO: 23, and a variable light chain region CDR3 comprising the amino acid sequence of SEQ ID NO: 24; or (b) (I) a first expression vector comprising a polynucleotide encoding a variable heavy chain region that is at least 95% identical to the amino acid sequence of SEQ ID NO: 17, wherein the variable heavy chain region comprises a variable heavy chain region CDR1 comprising the amino acid sequence of SEQ ID NO: 19, a variable heavy chain region CDR2 comprising the amino acid sequence of SEQ ID NO: 20, and a variable heavy chain region CDR3 comprising the amino acid sequence of SEQ ID NO: 21; and (II) a second expression vector comprising a polynucleotide encoding a variable light chain region that is at least 95% identical to the amino acid sequence of SEQ ID NO: 18, wherein the variable light chain region comprises a variable light chain region CDR1 comprising the amino acid sequence of SEQ ID NO: 22, a variable light chain region CDR2 comprising the amino acid sequence of SEQ ID NO: 23, and a variable light chain region CDR3 comprising the amino acid sequence of SEQ ID NO: 24. In a specific embodiment, the first and second expression vectors each comprise one or more regulatory regions operably linked to the polynucleotide.

In a specific embodiment, the host cell comprises: (a) (I) a first expression vector comprising a polynucleotide encoding a variable heavy chain region comprising a variable heavy chain region complementarity determining region (CDR) 1 comprising the amino acid sequence of SEQ ID NO: 51, a variable heavy chain region CDR2 comprising the amino acid sequence of SEQ ID NO: 52, and a variable heavy chain region CDR3 comprising the amino acid sequence of SEQ ID NO: 53; and (II) a second expression vector comprising a polynucleotide encoding a variable light chain region comprising a variable light chain region complementarity determining region (CDR) 1 comprising the amino acid sequence of SEQ ID NO: 54, (v) a variable light chain region CDR2 comprising the amino acid sequence of SEQ ID NO: 55, and (vi) a variable light chain region CDR3 comprising the amino acid sequence of SEQ ID NO: 56; or (b) (I) a first expression vector comprising a polynucleotide encoding a variable heavy chain region that is at least 95% identical to the amino acid sequence of SEQ ID NO: 49, wherein the variable heavy chain region comprises a variable heavy chain region CDR1 comprising the amino acid sequence of SEQ ID NO: 51, a variable heavy chain region CDR2 comprising the amino acid sequence of SEQ ID NO: 52, and a variable heavy chain region CDR3 comprising the amino acid sequence of SEQ ID NO: 53; and (II) a second expression vector comprising a polynucleotide encoding a variable light chain region that is at least 95% identical to the amino acid sequence of SEQ ID NO: 50, wherein the variable light chain region comprises a variable light chain region CDR1 comprising the amino acid sequence of SEQ ID NO: 54, a variable light chain region CDR2 comprising the amino acid sequence of SEQ ID NO: 55, and a variable light chain region CDR3 comprising the amino acid sequence of SEQ ID NO: 56. In a specific embodiment, the first and second expression vectors each comprise one or more regulatory regions operably linked to the polynucleotide.

In another specific embodiment, a host cell(s) comprises a polynucleotide sequence encoding a variable heavy chain region, wherein the variable heavy chain region comprises the amino acid sequence of SEQ ID NO:168, 169, 170, 171, 172, 173, 174 or 175. In another specific embodiment, a host cell(s) comprises a polynucleotide sequence encoding a variable light chain region, wherein the variable light chain region comprises the amino acid sequence of SEQ ID NO: 177, 178, 179, 180, 181, 182, 183, or 184.

In another specific embodiment, a host cell(s) comprises a polynucleotide sequence encoding a variable heavy chain region and a polynucleotide sequence encoding a variable light chain region, wherein the variable heavy chain region comprises the amino acid sequence of SEQ ID NO: 168, 169, 170, 171, 172, 173, 174 or 175, and wherein the variable light chain region comprises the amino acid sequence of SEQ ID NO: 177, 178, 179, 180, 181, 182, 183, or 184.

In another specific embodiment, a host cell(s) comprises a polynucleotide sequence encoding a heavy chain, wherein the heavy chain comprises the amino acid sequence of SEQ ID NO: 185, 186, 187, 188, 189, 190, 191, 192, or 193. In another specific embodiment, a host cell(s) comprises a polynucleotide sequence encoding a light chain, wherein the light chain comprises the amino acid sequence of SEQ ID NO:194, 195, 196, 197, 198, 199, 200, 201, or 202.

In another specific embodiment, a host cell(s) comprises a polynucleotide sequence encoding a heavy chain and a polynucleotide sequence encoding a light chain, wherein the heavy chain comprises the amino acid sequence of SEQ ID NO: 186, 187, 188, 189, 190, 191, 192, or 193, and wherein the light chain comprises the amino acid sequence of SEQ ID NO: 195, 196, 197, 198, 199, 200, 201, or 202.

In another specific embodiment, a host cell(s) comprises a polynucleotide sequence encoding a heavy chain and a polynucleotide sequence encoding a light chain, wherein the heavy chain comprises the amino acid sequence of SEQ ID NO:185, and wherein the light chain comprises the amino acid sequence of SEQ ID NO:194.

In another aspect, provided herein are compositions comprising an antibody described herein (e.g., an antibody described in Section 5.1, infra). Such compositions may comprise an additional agent such as an antiviral or an antibody that binds to hemagglutinin (HA). The compositions described herein may be used in the methods of prevention, treatment, or diagnosis described herein. In a particular embodiment, the compositions may be used to prevent an influenza virus disease (e.g., influenza B virus disease). In another particular embodiment, the compositions may be used to treat an influenza virus infection (e.g., an influenza B virus infection) or an influenza virus disease (e.g., an influenza B virus disease).

In another aspect, provided herein are methods for preventing influenza virus disease (e.g., influenza B virus disease) comprising administering to a subject in need thereof an antibody described herein, or a composition comprising such an antibody. See, e.g., Section 5.5, infra, for methods of preventing influenza virus disease (e.g., influenza B virus disease). In a specific embodiment, the method further comprises administering to the subject an antibody that binds to a hemagglutinin (HA) of an influenza virus. In certain embodiments, such an antibody binds to the globular head domain of the influenza virus HA. In other embodiments, such an antibody binds to the stem domain of the influenza virus HA. In specific embodiments, the method further comprises administering two antibodies that bind to HA of an influenza virus, wherein one of these antibodies binds to the globular head domain of HA and the other antibody binds to the stem domain of HA. In a specific embodiment, the method further comprises administering to the subject an antibody that binds to an NA of an influenza A strain. In a specific embodiment, the antibody is administered intranasally to subject. In particular embodiments, the antibody that binds to NA of an influenza B virus is administered intranasally to the subject. In a specific embodiment, the antibody is administered parenterally to the subject. In particular embodiments, the antibody that binds to NA of an influenza B virus is administered parentally to the subject. In a specific embodiment, the subject is a human. In a specific embodiment, the subject is a human infant or human toddler. In a specific embodiment, the subject is an elderly human.

In another aspect, provided herein are methods for treating an influenza virus (e.g., influenza B virus) infection or an influenza virus disease (e.g., an influenza B virus disease) comprising administering to a subject in need thereof an antibody described herein, or composition comprising such an antibody. See, e.g., Section 5.5, infra, for methods of treating an influenza virus (e.g., influenza B virus) infection or an influenza virus disease (e.g., influenza B virus disease). In a specific embodiment, the antibody is administered to the subject within 72 hours of the onset of symptoms of an influenza virus infection or an influenza virus disease. In a specific embodiment, the antibody is administered 12 to 72 hours after the onset of symptoms of an influenza virus infection or an influenza virus disease. In a specific embodiment, the antibody is administered 12 to 48 hours after the onset of symptoms of an influenza virus infection or an influenza virus disease. In a specific embodiment, the subject is diagnosed with an influenza virus infection or an influenza virus disease. In a specific embodiment, the influenza virus infection or influenza virus disease is diagnosed as an influenza B virus infection or influenza virus disease caused by an influenza B virus. In a specific embodiment, the subject is refractory to treatment with an antiviral agent. In a specific embodiment, the subject is refractory to treatment with an NA inhibitor. In a specific embodiment, the subject is refractory to oseltamivir or zanamivir. In a specific embodiment, the method further comprises administering to the subject an antiviral agent, such as, e.g., an NA inhibitor (such as, e.g., oseltamivir or zanamivir) or baloxavir marboxil. In a specific embodiment, the method further comprises administering to the subject an antiviral agent, such as, e.g., a cap-dependent endonuclease inhibitor or polymerase inhibitor. In a specific embodiment, the method further comprises administering to the subject an antibody that binds to a hemagglutinin (HA) of an influenza virus. In certain embodiments, such an antibody binds to the globular head domain of the influenza virus HA. In other embodiments, such an antibody binds to the stem domain of the influenza virus HA. In specific embodiments, the method further comprises administering two antibodies that bind to HA of an influenza virus, wherein one of these antibodies binds to the globular head domain of HA and the other antibody binds to the stem domain of HA. In a specific embodiment, the method further comprises administering to the subject an antibody that binds to an NA of an influenza A strain. In a specific embodiment, the antibody is administered intranasally to subject. In a specific embodiment, the antibody is administered parenterally to the subject. In a specific embodiment, the subject is a human. In a specific embodiment, the subject is a human infant or human toddler. In a specific embodiment, the subject is an elderly human.

In another aspect, provided herein are methods for detecting an influenza B virus, or diagnosing an influenza B virus infection. See, e.g., Section 5.6, infra, for more regarding such methods.

In another aspect, provided herein are influenza virus neuraminidase polypeptides as well as antigenic peptides which may be used as immunogens to induce an immune response to influenza virus (e.g., influenza B virus).

In another aspect, provided herein are kits comprising an antibody described herein (see, e.g., Sections 5.1 and 5.2). In a specific embodiment, provided herein is a kit comprising an antibody described herein, and optionally instructions for use of the antibody in the prevention or treatment of an influenza virus infection or an influenza virus disease, or in the detection of an influenza B virus.

In another aspect, provided herein is an isolated influenza virus neuraminidase antigenic peptide comprising an epitope of the antibody 1F2, 1F4, or 4B2.

4. DESCRIPTION OF THE FIGURES

Figure 1B:
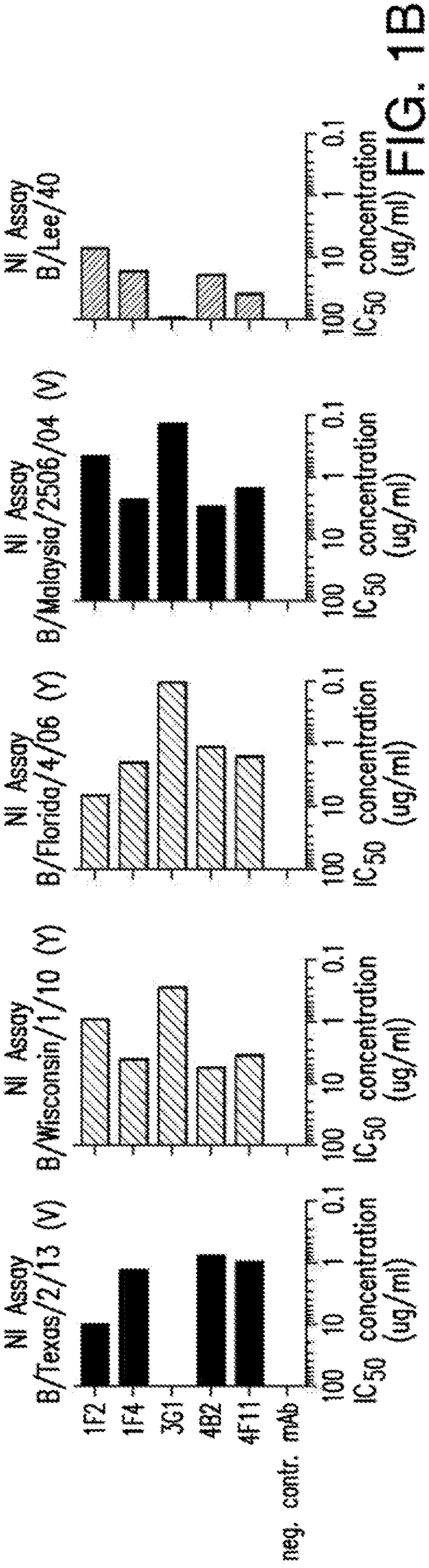
Figure 1C:
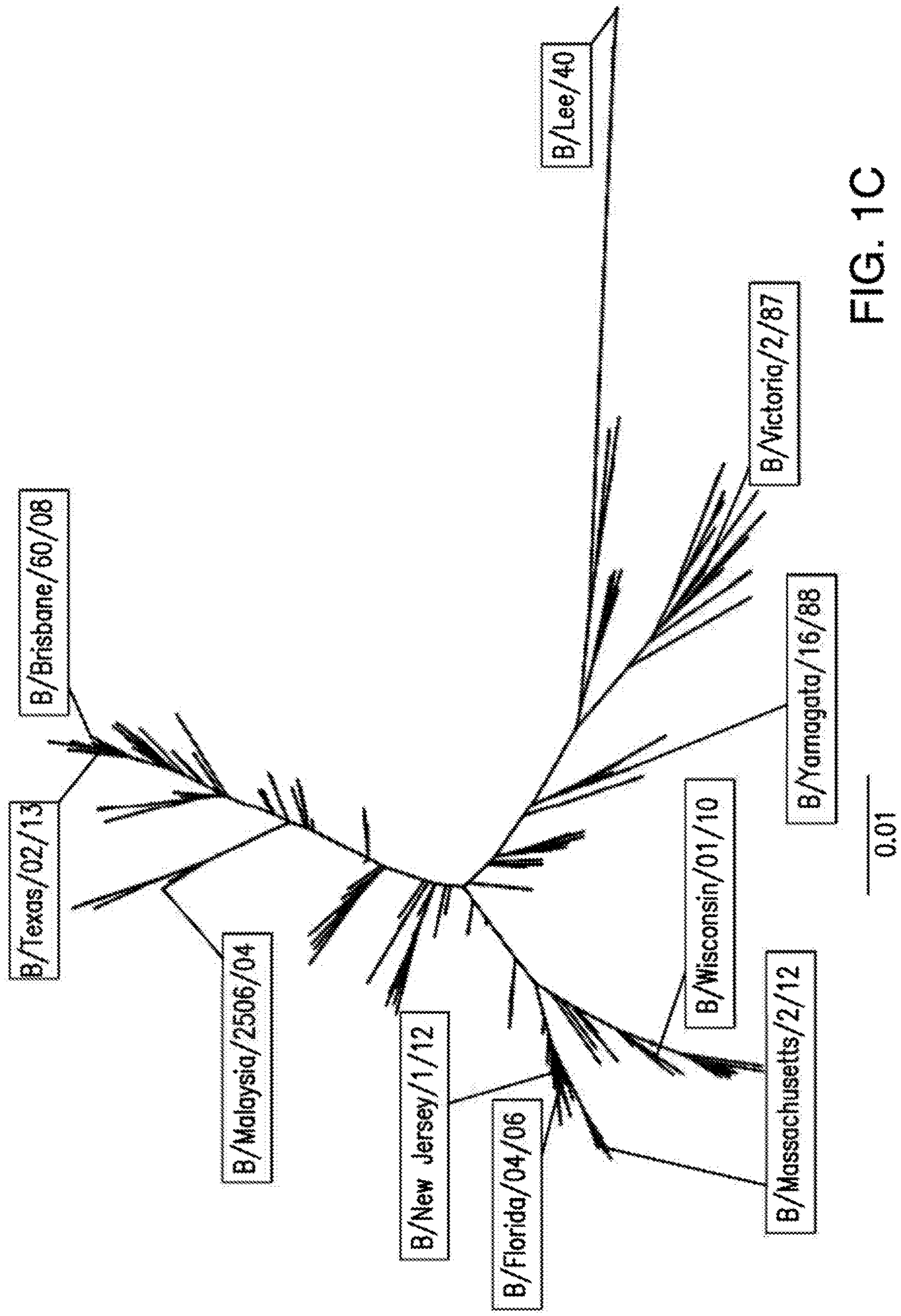

FIGS. 1A-C. In vitro binding of IBV anti-NA mAbs. FIG. 1A: Bar graphs represent the minimal binding concentrations of anti-NA mAbs to either rNA (top, coated at 2 ug/mL), or purified whole virus (bottom, coated at 5 ug/mL) as measured by ELISA. rHA from B/Yamagata/16/88 was used as a negative control substrate. Binding at concentrations higher than 10 ug/ml was detected for some mAb/NA combinations but is not displayed. FIG. 1B: MAbs were tested via ELLA to assess NI activity; bar graphs represent $IC_{50}$ values. All samples were analyzed in duplicate with the mean and standard error of the mean displayed graphically. Victoria lineage strains (with lineage referring to the HA) are marked with a "(V)", Yamagata lineage strains are marked with a "(Y)", and the ancestral B/Lee strain is labeled B/Lee/40. MAb 8H9 (anti-H6, murine IgG1) was used as a negative control. FIG. 1C: Phylogenetic tree based on the amino acid sequence of the B NA of 280 randomly subsampled IBV strains spanning all years since IBV was first isolated (1940-present). The scale bar represents a 1% difference in amino acid sequence.

Figure 2A:
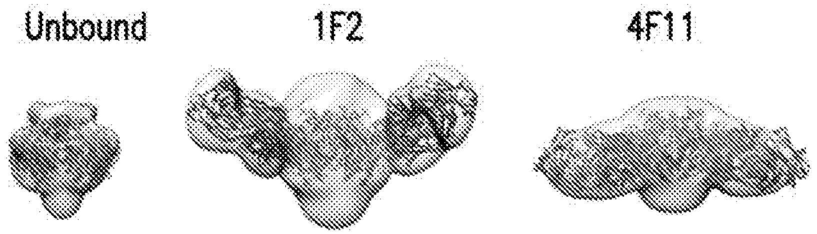
Figure 2B:
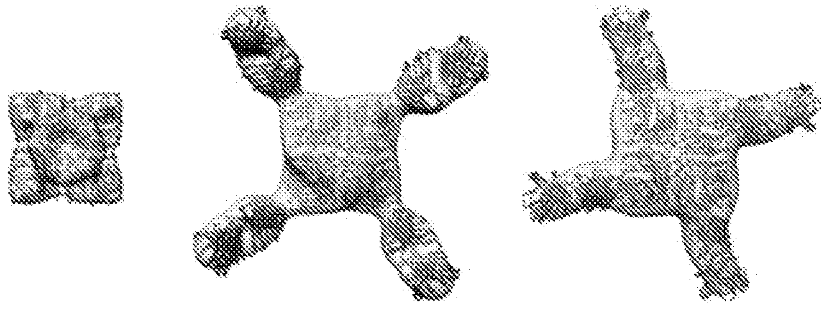
Figure 2C:
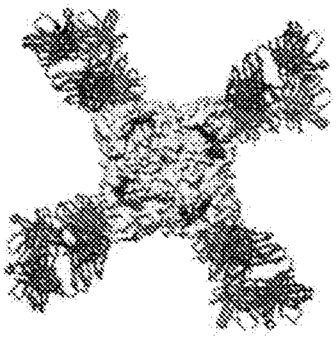
Figure 2D:
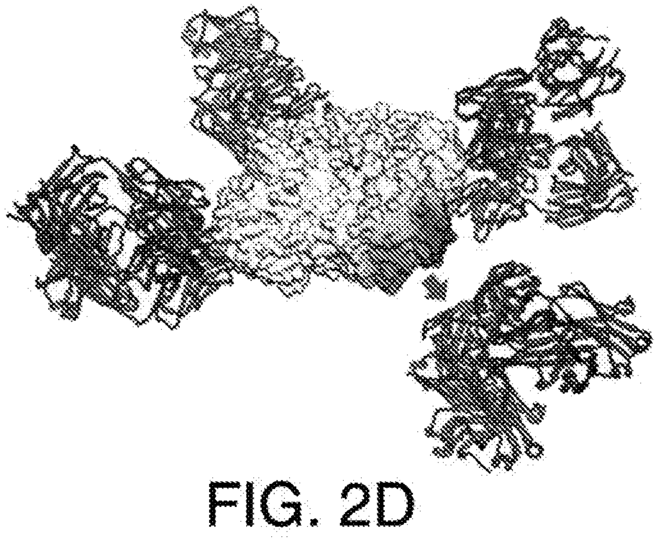
Figure 2E:
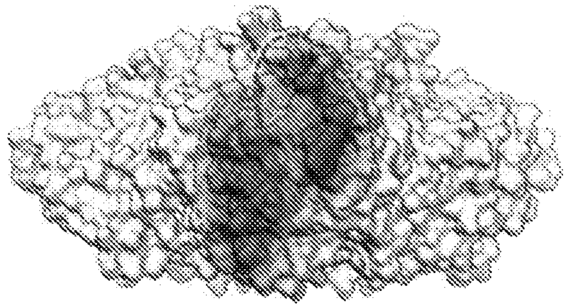

FIGS. 2A-2E. Negative stain electron microscopic analysis of NA structures reveals binding footprints for 1F2 and 4F11. Side view (FIG. 2A) or top view (FIG. 2B) isosurface representations of unbound, 1F2, and 4F11 bound NA density maps (from left to right) fitted with coordinates for the NA tetramer and Fab (1F2 in the middle and 4F11 on the right) x-ray coordinates. FIG. 2A and FIG. 2B are superimposed in top (FIG. 2C) and oblique (FIG. 2D) views of the IBV NA-Fab complexes. The top view also highlights the location of active site and framework residues. In the oblique view, the 1F2 and 4F11 binding footprints are highlighted on the surface of the NA tetramer, with the corresponding Fab coordinates displaced away from the highlighted epitope region for purposes of visualization (grey arrow, FIG. 2D). Binding footprints of both Fabs are shown on a single NA tetramer to highlight their non-overlapping, but spatially adjacent locations (FIG. 2E). Residues within the binding footprint are colored as a heat map based on percent amino acid conservation.

Figure 3A:
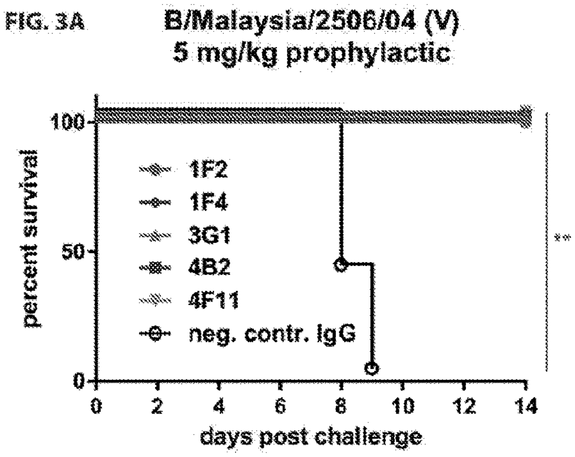
Figure 3D:
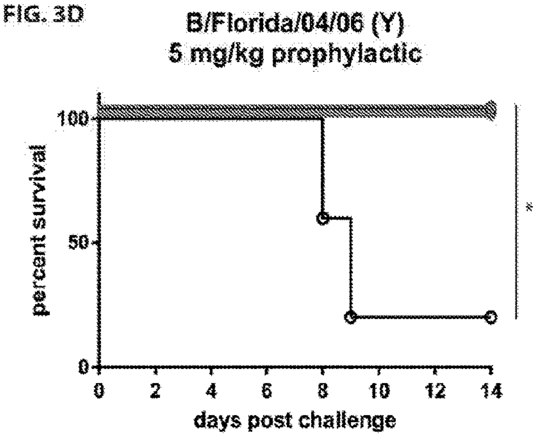

FIGS. 3A-3F. In vivo efficacy of IBV anti-NA mAbs. To test prophylactic efficacy, female BALB/c mice (5 per group) were administered either 5, 1, or 0.5 mg/kg of mAb intraperitoneally 2 h prior to a 5 $mLD_{50}$ challenge with B/Malaysia/2506/04 virus (FIG. 3A-C) or administered 5 mg/kg of mAb intraperitoneally 2 h prior to a 5 mLD50 challenge with B/Florida/04/06 virus (FIG. 3D). To test therapeutic efficacy, mice were administered 5 mg/kg of each antibody either 24 (FIG. 3E) or 48 (FIG. 3F) h after challenge with 5 $mLD_{50}$ B/Malaysia/2506/04 virus. Murine mAb 8H9 was used as a negative control in all experiments.

FIGS. 4A-4F. Non-neutralizing IBV anti-NA mAbs reduce viral lung titers in mice, activate ADCC, inhibit activity of a drug-resistant IBV, and demonstrate superior effectiveness to oseltamivir. (FIG. 4A) Female BALB/c mice (3 per group) were administered 5 mg/kg antibody prophylactically, challenged with B/Malaysia/2506/04 virus in identical fashion to FIG. 3A, and sacrificed on day 3 or 6 post-infection for lung titer analysis. Lung titers in groups treated with anti-NA mAbs are most significantly reduced on day 6 post-infection compared to negative control mAb 8H9. When added to both the infectious inoculum and the solid agar overlay in a PRNA, IBV anti-NA mAbs did not reduce plaque number (FIG. 4B)—but reduced plaque size (FIG. 4C), of B/Malaysia/2504/06 virus in a titratable fashion compared to negative control mAb 8H9. The exception was 3G1, which in addition to reducing plaque size, was able to also reduce plaque number up to approximately 50%. A neutralizing murine mAb against the IBV HA was used as a positive control. (FIG. 4D) Anti-NA mAbs incubated with MDCK cells infected with B/Malaysia/2504/06 virus (MOI=3) were able to engage Fc receptors and activate ADCC reporter activity in vitro. Fold induction is defined as relative light units (RLU) (induced by antibody)/RLU (no antibody control background). Murine mAb 2G12 (anti-Ebolavirus Gp) is used as a negative control. (FIG. 4E) NI assay against wild type (W) and oseltamivir-resistant (R) B/Perth/211/2001 virus. Bar graphs represent $IC_{50}$ values. (FIG. 4F) Female BALB/c mice (5 per group) were administered either 5 mg/kg of mAb 1F2 intraperitoneally, 5 mg/kg negative control mAb 8H9 intraperitoneally, or placed on a twice daily, 20 mg/kg, regimen of oseltamivir delivered via oral gavage and initiated at 72 hpi. Percent survival is shown. Statistical significance is indicated where tested as follows: n.s. is $p>0.05$, * is $p\leq0.05$,  is $p\leq0.01$, * is $p\leq0.001$ and **** is $p\leq0.0001$.

Figure 5A:
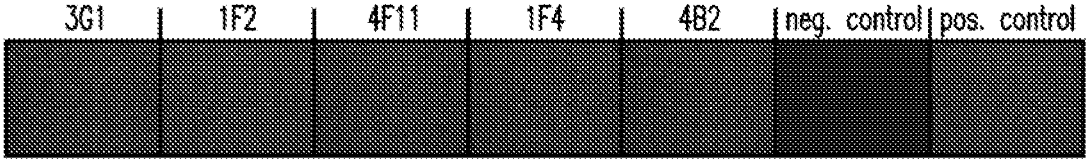
Figure 5B:
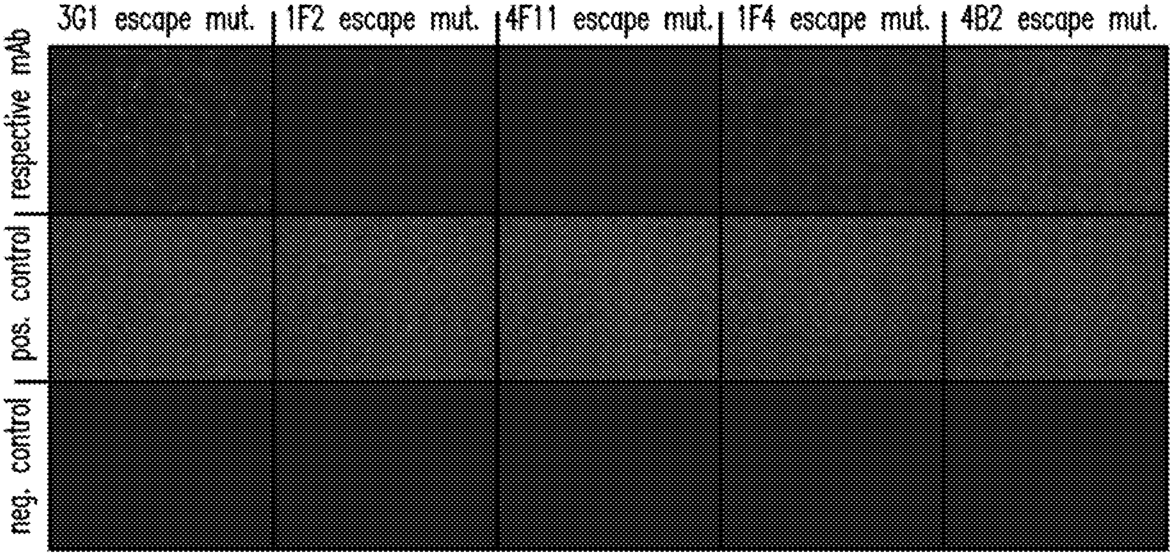
Figure 5C:
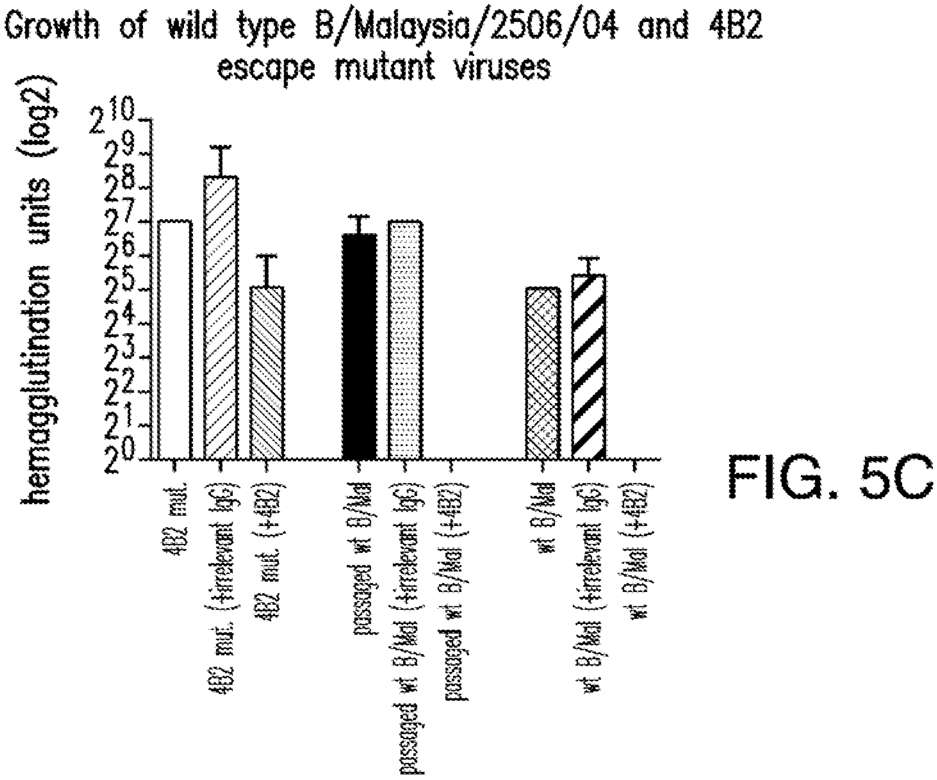
Figures 5D, 5E:
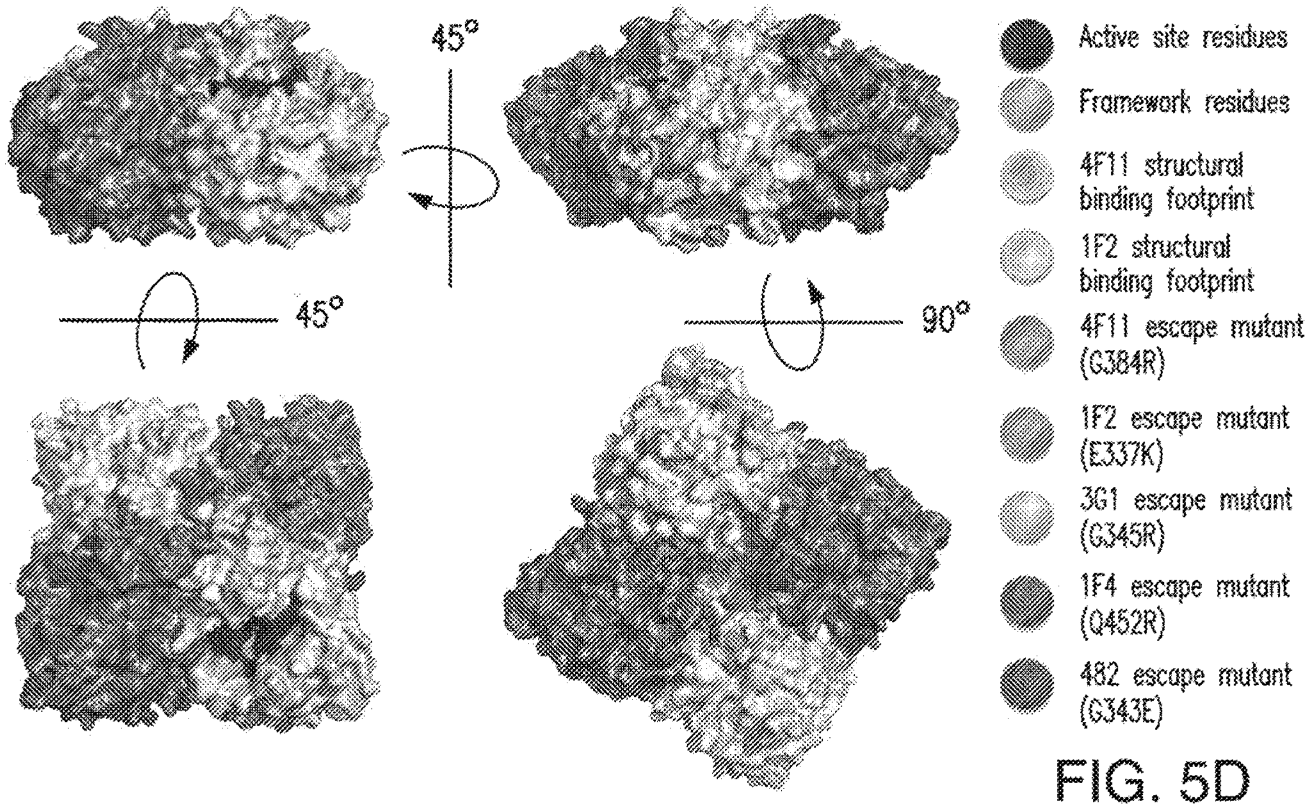

FIGS. 5A-5E: IBV escape mutants reveal amino acid residues critical for mAb binding. FIG. 5A: To demonstrate mAb reactivity via immunofluorescence, MDCK cells were infected with wt B/Malaysia/2506/04 virus (MOI=10), fixed, and stained using anti-NA mAbs (30 ug/ml). All mAbs displayed clear surface staining, allowing this assay to be used as a screen for potential binding mutants. A polyclonal cocktail of purified mouse mAb IgGs against the IBV HA was used as a positive infection control (pos. control). An irrelevant mouse mAb, 8H9 was used as a negative control (neg. control). FIG. 5B: MDCK cells were infected with the generated B/Malaysia/2506/04 escape mutant viruses and stained with the respective mAb to which the escape mutant was generated, in a similar fashion to FIG. 5A. All mutant viruses—except that generated to mAb 4B2—displayed clear loss of binding to the corresponding mAb. FIG. 5C: HA titers of wt B/Malaysia/2506/04 virus (wt B/Mal), 4B2 escape mutant virus (4B2 mut.), and passaged wt B/Malaysia/2506/04 virus (passaged wt B/Mal) in the presence of mAb 4B2 at 10 ug/ml, irrelevant mouse mAb 3C12 (anti-N8) at 10 ug/ml, or no mAb at 72 hpi. Only the generated 4B2 escape mutant virus grew to detectable titers in the presence of 4B2. Passaged wt B/Malaysia/2506/04 virus, as explained in detail in the materials and methods section, is a control virus produced by serially passaging wt B/Malaysia/2506/04 virus in MDCK cells in the presence of irrelevant mouse mAb 3C12 alongside wt B/Malaysia/2506/04 virus in the presence of increasing concentrations of 4B2. FIG. 5D: Critical binding residues identified in IBV escape mutants—along with the structurally defined binding footprints from FIG. 2 and the NA enzymatic active site/framework residues—were mapped on one of the four monomers of the 3D structure of the NA from B/Brisbane/60/2008 virus (PDB ID: 4CPL). The remaining three monomers of the tetramer are shown in either light or dark grey. Degrees of rotation are approximate. FIG. 5E: List of amino acid residues (position, identity, and percent conservation) identified as critical binding residues by escape mutant generation. Percent conservation was determined using 944 subsampled IBVs. B/Malaysia/2506/04 numbering is used throughout.

Figure 6A:
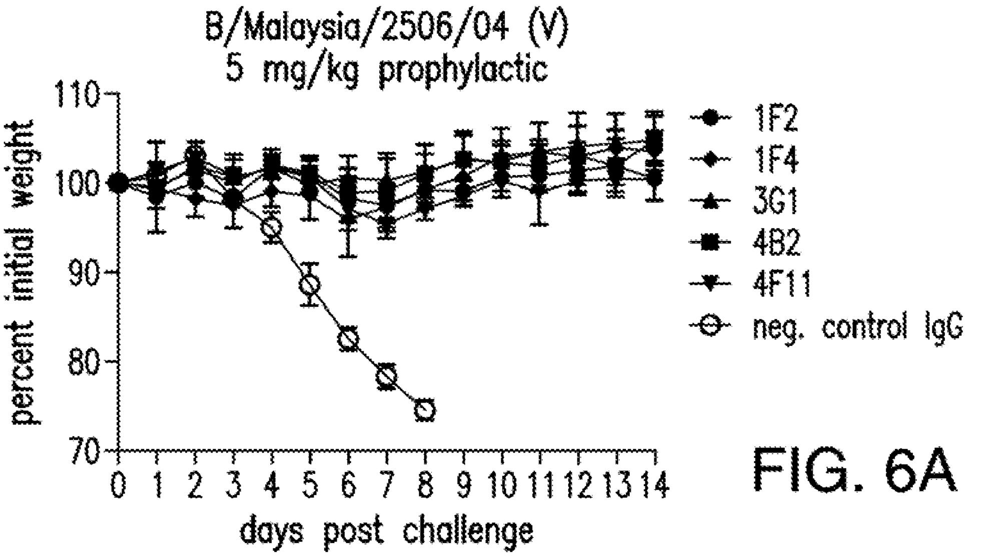
Figure 6B:
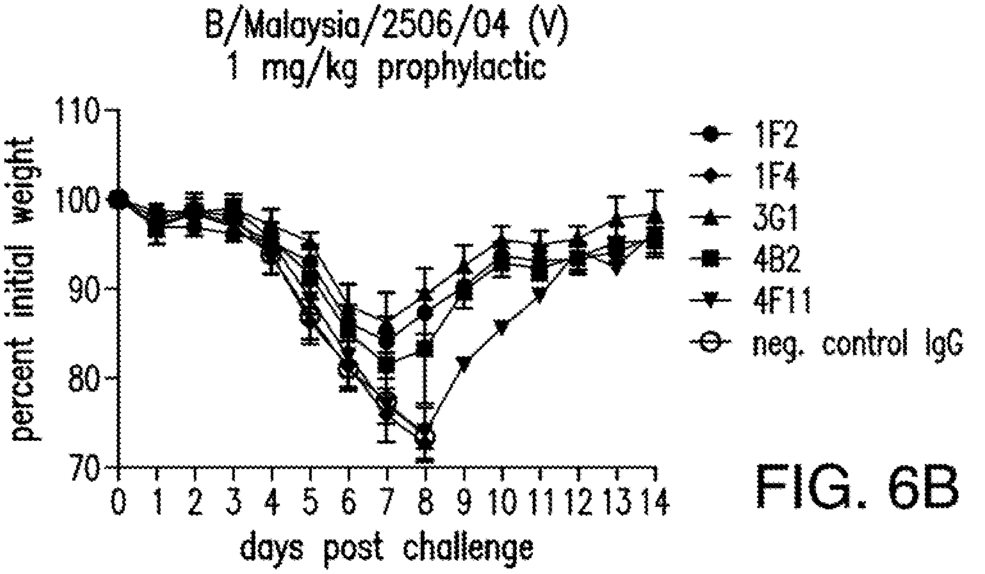
Figure 6C:
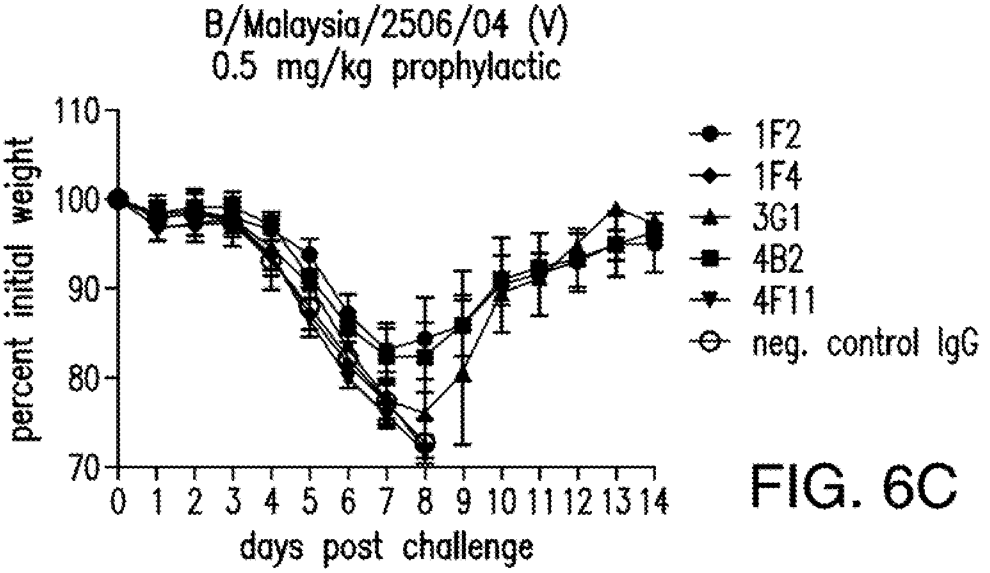
Figure 6D:
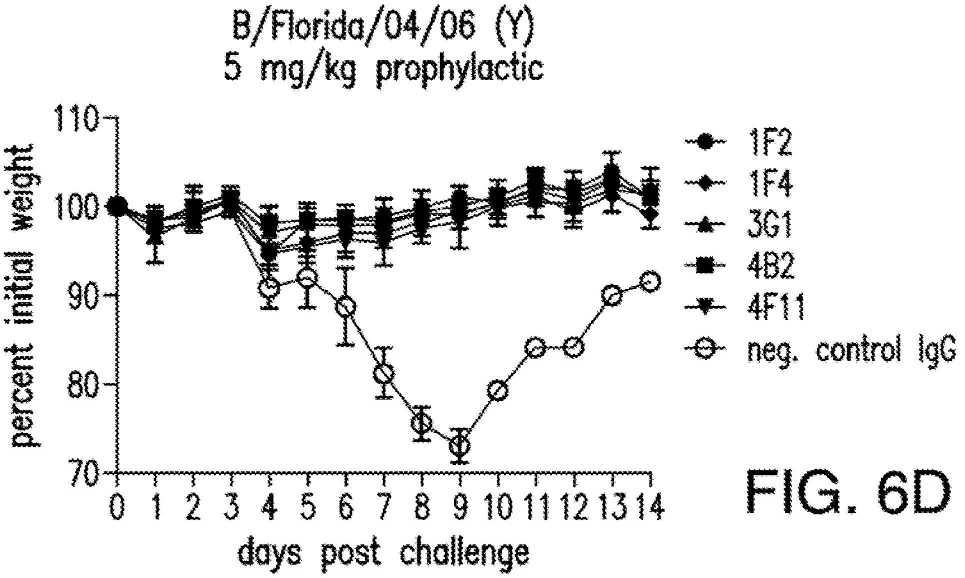

FIGS. 6A-6F: IBV anti-NA mAbs protect mice from morbidity when administered prophylactically or therapeutically. Displayed are the weight loss curves corresponding to the survival curves in FIG. 3. Mice were administered either 5, 1, or 0.5 mg/kg of mAb intraperitoneally 2 h prior to a 5 $mLD_{50}$ challenge with B/Malaysia/2506/04 virus (FIGS. 6A-6C) or administered 5 mg/kg of mAb intraperitoneally 2 hours prior to a 5 mLD50 challenge with B/Florida/04/06 virus (FIG. 6D). In therapeutic studies, mice were administered 5 mg/kg of each antibody either 24 (FIG. 6E) or 48 (FIG. 6F) h after challenge with 5 $mLD_{50}$ of B/Malaysia/2506/04 virus. Percent weight is calculated based on the initial body weight on day 0. Mice that lost more than 75% of their initial body weights were humanely euthanized, and the remaining curves were generated from the weights of the surviving mice only. Murine mAb 8H9 (anti-H6) was used as a negative control in all experiments.

Figures 7A, 7B, 7C, 7D, 7E:
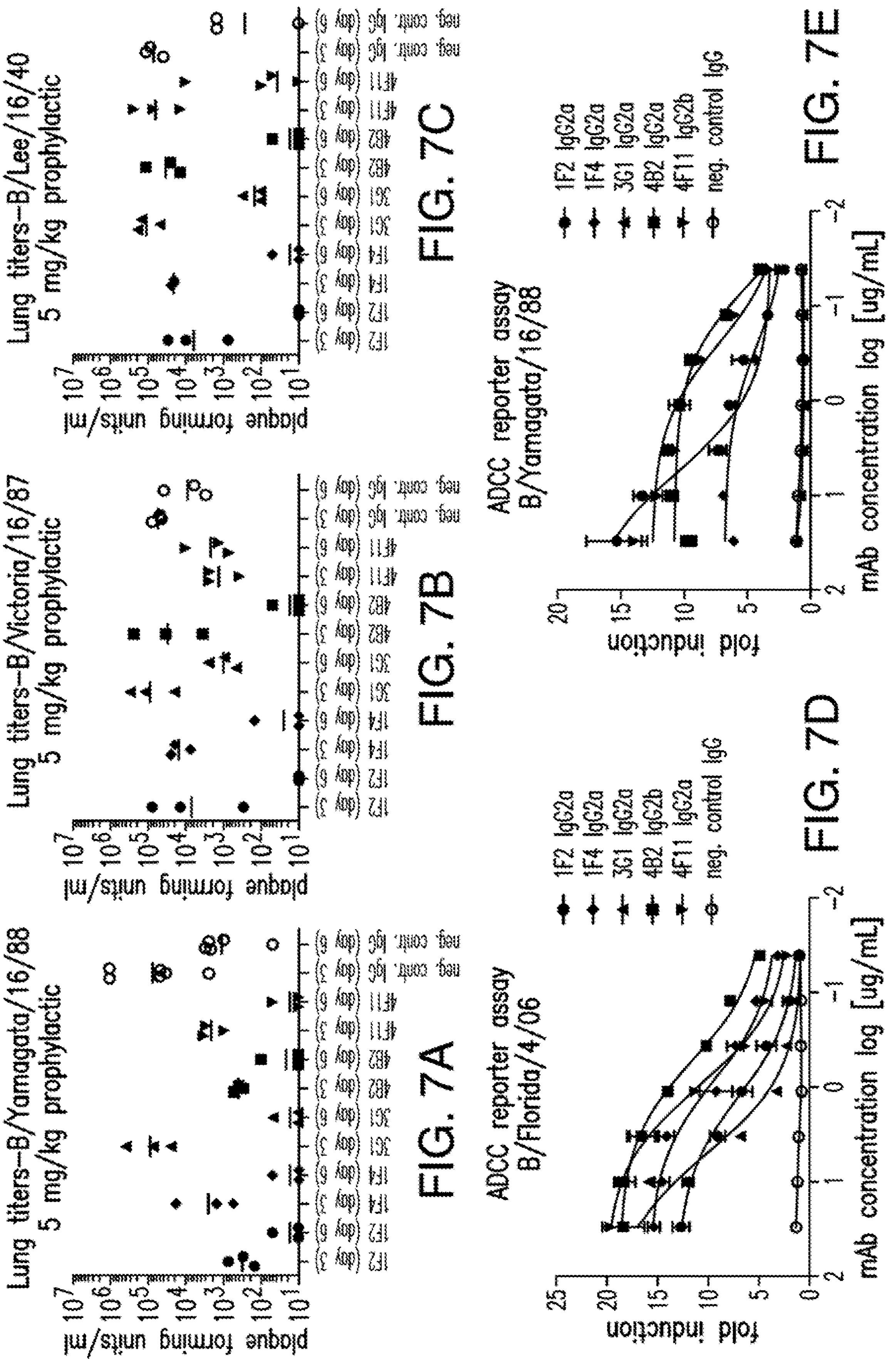
Figure 7F:
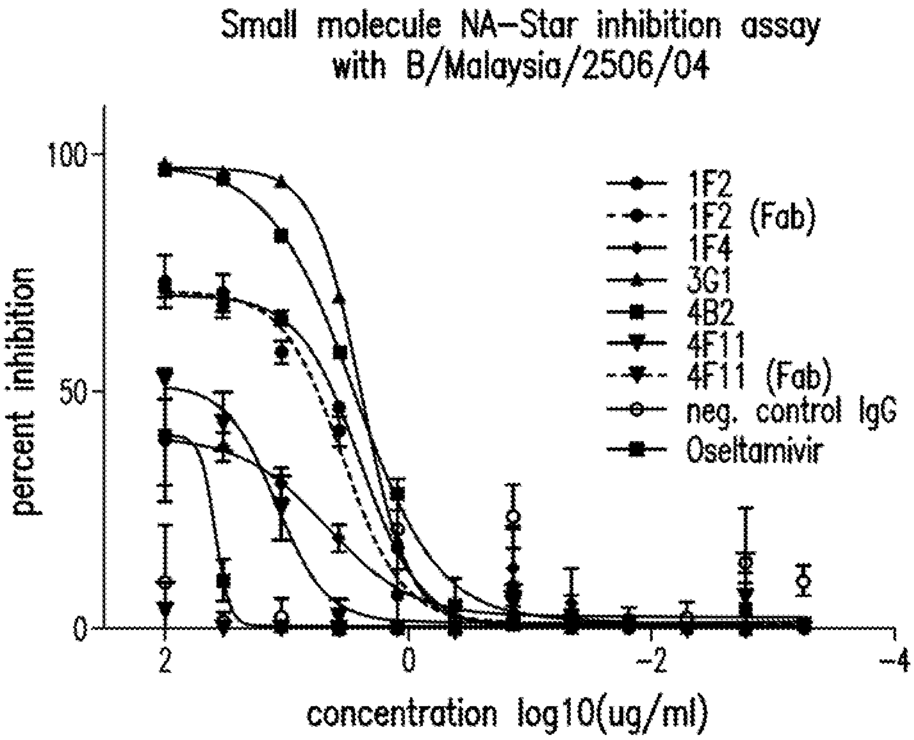
Figure 7G:
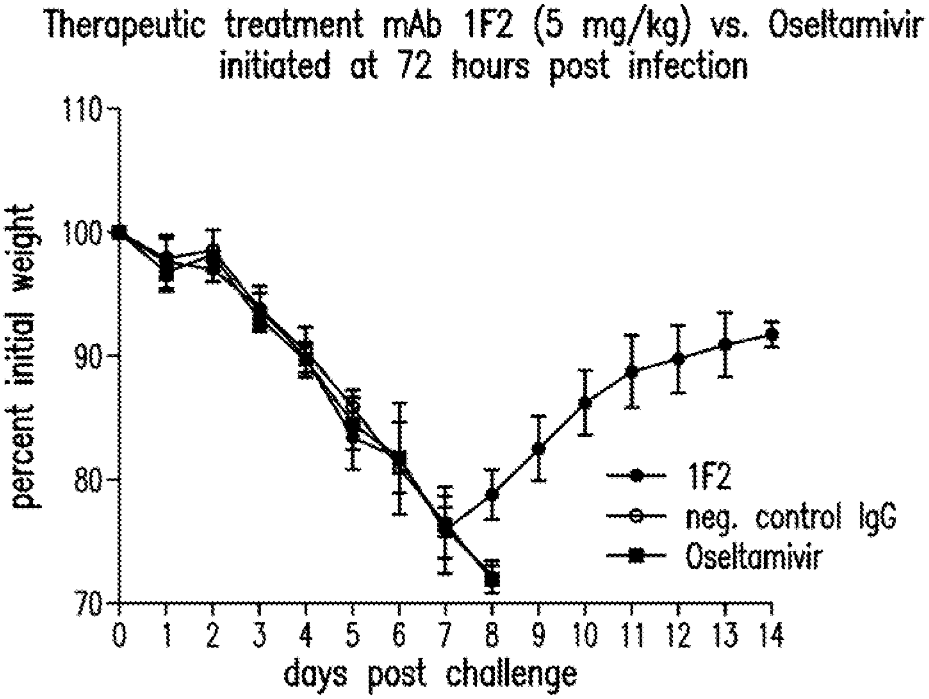

FIGS. 7A-7G. IBV anti-NA mAbs reduce viral lung titers in mice, activate ADCC, inhibit NA activity of drug-resistant IBV, and demonstrate superior effectiveness to oseltamivir. FIGS. 7A-7C: Female BALB/c mice (3 per group) were administered 5 mg/kg antibody prophylactically, challenged with B/Yamagata/16/88, B/Victoria/2/87, or B/Lee/40 viruses respectively and in identical fashion to FIG. 4A. Mice were sacrificed on day 3 or 6 post-infection for lung titer analysis. Lung titers in groups treated with anti-NA mAbs are most reduced on day 6 post-infection compared to negative control mAb 8H9. FIGS. 7D and 7E: Anti-NA mAb incubated with MDCK cells infected with B/Florida/04/06 or B/Yamagata/16/88 viruses, respectively (MOI=3), are able to engage Fc receptors and activate ADCC in vitro. Fold induction is defined as RLU (induced by antibody)/RLU (no antibody control background). Murine mAb 2G12 (anti-Ebolavirus Gp) is used as a negative control. FIG. 7F: NI activity against B/Malaysia/2506/04 using the NA-Star assay. Data points are presented as percent inhibition. FIG. 7G: Female BALB/c mice (5 per group) were administered either 5 mg/kg of mAb 1F2 intraperitoneally, 5 mg/kg negative control mAb 8H9 intraperitoneally, or placed on a twice daily, 20 mg/kg, 6 day-long regimen of oseltamivir delivered via oral gavage and initiated at 72 hpi. Percent weight is shown and is calculated based on the initial body weight on day 0.

FIG. 8. Polynucleotide sequences of 1F2 variable regions. Polynucleotide sequences of 1F2 heavy chain variable region (SEQ ID NO: 81) and 1F2 light chain variable region (SEQ ID NO: 82).

FIG. 9. Amino acid sequences of 1F2 variable regions. Amino acid sequences of 1F2 heavy chain variable region (SEQ ID NO:1) and 1F2 light chain variable region (SEQ ID NO:2). Underlined amino acids are the CDRs according to the IMGT delineation system in order from HCDR1 (SEQ ID NO:3), HCDR2 (SEQ ID NO:4), HCDR3 (SEQ ID NO: 5), LCDR1 (SEQ ID NO: 6), LCDR2 (SEQ ID NO: 7), LCDR3 (SEQ ID NO:8). Non-underlined amino acids are the FRs (SEQ ID NOs: 9-16) according to the IMGT delineation system.

FIG. 10. Polynucleotide sequences of 1F4 variable regions. Polynucleotide sequences of 1F4 heavy chain variable region (SEQ ID NO: 83) and 1F4 light chain variable region (SEQ ID NO: 84).

FIG. 11. Amino acid sequences of 1F4 variable regions. Amino acid sequences of 1F4 heavy chain variable region (SEQ ID NO:17) and 1F4 light chain variable region (SEQ ID NO: 18). Underlined amino acids are the CDRs according to the IMGT delineation system in order from HCDR1 (SEQ ID NO:19), HCDR2 (SEQ ID NO: 20), HCDR3 (SEQ ID NO: 21), LCDR1 (SEQ ID NO: 22), LCDR2 (SEQ ID NO: 23), LCDR3 (SEQ ID NO: 24). Non-underlined amino acids are the FRs (SEQ ID NOs: 25-32) according to the IMGT delineation system.

FIG. 12. Polynucleotide sequences of 3G1 variable regions. Polynucleotide sequences of 3G1 heavy chain variable region (SEQ ID NO: 85) and 3G1 light chain variable region (SEQ ID NO: 86).

FIG. 13. Amino acid sequences of 3G1 variable regions. Amino acid sequences of 3G1 heavy chain variable region (SEQ ID NO: 33) and 3G1 light chain variable region (SEQ ID NO: 34). Underlined amino acids are the CDRs according to the IMGT delineation system in order from HCDR1 (SEQ ID NO: 35), HCDR2 (SEQ ID NO: 36), HCDR3 (SEQ ID NO: 37), LCDR1 (SEQ ID NO: 38), LCDR2 (SEQ ID NO: 39), LCDR3 (SEQ ID NO: 40). Non-underlined amino acids are the FRs (SEQ ID NOs: 41-48) according to the IMGT delineation system.

FIG. 14. Polynucleotide sequences of 4B2 variable regions. Polynucleotide sequences of 4B2 heavy chain variable region (SEQ ID NO: 87) and 4B2 light chain variable region (SEQ ID NO: 88).

FIG. 15. Amino acid sequences of 4B2 variable regions. Amino acid sequences of 4B2 heavy chain variable region (SEQ ID NO: 49) and 4B2 light chain variable region (SEQ ID NO: 50). Underlined amino acids are the CDRs according to the IMGT delineation system in order from HCDR1 (SEQ ID NO: 51), HCDR2 (SEQ ID NO: 52), HCDR3 (SEQ ID NO: 53), LCDR1 (SEQ ID NO: 54), LCDR2 (SEQ ID NO: 55), LCDR3 (SEQ ID NO: 56). Non-underlined amino acids are the FRs (SEQ ID NOs: 57-64) according to the IMGT delineation system.

FIG. 16. Polynucleotide sequences of 4F11 variable regions. Polynucleotide sequences of 4F11 heavy chain variable region (SEQ ID NO: 89) and 4F11 light chain variable region (SEQ ID NO: 90).

FIG. 17. Amino acid sequences of 4F11 variable regions. Amino acid sequences of 4F11 heavy chain variable region (SEQ ID NO: 65) and 4F11 light chain variable region (SEQ ID NO: 66). Underlined amino acids are the CDRs according to the IMGT delineation system in order from HCDR1 (SEQ ID NO: 67), HCDR2 (SEQ ID NO: 68), HCDR3 (SEQ ID NO: 69), LCDR1 (SEQ ID NO: 70), LCDR2 (SEQ ID NO: 71), LCDR3 (SEQ ID NO: 72). Non-underlined amino acids are the FRs (SEQ ID NOs: 73-80) according to the IMGT delineation system.

Figure 18A:
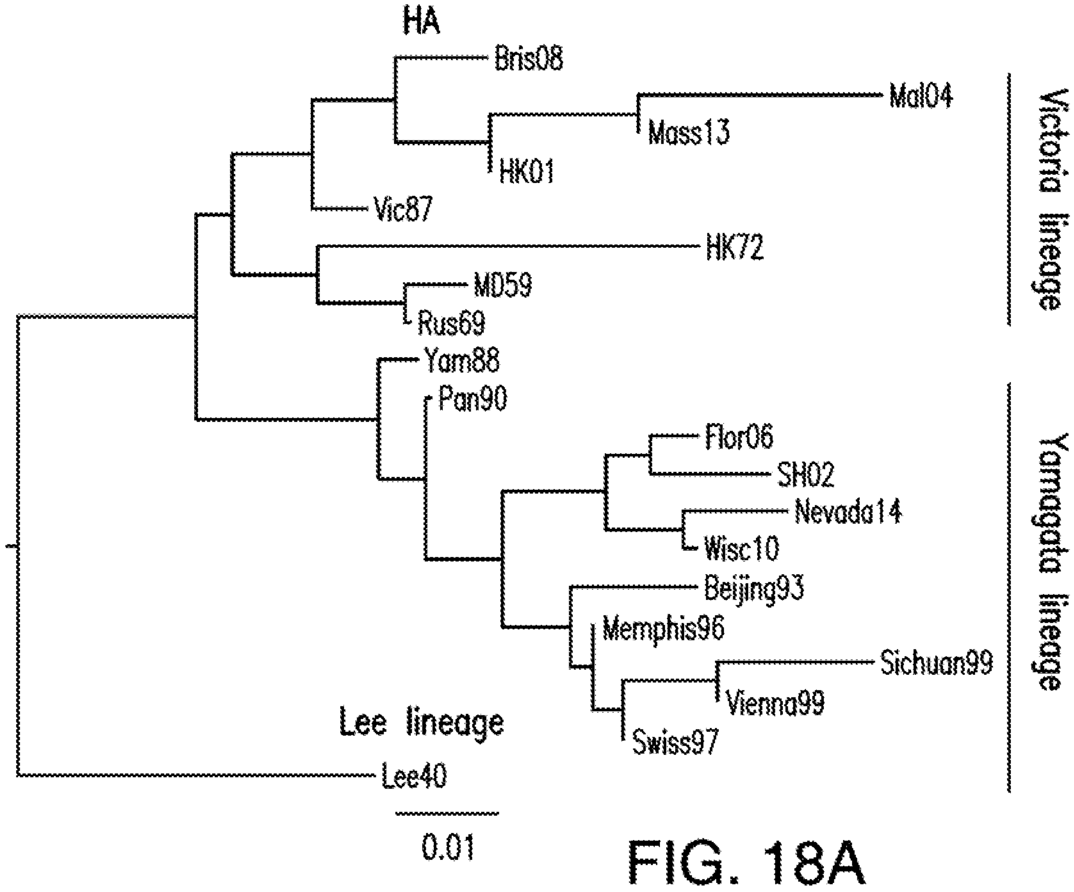
Figure 18B:
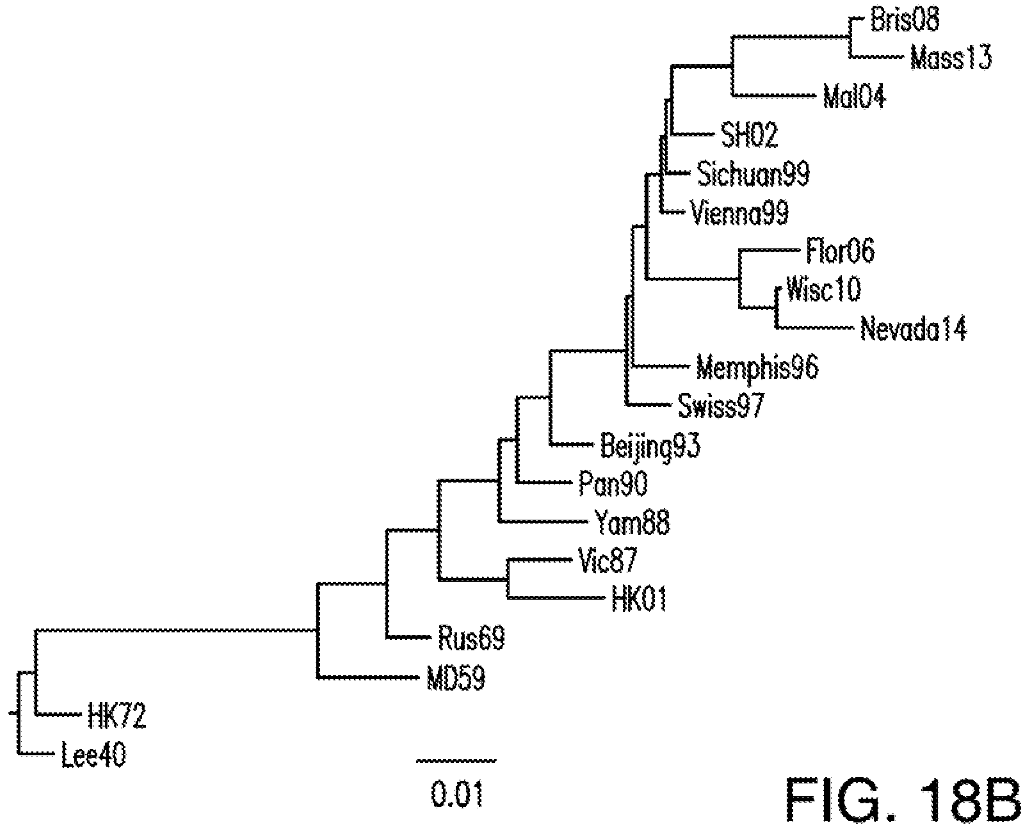

FIG. 18A-18B. Phylogenic analysis of HA and NA from influenza B virus. FIG. 18A: Phylogenetic tree of influenza B virus HA sequences from Victoria, Yamagata lineages and Lee lineages. FIG. 18B: Phylogenetic tree of influenza B virus NA sequences from Victoria, Yamagata lineages and Lee lineages. Note that NA of influenza B virus has not diverged into clear antigenic lineages.

Figure 19A:
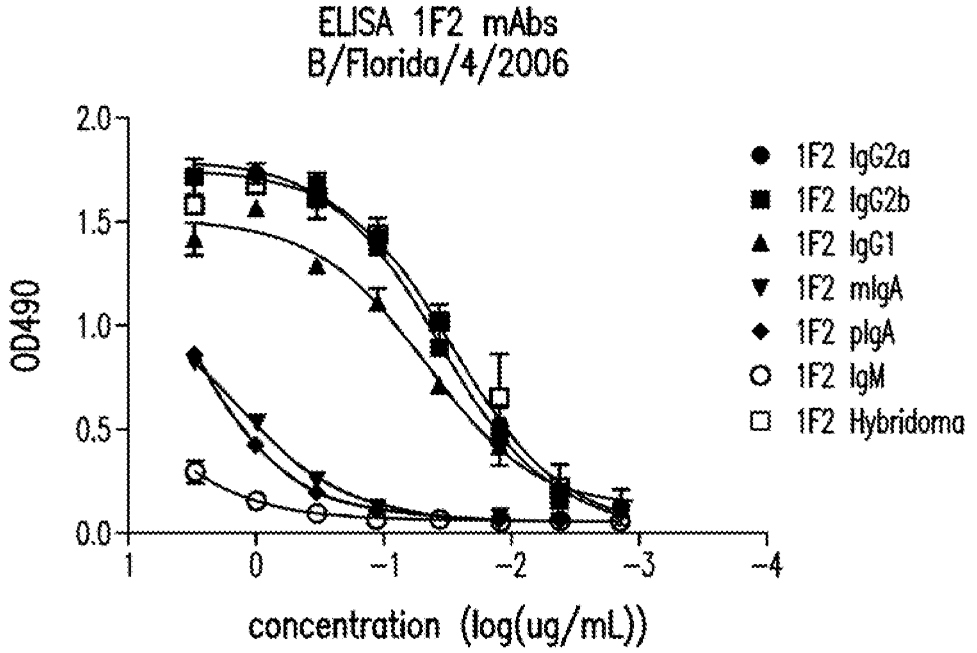
Figure 19B:
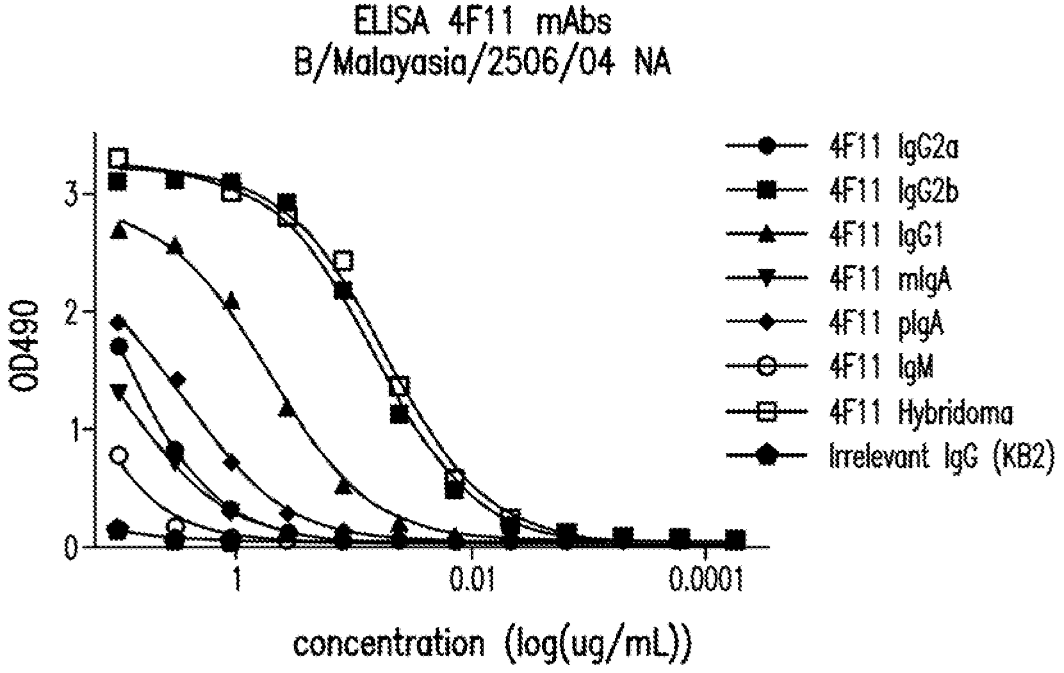

FIG. 19A-19B: ELISA assay. FIG. 19A: Plates were coated with recombinant NA (rNA; B/Florida/4/2006) at a concentration 2 μg/mL. Binding of 1F2 antibody isotypes was tested starting at 3 μg/mL and followed by 3-fold serial dilutions. Original, hybridoma-produced 1F2 is an IgG2a. FIG. 19B: Plates were coated with recombinant NA (B/Malaysia/2506/04) at a concentration 2 μg/mL. Binding of 4F11 antibody isotypes was tested starting at 90 μg/mL followed by 3-fold serial dilutions. Original, hybridoma-produced 4F11 is an IgG2b.

Figure 20A:
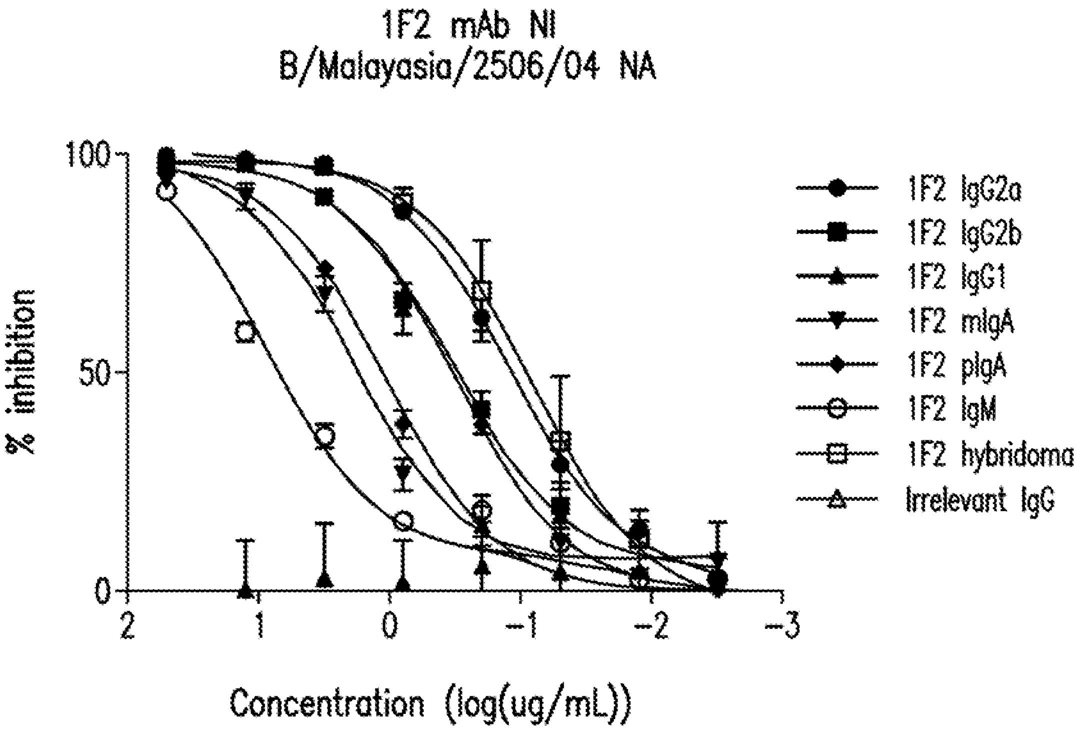
Figure 20B:
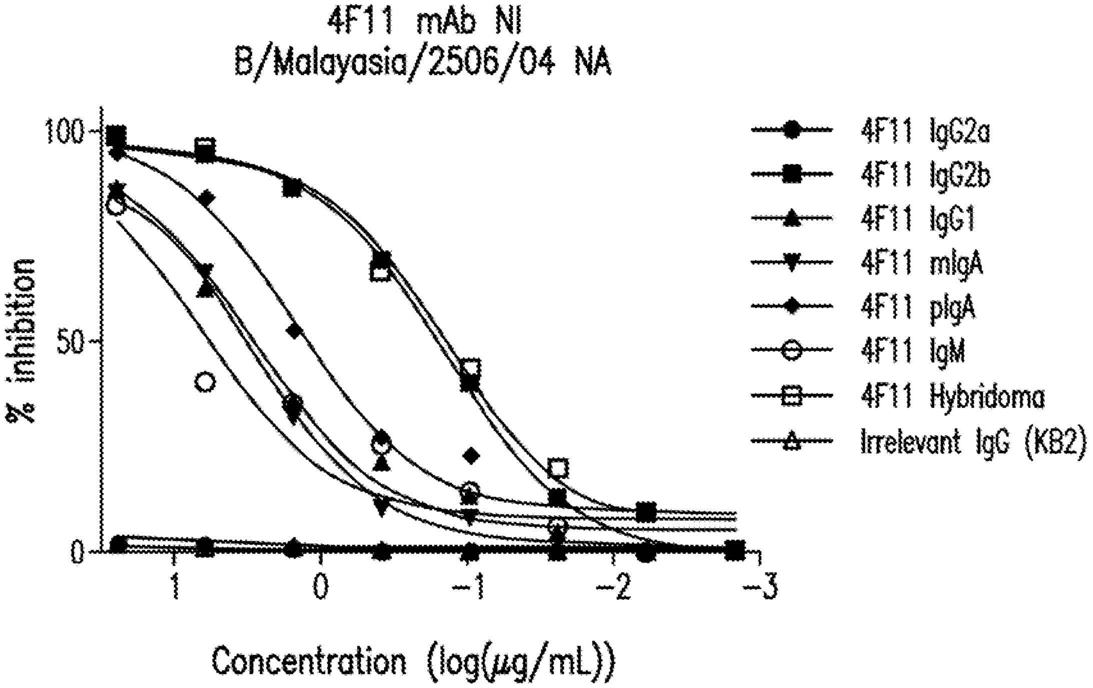

FIG. 20A-20B: All 1F2 and 4F11 isotypes were tested for their neuraminidase inhibition potential using enzyme-linked lectin assay (ELLA). FIG. 20A: All the 1F2 isotypes were tested against B/Malaysia/2506/04 virus. Of note, hybridoma-produced 1F2 IgG2a performed very similarly to recombinantly produced 1F2 IgG2a. FIG. 20B: All the 4F11 isotypes were tested against B/Malaysia/2506/04 virus. Of note, hybridoma-produced 4F11 IgG2b performed very similarly to recombinantly produced 4F11 IgG2b. Recombinantly produced 4F11 IgG2a did not show any activity.

Figure 21A:
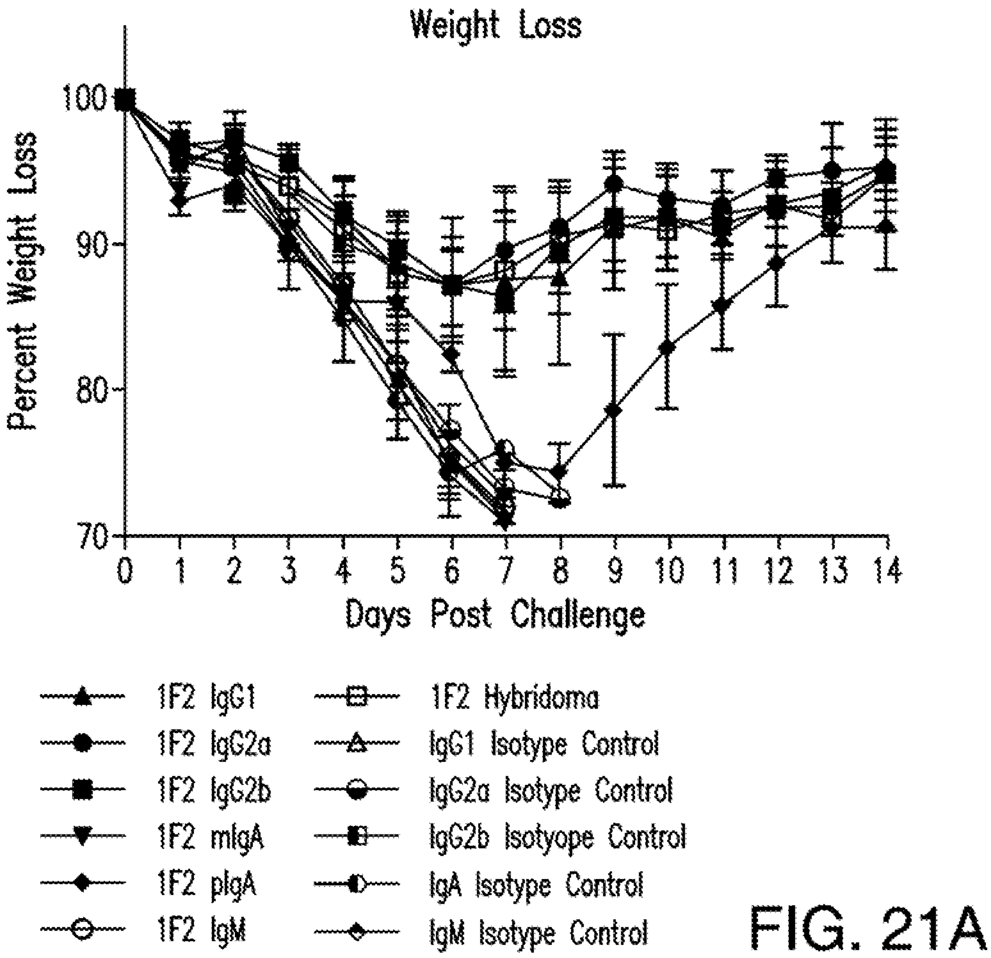
Figure 21B:
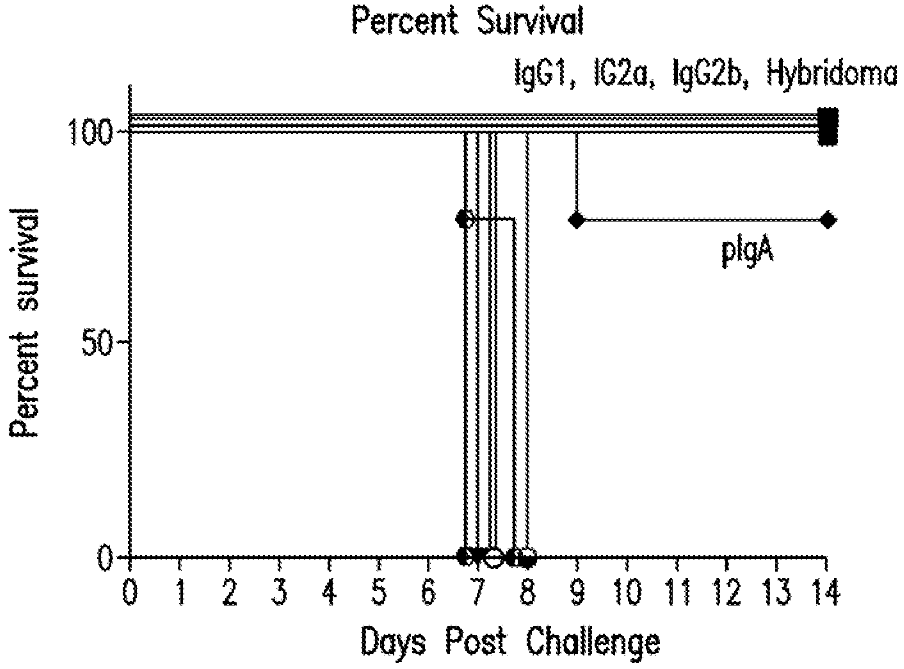

FIG. 21A-21B: Mouse prophylactic challenge study with B/Malaysia/2506/04 (V) virus. All 1F2 isotypes were tested in vivo in a prophylactic setting in mice. 5 mg/kg of each mAb was administered interperitoneally (IP) 2 hours prior to intranasal (IN) challenge with 5×LD50 of B/Malaysia/2506/04. The weight loss (FIG. 21A) and survival (FIG. 21B) were followed for 14 days. 75% initial weight was set as a humane end point. All the IgG subtypes as well as polymeric IgA proved protective with 100% protection from mortality in case of IgGs and 80% protection from mortality in case of pIgA.

Figure 22:
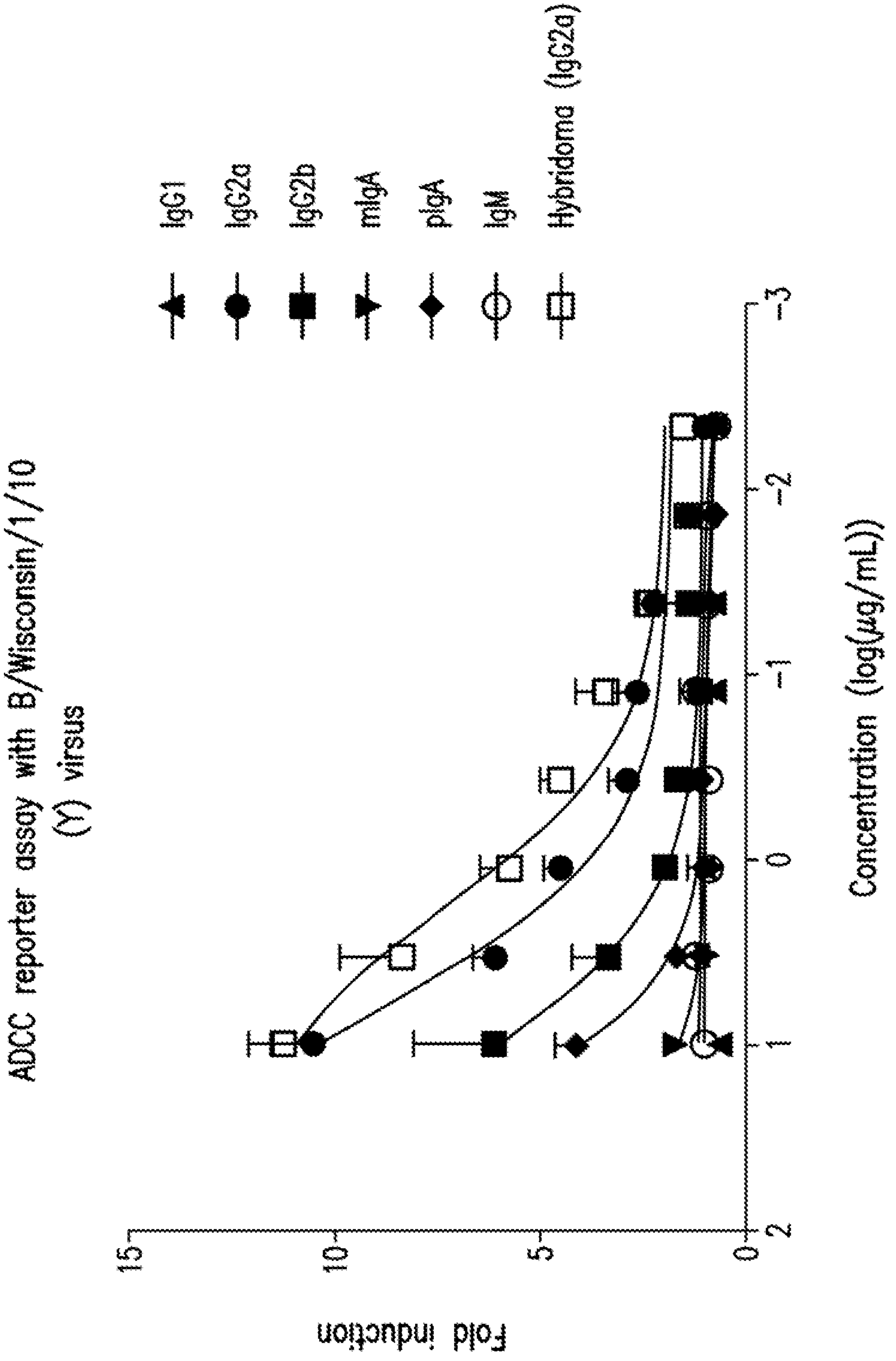

FIG. 22: All 1F2 isotypes were assessed for ADCC activity using an ADCC assay kit (Promega). MDCK cells infected with B/Wisconsin/1/10 were used as target cells. The IgG2a, IgG2b and polymeric IgA gave positive signal expressed as fold induction over the background. IgG1, monomeric IgA and IgM did not show any activity. This was in agreement with what has been known about the effector functions of antibody isotypes in mice. Without being bound by any particular theory, based on this data, it can be said that the IgG1 isotype did not rely on its ADCC activity for in vivo protection in mouse challenge.

Figure 23A:
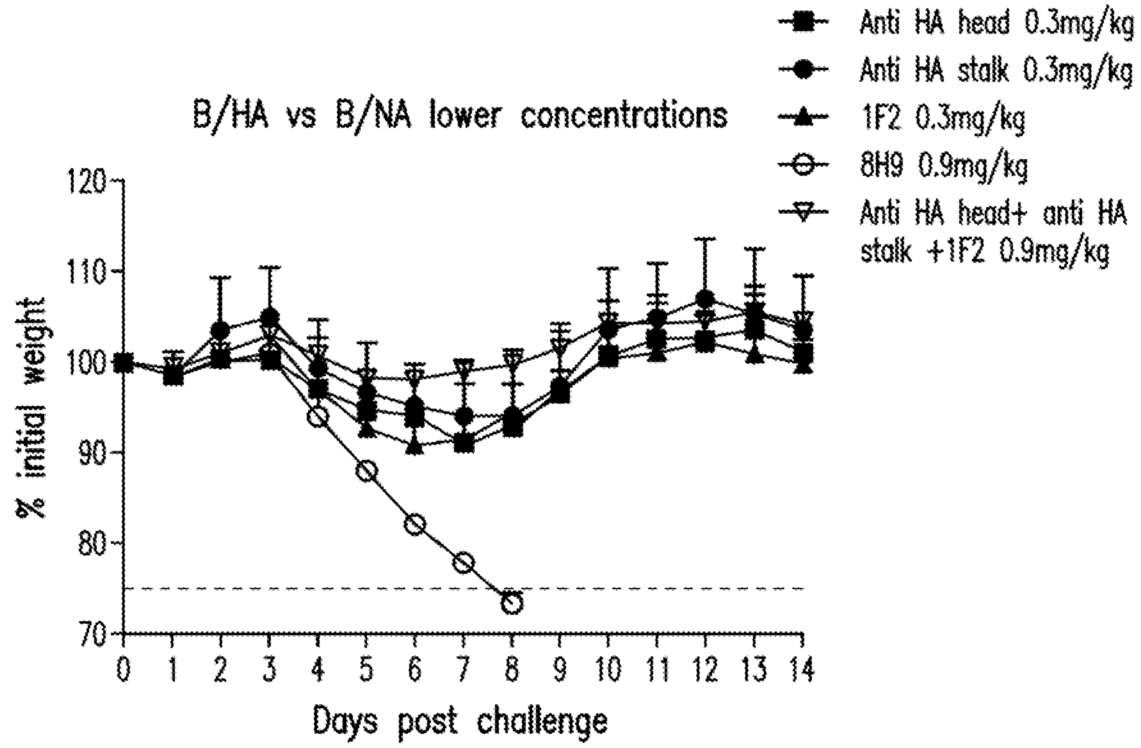
Figure 23B:
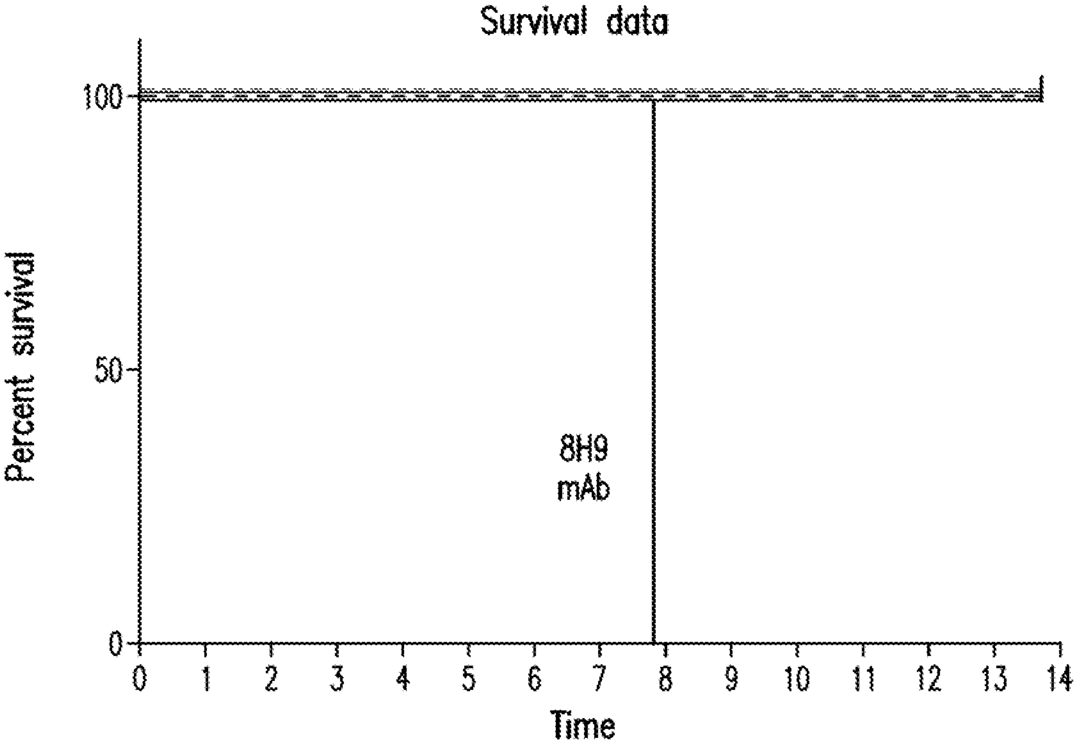

FIG. 23A-23B: Comparison of anti-head B/HA mAb, anti-stalk B/HA mAb, and anti-B/NA mAb 1F2 to the combination of all three of them in prophylactic settings. The antibodies were administered at indicated concentrations (with 8H9, which is anti-H6 specific mAb, being a negative control) IP 2 hours prior to IN challenge with 5×LD50 B/Malaysia/2506/04. FIG. 23A: the weight loss observed post challenge. FIG. 23B: the survival curves post challenge.

FIG. 24A-24E: Competition between different mAbs for binding to BNA. Antibodies 1F2 (FIG. 24A), 1F4 (FIG. 24B), 3G1 (FIG. 24C), 4B2 (FIG. 24D), and 4F11 (FIG. 24E) were competed against themselves and each other using an ELISA-based assay. Technical duplicates were performed.

FIG. 25A-25E: Neuraminidase inhibition assay against the escape mutants raised with the five mAbs. Escape mutants generated with 1F2 (FIG. 25A), 1F4 (FIG. 25B), 3G1 (FIG. 25C), 4B2 (FIG. 25D), and 4F11 (FIG. 25E) were each tested for sensitivity to the panel of five mAbs. The means obtained from technical duplicates are displayed graphically.

Figure 26:
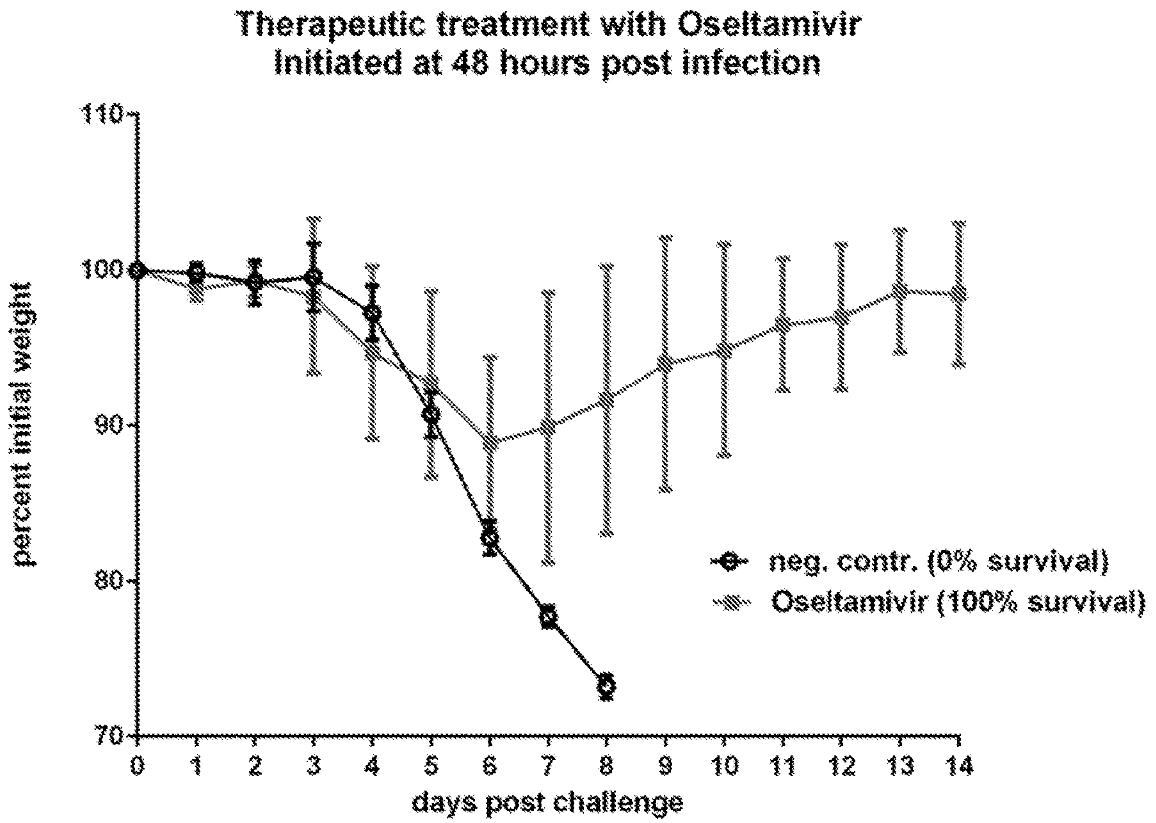

FIG. 26: Oseltamivir treatment of mice initiated 48 hours post infection with B/Malaysia/2506/04 virus does not protect from weight loss but leads to survival of the infection. Female BALB/c mice (5 per group) were administered 5 mg/kg negative control mAb 8H9 intraperitoneally or were placed on a twice daily, 20 mg/kg, 6 day-long regimen of oseltamivir delivered via oral gavage and initiated at 48 hpi. Percent weight is shown and is calculated based on the initial body weight on day 0. Percentages next to the legend indicate survival.

FIG. 27. Stability early versus stability late plot for identification of stable binder (best binders circled) against all four antigens. In total, 25+1 samples were analyzed and ranked with respect to binding stability against 4 different antigens. The assay was performed at 25° C. The data used to generate these plots are shown in the table in FIG. 28. Variants of interest are shown using the key shown.

FIG. 28. Table of off-rate ranking results obtained for the binding of 1F2 antibody variants binding to either B/Brisbane, B/Yamagata, B/Wisconsin or the B/Malaysia.

Figure 29:
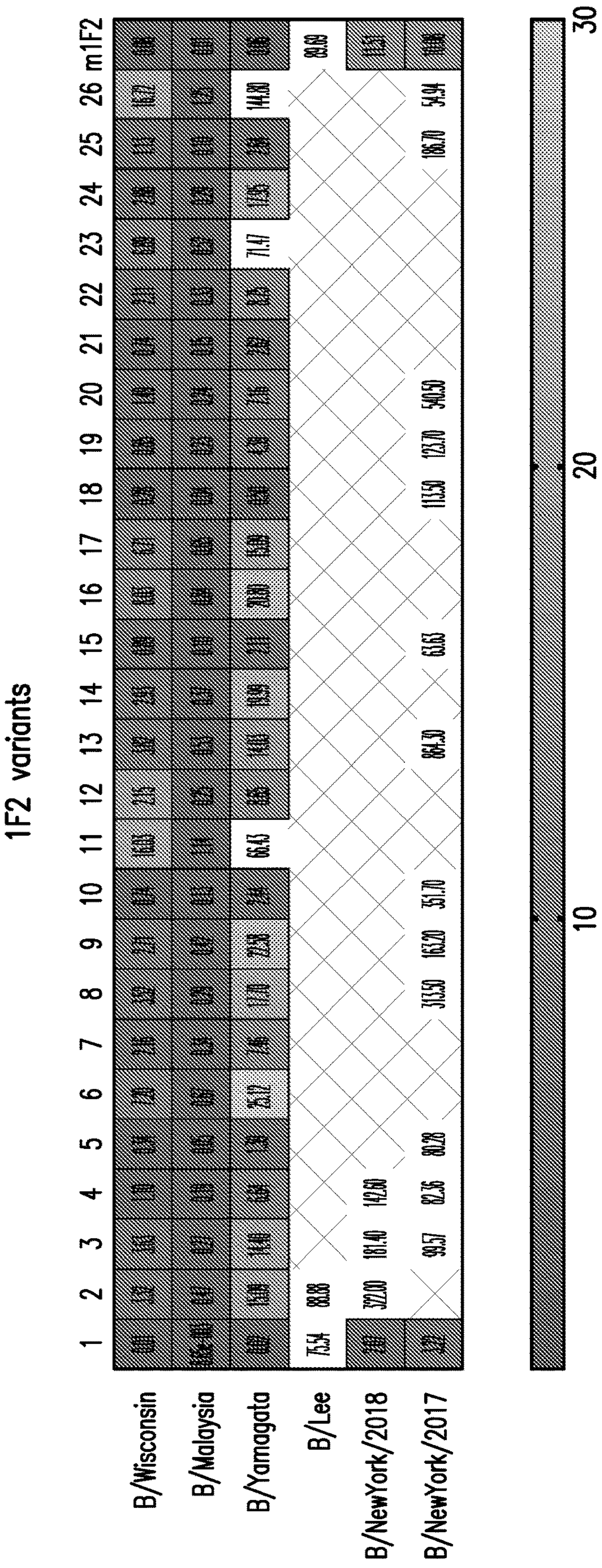

FIG. 29. Neuraminidase inhibition screening of 1F2 humanized monoclonal antibody (mAb) variants. The variants used in 1-26 as numbered at the top of FIG. 29 are provided in Table 8.

FIG. 30. Humanized variants of 1F2 variable heavy chain region. VH0 (SEQ ID NO:1) is the murine variable region of 1F2. IGHV1-46 (SEQ ID NO:166) and IVHV1-2 (SEQ ID NO:167) are human germline sequences. VH1 to VH8 (SEQ ID Nos:168 to 175) are humanized variable heavy regions of 1F2. The CDRs are underline and the framework regions are the sequences surrounding the CDRs.

FIG. 31. Humanized variants of 1F2 variable light chain region. VL0 (SEQ ID NO:2) is the murine variable region of 1F2. IGKV1-8 (SEQ ID NO:176) is a human germline sequence. VL1 to VL8 (SEQ ID Nos:177 to 184) are humanized variable light regions of 1F2. The CDRs are underline and the framework regions are the sequences surrounding the CDRs.

4.1 SEQUENCE INFORMATION

| SEQ ID NO. | NAME | SEQUENCE |
|---|---|---|
| 1 | 1F2 VH | QVHLQQSGPEVARPG ASVKLSCKASGYTFT DYYLNWVKQRPRQGL EWIGQIHPGSTNTYY NEKFKGKATLTADKS SSTAYMQLSSLTSED SAVYFCARSLGDGYY VYAMDYVVGQGTAVT VSS |
| 2 | 1F2 VL | DIVMTQSQKFMSTSV GDRVSVTCKASQNVV TNVVWYQQKPGQSPK PLIYSASYRYSGVPD RFTGSGSGTDFTLTI SNVQSEDLAEYCCQQ YHSYPFTFGSGTKLE VK |

-continued

| SEQ ID NO. | NAME | SEQUENCE |
|---|---|---|
| 3 | 1F2 HCDR1 (IMGT) | GYTFTDYY |
| 4 | 1F2 HCDR2 (IMGT) | IHPGSTNT |
| 5 | 1F2 HCDR3 (IMGT) | ARSLGDGYYVYAMDY |
| 6 | 1F2 LCDR1 (IMGT) | QNVVTN |
| 7 | 1F2 LCDR2 (IMGT) | SAS |
| 8 | 1F2 LCDR3 (IMGT) | QQYHSYPFT |
| 9 | 1F2 VH FR1 (IMGT) | QVHLQQSGPEVARPG ASVKLSCKAS |
| 10 | 1F2 VH FR2 (IMGT) | LNWVKQRPRQGLEWI GQ |
| 11 | 1F2 VH FR3 (IMGT) | YYNEKFKGKATLTAD KSSSTAYMQLSSLTS EDSAVYFC |
| 12 | 1F2 VH FR4 (IMGT) | WGQGTAVTVSS |
| 13 | 1F2 VL FR1 (IMGT) | DIVMTQSQKFMSTSV GDRVSVTCKAS |
| 14 | 1F2 VL FR2 (IMGT) | VVWYQQKPGQSPKPL IY |
| 15 | 1F2 VL FR3 (IMGT) | YRYSGVPDRFTGSGS GTDFTLTISNVQSED LAEYCC |
| 16 | 1F2 VL FR4 (IMGT) | FGSGTKLEVK |
| 17 | 1F4 VH | QVHLQQSGSELRSPG SSVKLSCKDFDSEVF PIVYMRWIRQKPGHG FEWIGDILPSFGRTI YGEKFEDKATLDADT VSNTAYLELNSLTSE DSAIYYCARGDHGNW LAYWGQGTLVTVSA |
| 18 | 1F4 VL | DIVMTQSHKFMSTSV GDRVTITCKASQDVS TAVAWYQQKPGQSPK LLIYWASTRHTGVPN RFTGIISGTDYTLTI SSVQAEDLALYYCQQ HYSAPWTFGGGTKLE IK |
| 19 | 1F4 HCDR1 (IMGT) | DSEVFPIVY |
| 20 | 1F4 HCDR2 (IMGT) | ILPSFGRT |
| 21 | 1F4 HCDR3 (IMGT) | ARGDHGNWLAY |
| 22 | 1F4 LCDR1 (IMGT) | QDVSTA |

-continued

| SEQ ID NO. | NAME | SEQUENCE |
|---|---|---|
| 23 | 1F4 LCDR2 (IMGT) | WAS |
| 24 | 1F4 LCDR3 (IMGT) | QQHYSAPWT |
| 25 | 1F4 VH FR1 (IMGT) | QVHLQQSGSELRSPG SSVKLSCKDF |
| 26 | 1F4 VH FR2 (IMGT) | MRWIRQKPGHGFEWI GD |
| 27 | 1F4 VH FR3 (IMGT) | IYGEKFEDKATLDAD TVSNTAYLELNSLTS EDSAIYYC |
| 28 | 1F4 VHFR4 (IMGT) | WGQGTLVTVSA |
| 29 | 1F4 VLFR1 (IMGT) | DIVMTQSHKFMSTSV GDRVTITCKAS |
| 30 | 1F4 VL FR2 (IMGT) | VAWYQQKPGQSPKLL IY |
| 31 | 1F4 VL FR3 (IMGT) | TRHTGVPNRFTGIIS GTDYTLTISSVQAED LALYYC |
| 32 | 1F4 VL FR4 (IMGT) | FGGGTKLEIK |
| 33 | 3G1 VH | QVQLQQSGAELMKPG ASVKISCKATGYKFT SYWIGWVKQRPGHGL EWCGEIFPGSGSINY NEKFKGKATFTADTS SNTAYLQLTSLTSED SAVYYCARGEDYYGS SYGAMDYVVGQGTSL TVSS |
| 34 | 3G1 VL | DVQITQSPSYLAASP GETITINCRASKSIS KYVAWYQEKPGRTNK VLIYSGSILSFGNPS RFSGSGSGTDFTLTI SSLEPEDFAMYYCQQ HNEYPWTFGGGTKLE IK |
| 35 | 3G1 HCDR1 (IMGT) | GYKFTSYW |
| 36 | 3G1 HCDR2 (IMGT) | IFPGSGSI |
| 37 | 3G1 HCDR3 (IMGT) | ARGEDYYGSSYGAMD Y |
| 38 | 3G1 LCDR1 (IMGT) | KSISKY |
| 39 | 3G1 LCDR2 (IMGT) | SGS |
| 40 | 3G1 LCDR3 (IMGT) | QQHNEYPWT |
| 41 | 3G1 VHFR1 (IMGT) | QVQLQQSGAELMKPG ASVKISCKAT |
| 42 | 3G1 VHFR2 (IMGT) | IGWVKQRPGHGLEWC GE |

-continued

| SEQ ID NO. | NAME | SEQUENCE |
|---|---|---|
| 43 | 3G1 VHFR3 (IMGT) | NYNEKFKGKATFTAD TSSNTAYLQLTSLTS EDSAVYYC |
| 44 | 3G1 VH FR4 (IMGT) | WGQGTSLTVSS |
| 45 | 3G1 VL FR1 (IMGT) | DVQITQSPSYLAASP GETITINCRAS |
| 46 | 3G1 VL FR2 (IMGT) | VAWYQEKPGRTNKVL IY |
| 47 | 3G1 VL FR3 (IMGT) | ILSFGNPSRFSGSGS GTDFTLTISSLEPED FAMYYC |
| 48 | 3G1 VL FR4 (IMGT) | FGGGTKLEIK |
| 49 | 4B2 VH | QIQLVQSGPELKKPG ETVKISCKASGFTFT DYPMHWVKQAPGKSL KWMGWINTETEEPTY SDDFKGRFALSLETS ASTTYLQINNLKNED TATYFCARSGYYYGS TYAWFGYWGQGTLVT VSA |
| 50 | 4B2 VL | DVVMTQIPLSLPVSL GDQASISCRSSQSLI HTNGDTFLHWYLQKP GQSPKLLIYKVSNRF SGVPDRFTGGGSGTD FTLKISRVEAEDLGI YFCSQSALFPYTFGG GTNLEIK |
| 51 | 4B2 HCDR1 (IMGT) | GFTFTDYP |
| 52 | 4B2 HCDR2 (IMGT) | INTETEEP |
| 53 | 4B2 HCDR3 (IMGT) | ARSGYYYGSTYAWFG Y |
| 54 | 4B2 LCDR1 (IMGT) | QSLIHTNGDTF |
| 55 | 4B2 LCDR2 (IMGT) | KVS |
| 56 | 4B2 LCDR3 (IMGT) | SQSALFPYT |
| 57 | 4B2 VH FR1 (IMGT) | QIQLVQSGPELKKPG ETVKISCKAS |
| 58 | 4B2 VH FR2 (IMGT) | MHWVKQAPGKSLKWM GW |
| 59 | 4B2 VH FR3 (IMGT) | TYSDDFKGRFALSLE TSASTTYLQINNLKN EDTATYFC |
| 60 | 4B2 VH FR4 (IMGT) | WGQGTLVTVSA |
| 61 | 4B2 VL FR1 (IMGT) | DVVMTQIPLSLPVSL GDQASISCRSS |
| 62 | 4B2 VL FR2 (IMGT) | LHWYLQKPGQSPKLL IY |

-continued

| SEQ ID NO. | NAME | SEQUENCE |
|---|---|---|
| 63 | 4B2 VL FR3 (IMGT) | NRFSGVPDRFTGGGSGTDFTLKISRVEAEDLGIYFC |
| 64 | 4B2 VL FR4 (IMGT) | FGGGTNLEIK |
| 65 | 4F11 VH | DVKLVESGGDLVKPGGSLKLSCAASGFTFSAYSMSWVRQTPERRLEWVATINTGGSFTYYPDSVKGRFTISRDNAKNTLYLQMSSLKSEDTAMYFCTRVSDYGNSAYFPYWGQGTLVIVSA |
| 66 | 4F11 VL | QVVLTQSPALISASPGEKVTMTCSASSNVNYMSWYQQRPRSSPKPWIYLTSKLASGVPPRFSGSGSGTSYSLTISSMEAEDVATYYCQQWSSDPQTFGGGTKVEIK |
| 67 | 4F11 HCDR1 (IMGT) | GFTFSAYS |
| 68 | 4F11 HCDR2 (IMGT) | INTGGSFT |
| 69 | 4F11 HCDR3 (IMGT) | TRVSDYGNSAYFPY |
| 70 | 4F11 LCDR1 (IMGT) | SNVNY |
| 71 | 4F11 LCDR2 (IMGT) | LTS |
| 72 | 4F11 LCDR3 (IMGT) | QQWSSDPQT |
| 73 | 4F11 VH FR1 (IMGT) | DVKLVESGGDLVKPGGSLKLSCAAS |
| 74 | 4F11 VH FR2 (IMGT) | MSWVRQTPERRLEWVAT |
| 75 | 4F11 VH FR3 (IMGT) | YYPDSVKGRFTISRDNAKNTLYLQMSSLKSEDTAMYFC |
| 76 | 4F11 VHFR4 (IMGT) | WGQGTLVIVSA |
| 77 | 4F11 VL FR1 (IMGT) | QVVLTQSPALISASPGEKVTMTCSAS |
| 78 | 4F11 VL FR2 (IMGT) | MSWYQQRPRSSPKPWIY |
| 79 | 4F11 VL FR3 (IMGT) | KLASGVPPRFSGSGSGTSYSLTISSMEAEDVATYYC |
| 80 | 4F11 VL FR4 (IMGT) | FGGGTKVEIK |
| 81 | 1F2 VH | caggttcacctgcagcagtctggacctgaggtggcgaggcccggggcttcagtgaagctgtcctgcaaggcttctggctacaccttcactgactactatcttaactgggtgaagcagaggcctagacagggccttgagtggattggacagattcatcctggaagtactaatacttactacaatgagaagttcaagggcaaggccacactgactgcagacaaatcctccagcacagcctacatgcagctcagcagcctgacatctgaggactctgcagtctatttctgtgcaagatcgcttggtgatggttactacgtctatgctatggactactggggtcagggaaccgcagtcaccgtctcctca |
| 82 | 1F2 VL | GACATTGTGATGACCCAGTCTCAAAAATTCATGTCCACATCAGTAGGAGACAGGGTCAGCGTCACCTGCAAGGCCAGTCAGAATGTGGTTACTAATGTAGTCTGGTATCAACAGAAACCAGGTCAGTCTCCTAAACCACTGATTTACTCGGCATCCTACCGGTACAGTGGAGTCCCTGATCGCTTCACAGGCAGTGGATCTGGGACAGATTTCACTCTCACCATCAGCAATGTGCAGTCTGAAGACTTGGCAGAGTACTGCTGTCAGCAATATCACAGCTATCCATTCACGTTCGGCTCGGGGACAAAGTTGGAAGTAAAA |
| 83 | 1F4 VH | CAGGTTCACCTACAACAGTCTGGTTCTGAACTGAGGAGTCCTGGGTCTTCAGTAAAGCTTTCATGCAAGGATTTTGATTCAGAAGTCTTCCCTATTGTTTATATGAGATGGATTAGGCAGAAGCCTGGCCATGGATTTGAATGGATTGGAGACATACTCCCAAGTTTTGGTAGAACAATCTATGGAGAGAAGTTTGAGGACAAAGCCACACTAGATGCAGACACAGTGTCCAACACAGCCTACTTGGAGCTCAACAGTCTGACATCTGAGGACTCTGCTATCTACTACTGTGCAAGGGGGGACCATGGTAACTGGCTTGCTTACTGGGGCCAAGGGACTCTGGTCACTGTCTCTGCA |
| 84 | 1F4 VL | gacattgtgatgacccagtctcacaaattcatgtccacatcagttggagacagggtcacc |

-continued

| SEQ ID NO. | NAME | SEQUENCE |
|---|---|---|
| | | atcacctgcaaggccagtcaggatgtgagtactgctgtagcctggtatcaacaaaaaccaggccaatctcctaaactactgatttactgggcatccacccggcacactggagtccctaatcgcttcacaggcattatatctgggacagattacactctcactatcagcagtgtgcaggctgaagacctggcactttattactgtcagcaacattatagcgctccgtggacgttcggtggaggcaccaagctggaaatcaaa |
| 85 | 3G1 VH | CAGGTTCAGCTGCAGCAGTCTGGAGCTGAATTGATGAAGCCTGGGGCCTCAGTGAAGATTTCCTGCAAGGCTACTGGGTACAAATTCACTAGTTATTGGATAGGGTGGGTAAAGCAGAGGCCGGGACATGGCCTTGAGTGGTGTGGAGAGATTTTTCCTGGAAGTGGCAGTATTAACTATAATGAGAAATTTAAGGGCAAGGCCACATTCACTGCAGATACATCCTCCAACACAGCCTACTTGCAACTGACCAGCCTGACATCTGAGGACTCTGCCGTCTATTACTGTGCAAGAGGGGAGGATTATTACGGTAGTAGTTACGGTGCTATGGACTACTGGGGTCAAGGAACCTCACTCACCGTCTCCTCA |
| 86 | 3G1 VL | GATGTCCAGATAACCCAGTCTCCATCTTATCTTGCTGCATCTCCTGGAGAAACCATTACTATTAATTGCAGGGCAAGTAAGAGCATCAGCAAATATGTAGCCTGGTATCAAGAGAAACCTGGGAGAACTAACAAGGTTCTTATATATTCTGGATCAATCTTGTCATTTGGAAATCCATCAAGGTTCAGTGGCAGTGGATCTGGTACAGATTTCACTCTCACCATCAGTAGCCTGGAGCCTGAAGATTTTGCAATGTATTACTGTCAACAGCATAATGAATACCCGTGGACGTTCGGTGGAGGCACCAAGCTGGAAATCAAA |
| 87 | 4B2 VH | cagatccagttggtgcagtctggacctgagctgaagaagcctggagagacagtcaagatctcctgcaaggcttctggttttaccttcacagactatccaatgcactgggtgaagcaggctccaggaaagagtttaaagtggatgggttggataaacactgagactgaagagccaacatattcagatgacttcaagggacggtttgccttgtctttggaaacctctgccagcacaacctatttgcagatcaacaatctcaaaaatgaggacacggctacatatttctgtgctagatcaggttattactatggtagtacctacgcctggtttggttactggggccaagggactctggtcactgtctctgca |
| 88 | 4B2 VL | GATGTTGTGATGACCCAAATTCCACTCTCCCTGCCTGTCAGTCTCGGAGATCAGGCCTCCATCTCTTGCAGATCTAGTCAGAGCCTTATACACACTAATGGAGACACCTTTTTACATTGGTACCTGCAGAAGCCAGGCCAGTCTCCAAAGCTCCTGATCTACAAAGTTTCCAACCGATTTTCTGGGGTCCCAGACAGGTTCACTGGCGGTGGATCAGGGACAGATTTCACACTCAAGATCAGCAGAGTGGAGGCTGAGGATCTGGGAATTTATTTCTGCTCTCAAAGTGCACTTTTTCCGTACACGTTCGGAGGGGGGACCAACCTGGAAATAAAA |
| 89 | 4F11 VH | gacgtgaaactggtggaatctgggggagacttagtgaagcctggagggtccctgaaactctcctgtgcagcctctggattcactttcagtgcctattccatgtcttgggttcgccagactccggagaggaggctggagtgggtcgcaaccattaatactggtggtagtttcacctactatccagacagtgtgaagggccgattcaccatctccagagacaatgccaagaacaccctgtacctgcaaatgagcagtctgaagtctgaggacacagccatgtatttctgtacaagagtttccgactacggtaatagcgcctactttccttactggggccaagggactctggtcattgtctctgca |
| 90 | 4F11 VL | CAAGTTGTTCTCACCCAGTCTCCAGCACTCATATCTGCGTCTCCAGGGGAGAAGGTCACCATGACCTGCAGTGCC |

-continued

| SEQ ID NO. | NAME | SEQUENCE |
|---|---|---|
| | | AGCTCAAATGTAAAT TACATGTCCTGGTAC CAGCAGAGGCCAAGA TCCTCCCCCAAACCC TGGATTTATCTCACA TCCAAACTGGCTTCT GGAGTCCCTCCTCGT TTCAGTGGCAGTGGG TCTGGGACCTCTTAC TCTCTCACAATCAGC AGCATGGAGGCTGAA GATGTTGCCACTTAT TACTGCCAGCAGTGG AGCAGTGACCCCCAG ACGTTCGGAGGGGGG ACCAAGGTGGAAATA AAA |
| 91 | 5' consensus anchor primer | GGCCACGCGTCGACT AGTACGGGNNGGGNN GGGNNG, Wherein N is C, U, or A |
| 92 | constant region specific reverse primer IgG2a | CCTTGACCAGGCATC CTAGAGTC |
| 93 | constant region specific reverse primer IgG2b | GGAGGTGTGCACACT GCTGGACAG |
| 94 | IF2 VHCDR1 (Chothia) | GYTFTDY |
| 95 | IF2 VHCDR2 (Chothia) | HPGSTN |
| 96 | IF2 VHCDR3 (Chothia) | SLGDGYYVYAMDY |
| 97 | IF2 VLCDR1 (Chothia) | KASQNVVTNVV |
| 98 | 1F2 VLCDR2 (Chothia) | SASYRYS |
| 99 | IF2 VLCDR3 (Chothia) | QQYHSYPFT |
| 100 | IF2 VHCDR1 (ABM) | GYTFTDYYLN |
| 101 | IF2 VHCDR2 (ABM) | QIHPGSTNTY |
| 102 | IF2 VHCDR3 (ABM) | SLGDGYYVYAMDY |
| 103 | IF2 VLCDR1 (ABM) | KASQNWTNW |

-continued

| SEQ ID NO. | NAME | SEQUENCE |
|---|---|---|
| 104 | IF2 VLCDR2 (ABM) | SASYRYS |
| 105 | IF2 VLCDR3 (ABM) | QQYHSYPFT |
| 106 | IF2 VHCDR1 (Kabat) | DYYLN |
| 107 | IF2 VHCDR2 (Kabat) | QIHPGSTNTYYNEKF KG |
| 108 | IF2 VHCDR3 (Kabat) | SLGDGYYVYAMDY |
| 109 | IF2 VLCDR1 (Kabat) | KASQNVVTNVV |
| 110 | IF2 VLCDR2 (Kabat) | SASYRYS |
| 111 | IF2 VLCDR3 (Kabat) | QQYHSYPFT |
| 112 | IF4 VHCDR1 (Chothia) | DSEVFP1V |
| 113 | IF4 VHCDR2 (Chothia) | LPSFGR |
| 114 | IF4 VHCDR3 (Chothia) | GDHGNWLAY |
| 115 | IF4 VLCDR1 (Chothia) | KASQDVSTAVA |
| 116 | IF4 VLCDR2 (Chothia) | WASTRHT |
| 117 | IF4 VLCDR3 (Chothia) | QQHYSAPWT |
| 118 | IF4 VHCDR1 (ABM) | DSEVFPIVYMR |
| 119 | IF4 VHCDR2 (ABM) | DILPSFGRTI |
| 120 | IF4 VHCDR3 (ABM) | GDHGNWLAY |
| 121 | 1F4 VLCDR1 (ABM) | KASQDVSTAVA |
| 122 | 1F4 VLCDR2 (ABM) | WASTRHT |

-continued

| SEQ ID NO. | NAME | SEQUENCE |
|---|---|---|
| 123 | IF4 VLCDR3 (ABM) | QQHYSAPWT |
| 124 | IF4 VHCDR1 (Kabat) | P1VYMR |
| 125 | IF4 VHCDR2 (Kabat) | D1LPSFGRTIYG EKFED |
| 126 | IF4 VHCDR3 (Kabat) | GDHGNWLAY |
| 127 | IF4 VLCDR1 (Kabat) | KASQDVSTAVA |
| 128 | IF4 VLCDR2 (Kabat) | WASTRHT |
| 129 | IF4 VLCDR3 (Kabat) | QQHYSAPWT |
| 130 | 4B2 VHCDR1 (Chothia) | GFTFTDY |
| 131 | 4B2 VHCDR2 (Chothia) | NTETEE |
| 132 | 4B2 VHCDR3 (Chothia) | SGYYYGSTYAW FGY |
| 133 | 4B2 VLCDR1 (Chothia) | RSSQSLIHTNGD TFLH |
| 134 | 4B2 VLCDR2 (Chothia) | KVSNRFS |
| 135 | 4B2 VLCDR3 (Chothia) | SQSALFPYT |
| 136 | 4B2 VHCDR1 (ABM) | GFTFTDYPMH |
| 137 | 4B2 VHCDR2 (ABM) | WINTETEEPT |
| 138 | 4B2 VHCDR3 (ABM) | SGYYYGSTYAWFGY |
| 139 | 4B2 VLCDR1 (ABM) | RSSQSLIHTNGDT FLH |
| 140 | 4B2 VLCDR2 (ABM) | KVSNRFS |

-continued

| SEQ ID NO. | NAME | SEQUENCE |
|---|---|---|
| 141 | 4B2 VLCDR3 (ABM) | SQSALFPYT |
| 142 | 4B2 VHCDR1 (Kabat) | DYPMH |
| 143 | 4B2 VHCDR2 (Kabat) | WINTETEEPTYSD DFKG |
| 144 | 4B2 VHCDR3 (Kabat) | SGYYYGSTYAW FGY |
| 145 | 4B2 VLCDR1 (Kabat) | RSSQSLIHTNGDT FLH |
| 146 | 4B2 VLCDR2 (Kabat) | KVSNRFS |
| 147 | 4B2 VLCDR3 (Kabat) | SQSALFPYT |
| 148 | 4F11 VHCDR1 (Chothia) | GFTFSAY |
| 149 | 4F11 VHCDR2 (Chothia) | NTGGSF |
| 150 | 4F11 VHCDR3 (Chothia) | VSDYGNSAYFPY |
| 151 | 4F11 VLCDR1 (Chothia) | SASSNVNYMS |
| 152 | 4F11 VLCDR2 (Chothia) | LTSKLAS |
| 153 | 4F11 VLCDR3 (Chothia) | QQWSSDPQT |
| 154 | 4F11 VHCDR1 (ABM) | GFTFSAYSMS |
| 155 | 4F11 VHCDR2 (ABM) | TINTGGSFTY |
| 156 | 4F11 VHCDR3 (ABM) | VSDYGNSAYFPY |
| 157 | 4F11 VLCDR1 (ABM) | SASSNVNYMS |
| 158 | 4F11 VLCDR2 (ABM) | LTSKLAS |
| 159 | 4F11 VLCDR3 (ABM) | QQWSSDPQT |

-continued

| SEQ ID NO. | NAME | SEQUENCE |
|---|---|---|
| 160 | 4F11 VHCDR1 (Kabat) | SAYSMS |
| 161 | 4F11 VHCDR2 (Kabat) | TINTGGSFTYYPDSVKG |
| 162 | 4F11 VHCDR3 (Kabat) | VSDYGNSAYFPY |
| 163 | 4F11 VLCDR1 (Kabat) | SASSNVNYMS |
| 164 | 4F11 VLCDR2 (Kabat) | LTSKLAS |
| 165 | 4F11 VLCDR3 (Kabat) | QQWSSDPQT |
| 166 | IGHV1-46 | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCAR |
| 167 | IGHV1-2 | QVQLVQSGAEVKKPGASVKVSCKASGYTFTGYYMHWVRQAPGQGLEWMGRINPNSGGTNYAQKFQGRVTMTRDTSISTAYMELSRLRSDDTAVYYCAR |
| 168 | 1F2 VH1 | QVQLQESGAEVKKPGASVKVSCKASGYTFTDYYLNWVRQAPGQGLEWMGQIHPGSTNTYYNEKFKGRVTMTRDTSTSTVYMELSSLRSEDTAVYYCARSLGDGYYVYAMDYWGQGTTVTVSS |
| 169 | 1F2 VH2 | QVQLVQSGAEVKKPGASVKVSCKASGYTFTDYYLNWVRQAPGQGLEWMGQIHPGSTNTYYNEKFKGRVTMTRDTSISTAYMELSRLRSDDTAVYFCARSLGDGYYVYAMDYWGQGTTVTVSS |
| 170 | 1F2 VH3 | EVQLVESGPEVKKPGATVKISCKVSGYTFTDYYLNWVQQAPGRGLEWMGQIHPGSTNTYYNEKFKGRVTMTADTSTGTAYMQLSSLTSEDTAVYFCARSLGDGYYVYAMDYWGQGTTVTVAS |
| 171 | 1F2 VH4 | QVQLVQSGAEVKKPGSSVKVSCKASGYTFTDYYLNWVRQAPGQGLEWMGQIHPGSTNTYYNEKFKGRVTITADKSTSTAYMELSSLRSEDTAVYYCARSLGDGYYVYAMDYWGQGTTVTVSS |
| 172 | 1F2 VH5 | QVQLVQSGAEVKKPGASVKVSCKASGYTFTDYYLNWVRQAPGQGLEWMGQIHPGSTNTYYNEKFKGRVTMTRDTSTSTVYMELSSLRSEDTAVYYCARSLGDGYYVYAMDYWGQGTLVTVSS |
| 173 | 1F2 VH6 | QVHLQESGAEVKKPGASVKVSCKASGYTFTDYYLNWVRQRPRQGLEWMGQIHPGSTNTYYNEKFKGRVTMTRDTSTSTVYMQLSSLTSEDTAVYFCARSLGDGYYVYAMDYWGQGTAVTVSS |
| 174 | 1F2 VH7 | QVQLQQSGPEVAKPGASVKLSCKASGYTFTDYYLNWVRQAPGQGLEWLGQIHPGSTNTYYNEKFKGRVTMTRDTSTSTVYMELSSLTSEDTAVYYCARSLGDGYYVYAMDYWGQGTAVTVSS |
| 175 | 1F2 VH8 | QVHLQQSGPEVAKPGASVKVSCKASGYTFTDYYLNWVRQAPGQGLEWLGQIHPGSTNTYYNEKFKGRVTMTADKSTSTVYMELSSLRSEDTAVYFCARSLGDGYYVYAMDYWGQGTAVTVSS |
| 176 | IGKVH8 | AIRMTQSPSSFSASTGDRVTITCRASQGISSYLAWYQQKPGKAPKLLIYAASTLQSGVPSRFSGSGSGTDFTLTISCLQSEDFATYYCQQYYSYP |
| 177 | 1F2 VL1 | DIQMTQSPSFLSASVGDRVTITCKASQNVVTNVVWYQQKPGKAPKLLIYSASYRYSGVPSRFSGSGSGTEFTLTISSLQPEDFATYSCQQYHSYPFTFGQGTRLEIK |
| 178 | 1F2 VL2 | DWMTQSPDSLAVSLGERVTINCKASQNVVTNVVWYQQKPGQSPKLLIYSASYRYSGVPDRFSGSGSGTDFTLTISSLQAEDVAVYYCQQYHSYPFTFGQGTKLEIK |
| 179 | 1F2 VL3 | DWMTQSPSSLSASVGDRVSITCKASQNVVTNVVWYQQKPGKAPKLLVYSASYRYSGVPSR |

-continued

| SEQ ID NO. | NAME | SEQUENCE |
|---|---|---|
| | | FSGSGSGTDFTLTIS<br>SLQPEDFATYCCQQY<br>HSYPFTFGQGTKLDI<br>K |
| 180 | 1F2 VL4 | DIQMTQSPSSLSASV<br>GDRVTITCKASQNVV<br>TNVVWYQQKPGQAPK<br>LLIYSASYRYSGVPS<br>RFSGSGSGTEFTFTI<br>SSLQPEDLATYSCQQ<br>YHSYPFTFGQGTKLE<br>IK |
| 181 | 1F2 VL5 | AIRMTQSPSSFSAST<br>GDRVTITCKASQNVV<br>TNVVWYQQKPGKAPK<br>LLIYSASYRYSGVPS<br>RFSGSGSGTDFTLTI<br>SCLQSEDFATYYCQQ<br>YHSYPFTFGQGTKLE<br>IK |
| 182 | 1F2 VL6 | DIQLTQSPKFLSASV<br>GDRVTITCKASQNVV<br>TNVVWYQQKPGKAPK<br>LLIYSASYRYSGVPD<br>RFSGSGSGTEFTLTI<br>SSLQPEDFAEYSCQQ<br>YHSYPFTFGSGTKLE<br>VK |
| 183 | 1F2 VL7 | DIVMTQSPSFLSASV<br>GDRVTITCKASQNVV<br>TNVVWYQQKPGKAPK<br>PLIYSASYRYSGVPS<br>RFSGSGSGTEFTLTI<br>SSLQPEDLAEYYCQQ<br>YHSYPFTFGSGTKLE<br>VK |
| 184 | 1F2 VL8 | DIQMTQSPSTLSASV<br>GDRVTITCKASQNVV<br>TNVVWYQQKPGQAPK<br>LLIYSASYRYSGVPS<br>RFSGSGSGTEFTFTI<br>SSLQSEDLAEYYCQQ<br>YHSYPFTFGSGTKLE<br>VK |
| 185 | 1F2 HC0 | MGWTLVFLFLLSVTA<br>GVHSQVHLQQSGPEV<br>ARPGASVKLSCKASG<br>YTFTDYYLNWVKQRP<br>RQGLEWIGQIHPGST<br>NTYYNEKFKGKATLT<br>ADKSSSTAYMQLSSL<br>TSEDSAVYFCARSLG<br>DGYYVYAMDYWGQGT<br>AVTVSSASTKGPSVF<br>PLAPSSKSTSGGTAA<br>LGCLVKDYFPEPVTV<br>SWNSGALTSGVHTFP<br>AVLQSSGLYSLSSVV<br>TVPSSSLGTQTYICN<br>VNHKPSNTKVDKKVE<br>PKSCDKTHTCPPCPA<br>PELLGGPSVFLFPPK<br>PKDTLMISRTPEVTC<br>VVVDVSHEDPEVKFN<br>WYVDGVEVHNAKTKP<br>REEQYNSTYRVVSVL<br>TVLHQDWLNGKEYKC<br>KVSNKALPAPIEKTI<br>SKAKGQPREPQVYTL |

-continued

| SEQ ID NO. | NAME | SEQUENCE |
|---|---|---|
| | | PPSRDELTKNQVSLT<br>CLVKGFYPSDIAVEW<br>ESNGQPENNYKTTPP<br>VLDSDGSFFLYSKLT<br>VDKSRWQQGNVFSCS<br>VMHEALHNHYTQKSL<br>SLSPGK |
| 186 | 1F2 HC1 | MGWTLVFLFLLSVTA<br>GVHSQVQLQESGAEV<br>KKPGASVKVSCKASG<br>YTFTDYYLNWVRQAP<br>GQGLEWMGQIHPGST<br>NTYYNEKFKGRVTMT<br>RDTSTSTVYMELSSL<br>RSEDTAVYYCARSLG<br>DGYYVYAMDYWGQGT<br>TVTVSSASTKGPSVF<br>PLAPSSKSTSGGTAA<br>LGCLVKDYFPEPVTV<br>SWNSGALTSGVHTFP<br>AVLQSSGLYSLSSVV<br>TVPSSSLGTQTYICN<br>VNHKPSNTKVDKKVE<br>PKSCDKTHTCPPCPA<br>PELLGGPSVFLFPPK<br>PKDTLMISRTPEVTC<br>VVVDVSHEDPEVKFN<br>WYVDGVEVHNAKTKP<br>REEQYNSTYRVVSVL<br>TVLHQDWLNGKEYKC<br>KVSNKALPAPIEKTI<br>SKAKGQPREPQVYTL<br>PPSRDELTKNQVSLT<br>CLVKGFYPSDIAVEW<br>ESNGQPENNYKTTPP<br>VLDSDGSFFLYSKLT<br>VDKSRWQQGNVFSCS<br>VMHEALHNHYTQKSL<br>SLSPGK |
| 187 | 1F2 HC2 | MGWTLVFLFLLSVTA<br>GVHSQVQLVQSGAEV<br>KKPGASVKVSCKASG<br>YTFTDYYLNWVRQAP<br>GQGLEWMGQIHPGST<br>NTYYNEKFKGRVTMT<br>RDTSISTAYMELSRL<br>RSDDTAVYFCARSLG<br>DGYYVYAMDYWGQGT<br>TVTVSSASTKGPSVF<br>PLAPSSKSTSGGTAA<br>LGCLVKDYFPEPVTV<br>SWNSGALTSGVHTFP<br>AVLQSSGLYSLSSVV<br>TVPSSSLGTQTYICN<br>VNHKPSNTKVDKKVE<br>PKSCDKTHTCPPCPA<br>PELLGGPSVFLFPPK<br>PKDTLMISRTPEVTC<br>VVVDVSHEDPEVKFN<br>WYVDGVEVHNAKTKP<br>REEQYNSTYRVVSVL<br>TVLHQDWLNGKEYKC<br>KVSNKALPAPIEKTI<br>SKAKGQPREPQVYTL<br>PPSRDELTKNQVSLT<br>CLVKGFYPSDIAVEW<br>ESNGQPENNYKTTPP<br>VLDSDGSFFLYSKLT<br>VDKSRWQQGNVFSCS<br>VMHEALHNHYTQKSL<br>SLSPGK |

-continued

| SEQ ID NO. | NAME | SEQUENCE |
|---|---|---|
| 188 | 1F2 HC3 | MGWTLVFLFLLSVTA<br>GVHSEVQLVESGPEV<br>KKPGATVKISCKVSG<br>YTFTDYYLNWVQQAP<br>GRGLEWMGQIHPGST<br>NTYYNEKFKGRVTMT<br>ADTSTGTAYMQLSSL<br>TSEDTAVYFCARSLG<br>DGYYVYAMDYWGQGT<br>TVTVASASTKGPSVF<br>PLAPSSKSTSGGTAA<br>LGCLVKDYFPEPVTV<br>SWNSGALTSGVHTFP<br>AVLQSSGLYSLSSVV<br>TVPSSSLGTQTYICN<br>VNHKPSNTKVDKKVE<br>PKSCDKTHTCPPCPA<br>PELLGGPSVFLFPPK<br>PKDTLMISRTPEVTC<br>VVVDVSHEDPEVKFN<br>WYVDGVEVHNAKTKP<br>REEQYNSTYRVVSVL<br>TVLHQDWLNGKEYKC<br>KVSNKALPAPIEKTI<br>SKAKGQPREPQVYTL<br>PPSRDELTKNQVSLT<br>CLVKGFYPSDIAVEW<br>ESNGQPENNYKTTPP<br>VLDSDGSFFLYSKLT<br>VDKSRWQQGNVFSCS<br>VMHEALHNHYTQKSL<br>SLSPGK |
| 189 | 1F2 HC4 | MGWTLVFLFLLSVTA<br>GVHSQVQLVQSGAEV<br>KKPGSSVKVSCKASG<br>YTFTDYYLNWVRQAP<br>GQGLEWMGQIHPGST<br>NTYYNEKFKGRVTIT<br>ADKSTSTAYMELSSL<br>RSEDTAVYYCARSLG<br>DGYYVYAMDYWGQGT<br>TVTVSSASTKGPSVF<br>PLAPSSKSTSGGTAA<br>LGCLVKDYFPEPVTV<br>SWNSGALTSGVHTFP<br>AVLQSSGLYSLSSVV<br>TVPSSSLGTQTYICN<br>VNHKPSNTKVDKKVE<br>PKSCDKTHTCPPCPA<br>PELLGGPSVFLFPPK<br>PKDTLMISRTPEVTC<br>VVVDVSHEDPEVKFN<br>WYVDGVEVHNAKTKP<br>REEQYNSTYRVVSVL<br>TVLHQDWLNGKEYKC<br>KVSNKALPAPIEKTI<br>SKAKGQPREPQVYTL<br>PPSRDELTKNQVSLT<br>CLVKGFYPSDIAVEW<br>ESNGQPENNYKTTPP<br>VLDSDGSFFLYSKLT<br>VDKSRWQQGNVFSCS<br>VMHEALHNHYTQKSL<br>SLSPGK |
| 190 | 1F2 HC5 | MGWTLVFLFLLSVTA<br>GVHSQVQLVQSGAEV<br>KKPGASVKVSCKASG<br>YTFTDYYLNWVRQAP<br>GQGLEWMGQIHPGST<br>NTYYNEKFKGRVTMT<br>RDTSTSTVYMELSSL<br>RSEDTAVYYCARSLG<br>DGYYVYAMDYWGQGT<br>LVTVSSASTKGPSVF<br>PLAPSSKSTSGGTAA<br>LGCLVKDYFPEPVTV<br>SWNSGALTSGVHTFP<br>AVLQSSGLYSLSSVV<br>TVPSSSLGTQTYICN<br>VNHKPSNTKVDKKVE<br>PKSCDKTHTCPPCPA<br>PELLGGPSVFLFPPK<br>PKDTLMISRTPEVTC<br>VVVDVSHEDPEVKFN<br>WYVDGVEVHNAKTKP<br>REEQYNSTYRVVSVL<br>TVLHQDWLNGKEYKC<br>KVSNKALPAPIEKTI<br>SKAKGQPREPQVYTL<br>PPSRDELTKNQVSLT<br>CLVKGFYPSDIAVEW<br>ESNGQPENNYKTTPP<br>VLDSDGSFFLYSKLT<br>VDKSRWQQGNVFSCS<br>VMHEALHNHYTQKSL<br>SLSPGK |
| 191 | 1F2 HC6 | MGWTLWLFLLSVTAG<br>VHSQVHLQESGAEVK<br>KPGASVKVSCKASGY<br>TFTDYYLNWVRQRPR<br>QGLEWMGQIHPGSTN<br>TYYNEKFKGRVTMTR<br>DTSTSTVYMQLSSLT<br>SEDTAVYFCARSLGD<br>GYYVYAMDYWGQGTA<br>VTVSSASTKGPSVFP<br>LAPSSKSTSGGTAAL<br>GCLVKDYFPEPVTVS<br>WNSGALTSGVHTFPA<br>VLQSSGLYSLSSVVT<br>WSSSLGTQTYICNVN<br>HKPSNTKVDKKVEPK<br>SCDKTHTCPPCPAPE<br>LLGGPSVFLFPPKPK<br>DTLMISRTPEVTCVV<br>VDVSHEDPEVKFNWY<br>VDGVEVHNAKTKPRE<br>EQYNSTYRVVSVLTV<br>LHQDWLNGKEYKCKV<br>SNKALPAPIEKTISK<br>AKGQPREPQVYTLPP<br>SRDELTKNQVSLTCL<br>VKGFYPSDIAVEWES<br>NGQPENNYKTTPPVL<br>DSDGSFFLYSKLTVD<br>KSRWQQGNVFSCSVM<br>HEALHNHYTQKSLSL<br>SPGK |
| 192 | 1F2 HC7 | MGWTLWLFLLSVTAG<br>VHSQVQLQQSGPEVA<br>KPGASVKISCKASGY<br>TFTDYYLNWVRQAPG<br>QGLEWIGQIHPGSTN<br>TYYNEKFKGRVTMTR<br>DTSTSTVYMELSSLT<br>SEDTAVYYCARSLGD<br>GYYVYAMDYWGQGTA<br>VTVSSASTKGPSVFP<br>LAPSSKSTSGGTAAL<br>GCLVKDYFPEPVTVS<br>WNSGALTSGVHTFPA<br>VLQSSGLYSLSSVVT<br>VPSSSLGTQTYICNV<br>NHKPSNTKVDKKVEP<br>KSCDKTHTCPPCPAP<br>ELLGGPSVFLFPPKP |

-continued

| SEQ ID NO. | NAME | SEQUENCE |
|---|---|---|
| | | KDTLMISRTPEVTCV VVDVSHEDPEVKFNW YVDGVEVHNAKTKPR EEQYNSTYRVVSVLT VLHQDWLNGKEYKCK VSNKALPAPIEKTIS KAKGQPREPQVYTLP PSRDELTKNQVSLTC LVKGFYPSDIAVEWE SNGQPENNYKTTPPV LDSDGSFFLYSKLTV DKSRWQQGNVFSCSV MHEALHNHYTQKSLS LSPGK |
| 193 | 1F2 HC8 | MGWTLVFLFLLSVTA GVHSQVHLQQSGPEV AKPGASVKVSCKASG YTFTDYYLNWVRQAP GQGLEWLGQIHPGST NTYYNEKFKGRVTMT ADKSTSTVYMELSSL RSEDTAVYFCARSLG DGYYVYAMDYWGQGT AVTVSSASTKGPSVF PLAPSSKSTSGGTAA LGCLVKDYFPEPVTV SWNSGALTSGVHTFP AVLQSSGLYSLSSVV TVPSSSLGTQTYICN VNHKPSNTKVDKKVE PKSCDKTHTCPPCPA PELLGGPSVFLFPPK PKDTLMISRTPEVTC VVVDVSHEDPEVKFN WYVDGVEVHNAKTKP REEQYNSTYRVVSVL TVLHQDWLNGKEYKC KVSNKALPAPIEKTI SKAKGQPREPQVYTL PPSRDELTKNQVSLT CLVKGFYPSDIAVEW ESNGQPENNYKTTPP VLDSDGSFFLYSKLT VDKSRWQQGNVFSCS VMHEALHNHYTQKSL SLSPGK |
| 194 | 1F2 LC0 | MVSSAQFLGLLLLCF QGTRCDIVMTQSQKF MSTSVGDRVSVTCKA SQNVVTNVVWYQQKP GQSPKPLIYSASYRY SGVPDRFTGSGSGTD FTLTISNVQSEDLAE YCCQQYHSYPFTFGS GTKLEVKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC |
| 195 | 1F2 LC1 | MVSSAQFLGLLLLCF QGTRCDIQMTQSPSF LSASVGDRVTITCKA SQNVVTNVVWYQQKP GKAPKLLIYSASYRY SGVPSRFSGSGSGTE FTLTISSLQPEDFAT YSCQQYHSYPFTFGQ GTRLEIKRTVAAPSV FIFPPSDEQLKSGTA |

-continued

| SEQ ID NO. | NAME | SEQUENCE |
|---|---|---|
| | | SVVCLLNNFYPREAK VQWKVDNALQSGNSQ ESVTEQDSKDSTYSL SSTLTLSKADYEKHK VYACEVTHQGLSSPV TKSFNRGEC |
| 196 | 1F2 LC2 | MVSSAQFLGLLLLCF QGTRCDWMTQSPDSL AVSLGERVTINCKAS QNVVTNVVWYQQKPG QSPKLLIYSASYRYS GVPDRFSGSGSGTDF ILTISSLQAEDVAVY YCQQYHSYPFTFGQG TKLEIKRTVAAPSVF IFPPSDEQLKSGTAS VVCLLNNFYPREAKV QWKVDNALQSGNSQE SVTEQDSKDSTYSLS STLTLSKADYEKHKV YACEVTHQGLSSPVT KSFNRGEC |
| 197 | 1F2 LC3 | MVSSAQFLGLLLLCF QGTRCDWMTQSPSSL SASVGDRVSITCKAS QNVVTNVVWYQQKPG KAPKLLVYSASYRYS GVPSRFSGSGSGTDF TLTISSLQPEDFATY CCQQYHSYPFTFGQG TKLDIKRTVAAPSVF IFPPSDEQLKSGTAS VVCLLNNFYPREAKV QWKVDNALQSGNSQE SVTEQDSKDSTYSLS STLTLSKADYEKHKV YACEVTHQGLSSPVT KSFNRGEC |
| 198 | 1F2 LC4 | MVSSAQFLGLLLLCF QGTRCDIQMTQSPSS LSASVGDRVTITCKA SQNVVTNVVWYQQKP GQAPKLLIYSASYRY SGVPSRFSGSGSGTE FTFTISSLQPEDLAT YSCQQYHSYPFTFGQ GTKLEIKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC |
| 199 | 1F2 LC5 | MVSSAQFLGLLLLCF QGTRCAIRMTQSPSS FSASTGDRVTITCKA SQNVVTNVVWYQQKP GKAPKLLIYSASYRY SGVPSRFSGSGSGTD FTLTISCLQSEDFAT YYCQQYHSYPFTFGQ GTKLEIKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC |

-continued

| SEQ ID NO. | NAME | SEQUENCE |
|---|---|---|
| 200 | 1F2 LC6 | MVSSAQFLGLLLLCF QGTRCDIQITQSPKF LSASVGDRVTITCKA SQNVVTNVVWYQQKP GKAPKLLIYSASYRY SGVPDRFSGSGSGTE FTLTISSLQPEDFAE YSCQQYHSYPFTFGS GTKLEVKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC |
| 201 | 1F2 LC7 | MVSSAQFLGLLLLCF QGTRCDIVMTQSPSF LSASVGDRVTITCKA SQNVVTNVVWYQQKP GKAPKPLIYSASYRY SGVPSRFSGSGSGTE FTLTISSLQPEDLAE YYCQQYHSYPFTFGS GTKLEVKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC |
| 202 | 1F2 LC8 | MVSSAQFLGLLLLCF QGTRCDIQMTQSPST LSASVGDRVTITCKA SQNVVTNVVWYQQKP GQAPKLLIYSASYRY SGVPSRFSGSGSGTE FTFTISSLQSEDLAE YYCQQYHSYPFTFGS GTKLEVKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC |
| 203 | 1F2 Heavy Chain Signal Peptide | MGWTLVFLFLLSVTA GVHS |
| 204 | 1F2 Light Chain Signal Peptide | MVSSAQFLGLLLLCF QGTRC |

5. DETAILED DESCRIPTION

In one aspect, provided herein are antibodies (see, e.g., Sections 5.1 and 5.2, infra) that bind to NA of influenza B virus strains and compositions comprising such antibodies (see, e.g., Section 5.4, infra). In one embodiment, an antibody described herein binds to an NA of an influenza B virus strain of the Victoria lineage and an NA of an influenza B virus strain of the Yamagata lineage, and the antibody inhibits the enzymatic activity of the NA of the influenza B virus strains of the Victoria and Yamagata lineages. In another embodiment, an antibody described herein cross-reacts with an NA of two or more influenza B virus strains of the Victoria lineage and two or more influenza B virus strains of the Yamagata lineage, and the antibody inhibits the enzymatic activity of the NA of the influenza B virus strains of the Victoria and Yamagata lineages. In specific embodiments, the antibodies described herein comprises the variable regions or complementarity determining regions (CDRs) of the 1F2, 1F4, 3G1, 4B2, or 4F11 antibody.

In another aspect, provided herein are polynucleotides encoding antibodies described herein (see, e.g., 5.2, infra). In another aspect, provided herein are expression vectors comprising a polynucleotide encoding an antibody described herein (see, e.g., Section 5.2, infra). In another aspect, provided herein are host cells comprising a polynucleotide encoding an antibody described herein (see, e.g., Section 5.3, infra). In a specific embodiment, provided herein are host cells engineered to express an antibody described herein (e.g., Section 5.3, infra). The host cells may be used to produce the antibody using techniques known to one of skill in the art or described herein (see, e.g., Section 5.3, infra).

In another aspect, provided herein are methods for preventing influenza virus disease (e.g., influenza B virus disease) comprising administering to a subject in need thereof an antibody described herein, or a composition comprising such an antibody. See, e.g., Section 5.5, infra, for methods of preventing influenza virus disease (e.g., influenza B virus disease). In another aspect, provided herein are methods for treating an influenza virus (e.g., influenza B virus) infection or a influenza virus disease (e.g., an influenza B virus disease) comprising administering to a subject in need thereof an antibody described herein, or composition comprising such an antibody. See, e.g., Section 5.5, infra, for methods of treating an influenza virus (e.g., influenza B virus) infection or an influenza virus disease (e.g., influenza B virus disease).

In another aspect, provided herein are methods for detecting an influenza B virus, or diagnosing an influenza B virus infection. See, e.g., Section 5.6, infra, for more regarding such methods.

In another aspect, provided herein are influenza virus neuraminidase polypeptides as well as antigenic peptides which may be used as immunogens to induce an immune response to influenza virus (e.g., influenza B virus). Such immunogens may be used to prevent an influenza virus disease (e.g., an influenza B virus disease).

In another aspect, provided herein are kits comprising an antibody described herein (see, e.g., Sections 5.1 and 5.2). See, e.g., Section 5.8, infra, regarding kits.

5.1 Antibodies

In one aspect, provided herein are antibodies (e.g., monoclonal antibodies, such as chimeric or humanized antibodies, and antigen-binding fragments) that bind to an influenza B virus neuraminidase (NA). In a specific embodiment, provided herein is an antibody that binds to NA of one, two, three or more of the influenza B virus strains described herein (e.g., the influenza B virus strains described in Section 6 and/or Section 7, infra). In a specific embodiment, an antibody described herein is isolated or purified.

Antibodies can include, for example, monoclonal antibodies, recombinantly produced antibodies, monospecific antibodies, multispecific antibodies (including bispecific antibodies), human antibodies, humanized antibodies, chimeric antibodies, synthetic antibodies, tetrameric antibodies comprising two heavy chain and two light chain molecule, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv), camelized antibodies, affybodies, Fab fragments, F(ab') fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA or IgY), any class, (e.g., IgG1, IgG2, IgG3, IgG4, IgA1 or IgA2), or any subclass (e.g., IgG2a or IgG2b) of immunoglobulin molecule. In certain embodiments, antibodies described herein are IgG antibodies, or a class (e.g., human IgG1 or IgG4) or subclass thereof.

In certain embodiments, antibodies described herein are IgA antibodies. In a specific embodiment, an antibody includes any molecule with an antigen-binding site that binds an antigen. In some embodiments, an antibody includes an antigen-binding fragment (e.g., the region(s) of an immunoglobulin that binds to an antigen or an epitope, such as a sequence comprising complementarity determining regions (e.g., the heavy and/or light chain variable regions)). In other embodiments, an antibody does not include antigen-binding fragments.

In a specific embodiment, an antibody described herein is a monoclonal antibody. As used herein, the term "monoclonal antibody" refers to an antibody obtained from a population of homogenous or substantially homogeneous antibodies. The term "monoclonal" is not limited to any particular method for making the antibody. Generally, a population of monoclonal antibodies can be generated by cells, a population of cells, or a cell line. In specific embodiments, a "monoclonal antibody," as used herein, is an antibody produced by a single cell (e.g., hybridoma or host cell producing a recombinant antibody), wherein the antibody binds to an influenza B virus NA as determined, e.g., by ELISA or other antigen-binding or competitive binding assay known in the art or in the Examples provided herein. In particular embodiments, a monoclonal antibody can be a chimeric antibody, a human antibody, or a humanized antibody.

In certain embodiments, a monoclonal antibody is a monovalent antibody or multivalent (e.g., bivalent) antibody. In particular embodiments, a monoclonal antibody is a monospecific or multispecific antibody (e.g., bispecific antibody). Monoclonal antibodies described herein can, for example, be made by the hybridoma method as described in Kohler et al.; Nature, 256:495 (1975) or can, e.g., be isolated from phage libraries using the techniques as described herein, for example. Other methods for the preparation of clonal cell lines and of monoclonal antibodies expressed thereby are well known in the art (see, for example, Chapter 11 in: *Short Protocols in Molecular Biology*, (2002) 5th Ed., Ausubel et al., eds., John Wiley and Sons, New York).

In a specific embodiment, an antibody described herein is an immunoglobulin, such as an IgG, IgE, IgM, IgD, IgA or IgY. In a particular embodiment, an antibody described herein is an IgG2a. In some embodiments, an antibody described herein is an IgG1 or IgG4. In another embodiment, antibody described herein is an antigen-binding fragment, such as, e.g., an Fab fragment or $F(ab')_2$ fragment. In another embodiment, an antibody described herein is an scFv.

As used herein, the terms "NA" and "neuraminidase" refer to any influenza virus neuraminidase known to those of skill in the art. In certain embodiments, the neuraminidase is an influenza A neuraminidase or an influenza B neuraminidase. A typical neuraminidase comprises domains known to those of skill in the art including a cytoplasmic domain, a transmembrane domain, a stalk domain or hypervariable region, and a globular head domain.

For example, the domains of influenza B/Memphis/3/1989 include: the intravirion domain from amino acid residues 1 to 6, the transmembrane domain from amino acid residues 7 to 38, the hypervariable region or stalk domain from amino acid residues 39 to 68, and the globular head domain from amino acid residues 69 to 465. See UniProtKB—P16199 (NRAM_INBMF). In certain embodiments, the terms "neuraminidase" and "NA" may encompass neuraminidase polypeptides that are modified by post-translational processing such as disulfide bond formation, glycosylation (e.g., N-linked glycosylation), protease cleavage and lipid modification (e.g., S-palmitoylation). In some embodiments, the terms "neuraminidase" and "NA" may encompass monomeric, dimeric, or trimeric forms of influenza virus neuraminidase. In a specific embodiment, the terms "neuraminidase" and "NA" encompass tetrameric forms of influenza virus neuraminidase.

NA has enzymatic activity. In particular, NA cleaves terminal sialic acid residues that serve as receptors for hemagglutinin, promoting the release of the virus from host cells.

In a specific embodiment, the neuraminidase is an influenza B virus NA. The NA may be from any influenza B virus known to one of skill in the art (e.g., in GenBank, UniProt, or the scientific literature). Examples of influenza B viruses are B/Wisconsin/1/10, B/Florida/04/06, B/Yamagata/16/88, B/Massachusetts/2/12, B/Brisbane/60/08, B/Malaysia/2506/04, B/Texas/2/13, B/New Jersey/i/12, B/Victoria/2/81, B/Lee/40, B/Beijing/i/1987, B/USSR/100/1983, B/Singapore/222/1979, B/Victoria/3/1985, B/Hong Kong/8/1973, B/Oregon/5/1980, B/Leningrad/179/1986, B/Memphis/6/1986, B/England/222/1982, B/Singapore/222/1979, B/Victoria/2/1987, B/New York/PV000094/2017, and B/New York/PV01181/2018. Specific examples of NA of influenza B viruses include, for example, the amino acid and nucleic acid sequences of NA of B/Arizona/36/2016, which may be found at GenBank Accession No. CY209719.1; the amino acid and nucleic acid sequences of NA of B/Pennsylvania/34/2015, which may be found at GenBank Accession No. KY090574.1; the amino acid sequence of NA of B/Beijing/1/1987, which may be found on UniProtKB-P27907; the amino acid sequence of NA of B/USSR/100/1983, which may be found on UniProtKB-P16205; the amino acid sequence of NA of B/Singapore/222/1979, which may be found on UniProtKB-P16203; the amino acid sequence of NA of B/Victoria/3/1985, which may be found on UniProtKB-P16207; the amino acid sequence of NA of B/Memphis/3/1989, which may be found on UniProtKB—P16199; and the amino acid sequence of NA of B/Yamagata/16/1988, which may be found on UniProtKB-Q90021. In a specific embodiment, the NA of an influenza B virus strain is an NA of an influenza B virus of the Victoria lineage. In another specific embodiment, the NA of an influenza B virus strain is an NA of an influenza B virus of the Yamagata lineage. In another specific embodiment, the NA of an influenza B virus strain is an NA of the B/Lee/40 strain. In another specific embodiment, the NA of an influenza B virus strain is an NA of the B/Lee/40 ancestral strain.

The lineage of an influenza virus can be determined by one of skill in the art. Examples of influenza B virus strains of the Victoria lineage include, e.g., B/Brisbane/60/08, B/Malaysia/2506/04, B/Texas/2/13, B/New Jersey/i/12, and B/Victoria/2/81. Examples of influenza B virus strains of the Yamagata lineage include, e.g., B/Wisconsin/1/10, B/Florida/04/06, B/Yamagata/16/88, and B/Massachusetts/2/12. See, e.g., FIG. 18 for information regarding the divergence of NA of influenza B virus.

In another aspect, the antibodies provided herein bind to an influenza B virus NA with a certain affinity. "Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), equilibrium association constant ($K_A$), and $IC_{50}$. The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIAcore™, Kinexa, or biolayer interferometry. See, e.g., the techniques described in Section 6 or 7, infra. Affinity can be measured by common methods known in the art, including those described herein. For example, individual association ($k_{on}$) and dissociation ($k_{off}$) rate constants can be calculated from the resulting binding curves using the BIAevaluation software available through the vendor. Data can then be fit to a 1:1 binding model, which includes a term to correct for mass transport limited binding, should it be detected. From these rate constants, the apparent dissociation binding constant ($K_D$) for the interaction of the antibody (e.g., IgG) with the antigen (e.g., influenza B virus NA) can be calculated from the quotient of $k_{off}/k_{on}$. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the described herein.

In certain embodiments, provided herein are antibodies that bind to an influenza B virus NA with a dissociation rate constant ($k_{off}$) of $8.5\times10^{-5-}$ $s^{-1}$ or less, $5\times10^{-5-}$ $s^{-1}$ or less, $2.5\times10^{-5-}$ $s^{-1}$ or less, $1\times10^{-5-}$ $s^{-1}$ or less, $8.5\times10^{-6-}$ $s^{-1}$ or less, $5\times10^{-6-}$ $s^{-1}$ or less, $2.5\times10^{-6-}$ $s^{-1}$ or less, $1\times10^{-6-}$ $s^{-1}$ or less, $8.5\times10^{-7-}$ $s^{-1}$ or less, $5\times10^{-7-}$ $s^{-1}$ or less, $2.5\times10^{-7-}$ $s^{-1}$ or less, $1\times10^{-7-}$ $s^{-1}$ or less, $8.5\times10^{-8-}$ $s^{-1}$ or less, $5\times10^{-8-}$ $s^{-1}$ or less, $2.5\times10^{-8-}$ $s^{-1}$ or less, $1\times10^{-8}$-$s^{-1}$ or less, $8.5\times10^{-9-}$ $s^{-1}$ or less, $5\times10^{-9}$ $s^{-1}$ or less, $2.5\times10^{-9-}$ $s^{-1}$ or less, or $1\times10^{-9-}$ $s^{-1}$ or less. In some embodiments, an antibody provided herein binds to an influenza B virus NA with a $k_{off}$ of between $9.5\times10^{-5-}$ $s^{-1}$ to $1\times10^{-9-}$ $s^{-1}$, $8.5\times10^{-5-}$ $s^{-1}$ to $1\times10^{-9-}$ $s^{-1}$, $5\times10^{-5-}$ $s^{-1}$ to $1\times10^{-9-}$ $s^{-1}$, $9.5\times10^{-5-}$ $s^{-1}$ to $1\times10^{-8-}$ $s^{-1}$, $5\times10^{-5}$ $s^{-1}$ to $1\times10^{-8-}$ $s^{-1}$, $9.5\times10^{-5-}$ $s^{-1}$ to $1\times10^{-7-}$ $s^{-1}$, $5\times10^{-5-}$ $s^{-1}$ to $1\times10^{-7-}$ $s^{-1}$, $9.5\times10^{-5-}$ $s^{-1}$ to $5\times10^{-6-}$ $s^{-1}$, or $9.5\times10^{-5-}$ $s^{-1}$ to $1\times10^{-5-}$ $s^{-1}$.

In a specific embodiment, provided herein are antibodies that bind to an influenza B virus with a $k_{off}$ within the range or as disclosed in Table 6 or 7. In a specific embodiment, provided herein are antibodies that bind to an influenza B virus with a $k_{off}$ within the range or as disclosed in table in FIG. 28. In certain embodiments, the $k_{off}$ is determined using a monovalent antibody, such as a Fab fragment, as measured by, e.g., BIAcore™ surface plasmon resonance technology, Kinexa, or biolayer interferometry.

In certain embodiments, provided herein are antibodies that bind to an influenza B virus NA with an association rate constant ($k_{on}$) of at least $10^5$ $M^{-1}s^{-1}$, at least $5\times10^5$ $M^{-1}s^{-1}$, at least $10^6$ $M^{-1}s^{-1}$, at least $5\times10^6$ $M^{-1}s^{-1}$, at least $10^7$ $M^{-1}s^{-1}$, at least $5\times10^7$ $M^{-1}s^{-1}$, at least $10^8$ $M^{-1}s^{-1}$, at least 5 $10^8$ $M^{-1}s^{-1}$ or at least $10^9$ $M^{-1}s^{-1}$. In some embodiments, an antibody provided herein binds to an influenza B virus NA with a $k_{on}$ of between $1\times10^5$ $M^{-1}s^{-1}$ to $5\times10^5$ $M^{-1}s^{-1}$, $1\times10^5$ $M^{-1}s^{-1}$ to $1\times10^6$ $M^{-1}s^{-1}$, $1\times10^5$ $M^{-1}s^{-1}$ to $5\times10^6$ $M^{-1}s^{-1}$, $1\times10^5$ $M^{-1}s^{-}$ to $1\times10^7$ $M^{-1}s^{-1}$, $1\times10^5$ $M^{-1}s^{-1}$ to $5\times10^7$ $M^{-1}s^{-1}$, $1\times10^5$ $M^{-1}s^{-1}$ to $10^8$ $M^{-1}s^{-1}$, $1\times10^5$ $M^{-1}s^{-1}$ to $1\times10^9$ $M^{-1}s^{-1}$, $1\times10^6$ $M^{-1}s^{-}$ to $1\times10^7$ $M^{-1}s^{-1}$, $1\times10^6$ $M^{-1}s^{-1}$ to $1\times10^8$ $M^{-1}s^{-1}$, $1\times10^6$ $M^{-1}s^{-1}$ to $1\times10^9$ $M^{-1}s^{-1}$, $1\times10^7$ $M^{-1}s^{-1}$ to $1\times10^8$ $M^{-1}s^{-1}$, $1\times10^7$ $M^{-1}s^{-1}$ to $1\times10^9$ $M^{-1}s^{-1}$, $1\times10^8$ $M^{-1}s^{-1}$ to $1\times10^9$ $M^{-1}s^{-1}$. In a specific embodiment, provided herein are antibodies that bind to an influenza B virus with a $k_{off}$ or $k_{on}$ within the range or as disclosed in Table 6 or 7. In certain embodiments, the $k_{on}$ is determined using a monovalent antibody, such as a Fab fragment, as measured by, e.g., BIAcore™ surface plasmon resonance technology, Kinexa, or biolayer interferometry.

In certain embodiments, provided herein are antibodies that bind to an influenza B virus NA with a $K_D$ of less than 375 pM, 350 pM, 325 pM, 300 pM, 275 pM, 250 pM, 225 pM, 200 pM, 175 pM, 150 pM, 125 pM, 100 pM, 75 pM, 50 pM, 45 pM, 40 pM, or 35 pM. In some embodiments, an antibody provided herein binds to an influenza B virus NA with a $k_D$ of 375 pM, 350 pM, 325 pM, 300 pM, 275 pM, 250 pM, 225 pM, 200 pM, 175 pM, 150 pM, 125 pM, 100 pM, 75 pM, or 50 pM, or between 375 pM to 300 pM, 375 pM to 200 pM, 375 pM to 100 pM, 350 pM to 250 pM, 350 pM to 200 pM, 300 pM to 150 pM, 300 pM to 100 pM, 300 pM to 50 pM, 300 pM to 200 pM, 300 pM to 150 pM, 300 pM to 100 pM, 300 pM to 50 pM, 275 pM to 200 pM, 275 pM to 175 pM, 275 pM to 150 pM, 275 pM to 100 pM, 275 pM to 50 pM, 250 pM to 200 pM, 250 pM to 150 pM, 250 pM to 100 pM, 250 pM to 50 pM, 200 pM to 150 pM, 200 pM to 100 pM, 200 to 50 pM, 150 pM to 100 pM, 150 pM to 50 pM, 100 pM to 50 pM, 200 to 40 pM, 150 pM to 40 pM, 150 pM to 40 pM, or 100 pM to 35 pM.

In certain embodiments, the $k_D$ is calculated as the quotient of $k_{off}/k_{on}$, and the $k_{on}$ and $k_{off}$ are determined using a monovalent antibody, such as a Fab fragment, as measured by, e.g., BIAcore™ surface plasmon resonance technology, Kinexa, or biolayer interferometry. In a specific embodiment, the $K_D$ of an antibody described herein is between $1\times10^{-9}$ M and $10\times10^{-10}$ M, determined using, e.g., biolayer interferometry. In another embodiment, the $K_D$ of an antibody described herein is between $2.42\times10^{-12}$ M and $8.9\times10^{-12}$ M, determined using, e.g., biolayer interferometry. In a specific embodiment, provided herein are antibodies that bind to an influenza B virus with a $K_D$ as disclosed in Table 6 or 7.

In one embodiment, provided herein are antibodies (e.g., monoclonal antibodies, such as human, chimeric or humanized antibodies, and antigen-binding fragments) that bind to the NA of different strains of influenza B virus (e.g., 2, 3, 4, 5, 6 or more influenza B virus strains) as assessed by a technique known to one of skill in the art, such as an immunoassay, surface plasmon resonance, or kinetic exclusion assay, or described herein. In another embodiment, provided herein are antibodies (e.g., monoclonal antibodies, such as chimeric or humanized antibodies, and antigen-binding fragments) thereof that bind to NA of influenza B virus strains of both the Victoria and Yamagata lineages (e.g., 1, 2, 3, 4, 5, 6 or more influenza B virus strain of each lineage) as assessed by a technique known to one of skill in the art, such as an immunoassay, surface plasmon resonance, kinetic exclusion assay, biolayer interferometry, or described herein.

In another embodiment, provided herein are antibodies (e.g., monoclonal antibodies, such as human, chimeric or humanized antibodies, and antigen-binding fragments) that (i) bind to the NA of different strains of influenza B virus (e.g., 2, 3, 4, 5, 6 or more strains) as assessed by a technique known to one of skill in the art, such as an immunoassay, surface plasmon resonance, or kinetic exclusion assay, or described herein; and (ii) inhibit Influenza B virus NA enzymatic activity as assessed by a technique known to one of skill in the art, such as the NA-Star assay (Applied Biosystems) or enzyme-linked lectin assay (ELLA), such as described infra. In another embodiment, provided herein are antibodies (e.g., monoclonal antibodies, such as chimeric or humanized antibodies, and antigen-binding fragments) that (i) bind to NA of influenza B virus strains of both the Victoria and Yamagata lineages (e.g., 1, 2, 3, 4, 5, 6 or more influenza B virus strain of each lineage) as assessed by a technique known to one of skill in the art, such as an immunoassay, surface plasmon resonance, or kinetic exclusion assay, or described herein; and (ii) inhibit Influenza B virus NA enzymatic activity as assessed by a technique known to one of skill in the art, such as the NA-Star assay (Applied Biosystems) or enzyme-linked lectin assay (ELLA), such as described infra.

In another embodiment, provided herein are antibodies (e.g., monoclonal antibodies, such as chimeric or humanized antibodies, and antigen-binding fragments) that (i) bind to NA of influenza B virus strains of the Victoria or Yamagata lineages (e.g., 1, 2, 3, 4, 5, 6 or more influenza B virus strains of each lineage) and the NA of B/Lee/40 strain as assessed by a technique known to one of skill in the art, such as an immunoassay, surface plasmon resonance, or kinetic exclusion assay, or described herein. In another embodiment, provided herein are antibodies (e.g., monoclonal antibodies, such as chimeric or humanized antibodies, and antigen-binding fragments) that (i) bind to NA of influenza B virus strains of the Victoria or Yamagata lineages (e.g., 1, 2, 3, 4, 5, 6 or more influenza B virus strains of each lineage) and the NA of B/Lee/40 strain as assessed by a technique known to one of skill in the art, such as an immunoassay, surface plasmon resonance, or kinetic exclusion assay, or described herein; and (ii) inhibit Influenza B virus NA enzymatic activity as assessed by a technique known to one of skill in the art, such as the NA-Star assay (Applied Biosystems) or enzyme-linked lectin assay (ELLA), such as described infra.

In another embodiment, provided herein are antibodies (e.g., monoclonal antibodies, such as chimeric or humanized antibodies, and antigen-binding fragments) that bind to NA of influenza B virus strains of both the Victoria and Yamagata lineages and the B/Lee/40 strain as assessed by a technique known to one of skill in the art, such as an immunoassay, surface plasmon resonance, kinetic exclusion assay, or biolayer interferometry, or described herein. In another embodiment, provided herein are antibodies (e.g., monoclonal antibodies, such as chimeric or humanized antibodies, and antigen-binding fragments) that (i) bind to NA of influenza B virus strains of both the Victoria and Yamagata lineages and the B/Lee/40 strain as assessed by a technique known to one of skill in the art, such as an immunoassay, surface plasmon resonance, kinetic exclusion assay, or biolayer interferometry, or described herein; and inhibit Influenza B virus NA enzymatic activity as assessed by a technique known to one of skill in the art, such as the NA-Star assay (Applied Biosystems) or enzyme-linked lectin assay (ELLA), such as described infra.

In another embodiment, provided herein are antibodies (e.g., monoclonal antibodies, such as chimeric or humanized antibodies, and antigen-binding fragments) that bind to NA of different strains of influenza B virus (e.g., 2, 3, 4, 5, 6 or more influenza B virus strains) spanning over a decade (e.g., 25-30 years, 25-50 years, 50-70 years, 50-75 years, 60-70 years, 70-73 years, 25 years or more, 30 years or more, 40 years or more, 50 years or more, 70 years or more, 15 years, 25 years, 30 years, 35 years, 40 years, 45 years, 50 years, 55 years, 60 years, 65 years, 70 years, or 73 years) of antigenic drift as assessed by a technique known to one of skill in the art, such as an immunoassay, surface plasmon resonance, kinetic exclusion assay, or biolayer interferometry, or described herein. In another embodiment, provided herein are antibodies (e.g., monoclonal antibodies, such as chimeric or humanized antibodies, and antigen-binding fragments) that bind to influenza B virus NA of both the Victoria and Yamagata lineages (e.g., 1, 2, 3, 4, 5, 6 or more influenza B virus strains of each lineage) that span over a decade (e.g., 25-30 years, 25-50 years, 50-70 years, 50-75 years, 60-70 years, 70-73 years, 25 years or more, 30 years or more, 40 years or more, 50 years or more, 70 years or more, 15 years, 25 years, 30 years, 35 years, 40 years, 45 years, 50 years, 55 years, 60 years, 65 years, 70 years, or 73 years) of antigenic drift as assessed by a technique known to one of skill in the art, such as an immunoassay, surface plasmon resonance, kinetic exclusion assay, or biolayer interferometry, or described herein. In another embodiment, provided herein are antibodies (e.g., monoclonal antibodies, such as chimeric or humanized antibodies, and antigen-binding fragments) that bind to influenza B virus NA of both the Victoria and Yamagata lineages (e.g., 1, 2, 3, 4, 5, 6 or more influenza B virus strains of each lineage) that span over a decade (e.g., 25-30 years, 25-50 years, 50-70 years, 50-75 years, 60-70 years, 70-73 years, 25 years or more, 30 years or more, 40 years or more, 50 years or more, 70 years or more, 15 years, 25 years, 30 years, 35 years, 40 years, 45 years, 50 years, 55 years, 60 years, 65 years, 70 years, or 73 years) of antigenic drift as assessed by a technique known to one of skill in the art, such as an immunoassay, surface plasmon resonance, or kinetic exclusion assay, or described herein. In another embodiment, provided herein are antibodies (e.g., monoclonal antibodies, such as chimeric or humanized antibodies, and antigen-binding fragments) that (i) bind to influenza B virus NA of both the Victoria and Yamagata lineages (e.g., 1, 2, 3, 4, 5, 6 or more influenza B virus strains of each lineage) that span over a decade (e.g., 25-30 years, 25-50 years, 50-70 years, 50-75 years, 60-70 years, 70-73 years, 25 years or more, 30 years or more, 40 years or more, 50 years or more, 70 years or more, 15 years, 25 years, 30 years, 35 years, 40 years, 45 years, 50 years, 55 years, 60 years, 65 years, 70 years, or 73 years) of antigenic drift as assessed by a technique known to one of skill in the art, such as an immunoassay, surface plasmon resonance, or kinetic exclusion assay, or described herein; and (ii) inhibit Influenza B virus NA enzymatic activity as assessed by a technique known to one of skill in the art, such as the NA-Star assay (Applied Biosystems) or enzyme-linked lectin assay (ELLA), such as described infra.

In another embodiment, provided herein are antibodies (e.g., monoclonal antibodies, such as chimeric or humanized antibodies, and antigen-binding fragments) that bind to NA of different strains of influenza B virus (e.g., 2, 3, 4, 5, 6 or more influenza B virus strains) spanning over a decade (e.g., 25-30 years, 25-50 years, 50-70 years, 50-75 years, 60-70 years, 70-73 years, 25 years or more, 30 years or more, 40 years or more, 50 years or more, 70 years or more, 15 years, 25 years, 30 years, 35 years, 40 years, 45 years, 50 years, 55 years, 60 years, 65 years, 70 years, or 73 years) of antigenic drift as assessed by a technique known to one of skill in the art, such as an immunoassay, surface plasmon resonance, kinetic exclusion assay, or biolayer interferometry, or described herein. In another embodiment, provided herein are antibodies (e.g., monoclonal antibodies, such as chimeric or humanized antibodies, and antigen-binding fragments) that bind to influenza B virus NA of both the Victoria and Yamagata lineages (e.g., 1, 2, 3, 4, 5, 6 or more influenza B virus strains of each lineage) that span over a decade (e.g., 25-30 years, 25-50 years, 50-70 years, 50-75 years, 60-70 years, 70-73 years, 25 years or more, 30 years or more, 40 years or more, 50 years or more, 70 years or more, 15 years, 25 years, 30 years, 35 years, 40 years, 45 years, 50 years, 55 years, 60 years, 65 years, 70 years, or 73 years) of antigenic drift as assessed by a technique known to one of skill in the art, such as an immunoassay, surface plasmon resonance, kinetic exclusion assay, or biolayer interferometry, or described herein. In another embodiment, provided herein are antibodies (e.g., monoclonal antibodies, such as chimeric or humanized antibodies, and antigen-binding fragments) that (i) bind to influenza B virus NA of both the Victoria and Yamagata lineages (e.g., 2, 3, 4, 5, 6 or more influenza B virus strain of each lineage) that span over a decade (e.g., 25-30 years, 25-50 years, 50-70 years, 50-75 years, 60-70 years, 70-73 years, 25 years or more, 30 years or more, 40 years or more, 50 years or more, 70 years or more, 15 years, 25 years, 30 years, 35 years, 40 years, 45 years, 50 years, 55 years, 60 years, 65 years, 70 years, or 73 years) of antigenic drift as assessed by a technique known to one of skill in the art, such as an immunoassay, surface plasmon resonance, or kinetic exclusion assay, or biolayer interferometry, or described herein; and (ii) inhibit Influenza B virus NA enzymatic activity as assessed by a technique known to one of skill in the art, such as the NA-Star assay (Applied Biosystems) or enzyme-linked lectin assay (ELLA), such as described infra.

In another embodiment, provided herein are antibodies (e.g., monoclonal antibodies, such as chimeric or humanized antibodies, and antigen-binding fragments) that (i) bind to NA of different strains of influenza B virus (e.g., 2, 3, 4, 5, 6 or more influenza B virus strains) spanning over a decade (e.g., 25-30 years, 25-50 years, 50-70 years, 50-75 years, 60-70 years, 70-73 years, 25 years or more, 30 years or more, 40 years or more, 50 years or more, 70 years or more, 15 years, 25 years, 30 years, 35 years, 40 years, 45 years, 50 years, 55 years, 60 years, 65 years, 70 years, or 73 years) of antigenic drift as assessed by a technique known to one of skill in the art, such as an immunoassay, surface plasmon resonance, kinetic exclusion assay, or biolayer interferometry, or described herein; and (ii) bind to the NA of B/Lee/40 as assessed by a technique known to one of skill in the art, such as an immunoassay, surface plasmon resonance, kinetic exclusion assay, or biolayer interferometry, or described herein. In another embodiment, provided herein are antibodies (e.g., monoclonal antibodies, such as chimeric or humanized antibodies, and antigen-binding fragments) that: (i) bind to influenza B virus NA of both the Victoria and Yamagata lineages (e.g., 1, 2, 3, 4, 5, 6 or more influenza B virus strains of each lineage) that span over a decade (e.g., 25-30 years, 25-50 years, 50-70 years, 50-75 years, 60-70 years, 70-73 years, 25 years or more, 30 years or more, 40 years or more, 50 years or more, 70 years or more, 15 years, 25 years, 30 years, 35 years, 40 years, 45 years, 50 years, 55 years, 60 years, 65 years, 70 years, or 73 years) of antigenic drift as assessed by a technique known to one of skill in the art, such as an immunoassay, surface plasmon resonance, kinetic exclusion assay, or biolayer interferometry, or described herein; and (ii) bind to the NA of B/Lee/40 as assessed by a technique known to one of skill in the art, such as an immunoassay, surface plasmon resonance, kinetic exclusion assay, or biolayer interferometry, or described herein. In another embodiment, provided herein are antibodies (e.g., monoclonal antibodies, such as chimeric or humanized antibodies, and antigen-binding fragments) that (i) bind to influenza B virus NA of both the Victoria and Yamagata lineages (e.g., 2, 3, 4, 5, 6 or more influenza B virus strain of each lineage) that span over a decade (e.g., 25-30 years, 25-50 years, 50-70 years, 50-75 years, 60-70 years, 70-73 years, 25 years or more, 30 years or more, 40 years or more, 50 years or more, 70 years or more, 15 years, 25 years, 30 years, 35 years, 40 years, 45 years, 50 years, 55 years, 60 years, 65 years, 70 years, or 73 years) of antigenic drift as assessed by a technique known to one of skill in the art, such as an immunoassay, surface plasmon resonance, kinetic exclusion assay, or biolayer interferometry, or described herein; (ii) bind to the NA of B/Lee/40 as assessed by a technique known to one of skill in the art, such as an immunoassay, surface plasmon resonance, kinetic exclusion assay, or biolayer interferometry, or described herein; and (iii) inhibit Influenza B virus NA enzymatic activity as assessed by a technique known to one of skill in the art, such as the NA-Star assay (Applied Biosystems) or enzyme-linked lectin assay (ELLA), such as described infra.

In another embodiment, provided herein are antibodies (e.g., monoclonal antibodies, such as chimeric or humanized antibodies, and antigen-binding fragments) that (i) bind to NA of different strains of influenza B virus spanning over a decade (e.g., 25-30 years, 25-50 years, 50-70 years, 50-75 years, 60-70 years, 70-73 years, 25 years or more, 30 years or more, 40 years or more, 50 years or more, 70 years or more, 15 years, 25 years, 30 years, 35 years, 40 years, 45 years, 50 years, 55 years, 60 years, 65 years, 70 years, or 73 years) of antigenic drift as assessed by a technique known to one of skill in the art, such as an immunoassay, surface plasmon resonance, kinetic exclusion assay, or biolayer interferometry, or described herein; and (ii) inhibit Influenza B virus NA enzymatic activity as assessed by a technique known to one of skill in the art, such as the NA-Star assay (Applied Biosystems) or enzyme-linked lectin assay (ELLA), such as described infra. In another embodiment, provided herein are antibodies (e.g., monoclonal antibodies, such as chimeric or humanized antibodies, and antigen-binding fragments) that (i) bind to influenza B virus NA of both the Victoria and Yamagata lineages and spanning over a decade (e.g., 25-30 years, 25-50 years, 50-70 years, 50-75 years, 60-70 years, 70-73 years, 25 years or more, 30 years or more, 40 years or more, 50 years or more, 70 years or more, 15 years, 25 years, 30 years, 35 years, 40 years, 45 years, 50 years, 55 years, 60 years, 65 years, 70 years, or 73 years) of antigenic drift as assessed by a technique known to one of skill in the art, such as an immunoassay, surface plasmon resonance, kinetic exclusion assay, or biolayer interferometry, or described herein; and (ii) inhibit Influenza B virus NA enzymatic activity as assessed by a technique known to one of skill in the art, such as the NA-Star assay (Applied Biosystems) or enzyme-linked lectin assay (ELLA), such as described infra.

In another embodiment, provided herein are antibodies (e.g., monoclonal antibodies, such as chimeric or humanized antibodies, and antigen-binding fragments) that (i) bind to NA of different strains of influenza B virus spanning over a decade (e.g., 25-30 years, 25-50 years, 50-70 years, 50-75 years, 60-70 years, 70-73 years, 25 years or more, 30 years or more, 40 years or more, 50 years or more, 70 years or more, 15 years, 25 years, 30 years, 35 years, 40 years, 45 years, 50 years, 55 years, 60 years, 65 years, 70 years, or 73 years) of antigenic drift as assessed by a technique known to one of skill in the art, such as an immunoassay, surface plasmon resonance, kinetic exclusion assay, or biolayer interferometry, or described herein; (ii) bind to the NA of B/Lee/40 as assessed by a technique known to one of skill in the art, such as an immunoassay, surface plasmon resonance, kinetic exclusion assay, or biolayer interferometry, or described herein; and (iii) inhibit Influenza B virus NA enzymatic activity as assessed by a technique known to one of skill in the art, such as the NA-Star assay (Applied Biosystems) or enzyme-linked lectin assay (ELLA), such as described infra. In another embodiment, provided herein are antibodies (e.g., monoclonal antibodies, such as chimeric or humanized antibodies, and antigen-binding fragments) that (i) bind to influenza B virus NA of both the Victoria and Yamagata lineages that span over a decade (e.g., 25-30 years, 25-50 years, 50-70 years, 50-75 years, 60-70 years, 70-73 years, 25 years or more, 30 years or more, 40 years or more, 50 years or more, 70 years or more, 15 years, 25 years, 30 years, 35 years, 40 years, 45 years, 50 years, 55 years, 60 years, 65 years, 70 years, or 73 years) of antigenic drift as assessed by a technique known to one of skill in the art, such as an immunoassay, surface plasmon resonance, kinetic exclusion assay, or biolayer interferometry, or described herein; (ii) bind to the NA of B/Lee/40 as assessed by a technique known to one of skill in the art, such as an immunoassay, surface plasmon resonance, kinetic exclusion assay, or biolayer interferometry, or described herein; and (iii) inhibit Influenza B virus NA enzymatic activity as assessed by a technique known to one of skill in the art, such as the NA-Star assay (Applied Biosystems) or enzyme-linked lectin assay (ELLA), such as described infra.

In a specific embodiment, provided herein are antibodies (e.g., monoclonal antibodies, such as chimeric or humanized antibodies, and antigen-binding fragments) that (i) bind to influenza B virus NA of both the Victoria and Yamagata lineages (e.g., 1, 2, 3, 4, 5, 6, 7 or more strains of each lineage) that span 73 years of antigenic drift as assessed by a technique known to one of skill in the art, such as an immunoassay, surface plasmon resonance, kinetic exclusion assay, or biolayer interferometry, or described herein, and (ii) inhibit Influenza B virus NA enzymatic activity as assessed by a technique known in art, such as the NA-Star assay (Applied Biosystems) or enzyme-linked lectin assay (ELLA), such as described infra. In another specific embodiment, provided herein are antibodies (e.g., monoclonal antibodies, such as chimeric or humanized antibodies, and antigen-binding fragments) that (i) bind to influenza B virus NA of both the Victoria and Yamagata lineages (e.g., 2, 3, 4, 5, 6, 7 or more strains of each lineage) that span 73 years of antigenic drift as assessed by a technique known to one of skill in the art, such as an immunoassay, surface plasmon resonance, kinetic exclusion assay, or biolayer interferometry, or described herein, (ii) bind to the NA of B/Lee/40 as assessed by a technique known to one of skill in the art, such as an immunoassay, surface plasmon resonance, kinetic exclusion assay, or biolayer interferometry, or described herein; and (iii) inhibit Influenza B virus NA enzymatic activity as assessed by a technique known in art, such as the NA-Star assay (Applied Biosystems) or enzyme-linked lectin assay (ELLA), such as described infra.

In certain embodiments, an antibody described herein has a higher affinity for an NA of one lineage of influenza B virus (e.g., the Victoria or Yamagata lineage) than for an NA from another lineage of influenza B virus. In some embodiments, the affinity of an antibody described herein for an NA from one lineage of influenza B virus (e.g., the Victoria or Yamagata lineage) is 1-fold, 1.5-fold, 2-fold, 3-fold, 4-fold, 5-fold, 6-fold, 7-fold, 8-fold, 9-fold, 10-fold, greater than 10-fold, 1- to 2-fold, 1- to 5-fold, 1- to 10-fold, 2- to 5-fold, 2- to 10-fold, 5- to 10-fold, 10- to 15-fold, or 10- to 20-fold greater than the affinity of the antibody to for an NA of another lineage of influenza B virus as assessed by techniques known in the art, e.g., ELISA, Western blot, biolayer interferometry, FACS or BIACore, or described herein. In certain embodiments, the affinity of an antibody described herein for an NA of one lineage of influenza B virus (e.g., the Victoria or Yamagata lineage) is 0.5 log, 1 log, 1.5 log, 2 log, 2.5 log, 3 log, 3.5 log, or 4 log greater than the affinity of the antibody for an NA of another lineage of influenza B virus as assessed by techniques known in the art, e.g., ELISA, Western blot, biolayer interferometry, FACS or BIACore, or described herein. In some embodiments, an antibody described herein has a 5%, 10%, 15%, 20%, 25%, 30%, 35%, 40%, 45%, 50%, 55%, 60%, 65%, 70% or higher affinity for an NA of one lineage of influenza B virus (e.g., the Victoria or Yamagata lineage) than the affinity of the antibody for an NA of another lineage of influenza B virus as measured by, e.g., a radioimmunoassay, surface plasmon resonance, kinetic exclusion assay, or biolayer interferometry, or described herein.

In some embodiments, provided herein is an antibody that selectively binds to NA of one, two, three or more strains of influenza B virus of a particular lineage (e.g., the Victoria or Yamagata lineage) relative to an NA of an influenza B virus strain of a different lineage as assessed by techniques known in the art, e.g., ELISA, Western blot, biolayer interferometry, FACS or BIACore, or described herein. In other words, the antibody binds to an NA from one, two, three or more strains of influenza B virus of a particular lineage (e.g., the Victoria or Yamagata lineage) with a higher affinity than the antibody binds to an NA of an influenza B virus strain of a different lineage as assessed by techniques known in the art, e.g., ELISA, Western blot, biolayer interferometry, FACS or BIACore, or described herein. In certain embodiments, an antibody described herein binds to an NA of one, two, three or more strains of influenza B virus of a particular lineage (e.g., the Victoria or Yamagata lineage) with a 1-fold, 1.5-fold, 2-fold, 3-fold, 4-fold, 5-fold, 6-fold, 7-fold, 8-fold, 9-fold, 10-fold, greater than 10-fold, 1- to 2-fold, 1- to 5-fold, 1- to 10-fold, 2- to 5-fold, 2- to 10-fold, 5- to 10-fold, 10- to 15-fold, or 10- to 20-fold greater affinity than that which the antibody binds to an NA of an influenza B virus strain of a different lineage as assessed by techniques known in the art, e.g., ELISA, Western blot, biolayer interferometry, FACS or BIACore, or described herein. In some embodiments, an antibody described herein binds to an NA of one, two, three or more strains of influenza B virus of a particular lineage (e.g., the Victoria or Yamagata lineage) with a 0.5 log, 1 log, 1.5 log, 2 log, 2.5 log, 3 log, 3.5 log, or 4 log greater affinity than that which the antibody binds to an NA of an influenza B virus strain of a different lineage as assessed by techniques known in the art, e.g., ELISA, Western blot, biolayer interferometry, FACS or BIACore, or described herein. In some embodiments, an antibody described herein binds to an NA of one, two, three or more strains of influenza B virus of a particular lineage (e.g., the Victoria or Yamagata lineage) with a 5% 10%, 15%, 20%, 25%, 30%, 35%, 40%, 45%, 50%, 55%, 60%, 65%, 70% or higher affinity than that which the antibody binds to an NA of an influenza B virus strain of a different lineage as measured by, e.g., a radioimmunoassay, surface plasmon resonance, biolayer interferometry, or kinetic exclusion assay.

In another embodiment, an antibody described herein binds to a recombinant NA protein (e.g., a recombinant form of an influenza B virus NA, or a soluble form thereof) such as described herein (e.g., in Section, 6, and/or 7, infra. In a particular embodiment, an antibody described herein binds to a recombinant NA protein described in Section 6 or Section 7, infra.

In another embodiment, an antibody described herein binds to an influenza B virus NA present in the virion particle. In a particular embodiment, an antibody described herein binds to an influenza B virus NA present in the virion particle as described in Section 6 or Section 7, infra. In a particular embodiment, an antibody described herein binds to a protein (e.g., influenza B virus NA) on the surface of a cell infected with an influenza B virus.

In another embodiment, an antibody described herein binds to a recombinant NA protein such as described in Section 6 and/or Section 7, infra and binds to an influenza B virus NA present in the virion particle. In a particular embodiment, an antibody described herein binds to a recombinant NA protein described in Section 6 and/or Section 7, infra and binds to an influenza B virus NA present in the virion particle as described in Section 6 and/or Section 7, infra. In another embodiment, an antibody described herein binds to a recombinant NA protein, such as described in Section 6 and/or 7, infra, binds to an influenza B virus NA present in the virion particle such as described in Section 6 and/or 7, infra, and binds to influenza B virus NA on the surface of a cell infected with influenza B virus. In some embodiments, an antibody described herein does not cross-react with an NA from an influenza A virus as assessed by techniques known in the art, e.g., ELISA, Western blot, biolayer interferometry, FACS or BIACore, or described herein. In certain embodiments, provided herein is an antibody that selectively binds to NA of one, two, three or more strains of influenza B virus relative to an NA of influenza A virus as assessed by techniques known in the art, e.g., ELISA, Western blot, biolayer interferometry, FACS or BIACore, or described herein. In other words, the antibody binds to NA from one, two, three or more strains of influenza B virus with a higher affinity than the antibody binds to an NA of influenza A virus as assessed by techniques known in the art, e.g., ELISA, Western blot, biolayer interferometry, FACS or BIACore, or described herein. In some embodiments, an antibody described herein binds to NA of one, two, three or more strains of influenza B virus with a 1-fold, 1.5-fold, 2-fold, 3-fold, 4-fold, 5-fold, 6-fold, 7-fold, 8-fold, 9-fold, 10-fold, greater than 10-fold, 1- to 2-fold, 1- to 5-fold, 1- to 10-fold, 2- to 5-fold, 2- to 10-fold, 5- to 10-fold, 10- to 15-fold, or 10- to 20-fold greater affinity than that which the antibody binds to an NA of influenza A virus as assessed by techniques known in the art, e.g., ELISA, Western blot, biolayer interferometry, FACS or BIACore, or described herein.

In certain embodiments, an antibody described herein binds to NA of one, two, three or more strains of influenza B virus with a 0.5 log, 1 log, 1.5 log, 2 log, 2.5 log, 3 log, 3.5 log, or 4 log greater affinity than that which the antibody binds to an NA of influenza A virus as assessed by techniques known in the art, e.g., ELISA, Western blot, biolayer interferometry, FACS or BIACore, or described herein. In certain embodiments, an antibody described herein binds to NA of one, two, three or more strains of influenza B virus with a 5%, 10%, 15%, 20%, 25%, 30%, 35%, 40%, 45%, 50%, 55%, 60%, 65%, 70% or higher affinity than that which the antibody binds to an NA of influenza A virus as measured by, e.g., a radioimmunoassay, surface plasmon resonance, kinetic exclusion assay, or biolayer interferometry, or described herein.

In another embodiment, provided herein is an antibody that selectively binds to NA of one, two, three or more strains of influenza B virus relative to a non-influenza virus antigen as assessed by techniques known in the art, e.g., ELISA, Western blot, biolayer interferometry, FACS or BIACore, or described herein. In other words, the antibody binds to NA from one, two, three or more strains of influenza B virus with a higher affinity than the antibody binds to a non-influenza virus antigen as assessed by techniques known in the art, e.g., ELISA, Western blot, biolayer interferometry, FACS or BIACore, or described herein. In some embodiments, an antibody described herein binds to NA of one, two, three or more strains of influenza B virus with a 1-fold, 1.5-fold, 2-fold, 3-fold, 4-fold, 5-fold, 6-fold, 7-fold, 8-fold, 9-fold, 10-fold, greater than 10-fold, 1- to 2-fold, 1- to 5-fold, 1- to 10-fold, 2- to 5-fold, 2- to 10-fold, 5- to 10-fold, 10- to 15-fold, or 10- to 20-fold greater affinity than that which the antibody binds to a non-influenza virus antigen as assessed by techniques known in the art, e.g., ELISA, Western blot, biolayer interferometry, FACS or BIACore, or described herein. In certain embodiments, an antibody described herein binds to NA of one, two, three or more strains of influenza B virus with a 0.5 log, 1 log, 1.5 log, 2 log, 2.5 log, 3 log, 3.5 log, or 4 log greater affinity than that which the antibody binds to a non-influenza virus antigen as assessed by techniques known in the art, e.g., ELISA, Western blot, biolayer interferometry, FACS or BIACore, or described herein. In some embodiments, an antibody described herein binds to NA of one, two, three or more strains of influenza B virus with a 5%, 10%, 15%, 20%, 25%, 30%, 35%, 40%, 45%, 50%, 55%, 60%, 65%, 70% or higher affinity than that which the antibody binds to a non-influenza virus antigen as measured by, e.g., a radioimmunoassay, surface plasmon resonance, kinetic exclusion assay, or biolayer interferometry, or described herein.

The inhibition of NA enzymatic acivity may be complete or partial as assessed by a technique known to one of skill in the art or described herein (e.g., an assay described in Section 6 and/or Section 7 and/or Section 9, infra). In certain aspects, the binding of an antibody provided herein to an influenza B virus NA partially inhibits the enzymatic activity of the NA as measured by a method known to one of skill in the art or described herein (e.g., in Section 6 and/or Section 7 and/or Section 9, infra). In some aspects, the binding of an antibody provided herein to an influenza B virus completely inhibits the enzymatic activity of the NA as measured by a method known to one of skill in the art or described herein (e.g., in Section 6 and/or Section 7 and/or Section 9, infra).

In certain embodiments, an antibody described herein inhibits influenza B virus NA enzymatic activity by 20%, 25%, 30%, 35%, 40%, 45%, 50%, 55%, 60%, 65%, 70%, 75%, 80%, 85%, 90%, 95% or more relative to Influenza B virus NA enzymatic activity in the presence of a negative control, such as a control IgG, as measured by a technique known to one of skill in the art, such as the NA-Star assay (Applied Biosystems) or ELLA assay, or described herein. In some embodiments, an antibody described herein inhibits influenza B virus Influenza B virus NA enzymatic activity by 20% to 40%, 25% to 50%, 25% to 75%, 50% to 75%, 25% to 50%, 75% to 90%, 50% to 90%, or 85% to 95% relative to Influenza B virus NA enzymatic activity in the presence of a negative control, such as a control IgG, as measured by a technique known to one of skill in the art, such as the NA-Star assay (Applied Biosystems) or ELLA assay, or described herein.

In another aspect, an antibody provided herein demonstrates antibody dependent cell-mediated cytotoxicity (ADCC). In a specific embodiment, an antibody provided herein demonstrates ADCC activity in an in vitro assay known to one of skill in the art or described herein (e.g., in Section 6 and/or Section 7, infra). For example, ADCC activity may be assessed using Promega's ADCC Reporter Assay Core Kit.

In another aspect, an antibody provided herein demonstrates antibody-dependent cellular phagocytosis (ADCP) as assessed by a technique known to one of skill in the art.

In another aspect, an antibody provided herein has one, two or more, or all of the characteristics/properties of one of the antibodies described in Section 6 and/or Section 7 and/or Section 8 and/or Section 9, infra. In a specific embodiment, an antibody described herein has one, two or more, or all of the characteristics/properties of the 1F2 antibody described herein. In another specific embodiment, an antibody described herein has one, two or more, or all of the characteristics/properties of a 1F2 antibody variant described herein. In another specific embodiment, an antibody provided herein has one, two or more, or all of the characteristics/properties of the 1F4 antibody described herein. In another specific embodiment, an antibody provided herein has one, two or more, or all of the characteristics/properties of the 3G1 antibody described herein. In another specific embodiment, an antibody provided herein has one, two or more, or all of the characteristics/properties of the 4B2 antibody described herein. In another specific embodiment, an antibody provided herein has one, two or more, or all of the characteristics/properties of the 4F11 antibody described herein.

In another aspect, provided herein are antibodies that bind to the globular head domain of an NA of an influenza B virus, as assessed by a technique known to one of skill in the art or described herein. In a specific embodiment, provided herein is an antibody that binds to the globular head domain of an NA of an influenza B virus described herein (e.g., in Section 6 and/or Section 7, infra), as assessed by a technique known to one of skill in the art or described herein. In another specific embodiment, provided herein is an antibody that binds to an epitope that includes an amino acid residue (s) in the enzymatic active site of an NA of an influenza B virus, as assessed by a technique known to one of skill in the art or described herein. In another specific embodiment, provided herein is an antibody that binds to an epitope that includes amino acid residues outside of the enzymatic active site an NA of an influenza B virus described herein (e.g., in Section 6 and/or Section 7, infra), as assessed by a technique known to one of skill in the art or described herein. The enzymatic active site amino acid residues of influenza B virus NA include those known to one of skill in the art. For example, the enzymatic active site includes amino acid residues 118, 151, 152, 224, 276, 292, 371, and 406 using the N2 numbering system. In another example, the enzymatic active site includes amino acid residues 116, 150, 151, 223, 276, 292, 374, and 409 using the N2 numbering system. In another specific embodiment, provided herein is an antibody that binds to an epitope comprising an amino acid residue(s) found in the globular head domain of an NA of an influenza B virus, but not within the enzymatic active site of the NA, as assessed by a technique known to one of skill in the art or described herein.

With respect to the positions of the amino acid residues in different influenza B virus strains, a person of ordinary skill in the art would be able to determine the corresponding and/or equivalent residues in other influenza B virus isolates and be able to determine the corresponding and/or equivalent residues in isoforms therein.

In certain embodiments, provided herein are antibodies that: (i) bind to a non-linear epitope of NA of an influenza B virus and (ii) inhibit NA enzymatic activity, as assessed by a technique known to one of skill in the art or described herein. In a specific embodiment, provided herein is an antibody that: (i) binds to a non-linear epitope in the globular head of an influenza B virus and (ii) inhibits NA enzymatic activity, as assessed by a technique known to one of skill in the art or described herein. In a specific embodiment, provided herein is an antibody that: (i) binds to a non-linear epitope comprising amino acid residues in the enzymatic active site of an influenza B virus NA and (ii) inhibits NA enzymatic activity, as assessed by a technique known to one of skill in the art or described herein. In another specific embodiment, provided herein is an antibody that: (i) binds to a non-linear epitope comprising amino acid residues found in the globular head domain of an NA of an influenza B virus, but not within the enzymatic active site of the NA and (ii) inhibits NA enzymatic activity, as assessed by a technique known to one of skill in the art or described herein.

In another aspect, an antibody described herein is the 1F2, 1F4, 3G1, 4B2, or 4F11 antibody provided herein or an antigen-binding fragment thereof. In another aspect, an antibody described herein is a 1F2 variant provided herein or an antigen-binding fragment thereof. In another aspect, an antibody provided herein comprises the variable heavy chain region ("VH" domain) or variable light chain region ("VL" domain) of the 1F2, 1F4, 3G1, 4B2, or 4F11 antibody. In another aspect, an antibody provided herein comprises the variable heavy chain region ("VH" domain) or variable light chain region ("VL" domain) of a 1F2 variant provided herein. In another aspect, an antibody provided herein comprises the variable heavy chain region ("VH" domain) and variable light chain region ("VL" domain) of the 1F2, 1F4, 3G1, 4B2, or 4F11 antibody. In another aspect, an antibody provided herein comprises the variable heavy chain region ("VH" domain) and variable light chain region ("VL" domain) of a 1F2 variant provided herein.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids in a mature heavy chain and about the amino-terminal 90 to 100 amino acids in a mature light chain, which differs extensively in sequence among antibodies and is used in the binding and specificity of a particular antibody for its particular antigen. The variability in sequence is concentrated in those regions called complementarity determining regions (CDRs) while the more highly conserved regions in the variable domain are called framework regions (FR). CDRs are flanked by FRs. Generally, the spatial orientation of CDRs and FRs are as follows, in an N-terminal to C-terminal direction: FR1-CDR1-FR2-CDR2-FR3-CDR3-FR4. Without wishing to be bound by any particular mechanism or theory, it is believed that the CDRs of the light and heavy chains are primarily responsible for the interaction and specificity of the antibody with antigen. In certain embodiments, the variable region is a rodent (e.g., mouse or rat) variable region. In certain embodiments, the variable region is a human variable region. In certain embodiments, the variable region comprises rodent (e.g., mouse or rat) CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

In another aspect, an antibody provided herein comprises one, two or three of the complementarity determining regions (CDRs) of the variable heavy chain region ("VH" domain) or one, two or three of the CDRs of the variable light chain region ("VL" domain) of the 1F2, 1F4, 3G1, 4B2, or 4F11 antibody. In another aspect, an antibody provided herein comprises one, two or three of the complementarity determining regions (CDRs) of the variable heavy chain region ("VH" domain) and one, two or three of the CDRs of the variable light chain region ("VL" domain) of the 1F2, 1F4, 3G1, 4B2, or 4F11 antibody. In another aspect, an antibody provided herein comprises the complementarity determining regions (CDRs) of the variable heavy chain region ("VH" domain) and the CDRs of the variable light chain region ("VL" domain) of the 1F2, 1F4, 3G1, 4B2, or 4F11 antibody. In some embodiments, the antibody further comprises framework regions from a non-murine antibody (e.g., a human antibody) or framework regions derived from a non-murine antibody (e.g., a human antibody).

In another aspect, an antibody provided herein comprises a variable heavy chain region that comprises the amino acid sequence of a variable heavy chain region provided in FIG. 30. In a specific embodiment, an antibody provided herein comprises a variable heavy chain region that comprises the amino acid sequence of a variable heavy chain region of any one of VH1 to VH8 provided in FIG. 30. In another aspect, an antibody provided herein comprises a variable light chain region that comprises the amino acid sequence of a variable light chain region provided in FIG. 31. In a specific embodiment, an antibody provided herein comprises a variable heavy light region that comprises the amino acid sequence of a variable light chain region of any one of VL1 to VL8 provided in FIG. 31.

In another aspect, an antibody provided herein comprises: (a) a variable heavy chain region that comprises the amino acid sequence of a variable heavy chain region provided in FIG. 30; and (b) a variable light chain region that comprises the amino acid sequence of a variable light chain region provided in FIG. 31. In a specific embodiment, an antibody provided herein comprises: (a) a variable heavy chain region that comprises the amino acid sequence of a variable heavy chain region of any one of VH1 to VH8 provided in FIG. 30; and (b) a variable heavy light region that comprises the amino acid sequence of a variable light chain region of any one of VL1 to VL8 provided in FIG. 31.

In certain aspects, the CDRs of an antibody can be determined according to the Kabat numbering system. The terms "Kabat numbering," and like terms are recognized in the art and refer to a system of numbering amino acid residues in the heavy and light chain variable regions of an antibody, or an antigen-binding portion thereof. In certain aspects, the CDRs of an antibody can be determined according to the Kabat numbering system (see, e.g., Kabat et al. (1971) Ann. NY Acad. Sci. 190:382-391 and, Kabat et al. (1991) Sequences of Proteins of Immunological Interest, Fifth Edition, U.S. Department of Health and Human Services, NIH Publication No. 91-3242). With respect to the Kabat numbering system, (i) the VH CDR1 is typically present at amino acid positions 31 to 35 of the heavy chain, which can optionally include one or two additional amino acids following amino acid position 35 (referred to in the Kabat numbering scheme as 35A and 35B); (ii) the VH CDR2 is typically present at amino acid positions 50 to 65 of the heavy chain; and (iii) the VH CDR2 is typically present at amino acid positions 95 to 102 of the heavy chain (Kabat, Elvin A. et al., Sequences of Proteins of Immunological Interest. Bethesda: National Institutes of Health, 1983). With respect to the Kabat numbering system, (i) the VL CDR1 is typically present at amino acid positions 24 to 34 of the light chain; (ii) the VL CDR2 is typically present at amino acid positions 50 to 56 of the light chain; and (iii) the VL CDR3 is typically present at amino acid positions 89 to 97 of the light chain (Kabat, Elvin A. et al., Sequences of Proteins of Immunological Interest. Bethesda: National Institutes of Health, 1983). As is well known to those of skill in the art, using the Kabat numbering system, the actual linear amino acid sequence of the antibody variable domain can contain fewer or additional amino acids due to a shortening or lengthening of a FR and/or CDR and, as such, an amino acid's Kabat number is not necessarily the same as its linear amino acid number.

In certain aspects, the CDRs of an antibody can be determined according to the Chothia numbering scheme, which refers to the location of immunoglobulin structural loops (see, e.g., Chothia and Lesk, 1987, J. Mol. Biol., 196:901-917; Al-Lazikani et al., 1997, J. Mol. Biol., 273: 927-948; Chothia et al., 1992, J. Mol. Biol., 227:799-817; Tramontano A et al., 1990, J. Mol. Biol. 215(1):175-82; and U.S. Pat. No. 7,709,226). The Chothia definition is based on the location of the structural loop regions (Chothia et al., (1987) J Mol Biol 196: 901-917; and U.S. Pat. No. 7,709,226). The term "Chothia CDRs," and like terms are recognized in the art and refer to antibody CDR sequences as determined according to the method of Chothia and Lesk, 1987, J. Mol. Biol., 196:901-917, which will be referred to herein as the "Chothia CDRs" (see also, e.g., U.S. Pat. No. 7,709,226 and Martin, A., "Protein Sequence and Structure Analysis of Antibody Variable Domains," in Antibody Engineering, Kontermann and Dubel, eds., Chapter 31, pp. 422-439, Springer-Verlag, Berlin (2001)). With respect to the Chothia numbering system, using the Kabat numbering system of numbering amino acid residues in the VH region, (i) the VH CDR1 is typically present at amino acid positions 26 to 32 of the heavy chain; (ii) the VH CDR2 is typically present at amino acid positions 53 to 55 of the heavy chain; and (iii) the VH CDR3 is typically present at amino acid positions 96 to 101 of the heavy chain. In a specific embodiment, with respect to the Chothia numbering system, using the Kabat numbering system of numbering amino acid residues in the VH region, (i) the VH CDR1 is typically present at amino acid positions 26 to 32 or 34 of the heavy chain; (ii) the VH CDR2 is typically present at amino acid positions 52 to 56 (in one embodiment, CDR2 is at positions 52A-56, wherein 52A follows position 52) of the heavy chain; and (iii) the VH CDR3 is typically present at amino acid positions 95 to 102 of the heavy chain (in one embodiment, there is no amino acid at positions numbered 96-100). With respect to the Chothia numbering system, using the Kabat numbering system of numbering amino acid residues in the VL region, (i) the VL CDR1 is typically present at amino acid positions 26 to 33 of the light chain; (ii) the VL CDR2 is typically present at amino acid positions 50 to 52 of the light chain; and (iii) the VL CDR3 is typically present at amino acid positions 91 to 96 of the light chain. In a specific embodiment, with respect to the Chothia numbering system, using the Kabat numbering system of numbering amino acid residues in the VL region, (i) the VL CDR1 is typically present at amino acid positions 24 to 34 of the light chain; (ii) the VL CDR2 is typically present at amino acid positions 50 to 56 of the light chain; and (iii) the VL CDR3 is typically present at amino acid positions 89 to 97 of the light chain (in one embodiment, there is no amino acid at positions numbered 96-100). These Chothia CDR positions may vary depending on the antibody, and may be determined according to methods known in the art.

In certain aspects, the CDRs of an antibody can be determined according to the IMGT numbering system as described in Lefranc, M.-P., 1999, The Immunologist, 7:132-136 and Lefranc, M.-P. et al., 1999, Nucleic Acids Res., 27:209-212. The IMGT definition is from the IMGT ("IMGT®, the international ImMunoGeneTics information System® website imgt.org, founder and director: Marie-Paule Lefranc, Montpellier, France; see, e.g., Lefranc, M.-P., 1999, The Immunologist, 7:132-136 and Lefranc, M.-P. et al., 1999, Nucleic Acids Res., 27:209-212, both of which are incorporated herein by reference in their entirety). With respect to the IMGT numbering system, (i) the VH CDR1 is typically present at amino acid positions 25 to 35 of the heavy chain; (ii) the VH CDR2 is typically present at amino acid positions 51 to 57 of the heavy chain; and (iii) the VH CDR2 is typically present at amino acid positions 93 to 102 of the heavy chain. With respect to the IMGT numbering system, (i) the VL CDR1 is typically present at amino acid positions 27 to 32 of the light chain; (ii) the VL CDR2 is typically present at amino acid positions 50 to 52 of the light chain; and (iii) the VL CDR3 is typically present at amino acid positions 89 to 97 of the light chain.

In certain aspects, the CDRs of an antibody can be determined according to MacCallum et al., 1996, J. Mol. Biol., 262:732-745. See also, e.g., Martin, A., "Protein Sequence and Structure Analysis of Antibody Variable Domains," in Antibody Engineering, Kontermann and Dubel, eds., Chapter 31, pp. 422-439, Springer-Verlag, Berlin (2001).

In certain aspects, the CDRs of an antibody can be determined according to the AbM numbering scheme, which refers AbM hypervariable regions which represent a compromise between the Kabat CDRs and Chothia structural loops, and are used by Oxford Molecular's AbM antibody modeling software.

In a specific aspect, an antibody provided herein is the antibody designated 1F2 or an antigen-binding fragment thereof. The 1F2 antibody is a murine IgG2a antibody. The deduced nucleotide sequences of the variable heavy chain region ("VH" domain) and variable light chain region ("VL" domain) of the antibody 1F2 are shown in FIG. 8 and Table 1A. The deduced amino acid sequences of the VH and VL domains of the antibody 1F2 are shown in FIG. 9 and Table 1A. The CDRs and framework regions of the VH domain and VL domain are indicated in FIG. 9. In addition, Table 1A, infra, sets forth the nucleic acid and amino acid sequences of the CDRs and framework regions of the variable regions of the antibody 1F2. The CDRs and framework regions in Table 1A were determined using the International ImMunoGeneTics ("IMGT") numbering system. See Lefranc et al., Dev. Comp. Immunol. 27:55-77 (2003), which is incorporated herein by reference in its entirety, for a description of the IMGT numbering system. As an alternative to the IMGT numbering system, the Kabat numbering system can be used. See Table 1B for the CDR's of antibody IF2 as determined using the Kabat numbering system. Table 2 of Lefranc et al. shows the correspondence between the IMGT and the Kabat numberings. Another alternative to the IMGT numbering system is Chothia. See Chothia and Lesk, J. Mol. Biol. 196:901-917 (1987), which is incorporated herein by reference in its entirety. See Table 1B for the CDR's of antibody IF2 as determined using the Chothia numbering system. Futher, Oxford's AbM system may be used instead of the IMGT numbering system. See Table 1B for the CDR's of antibody IF2 as determined using the ABM numbering system. A person of ordinary skill in the art would be able to determine the CDRs and framework regions of the variable regions of the 1F2 antibody sequence based on known numbering systems, such as the Kabat numbering system, Chothia system, Oxford's AbM system, and/or contact system.

TABLE 1A

| DESCRIPTION OF SEQUENCE | VARIABLE REGION AMINO ACID SEQUENCE |
|---|---|
| 1F2 VH AMINO ACID SEQUENCE | QVHLQQSGPEVARPGASVKLSCKASGYTFTDYYLNWVKQRPRQGL EWIGQIHPGSTNTYYNEKFKGKATLTADKSSSTAYMQLSSLTSEDSA VYFCARSLGDGYYVYAMDYWGQGTAVTVSS (SEQ ID NO: 1) |
| 1F2 VL AMINO ACID SEQUENCE | DIVMTQSQKFMSTSVGDRVSVTCKASQNVVTNVVWYQQKPGQSPK PLIYSASYRYSGVPDRFTGSGSGTDFTLTISNVQSEDLAEYCCQQYHS YPFTFGSGTKLEVK (SEQ ID NO: 2) |

| DESCRIPTION OF SEQUENCE | CDR1 AMINO ACID SEQUENCE | CDR2 AMINO ACID SEQUENCE | CDR3 AMINO ACID SEQUENCE |
|---|---|---|---|
| 1F2 VH CDRs (IMGT DELINEATION) | GYTFTDYY (SEQ ID NO: 3) | IHPGSTNT (SEQ ID NO: 4) | ARSLGDGYYVYAMDY (SEQ ID NO: 5) |
| 1F2 VL CDRs (IMGT DELINEATION) | QNVVTN (SEQ ID NO: 6) | SAS (SEQ ID NO: 7) | QQYHSYPFT (SEQ ID NO: 8) |

| DESCRIPTION OF SEQUENCE | FR1 AMINO ACID SEQUENCE | FR2 AMINO ACID SEQUENCE | FR3 AMINO ACID SEQUENCE | FR4 AMINO ACID SEQUENCE |
|---|---|---|---|---|
| 1F2 VH FRs (IMGT DELINEATION) | QVHLQQSGPEVA RPGASVKLSCKA S (SEQ ID NO: 9) | LNWVKQRPRQG L EWIGQ (SEQ ID NO: 10) | YYNEKFKGKATL TADKSSSTAYMQ LSSLTSEDSAVYF C (SEQ ID NO: 11) | WGQGTAVTVSS (SEQ ID NO: 12) |
| 1F2 VL FRs (IMGT DELINEATION) | DIVMTQSQKFMS TSVGDRVSVTCK A S (SEQ ID NO: 13) | VVWYQQKPGQS P KPLIY (SEQ ID NO: 14) | YRYSGVPDRFTG S GSGTDFTLTISNV Q SEDLAEYCC (SEQ ID NO: 15) | FGSGTKLEVK (SEQ ID NO: 16) |

TABLE 1A-continued

| DESCRIPTION OF SEQUENCE | VARIABLE REGION POLYNUCLEOTIDE SEQUENCE |
|---|---|
| 1F2 VH | caggttcacctgcagcagtctggacctgaggtggcgaggcccggggcttcagtgaagctgtcctgcaaggct tctggctacaccttcactgactactatcttaactgggtgaagcagaggcctagacagggccttgagtggattgg acagattcatcctggaagtactaatacttactacaatgagaagttcaagggcaaggccacactgactgcagaca aatcctccagcacagcctacatgcagctcagcagcctgacatctgaggactctgcagtctatttctgtgcaagat cgcttggtgatggttactacgtctatgctatggactactggggtcagggaaccgcagtcaccgtctcctca (SEQ ID NO: 81) |
| 1F2 VL | GACATTGTGATGACCCAGTCTCAAAAATTCATGTCCACATCAGTA GGAGACAGGGTCAGCGTCACCTGCAAGGCCAGTCAGAATGTGGTT ACTAATGTAGTCTGGTATCAACAGAAACCAGGTCAGTCTCCTAAA CCACTGATTTACTCGGCATCCTACCGGTACAGTGGAGTCCCTGATC GCTTCACAGGCAGTGGATCTGGGACAGATTTCACTCTCACCATCA GCAATGTGCAGTCTGAAGACTTGGCAGAGTACTGCTGTCAGCAAT ATCACAGCTATCCATTCACGTTCGGCTCGGGGACAAAGTTGGAAG TAAAA (SEQ ID NO: 82) |

TABLE 1B

CDRs for antibody IF2 as determined by Chothia, ABM and Kabat.

| | Chothia numbering system | ABM numbering system | Kabat numbering system |
|---|---|---|---|
| VHCDR1 | GYTFTDY (SEQ ID NO: 94) | GYTFTDYYLN (SEQ ID NO: 100) | DYYLN (SEQ ID NO: 106) |
| VHCDR2 | HPGSTN (SEQ ID NO: 95) | QIHPGSTNTY (SEQ ID NO: 101) | QIHPGSTNTYYNEKFKG (SEQ ID NO: 107) |
| VHCDR3 | SLGDGYYVYAMDY (SEQ ID NO: 96) | SLGDGYYVYAMDY (SEQ ID NO: 102) | SLGDGYYVYAMDY (SEQ ID NO: 108) |
| VLCDR1 | KASQNVVTNVV (SEQ ID NO: 97) | KASQNVVTNVV (SEQ ID NO: 103) | KASQNVVTNVV (SEQ ID NO: 109) |
| VLCDR2 | SASYRYS (SEQ ID NO: 98) | SASYRYS (SEQ ID NO: 104) | SASYRYS (SEQ ID NO: 110) |
| VLCDR3 | QQYHSYPFT (SEQ ID NO: 99) | QQYHSYPFT (SEQ ID NO: 105) | QQYHSYPFT (SEQ ID NO: 111) |

In a specific aspect, an antibody provided herein is the antibody designated 1F4 or an antigen-binding fragment thereof. The 1F4 antibody is a murine IgG2a antibody. The deduced nucleotide sequences of the variable heavy chain region ("VH" domain) and variable light chain region ("VL" domain) of the antibody 1F4 are shown in FIG. 10 and Table 2A. The deduced amino acid sequences of the VH and VL domains of the antibody 1F4 are shown in FIG. 11 and Table 2A. The CDRs and framework regions of the VH domain and VL domain are indicated in FIG. 11. In addition, Table 2A, infra, sets forth the nucleic acid and amino acid sequences of the CDRs and framework regions of the variable regions of the antibody 1F4. The CDRs and framework regions in Table 2A were determined using the International ImMunoGeneTics ("IMGT") numbering system. See Lefranc et al., Dev. Comp. Immunol. 27:55-77 (2003), which is incorporated herein by reference in its entirety, for a description of the IMGT numbering system. As an alternative to the IMGT numbering system, the Kabat numbering system can be used. See Table 2B for the CDRs of antibody IF4 as determined by the Kabat numbering system. Table 2 of Lefranc et al. shows the correspondence between the IMGT and the Kabat numberings. Another alternative to the MGT numbering system is Chothia. See Chothia and Lesk, J. Mol. Biol. 196:901-917 (1987), which is incorporated herein by reference in its entirety. See Table 2B for the CDRs of antibody IF4 as determined by the Chothia numbering system. Further, Oxford's AbM system may be used instead of the IMGT numbering system. See Table 2B for the CDRs of antibody IF4 as determined by the ABM numbering system. A person of ordinary skill in the art would be able to determine the CDRs and framework regions of the variable regions of the 1F4 antibody sequence based on known numbering systems, such as the Kabat numbering system, Chothia system, Oxford's AbM system and/or contact system.

TABLE 2A

| DESCRIPTION OF SEQUENCE | VARIABLE REGION AMINO ACID SEQUENCE |
|---|---|
| 1F4 VH | QVHLQQSGSELRSPGSSVKLSCKDFDSEVFPIVYMRWIRQKPGHGFE WIGDILPSFGRTIYGEKFEDKATLDADTVSNTAYLELNSLTSEDSAIY YCARGDHGNWLAYWGQGTLVTVSA (SEQ ID NO: 17) |

TABLE 2A-continued

| | |
|---|---|
| 1F4 VL | DIVMTQSHKFMSTSVGDRVTITCKASQDVSTAVAWYQQKPGQSPK LLIYWASTRHTGVPNRFTGIISGTDYTLTISSVQAEDLALYYCQQHY SAPWTFGGGTKLEIKSEQ ID NO: 18) |

| DESCRIPTION OF SEQUENCE | CDR1 AMINO ACID SEQUENCE | CDR2 AMINO ACID SEQUENCE | CDR3 AMINO ACID SEQUENCE |
|---|---|---|---|
| 1F4 VH CDRs (IMGT DELINEATION) | DSEVFPIVY (SEQ ID NO: 19) | ILPSFGRT (SEQ ID NO: 20) | ARGDHGNWLAY (SEQ ID NO: 21) |
| 1F4 VL CDRs (IMGT DELINEATION) | QDVSTA (SEQ ID NO: 22) | WAS (SEQ ID NO: 23) | QQHYSAPWT (SEQ ID NO: 24) |

| DESCRIPTION OF SEQUENCE | FR1 AMINO ACID SEQUENCE | FR2 AMINO ACID SEQUENCE | FR3 AMINO ACID SEQUENCE | FR4 AMINO ACID SEQUENCE |
|---|---|---|---|---|
| 1F4 VH FRs (IMGT DELINEATION) | QVHLQQSGSEL RSPGSSVKLSCK DF (SEQ ID NO: 25) | MRWIRQKPGHG FEWIGD (SEQ ID NO: 26) | IYGEKFEDKATL DADTVSNTAYL ELNSLTSEDSAIY YC (SEQ ID NO: 27) | WGQGTLVTVSA (SEQ ID NO: 28) |
| 1F4 VL FRs (IMGT DELINEATION) | DIVMTQSHKFM ST SVGDRVTITCKA S (SEQ ID NO: 29) | VAWYQQKPGQS P KLLIY (SEQ ID NO: 30) | TRHTGVPNRFTG IISGTDYTLTISSV QAEDLALYYC (SEQ ID NO: 31) | FGGGTKLEIK (SEQ ID NO: 32) |

| DESCRIPTION OF SEQUENCE | VARIABLE REGION POLYNUCLEOTIDE SEQUENCE |
|---|---|
| 1F4 VH | CAGGTTCACCTACAACAGTCTGGTTCTGAACTGAGGAGTCCTGGGTCTTCAG TAAAGCTTTCATGCAAGGATTTTGATTCAGAAGTCTTCCCTATTGTTTATAT GAGATGGATTAGGCAGAAGCCTGGCCATGGATTTGAATGGATTGGAGACAT ACTCCCAAGTTTTGGTAGAACAATCTATGGAGAGAAGTTTGAGGACAAAGC CACACTAGATGCAGACACAGTGTCCAACACAGCCTACTTGGAGCTCAACAG TCTGACATCTGAGGACTCTGCTATCTACTACTGTGCAAGGGGGGACCATGG TAACTGGCTTGCTTACTGGGGCCAAGGGACTCTGGTCACTGTCTCTGCA (SEQ ID NO: 83) |
| 1F4 VL | gacattgtgatgacccagtctcacaaattcatgtccacatcagttggagacagggtcaccatcacctgcaaggcca gtcaggatgtgagtactgctgtagcctggtatcaacaaaaaccaggccaatctcctaaactactgatttactgggc atccacccggcacactggagtccctaatcgcttcacaggcattatatctgggacagattacactctcactatcagc agtgtgcaggctgaagacctggcactttattactgtcagcaacattatagcgctccgtggacgttcggtggaggca ccaagctggaaatcaaa (SEQ ID NO: 84) |

TABLE 2B

CDRs for antibody IF4 as determined by Chothia, ABM and Kabat.

| | Chothia numbering system | ABM numbering system | Kabat numbering system |
|---|---|---|---|
| VHCDR1 | DSEVFPIV (SEQ ID NO: 112) | DSEVFPIVYMR(SEQ ID NO: 118) | PIVYMR (SEQ ID NO: 124) |
| VHCDR2 | LPSFGR (SEQ ID NO: 113) | DILPSFGRTI (SEQ ID NO: 119) | DILPSFGRTIYGEKFED (SEQ ID NO: 125) |
| VHCDR3 | GDHGNWLAY (SEQ ID NO: 114) | GDHGNWLAY (SEQ ID NO: 120) | GDHGNWLAY (SEQ ID NO: 126) |
| VLCDR1 | KASQDVSTAVA(SEQ ID NO: 115) | KASQDVSTAVA (SEQ ID NO: 121) | KASQDVSTAVA (SEQ ID NO: 127) |
| VLCDR2 | WASTRHT (SEQ ID NO: 116) | WASTRHT (SEQ ID NO: 122) | WASTRHT (SEQ ID NO: 128) |
| VLCDR3 | QQHYSAPWT (SEQ ID NO: 117) | QQHYSAPWT (SEQ ID NO: 123) | QQHYSAPWT (SEQ ID NO: 129) |

In a specific aspect, an antibody provided herein is the antibody designated 3G1 or an antigen-binding fragment thereof. The 3G1 antibody is a murine IgG2a antibody. The deduced nucleotide sequences of the variable heavy chain region ("VH" domain) and variable light chain region ("VL" domain) of the antibody 3G1 are shown in FIG. 12 and Table 3. The deduced amino acid sequences of the VH and VL domains of the antibody 3G1 are shown in FIG. 13 and Table 3. The CDRs and framework regions of the VH domain and VL domain are indicated in FIG. 13. In addition, Table 3, infra, sets forth the nucleic acid and amino acid sequences of the CDRs and framework regions of the variable regions of the antibody 3G1. The CDRs and framework regions in Table 3 were determined using the International ImMunoGeneTics ("IMGT") numbering system. See Lefranc et al., Dev. Comp. Immunol. 27:55-77 (2003), which is incorporated herein by reference in its entirety, for a description of the IMGT numbering system. As an alternative to the IMGT numbering system, the Kabat numbering system can be used. Table 2 of Lefranc et al. shows the correspondence between the IMGT and the Kabat numberings. Another alternative to the IMGT numbering system is Chothia. See Chothia and Lesk, J. Mol. Biol. 196:901-917 (1987), which is incorporated herein by reference in its entirety. Further, Oxford's AbM system may be used instead of the IMGT numbering system. A person of ordinary skill in the art would be able to determine the CDRs and framework regions of the variable regions of the 3G1 antibody sequence based on the Kabat numbering system, Chothia system, and/or Oxford's AbM system.

TABLE 3

| DESCRIPTION OF SEQUENCE | VARIABLE REGION AMINO ACID SEQUENCE |
|---|---|
| 3G1 VH | QVQLQQSGAELMKPGASVKISCKATGYKFTSYWIGWVKQRPGH GLEWCGEIFPGSGSINYNEKFKGKATFTADTSSNTAYLQLTSLTS EDSAVYYCARGEDYYGSSYGAMDYWGQGTSLTVSS (SEQ ID NO: 33) |
| 3G1 VL | DVQITQSPSYLAASPGETITINCRASKSISKYVAWYQEKPGRTNK VLIYSGSILSFGNPSRFSGSGSGTDFTLTISSLEPEDFAMYYCQQH NEYPWTFGGGTKLEIK (SEQ ID NO: 34) |

| DESCRIPTION OF SEQUENCE | CDR1 AMINO ACID SEQUENCE | CDR2 AMINO ACID SEQUENCE | CDR3 AMINO ACID SEQUENCE |
|---|---|---|---|
| 3G1 VH CDRs (IMGT DELINEATION) | GYKFTSYW (SEQ ID NO: 35) | IFPGSGSI (SEQ ID NO: 36) | ARGEDYYGSSYGAM DY (SEQ ID NO: 37) |
| 3G1 VL CDRs (IMGT DELINEATION) | KSISKY (SEQ ID NO: 38) | SGS (SEQ ID NO: 39) | QQHNEYPWT (SEQ ID NO: 40) |

| DESCRIPTION OF SEQUENCE | FR1 AMINO ACID SEQUENCE | FR2 AMINO ACID SEQUENCE | FR3 AMINO ACID SEQUENCE | FR4 AMINO ACID SEQUENCE |
|---|---|---|---|---|
| 3G1 VH FRs (IMGT DELINEATION) | QVQLQQSGAEL M KPGASVKISCKA T (SEQ ID NO: 41) | IGWVKQRPGHG L EWCGE (SEQ ID NO: 42) | NYNEKFKGKAT FT ADTSSNTAYLQL TS LTSEDSAVYYC (SEQ ID NO: 43) | WGQGTSLTVSS (SEQ ID NO: 44) |
| 3G1 VL FRs (IMGT DELINEATION) | DVQITQSPSYLA AS PGETITINCRAS (SEQ ID NO: 45) | VAWYQEKPGRT N KVLIY (SEQ ID NO: 46) | ILSFGNPSRFSGS G SGTDFTLTISSLE PE DFAMYYC (SEQ ID NO: 47) | FGGGTKLEIK (SEQ ID NO: 48) |

| DESCRIPTION OF SEQUENCE | VARIABLE REGION POLYNUCLEOTIDE SEQUENCE |
|---|---|
| 3G1 VH | CAGGTTCAGCTGCAGCAGTCTGGAGCTGAATTGATGAAGCCT GGGGCCTCAGTGAAGATTTCCTGCAAGGCTACTGGGTACAAA TTCACTAGTTATTGGATAGGGTGGGTAAAGCAGAGGCCGGGA CATGGCCTTGAGTGGTGTGGAGAGATTTTTCCTGGAAGTGGC AGTATTAACTATAATGAGAAATTTAAGGGCAAGGCCACATTC ACTGCAGATACATCCTCCAACACAGCCTACTTGCAACTGACC AGCCTGACATCTGAGGACTCTGCCGTCTATTACTGTGCAAGAG GGGAGGATTATTACGGTAGTAGTTACGGTGCTATGGACTACT GGGGTCAAGGAACCTCACTCACCGTCTCCTCA (SEQ ID NO: 85) |
| 3G1 VL | GATGTCCAGATAACCCAGTCTCCATCTTATCTTGCTGCATCTC CTGGAGAAACCATTACTATTAATTGCAGGGCAAGTAAGAGCA TCAGCAAATATGTAGCCTGGTATCAAGAGAAACCTGGGAGAA CTAACAAGGTTCTTATATATTCTGGATCAATCTTGTCATTTGG AAATCCATCAAGGTTCAGTGGCAGTGGATCTGGTACAGATTT CACTCTCACCATCAGTAGCCTGGAGCCTGAAGATTTTGCAATG TATTACTGTCAACAGCATAATGAATACCCGTGGACGTTCGGTG GAGGCACCAAGCTGGAAATCAAA (SEQ ID NO: 86) |

In a specific aspect, an antibody provided herein is the antibody designated 4B2 or an antigen-binding fragment thereof. The 4B2 antibody is a murine IgG2a antibody. The deduced nucleotide sequences of the variable heavy chain region ("VH" domain) and variable light chain region ("VL" domain) of the antibody 4B2 are shown in FIG. 14 and Table 4A. The deduced amino acid sequences of the VH and VL domains of the antibody 4B2 are shown in FIG. 15 and Table 4. The CDRs and framework regions of the VH domain and VL domain are indicated in FIG. 15. In addition, Table 4A, infra, sets forth the nucleic acid and amino acid sequences of the CDRs and framework regions of the variable regions of the antibody 4B2. The CDRs and framework regions in Table 4A were determined using the International ImMunoGeneTics ("IMGT") numbering system. See Lefranc et al., Dev. Comp. Immunol. 27:55-77 (2003), which is incorporated herein by reference in its entirety, for a description of the IMGT numbering system. As an alternative to the IMGT numbering system, the Kabat numbering system can be used. See Table 4B for the CDRs of antibody 4B2 as determined by the Kabat numbering system. Table 2 of Lefranc et al. shows the correspondence between the IMGT and the Kabat numberings. Another alternative to the IMGT numbering system is Chothia. See Chothia and Lesk, J. Mol. Biol. 196:901-917 (1987), which is incorporated herein by reference in its entirety. See Table 4B for the CDRs of antibody 4B2 as determined by the Chothia numbering system. Futher, Oxford's AbM system may be used instead of the IMGT numbering system. See Table 4B for the CDRs of antibody 4B2 as determined by the ABM numbering system. A person of ordinary skill in the art would be able to determine the CDRs and framework regions of the variable regions of the 4B2 antibody sequence based on known numbering systems, such as the Kabat numbering system, Chothia system, Oxford's AbM system and/or contact system.

TABLE 4A

| DESCRIPTION OF SEQUENCE | VARIABLE REGION AMINO ACID SEQUENCE |
|---|---|
| 4B2 VH | QIQLVQSGPELKKPGETVKISCKASGFTFTDYPMHWVKQAPGKSL KWMGWINTETEEPTYSDDFKGRFALSLETSASTTYLQINNLKNED TATYFCARSGYYYGSTYAWFGYWGQGTLVTVSA (SEQ ID NO: 49) |
| 4B2 VL | DVVMTQIPLSLPVSLGDQASISCRSSQSLIHTNGDTFLHWYLQKPG QSPKWYKVSNRFSGVPDRFTGGGSGTDFTLKISRVEAEDLGIYF CSQSALFPYTFGGGTNLEIK (SEQ ID NO: 50) |

| DESCRIPTION OF SEQUENCE | CDR1 AMINO ACID SEQUENCE | CDR2 AMINO ACID SEQUENCE | CDR3 AMINO ACID SEQUENCE |
|---|---|---|---|
| 4B2 VH CDRs (IMGT DELINEATION) | GFTFTDYP (SEQ ID NO: 51) | INTETEEP (SEQ ID NO: 52) | ARSGYYYGSTYAWF GY (SEQ ID NO: 53) |
| 4B2 VL CDRs (IMGT DELINEATION) | QSLIHTNGDTF (SEQ ID NO: 54) | KVS (SEQ ID NO: 55) | SQSALFPYT (SEQ ID NO: 56) |

| DESCRIPTION OF SEQUENCE | FR1 AMINO ACID SEQUENCE | FR2 AMINO ACID SEQUENCE | FR3 AMINO ACID SEQUENCE | FR4 AMINO ACID SEQUENCE |
|---|---|---|---|---|
| 4B2 VH FRs (IMGT DELINEATION) | QIQLVQSGPELK KP GETVKISCKAS (SEQ ID NO: 57) | MHWVKQAPGKS L KWMGW (SEQ ID NO: 58) | TYSDDFKGRFAL SLETSASTTYLQI NNLKNEDTATY FC (SEQ ID NO: 59) | WGQGTLVTVSA (SEQ ID NO: 60) |
| 4B2 VL FRs (IMGT DELINEATION) | DVVMTQIPLSLP VSLGDQASISCR SS (SEQ ID NO: 61) | LHWYLQKPGQS PK LLIY (SEQ ID NO: 62) | NRFSGVPDRFTG GGSGTDFTLKIS RVE AEDLGIYFC (SEQ ID NO: 63) | FGGGTNLEIK (SEQ ID NO: 64) |

| DESCRIPTION OF SEQUENCE | VARIABLE REGION POLYNUCLEOTIDE SEQUENCE |
|---|---|
| 4B2 VH | cagatccagttggtgcagtctggacctgagctgaagaagcctggagagacagtcaagatctcctgcaag gcttctggttttaccttcacagactatccaatgcactgggtgaagcaggctccaggaaagagtttaaagtg gatgggttggataaacactgagactgaagagccaacatattcagatgacttcaagggacggtttgccttgt ctttggaaacctctgccagcacaacctatttgcagatcaacaatctcaaaaatgaggacacggctacatat ttctgtgctagatcaggttattactatggtagtacctacgcctggtttggttactggggccaagggactctgg tcactgtctctgca (SEQ ID NO: 87) |
| 4B2 VL | GATGTTGTGATGACCCAAATTCCACTCTCCCTGCCTGTCAGTCT CGGAGATCAGGCCTCCATCTCTTGCAGATCTAGTCAGAGCCTT ATACACACTAATGGAGACACCTTTTTACATTGGTACCTGCAGA AGCCAGGCCAGTCTCCAAAGCTCCTGATCTACAAAGTTTCCAA CCGATTTTCTGGGGTCCCAGACAGGTTCACTGGCGGTGGATCA GGGACAGATTTCACACTCAAGATCAGCAGAGTGGAGGCTGAG GATCTGGGAATTTATTTCTGCTCTCAAAGTGCACTTTTTCCGTA CACGTTCGGAGGGGGGACCAACCTGGAAATAAAA (SEQ ID NO: 88) |

TABLE 4B

CDRs for antibody 4B2 as determined by Chothia, ABM and Kabat.

| | Chothia numbering system | ABM numbering system | Kabat numbering system |
|---|---|---|---|
| VHCDR1 | GFTFTDY (SEQ ID NO: 130) | GFTFTDYPMH (SEQ ID NO: 136) | DYPMH (SEQ ID NO: 142) |
| VHCDR2 | NTETEE (SEQ ID NO: 131) | WINTETEEPT (SEQ ID NO: 137) | WINTETEEPTYSDDFKG (SEQ ID NO: 143) |
| VHCDR3 | SGYYYGSTYAWFGY (SEQ ID NO: 132) | SGYYYGSTYAWFGY (SEQ ID NO: 138) | SGYYYGSTYAWFGY (SEQ ID NO: 144) |
| VLCDR1 | RSSQSLIHTNGDTFLH (SEQ ID NO: 133) | RSSQSLIHTNGDTFLH (SEQ ID NO: 139) | RSSQSLIHTNGDTFLH (SEQ ID NO: 145) |
| VLCDR2 | KVSNRFS (SEQ ID NO: 134) | KVSNRFS (SEQ ID NO: 140) | KVSNRFS (SEQ ID NO: 146) |
| VLCDR3 | SQSALFPYT (SEQ ID NO: 135) | SQSALFPYT (SEQ ID NO: 141) | SQSALFPYT (SEQ ID NO: 147) |

In a specific aspect, an antibody provided herein is the antibody designated 4F11 or an antigen-binding fragment thereof. The 4F11 antibody is a murine IgG2b antibody. The deduced nucleotide sequences of the variable heavy chain region ("VH" domain) and variable light chain region ("VL" domain) of the antibody 4F11 are shown in FIG. 16 and Table 5A. The deduced amino acid sequences of the VH and VL domains of the antibody 4F11 are shown in FIG. 17 and Table 5A. The CDRs and framework regions of the VH domain and VL domain are indicated in FIG. 17. In addition, Table 5A, infra, sets forth the nucleic acid and amino acid sequences of the CDRs and framework regions of the variable regions of the antibody 4F11. The CDRs and framework regions in Table 5A were determined using the International ImMunoGeneTics ("IMGT") numbering system. See Lefranc et al., Dev. Comp. Immunol. 27:55-77 (2003), which is incorporated herein by reference in its entirety, for a description of the IMGT numbering system. As an alternative to the IMGT numbering system, the Kabat numbering system can be used. See Table 5B for the CDRs of antibody 4F11 as determined by the Kabat numbering system. Table 2 of Lefranc et al. shows the correspondence between the IMGT and the Kabat numberings. Another alternative to the IMGT numbering system is Chothia. See Chothia and Lesk, J. Mol. Biol. 196:901-917 (1987), which is incorporated herein by reference in its entirety. See Table 5B for the CDRs of antibody 4F11 as determined by the Chothia numbering system. Further, Oxford's AbM system may be used instead of the IMGT numbering system. See Table 5B for the CDRs 4 of antibody 4F11 as determined by the ABM numbering system. A person of ordinary skill in the art would be able to determine the CDRs and framework regions of the variable regions of the 4F11 antibody sequence based on known numbering systems, such as the Kabat numbering system, Chothia system, Oxford's AbM system and/or contact system.

TABLE 5A

| DESCRIPTION OF SEQUENCE | VARIABLE REGION AMINO ACID SEQUENCE |
|---|---|
| 4F11 VH | DVKLVESGGDLVKPGGSLKLSCAASGFTFSAYSMSWVRQTPERR LEWVATINTGGSFTYYPDSVKGRFTISRDNAKNTLYLQMSSLKS EDTAMYFCTRVSDYGNSAYFPYWGQGTLVIVSA (SEQ ID NO: 65) |
| 4F11 VL | QVVLTQSPALISASPGEKVTMTCSASSNVNYMSWYQQRPRSSPK PWIYLTSKLASGVPPRFSGSGSGTSYSLTISSMEAEDVATYYCQQ WSSDPQTFGGGTKVEIK (SEQ ID NO: 66) |

| DESCRIPTION OF SEQUENCE | CDR1 AMINO ACID SEQUENCE | CDR2 AMINO ACID SEQUENCE | CDR3 AMINO ACID SEQUENCE |
|---|---|---|---|
| 4F11 VH CDRs (IMGT DELINEATION) | GFTFSAYS (SEQ ID NO: 67) | INTGGSFT (SEQ ID NO: 68) | TRVSDYGNSAYFPY (SEQ ID NO: 69) |
| 4F11 VL CDRs (IMGT DELINEATION) | SNVNY (SEQ ID NO: 70) | LTS QQWS (SEQ ID NO: 71) | SDPQT (SEQ ID NO: 72) |

| DESCRIPTION OF SEQUENCE | FR1 AMINO ACID SEQUENCE | FR2 AMINO ACID SEQUENCE | FR3 AMINO ACID SEQUENCE | FR4 AMINO ACID SEQUENCE |
|---|---|---|---|---|
| 4F11 VH FRs (IMGT DELINEATION) | DVKLVESGGDL VK PGGSLKLSCAAS (SEQ ID NO: 73) | MSWVRQTPERR L EWVAT (SEQ ID NO: 74) | YYPD SVKGRFTI SR DNAKNTLYLQM SS LKSEDTAMYFC (SEQ ID NO: 75) | WGQGTLVIVSA (SEQ ID NO: 76) |

TABLE 5A-continued

| | | | | |
|---|---|---|---|---|
| 4F11 VL FRs (IMGT DELINEATION) | QVVLTQSPALIS AS PGEKVTMTCSAS (SEQ ID NO: 77) | MSWYQQRPRSS P KPWIY (SEQ ID NO: 78) | KLASGVPPRFSG S GSGTSYSLTISSM E AEDVATYYC (SEQ ID NO: 79) | FGGGTKVEIK (SEQ ID NO: 80) |

| DESCRIPTION OF SEQUENCE | VARIABLE REGION POLYNUCLEOTIDE SEQUENCE |
|---|---|
| 4F11 VH | gacgtgaaactggtggaatctgggggagacttagtgaagcctggagggtccctgaaactctcctgtgca gcctctggattcactttcagtgcctattccatgtcttgggttcgccagactccggagaggaggctggagtg ggtcgcaaccattaatactggtggtagtttcacctactatccagacagtgtgaagggccgattcaccatct ccagagacaatgccaagaacaccctgtacctgcaaatgagcagtctgaagtctgaggacacagccatg tatttctgtacaagagtttccgactacggtaatagcgcctactttccttactggggccaagggactctggtc attgtctctgca (SEQ ID NO: 89) |
| 4F11 VL | CAAGTTGTTCTCACCCAGTCTCCAGCACTCATATCTGCGTCTCC AGGGGAGAAGGTCACCATGACCTGCAGTGCCAGCTCAAATGT AAATTACATGTCCTGGTACCAGCAGAGGCCAAGATCCTCCCCC AAACCCTGGATTTATCTCACATCCAAACTGGCTTCTGGAGTCCC TCCTCGTTTCAGTGGCAGTGGGTCTGGGACCTCTTACTCTCTCA CAATCAGCAGCATGGAGGCTGAAGATGTTGCCACTTATTACTG CCAGCAGTGGAGCAGTGACCCCCAGACGTTCGGAGGGGGGAC CAAGGTGGAAATAAAA (SEQ ID NO: 90) |

TABLE 5B

CDRs for antibody 4F11 as determined by Chothia, ABM and Kabat.

| | Chothia numbering system | ABM numbering system | Kabat numbering system |
|---|---|---|---|
| VHCDR1 | GFTFSAY (SEQ ID NO: 148) | GFTFSAYSMS (SEQ ID NO: 154) | SAYSMS (SEQ ID NO: 160) |
| VHCDR2 | NTGGSF (SEQ ID NO: 149) | TINTGGSFTY (SEQ ID NO: 155) | TINTGGSFTYYPDSVKG (SEQ ID NO: 161) |
| VHCDR3 | VSDYGNSAYFPY (SEQ ID NO: 150) | VSDYGNSAYFPY (SEQ ID NO: 156) | VSDYGNSAYFPY (SEQ ID NO: 162) |
| VLCDR1 | SASSNVNYMS (SEQ ID NO: 151) | SASSNVNYMS (SEQ ID NO: 157) | SASSNVNYMS (SEQ ID NO: 163) |
| VLCDR2 | LTSKLAS (SEQ ID NO: 152) | LTSKLAS (SEQ ID NO: 158) | LTSKLAS (SEQ ID NO: 164) |
| VLCDR3 | QQWSSDPQT (SEQ ID NO: 153) | QQWSSDPQT (SEQ ID NO: 159) | QQWSSDPQT (SEQ ID NO: 165) |

In a specific embodiment, the position of a CDR along the VH and/or VL domain of an antibody described herein may vary by one, two, three or four amino acid positions so long as binding to influenza B virus NA (e.g., NA of an influenza B virus strain of the Victoria lineage, such as NA of B/Malaysia/2506/04, B/Victoria/2/87, or B/Brisbane/60/08, and/or NA of an influenza B virus strain of the Yamagata lineage, such as B/Yamagata/16/88 or another strain described herein, such as in Section 6 and/or Section 7, infra) is maintained or substantially maintained (for example, by at least 50%, at least 60%, at least 70%, at least 80%, at least 90%, at least 95% in an assay known in the art or described herein, such as an ELISA). For example, in one embodiment, the position defining a CDR of antibody 1F2 may vary by shifting the N-terminal and/or C-terminal boundary of the CDR by one, two, three, or four amino acids, relative to the CDR position depicted in FIG. 9, so long as binding to influenza B virus NA (e.g., NA of an influenza B virus strain of the Victoria lineage, such as NA of B/Malaysia/2506/04, B/Victoria/2/87, or B/Brisbane/60/08, and/or NA of an influenza B virus strain of the Yamagata lineage, such as B/Yamagata/16/88 or another strain described herein, such as in Section 6 and/or Section 7, infra) is maintained or substantially maintained (for example, by at least 50%, at least 60%, at least 70%, at least 80%, at least 90%, at least 95% in an assay known in the art or described herein, such as an ELISA). In another example, in one embodiment, the position defining a CDR of antibody 1F4 may vary by shifting the N-terminal and/or C-terminal boundary of the CDR by one, two, three, or four amino acids, relative to the CDR position depicted in FIG. 11, so long as binding to influenza B virus NA (e.g., NA of an influenza B virus strain of the Victoria lineage, such as NA of B/Malaysia/2506/04, B/Victoria/2/87, or B/Brisbane/60/08, and/or NA of an influenza B virus strain of the Yamagata lineage, such as B/Yamagata/16/88 or another strain described herein, such as in Section 6 and/or Section 7, infra) is maintained or substantially maintained (for example, by at least 50%, at least 60%, at least 70%, at least 80%, at least 90%, at least 95% in an assay known in the art or described herein, such as an ELISA). In another example, in one embodiment, the position defining a CDR of antibody 3G1 may vary by shifting the N-terminal and/or C-terminal boundary of the CDR by one, two, three, or four amino acids, relative to the CDR position depicted in FIG. 13, so long as binding to influenza B virus NA (e.g., NA of an influenza B virus strain of the Victoria lineage, such as NA of B/Malaysia/2506/04, B/Victoria/2/87, or B/Brisbane/60/08, and/or NA of an influenza B virus strain of the Yamagata lineage, such as B/Yamagata/16/88 or another strain described herein, such as in Section 6 and/or Section 7, infra) is maintained or substantially maintained (for example, by at least 50%, at least 60%, at least 70%, at least 80%, at least 90%, at least 95% in an assay known in the art or described herein, such as an ELISA). In another example, in one embodiment, the position defining a CDR of antibody 4B2 may vary by shifting the N-terminal and/or C-terminal boundary of the CDR by one, two, three, or four amino acids, relative to the CDR position depicted in FIG. 15, so long as binding to influenza B virus NA (e.g., NA of an influenza B virus strain of the Victoria lineage, such as NA of B/Malaysia/2506/04, B/Victoria/2/87, or B/Brisbane/60/08, and/or NA of an influenza B virus strain of the Yamagata lineage, such as B/Yamagata/16/88 or another strain described herein, such as in Section 6 and/or Section 7, infra) is maintained or substantially maintained (for example, by at least 50%, at least 60%, at least 70%, at least 80%, at least 90%, at least 95% in an assay known in the art or described herein, such as an ELISA). In another example, in one embodiment, the position defining a CDR of antibody 4F11 may vary by shifting the N-terminal and/or C-terminal boundary of the CDR by one, two, three, or four amino acids, relative to the CDR position depicted in FIG. 17, so long as binding to influenza B virus NA (e.g., NA of an influenza B virus strain of the Victoria lineage, such as NA of B/Malaysia/2506/04, B/Victoria/2/87, or B/Brisbane/60/08, and/or NA of an influenza B virus strain of the Yamagata lineage, such as B/Yamagata/16/88 or another strain described herein, such as in Section 6 and/or Section 7, infra) is maintained or substantially maintained (for example, by at least 50%, at least 60%, at least 70%, at least 80%, at least 90%, at least 95% in an assay known in the art or described herein, such as an ELISA).

In another aspect, provided herein are antibodies that bind to an influenza B virus NA comprising one, two or three complementarity determining regions (CDRs) of the variable heavy chain region of the antibody 1F2, 1F4, 3G1, 4B2, or 4F11 and one, two or three CDRs of the variable light chain region of the antibody 1F2, 1F4, 3G1, 4B2, or 4F11. In certain embodiments, an antibody that binds to an influenza B virus NA (e.g., an influenza B virus NA described in Section 6 and/or Section 7 and/or Section 8, infra), comprises (or alternatively, consists of) a VH CDR1 and a VL CDR1; a VH CDR1 and a VL CDR2; a VH CDR1 and a VL CDR3; a VH CDR2 and a VL CDR1; VH CDR2 and a VL CDR2; a VH CDR2 and a VL CDR3; a VH CDR3 and a VL CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1; a VH CDR2, a VH CDR3 and a VL CDR2; a VH CDR2, a VH CDR3 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR3, a VL CDR1 and a VL CDR2; a VH CDR1, a VH CDR3, a VL CDR1 and a VL CDR3; a VH CDR2, a VH CDR3, a VL CDR1 and a VL CDR2; a VH CDR2, a VH CDR3, a VL CDR1 and a VL CDR3; a VH CDR2, a VH CDR3, a VL CDR2 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; a VH CDR1, VH CDR2, a VH CDR3, a VL CDR1, a VL CDR2, and a VL CDR3; or any combination thereof of the VH CDRs and VL CDRs of the antibody 1F2, 1F4, 3G1, 4B2, or 4F11.

In a specific aspect, provided herein are antibodies that bind to an influenza B virus NA comprising one, two or three complementarity determining regions (CDRs) of the variable heavy chain region of the antibody 1F2 and one, two or three CDRs of the variable light chain region of the antibody 1F2. In certain embodiments, an antibody that binds to an influenza B virus NA (e.g., an influenza B virus NA described in Section 6 and/or Section 7 and/or Section 8, infra), comprises (or alternatively, consists of) a VH CDR1 and a VL CDR1; a VH CDR1 and a VL CDR2; a VH CDR1 and a VL CDR3; a VH CDR2 and a VL CDR1; VH CDR2 and a VL CDR2; a VH CDR2 and a VL CDR3; a VH CDR3 and a VL CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1; a VH CDR2, a VH CDR3 and a VL CDR2; a VH CDR2, a VH CDR3 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR3, a VL CDR1 and a VL CDR2; a VH CDR1, a VH CDR3, a VL CDR1 and a VL CDR3; a VH CDR2, a VH CDR3, a VL CDR1 and a VL CDR2; a VH CDR2, a VH CDR3, a VL CDR1 and a VL CDR3; a VH CDR2, a VH CDR3, a VL CDR2 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; a VH CDR1, VH CDR2, a VH CDR3, a VL CDR1, a VL CDR2, and a VL CDR3; or any combination thereof of the VH CDRs and VL CDRs of the antibody 1F2.

In a specific aspect, provided herein are antibodies that bind to an influenza B virus NA comprising one, two or three complementarity determining regions (CDRs) of the variable heavy chain region of the antibody 1F4 and one, two or three CDRs of the variable light chain region of the antibody 1F4. In certain embodiments, an antibody that binds to an influenza B virus NA (e.g., an influenza B virus NA described in Section 6 and/or Section 7, infra), comprises (or alternatively, consists of) a VH CDR1 and a VL CDR1; a VH CDR1 and a VL CDR2; a VH CDR1 and a VL CDR3; a VH CDR2 and a VL CDR1; VH CDR2 and a VL CDR2; a VH CDR2 and a VL CDR3; a VH CDR3 and a VL CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1; a VH CDR2, a VH CDR3 and a VL CDR2; a VH CDR2, a VH CDR3 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR3, a VL CDR1 and a VL CDR2; a VH CDR1, a VH CDR3, a VL CDR1 and a VL CDR3; a VH CDR2, a VH CDR3, a VL CDR1 and a VL CDR2; a VH CDR2, a VH CDR3, a VL CDR1 and a VL CDR3; a VH CDR2, a VH CDR3, a VL CDR2 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; a VH CDR1, VH CDR2, a VH CDR3, a VL CDR1, a VL CDR2, and a VL CDR3; or any combination thereof of the VH CDRs and VL CDRs of the antibody 1F4.

In a specific aspect, provided herein are antibodies that bind to an influenza B virus NA comprising one, two or three complementarity determining regions (CDRs) of the variable heavy chain region of the antibody 3G1 and one, two or three CDRs of the variable light chain region of the antibody 3G1. In certain embodiments, an antibody that binds to an influenza B virus NA (e.g., an influenza B virus NA described in Section 6 and/or Section 7, infra), comprises (or alternatively, consists of) a VH CDR1 and a VL CDR1; a VH CDR1 and a VL CDR2; a VH CDR1 and a VL CDR3; a VH CDR2 and a VL CDR1; VH CDR2 and a VL CDR2; a VH CDR2 and a VL CDR3; a VH CDR3 and a VL CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1; a VH CDR2, a VH CDR3 and a VL CDR2; a VH CDR2, a VH CDR3 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR3, a VL CDR1 and a VL CDR2; a VH CDR1, a VH CDR3, a VL CDR1 and a VL CDR3; a VH CDR2, a VH CDR3, a VL CDR1 and a VL CDR2; a VH CDR2, a VH CDR3, a VL CDR1 and a VL CDR3; a VH CDR2, a VH CDR3, a VL CDR2 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; a VH CDR1, VH CDR2, a VH CDR3, a VL CDR1, a VL CDR2, and a VL CDR3; or any combination thereof of the VH CDRs and VL CDRs of the antibody 3G1.

In a specific aspect, provided herein are antibodies that bind to an influenza B virus NA comprising one, two or three complementarity determining regions (CDRs) of the variable heavy chain region of the antibody 4B2 and one, two or three CDRs of the variable light chain region of the antibody 4B2. In certain embodiments, an antibody that binds to an influenza B virus NA (e.g., an influenza B virus NA described in Section 6 and/or Section 7, infra), comprises (or alternatively, consists of) a VH CDR1 and a VL CDR1; a VH CDR1 and a VL CDR2; a VH CDR1 and a VL CDR3; a VH CDR2 and a VL CDR1; VH CDR2 and a VL CDR2; a VH CDR2 and a VL CDR3; a VH CDR3 and a VL CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1; a VH CDR2, a VH CDR3 and a VL CDR2; a VH CDR2, a VH CDR3 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR3, a VL CDR1 and a VL CDR2; a VH CDR1, a VH CDR3, a VL CDR1 and a VL CDR3; a VH CDR2, a VH CDR3, a VL CDR1 and a VL CDR2; a VH CDR2, a VH CDR3, a VL CDR1 and a VL CDR3; a VH CDR2, a VH CDR3, a VL CDR2 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; a VH CDR1, VH CDR2, a VH CDR3, a VL CDR1, a VL CDR2, and a VL CDR3; or any combination thereof of the VH CDRs and VL CDRs of the antibody 4B2.

In a specific aspect, provided herein are antibodies that bind to an influenza B virus NA comprising one, two or three complementarity determining regions (CDRs) of the variable heavy chain region of the antibody 4F11 and one, two or three CDRs of the variable light chain region of the antibody 4F11. In certain embodiments, an antibody that binds to an influenza B virus NA (e.g., an influenza B virus NA described in Section 6 and/or Section 7, infra), comprises (or alternatively, consists of) a VH CDR1 and a VL CDR1; a VH CDR1 and a VL CDR2; a VH CDR1 and a VL CDR3; a VH CDR2 and a VL CDR1; VH CDR2 and a VL CDR2; a VH CDR2 and a VL CDR3; a VH CDR3 and a VL CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1; a VH CDR2, a VH CDR3 and a VL CDR2; a VH CDR2, a VH CDR3 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR3, a VL CDR1 and a VL CDR2; a VH CDR1, a VH CDR3, a VL CDR1 and a VL CDR3; a VH CDR2, a VH CDR3, a VL CDR1 and a VL CDR2; a VH CDR2, a VH CDR3, a VL CDR1 and a VL CDR3; a VH CDR2, a VH CDR3, a VL CDR2 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; a VH CDR1, VH CDR2, a VH CDR3, a VL CDR1, a VL CDR2, and a VL CDR3; or any combination thereof of the VH CDRs and VL CDRs of the antibody 4F11.

In another embodiment, an antibody, which binds to an influenza B virus NA (e.g., an influenza B virus NA discussed in Section 6 and/or Section 7 and/or Section 8, infra), comprises one, two, three, four, five or all six complementarity determining regions (CDRs) of the antibody 1F2. In certain embodiments, an antibody, which binds to influenza B virus NA, comprises one, two, three, four, five or all six CDRs of the antibody IF2 as determined by IMGT numbering system, Kabat numbering system, Chothia numbering system or ABM numbering system. In some embodiments, an antibody, which binds to influenza B virus NA, comprises a VL domain or light chain comprising the VL CDR1, VL CDR2 and VL CDR3 of the antibody IF2, as determined by a known numbering system known in the art, such as set forth in Table 1A and 1B. In certain embodiments, an antibody, which binds to influenza B virus NA (e.g., influenza B virus NA discussed in Section 6 and/or Section 7 and/or Section 8, infra), comprises VL domain or light chain comprising a VL complementarity determining region (CDR)1, VL CDR2, and VL CDR3 comprising the amino acid sequences of SEQ ID NOs: 6-8, respectively. In certain embodiments, the light chain or VL domain comprises one, two or three of framework region (FR)1, FR2, FR3, and FR4 comprising the amino acid sequences of SEQ ID NO: 13-16, respectively. In some embodiments, the light chain or VL domain comprises framework region (FR)1, FR2, FR3, and FR4 comprising the amino acid sequences of SEQ ID NO: 13-16, respectively. In other embodiments, the light chain or VL domain comprises human framework regions or framework regions derived from a human antibody. In some embodiments, the light chain or VL domain comprises human framework regions or framework regions derived from IGKV1-8. In some embodiments, a light chain or VL domain comprises a signal peptide, such as set forth in SEQ ID NO:204.

In certain embodiments, an antibody, which binds to an influenza B virus NA, comprises a VH domain or heavy chain comprising the VH CDR1, VH CDR2, and VH CDR3 of antibody 1F2, as determined by a numbering system known in the art, such as set forth in Table 1A or Table 1B. In some embodiments, an antibody, which binds to influenza B virus NA (e.g., an influenza B virus NA discussed in Section 6 and/or 7, infra), comprises a VH domain or heavy chain comprising a VH CDR1, VH CDR2, and VH CDR3 comprising the amino acid sequences of SEQ ID NOs: 3-5, respectively. In certain embodiments, the heavy chain or VH domain comprises one, two or three of framework region (FR)1, FR2, FR3, and FR4 comprising the amino acid sequences of SEQ ID NO: 9-12, respectively. In some embodiments, the heavy chain or VH domain comprises framework region (FR)1, FR2, FR3, and FR4 comprising the amino acid sequences of SEQ ID NO: 9-12, respectively. In other embodiments, the heavy chain or VH domain comprises human framework regions or framework regions derived from a human antibody. In some embodiments, the heavy chain or VH domain comprises human framework regions or framework regions derived from IGHV1-46 or IGHV1-2. In certain embodiments, a heavy chain or VH domain comprises a signal peptide, such as set forth in SEQ ID NO:203.

In one embodiment, an antibody, which binds to influenza B virus NA, comprises: (a) a VL domain or light chain comprising VL CDR1, VL CDR2, VL CDR3 of antibody IF2, as determined by any numbering system known in the art, such as set forth in Tables 1A and 1B; and (b) a VH domain or a heavy chain comprising VH CDR1, VH CDR2, VH CDR3, as determined by any numbering system known in the art such as set forth in Tables 1A and 1B. In specific embodiments, an antibody, which binds to influenza B virus NA (e.g., an influenza B virus NA discussed in Section 6 and/or 7, infra), comprises: VL domain or light chain comprising a VL complementarity determining region (CDR)1, VL CDR2, and VL CDR3 comprising the amino acid sequences of SEQ ID NOs: 6-8, respectively; and a VH domain or heavy chain comprising a VH CDR1, VH CDR2, and VH CDR3 comprising the amino acid sequences of SEQ ID NOs: 3-5, respectively. In certain embodiments, the light chain or VL domain comprises one, two or three of framework region (FR)1, FR2, FR3, and FR4 comprising the amino acid sequences of SEQ ID NO: 13-16, respectively, and the heavy chain or VH domain comprises one, two or three of framework regions (FR)1, FR2, FR3, and FR4 comprising the amino acid sequences of SEQ ID NO: 9-12, respectively. In some embodiments, the light chain or VL domain comprises framework region (FR)1, FR2, FR3, and FR4 comprising the amino acid sequences of SEQ ID NO: 13-16, respectively, and the heavy chain or VH domain comprises framework regions (FR)1, FR2, FR3, and FR4 comprising the amino acid sequences of SEQ ID NO: 9-12, respectively. In other embodiments, the light chain or VL domain and heavy chain or VH domain comprises human framework regions or framework regions derived from a human antibody. In some embodiments, the heavy chain or VH domain comprises framework regions derived from IGHV1-46 or IGHV1-2, and the light chain or VL domain comprises framework regions derived from IGKV1-8. In certain embodiments, a heavy chain or VH domain comprises a signal peptide, such as set forth in SEQ ID NO:203. In some embodiments, a light chain or VL domain comprises a signal peptide, such as set forth in SEQ ID NO:204.

In a specific embodiment, an antibody, which binds to an influenza B virus NA, comprises a variable heavy chain region that comprises the amino acid sequence of SEQ ID NO: 168, 169, 170, 171, 172, 173, 174 or 175. In another specific embodiment, an antibody, which binds to an influenza B virus NA, comprises a variable light chain region that comprises the amino acid sequence of SEQ ID NO: 177, 178, 179, 180, 181, 182, 183, or 184. In another specific embodiment, an antibody, which binds to an influenza B virus NA, comprises: (a) a variable heavy chain region that comprises the amino acid sequence of SEQ ID NO: 168, 169, 170, 171, 172, 173, 174 or 175; and (b) a variable light chain region that comprises the amino acid sequence of SEQ ID NO: 177, 178, 179, 180, 181, 182, 183, or 184. In certain embodiments, a variable heavy chain region comprises a signal peptide, such as set forth in SEQ ID NO:203. In some embodiments, a variable light chain region comprises a signal peptide, such as set forth in SEQ ID NO:204.

In a specific embodiment, an antibody, which binds to an influenza B virus NA, comprises a heavy chain that comprises the amino acid sequence of SEQ ID NO: 168, 169, 170, 171, 172, 173, 174 or 175. In another specific embodiment, an antibody, which binds to an influenza B virus NA, comprises a light chain that comprises the amino acid sequence of SEQ ID NO: 177, 178, 179, 180, 181, 182, 183, or 184. In another specific embodiment, an antibody, which binds to an influenza B virus NA, comprises: (a) a heavy chain that comprises the amino acid sequence of SEQ ID NO: 168, 169, 170, 171, 172, 173, 174 or 175; and (b) a light chain that comprises the amino acid sequence of SEQ ID NO: 177, 178, 179, 180, 181, 182, 183, or 184. In certain embodiments, a heavy chain comprises a signal peptide, such as set forth in SEQ ID NO:203. In some embodiments, a light chain comprises a signal peptide, such as set forth in SEQ ID NO:204.

In another embodiment, an antibody, which binds to an influenza B virus NA (e.g., an influenza B virus NA discussed in Section 6 and/or Section 7, infra), comprises one, two, three, four, five or all six complementarity determining regions (CDRs) of the antibody 1F4. In certain embodiments, an antibody, which binds to an influenza B virus NA, comprises one, two, three, four, five or all six CDRs of the antibody 1F4, as determined by the IMGT numbering system, Kabat numbering system, Chothia numbering system or ABM numbering system. In some embodiments, an antibody, which binds to an influenza B virus NA, comprises a VL domain or light chain comprising the VL CDR1, VL CDR2, and VL CDR3 of antibody 1F4, as determined by a numbering system known in the art, such as set forth in Table 2A or Table 2B. In certain embodiments, an antibody, which binds to influenza B virus NA (e.g., influenza B virus NA discussed in Section 6 and/or 7, infra), comprises VL domain or light chain comprising a VL complementarity determining region (CDR)1, VL CDR2, and VL CDR3 comprising the amino acid sequences of SEQ ID NOs: 22-24, respectively. In certain embodiments, the light chain or VL domain comprises one, two or three of framework region (FR)1, FR2, FR3, and FR4 comprising the amino acid sequences of SEQ ID NO: 29-32, respectively. In some embodiments, the light chain or VL domain comprises framework region (FR)1, FR2, FR3, and FR4 comprising the amino acid sequences of SEQ ID NO: 29-32, respectively. In other embodiments, the light chain or VL domain comprises human framework regions or framework regions derived from a human antibody.

In certain embodiments, an antibody, which binds to an influenza B virus NA, comprises a VH domain or heavy chain comprising the VH CDR1, VH CDR2, and VH CDR3 of antibody 1F4, as determined by a numbering system known in the art, such as set forth in Table 2A or Table 2B. In some embodiments, an antibody, which binds to influenza B virus NA (e.g., an influenza B virus NA discussed in Section 6 and/or 7, infra), comprises a VH domain or heavy chain comprising a VH CDR1, VH CDR2, and VH CDR3 comprising the amino acid sequences of SEQ ID NOs: 19-21, respectively. In certain embodiments, the heavy chain or VH domain comprises one, two or three of framework region (FR)1, FR2, FR3, and FR4 comprising the amino acid sequences of SEQ ID NO: 25-28, respectively. In some embodiments, the heavy chain or VH domain comprises framework region (FR)1, FR2, FR3, and FR4 comprising the amino acid sequences of SEQ ID NOs:25-28, respectively. In other embodiments, the heavy chain or VH domain comprises human framework regions or framework regions derived from a human antibody.

In one embodiment, an antibody, which binds to influenza B virus NA, comprises: (a) a VL domain or light chain comprising VL CDR1, VL CDR2, and VL CDR3 of antibody 1F4 as determined by any numbering system known in the art, such as set forth in Tables 2A and 2B; and (b) a VH domain or heavy chain comprising VH CDR3, VH CDR2, and VH CDR3 of antibody 1F4 as determined by any numbering system known in the art, such as set forth in Tables 2A and 2B. In specific embodiments, an antibody, which binds to influenza B virus NA (e.g., an influenza B virus NA discussed in Section 6 and/or 7, infra), comprises: VL domain or light chain comprising a VL complementarity determining region (CDR)1, VL CDR2, and VL CDR3 comprising the amino acid sequences of SEQ ID NOs: 22-24, respectively; and a VH domain or heavy chain comprising a VH CDR1, VH CDR2, and VH CDR3 comprising the amino acid sequences of SEQ ID NOs: 19-21, respectively. In certain embodiments, the light chain or VL domain comprises one, two or three of framework region (FR)1, FR2, FR3, and FR4 comprising the amino acid sequences of SEQ ID NOs: 29-32, respectively, and the heavy chain or VH domain comprises one, two or three of framework regions (FR)1, FR2, FR3, and FR4 comprising the amino acid sequences of SEQ ID NOs: 25-28, respectively. In some embodiments, the light chain or VL domain comprises framework region (FR)1, FR2, FR3, and FR4 comprising the amino acid sequences of SEQ ID NOs:29-32, respectively, and the heavy chain or VH domain comprises framework regions (FR)1, FR2, FR3, and FR4 comprising the amino acid sequences of SEQ ID NO: 25-28, respectively. In other embodiments, the light chain or VL domain and heavy chain or VH domain comprises human framework regions or framework regions derived from a human antibody.

In another embodiment, an antibody, which binds to an influenza B virus NA (e.g., an influenza B virus NA discussed in Section 6 and/or 7, infra), comprises one, two, three, four, five or all six complementarity determining regions (CDRs) of the antibody 3G1. In certain embodiments, an antibody, which binds to influenza B virus NA (e.g., influenza B virus NA), comprises VL domain or light chain comprising a VL complementarity determining region (CDR)1, VL CDR2, and VL CDR3 comprising the amino acid sequences of SEQ ID NOs: 38-40, respectively. In certain embodiments, the light chain or VL domain comprises one, two or three of framework region (FR)1, FR2, FR3, and FR4 comprising the amino acid sequences of SEQ ID NO: 45-48, respectively. In some embodiments, the light chain or VL domain comprises framework region (FR)1, FR2, FR3, and FR4 comprising the amino acid sequences of SEQ ID NO: 45-48, respectively. In other embodiments, the light chain or VL domain comprises human framework regions or framework regions derived from a human antibody.

In some embodiments, an antibody, which binds to influenza B virus NA (e.g., an influenza B virus NA discussed in Section 6 and/or 7, infra), comprises a VH domain or heavy chain comprising a VH CDR1, VH CDR2, and VH CDR3 comprising the amino acid sequences of SEQ ID NOs: 35-37, respectively. In certain embodiments, the heavy chain or VH domain comprises one, two or three of framework region (FR)1, FR2, FR3, and FR4 comprising the amino acid sequences of SEQ ID NO: 41-44, respectively. In some embodiments, the heavy chain or VH domain comprises framework region (FR)1, FR2, FR3, and FR4 comprising the amino acid sequences of SEQ ID NO: 41-44, respectively. In other embodiments, the heavy chain or VH domain comprises human framework regions or framework regions derived from a human antibody.

In specific embodiments, an antibody, which binds to influenza B virus NA (e.g., an influenza B virus NA discussed in Section 6 and/or 7, infra), comprises: VL domain or light chain comprising a VL complementarity determining region (CDR)1, VL CDR2, and VL CDR3 comprising the amino acid sequences of SEQ ID NOs: 38-40, respectively; and a VH domain or heavy chain comprising a VH CDR1, VH CDR2, and VH CDR3 comprising the amino acid sequences of SEQ ID NOs: 35-37, respectively. In certain embodiments, the light chain or VL domain comprises one, two or three of framework region (FR)1, FR2, FR3, and FR4 comprising the amino acid sequences of SEQ ID NO: 45-48, respectively, and the heavy chain or VH domain comprises one, two or three of framework regions (FR)1, FR2, FR3, and FR4 comprising the amino acid sequences of SEQ ID NO: 41-44, respectively. In some embodiments, the light chain or VL domain comprises framework region (FR)1, FR2, FR3, and FR4 comprising the amino acid sequences of SEQ ID NO: 45-48, respectively, and the heavy chain or VH domain comprises framework regions (FR)1, FR2, FR3, and FR4 comprising the amino acid sequences of SEQ ID NO: 41-44, respectively. In other embodiments, the light chain or VL domain and heavy chain or VH domain comprises human framework regions or framework regions derived from a human antibody.

In another embodiment, an antibody, which binds to an influenza B virus NA (e.g., an influenza B virus NA discussed in Section 6 and/or 7, infra), comprises one, two, three, four, five or all six complementarity determining regions (CDRs) of the antibody 4B2. In certain embodiments, an antibody, which binds to an influenza B virus NA, comprises one, two, three, four, five or all six CDRs of the antibody 4B2, as determined by the IMGT numbering system, Kabat numbering system, Chothia numbering system or ABM numbering system. In some embodiments, an antibody, which binds to an influenza B virus NA, comprises a VL domain or light chain comprising the VL CDR1, VL CDR2, and VL CDR3 of antibody 4B2, as determined by a numbering system known in the art, such as set forth in Table 4A or Table 4B. In certain embodiments, an antibody, which binds to influenza B virus NA (e.g., influenza B virus NA discussed in Section 6 and/or 7, infra), comprises VL domain or light chain comprising a VL complementarity determining region (CDR)1, VL CDR2, and VL CDR3 comprising the amino acid sequences of SEQ ID NOs: 54-56, respectively. In certain embodiments, the light chain or VL domain comprises one, two or three of framework region (FR)1, FR2, FR3, and FR4 comprising the amino acid sequences of SEQ ID NO: 61-64, respectively. In some embodiments, the light chain or VL domain comprises framework region (FR)1, FR2, FR3, and FR4 comprising the amino acid sequences of SEQ ID NO: 61-64, respectively. In other embodiments, the light chain or VL domain comprises human framework regions or framework regions derived from a human antibody.

In certain embodiments, an antibody, which binds to an influenza B virus NA, comprises a VH domain or heavy chain comprising the VH CDR1, VH CDR2, and VH CDR3 of antibody 4B2, as determined by a numbering system known in the art, such as set forth in Table 4A or Table 4B. In some embodiments, an antibody, which binds to influenza B virus NA (e.g., an influenza B virus NA discussed in Section 6 and/or 7, infra), comprises a VH domain or heavy chain comprising a VH CDR1, VH CDR2, and VH CDR3 comprising the amino acid sequences of SEQ ID NOs: 51-53, respectively. In certain embodiments, the heavy chain or VH domain comprises one, two or three of framework region (FR)1, FR2, FR3, and FR4 comprising the amino acid sequences of SEQ ID NO: 57-60, respectively. In some embodiments, the heavy chain or VH domain comprises framework region (FR)1, FR2, FR3, and FR4 comprising the amino acid sequences of SEQ ID NO: 57-60, respectively. In other embodiments, the heavy chain or VH domain comprises human framework regions or framework regions derived from a human antibody.

In one embodiment, an antibody, which binds to influenza B virus NA, comprises: (a) a VL domain or light chain comprising VL CDR1, VL CDR2, and VL CDR3 of antibody 4B2 as determined by any numbering system known in the art, such as set forth in Tables 4A and 4B; and (b) a VH domain or heavy chain comprising VH CDR3, VH CDR2, and VH CDR3 of antibody 4B2 as determined by any numbering system known in the art, such as set forth in Tables 4A and 4B. In specific embodiments, an antibody, which binds to influenza B virus NA (e.g., an influenza B virus NA discussed in Section 6 and/or 7, infra), comprises: VL domain or light chain comprising a VL complementarity determining region (CDR)1, VL CDR2, and VL CDR3 comprising the amino acid sequences of SEQ ID NOs: 54-56, respectively; and a VH domain or heavy chain comprising a VH CDR1, VH CDR2, and VH CDR3 comprising the amino acid sequences of SEQ ID NOs: 51-53, respectively. In certain embodiments, the light chain or VL domain comprises one, two or three of framework region (FR)1, FR2, FR3, and FR4 comprising the amino acid sequences of SEQ ID NO: 61-64, respectively, and the heavy chain or VH domain comprises one, two or three of framework regions (FR)1, FR2, FR3, and FR4 comprising the amino acid sequences of SEQ ID NOs: 57-60, respectively. In some embodiments, the light chain or VL domain comprises framework region (FR)1, FR2, FR3, and FR4 comprising the amino acid sequences of SEQ ID NOs: 61-64, respectively, and the heavy chain or VH domain comprises framework regions (FR)1, FR2, FR3, and FR4 comprising the amino acid sequences of SEQ ID NOs: 57-60, respectively. In other embodiments, the light chain or VL domain and heavy chain or VH domain comprises human framework regions or framework regions derived from a human antibody.

In another embodiment, an antibody, which binds to an influenza B virus NA (e.g., an influenza B virus NA discussed in Section 6 and/or 7, infra), comprises one, two, three, four, five or all six complementarity determining regions (CDRs) of the antibody 4F11. In certain embodiments, an antibody, which binds to an influenza B virus NA, comprises one, two, three, four, five or all six CDRs of the antibody 4F11, as determined by the IMGT numbering system, Kabat numbering system, Chothia numbering system or ABM numbering system. In some embodiments, an antibody, which binds to an influenza B virus NA, comprises a VL domain or light chain comprising the VL CDR1, VL CDR2, and VL CDR3 of antibody 4F11, as determined by a numbering system known in the art, such as set forth in Table 5A or Table 5B. In certain embodiments, an antibody, which binds to influenza B virus NA (e.g., influenza B virus NA), comprises VL domain or light chain comprising a VL complementarity determining region (CDR)1, VL CDR2, and VL CDR3 comprising the amino acid sequences of SEQ ID NOs: 70-72, respectively. In certain embodiments, the light chain or VL domain comprises one, two or three of framework region (FR)1, FR2, FR3, and FR4 comprising the amino acid sequences of SEQ ID NO: 77-80, respectively. In some embodiments, the light chain or VL domain comprises framework region (FR)1, FR2, FR3, and FR4 comprising the amino acid sequences of SEQ ID NO: 77-80, respectively. In other embodiments, the light chain or VL domain comprises human framework regions or framework regions derived from a human antibody.

In certain embodiments, an antibody, which binds to an influenza B virus NA, comprises a VH domain or heavy chain comprising the VH CDR1, VH CDR2, and VH CDR3 of antibody 4F11, as determined by a numbering system known in the art, such as set forth in Table 5A or Table 5B. In some embodiments, an antibody, which binds to influenza B virus NA (e.g., an influenza B virus NA discussed in Section 6 and/or 7, infra), comprises a VH domain or heavy chain comprising a VH CDR1, VH CDR2, and VH CDR3 comprising the amino acid sequences of SEQ ID NOs: 67-69, respectively. In certain embodiments, the heavy chain or VH domain comprises one, two or three of framework region (FR)1, FR2, FR3, and FR4 comprising the amino acid sequences of SEQ ID NOs: 73-76, respectively. In some embodiments, the heavy chain or VH domain comprises framework region (FR)1, FR2, FR3, and FR4 comprising the amino acid sequences of SEQ ID NOs: 73-76, respectively. In other embodiments, the heavy chain or VH domain comprises human framework regions or framework regions derived from a human antibody.

In one embodiment, an antibody, which binds to influenza B virus NA, comprises: (a) a VL domain or light chain comprising VL CDR1, VL CDR2, and VL CDR3 of antibody 4F11 as determined by any numbering system known in the art, such as set forth in Tables 5A and 5B; and (b) a VH domain or heavy chain comprising VH CDR3, VH CDR2, and VH CDR3 of antibody 4F11 as determined by any numbering system known in the art, such as set forth in Tables 5A and 5B. In specific embodiments, an antibody, which binds to influenza B virus NA (e.g., an influenza B virus NA discussed in Section 6 and/or 7, infra), comprises: VL domain or light chain comprising a VL complementarity determining region (CDR)1, VL CDR2, and VL CDR3 comprising the amino acid sequences of SEQ ID NOs: 70-72, respectively; and a VH domain or heavy chain comprising a VH CDR1, VH CDR2, and VH CDR3 comprising the amino acid sequences of SEQ ID NOs: 67-69, respectively. In certain embodiments, the light chain or VL domain comprises one, two or three of framework region (FR)1, FR2, FR3, and FR4 comprising the amino acid sequences of SEQ ID NOs: 77-80, respectively, and the heavy chain or VH domain comprises one, two or three of framework regions (FR)1, FR2, FR3, and FR4 comprising the amino acid sequences of SEQ ID NOs: 73-76, respectively. In some embodiments, the light chain or VL domain comprises framework region (FR)1, FR2, FR3, and FR4 comprising the amino acid sequences of SEQ ID NOs: 77-80, respectively, and the heavy chain or VH domain comprises framework regions (FR)1, FR2, FR3, and FR4 comprising the amino acid sequences of SEQ ID NOs: 73-76, respectively. In other embodiments, the light chain or VL domain and heavy chain or VH domain comprises human framework regions or framework regions derived from a human antibody.

In some embodiments, an antibody described herein, which binds to an influenza B virus NA (e.g., NA of an influenza B virus strain described in Section 6 and/or Section 7, infra), comprises a VL domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 2. In certain embodiments, an antibody described herein, which binds to an influenza B virus NA (e.g., NA of an influenza B virus strain described in Section 6 and/or Section 7, infra), comprises a VH domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 1. In some embodiments, an antibody, which binds to an influenza B virus NA (e.g., NA of an influenza B virus strain described in Section 6 and/or Section 7, infra), comprises a VL domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 2; and a VH domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 1. In accordance with these embodiments, the CDRs of the antibody may, in certain embodiments, be identical to one, two, three, four, five, or all six of the CDRs of the antibody 1F2.

In a specific embodiment, an antibody described herein does not comprise any one, two, three, or all of the following: (i) isoleucine at amino acid position 98 in VHCDR3 of SEQ ID NO: 1, (ii) a phenylalanine at amino acid position 88 of SEQ ID NO: 1, (iii) valine at amino acid position 110 in VH CDR3 of SEQ ID NO: 1, or (iv) cysteine at amino acid position 111 in VH CDR3 of SEQ ID NO: 1.

In some embodiments, an antibody described herein, which binds to an influenza B virus NA (e.g., NA of an influenza B virus strain described in Section 6 and/or Section 7, infra), comprises a VL domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 18. In certain embodiments, an antibody described herein, which binds to an influenza B virus NA (e.g., NA of an influenza B virus strain described in Section 6 and/or Section 7, infra), comprises a VH domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 17. In some embodiments, an antibody which binds to an influenza B virus NA (e.g., NA of an influenza B virus strain described in Section 6 and/or Section 7, infra), comprises a VL domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 18; and a VH domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 17. In accordance with these embodiments, the CDRs of the antibody may, in certain embodiments, be identical to one, two, three, four, five, or all six of the CDRs of the antibody 1F4.

In a specific embodiment, an antibody described herein does not comprise an asparagine at amino acid position 32 of VLCDR1 of SEQ ID NO: 18, an arginine at amino acid position 83 in the framework region 3 of SEQ ID NO: 18, or both.

In some embodiments, an antibody described herein, which binds to an influenza B virus NA (e.g., NA of an influenza B virus strain described in Section 6 and/or Section 7, infra), comprises a VL domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 50. In certain embodiments, an antibody described herein, which binds to an influenza B virus NA (e.g., NA of an influenza B virus strain described in Section 6 and/or Section 7, infra), comprises a VH domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 49. In some embodiments, an antibody, which binds to an influenza B virus NA (e.g., NA of an influenza B virus strain described in Section 6 and/or Section 7, infra), comprises a VL domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 50; and a VH domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 49. In accordance with these embodiments, the CDRs of the antibody (or an antigen-binding fragment thereof) may, in certain embodiments, be identical to one, two, three, four, five, or all six of the CDRs of the antibody 4B2.

In a specific embodiment, an antibody described herein does not comprise any one, two, three or all of the following: a serine at amino acid position 68 in framework region 3 of SEQ ID NO: 49, a proline at amino acid position 69 in framework region 3 of SEQ ID NO: 49, a serine at amino acid position 92 in framework region of SEQ ID NO: 49, or a valine at amino acid position 97 in VHCDR3 of SEQ ID NO: 49.

In some embodiments, an antibody (e.g., a monoclonal antibody, such as a chimeric or humanized antibody, or an antigen-binding fragment thereof) described herein, which binds to an influenza B virus NA (e.g., NA of an influenza B virus strain described in Section 6 and/or Section 7, infra), comprises a VL domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 66. In certain embodiments, an antibody described herein, which binds to an influenza B virus NA (e.g., NA of an influenza B virus strain described in Section 6 and/or Section 7, infra), comprises a VH domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 65. In some embodiments, an antibody, which binds to an influenza B virus NA (e.g., NA of an influenza B virus strain described in Section 6 and/or Section 7, infra), comprises a VL domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 66; and a VH domain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 65. In accordance with these embodiments, the CDRs of the antibody may, in certain embodiments, be identical to one, two, three, four, five, or all six of the CDRs of the antibody 4F11.

In a specific embodiment, an antibody described herein does not comprise a phenylalanine at amino acid position 120 of SEQ ID NO: 65.

In some embodiments, an antibody described herein, which binds to an influenza B virus NA, comprises a VL domain comprising the amino acid sequence of SEQ ID NO:2; and/or a VH domain comprising the amino acid sequence of SEQ ID NO: 1. In certain embodiments, an antibody described herein, which binds to an influenza B virus NA, comprises a VL domain comprising the amino acid sequence of SEQ ID NO: 18; and/or a VH domain comprising the amino acid sequence of SEQ ID NO: 17. In certain embodiments, an antibody described herein, which binds to an influenza B virus NA, comprises a VL domain comprising the amino acid sequence of SEQ ID NO:34; and/or a VH domain comprising the amino acid sequence of SEQ ID NO: 33. In some embodiments, an antibody described herein, which binds to an influenza B virus NA, comprises a VL domain comprising the amino acid sequence of SEQ ID NO: 50; and/or a VH domain comprising the amino acid sequence of SEQ ID NO: 49. In certain embodiments, an antibody described herein, which binds to an influenza B virus NA, comprises a VL domain comprising the amino acid sequence of SEQ ID NO: 66; and/or a VH domain comprising the amino acid sequence of SEQ ID NO: 65.

In some embodiments, an antibody described herein, which binds to an influenza B virus NA (e.g., NA of an influenza B virus strain described in Section 6 and/or Section 7, infra), comprises a light chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 2. In certain embodiments, an antibody described herein, which binds to an influenza B virus NA (e.g., NA of an influenza B virus strain described in Section 6 and/or Section 7, infra), comprises a heavy chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 1. In some embodiments, an antibody, which binds to an influenza B virus NA (e.g., NA of an influenza B virus strain described in Section 6 and/or Section 7, infra), comprises a light chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 2; and a heavy chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 1. In accordance with these embodiments, the CDRs of the antibody may, in certain embodiments, identical to one, two, three, four, five, or all six of the CDRs of the antibody 1F2.

In some embodiments, an antibody described herein, which binds to an influenza B virus NA (e.g., NA of an influenza B virus strain described in Section 6 and/or Section 7, infra), comprises a light chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 18. In certain embodiments, an antibody described herein, which binds to an influenza B virus NA (e.g., NA of an influenza B virus strain described in Section 6 and/or Section 7, infra), comprises a heavy chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 17. In some embodiments, an antibody, which binds to an influenza B virus NA (e.g., NA of an influenza B virus strain described in Section 6 and/or Section 7, infra), comprises a light chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 18; and a heavy chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 17. In accordance with these embodiments, the CDRs of the antibody may, in certain embodiments, identical to one, two, three, four, five, or all six of the CDRs of the antibody 1F4.

In some embodiments, an antibody described herein, which binds to an influenza B virus NA (e.g., NA of an influenza B virus strain described in Section 6 and/or Section 7, infra), comprises a light chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 34. In certain embodiments, an antibody described herein, which binds to an influenza B virus NA (e.g., NA of an influenza B virus strain described in Section 6 and/or Section 7, infra), comprises a heavy chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 33. In some embodiments, an antibody, which binds to an influenza B virus NA (e.g., NA of an influenza B virus strain described in Section 6 and/or Section 7, infra), comprises a light chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 34; and a heavy chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 33. In accordance with these embodiments, the CDRs of the antibody may, in certain embodiments, identical to one, two, three, four, five, or all six of the CDRs of the antibody 3G1.

In some embodiments, an antibody described herein, which binds to an influenza B virus NA (e.g., NA of an influenza B virus strain described in Section 6 and/or Section 7, infra), comprises a light chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 50. In certain embodiments, an antibody described herein, which binds to an influenza B virus NA (e.g., NA of an influenza B virus strain described in Section 6 and/or Section 7, infra), comprises a heavy chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 49. In some embodiments, an antibody, which binds to an influenza B virus NA (e.g., NA of an influenza B virus strain described in Section 6 and/or Section 7, infra), comprises a light chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 50; and a heavy chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 49. In accordance with these embodiments, the CDRs of the antibody may, in certain embodiments, identical to one, two, three, four, five, or all six of the CDRs of the antibody 4B2.

In some embodiments, an antibody described herein, which binds to an influenza B virus NA (e.g., NA of an influenza B virus strain described in Section 6 and/or Section 7, infra), comprises a light chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 66. In certain embodiments, an antibody described herein, which binds to an influenza B virus NA (e.g., NA of an influenza B virus strain described in Section 6 and/or Section 7, infra), comprises a heavy chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 65. In some embodiments, an antibody, which binds to an influenza B virus NA (e.g., NA of an influenza B virus strain described in Section 6 and/or Section 7, infra), comprises a light chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 66; and a heavy chain comprising an amino acid sequence that is at least 80%, 85%, 86%, 87%, 88%, 89%, 90%, 91%, 92%, 93%, 94% 95%, 96%, 97% or 98% identical to the amino acid sequence of SEQ ID NO: 65. In accordance with these embodiments, the CDRs of the antibody may, in certain embodiments, identical to one, two, three, four, five, or all six of the CDRs of the antibody 4F11.

In some embodiments, an antibody described herein, which binds to an influenza B virus NA, comprises a light chain comprising the amino acid sequence of SEQ ID NO: 2; and/or a heavy chain comprising the amino acid sequence of SEQ ID NO: 1. In certain embodiments, an antibody described herein, which binds to an influenza B virus NA, comprises a light chain comprising the amino acid sequence of SEQ ID NO: 18; and/or a heavy chain comprising the amino acid sequence of SEQ ID NO: 17. In certain embodiments, an antibody described herein, which binds to an influenza B virus NA, comprises a light chain comprising the amino acid sequence of SEQ ID NO:34; and/or a heavy chain comprising the amino acid sequence of SEQ ID NO: 33. In some embodiments, an antibody described herein, which binds to an influenza B virus NA, comprises a light chain comprising the amino acid sequence of SEQ ID NO: 50; and/or a heavy chain comprising the amino acid sequence of SEQ ID NO: 49. In certain embodiments, an antibody described herein, which binds to an influenza B virus NA, comprises a light chain comprising the amino acid sequence of SEQ ID NO: 66; and/or a heavy chain comprising the amino acid sequence of SEQ ID NO: 65.

Techniques known to one of skill in the art can be used to determine the percent identity between two amino acid sequences or between two nucleotide sequences. Generally, to determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length. In a certain embodiment, the percent identity is determined over the entire length of an amino acid sequence or nucleotide sequence.

The determination of percent identity between two sequences (e.g., amino acid sequences or nucleic acid sequences) can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another preferred, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

In some embodiments, an antibody described herein, which binds to an influenza B virus NA (e.g., NA of an influenza B virus strain in Section 6 and/or Section 7 and/or Section 8, infra), comprises the VH or VL of 1F2 with one or more (e.g., 1, 2, 3, 4, 5, 6, 7, 8, 9, 10, 15 or 20) amino acid substitutions (e.g., conservative amino acid substitutions), deletions, or additions relative to the amino acid sequence of the SEQ ID NO: 1 or 2. In a specific embodiment, an antibody described herein, which binds to an influenza B virus NA (e.g., NA of an influenza B virus strain in Section 6 and/or Section 7, infra), comprises the VH or VL of 1F2 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 1 or 2. In certain embodiments, an antibody described herein, which binds to an influenza B virus NA (e.g., NA of an influenza B virus strain in Section 6 and/or Section 7 and/or Section 8, infra), comprises the VH or VL of 1F2 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 1 or 2, wherein the one or more amino acid substitutions is in one, two, three or more of the framework regions. In specific embodiments, none of the amino acid substitutions are located within the CDRs (e.g., SEQ ID NOs: 3-8). In specific embodiments, all of the amino acid substitutions are in the framework regions (e.g., SEQ ID NOs: 9-16).

In some embodiments, an antibody described herein, which binds to an influenza B virus NA (e.g., NA of an influenza B virus strain in Section 6 and/or Section 7 and/or Section 8, infra), comprises (1) the VH domain of 1F2 with one or more (e.g., 1, 2, 3, 4, 5, 6, 7, 8, 9, 10, 15 or 20) amino acid substitutions (e.g., conservative amino acid substitutions), deletions, or additions relative to the amino acid sequence of the SEQ ID NO: 1 and (2) the VL domain of 1F2 with one or more (e.g., 1, 2, 3, 4, 5, 6, 7, 8, 9, 10, 15 or 20) amino acid substitutions (e.g., conservative amino acid substitutions), deletions, or additions relative to the amino acid sequence of the SEQ ID NO: 2. In a specific embodiment, an antibody described herein, which binds to an influenza B virus NA (e.g., NA of an influenza B virus strain in Section 6 and/or Section 7 and/or Section 8, infra), comprises (1) the VH domain of 1F2 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 1 and (2) the VL domain of 1F2 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 2. In certain embodiments, an antibody described herein, which binds to an influenza B virus NA (e.g., NA of an influenza B virus strain in Section 6 and/or Section 7 and/or Section 8, infra), comprises (1) the VH domain of 1F2 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 1, wherein the one or more amino acid substitutions is in one, two, three or more of the framework regions; and (2) the VL domain of 1F2 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 2, wherein the one or more amino acid substitutions is in one, two, three or more of the framework regions. In specific embodiments, none of the amino acid substitutions are located within the CDRs (e.g., SEQ ID NOs: 3-8). In specific embodiments, all of the amino acid substitutions are in the framework regions (e.g., SEQ ID NOs: 9-16).

In certain embodiments, an antibody described herein, which binds to an influenza B virus NA (e.g., NA of an influenza B virus strain described in Section 6 and/or Section 7 and/or Section 8, infra), comprises one or more (e.g., 1, 2, 3, 4, 5 or 6) amino acid substitutions (e.g., conservative amino acid substitutions) in the amino acid sequence of one, two or more of the following: the VL CDR1, the VL CDR2, the VL CDR3, the VL CDR1 and VL CDR2, the VL CDR2 and VL CDR3, the VL CDR1 and VL CDR3, or the VL CDR1, VL CDR2 and VL CDR3 of the antibody 1F2. In some embodiments, an antibody described herein, which binds to an influenza B virus NA (e.g., NA of an influenza B virus strain described in Section 6 and/or Section 7 and/or Section 8, infra), comprises one or more (e.g., 1, 2, 3, 4, 5 or 6) amino acid substitutions (e.g., conservative amino acid substitutions) in the amino acid sequence of one, two or more of the following: the VH CDR1, the VH CDR2, the VH CDR3, the VH CDR1 and VH CDR2, the VH CDR2 and VH CDR3, the VH CDR1 and VH CDR3, or the VH CDR1, VH CDR2 and VH CDR3 of the antibody 1F2. In certain embodiments, an antibody described herein, which binds to an influenza B virus NA (e.g., NA of an influenza B virus strain described in Section 6 and/or Section 7 and/or Section 8, infra), comprises one or more (e.g., 1, 2, 3, 4, 5 or 6) amino acid substitutions (e.g., conservative amino acid substitutions) in the amino acid sequence of one, two or more of the following: the VL CDR1; the VL CDR2; the VL CDR3; the VH CDR1; the VH CDR2; and/or the VH CDR3 of the antibody 1F2.

As used herein, a "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In some embodiments, an antibody described herein, which binds to an influenza B virus NA (e.g., NA of an influenza B virus strain in Section 6 and/or Section 7, infra), comprises the VH or VL of 1F4 with one or more (e.g., 1, 2, 3, 4, 5, 6, 7, 8, 9, 10, 15 or 20) amino acid substitutions (e.g., conservative amino acid substitutions), deletions, or additions relative to the amino acid sequence of the SEQ ID NO: 17 or 18. In a specific embodiment, an antibody described herein, which binds to an influenza B virus NA (e.g., NA of an influenza B virus strain in Section 6 and/or Section 7, infra), comprises the VH or VL of 1F4 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 17 or 18. In certain embodiments, an antibody described herein, which binds to an influenza B virus NA (e.g., NA of an influenza B virus strain in Section 6 and/or Section 7, infra), comprises the VH or VL of 1F4 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 17 or 18, wherein the one or more amino acid substitutions is in one, two, three or more of the framework regions. In specific embodiments, none of the amino acid substitutions are located within the CDRs (e.g., SEQ ID NOs: 19-24). In specific embodiments, all of the amino acid substitutions are in the framework regions (e.g., SEQ ID NOs: 25-32).

In some embodiments, an antibody described herein, which binds to an influenza B virus NA (e.g., NA of an influenza B virus strain in Section 6 and/or Section 7, infra), comprises (1) the VH domain of 1F4 with one or more (e.g., 1, 2, 3, 4, 5, 6, 7, 8, 9, 10, 15 or 20) amino acid substitutions (e.g., conservative amino acid substitutions), deletions, or additions relative to the amino acid sequence of the SEQ ID NO: 17 and (2) the VL domain of 1F4 with one or more (e.g., 1, 2, 3, 4, 5, 6, 7, 8, 9, 10, 15 or 20) amino acid substitutions (e.g., conservative amino acid substitutions), deletions, or additions relative to the amino acid sequence of the SEQ ID NO: 18. In a specific embodiment, an antibody described herein, which binds to an influenza B virus NA (e.g., NA of an influenza B virus strain in Section 6 and/or Section 7, infra), comprises (1) the VH domain of 1F4 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 17 and (2) the VL domain of 1F4 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 18. In certain embodiments, an antibody described herein, which binds to an influenza B virus NA (e.g., NA of an influenza B virus strain in Section 6 and/or Section 7, infra), comprises (1) the VH domain of 1F4 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 17, wherein the one or more amino acid substitutions is in one, two, three or more of the framework regions; and (2) the VL domain of 1F4 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 18, wherein the one or more amino acid substitutions is in one, two, three or more of the framework regions. In specific embodiments, none of the amino acid substitutions are located within the CDRs (e.g., SEQ ID NOs: 19-24). In specific embodiments, all of the amino acid substitutions are in the framework regions (e.g., SEQ ID NOs: 25-32).

In certain embodiments, an antibody described herein, which binds to an influenza B virus NA (e.g., NA of an influenza B virus strain described in Section 6 and/or Section 7, infra), comprises one or more (e.g., 1, 2, 3, 4, 5 or 6) amino acid substitutions (e.g., conservative amino acid substitutions) in the amino acid sequence of one, two or more of the following: the VL CDR1, the VL CDR2, the VL CDR3, the VL CDR1 and VL CDR2, the VL CDR2 and VL CDR3, the VL CDR1 and VL CDR3, or the VL CDR1, VL CDR2 and VL CDR3 of the antibody 1F4. In some embodiments, an antibody described herein, which binds to an influenza B virus NA (e.g., NA of an influenza B virus strain described in Section 6 and/or Section 7, infra), comprises one or more (e.g., 1, 2, 3, 4, 5 or 6) amino acid substitutions (e.g., conservative amino acid substitutions) in the amino acid sequence of one, two or more of the following: the VH CDR1, the VH CDR2, the VH CDR3, the VH CDR1 and VH CDR2, the VH CDR2 and VH CDR3, the VH CDR1 and VH CDR3, or the VH CDR1, VH CDR2 and VH CDR3 of the antibody 1F4. In certain embodiments, an antibody described herein, which binds to an influenza B virus NA (e.g., NA of an influenza B virus strain described in Section 6 and/or Section 7, infra), comprises one or more (e.g., 1, 2, 3, 4, 5 or 6) amino acid substitutions (e.g., conservative amino acid substitutions) in the amino acid sequence of one, two or more of the following: the VL CDR1; the VL CDR2; the VL CDR3; the VH CDR1; the VH CDR2; and/or the VH CDR3 of the antibody 1F4.

In some embodiments, an antibody described herein, which binds to an influenza B virus NA (e.g., NA of an influenza B virus strain in Section 6 and/or Section 7, infra), comprises the VH or VL of 3G1 with one or more (e.g., 1, 2, 3, 4, 5, 6, 7, 8, 9, 10, 15 or 20) amino acid substitutions (e.g., conservative amino acid substitutions), deletions, or additions relative to the amino acid sequence of the SEQ ID NO: 33 or 34. In a specific embodiment, an antibody described herein, which binds to an influenza B virus NA (e.g., NA of an influenza B virus strain in Section 6 and/or Section 7, infra), comprises the VH or VL of 3G1 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 33 or 34. In certain embodiments, an antibody described herein, which binds to an influenza B virus NA (e.g., NA of an influenza B virus strain in Section 6 and/or Section 7, infra), comprises the VH or VL of 3G1 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 33 or 34, wherein the one or more amino acid substitutions is in one, two, three or more of the framework regions. In specific embodiments, none of the amino acid substitutions are located within the CDRs (e.g., SEQ ID NOs: 35-40). In specific embodiments, all of the amino acid substitutions are in the framework regions (e.g., SEQ ID NOs: 41-48).

In some embodiments, an antibody described herein, which binds to an influenza B virus NA (e.g., NA of an influenza B virus strain in Section 6 and/or Section 7, infra), comprises the VH or VL of 4B2 with one or more (e.g., 1, 2, 3, 4, 5, 6, 7, 8, 9, 10, 15 or 20) amino acid substitutions (e.g., conservative amino acid substitutions), deletions, or additions relative to the amino acid sequence of the SEQ ID NO: 49 or 50. In a specific embodiment, an antibody described herein, which binds to an influenza B virus NA (e.g., NA of an influenza B virus strain in Section 6 and/or Section 7, infra), comprises the VH or VL of 4B2 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 49 or 50. In certain embodiments, an antibody described herein, which binds to an influenza B virus NA (e.g., NA of an influenza B virus strain in Section 6 and/or Section 7, infra), comprises the VH or VL of 4B2 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 49 or 50, wherein the one or more amino acid substitutions is in one, two, three or more of the framework regions. In specific embodiments, none of the amino acid substitutions are located within the CDRs (e.g., SEQ ID NO: 51-56). In specific embodiments, all of the amino acid substitutions are in the framework regions (e.g., SEQ ID NO: 57-64).

In some embodiments, an antibody described herein, which binds to an influenza B virus NA (e.g., NA of an influenza B virus strain in Section 6 and/or Section 7, infra), comprises (1) the VH domain of 4B2 with one or more (e.g., 1, 2, 3, 4, 5, 6, 7, 8, 9, 10, 15 or 20) amino acid substitutions (e.g., conservative amino acid substitutions), deletions, or additions relative to the amino acid sequence of the SEQ ID NO: 49 and (2) the VL domain of 4B2 with one or more (e.g., 1, 2, 3, 4, 5, 6, 7, 8, 9, 10, 15 or 20) amino acid substitutions (e.g., conservative amino acid substitutions), deletions, or additions relative to the amino acid sequence of the SEQ ID NO: 50. In a specific embodiment, an antibody described herein, which binds to an influenza B virus NA (e.g., NA of an influenza B virus strain in Section 6 and/or Section 7, infra), comprises (1) the VH domain of 4B2 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 49 and (2) the VL domain of 4B2 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 50. In certain embodiments, an antibody described herein, which binds to an influenza B virus NA (e.g., NA of an influenza B virus strain in Section 6 and/or Section 7, infra), comprises (1) the VH domain of 4B2 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 49, wherein the one or more amino acid substitutions is in one, two, three or more of the framework regions; and (2) the VL domain of 4B2 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 50, wherein the one or more amino acid substitutions is in one, two, three or more of the framework regions. In specific embodiments, none of the amino acid substitutions are located within the CDRs (e.g., SEQ ID NOs: 51-56). In specific embodiments, all of the amino acid substitutions are in the framework regions (e.g., SEQ ID NOs: 57-64).

In certain embodiments, an antibody described herein, which binds to an influenza B virus NA (e.g., NA of an influenza B virus strain described in Section 6 and/or Section 7, infra), comprises one or more (e.g., 1, 2, 3, 4, 5 or 6) amino acid substitutions (e.g., conservative amino acid substitutions) in the amino acid sequence of one, two or more of the following: the VL CDR1, the VL CDR2, the VL CDR3, the VL CDR1 and VL CDR2, the VL CDR2 and VL CDR3, the VL CDR1 and VL CDR3, or the VL CDR1, VL CDR2 and VL CDR3 of the antibody 4B2. In some embodiments, an antibody described herein, which binds to an influenza B virus NA (e.g., NA of an influenza B virus strain described in Section 6 and/or Section 7, infra), comprises one or more (e.g., 1, 2, 3, 4, 5 or 6) amino acid substitutions (e.g., conservative amino acid substitutions) in the amino acid sequence of one, two or more of the following: the VH CDR1, the VH CDR2, the VH CDR3, the VH CDR1 and VH CDR2, the VH CDR2 and VH CDR3, the VH CDR1 and VH CDR3, or the VH CDR1, VH CDR2 and VH CDR3 of the antibody 4B2. In certain embodiments, an antibody described herein, which binds to an influenza B virus NA (e.g., NA of an influenza B virus strain described in Section 6 and/or Section 7, infra), comprises one or more (e.g., 1, 2, 3, 4, 5 or 6) amino acid substitutions (e.g., conservative amino acid substitutions) in the amino acid sequence of one, two or more of the following: the VL CDR1; the VL CDR2; the VL CDR3; the VH CDR1; the VH CDR2; and/or the VH CDR3 of the antibody 4B2.

In some embodiments, an antibody described herein, which binds to an influenza B virus NA (e.g., NA of an influenza B virus strain in Section 6 and/or Section 7, infra), comprises the VH or VL of 4F11 with one or more (e.g., 1, 2, 3, 4, 5, 6, 7, 8, 9, 10, 15 or 20) amino acid substitutions (e.g., conservative amino acid substitutions), deletions, or additions relative to the amino acid sequence of the SEQ ID NO: 65 or 66. In a specific embodiment, an antibody described herein, which binds to an influenza B virus NA (e.g., NA of an influenza B virus strain in Section 6 and/or Section 7, infra), comprises the VH or VL of 4F11 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 65 or 66. In certain embodiments, an antibody described herein, which binds to an influenza B virus NA (e.g., NA of an influenza B virus strain in Section 6 and/or Section 7, infra), comprises the VH or VL of 4F11 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 65 or 66, wherein the one or more amino acid substitutions is in one, two, three or more of the framework regions. In specific embodiments, none of the amino acid substitutions are located within the CDRs (e.g., SEQ ID NOs: 67-72). In specific embodiments, all of the amino acid substitutions are in the framework regions (e.g., SEQ ID NOs: 73-80).

In some embodiments, an antibody described herein, which binds to an influenza B virus NA (e.g., NA of an influenza B virus strain in Section 6 and/or Section 7, infra), comprises (1) the VH domain of 4F11 with one or more (e.g., 1, 2, 3, 4, 5, 6, 7, 8, 9, 10, 15 or 20) amino acid substitutions (e.g., conservative amino acid substitutions), deletions, or additions relative to the amino acid sequence of the SEQ ID NO: 65 and (2) the VL domain of 4F11 with one or more (e.g., 1, 2, 3, 4, 5, 6, 7, 8, 9, 10, 15 or 20) amino acid substitutions (e.g., conservative amino acid substitutions), deletions, or additions relative to the amino acid sequence of the SEQ ID NO: 66. In a specific embodiment, an antibody described herein, which binds to an influenza B virus NA (e.g., NA of an influenza B virus strain in Section 6 and/or Section 7, infra), comprises (1) the VH domain of 4F11 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 65 and (2) the VL domain of 4F11 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 66. In certain embodiments, an antibody described herein, which binds to an influenza B virus NA (e.g., NA of an influenza B virus strain in Section 6 and/or Section 7, infra), comprises (1) the VH domain of 4F11 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 65, wherein the one or more amino acid substitutions is in one, two, three or more of the framework regions; and (2) the VL domain of 4F11 with one or more (e.g., 1, 2, 3, 4, 5, 6, 7, 8, 9, 10, 15 or 20) amino acid substitutions (e.g., conservative amino acid substitutions) relative to the amino acid sequence of the SEQ ID NO: 66, wherein the one or more amino acid substitutions is in one, two, three or more of the framework regions. In specific embodiments, none of the amino acid substitutions are located within the CDRs (e.g., SEQ ID NO: 67-72). In specific embodiments, all of the amino acid substitutions are in the framework regions (e.g., SEQ ID NOs:73-80).

In certain embodiments, an antibody described herein, which binds to an influenza B virus NA (e.g., NA of an influenza B virus strain described in Section 6 and/or Section 7, infra), comprises one or more (e.g., 1, 2, 3, 4, 5 or 6) amino acid substitutions (e.g., conservative amino acid substitutions) in the amino acid sequence of one, two or more of the following: the VL CDR1, the VL CDR2, the VL CDR3, the VL CDR1 and VL CDR2, the VL CDR2 and VL CDR3, the VL CDR1 and VL CDR3, or the VL CDR1, VL CDR2 and VL CDR3 of the antibody 4F11. In some embodiments, an antibody described herein, which binds to an influenza B virus NA (e.g., NA of an influenza B virus strain described in Section 6 and/or Section 7, infra), comprises one or more (e.g., 1, 2, 3, 4, 5 or 6) amino acid substitutions (e.g., conservative amino acid substitutions) in the amino acid sequence of one, two or more of the following: the VH CDR1, the VH CDR2, the VH CDR3, the VH CDR1 and VH CDR2, the VH CDR2 and VH CDR3, the VH CDR1 and VH CDR3, or the VH CDR1, VH CDR2 and VH CDR3 of the antibody 4F11. In certain embodiments, an antibody described herein, which binds to an influenza B virus NA (e.g., NA of an influenza B virus strain described in Section 6 and/or Section 7, infra), comprises one or more (e.g., 1, 2, 3, 4, 5 or 6) amino acid substitutions (e.g., conservative amino acid substitutions) in the amino acid sequence of one, two or more of the following: the VL CDR1; the VL CDR2; the VL CDR3; the VH CDR1; the VH CDR2; and/or the VH CDR3 of the antibody 4F11.

In another aspect, provided herein are antibodies that bind to the same or an overlapping epitope of an antibody described herein (e.g., an antibody described in Section 6 and/or Section 7, infra), e.g., antibodies that compete for binding to an influenza B virus NA with an antibody described herein, or antibodies which bind to an epitope which overlaps with an epitope to which an antibody described herein binds. As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain aspects, epitope mapping assays, well known to one of skill in the art, can be performed to ascertain the epitope (e.g., conformational epitope) to which an antibody described herein binds. In certain embodiments, the epitope can be determined by, e.g., structural mapping using negative electron microscopy (see, e.g., Section 6, infra), X-ray diffraction crystallography studies (see, e.g., Blechman et al., 1993, J. Biol. Chem. 268:4399-4406; Cho et al., 2003, Nature, 421:756-760), ELISA assays, hydrogen/deuterium exchange coupled with mass spectrometry (e.g., MALDI mass spectrometry), array-based oligo-peptide scanning assays, mutagenesis mapping (e.g., site-directed mutagenesis mapping) and/or escape binding assays, such as described in Section 6 and/or Section 7, infra. In a specific embodiment, the epitope of an antibody is determined using one or more of the methods described in Section 6 and/or Section 7, infra.

Antibodies that recognize such epitopes can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as influenza B virus NA. Numerous types of competitive binding assays are known, for example: solid phase direct or indirect radioimmunoassay (RIA), solid phase direct or indirect enzyme immunoassay (EIA), sandwich competition assay (see Stahli et al., (1983) Methods in Enzymology 9:242); solid phase direct biotin-avidin EIA (see Kirkland et al., (1986) J. Immunol. 137:3614); solid phase direct labeled assay, solid phase direct labeled sandwich assay (see Harlow and Lane, (1988) Antibodies: A Laboratory Manual, Cold Spring Harbor Press); solid phase direct label RIA using I-125 label (see Morel et al., (1988) Mol. Immunol. 25(1):7); solid phase direct biotin-avidin EIA (Cheung et al., (1990) Virology 176:546); and direct labeled RIA. (Moldenhauer et al., (1990) Scand J. Immunol. 32:77). See, e.g., Section 6, infra, for a method for assessing competitive binding that may be used. Typically, such an assay involves the use of purified antigen (e.g., influenza B virus NA) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener et al., J. Immunol., 1983, 130:2308-2315; Wagener et al., J. Immunol. Methods, 1984, 68:269-274; Kuroki et al., Cancer Res., 1990, 50:4872-4879; Kuroki et al., Immunol. Invest., 1992, 21:523-538; Kuroki et al., Hybridoma, 1992, 11:391-407, and *Using Antibodies: A Laboratory Manual*, Ed Harlow and David Lane editors (Cold Springs Harbor Laboratory Press, Cold Springs Harbor, N.Y., 1999), pp. 386-389.

In certain aspects, competition binding assays can be used to determine whether an antibody is competitively blocked, e.g., in a dose dependent manner, by another antibody for example, an antibody binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. In a particular embodiment, an antibody can be tested in competition binding assays with an antibody described herein, e.g., antibody 1F2, 1F4, 3G1, 4B2, or 4F11, an antibody comprising VH CDRs and VL CDRs of antibody 1F2, 1F4, 3G1, 4B2, or 4F11, or a humanized monoclonal antibody comprising VH CDRs and VL CDRs of antibody 1F2, 1F4, 3G1, 4B2, or 4F11. In a specific embodiment, an antibody can be tested in competition binding assays with an antibody described herein that comprises: (a) a variable heavy chain region comprising the amino acid sequence of SEQ ID NO: 168, 169, 170, 171, 172, 173, 174 or 175; and (b) a variable light chain region comprising the amino acid sequence of SEQ ID NO: 177, 178, 179, 180, 181, 182, 183, or 184. In a particular embodiment, a humanized antibody derived from a mouse monoclonal antibody is able to compete (e.g., in a dose dependent manner) with the mouse monoclonal antibody.

In a specific embodiment, provided herein is an antibody, which binds to an influenza B virus NA (e.g., NA of an influenza B virus described in Section 6 and/or Section 7 and/or Section 8, infra), wherein said antibody competes (e.g., in a dose-dependent manner) for binding to the influenza B virus NA with a reference antibody comprising: a VL domain or light chain comprising a VL CDR1, VL CDR2, and VL CDR3 having the amino acid sequences of SEQ ID NOs: 6-8, respectively; and a VH domain or heavy chain comprising a VH CDR1, VH CDR2, and VH CDR3 having the amino acid sequences of SEQ ID NOs: 3-5, respectively. In another specific embodiment, provided herein is an antibody, which binds to an influenza B virus NA (e.g., NA of an influenza B virus described in Section 6 and/or Section 7 and/or Section 8, infra), wherein said antibody competes (e.g., in a dose-dependent manner) for binding to the influenza B virus NA with a reference antibody comprising: a VL domain or light chain comprising a VL CDR1, VL CDR2, and VL CDR3 having the amino acid sequences of SEQ ID NOs: 22-24, respectively; and a VH domain or heavy chain comprising a VH CDR1, VH CDR2, and VH CDR3 having the amino acid sequences of SEQ ID NOs: 19-21, respectively. In another specific embodiment, provided herein is an antibody, which binds to an influenza B virus NA (e.g., NA of an influenza B virus described in Section 6 and/or Section 7, infra), wherein said antibody competes (e.g., in a dose-dependent manner) for binding to the influenza B virus NA with a reference antibody comprising: a VL domain or light chain comprising a VL CDR1, VL CDR2, and VL CDR3 having the amino acid sequences of SEQ ID NOs: 54-56, respectively; and a VH domain or heavy chain comprising a VH CDR1, VH CDR2, and VH CDR3 having the amino acid sequences of SEQ ID NOs: 51-53, respectively. In a specific embodiment, provided herein is an antibody, which binds to an influenza B virus NA (e.g., NA of an influenza B virus described in Section 6 and/or Section 7 and/or Section 8, infra), wherein said antibody competes (e.g., in a dose-dependent manner) for binding to the influenza B virus NA with a reference antibody comprising: a VL domain or light chain comprising a VL CDR1, VL CDR2, and VL CDR3 having the amino acid sequences of SEQ ID NOs: 70-72, respectively; and a VH domain or heavy chain comprising a VH CDR1, VH CDR2, and VH CDR3 having the amino acid sequences of SEQ ID NOs: 67-69, respectively.

In another embodiment, provided herein is an antibody, which binds to an influenza B virus NA (e.g., NA of an influenza B virus described in Section 6 and/or Section 7 and/or Section 8, infra), wherein said antibody competes (e.g., in a dose-dependent manner) for binding to the influenza B virus NA with a reference antibody comprising a VL domain comprising the amino acid sequence of SEQ ID NO: 2; and VH domain comprising the amino acid sequence of SEQ ID NO: 1. In a specific embodiment, provided herein is an antibody, which binds to an influenza B virus NA (e.g., NA of an influenza B virus described in Section 6 and/or Section 7 and/or Section 8, infra), wherein said antibody competes (e.g., in a dose-dependent manner) for binding to the influenza B virus NA with a reference antibody comprising: (a) a variable heavy chain region comprising the amino acid sequence of SEQ ID NO: 168, 169, 170, 171, 172, 173, 174 or 175; and (b) a variable light chain region comprising the amino acid sequence of SEQ ID NO: 177, 178, 179, 180, 181, 182, 183, or 184. In another embodiment, provided herein is an antibody, which binds to an influenza B virus NA (e.g., NA of an influenza B virus described in Section 6 and/or Section 7, infra), wherein said antibody competes (e.g., in a dose-dependent manner) for binding to the influenza B virus NA with a reference antibody comprising a VL domain comprising the amino acid sequence of SEQ ID NO: 18; and VH domain comprising the amino acid sequence of SEQ ID NO: 17. In another embodiment, provided herein is an antibody, which binds to an influenza B virus NA (e.g., NA of an influenza B virus described in Section 6 and/or Section 7, infra), wherein said antibody competes (e.g., in a dose-dependent manner) for binding to the influenza B virus NA with a reference antibody comprising a VL domain comprising the amino acid sequence of SEQ ID NO: 34; and VH domain comprising the amino acid sequence of SEQ ID NO: 33. In another embodiment, provided herein is an antibody, which binds to an influenza B virus NA (e.g., NA of an influenza B virus described in Section 6 and/or Section 7, infra), wherein said antibody competes (e.g., in a dose-dependent manner) for binding to the influenza B virus NA with a reference antibody comprising a VL domain comprising the amino acid sequence of SEQ ID NO: 50; and VH domain comprising the amino acid sequence of SEQ ID NO: 49. In another embodiment, provided herein is an antibody, which binds to an influenza B virus NA (e.g., NA of an influenza B virus described in Section 6 and/or Section 7, infra), wherein said competes (e.g., in a dose-dependent manner) for binding to the influenza B virus NA with a reference antibody comprising a VL domain comprising the amino acid sequence of SEQ ID NO: 66; and VH domain comprising the amino acid sequence of SEQ ID NO: 65.

In one embodiment, an antibody described herein binds to the same epitope as the 1F2 antibody described herein. In another embodiment, an antibody described herein binds to the same epitope as the 1F4 antibody described herein. In another embodiment, an antibody described herein binds to the same epitope as the 3G1 antibody described herein. In another embodiment, an antibody described herein binds to the same epitope as the 4B2 antibody described herein. In another embodiment, an antibody described herein binds to the same epitope as the 4F11 antibody described herein.

In another embodiment, an antibody described herein binds to an epitope comprising at least 1, 2, 3, 4, 5, 6, 7, 8, 9, 10, 11, 12, 13, 14, 15, 16, 17, 18, 19, 20, or 21 amino acid residues of the amino acid residues 247, 265-271, 302-305, 308-315, 339, and 387 of an NA of an influenza B virus. In another embodiment, an antibody described herein binds to an epitope comprising at least 1, 2, 3, 4, 5, 6, 7, 8, 9, 10, 11, 12, 13, 14, 15, 16, 17, 18, 19, 20, or 21 amino acid residues of the amino acid residues 247, 265-271, 302-305, 308-315, 339, and 387 of the NA of B/Malaysia/2506/04 virus. In another embodiment, an antibody described herein binds to an epitope comprising at least 1, 2, 3, 4, 5, 6, 7, 8, 9, 10, 11, 12, 13, 14, 15, 16, 17, 18, 19, 20, or 21 amino acid residues of the amino acid residues corresponding to amino acid residues 247, 265-271, 302-305, 308-315, 339, and 387 of the NA of B/Malaysia/2506/04 virus.

In another embodiment, an antibody described herein binds to an epitope comprising amino acid residues 247, 265-271, 302-305, 308-315, 339, and 387 of an NA of an influenza B virus. In another embodiment, an antibody described herein binds to an epitope comprising amino acid residues 247, 265-271, 302-305, 308-315, 339, and 387 of the NA of B/Malaysia/2506/04 virus. In another embodiment, an antibody described herein binds to an epitope comprising amino acid residues corresponding to amino acid residues 247, 265-271, 302-305, 308-315, 339, and 387 of the NA of B/Malaysia/2506/04 virus.

In another embodiment, an antibody described herein binds to an epitope comprising amino acid residue 387 of an NA of an influenza B virus. In another embodiment, an antibody described herein binds to an epitope comprising amino acid residue 387 of the NA of B/Malaysia/2506/04 virus. In another embodiment, an antibody described herein binds to an epitope comprising an amino acid residue corresponding to the amino acid residue 387 of the NA of B/Malaysia/2506/04 virus.

In another embodiment, an antibody described herein binds to an epitope comprising at least 1 or 2 amino acid residues of the amino acid residues 333, 334, and 341 of an NA of an influenza B virus. In another embodiment, an antibody described herein binds to an epitope comprising at least 1 or 2 amino acid residues of the amino acid residues 333, 334, and 341 of the NA of B/Malaysia/2506/04 virus. In another embodiment, an antibody described herein binds to an epitope comprising at least 1 or 2 amino acid residues of the amino acid residues corresponding to amino acid residues 333, 334, and 341 of the NA of B/Malaysia/2506/04 virus.

In another embodiment, an antibody described herein binds to an epitope comprising amino acid residues 333, 334, and 341 of an NA of an influenza B virus. In another embodiment, an antibody described herein binds to an epitope comprising amino acid residues 333, 334, and 341 of the NA of B/Malaysia/2506/04 virus. In another embodiment, an antibody described herein binds to an epitope comprising amino acid residues corresponding to amino acid residues 333, 334, and 341 of the NA of B/Malaysia/2506/04 virus.

In another embodiment, an antibody described herein binds to an epitope comprising amino acid residue 337 of an NA of an influenza B virus. In another embodiment, an antibody described herein binds to an epitope comprising amino acid residue 337 of the NA of B/Malaysia/2506/04 virus. In another embodiment, an antibody described herein binds to an epitope comprising an amino acid residue corresponding to the amino acid residue 337 of the NA of B/Malaysia/2506/04 virus.

In another embodiment, an antibody described herein binds to an epitope comprising at least 1, 2 or 3 amino acid residues of the amino acid residues 335-388 of an NA of an influenza B virus. In another embodiment, an antibody described herein binds to an epitope comprising at least 1, 2 or 3 amino acid residues of the amino acid residues 335-388 of the NA of B/Malaysia/2506/04 virus. In another embodiment, an antibody described herein binds to an epitope comprising at least 1, 2 or 3 amino acid residues of the amino acid residues corresponding to amino acid residues 335-388 of the NA of B/Malaysia/2506/04 virus.

In another embodiment, an antibody described herein binds to an epitope comprising amino acid residues 335-388 of an NA of an influenza B virus. In another embodiment, an antibody described herein binds to an epitope comprising amino acid residues 335-388 of the NA of B/Malaysia/2506/04 virus. In another embodiment, an antibody described herein binds to an epitope comprising amino acid residues corresponding to amino acid residues 335-388 of the NA of B/Malaysia/2506/04 virus.

In another embodiment, an antibody described herein binds to an epitope comprising amino acid residue 384 of an NA of an influenza B virus. In another embodiment, an antibody described herein binds to an epitope comprising amino acid residue 384 of the NA of B/Malaysia/2506/04 virus. In another embodiment, an antibody described herein binds to an epitope comprising an amino acid residue corresponding to amino acid residue 384 of the NA of B/Malaysia/2506/04 virus.

In another embodiment, an antibody described herein binds to an epitope comprising amino acid residue 345 of an NA of an influenza B virus. In another embodiment, an antibody described herein binds to an epitope comprising amino acid residue 345 of the NA of B/Malaysia/2506/04 virus. In another embodiment, an antibody described herein binds to an epitope comprising an amino acid residue corresponding to the amino acid residue 345 of the NA of B/Malaysia/2506/04 virus.

In another embodiment, an antibody described herein binds to an epitope comprising amino acid residue 338 of an NA of an influenza B virus. In another embodiment, an antibody described herein binds to an epitope comprising amino acid residue 338 of the NA of B/Malaysia/2506/04 virus. In another embodiment, an antibody described herein binds to an epitope comprising an amino acid residue corresponding to the amino acid residue 338 of the NA of B/Malaysia/2506/04 virus.

In another embodiment, an antibody described herein binds to an epitope comprising amino acid residue 352 of an NA of an influenza B virus. In another embodiment, an antibody described herein binds to an epitope comprising amino acid residue 352 of the NA of B/Malaysia/2506/04 virus. In another embodiment, an antibody described herein binds to an epitope comprising an amino acid residue corresponding to the amino acid residue 352 of the NA of B/Malaysia/2506/04 virus.

In another embodiment, an antibody described herein binds to an epitope comprising amino acid residue 385 of an NA of an influenza B virus. In another embodiment, an antibody described herein binds to an epitope comprising amino acid residue 385 of the NA of B/Malaysia/2506/04 virus. In another embodiment, an antibody described herein binds to an epitope comprising an amino acid residue corresponding to the amino acid residue 385 of the NA of B/Malaysia/2506/04 virus.

In another embodiment, an antibody described herein binds to an epitope comprising amino acid residue 346 of an NA of an influenza B virus. In another embodiment, an antibody described herein binds to an epitope comprising amino acid residue 346 of the NA of B/Malaysia/2506/04 virus. In another embodiment, an antibody described herein binds to an epitope comprising an amino acid residue corresponding to the amino acid residue 346 of the NA of B/Malaysia/2506/04 virus.

In another embodiment, an antibody described herein binds to an epitope comprising amino acid residue 453 of an NA of an influenza B virus. In another embodiment, an antibody described herein binds to an epitope comprising amino acid residue 453 of the NA of B/Malaysia/2506/04 virus. In another embodiment, an antibody described herein binds to an epitope comprising an amino acid residue corresponding to the amino acid residue 453 of the NA of B/Malaysia/2506/04 virus.

In another embodiment, an antibody described herein binds to an epitope comprising amino acid residue 344 of an NA of an influenza B virus. In another embodiment, an antibody described herein binds to an epitope comprising amino acid residue 344 of the NA of B/Malaysia/2506/04 virus. In another embodiment, an antibody described herein binds to an epitope comprising an amino acid residue corresponding to the amino acid residue 344 of the NA of B/Malaysia/2506/04 virus.

In another embodiment, an antibody described herein binds to an epitope comprising amino acid residue 343 of an NA of an influenza B virus. In another embodiment, an antibody described herein binds to an epitope comprising amino acid residue 343 of the NA of B/Malaysia/2506/04 virus. In another embodiment, an antibody described herein binds to an epitope comprising an amino acid residue corresponding to the amino acid residue 343 of the NA of B/Malaysia/2506/04 virus. In a specific embodiment, an antibody described herein binds to an epitope described in Section 6 or 7, infra. In another specific embodiment, an antibody provided herein competes for binding to recombinant NA or influenza B virus NA with an antibody comprising either the variable regions (VL and VH domains) or light and heavy chains of the antibody 1F1, 1F4, 3G1, 4B2, or 4F11, such as described in Section 6, infra. In another particular embodiment, an antibody competes for binding to recombinant NA or influenza B virus NA with the antibody 1F1, 1F4, 3G1, 4B2, or 4F11 as described in Section 6, infra.

In a particular embodiment, the competition between an antibody for binding to recombinant NA or influenza B virus NA with the antibody 1F1, 1F4, 3G1, 4B2, or 4F11 is not asymmetrical.

In certain embodiments, an antibody described herein, which binds to an influenza B virus NA, comprises a VH domain or heavy chain comprising FR1, FR2, FR3 and FR4 of the antibody 1F1, 1F4, 3G1, 4B2, or 4F11. In certain embodiments, an antibody described herein, which binds to an influenza B virus NA, comprises a VH domain or heavy chain comprising FR1, FR2, FR3 and FR4 of a 1F2 variant (such as VH1, VH2, VH3, VH4, VH5, VH6, VH7, or VH8 (SEQ ID Nos: 168, 169, 170, 171, 172, 173, 174 or 175, respectively). In some embodiments, an antibody described herein, which binds to an influenza B virus NA, comprises a VL domain or light chain comprising FR1, FR2, FR3 and FR4 of the antibody 1F1, 1F4, 3G1, 4B2, or 4F11. In certain embodiments, an antibody described herein, which binds to an influenza B virus NA, comprises a VL domain or light chain comprising FR1, FR2, FR3 and FR4 of a 1F2 variant (such as VL1, VL2, VL3, VL4, VL5, VL6, VH7, or VL8 (SEQ ID Nos: 177, 178, 179, 180, 181, 182, 183, or 184, respectively). In a specific embodiment, an antibody described herein, which binds to an influenza virus HA, comprises framework regions of the antibody 1F1, 1F4, 3G1, 4B2, or 4F11.

In specific embodiments, an antibody described herein, which binds to an influenza B virus NA, comprises framework regions (e.g., framework regions of the VL domain and/or VH domain) that are human framework regions or derived from human framework regions. The framework region may be naturally occurring or consensus framework regions (see, e.g., Sui et al., 2009, Nature Structural & Molecular Biology 16:265-273). Non-limiting examples of human framework regions are described in the art, e.g., see Kabat et al. (1991) *Sequences of Proteins of Immunological Interest*, Fifth Edition, U.S. Department of Health and Human Services, NIH Publication No. 91-3242). In certain embodiment, an antibody described herein comprises framework regions (e.g., framework regions of the VL domain and/or VH domain) that are primate (e.g., non-human primate) framework regions or derived from primate (e.g., non-human primate) framework regions.

For example, CDRs from antigen-specific non-human antibodies, typically of rodent origin (e.g., mouse or rat), are grafted onto homologous human or non-human primate acceptor frameworks. In one embodiment, the non-human primate acceptor frameworks are from Old World apes. In a specific embodiment, the Old World ape acceptor framework is from Pan troglodytes, *Pan paniscus* or *Gorilla gorilla*. In a particular embodiment, the non-human primate acceptor frameworks are from the chimpanzee Pan troglodytes. In a particular embodiment, the non-human primate acceptor frameworks are Old World monkey acceptor frameworks. In a specific embodiment, the Old World monkey acceptor frameworks are from the genus *Macaca*. In a certain embodiment, the non-human primate acceptor frameworks are is derived from the cynomolgus monkey *Macaca cynomolgus*. Non-human primate framework sequences are described in U.S. Patent Application Publication No. US 2005/0208625.

In specific aspects, provided herein is an antibody comprising an antibody light chain and heavy chain, e.g., a separate light chain and heavy chain.

With respect to the light chain, in a specific embodiment, the light chain of an antibody described herein is a kappa light chain. In another specific embodiment, the light chain of an antibody described herein is a lambda light chain. In yet another specific embodiment, the light chain of an antibody described herein is a human kappa light chain or a human lambda light chain. In a particular embodiment, an antibody described herein, which binds to an influenza B virus NA, comprises a light chain wherein the amino acid sequence of the VL domain can comprise any amino acid sequence described herein, and wherein the constant region of the light chain comprises the amino acid sequence of a human kappa or lamda light chain constant region. Non-limiting examples of human constant region sequences have been described in the art, e.g., see U.S. Pat. No. 5,693,780 and Kabat et al. (1991) *Sequences of Proteins of Immunological Interest*, Fifth Edition, U.S. Department of Health and Human Services, NIH Publication No. 91-3242.

In a specific embodiment, an antibody described herein comprises (i) a heavy chain comprising a VH domain described herein and a constant region; or (ii) a light chain comprising a VL domain described herein and a constant region. In a specific embodiment, an antibody described herein comprises (i) a heavy chain comprising a VH domain described herein and a constant region; and (ii) a light chain comprising a VL domain described herein and a constant region. As used herein, the term "constant region" or "constant domain" is interchangeable and has its meaning common in the art. The constant region refers to an antibody portion, e.g., a carboxyl terminal portion of a light and/or heavy chain which is not directly involved in binding of an antibody to antigen but which can exhibit various effector functions, such as interaction with the Fc receptor. The terms refer to a portion of an immunoglobulin molecule having a generally more conserved amino acid sequence relative to an immunoglobulin variable domain.

As used herein, the term "heavy chain" when used in reference to an antibody can refer to any distinct types, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG1, IgG2, IgG3 and IgG4.

As used herein, the term "light chain" when used in reference to an antibody can refer to any distinct types, e.g., kappa (κ) of lambda (λ) based on the amino acid sequence of the constant domains. Light chain amino acid sequences are well known in the art. In specific embodiments, the light chain is a human light chain.

With respect to the heavy chain, in a specific embodiment, the heavy chain of an antibody described herein can be an alpha (α), delta (δ), epsilon (ε), gamma (γ) or mu (μ) heavy chain. In another specific embodiment, the heavy chain of an antibody described can comprise a human alpha (α), delta (δ), epsilon (ε), gamma (γ) or mu (μ) heavy chain. In a particular embodiment, an antibody described herein, which binds to an influenza B virus NA, comprises a heavy chain wherein the amino acid sequence of the VH domain can comprise any amino acid sequence described herein, and wherein the constant region of the heavy chain comprises the amino acid sequence of a human gamma (γ) heavy chain constant region. Non-limiting examples of human constant region sequences have been described in the art, e.g., see U.S. Pat. No. 5,693,780 and Kabat et al. (1991) *Sequences of Proteins of Immunological Interest*, Fifth Edition, U.S. Department of Health and Human Services, NIH Publication No. 91-3242.

In a specific embodiment, an antibody described herein, which binds to an influenza B virus NA (e.g., NA of an influenza B virus strain described herein in Section 6 and/or Section 7, infra) comprises a VL domain and a VH domain comprising any amino acid sequences described herein, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In another specific embodiment, an antibody described herein, which binds to an influenza B virus NA (e.g., NA of an influenza B virus strain described herein in Section 6 and/or Section 7, infra) comprises a VL domain and a VH domain comprising any amino acid sequences described herein, and wherein the constant regions comprise the amino acid sequences of the constant regions of an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. In a particular embodiment, the constant regions comprise the amino acid sequences of the constant regions of a human IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule.

In particular embodiments, an antibody described herein is an IgG2a antibody, and optionally comprises a kappa light chain. In some embodiments, an antibody described herein is an IgG1 antibody.

In a specific embodiment, an antibody, which binds to influenza B virus NA, comprises a heavy chain that comprises the amino acid sequence of SEQ ID NO: 185, 186, 187, 188, 189, 190, 191, 192, or 193. In another specific embodiment, an antibody, which binds to influenza B virus NA, comprises a light chain that comprises the amino acid sequence of SEQ ID NO: 194, 195, 196, 197, 198, 199, 200, 201, or 202. In another specific embodiment, an antibody, which binds to influenza B virus NA, comprises: (a) a heavy chain that comprises the amino acid sequence of SEQ ID NO: 186, 187, 188, 189, 190, 191, 192, or 193; and (b) a light chain that comprises the amino acid sequence of SEQ ID NO: 195, 196, 197, 198, 199, 200, 201, or 202. In another specific embodiment, an antibody, which binds to influenza B virus NA, comprises: (a) a heavy chain that comprises the amino acid sequence of SEQ ID NO: 185; and (b) a light chain that comprises the amino acid sequence of SEQ ID NO: 194.

The antibodies described herein can be affinity matured using techniques known to one of skill in the art. The antibodies described herein can be chimerized using techniques known to one of skill in the art. A chimeric antibody is a molecule in which different portions of the antibody are derived from different immunoglobulin molecules. Methods for producing chimeric antibodies are known in the art. See, e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415, which are incorporated herein by reference in their entirety.

The antibodies described herein can be humanized. A humanized antibody is an antibody which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab')2, Fab, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibits cytotoxic activity, and the class is typically IgG1. Where such cytotoxic activity is not desirable, the constant domain may be of the IgG2 class. Examples of VL and VH constant domains that can be used in certain embodiments include, but are not limited to, C-kappa and C-gamma-1 (nG1m) described in Johnson et al. (1997) *J. Infect. Dis.* 176, 1215-1224 and those described in U.S. Pat. No. 5,824,307. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework and CDR sequences, more often 90%, and most preferably greater than 95%.

In a specific embodiment, provided herein is a humanized antibody comprising the VHCDR1, VHCDR2, VHCDR3, VLCDR1, VLCDR2, and VLCDR3 of the IF2 antibody described herein. In a specific embodiment, provided herein is a humanized antibody comprising the VHCDR1, VHCDR2, VHCDR3, VLCDR1, VLCDR2, and VLCDR3 of the IF4 antibody described herein. In a specific embodiment, provided herein is a humanized antibody comprising the VHCDR1, VHCDR2, VHCDR3, VLCDR1, VLCDR2, and VLCDR3 of the 4B2 antibody described herein. The antibodies provided herein include derivatives that are chemically modified, i.e., by the covalent attachment of any type of molecule to the antibody. For example, but not by way of limitation, the antibody derivatives include antibodies that have been chemically modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In particular embodiments, the glycosylation of antibodies described herein, in particular glycosylation of a variable region of an antibody described herein, is modified. For example, an aglycoslated antibody can be made (i.e., the antibody lacks glycosylation) or an antibody comprising a mutation or substitution at one or more glycosylation sites to eliminate glycosylation at the one or more glycosylation sites can be made. Glycosylation can be altered to, for example, increase the affinity of the antibody for an influenza B virus NA. Such carbohydrate modifications can be accomplished by, for example, altering one or more sites of glycosylation within the antibody sequence. For example, one or more amino acid substitutions can be made that result in elimination of one or more variable region (e.g., VL and/or VH CDRs or VL and/or VH FRs) glycosylation sites to thereby eliminate glycosylation at that site. Such aglycosylation can increase the affinity of the antibody for an influenza B virus NA. Such an approach is described in further detail in U.S. Pat. Nos. 5,714,350 and 6,350,861.

Glycosylation can occur via N-linked (or asparagine-linked) glycosylation or 0-linked glycosylation. N-linked glycosylation involves carbohydrate modification at the side-chain $NH_2$ group of an asparagine amino acid in a polypeptide. O-linked glycosylation involves carbohydrate modification at the hydroxyl group on the side chain of a serine, threonine, or hydroxylysine amino acid.

In certain embodiments, aglycosylated antibodies can be produced in bacterial cells which lack the necessary glycosylation machinery. Cells with altered glycosylation machinery have been described in the art and can be used as host cells in which to express recombinant antibodies described herein to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 03/035835; WO 99/54342.

Antibodies with reduced fucose content have been reported to have an increased affinity for Fc receptors, such as, e.g., FcγRIIIa. Accordingly, in certain embodiments, the antibodies described herein have reduced fucose content or no fucose content. Such antibodies can be produced using techniques known to one skilled in the art. For example, the antibodies can be expressed in cells deficient or lacking the ability to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

In certain embodiments, one, two or more mutations (e.g., amino acid substitutions) are introduced into the Fc region of an antibody described herein or a fragment thereof (e.g., CH2 domain (residues 231-340 of human IgG1) and/or CH3 domain (residues 341-447 of human IgG1) and/or the hinge region, with numbering according to the Kabat numbering system (e.g., the EU index in Kabat)) to increase the affinity of the antibody for an Fc receptor (e.g., an activated Fc receptor) on the surface of an effector cell. Mutations in the Fc region of an antibody or fragment thereof that increase the affinity of an antibody for an Fc receptor and techniques for introducting such mutations into the Fc receptor or fragment thereof are known to one of skill in the art. Examples of mutations in the Fc receptor of an antibody that can be made to increase the affinity of the antibody for an Fc receptor are described in, e.g., Smith, P., et al. (2012) PNAS. 109:6181-6186, which is incorporated herein by reference.

5.1.1 Antibodies with Increased Half-Lives

Provided herein are antibodies, wherein said antibodies are modified to have an extended (or increased) half-life in vivo. In particular, provided herein are modified antibodies which have a half-life in a subject, preferably a mammal and most preferably a human, of from about 3 days to about 180 days (or more), and in some embodiments greater than 3 days, greater than 7 days, greater than 10 days, greater than 15 days, greater than 20 days, greater than 25 days, greater than 30 days, greater than 35 days, greater than 40 days, greater than 45 days, greater than 50 days, at least about 60 days, greater than 75 days, greater than 90 days, greater than 105 days, greater than 120 days, greater than 135 days, greater than 150 days, greater than 165 days, or greater than 180 days.

In a specific embodiment, modified antibodies having an increased half-life in vivo are generated by introducing one or more amino acid modifications (i.e., substitutions, insertions or deletions) into an IgG constant domain, or FcRn-binding fragment thereof (preferably a Fc or hinge-Fc domain fragment). See, e.g., International Publication Nos. WO 02/060919; WO 98/23289; and WO 97/34631; and U.S. Pat. No. 6,277,375; each of which is incorporated herein by reference in its entirety. In a specific embodiment, the modified antibodies may have one or more amino acid modifications in the second constant CH2 domain (residues 231-340 of human IgG1) and/or the third constant CH3 domain (residues 341-447 of human IgG1), with numbering according to the Kabat numbering system (e.g., the EU index in Kabat).

In some embodiments, to prolong the in vivo serum circulation of antibodies, inert polymer molecules such as high molecular weight polyethyleneglycol (PEG) are attached to the antibodies with or without a multifunctional linker either through site-specific conjugation of the PEG to the N- or C-terminus of the antibodies or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein.

In another embodiment, antibodies are conjugated to albumin in order to make the antibody more stable in vivo or have a longer half-life in vivo. The techniques are well-known in the art, see, e.g., International Publication Nos. WO 93/15199, WO 93/15200, and WO 01/77137; and European Patent No. EP 413,622, all of which are incorporated herein by reference.

5.1.2 Antibody Conjugates

In some aspects, provided herein are antibodies, conjugated or recombinantly fused to a diagnostic, detectable or therapeutic agent or any other molecule. The conjugated or recombinantly fused antibodies can be useful, e.g., for monitoring or prognosing the onset, development, progression and/or severity of an influenza virus disease as part of a clinical testing procedure, such as determining the efficacy of a particular therapy. In certain aspects, the conjugated or recombinantly fused antibodies can be useful in preventing and/or treating an influenza virus disease or influenza virus infection. Antibodies described herein can also be conjugated to a molecule (e.g., polyethylene glycol) which can affect one or more biological and/or molecular properties of the antibodies, for example, stability (e.g., in serum), half-life, solubility, and antigenicity.

In specific embodiments, a conjugate comprises an antibody described herein and a molecule (e.g., therapeutic or drug moiety), wherein the antibody is linked directly to the molecule, or by way of one or more linkers. In certain embodiments, an antibody is covalently conjugated to a molecule. In a particular embodiment, an antibody is non-covalently conjugated to a molecule. In a specific embodiment, provided herein is an antibody drug conjugate comprising an antibody moiety and a drug (e.g., therapeutic or prophylactic agent), wherein the antibody moiety is an antibody described herein and wherein the conjugate may comprise one or more linkers.

In certain embodiments, an antibody described herein is conjugated to one or more molecules (e.g., therapeutic or drug moiety) directly or indirectly via one or more linker molecules. In particular embodiments, a linker comprises 1, 2, 3, 4, 5, 6, 7, 8, 9, 10, 11, 12, 13, 14, 15, or 20 amino acid residues. In certain embodiments, a linker consists of 1 to 10 amino acid residues, 1 to 15 amino acid residues, 5 to 20 amino acid residues, 10 to 25 amino acid residues, 10 to 30 amino acid residues, or 10 to 50 amino acid residues. In particular embodiments, a linker is an enzyme-cleavable linker or a disulfide linker. In a specific embodiment, the cleavable linker is cleavable via an enzyme such an aminopeptidase, an aminoesterase, a dipeptidyl carboxy peptidase, or a protease of the blood clotting cascade. In a specific embodiment, the linker that may be conjugated to the antibody does not interfere with the antibody binding to either recombinant NA, influenza B virus, or both, using techniques known in the art or described herein. In a specific embodiment, the molecule that may be conjugated to the antibody does not interfere with the antibody binding to either recombinant NA, influenza B virus, or both, using techniques known in the art or described herein.

In one embodiment, a linker is hydrolyzed at a pH in the range of 3.0 and pH 4.0 for about 1-24 hours, and at a temperature from about 20 to 50° C., preferably 37° C. In a specific embodiment, a linker is stable in the blood stream but is cleaved or hydrolyzed once it is inside the targeted cells. In certain embodiments, a linker comprises one or more triazole-containing linkers (see, e.g., International Patent Application Publication No. WO 2007/018431, which is incorporated by reference herein in its entirety). Non-limiting examples of linkers and spacers for incorporation into antibody-drug conjugates described herein are disclosed in International Patent Application Publication Nos. WO 2007/018431, WO 2004/043493, and WO 2002/083180.

In specific aspects, diagnosis and detection can be accomplished, for example, by coupling the antibody to a detectable substance(s) including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I $^{125}$I, $^{123}$I, and $^{121}$I,), carbon ($^{14}$C), sulfur ($^{35}$S), tritium ($^{3}$H), indium ($^{115}$In, $^{113}$In, $^{112}$In, and $^{111}$In,), technetium ($^{99}$Tc), thallium ($^{201}$Ti), gallium ($^{68}$Ga, $^{67}$Ga), palladium ($^{113}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$P, $^{97}$Ru, $^{68}$Ge $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; and positron emitting metals using various positron emission tomographies, and non-radioactive paramagnetic metal ions.

Provided are antibodies described herein conjugated or recombinantly fused to a therapeutic moiety (or one or more therapeutic moieties) and uses of such antibodies. The antibody can be conjugated or recombinantly fused to a therapeutic moiety, such as a cytotoxin, e.g., a cytostatic or cytocidal agent, a therapeutic agent or a radioactive metal ion, e.g., alpha-emitters.

Further, provided herein are uses of the antibodies conjugated or recombinantly fused to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, β-interferon, γ-interferon, α-interferon, interleukin-2 ("IL-2"), interleukin-4 ("IL-4"), interleukin-6 ("IL-6"), interleukin-7 ("IL-7"), interleukin 9 ("IL-9"), interleukin-10 ("IL-10"), interleukin-12 ("IL-12"), interleukin-15 ("IL-15"), interleukin-18 ("IL-18"), interleukin-23 ("IL-23"), granulocyte macrophage colony stimulating factor ("GM-CSF"), granulocyte colony stimulating factor ("G-CSF")), a growth factor, or a defensin. The therapeutic moiety or drug conjugated or recombinantly fused to an antibody should be chosen to achieve the desired prophylactic or therapeutic effect(s). In certain embodiments, an antibody conjugate may be used for the prophylactic or therapeutic uses described herein. In certain embodiments, the antibody is a modified antibody. A clinician or other medical personnel should consider the following when deciding on which therapeutic moiety or drug to conjugate or recombinantly fuse to an antibody: the nature of the disease, the severity of the disease, and the condition of the subject.

In addition, an antibody described herein can be conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$LU, $^{131}$Y, $^{131}$Ho, $^{131}$Sm, to polypeptides. In certain embodiments, the macrocyclic chelator is 1,4,7,10-tetraazacyclododecane-N,N',N",N"'-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Provided herein are antibodies recombinantly fused or chemically conjugated (including both covalent and non-covalent conjugations) to a heterologous protein or polypeptide (or fragment thereof, preferably to a polypeptide of about 10, about 20, about 30, about 40, about 50, about 60, about 70, about 80, about 90 or about 100 amino acids) to generate fusion proteins. In particular, provided herein are fusion proteins comprising an antigen-binding fragment of a monoclonal antibody (e.g., a Fab fragment, Fd fragment, Fv fragment, F(ab)2 fragment, a VH domain, a VH CDR, a VL domain or a VL CDR) and a heterologous protein, polypeptide, or peptide. In a specific embodiment, the heterologous protein, polypeptide, or peptide that the antibody is fused to is useful for targeting the antibody to a particular cell type.

In one embodiment, a fusion protein provided herein comprises the antibody 1F2, 1F4, 3G1, 4B2, or 4F11 and a heterologous polypeptide. In another embodiment, a fusion protein provided herein comprises an antigen-binding fragment of the antibody 1F2, 1F4, 3G1, 4B2, or 4F11 and a heterologous polypeptide. In another embodiment, a fusion protein provided herein comprises (i) a VH domain having the amino acid sequence of the VH domain of the antibody 1F2, 1F4, 3G1, 4B2, or 4F11, or a VL domain having the amino acid sequence of the VL domain of the antibody 1F2, 1F4, 3G1, 4B2, or 4F11; and (ii) a heterologous polypeptide. In another embodiment, a fusion protein provided herein comprises one, two, or more VH CDRs having the amino acid sequence of the VH CDRs of the antibody 1F2, 1F4, 3G1, 4B2, or 4F11 and a heterologous polypeptide. In another embodiment, a fusion protein comprises one, two, or more VL CDRs having the amino acid sequence of the VL CDRs of the antibody 1F2, 1F4, 3G1, 4B2, or 4F11 and a heterologous polypeptide. In certain embodiments, the above-referenced antibodies comprise a modified IgG (e.g., IgG1) constant domain, or FcRn binding fragment thereof (e.g., the Fc domain or hinge-Fc domain), described herein. In another embodiment, a fusion protein provided herein comprises at least one VH domain and at least one VL domain of the antibody 1F2 and a heterologous polypeptide. In another embodiment, a fusion protein provided herein comprises: (a) a VH domain comprising the amino acid sequence of SEQ ID NO: 168, 169, 170, 171, 172, 173, 174 or 175; (b) a VL domain comprising the amino acid sequence of SEQ ID NO: 177, 178, 179, 180, 181, 182, 183, or 184; and (c) a heterologous polypeptide. In yet another embodiment, a fusion protein provided herein comprises at least one VH CDR (or at least 2 or 3 VH CDRs) and at least one VL CDR (or at least 2 or 3 VL CDRs) of the antibody 1F2 and a heterologous polypeptide. In certain embodiments, the above-referenced antibodies comprise a modified IgG (e.g., IgG1) constant domain, or FcRn binding fragment thereof (e.g., the Fc domain or hinge-Fc domain), described herein. In certain embodiments, the above-referenced antibodies comprise a modified IgG (e.g., IgG1) constant domain, or FcRn binding fragment thereof (e.g., the Fc domain or hinge-Fc domain), described herein.

In another embodiment, a fusion protein provided herein comprises at least one VH domain and at least one VL domain of the antibody 1F4 and a heterologous polypeptide. In yet another embodiment, a fusion protein provided herein comprises at least one VH CDR and at least one VL CDR of the antibody 1F4 and a heterologous polypeptide. In certain embodiments, the above-referenced antibodies comprise a modified IgG (e.g., IgG1) constant domain, or FcRn binding fragment thereof (e.g., the Fc domain or hinge-Fc domain), described herein.

In another embodiment, a fusion protein provided herein comprises at least one VH domain and at least one VL domain of the antibody 3G1 and a heterologous polypeptide. In yet another embodiment, a fusion protein provided herein comprises at least one VH CDR and at least one VL CDR of the antibody 3G1 and a heterologous polypeptide. In certain embodiments, the above-referenced antibodies comprise a modified IgG (e.g., IgG1) constant domain, or FcRn binding fragment thereof (e.g., the Fc domain or hinge-Fc domain), described herein.

In another embodiment, a fusion protein provided herein comprises at least one VH domain and at least one VL domain of the antibody 4B2 and a heterologous polypeptide. In yet another embodiment, a fusion protein provided herein comprises at least one VH CDR and at least one VL CDR of the antibody 4B2 and a heterologous polypeptide. In certain embodiments, the above-referenced antibodies comprise a modified IgG (e.g., IgG1) constant domain, or FcRn binding fragment thereof (e.g., the Fc domain or hinge-Fc domain), described herein.

In another embodiment, a fusion protein provided herein comprises at least one VH domain and at least one VL domain of the antibody 4F11 and a heterologous polypeptide. In yet another embodiment, a fusion protein provided herein comprises at least one VH CDR and at least one VL CDR of the antibody 4F11 and a heterologous polypeptide. In certain embodiments, the above-referenced antibodies comprise a modified IgG (e.g., IgG1) constant domain, or FcRn binding fragment thereof (e.g., the Fc domain or hinge-Fc domain), described herein.

Moreover, antibodies can be fused to marker sequences, such as a peptide to facilitate purification. In preferred embodiments, the marker amino acid sequence is a hexa-histidine peptide (i.e., His-tag), such as the tag provided in a pQE vector (QIAGEN, Inc.), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

Methods for fusing or conjugating therapeutic moieties (including polypeptides) to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367, 166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154:5590-5600, 1995; Vil et al., Proc. Natl. Acad. Sci. USA, 89:11337-11341, 1992; which are incorporated herein by reference in their entireties.

In particular, fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of the monoclonal antibodies described herein (or an antigen-binding fragment thereof) (e.g., antibodies with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies, or the encoded antibodies, may be altered by being subjected to random mutagenesis by error-prone PCR, random nucleotide insertion or other methods prior to recombination. A polynucleotide encoding a monoclonal antibody described herein (or an antigen-binding fragment thereof) may be recombined with one or more components, motifs, sections, parts, domains, fragments, etc. of one or more heterologous molecules.

An antibody can also be conjugated to a second antibody to form an antibody heteroconjugate as described by Segal in U.S. Pat. No. 4,676,980, which is incorporated herein by reference in its entirety.

An antibody can also be linked directly or indirectly to one or more antibodies to produce bispecific/multispecific antibodies.

An antibody can also be attached to solid supports, which are particularly useful for immunoassays or purification of an antigen. Such solid supports include, but are not limited to, glass, cellulose, polyacrylamide, nylon, polystyrene, polyvinyl chloride or polypropylene.

5.2 Polynucleotides

In certain aspects, provided herein are polynucleotides comprising a nucleotide sequence encoding an antibody described herein or a fragment thereof (e.g., a VL domain and/or VH domain) that binds to an influenza B virus NA (e.g., NA of an influenza B virus strain described in Section 6 and/or Section 7 and/or Section 8, infra), and vectors, e.g., vectors comprising such polynucleotides for recombinant expression in host cells (e.g., *E. coli* and mammalian cells). Provided herein are polynucleotides comprising nucleotide sequences encoding any of the antibodies provided herein (see, e.g., Section 5.1), as well as vectors comprising such polynucleotide sequences, e.g., expression vectors for their efficient expression in host cells, e.g., mammalian cells.

As used herein, an "isolated" polynucleotide or nucleic acid molecule is one that is separated from other nucleic acid molecules that are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

As used herein, the terms "polynucleotide(s)" "nucleic acid" and "nucleotide" include deoxyribonucleotides, deoxyribonucleic acids, ribonucleotides, and ribonucleic acids, and polymeric forms thereof, and includes either single- or double-stranded forms. In certain embodiments, the terms "polynucleotide(s)" "nucleic acid" and "nucleotide" include known analogues of natural nucleotides, for example, peptide nucleic acids ("PNA"s), that have similar binding properties as the reference nucleic acid. In some embodiments, the terms "polynucleotide(s)" "nucleic acid" and "nucleotide" refer to deoxyribonucleic acids (e.g., cDNA or DNA). In other embodiments, the terms "polynucleotide(s)" "nucleic acid" and "nucleotide" refer to ribonucleic acids (e.g., mRNA or RNA).

In particular aspects, provided herein are polynucleotides comprising nucleotide sequences encoding antibodies (e.g., a murine, chimeric, or humanized antibody, or antigen-binding fragments thereof), which binds to an influenza B virus NA (e.g., NA of an influenza B virus strain described in Section 6 and/or Section 7, infra) and comprises an amino acid sequence as described herein, as well as antibodies which compete with such antibodies for binding to an influenza B virus NA (e.g., NA of an influenza B virus strain described in Section 6 and/or Section 7, infra) (e.g., in a dose-dependent manner), or which binds to the same epitope as that of such antibodies. In particular embodiments, a polynucleotide described herein an antibody which comprises a VL domain and a VH domain of antibody 1F2, 1F4, 3G1, 4B2, or 4F11.

In particular embodiments, a polynucleotide described herein comprises a nucleotide sequence encoding an antibody which comprises a VL domain comprising the amino acid sequence of SEQ ID NO: 2 and/or a VH domain comprising the amino acid of SEQ ID NO: 1. In certain embodiments, a polynucleotide described herein comprises a nucleotide sequence encoding such a VL domain (e.g., a VL domain comprising the amino acid sequence of SEQ ID NO: 2). In certain embodiments, a polynucleotide described herein comprises a nucleotide sequence encoding such a VH domain (e.g., a VH domain comprising the amino acid sequence of SEQ ID NO: 1). In some embodiments, a polynucleotide described herein comprises a nucleotide sequence encoding for an antibody that binds to influenza B virus NA (e.g., NA of an influenza B virus strain described in Section 6 and/or Section 7, infra), wherein the antibody comprises 1, 2, or 3 VH CDRs and/or 1, 2, or 3 VL CDRs of the antibody 1F2.

In particular embodiments, a polynucleotide described herein comprises a nucleotide sequence encoding an antibody which comprises a VH domain comprising the amino acid sequence of SEQ ID NO: 168, 169, 170, 171, 172, 173, 174 or 175 and/or a VL domain comprising the amino acid of SEQ ID NO: 177, 178, 179, 180, 181, 182, 183, or 184. In certain embodiments, a polynucleotide described herein comprises a nucleotide sequence encoding such a VL domain (e.g., a VL domain comprising the amino acid sequence of SEQ ID NO: 177, 178, 179, 180, 181, 182, 183, or 184). In certain embodiments, a polynucleotide described herein comprises a nucleotide sequence encoding such a VH domain (e.g., a VH domain comprising the amino acid sequence of SEQ ID NO: 168, 169, 170, 171, 172, 173, 174 or 175).

In particular embodiments, a polynucleotide described herein comprises a nucleotide sequence encoding an antibody which comprises a VL domain comprising the amino acid sequence of SEQ ID NO: 18 and/or a VH domain comprising the amino acid of SEQ ID NO: 17. In certain embodiments, a polynucleotide described herein comprises a nucleotide sequence encoding such a VL domain (e.g., a VL domain comprising the amino acid sequence of SEQ ID NO: 18). In certain embodiments, a polynucleotide described herein comprises a nucleotide sequence encoding such a VH domain (e.g., a VH domain comprising the amino acid sequence of SEQ ID NO: 17). In some embodiments, a polynucleotide described herein comprises a nucleotide sequence encoding for an antibody that binds to influenza B virus NA (e.g., NA of an influenza B virus strain described in Section 6 and/or Section 7, infra), wherein the antibody comprises 1, 2, or 3 VH CDRs and/or 1, 2, or 3 VL CDRs of the antibody 1F4.

In particular embodiments, a polynucleotide described herein comprises a nucleotide sequence encoding an antibody which comprises a VL domain comprising the amino acid sequence of SEQ ID NO: 34 and/or a VH domain comprising the amino acid of SEQ ID NO: 33. In certain embodiments, a polynucleotide described herein comprises a nucleotide sequence encoding such a VL domain (e.g., a VL domain comprising the amino acid sequence of SEQ ID NO: 34). In certain embodiments, a polynucleotide described herein comprises a nucleotide sequence encoding such a VH domain (e.g., a VH domain comprising the amino acid sequence of SEQ ID NO: 33). In some embodiments, a polynucleotide described herein comprises a nucleotide sequence encoding for an antibody that binds to influenza B virus NA (e.g., NA of an influenza B virus strain described in Section 6 and/or Section 7, infra), wherein the antibody comprises 1, 2, or 3 VH CDRs and/or 1, 2, or 3 VL CDRs of the antibody 3G1.

In particular embodiments, a polynucleotide described herein comprises a nucleotide sequence encoding an antibody which comprises a VL domain comprising the amino acid sequence of SEQ ID NO: 50 and/or a VH domain comprising the amino acid of SEQ ID NO: 49. In certain embodiments, a polynucleotide described herein comprises a nucleotide sequence encoding such a VL domain (e.g., a VL domain comprising the amino acid sequence of SEQ ID NO: 50). In certain embodiments, a polynucleotide described herein comprises a nucleotide sequence encoding such a VH domain (e.g., a VH domain comprising the amino acid sequence of SEQ ID NO: 49). In some embodiments, a polynucleotide described herein comprises a nucleotide sequence encoding for an antibody that binds to influenza B virus NA (e.g., NA of an influenza B virus strain described in Section 6 and/or Section 7, infra), wherein the antibody comprises 1, 2, or 3 VH CDRs and/or 1, 2, or 3 VL CDRs of the antibody 4B2.

In particular embodiments, a polynucleotide described herein comprises a nucleotide sequence encoding an antibody which comprises a VL domain comprising the amino acid sequence of SEQ ID NO: 66 and/or a VH domain comprising the amino acid of SEQ ID NO: 65. In certain embodiments, a polynucleotide described herein comprises a nucleotide sequence encoding such a VL domain (e.g., a VL domain comprising the amino acid sequence of SEQ ID NO: 66). In certain embodiments, a polynucleotide described herein comprises a nucleotide sequence encoding such a VH domain (e.g., a VH domain comprising the amino acid sequence of SEQ ID NO: 65). In some embodiments, a polynucleotide described herein comprises a nucleotide sequence encoding for an antibody that binds to influenza B virus NA (e.g., NA of an influenza B virus strain described in Section 6 and/or Section 7, infra), wherein the antibody comprises 1, 2, or 3 VH CDRs and/or 1, 2, or 3 VL CDRs of the antibody 4F11.

In particular embodiments, a polynucleotide described herein comprises a nucleotide sequence encoding an antibody, which binds to an influenza B virus NA (e.g., NA of an influenza B virus strain described in Section 6 and/or Section 7, infra), comprising VL CDRs and/or VH CDRs of antibody 1F2. For example, in a specific embodiment, a polynucleotide described herein comprises a nucleotide sequence encoding an antibody which comprises a VL domain comprising CDR1, CDR2, and CDR3 comprising the amino acid sequences of SEQ ID NOs: 6-8, respectively, and/or a VH domain comprising CDR1, CDR2, and CDR3 having the amino acid sequences of SEQ ID NOs: 3-5, respectively. In certain aspects, provided herein are polynucleotides comprising a nucleotide sequence encoding the light chain or heavy chain of an antibody described herein. The polynucleotides can comprise nucleotide sequences encoding a light chain or a VL domain, comprising the VL FRs and CDRs of an antibody described herein. The polynucleotides can comprise nucleotide sequences encoding a heavy chain, or a VH domain, comprising the VH FRs and CDRs of antibodies described herein. In specific embodiments, a polynucleotide described herein comprises a nucleotide sequence encoding a VL domain comprising the amino acid sequence of SEQ ID NO: 2. In specific embodiments, a polynucleotide described herein comprises a nucleotide sequence encoding a VH domain comprising the amino acid sequence of SEQ ID NO: 1. In specific embodiments, a polynucleotide described herein comprises a nucleotide sequence encoding a VL domain comprising the amino acid sequence of SEQ ID NO: 177, 178, 179, 180, 181, 182, 183, or 184. In specific embodiments, a polynucleotide described herein comprises a nucleotide sequence encoding a VH domain comprising the amino acid sequence of SEQ ID NO: 168, 169, 170, 171, 172, 173, 174 or 175. In particular embodiments, a polynucleotide described herein encodes an antibody, which binds to an influenza B virus NA (e.g., NA of an influenza B virus strain described in Section 6 and/or Section 7, infra), comprising VL CDRs and/or VH CDRs of antibody 1F4. For example, in a specific embodiment, a polynucleotide described herein comprises a nucleotide sequence encoding an antibody which comprises a VL domain comprising CDR1, CDR2, and CDR3 comprising the amino acid sequences of SEQ ID NOs: 22-24, respectively, and/or a VH domain comprising CDR1, CDR2, and CDR3 having the amino acid sequences of SEQ ID NOs: 19-21, respectively. In certain aspects, provided herein are polynucleotides comprising a nucleotide sequence encoding the light chain or heavy chain of an antibody described herein. The polynucleotides can comprise nucleotide sequences encoding a light chain or a VL domain, comprising the VL FRs and CDRs of an antibody described herein. The polynucleotides can comprise nucleotide sequences encoding a heavy chain, or a VH domain, comprising the VH FRs and CDRs of antibodies described herein. In specific embodiments, a polynucleotide described herein comprises a nucleotide sequence encoding a VL domain comprising the amino acid sequence of SEQ ID NO: 18. In specific embodiments, a polynucleotide described herein comprises a nucleotide sequence encoding a VH domain comprising the amino acid sequence of SEQ ID NO: 17.

In particular embodiments, a polynucleotide described herein comprises a nucleotide sequence encoding an antibody, which binds to an influenza B virus NA (e.g., NA of an influenza B virus strain described in Section 6 and/or Section 7, infra), comprising VL CDRs and/or VH CDRs of antibody 3G1. For example, in a specific embodiment, a polynucleotide described herein comprises a nucleotide sequence encoding an antibody which comprises a VL domain comprising CDR1, CDR2, and CDR3 comprising the amino acid sequences of SEQ ID NOs: 38-40, respectively, and/or a VH domain comprising CDR1, CDR2, and CDR3 having the amino acid sequences of SEQ ID NOs: 35-37, respectively. In certain aspects, provided herein are polynucleotides comprising a nucleotide sequence encoding the light chain or heavy chain of an antibody described herein. The polynucleotides can comprise nucleotide sequences encoding a light chain or a VL domain, comprising the VL FRs and CDRs of an antibody described herein. The polynucleotides can comprise nucleotide sequences encoding a heavy chain, or a VH domain, comprising the VH FRs and CDRs of antibodies described herein. In specific embodiments, a polynucleotide described herein comprises a nucleotide sequence encoding a VL domain comprising the amino acid sequence of SEQ ID NO: 34. In specific embodiments, a polynucleotide described herein comprises a nucleotide sequence encoding a VH domain comprising the amino acid sequence of SEQ ID NO: 33.

In particular embodiments, a polynucleotide described herein comprises a nucleotide sequence encoding an antibody, which binds to an influenza B virus NA (e.g., NA of an influenza B virus strain described in Section 6 and/or Section 7, infra), comprising VL CDRs and/or VH CDRs of antibody 4B2. For example, in a specific embodiment, a polynucleotide described herein comprises a nucleotide sequence encoding an antibody which comprises a VL domain comprising CDR1, CDR2, and CDR3 comprising the amino acid sequences of SEQ ID NOs: 54-56, respectively, and/or a VH domain comprising CDR1, CDR2, and CDR3 having the amino acid sequences of SEQ ID NOs: 51-53, respectively. In certain aspects, provided herein are polynucleotides comprising a nucleotide sequence encoding the light chain or heavy chain of an antibody described herein. The polynucleotides can comprise nucleotide sequences encoding a light chain or a VL domain, comprising the VL FRs and CDRs of an antibody described herein. The polynucleotides can comprise nucleotide sequences encoding a heavy chain, or a VH domain, comprising the VH FRs and CDRs of antibodies described herein. In specific embodiments, a polynucleotide described herein comprises a nucleotide sequence encoding a VL domain comprising the amino acid sequence of SEQ ID NO: 50. In specific embodiments, a polynucleotide described herein comprises a nucleotide sequence encoding a VH domain comprising the amino acid sequence of SEQ ID NO: 49.

In particular embodiments, a polynucleotide described herein comprises a nucleotide sequence encoding an antibody, which binds to an influenza B virus NA (e.g., NA of an influenza B virus strain described in Section 6 and/or Section 7, infra), comprising VL CDRs and/or VH CDRs of antibody 4F11. For example, in a specific embodiment, a polynucleotide described herein comprises a nucleotide sequence encoding an antibody which comprises a VL domain comprising CDR1, CDR2, and CDR3 comprising the amino acid sequences of SEQ ID NOs: 70-72, respectively, and/or a VH domain comprising CDR1, CDR2, and CDR3 having the amino acid sequences of SEQ ID NOs: 67-69, respectively. In certain aspects, provided herein are polynucleotides comprising a nucleotide sequence encoding the light chain or heavy chain of an antibody described herein. The polynucleotides can comprise nucleotide sequences encoding a light chain or a VL domain, comprising the VL FRs and CDRs of an antibody described herein. The polynucleotides can comprise nucleotide sequences encoding a heavy chain, or a VH domain, comprising the VH FRs and CDRs of antibodies described herein. In specific embodiments, a polynucleotide described herein encodes a VL domain comprising the amino acid sequence of SEQ ID NO: 66. In specific embodiments, a polynucleotide described herein encodes a VH domain comprising the amino acid sequence of SEQ ID NO: 65.

In particular embodiments, a polynucleotide described herein encodes a VL domain, wherein the polynucleotide comprises the nucleic acid sequence of SEQ ID NO: 82. In particular embodiments, a polynucleotide described herein encodes a VH domain, wherein the polynucleotide comprises the nucleic acid sequence of SEQ ID NO: 81. In certain embodiments, a polynucleotide encodes an antibody described herein, wherein the polynucleotide comprises the nucleic acid sequence of SEQ ID NO: 82 encoding a VL domain and the nucleic acid sequence of SEQ ID NO: 81 encoding a VH domain.

In particular embodiments, a polynucleotide described herein encodes a VL domain, wherein the polynucleotide comprises the nucleic acid sequence of SEQ ID NO: 84. In particular embodiments, a polynucleotide described herein encodes a VH domain, wherein the polynucleotide comprises the nucleic acid sequence of SEQ ID NO: 83. In certain embodiments, a polynucleotide encodes an antibody described herein, wherein the polynucleotide comprises the nucleic acid sequence of SEQ ID NO: 84 encoding a VL domain and the nucleic acid sequence of SEQ ID NO: 83 encoding a VH domain.

In particular embodiments, a polynucleotide described herein encodes a VL domain, wherein the polynucleotide comprises the nucleic acid sequence of SEQ ID NO: 86. In particular embodiments, a polynucleotide described herein encodes a VH domain, wherein the polynucleotide comprises the nucleic acid sequence of SEQ ID NO: 85. In certain embodiments, a polynucleotide encodes an antibody described herein, wherein the polynucleotide comprises the nucleic acid sequence of SEQ ID NO: 86 encoding a VL domain and the nucleic acid sequence of SEQ ID NO: 85 encoding a VH domain.

In particular embodiments, a polynucleotide described herein encodes a VL domain, wherein the polynucleotide comprises the nucleic acid sequence of SEQ ID NO: 88. In particular embodiments, a polynucleotide described herein encodes a VH domain, wherein the polynucleotide comprises the nucleic acid sequence of SEQ ID NO: 87. In certain embodiments, a polynucleotide encodes an antibody described herein, wherein the polynucleotide comprises the nucleic acid sequence of SEQ ID NO: 88 encoding a VL domain and the nucleic acid sequence of SEQ ID NO: 87 encoding a VH domain.

In particular embodiments, a polynucleotide described herein encodes a VL domain, wherein the polynucleotide comprises the nucleic acid sequence of SEQ ID NO: 90. In particular embodiments, a polynucleotide described herein encodes a VH domain, wherein the polynucleotide comprises the nucleic acid sequence of SEQ ID NO: 89. In certain embodiments, a polynucleotide encodes an antibody described herein, wherein the polynucleotide comprises the nucleic acid sequence of SEQ ID NO: 90 encoding a VL domain and the nucleic acid sequence of SEQ ID NO: 89 encoding a VH domain.

In particular embodiments, a polynucleotide described herein encodes a VL domain, wherein the polynucleotide comprises a nucleic acid sequence that is at least 80%, 85%, 90%, 91%, 92%, 93%, 94%, 95%, 96%, 97%, or 98% identical to the nucleic acid sequence of SEQ ID NO: 82, 84, 86, 88, or 90. In particular embodiments, a polynucleotide described herein encodes a VH domain, wherein the polynucleotide comprises a nucleic acid sequence that is at least 80%, 85%, 90%, 91%, 92%, 93%, 94%, 95%, 96%, 97%, or 98% identical to the nucleic acid sequence of SEQ ID NO: 81, 83, 85, 87, or 89.

In particular embodiments, a polynucleotide described herein comprises nucleic acid sequences that encode a VL domain and a VH domain, wherein the nucleic acid sequence encoding the VL domain is at least 80%, 85%, 90%, 91%, 92%, 93%, 94%, 95%, 96%, 97%, or 98% identical to the nucleic acid sequence of SEQ ID NO: 82 and the nucleic acid sequence encoding the VH domain is at least 80%, 85%, 90%, 91%, 92%, 93%, 94%, 95%, 96%, 97%, or 98% identical to the nucleic acid sequence of SEQ ID NO: 81.

In particular embodiments, a polynucleotide described herein comprises nucleic acid sequences that encode a VL domain and a VH domain, wherein the nucleic acid sequence encoding the VL domain is at least 80%, 85%, 90%, 91%, 92%, 93%, 94%, 95%, 96%, 97%, or 98% identical to the nucleic acid sequence of SEQ ID NO: 84 and the nucleic acid sequence encoding the VH domain is at least 80%, 85%, 90%, 91%, 92%, 93%, 94%, 95%, 96%, 97%, or 98% identical to the nucleic acid sequence of SEQ ID NO: 83.

In particular embodiments, a polynucleotide described herein comprises nucleic acid sequences that encode a VL domain and a VH domain, wherein the nucleic acid sequence encoding the VL domain is at least 80%, 85%, 90%, 91%, 92%, 93%, 94%, 95%, 96%, 97%, or 98% identical to the nucleic acid sequence of SEQ ID NO: 86 and the nucleic acid sequence encoding the VH domain is at least 80%, 85%, 90%, 91%, 92%, 93%, 94%, 95%, 96%, 97%, or 98% identical to the nucleic acid sequence of SEQ ID NO: 85.

In particular embodiments, a polynucleotide described herein comprises nucleic acid sequences that encode a VL domain and a VH domain, wherein the nucleic acid sequence encoding the VL domain is at least 80%, 85%, 90%, 91%, 92%, 93%, 94%, 95%, 96%, 97%, or 98% identical to the nucleic acid sequence of SEQ ID NO: 88 and the nucleic acid sequence encoding the VH domain is at least 80%, 85%, 90%, 91%, 92%, 93%, 94%, 95%, 96%, 97%, or 98% identical to the nucleic acid sequence of SEQ ID NO: 87.

In particular embodiments, a polynucleotide described herein comprises nucleic acid sequences that encode a VL domain and a VH domain, wherein the nucleic acid sequence encoding the VL domain is at least 80%, 85%, 90%, 91%, 92%, 93%, 94%, 95%, 96%, 97%, or 98% identical to the nucleic acid sequence of SEQ ID NO: 90 and the nucleic acid sequence encoding the VH domain is at least 80%, 85%, 90%, 91%, 92%, 93%, 94%, 95%, 96%, 97%, or 98% identical to the nucleic acid sequence of SEQ ID NO: 89.

In particular embodiments, a polynucleotide described herein encodes a light chain, wherein the polynucleotide comprises the nucleic acid sequence of SEQ ID NO: 82, 84, 86, 88, or 90. In particular embodiments, a polynucleotide described herein encodes a heavy chain, wherein the polynucleotide comprises the nucleic acid sequence of SEQ ID NO: 81, 83, 85, 87, or 89.

In particular embodiments, a polynucleotide(s) described herein encodes a light chain and a heavy chain, wherein the polynucleotide(s) comprises the nucleic acid sequence of SEQ ID NO: 82 and the nucleic acid sequence of SEQ ID NO: 81. In particular embodiments, a polynucleotide(s) described herein encodes a light chain and a heavy chain, wherein the polynucleotide(s) comprises the nucleic acid sequence of SEQ ID NO: 84 and the nucleic acid sequence of SEQ ID NO: 83. In particular embodiments, a polynucleotide(s) described herein encodes a light chain and a heavy chain, wherein the polynucleotide(s) comprises the nucleic acid sequence of SEQ ID NO: 86 and the nucleic acid sequence of SEQ ID NO: 85. In particular embodiments, a polynucleotide(s) described herein encodes a light chain and a heavy chain, wherein the polynucleotide(s) comprises the nucleic acid sequence of SEQ ID NO: 88 and the nucleic acid sequence of SEQ ID NO: 87. In particular embodiments, a polynucleotide(s) described herein encodes a light chain and a heavy chain, wherein the polynucleotide(s) comprises the nucleic acid sequence of SEQ ID NO: 90 and the nucleic acid sequence of SEQ ID NO: 89.

In particular embodiments, a polynucleotide described herein comprises nucleic acid sequences that encode a light chain and a heavy chain, wherein the nucleic acid sequence encoding the light chain comprises a nucleotide sequence that is at least 80%, 85%, 90%, 91%, 92%, 93%, 94%, 95%, 96%, 97%, or 98% identical to the nucleic acid sequence of SEQ ID NO: 82 and/or the nucleic acid sequence encoding the heavy chain comprises a nucleotide sequence that is at least 80%, 85%, 90%, 91%, 92%, 93%, 94%, 95%, 96%, 97%, or 98% identical to the nucleic acid sequence of SEQ ID NO: 81. In particular embodiments, a polynucleotide described herein comprises nucleic acid sequences that encode a light chain and a heavy chain, wherein the nucleic acid sequence encoding the light chain comprises a nucleotide sequence that is at least 80%, 85%, 90%, 91%, 92%, 93%, 94%, 95%, 96%, 97%, or 98% identical to the nucleic acid sequence of SEQ ID NO: 84 and/or the nucleic acid sequence encoding the heavy chain comprises a nucleotide sequence that is at least 80%, 85%, 90%, 91%, 92%, 93%, 94%, 95%, 96%, 97%, or 98% identical to the nucleic acid sequence of SEQ ID NO: 83. In particular embodiments, a polynucleotide described herein comprises nucleic acid sequences that encode a light chain and a heavy chain, wherein the nucleic acid sequence encoding the light chain comprises a nucleotide sequence that is at least 80%, 85%, 90%, 91%, 92%, 93%, 94%, 95%, 96%, 97%, or 98% identical to the nucleic acid sequence of SEQ ID NO: 86 and/or the nucleic acid sequence encoding the heavy chain comprises a nucleotide sequence that is at least 80%, 85%, 90%, 91%, 92%, 93%, 94%, 95%, 96%, 97%, or 98% identical to the nucleic acid sequence of SEQ ID NO: 85. In particular embodiments, a polynucleotide described herein comprises nucleic acid sequences that encode a light chain and a heavy chain, wherein the nucleic acid sequence encoding the light chain comprises a nucleotide sequence that is at least 80%, 85%, 90%, 91%, 92%, 93%, 94%, 95%, 96%, 97%, or 98% identical to the nucleic acid sequence of SEQ ID NO: 88 and/or the nucleic acid sequence encoding the heavy chain comprises a nucleotide sequence that is at least 80%, 85%, 90%, 91%, 92%, 93%, 94%, 95%, 96%, 97%, or 98% identical to the nucleic acid sequence of SEQ ID NO: 87. In particular embodiments, a polynucleotide described herein comprises nucleic acid sequences that encode a light chain and a heavy chain, wherein the nucleic acid sequence encoding the light chain comprises a nucleotide sequence that is at least 80%, 85%, 90%, 91%, 92%, 93%, 94%, 95%, 96%, 97%, or 98% identical to the nucleic acid sequence of SEQ ID NO: 90 and/or the nucleic acid sequence encoding the heavy chain comprises a nucleotide sequence that is at least 80%, 85%, 90%, 91%, 92%, 93%, 94%, 95%, 96%, 97%, or 98% identical to the nucleic acid sequence of SEQ ID NO: 89.

In specific embodiments, provided herein is a polynucleotide comprising a nucleotide sequence encoding a heavy chain, wherein the heavy chain comprises the amino acid sequence of SEQ ID NO: 185, 186, 187, 188, 189, 190, 191, 192, or 193. In specific embodiments, provided herein is a polynucleotide comprising a nucleotide sequence encoding a light chain, wherein the light chain comprises the amino acid sequence of SEQ ID NO: 194, 195, 196, 197, 198, 199, 200, 201, or 202. In specific embodiments, provided herein is a polynucleotide comprising a nucleotide sequence encoding a heavy chain and a nucleotide sequence encoding a light chain, wherein the heavy chain comprises the amino acid sequence of SEQ ID NO: 186, 187, 188, 189, 190, 191, 192, or 193, and wherein the light chain comprises the amino acid sequence of SEQ ID NO: 195, 196, 197, 198, 199, 200, 201, or 202. In specific embodiments, provided herein is a polynucleotide comprising a nucleotide sequence encoding a heavy chain and a nucleotide sequence encoding a light chain, wherein the heavy chain comprises the amino acid sequence of SEQ ID NO: 185, and wherein the light chain comprises the amino acid sequence of SEQ ID NO: 194.

In specific aspects, provided herein is a polynucleotide comprising a nucleotide sequence encoding an antibody provided herein (e.g., murine, chimeric, or humanized antibody) which competitively blocks (e.g., in a dose dependent manner), antibody 1F2, 1F4, 3G1, 4B2, or 4F11 from binding to an influenza B virus NA, as determined using assays known to one of skill in the art or described herein (e.g., ELISA competitive assays).

In a specific embodiment, a polynucleotide provided herein comprises a nucleotide sequence encoding a kappa light chain (e.g., human kappa light chain). In another specific embodiment, a polynucleotide provided herein comprises a nucleotide sequence encoding a lambda light chain (e.g., human lambda light chain).

In a specific embodiment, a polynucleotide provided herein comprises a nucleotide sequence encoding an IgG1 heavy chain (e.g., human IgG1 heavy chain) of an antibody described herein. In another specific embodiment, a polynucleotide provided herein comprises a nucleotide sequence encoding IgG4 heavy chain (e.g., human IgG4 heavy chain). In another specific embodiment, a polynucleotide provided herein comprises a nucleotide sequence encoding IgG2 heavy chain (e.g., human IgG2 heavy chain).

In a specific embodiment, a polynucleotide provided herein encodes an antigen-binding domain, e.g., an Fab or F(ab')2.

In another particular embodiment, a polynucleotide provided herein comprises a nucleotide sequence encoding an antibody described herein, which binds to an influenza B virus NA, wherein the antibody comprises a light chain and a heavy chain, and wherein (i) the light chain comprises a VL domain comprising a VL CDR1, VL CDR2, and VL CDR3 having the amino acid sequences of the VL CDRs of antibody 1F2; (ii) the heavy chain comprises a VH domain comprising a VH CDR1, VH CDR2, and VH CDR3 having the amino acid sequences of the VH CDRs of antibody 1F2; (iii) the light chain further comprises a constant light chain domain comprising the amino acid sequence of the constant domain of a human kappa light chain; and (iv) the heavy chain further comprises a constant heavy chain domain comprising the amino acid sequence of the constant domain of a human IgG1 heavy chain or human IgG2a heavy chain.

In another particular embodiment, a polynucleotide provided herein comprises a nucleotide sequence encoding an antibody described herein, which binds to an influenza B virus NA, wherein the antibody comprises a light chain and a heavy chain, and wherein (i) the light chain comprises a VL domain comprising a VL CDR1, VL CDR2, and VL CDR3 having the amino acid sequences of the VL CDRs of antibody 1F4; (ii) the heavy chain comprises a VH domain comprising a VH CDR1, VH CDR2, and VH CDR3 having the amino acid sequences of the VH CDRs of antibody 1F4; (iii) the light chain further comprises a constant light chain domain comprising the amino acid sequence of the constant domain of a human kappa light chain; and (iv) the heavy chain further comprises a constant heavy chain domain comprising the amino acid sequence of the constant domain of a human IgG1 heavy chain or human IgG2a heavy chain.

In another particular embodiment, a polynucleotide provided herein comprises a nucleotide sequence encoding an antibody described herein, which binds to an influenza B virus NA, wherein the antibody comprises a light chain and a heavy chain, and wherein (i) the light chain comprises a VL domain comprising a VL CDR1, VL CDR2, and VL CDR3 having the amino acid sequences of the VL CDRs of antibody 3G1; (ii) the heavy chain comprises a VH domain comprising a VH CDR1, VH CDR2, and VH CDR3 having the amino acid sequences of the VH CDRs of antibody 3G1; (iii) the light chain further comprises a constant light chain domain comprising the amino acid sequence of the constant domain of a human kappa light chain; and (iv) the heavy chain further comprises a constant heavy chain domain comprising the amino acid sequence of the constant domain of a human IgG1 heavy chain or human IgG2a heavy chain.

In another particular embodiment, a polynucleotide provided herein comprises a nucleotide sequence encoding an antibody described herein, which binds to an influenza B virus NA, wherein the antibody comprises a light chain and a heavy chain, and wherein (i) the light chain comprises a VL domain comprising a VL CDR1, VL CDR2, and VL CDR3 having the amino acid sequences of the VL CDRs of antibody 4B2; (ii) the heavy chain comprises a VH domain comprising a VH CDR1, VH CDR2, and VH CDR3 having the amino acid sequences of the VH CDRs of antibody 4B2; (iii) the light chain further comprises a constant light chain domain comprising the amino acid sequence of the constant domain of a human kappa light chain; and (iv) the heavy chain further comprises a constant heavy chain domain comprising the amino acid sequence of the constant domain of a human IgG1 heavy chain or human IgG2a heavy chain.

In another particular embodiment, a polynucleotide provided herein comprises a nucleotide sequence encoding an antibody described herein, which binds to an influenza B virus NA, wherein the antibody comprises a light chain and a heavy chain, and wherein (i) the light chain comprises a VL domain comprising a VL CDR1, VL CDR2, and VL CDR3 having the amino acid sequences of the VL CDRs of antibody 4F11; (ii) the heavy chain comprises a VH domain comprising a VH CDR1, VH CDR2, and VH CDR3 having the amino acid sequences of the VH CDRs of antibody 4F11; (iii) the light chain further comprises a constant light chain domain comprising the amino acid sequence of the constant domain of a human kappa light chain; and (iv) the heavy chain further comprises a constant heavy chain domain comprising the amino acid sequence of the constant domain of a human IgG1 heavy chain or human IgG2a heavy chain.

In certain embodiments, with respect to a polynucleotide provided herein comprising a nucleotide sequence encoding a VL domain and VH domain of any of the antibodies described herein, the polynucleotide of the VL domain further comprises primate (e.g., human) framework regions; and the VH domain further comprises primate (e.g., human) framework regions.

In a specific embodiment, provided herein are polynucleotides comprising a nucleotide sequence encoding an antibody, or a fragment or domain thereof (e.g., VL domain or VH domain), designated herein as antibody 1F2, 1F4, 3G1, 4B2, or 4F11.

Also provided are polynucleotides that hybridize under high stringency, intermediate or lower stringency hybridization conditions to antisense polynucleotides of polynucleotides that encode an antibody described herein or a fragment thereof (e.g., VL domain or VH domain). In specific embodiments, a polynucleotide described herein hybridizes under high stringency, or intermediate stringency hybridization conditions to an antisense polynucleotide of a polynucleotide encoding a VL domain, e.g., SEQ ID NO: 82, and/or VH domain, e.g., SEQ ID NO: 81, provided herein. In specific embodiments, a polynucleotide described herein hybridizes under high stringency, or intermediate stringency hybridization conditions to an antisense polynucleotide of a polynucleotide comprising SEQ ID NO: 81 or 82.

In specific embodiments, a polynucleotide described herein hybridizes under high stringency, or intermediate stringency hybridization conditions to an antisense polynucleotide of a polynucleotide encoding a VL domain, e.g., SEQ ID NO: 84, and/or VH domain, e.g., SEQ ID NO: 83, provided herein. In specific embodiments, a polynucleotide described herein hybridizes under high stringency, or intermediate stringency hybridization conditions to an antisense polynucleotide of a polynucleotide comprising SEQ ID NO: 83 or 84.

In specific embodiments, a polynucleotide described herein hybridizes under high stringency, or intermediate stringency hybridization conditions to an antisense polynucleotide of a polynucleotide encoding a VL domain, e.g., SEQ ID NO: 86, and/or VH domain, e.g., SEQ ID NO: 85, provided herein. In specific embodiments, a polynucleotide described herein hybridizes under high stringency, or intermediate stringency hybridization conditions to an antisense polynucleotide of a polynucleotide comprising SEQ ID NO: 85 or 86.

In specific embodiments, a polynucleotide described herein hybridizes under high stringency, or intermediate stringency hybridization conditions to an antisense polynucleotide of a polynucleotide encoding a VL domain, e.g., SEQ ID NO: 88, and/or VH domain, e.g., SEQ ID NO: 87, provided herein. In specific embodiments, a polynucleotide described herein hybridizes under high stringency, or intermediate stringency hybridization conditions to an antisense polynucleotide of a polynucleotide comprising SEQ ID NO: 87 or 88.

In specific embodiments, a polynucleotide described herein hybridizes under high stringency, or intermediate stringency hybridization conditions to an antisense polynucleotide of a polynucleotide encoding a VL domain, e.g., SEQ ID NO: 90, and/or VH domain, e.g., SEQ ID NO: 89, provided herein. In specific embodiments, a polynucleotide described herein hybridizes under high stringency, or intermediate stringency hybridization conditions to an antisense polynucleotide of a polynucleotide comprising SEQ ID NO: 89 or 90.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3.

Also provided herein are polynucleotides encoding an antibody that are optimized, e.g., by codon/RNA optimization, replacement with heterologous signal sequences, and elimination of mRNA instability elements. Methods to generate optimized nucleic acids encoding an antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of an antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an antibody encoded by polynucleotides that have not been optimized.

In certain embodiments, an optimized polynucleotide sequence encoding an antibody described herein or a fragment thereof (e.g., VL region and/or VH region) can hybridize to an antisense polynucleotide of an unoptimized polynucleotide encoding an antibody described herein or a fragment thereof (e.g., VL region and/or VH region). In specific embodiments, an optimized nucleotide sequence encoding an antibody described herein or a fragment thereof (e.g., VL region and/or VH region) hybridizes under high stringency conditions to an antisense polynucleotide of an unoptimized polynucleotide encoding an antibody described herein or a fragment thereof (e.g., VL region and/or VH region). In a specific embodiment, an optimized nucleotide sequence encoding an antibody described herein or a fragment thereof (e.g., VL region and/or VH region) hybridizes under intermediate or lower stringency hybridization conditions to an antisense polynucleotide of an unoptimized polynucleotide encoding an antibody described herein or a fragment thereof (e.g., VL region and/or VH region). Information regarding hybridization conditions have been described, see, e.g., U.S. Patent Application Publication No. US 2005/0048549 (e.g., paragraphs 72-73), which is incorporated herein by reference in its entirety.

The polynucleotides can be obtained, and the nucleotide sequence of the polynucleotides determined, by any method known in the art. Nucleotide sequences encoding antibodies described herein, and modified forms of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light domain and/or the variable heavy domain of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding an antibody can be readily isolated and sequenced using conventional procedures (e.g., by using oligonucleotide probes that are capable of binding specifically to genes encoding the heavy and light chains of the antibody). Hybridoma cells can serve as a source of such DNA. Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of antibodies in the recombinant host cells.

In phage display methods, functional antibody domains are displayed on the surface of phage particles which carry the polynucleotide sequences encoding them. In particular, a library of DNA sequences encoding VH and VL domains are generated (e.g., amplified from animal cDNA libraries such as human cDNA libraries or random libraries are generated by chemical synthesis). The DNA encoding the VH and VL domains are recombined together with an scFv linker by PCR and cloned into a phagemid vector. The vector is electroporated in *E. coli* and the *E. coli* is infected with helper phage. Phage expressing an antigen-binding domain that binds to a particular antigen can be selected or identified with antigen, e.g., using labeled antigen or antigen bound or captured to a solid surface or bead. After phage selection, the antibody coding regions from the phage can be isolated and used to generate whole antibodies, including human antibodies, or any other desired antigen-binding fragment, and expressed in any desired host, including mammalian cells, insect cells, plant cells, yeast, and bacteria, e.g., as described below. Techniques to recombinantly produced Fab, Fab' and $F(ab')_2$ fragments can also be employed using methods known in the art such as those disclosed in PCT Publication No. WO 92/22324; Mullinax et al., 1992, *BioTechniques,* 12(6):864-869; Sawai et al., 1995, *AJRI,* 34:26-34; and Better et al., 1988, *Science,* 240:1041-1043.

Antibodies can be isolated from antibody phage libraries generated using the techniques described in McCafferty et al., *Nature,* 348:552-554 (1990). Clackson et al., *Nature,* 352:624-628 (1991). Marks et al., *J. Mol. Biol.,* 222:581-597 (1991) describe the isolation of murine and human antibodies, respectively, using phage libraries. Chain shuffling can be used in the production of high affinity (nM range) human antibodies (Marks et al., *Bio Technology,* 10:779-783 (1992)), as well as combinatorial infection and in vivo recombination as a strategy for constructing very large phage libraries (Waterhouse et al., *Nuc. Acids. Res.,* 21:2265-2266 (1993)).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise a promoter, a secretion signal, a cloning site for the variable domain, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

In a specific embodiment, provided herein are two vectors (e.g., plasmids or viruses), wherein one vector comprises the VH domain of an antibody described herein, and the second vector comprises the VL domain of an antibody described herein.

In a non-limiting example, the Dyax (Cambridge, MA) technology platform can be used to convert Fab-phage or Fabs to complete IgG antibodies, such as the Dyax pR rapid reformatting vectors (RR). Briefly, by PCR, a Fab-encoding DNA fragment is inserted into a Dyax pR-RRV between a eukaryotic leader sequence and an IgG heavy chain constant region cDNA. Antibody expression is driven by the human cytomegalovirus (hCMV). In a second cloning step, bacterial regulatory elements are replaced by the appropriate eukaryotic sequences (i.e., the IRES (internal ribosome entry site) motif). The expression vector can also include the SV40 origin of replication. The Dyax pRh1(a,z), pRh1(f), pRh4 and pRm2a are expression vectors allowing expression of reformatted FAbs as human IgG1 (isotype a,z), human IgG1 (isotype F), human IgG4, and mouse IgG2a, respectively. Expressing vectors can be introduced into a suitable host cell (e.g., HEK293T cells, CHO cells)) for expression and purification.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

In some embodiments, a polynucleotide(s) encoding an antibody provided herein is isolated. In other embodiments, a polynucleotide(s) encoding an antibody provided herein is not isolated. In yet other embodiments, a polynucleotide(s) encoding an antibody provided herein is integrated, e.g., into chromosomal DNA or an expression vector. In specific embodiments, a polynucleotide(s) encoding an antibody provided herein is not integrated into chromosomal DNA.

5.3 Antibody Production

In one aspect, provided herein are methods for making an antibody described herein, which binds to an influenza B virus NA. In a specific embodiment, an antibody described herein (e.g., an antigen-binding fragment), which binds to an influenza B virus NA, may be prepared, expressed, created or isolated by any means that involves creation, e.g., via synthesis or genetic engineering of sequences. In a specific embodiment, such an antibody comprises sequences that are encoded by DNA sequences that do not naturally exist within the antibody germline repertoire of an animal or mammal (e.g., a human).

In certain aspects, a method for making an antibody described herein, which binds to an influenza B virus NA, comprises the step of culturing a cell (e.g., host cell or hybridoma cell) that expresses the antibody. In certain embodiments, the method for making an antibody described herein further comprises the step of purifying the antibody expressed by the cell. In certain aspects, a method for making an antibody described herein (e.g., an antigen-binding fragment thereof), which binds to an influenza B virus NA, comprises the step of culturing a cell (e.g., host cell or hybridoma cell) that comprises polynucleotides or vectors encoding the antibody. In a particular aspect, provided herein are methods for producing an antibody described herein (e.g., an antigen-binding fragment thereof), comprising expressing such antibody from a host cell.

In certain aspects, provided herein are cells (e.g., host cells) expressing (e.g., recombinantly expressing) the antibodies described herein (e.g., an antigen-binding fragment thereof) and related expression vectors. In another aspect, provided herein are vectors (e.g., expression vectors) comprising polynucleotides comprising nucleotide sequences encoding antibodies (e.g., an antigen-binding fragment) for recombinant expression in host cells, preferably in mammalian cells. Also provided herein are host cells comprising a polynucleotide encoding an antibody, or vectors comprising a polynucleotide encoding an antibody for recombinantly expressing an antibody described herein (e.g., antibody 1F2, 1F4, 3G1, 4B2, or 4F11, or another antibody described in Section 5.1 or 5.2, supra). In a specific embodiment, provided herein is a host cell comprising two vectors, wherein the first vector comprises a polynucleotide of an antibody described herein (e.g., antibody 1F2, 1F4, 3G1, 4B2, or 4F11, or another antibody described in Section 5.1 or 5.2, supra) and the second vector comprises a polynucleotide encoding an antibody for recombinantly expressing an antibody described herein (e.g., antibody 1F2, 1F4, 3G1, 4B2, or 4F11, or another antibody described in Section 5.1 or 5.2, supra). Examples of cells that may be used include those described in this section and in Section 6 and/or Section 7, infra. The cells may be primary cells or cell lines. In a particular aspect, provided herein are hybridoma cells expressing an antibody described herein, e.g., antibody 1F2, 1F4, 3G1, 4B2, or 4F11. In a particular embodiment, the host cell is isolated from other cells. In another embodiment, the host cell is not found within the body of a subject.

Antibodies described herein (e.g., monoclonal antibodies, such as chimeric or humanized antibodies, or an antigen-binding fragment thereof) that bind to an influenza B virus NA can be produced by any method known in the art for the synthesis of antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, NY; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, TRL Press; Eckstein (ed.) (1991) *Oligonucleotides and Analogues: A Practical Approach*, TRL Press; Birren et al. (eds.) (1999) *Genome Analysis: A Laboratory Manual*, Cold Spring Harbor Laboratory Press.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563 681 (Elsevier, N.Y., 1981). The term "monoclonal antibody" as used herein is not limited to antibodies produced through hybridoma technology.

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will bind to the protein (e.g., influenza B virus NA) used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

Additionally, a RIMMS (repetitive immunization multiple sites) technique can be used to immunize an animal (Kilptrack et al., 1997 Hybridoma 16:381-9, incorporated by reference in its entirety).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as those derived from MOPC-21 and MPC-11 mouse tumors available from the Salk Institute Cell Distribution Center, San Diego, CA, USA, and SP-2 or X63-Ag8.653 cells available from the American Type Culture Collection, Rockville, MD, USA. Human myeloma and mouse-human heteromyeloma cell lines also have been described for the production of human monoclonal antibodies (Kozbor, *J. Immunol.,* 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against an influenza B virus NA. The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (*Goding, Monoclonal Antibodies: Principles and Practice*, pp. 59-103 (Academic Press, 1986)). Suitable culture media for this purpose include, for example, D-MEM or RPMI 1640 medium. Alternatively, clonal cells can be isolated using a semi-solid agar supplemented with HAT (Stemcell Technologies). In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

In some embodiments, mice (or other animals, such as rats, monkeys, donkeys, pigs, sheep, goats, hamsters, or dogs) can be immunized with an antigen (e.g., an influenza B virus NA) and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP2/0 available from the American Type Culture Collection (ATCC®) (Manassas, VA), to form hybridomas. Hybridomas are selected and cloned by limited dilution.

In certain embodiments, lymph nodes of the immunized mice are harvested and fused with NS0 myeloma cells.

The hybridoma clones are then assayed by methods known in the art for cells that secrete antibodies capable of binding a polypeptide of the antigen (e.g., an influenza B virus NA). Ascites fluid, which generally contains high levels of antibodies, can be generated by immunizing mice with positive hybridoma clones.

Accordingly, described herein are methods of making antibodies described herein by culturing a hybridoma cell secreting an antibody. In certain embodiments, the method of making an antibody described herein further comprises the step of purifying the antibody.

In specific embodiments, the hybridoma is generated by fusing splenocytes isolated from a mouse (or other animal, such as rat, monkey, donkey, pig, sheep, or dog) immunized with an influenza B virus NA with myeloma cells and then screening the hybridomas resulting from the fusion for hybridoma clones that secrete an antibody able to bind to the influenza B virus NA. In certain embodiments, the hybridoma is generated by fusing lymph nodes isolated from a mouse (or other animal, such as rat, monkey, donkey, pig, sheep, or dog) immunized with an influenza B virus NA with myeloma cells, and then screening the hybridomas resulting from the fusion for hybridoma clones that secrete an antibody able to bind to the influenza B virus NA.

Antibodies described herein include antibody fragments that recognize an influenza B virus NA and can be generated by any technique known to those of skill in the art. For example, Fab and $F(ab')_2$ fragments described herein can be produced by proteolytic cleavage of immunoglobulin molecules, using enzymes such as papain (to produce Fab fragments) or pepsin (to produce $F(ab')_2$ fragments). A Fab fragment corresponds to one of the two identical arms of an antibody molecule and contains the complete light chain paired with the VH and CH1 domains of the heavy chain. A $F(ab')_2$ fragment contains the two antigen-binding arms of an antibody molecule linked by disulfide bonds in the hinge region.

Further, the antibodies described herein can also be generated using various phage display methods known in the art. In phage display methods, functional antibody domains are displayed on the surface of phage particles that carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce antibody fragments such as Fab, Fab' and F(ab')2 fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043.

In one aspect, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it can be preferable to use human, humanized or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741.

A chimeric antibody is a molecule in which different portions of the antibody are derived from different immunoglobulin molecules. For example, a chimeric antibody can contain a variable region of a mouse monoclonal antibody fused to a constant region of a human antibody. Methods for producing chimeric antibodies are known in the art. See, e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415.

In some embodiments, humanized antibodies are produced. A humanized antibody is capable of binding to a predetermined antigen and comprises a framework region having substantially the amino acid sequence of a human immunoglobulin and CDRs having substantially the amino acid sequence of a non-human immunoglobulin (e.g., a murine immunoglobulin). Humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), which is incorporated by reference herein in its entirety.

In some embodiments, humanized antibodies are produced. In particular embodiments, an antibody described herein, which binds to the same epitope of an influenza B virus NA as antibody 1F2, 1F4, 3G1, 4B2 or 4F11, is a humanized antibody. In particular embodiments, an antibody described herein, which competitively blocks (e.g., in a dose-dependent manner) antibody 1F2, 1F4, 3G1, 4B2 or 4F11 from binding to an influenza B virus NA, is a humanized antibody. In certain embodiments, an antibody described herein, which binds to an influenza B virus NA, is a humanized antibody derived from antibody 1F2, 1F4, 3G1, 4B2 or 4F11. For example, such a humanized antibody comprises a VL domain comprising VL CDR1, VL CDR2, and VL CDR3, and/or a VH domain comprising VH CDR1, VH CDR2, and VH CDR3, of the antibody from which it was derived (e.g., antibody 1F2, 1F4, 3G1, 4B2 or 4F11).

Human antibodies can be produced using any method known in the art. In certain embodiments, provided herein are human antibodies which can compete with antibody 1F2, 1F4, 3G1, 4B2 or 4F11 for specific binding to an influenza B virus NA. In certain embodiments, provided herein are human antibodies which bind to the same epitope of an influenza B virus NA as the epitope to which antibody 1F2, 1F4, 3G1, 4B2 or 4F11 binds. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., an influenza B virus NA). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, Int. Rev. Immunol. 13:65-93. For a detailed discussion of this technology for producing human antibodies and human monoclonal antibodies and protocols for producing such antibodies, see, e.g., PCT publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that bind to a target antigen (e.g., an influenza B virus NA). Such methods are known and are described in the art, see, e.g., Shinmoto et al., Cytotechnology, 2004, 46:19-23; Naganawa et al., Human Antibodies, 2005, 14:27-31.

In some embodiments, human antibodies can be generated by inserting polynucleotides encoding human CDRs (e.g., VL CDRs and/or VH CDRs) of an antibody into an expression vector containing nucleotide sequences encoding human framework region sequences. In certain embodiments, such expression vectors further comprise nucleotide sequences encoding a constant region of a human light and/or heavy chain. In some embodiments, human antibodies can be generated by inserting human CDRs (e.g., VL CDRs and/or VH CDRs) of an antibody obtained from a phage library into such human expression vectors.

In certain embodiments, a human antibody can be generated by selecting human CDR sequences that are homologous (or substantially homologous) to non-human CDR sequences of a non-human antibody and selecting human framework sequences that are homologous (or substantially homologous) to non-human framework sequences of a non-human antibody.

Single domain antibodies, for example, antibodies lacking the light chains, can be produced by methods well-known in the art. See Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301.

Bispecific antibodies are antibodies that have binding specificities for at least two different epitopes. Exemplary bispecific antibodies may bind to two different epitopes of an antigen or to two different epitopes of two different antigens. In specific embodiments, a bispecific antibody has two distinct antigen-binding domains, wherein each domain specifically binds to a different antigen. Other such antibodies may bind a first antigen (e.g., an influenza B virus NA) and further bind a second antigen. Bispecific antibodies can be prepared as full-length antibodies or antibody fragments (e.g., F(ab'): bispecific antibodies).

Methods for making bispecific antibodies are known in the art. (See, for example, Millstein et al., Nature, 305:537-539 (1983); Traunecker et al., EMBO J., 10:3655-3659 (1991); Suresh et al., Methods in Enzymology, 121:210 (1986); Kostelny et al., J. Immunol., 148(5):1547-1553 (1992); Hollinger et al., Proc. Natl. Acad. Sci. USA, 90:6444-6448 (1993); Gruber et al., J. Immunol., 152:5368 (1994); U.S. Pat. Nos. 4,474,893; 4,714,681; 4,925,648; 5,573,920; 5,601,81; 95,731,168; 4,676,980; and 4,676,980, WO 94/04690; WO 91/00360; WO 92/200373; WO 93/17715; WO 92/08802; and EP 03089.)

Further, antibodies that bind to an influenza B virus NA can, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8):2429-2438).

Recombinant expression of an antibody described herein (e.g., a full-length antibody, heavy and/or light chain of an antibody, or a single chain antibody described herein) that binds to an influenza B virus NA, can for example, involve construction of vectors (e.g., expression vectors) containing a polynucleotide that encodes the antibody or fragments thereof (e.g., VL domain and/or VH domain). Once a polynucleotide encoding an antibody molecule, heavy and/or light chain of an antibody, or antigen-binding fragment thereof described herein has been obtained, a vector for the production of the antibody molecule can be produced by recombinant DNA technology using techniques well-known in the art. Methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable domain of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036;

and U.S. Pat. No. 5,122,464) and the variable domain of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein or a fragment thereof. Thus, provided herein are host cells containing a polynucleotide encoding an antibody described herein or fragments thereof, or a heavy or light chain thereof, or antigen-binding fragment thereof, or a single chain antibody described herein, operably linked to a promoter for expression of such sequences in the host cell. In certain embodiments, e.g., for the expression of double-chained antibodies, vectors encoding both the heavy and light chains individually can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain of an antibody described herein, or a fragment thereof, and a second vector comprising a polynucleotide encoding a light chain of an antibody described herein, or a fragment thereof. In other embodiments, a first host cell comprises a first vector comprising a polynucleotide encoding a heavy chain of an antibody described herein, or a fragment thereof, and a second host cell comprises a second vector comprising a polynucleotide encoding a light chain of an antibody described herein.

A variety of host-expression vector systems can be utilized to express antibody molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, MDCK, HEK 293, NS0, PER.C6, VERO, CRL7O3O, HsS78Bst, HeLa, and NIH 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, a mammalian expression vector is pOptiVEC™ or pcDNA3.3. Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In certain embodiments, antibodies described herein are produced by CHO cells or NS0 cells. In a specific embodiment, the expression of nucleotide sequences encoding antibodies described herein (or fragments thereof) which bind to an influenza B virus NA is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruther et al., 1983, EMBO 12:1791), in which the antibody coding sequence can be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, Methods in Enzymol. 153:51-544).

As used herein, the term "host cell" refers to any type of cell, e.g., a primary cell or a cell from a cell line. In specific embodiments, the term "host cell" refers a cell transfected with a polynucleotide and the progeny or potential progeny of such a cell. Progeny of such a cell may not be identical to the parent cell transfected with the polynucleotide due to mutations or environmental influences that may occur in succeeding generations or integration of the polynucleotide into the host cell genome.

In addition, a host cell strain can be chosen which modulates the expression of the inserted sequences or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, COS, MDCK, HEK 293, NIH 3T3, W138, BT483, Hs578T, HTB2, BT2O and T47D, NS0 (a murine myeloma cell line that does not endogenously produce any immunoglobulin chains), CRL7O3O and HsS78Bst cells. In certain embodiments, humanized monoclonal antibodies described herein are produced in mammalian cells, such as CHO cells.

For long-term, high-yield production of recombinant proteins, stable expression is preferred. For example, cell lines that stably express the antibody molecule can be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the antibody molecule. Such engineered cell lines can be particularly useful in screening and evaluation of compositions that interact directly or indirectly with the antibody molecule.

A number of selection systems can be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-2 15); and hygro, which confers resistance to hygromycin (Santerre et al., 1984, Gene 30:147). Methods commonly known in the art of recombinant DNA technology can be routinely applied to select the desired recombinant clone, and such methods are described, for example, in Ausubel et al. (eds.), *Current Protocols in Molecular Biology*, John Wiley & Sons, N Y (1993); Kriegler, *Gene Transfer and Expression*, A Laboratory Manual, Stockton Press, N Y (1990); and in Chapters 12 and 13, Dracopoli et al. (eds.), *Current Protocols in Human Genetics*, John Wiley & Sons, N Y (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell can be co-transfected with two or more expression vectors described herein, the first vector encoding a heavy chain derived polypeptide and the second vector encoding a light chain derived polypeptide. In a specific embodiment, a host cell comprises two expression vectors: one vector comprising a polynucleotide sequence comprising a nucleotide sequence encoding a heavy chain variable region of an antibody described herein (e.g., 1F1, 1F4, 3G1, 4B2, or 4F11) and a second vector comprising a polynucleotide sequence comprising a nucleotide sequence encoding a light chain variable region of an antibody described herein (e.g., 1f1 1F4, 3G1, 4B2, or 4F11). The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES. Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody (e.g., a monoclonal antibody, such as a humanized or chimeric antibody or an antigen-binding fragment thereof) described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals that are involved in the synthesis of the protein. Accordingly, such preparations of the antibody have less than about 30%, 20%, 10%, 5% (by dry weight) of chemical precursors or compounds other than the antibody of interest. In a specific embodiment, antibodies described herein are isolated or purified.

5.4 Compositions

Provided herein are compositions (e.g., pharmaceutical compositions) comprising an antibody having the desired degree of purity in a physiologically acceptable carrier, excipient or stabilizer (*Remington's Pharmaceutical Sciences* (1990) Mack Publishing Co., Easton, PA). In a specific embodiment, a composition comprises an antibody described herein and an acceptable carrier or excipient. In a specific embodiment, the compositions comprise an antibody conjugated to a moiety such as described in Section 5.1.2, supra. In certain embodiments, the compositions comprise an antibody that has been modified to increase its half-life. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ PLURONICS™ or polyethylene glycol (PEG).

In a specific embodiment, pharmaceutical compositions comprise an antibody, and optionally one or more additional prophylactic or therapeutic agents, in a pharmaceutically acceptable carrier. In a specific embodiment, pharmaceutical compositions comprise an effective amount of an antibody, and optionally one or more additional prophylactic of therapeutic agents, in a pharmaceutically acceptable carrier. See Section 5.5.2, infra, for examples of prophylactic or therapeutic agents. In some embodiments, the antibody is the only active ingredient included in the pharmaceutical composition. In a specific embodiment, pharmaceutical compositions comprise an antibody conjugated to a moiety such as described in Section 5.1.2, and optionally one or more additional prophylactic or therapeutic agents, in a pharmaceutically acceptable carrier. In a specific embodiment, pharmaceutical compositions comprise an effective amount of an antibody conjugated to a moiety such as described in Section 5.12, and optionally one or more additional prophylactic of therapeutic agents, in a pharmaceutically acceptable carrier. See Section 5.5.2, infra, for examples of prophylactic or therapeutic agents. In some embodiments, the antibody conjugated to a moiety such as described in Section 5.1.2 is the only active ingredient included in the pharmaceutical composition. Pharmaceutical compositions described herein can be useful in the prevention and/or treatment of influenza virus (e.g., influenza B virus) infection or influenza virus disease (e.g., influenza B virus disease). Further, pharmaceutical compositions described herein can be useful in the prevention, treatment and/or management of influenza virus disease.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition may be formulated for any route of administration to a subject. Specific examples of routes of administration include intranasal, oral, pulmonary, transdermal, intradermal, parenteral, and mucosal. In a specific embodiment, the composition is formulated for intranasal or intramuscular administration. In a specific embodiment, the composition is formulation for intramuscular administration. In a specific embodiment, the composition is formulated for mucosal administration. In a particular embodiment, the composition is formulated for intranasal administration. For example, the composition may be formulated as an aersoal. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An antibody can be formulated as an aerosol for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

An antibody can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

In certain embodiments, a pharmaceutical composition comprising an antibody is a lyophilized powder, which can be reconstituted for administration as solutions, emulsions and other mixtures. It may also be reconstituted and formulated as solids or gels. The lyophilized powder is prepared by dissolving an antibody provided herein, or a pharmaceutically acceptable derivative thereof, in a suitable solvent. In some embodiments, the lyophilized powder is sterile. The solvent may contain an excipient that improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

An antibody can also, for example, be formulated in liposomes. Liposomes containing the molecule of interest are prepared by methods known in the art, such as described in Epstein et al. (1985) *Proc. Natl. Acad. Sci. USA* 82:3688; Hwang et al. (1980) *Proc. Natl. Acad. Sci. USA* 77:4030; and U.S. Pat. Nos. 4,485,045 and 4,544,545. Liposomes with enhanced circulation time are disclosed in U.S. Pat. No. 5,013,556. In one embodiment, liposomal suspensions may also be suitable as pharmaceutically acceptable carriers. These can be prepared according to methods known to those skilled in the art. For example, liposome formulations can be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound comprising an antibody described herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

An antibody can also be entrapped in a microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* (1990) Mack Publishing Co., Easton, PA.

Sustained-release preparations can also be prepared. Suitable examples of sustained-release preparations include semipermeable matrices of solid hydrophobic polymers containing the antagonist, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The antibodies and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

The compositions to be used for in vivo administration can be sterile. This is readily accomplished by filtration through, e.g., sterile filtration membranes.

In a specific embodiment, nucleic acids comprising sequences encoding an antibody described herein are administered to a subject by way of gene therapy. Gene therapy refers to therapy performed by the administration to a subject of an expressed or expressible nucleic acid. Encompassed herein are any of the methods for gene therapy available in the art. For general review of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5):155-215. For a review of methods of delivery of transgenes encoding antibodies, see, e.g., Deal, 2015, Curr. Opin. Immunol. 2015 August, 35:113-22; Deal, 2015, Curr Opin HIV AIDS. 2015 May, 10(3):190-7; Marschall, 2015, MAbs. 7(6):1010-35. In a specific embodiment, an mRNA encoding an antibody described herein is administered to a subject. Techniques known to one of skill in the art may be used to administer an mRNA encoding an antibody to a subject. For methods of delivery of mRNA encoding antibodies, see, e.g., U.S. Patent Application Publication No. US20130244282A1; U.S. Patent Application Publication No. US 2016/0158354A1; and International Patent Application No. WO2016014846A1, each of which is incorporated herein by reference in its entirety.

Methods commonly known in the art of recombinant DNA technology which can be used are described in Ausubel et al. (eds.), Current Protocols in Molecular Biology, John Wiley & Sons, N Y (1993); and Kriegler, Gene Transfer and Expression, A Laboratory Manual, Stockton Press, NY (1990).

5.5 Prophylactic and Therapeutic Uses of Antibodies

In one aspect, provided herein are methods for preventing influenza virus disease (e.g., disease caused by an influenza B virus) comprising administering an antibody described herein. In a specific embodiment, provided herein is a method for preventing influenza virus disease (e.g., disease caused by an influenza B virus) in a subject comprising administering to the subject an effective amount of an antibody described herein. In a specific embodiment, provided herein is a method for preventing influenza virus disease (e.g., disease caused by an influenza B virus) in a subject comprising administering to the subject a pharmaceutical composition comprising an effective amount of an antibody described herein. In a specific embodiment, the antibody is a protein or a protein conjugate. In a specific embodiment, the antibody is administered to the subjects as polynucleotide sequence comprising a nucleotide sequence encoding the antibody. In another specific embodiment, the antibody administered to the subject is a conjugated moiety such as described in Section 5.1.2. In a particular embodiment, the administration of an effective amount of the antibody to the subject inhibits or reduces in the development or onset of an influenza virus disease. In a specific embodiment, provided herein is a method for preventing influenza virus disease (e.g., disease caused by an influenza B virus) in a subject comprising administering to the subject an effective amount of an antibody described herein and another therapy, such as known to one of skill in the art or described herein (e.g., in Section 5.5.2, infra). In a specific embodiment, provided herein is a method for preventing influenza virus disease (e.g., disease caused by an influenza B virus) in a subject comprising administering to the subject a pharmaceutical composition comprising an effective amount of an antibody described herein, and another therapy, such as known to one of skill in the art or described herein (e.g., in Section 5.5.2, infra). In a particular embodiment, the administration of an effective amount of the antibody to the subject inhibits or reduces in the development or onset of an influenza virus disease. In another embodiment, the administration of an effective amount of the antibody to the subject inhibits or reduces onset, development and/or severity of a symptom thereof (e.g., fever, myalgia, edema, inflammatory infiltrates) of influenza virus disease. In another embodiment, the administration of an effective amount of the antibody inhibits or reduces in the recurrence of an influenza virus disease or a symptom associated therewith.

In specific embodiments, the administration of an effective amount of an antibody to a subject results in one, two, three, four, or more of the following: (i) the reduction or inhibition of the spread of influenza virus from one cell to another cell; (ii) the reduction or inhibition of the spread of influenza virus from one organ or tissue to another organ or tissue; (iii) the reduction or inhibition of the spread of influenza virus from one region of an organ or tissue to another region of the organ or tissue (e.g., the reduction in the spread of influenza virus from the upper to lower respiratory tract); (iv) the prevention of influenza virus disease after after exposure to an influenza virus; (v) the reduction or inhibition in influenza virus infection and/or replication; and/or (vi) prevention of the onset or development of one or more symptoms associated with influenza virus disease or infection.

In another aspect, provided herein are methods for treating an influenza virus (e.g., influenza B virus) infection or an influenza virus disease (e.g., disease caused by an influenza B virus) comprising administering an antibody described herein. In a specific embodiment, provided herein is a method for treating an influenza virus (e.g., influenza B virus) infection or an influenza virus disease (e.g., disease caused by an influenza B virus) in a subject comprising administering to the subject an effective amount of an antibody described herein. In another specific embodiment, provided herein is a method for treating an influenza virus (e.g., influenza B virus) infection or an influenza virus disease (e.g., disease caused by an influenza B virus) in a subject comprising administering to the subject a pharmaceutical composition comprising an effective amount of an antibody described herein. In another specific embodiment, provided herein is a method for treating an influenza virus (e.g., influenza B virus) infection or an influenza virus disease (e.g., disease caused by an influenza B virus) comprising administering to the subject an effective amount of an antibody described herein and another therapy, such as known to one of skill in the art or described herein (e.g., in Section 5.5.2, infra). In another specific embodiment, provided herein is a method for treating an influenza virus (e.g., influenza B virus) infection or an influenza virus disease (e.g., disease caused by an influenza B virus) in a subject comprising administering to the subject a pharmaceutical composition comprising an effective amount of an antibody described herein, and another therapy, such as known to one of skill in the art or described herein (e.g., in Section 5.5.2, infra). In a specific embodiment, the antibody is administered as a polynucleotide sequence comprising a nucleotide sequence encoding the antibody. In another specific embodiment, the antibody that is administered to the subject is conjugated to a moiety such as described in Section 5.1.2. In a particular embodiment, the administration of an effective amount of the antibody to the subject inhibits or reduces in the development of an influenza virus disease. In another embodiment, the administration of an effective amount of the antibody to the subject inhibits or reduces onset, development and/or severity of a symptom thereof (e.g., fever, myalgia, edema, inflammatory infiltrates) of influenza virus disease. In another embodiment, the administration of an effective amount of the antibody inhibits or reduces duration of an influenza virus disease or a symptom associated therewith. In another embodiment, the administration of an effective amount of the antibody reduces organ failure associated with an influenza virus infection or influenza virus disease. In another embodiment, the administration of an effective amount of the antibody reduces the hospitalization of the subject. In another embodiment, the administration of an effective amount of the antibody reduces the length of hospitalization of the subject. In another embodiment, the administration of an effective amount of the antibody increases the overall survival of subjects with an influenza virus infection or a disease associated therewith. In another embodiment, the administration of an effective amount of the antibody prevents the onset or progression of a secondary infection associated with an influenza virus infection.

In a specific embodiment, administration of an antibody(ies) to a subject reduces the incidence of hospitalization by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the incidence of hospitalization in the absence of administration of said antibody(ies).

In a specific embodiment, administration of an antibody(ies) to a subject reduces mortality by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the mortality in the absence of administration of said antibody(ies).

In certain embodiments, the administration of an effective amount of an antibody described herein to a subject results in one, two, three, four, five, or more of the following effects: (i) reduction or amelioration in the severity of an influenza virus infection, an influenza virus disease or a symptom associated therewith; (ii) reduction in the duration of an influenza virus infection, an influenza virus disease or a symptom associated therewith; (iii) prevention of the progression of an influenza virus infection, an influenza virus disease or a symptom associated therewith; (iv) regression of an influenza virus infection, an influenza virus disease or a symptom associated therewith; (v) prevention of the development or onset of an influenza virus infection, an influenza virus disease or a symptom associated therewith; (vi) prevention of the recurrence of an influenza virus infection, an influenza virus disease or a symptom associated therewith; (vii) reduction or prevention of the spread of an influenza virus from one cell to another cell, one tissue to another tissue, or one organ to another organ; (viii) prevention or reduction of the spread/transmission of an influenza virus from one subject to another subject; (ix) reduction in organ failure associated with an influenza virus infection or influenza virus disease; (x) reduction in the hospitalization of a subject; (xi) reduction in the hospitalization length; (xii) an increase in the survival of a subject with an influenza virus infection or a disease associated therewith; (xiii) elimination of an influenza virus infection or a disease associated therewith; (xiv) inhibition or reduction in influenza virus replication; (xv) inhibition or reduction in the binding or fusion of influenza virus to a host cell(s); (xvi) inhibition or reduction in the entry of an influenza virus into a host cell(s); (xvii) inhibition or reduction of replication of the influenza virus genome; (xviii) inhibition or reduction in the synthesis of influenza virus proteins; (xix) inhibition or reduction in the assembly of influenza virus particles; (xx) inhibition or reduction in the release of influenza virus particles from a host cell(s); (xxi) reduction in influenza virus titer; (xxii) the reduction in the number of symptoms associated with an influenza virus infection or an influenza virus disease; (xxiii) enhancement, improvement, supplementation, complementation, or augmentation of the prophylactic or therapeutic effect(s) of another therapy; (xxiv) prevention of the onset or progression of a secondary infection associated with an influenza virus infection; and/or (xxv) prevention of the onset or diminution of disease severity of bacterial pneumonias occurring secondary to influenza virus infections.

In a specific embodiment, the influenza virus disease prevented or treated is a respiratory illness caused by an influenza B virus.

In a specific embodiment, administration of an antibody(ies) prevents or inhibits influenza virus from binding to its host cell receptor by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to influenza virus binding to its host cell receptor in the absence of said antibody(ies) or in the presence of a negative control in an assay known to one of skill in the art or described herein.

In a specific embodiment, administration of an antibody(ies) inhibits or reduces influenza virus replication by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to replication of influenza virus in the absence of said antibody(ies) or in the presence of a negative control in an assay known to one of skill in the art or described herein. Inhibition of influenza virus replication can be determined by detecting the influenza virus titer in a biological specimen from a subject using methods known in the art (e.g., Northern blot analysis, RT-PCR, Western Blot analysis, etc.).

In a specific embodiment, administration of an antibody(ies) results in reduction of about 1-fold, about 1.5-fold, about 2-fold, about 3-fold, about 4-fold, about 5-fold, about 8-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, about 100-fold, about 105 fold, about 110-fold, about 115-fold, about 120 fold, about 125-fold or higher in influenza virus titer in the subject. The fold-reduction in influenza virus titer may be as compared to a negative control, as compared to another treatment, or as compared to the titer in the patient prior to antibody administration.

In a specific embodiment, administration of an antibody(ies) results in a reduction of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 5 logs, 2 to 10 logs, 2 to 5 logs, or 2 to 10 logs in influenza virus titer in the subject. The log-reduction in influenza virus titer may be as compared to a negative control, as compared to another treatment, or as compared to the titer in the patient prior to antibody administration.

In a specific embodiment, administration of an antibody(ies) inhibits or reduces influenza virus infection of a subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to influenza virus infection of a subject in the absence of said antibody(ies) or in the presence of a negative control in an assay known to one of skill in the art or described herein.

In a specific embodiment, administration of an antibody(ies) inhibits or reduces the spread of influenza virus in a subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the spread of influenza virus in a subject in the absence of said an antibody(ies) or in the presence of a negative control in an assay known to one of skill in the art or described herein.

In a specific embodiment, administration of an antibody(ies) inhibits or reduces the spread of influenza virus between a subject and at least one other subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the spread of influenza virus between a subject and at least one other subject in the absence of said antibody(ies) or in the presence of a negative control in an assay known to one of skill in the art or described herein.

In a specific embodiment, administration of an antibody(ies) to a subject reduces the number of and/or the frequency of symptoms of influenza virus disease or infection in the subject (exemplary symptoms of influenza virus disease include, but are not limited to, body aches (especially joints and throat), fever, nausea, headaches, irritated eyes, fatigue, sore throat, reddened eyes or skin, and abdominal pain).

An antibody(ies) may be administered alone or in combination with another/other type of therapy known in the art to reduce influenza virus infection, to reduce titers of influenza virus in a subject, to reduce the spread of influenza virus between subjects, to inhibit influenza virus replication, to inhibit influenza virus-induced fusion, and/or to inhibit binding of influenza virus to its host cell receptor.

One or more of the antibodies described herein may be used locally or systemically in the body as a prophylactic or therapeutic agent. The antibodies may also be advantageously utilized in combination with other antibodies (e.g., monoclonal or chimeric antibodies), or with lymphokines or hematopoietic growth factors (such as, e.g., IL-2, IL-3 and IL-7), which, for example, serve to increase the number or activity of effector cells that interact with the antibodies.

One or more antibodies described herein may also be advantageously utilized in combination with one or more agents used to treat influenza virus infection such as, for example antiviral agents. Specific antiviral agents include: oseltamavir (Tamiflu®), zanamivir (Relenza®), nucleoside analogs (e.g., zidovudine, acyclovir, gangcyclovir, vidarabine, idoxuridine, trifluridine, and ribavirin), foscarnet, amantadine, rimantadine (Flumadine®), saquinavir, indinavir, ritonavir, alpha-interferons and other interferons, AZT, influenza virus vaccines (e.g., Fluarix®, FluMist®, Fluvirin®, and Fluzone®), and baloxavir marboxil.

One or more of the antibodies described herein may be used advantageously in combination with one or more antibodies that bind to influenza virus (e.g., influenza B virus) HA. Such antibodies may bind to the globular head domain of HA or the stem domain of HA.

In some embodiments, an antibody (e.g., an antigen-binding fragment) acts synergistically with the one or more other therapies. Generally, administration of products of a species origin or species reactivity (in the case of antibodies) that is the same species as that of the patient is preferred. Thus, in a preferred embodiment, human or humanized antibodies are administered to a human patient for treatment or prophylaxis of an influenza virus infection or a disease associated therewith.

In one embodiment, provided herein are methods of prevention and/or treatment of an influenza virus disease that are an alternative to current therapies. In a specific embodiment, the current therapy has proven or may prove to be too toxic (i.e., results in unacceptable or unbearable side effects) for the patient. In another embodiment, an antibody described herein decreases the side effects as compared to the current therapy. In another embodiment, the patient has proven refractory to a current therapy. In such embodiments, encompassed herein is the administration of one or more antibodies described herein without any other anti-infection therapies.

Suitable regimens can be selected by one skilled in the art by considering such factors and by following, for example, dosages reported in the literature and recommended in the Physician's Desk Reference ($58^{th}$ ed., 2004, $73^{rd}$ ed., 2019 or $74^{th}$ ed., 2020). See Section 5.5.1 for exemplary dosage amounts and frequencies of administration of the monoclonal antibodies described herein.

In specific embodiment, an antibody described herein may be used as any line of therapy, including, but not limited to, a first, second, third, fourth and/or fifth line of therapy. Further, in another specific embodiment, an antibody described herein can be used before or after any adverse effects or intolerance of the therapies other than an antibody described herein occurs. Encompassed herein are methods for administering one or more antibodies described herein to prevent the onset of an influenza virus disease and/or to treat or lessen the recurrence of an influenza virus disease.

Further encompassed herein are methods for preventing and/or treating an influenza virus disease and/or a symptom relating thereto for which no other antiviral therapy is available.

5.5.1 Routes of Administration and Dosage

An antibody (e.g., a monoclonal antibody, such as a chimeric or humanized antibody, or an antigen-binding fragment thereof) or composition described herein may be delivered to a subject by a variety of routes. In a specific embodiment, an antibody conjugated to a moiety such as described in Section 5.1.2, or a polynucleotide encoding a sequence encoding an antibody may be administered to a subject by a variety of routes. These include, but are not limited to, intranasal, intratracheal, oral, intradermal, intramuscular, intraperitoneal, transdermal, intravenous, conjunctival and subcutaneous routes. Pulmonary administration can also be employed, e.g., by use of an inhaler or nebulizer, and formulation with an aerosolizing agent for use as a spray. In a specific embodiment, an antibody described herein is administered to a subject intranasally or intramuscularly.

The amount of an antibody (e.g., a monoclonal antibody, such as a chimeric or humanized antibody, or an antigen-binding fragment thereof), antibody conjugate or composition which will be effective in the treatment and/or prevention of an influenza virus infection or an influenza virus disease will depend on the nature of the disease and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, health), whether the patient is human or an animal, other medications administered, and whether treatment is prophylactic or therapeutic. Usually, the patient is a human but non-human mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

For passive immunization with an (e.g., a monoclonal antibody, such as a chimeric or humanized antibody, or an antigen-binding fragment thereof), the dosage ranges from about 0.0001 to 100 mg/kg, and more usually 0.01 to 5 mg/kg, of the patient body weight. For example, dosages can be 1 mg/kg body weight, 10 mg/kg body weight, or within the range of 1-10 mg/kg or in other words, 70 mg or 700 mg or within the range of 70-700 mg, respectively, for a 70 kg patient. In some embodiments, the dosage administered to the patient is about 3 mg/kg to about 60 mg/kg of the patient's body weight. Preferably, the dosage administered to a patient is between 0.025 mg/kg and 20 mg/kg of the patient's body weight, more preferably 1 mg/kg to 15 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of the antibodies described herein (e.g., a monoclonal antibody, such as a chimeric or humanized antibody, or an antigen-binding fragment thereof) may be reduced by enhancing uptake and tissue penetration (e.g., into the nasal passages and/or lung) of the antibodies by modifications such as, for example, lipidation.

An exemplary treatment regime entails administration once per every two weeks or once a month or once every 3 to 6 months for a period of one year or over several years, or over several year-intervals. In some methods, two or more antibodies with different binding specificities are administered simultaneously to a subject. An antibody is usually administered on multiple occasions. Intervals between single dosages can be weekly, monthly, every 3 months, every 6 months or yearly. Intervals can also be irregular as indicated by measuring blood levels of antibody to the influenza virus antigen (e.g., hemagglutinin) in the patient.

In a specific embodiment, an antibody described herein, or a composition thereof is administered once a month just prior to (e.g., within three months, within two months, within one month) or during the influenza season. In another specific embodiment, an antibody described herein, or a composition thereof is administered once a month just prior to (e.g., within three months, within two months, within one month) and one, two or more times during the influenza season. In another embodiment, an antibody described herein, or a composition thereof is administered every two months just prior to or during the influenza season. In another embodiment, an antibody described herein, or a composition thereof is administered every two months just prior to and one, two or more times during the influenza season. In another embodiment, an antibody described herein, or a composition thereof is administered every three months just prior to or during the influenza season. In a specific embodiment, an antibody described herein, or a composition thereof is administered once just prior to or during the influenza season. In a specific embodiment, an antibody described herein, or a composition thereof is administered once just prior to and one, two or more times during the influenza season. In another specific embodiment, an antibody described herein, or a composition thereof is administered twice, and most preferably once, during an influenza season. In some embodiments, an antibody described herein, or a composition thereof is administered just prior to the influenza season and can optionally be administered once during the influenza season. In some embodiments, an antibody described herein, or a composition thereof is administered just prior to the influenza season and is administered once or twice during the influenza season. In some embodiments in which an antibody described herein is administered to a subject mucosally, the antibody is administered once per week or once per month during the influenza season. In some embodiments, an antibody described herein, or a composition thereof is administered every 24 hours for at least three days, at least four days, at least five days, at least six days up to one week just prior to or during an influenza season. In specific embodiments, the daily administration of the antibody or composition thereof occurs soon after influenza virus infection is first recognized in a patient, but prior to presentation of clinically significant disease. The term "influenza season" refers to the season when influenza infection is most likely to occur. Typically, the influenza season in the northern hemisphere commences in November and lasts through April.

In some embodiments, the plasma level of an antibody described herein in a patient is measured prior to administration of a subsequent dose of an antibody described herein, or a composition thereof. The plasma level of the antibody may be considered in determining the eligibility of a patient to receive a subsequent dose of an antibody described herein. For example, a patient's plasma level of an antibody described herein may suggest not administering an antibody described herein; alternatively, a patient's plasma level of an antibody described herein may suggest administering an antibody described herein at a particular dosage, at a particular frequency, and/or for a certain period of time.

In certain embodiments, the route of administration for a dose of an antibody described herein, or a composition thereof to a patient is intranasal, intramuscular, intravenous, or a combination thereof, but other routes described herein are also acceptable. Each dose may or may not be administered by an identical route of administration. In some embodiments, an antibody described herein, or composition thereof, may be administered via multiple routes of administration simultaneously or subsequently to other doses of the same or a different antibody described herein.

5.5.2 Combination Therapy

In various embodiments, an antibody described herein or a nucleic acid encoding such an antibody may be administered to a subject in combination with one or more other therapies (e.g., antiviral or immunomodulatory therapies). In a specific embodiment, an antibody conjugated to a moiety such as described in Section 5.1.2 may be administered to a subject with one or more other therapies. In some embodiments, a pharmaceutical composition described herein may be administered to a subject in combination with one or more therapies. The one or more other therapies may be beneficial in the treatment or prevention of an influenza virus disease or may ameliorate a condition associated with an influenza virus disease. The one or more other therapies may be beneficial in the treatment or prevention of an influenza virus infection or a disease associated therewith.

In some embodiments, the one or more other therapies that are supportive measures, such as pain relievers, anti-fever medications, or therapies that alleviate or assist with breathing. Specific examples of supportive measures include humidification of the air by an ultrasonic nebulizer, aerolized racemic epinephrine, oral dexamethasone, intravenous fluids, intubation, fever reducers (e.g., ibuprofen, acetometaphin), and antibiotic and/or antifungal therapy (i.e., to prevent or treat secondary bacterial and/or fungal infections).

In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In specific embodiments, two or more therapies are administered within the same patent visit. In some embodiments, two or more therapies are administered concurrently. The two or more therapies can be administered in the same composition or a different composition. Further, the two or more therapies can be administered by the same route of administration of a different route of administration.

Any antiviral agents well-known to one of skill in the art may be used in combination with an antibody or pharmaceutical composition described herein. Non-limiting examples of antiviral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, antiviral agents include, but are not limited to, nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, alpha-interferons and other interferons, AZT, zanamivir, and oseltamivir. Other antiviral agents include influenza virus vaccines, e.g., Fluarix® (GlaxoSmithKline), FluMist® (MedImmune Vaccines), Fluvirin® (Chiron Corporation), or Fluzone® (Aventis Pasteur). In a specific embodiment, an antibody described herein is administered to a subject in combination with an NA inhibitor. In a particular embodiment, an antibody described herein is administered to a subject in combination with zanamivir, and oseltamivir. In another embodiment an antibody described herein is administered to a subject in combination with a cap-dependent endonuclease inhibitor or polymerase inhibitor. In another embodiment, an antibody described herein is administered to a subject in combination with baloxavir marboxil.

In specific embodiments, the antiviral agent is an immunomodulatory agent that is specific for a viral antigen. In particular embodiments, the viral antigen is an influenza virus polypeptide other than a NA polypeptide (e.g., an influenza virus HA polypeptide). In other embodiments, the viral antigen is an influenza B virus NA polypeptide or an influenza A virus NA polypeptide (e.g., an influenza virus neuraminidase polypeptide or antigenic peptide described herein).

In a specific embodiment, an antibody described herein is administered to a subject in combination with an antibody that binds to an influenza virus hemagglutinin (e.g., an antibody known to one of skill in the art or described in, e.g., U.S. Patent Application Publication No. 2016/0137721A1, International Patent Application Publication No. WO 2014/159960, U.S. Pat. No. 8,673,314 B2, International Patent Application Publication No. WO 2010/138564, U.S. Pat. No. 9,908,930 B2, each of which is incorporated herein by reference its entirety).

In a specific embodiment, an antibody described herein is administered to a subject in combination with an antibody that binds to an influenza A virus NA (e.g., an antibody known to one of skill in the art or described in, e.g., International Patent Application Publication No. WO 2016/118937, which is incorporated herein by reference in its entirety).

In a specific embodiment, an antibody described herein is administered to a subject in combination with an immunogenic composition described in, e.g., International Patent Application Publication No. WO 2016/118937, which is incorporated herein by reference in its entirety. In another specific embodiment, an antibody described herein is administered to a subject in combination with an immunogenic composition described in, e.g., U.S. Pat. No. 9,051,359, International Patent Application Publication No. WO 2010/117786, International Patent Application No. WO 2011/123495, U.S. Patent Application Publication No. 2013/0129761 A1, International Patent Application No. WO 2011/103453, U.S. Patent Application Publication No. 2015/0132330 A1, International Patent Application No. WO 2013/056122, U.S. Pat. No. 9,371,366, International Patent Application No. WO 2014/099931 or International Patent Application No. WO 2016/205347, each of which is incorporated herein by reference in its entirety. In another specific embodiment, an antibody described herein is administered to a subject in combination with a chimeric influenza virus hemagglutinin polypeptide known in the art or described in, e.g., International Patent Application No. WO 2011/103453, U.S. Patent Application Publication No. 2015/0132330 A1, International Patent Application No. WO 2013/056122, U.S. Pat. No. 9,371,366, International Patent Application No. WO 2014/099931, U.S. Pat. No. 10,131,695, International Patent Application No. WO 2013/043729, U.S. Pat. No. 9,968,670, International Patent Application No. WO 2014/099931, U.S. Patent Publication No. 2018-0008696 A1, International Patent Application No. WO 2016/118937, each of which is incorporated herein by reference in its entirety.

In a specific embodiment, one or more therapies that prevent or treat secondary responses to a primary influenza virus infection are administered in combination with one or more antibodies described herein (e.g., a monoclonal antibody, such as a chimeric or humanized antibody, or an antigen-binding fragment thereof). Examples of secondary responses to a primary influenza virus infection include, but are not limited to, asthma-like responsiveness to mucosal stimuli, elevated total respiratory resistance, increased susceptibility to secondary viral, bacterial, and fungal infections, and development of conditions such as, but not limited to, bronchiolitis, pneumonia, croup, and febrile bronchitis.

In a specific embodiment, one or more antibodies described herein (e.g., a monoclonal antibody, such as a chimeric or humanized antibody, or an antigen-binding fragment thereof) is used in combination with another antibody that binds to an influenza virus Group 1 HA to prevent and/or treat an influenza virus infection and/or influenza virus disease. In another specific embodiment, one or more antibodies described herein (e.g., a monoclonal antibody, such as a chimeric or humanized antibody, or an antigen-binding fragment thereof) is used in combination with an antibody that binds to an influenza virus Group 2 HA to prevent and/or treat an influenza virus infection and/or influenza virus disease. In another specific embodiment, one or more antibodies described herein (e.g., a monoclonal antibody, such as a chimeric or humanized antibody, or an antigen-binding fragment thereof) is used in combination with an antibody that binds to an influenza A virus neuraminidase to prevent and/or treat an influenza virus infection and/or influenza virus disease. In another specific embodiment, one or more antibodies described herein (e.g., a monoclonal antibody, such as a chimeric or humanized antibody, or an antigen-binding fragment thereof) is used in combination with an antibody that binds to an influenza A virus neuraminidase and an antibody that binds to an influenza virus Group 1 HA to prevent and/or treat an influenza virus infection and/or influenza virus disease.

In another specific embodiment, one or more antibodies described herein (e.g., a monoclonal antibody, such as a chimeric or humanized antibody, or an antigen-binding fragment thereof) is used in combination with an antibody that binds to an influenza A virus neuraminidase and an antibody that binds to an influenza virus Group 2 HA to prevent and/or treat an influenza virus infection and/or influenza virus disease. See, e.g., Wan et al., 2013, Journal of Virology 87: 9250 and Wohlbold et al., 2016, Journal of Virology 90: 851 for examples of anti-NA antibodies. One or more of such anti-NA antibodies may be administered in combination with an antibody described herein for the prevention of an influenza virus disease, or the treatment of an influenza virus infection or influenza virus disease.

In a specific embodiment, one or more antibodies described herein (e.g., a monoclonal antibody, such as a chimeric or humanized antibody, or an antigen-binding fragment thereof) is used in combination with another antibody that binds to an influenza B virus HA globular head domain to prevent an influenza virus disease. In a specific embodiment, one or more antibodies described herein (e.g., a monoclonal antibody, such as a chimeric or humanized antibody, or an antigen-binding fragment thereof) is used in combination with another antibody that binds to an influenza B virus HA globular head domain to treat an influenza virus infection and/or influenza virus disease. In another specific embodiment, one or more antibodies described herein (e.g., a monoclonal antibody, such as a chimeric or humanized antibody, or an antigen-binding fragment thereof) is used in combination with another antibody that binds to an influenza B virus HA stem domain to prevent an influenza virus disease. In another specific embodiment, one or more antibodies described herein (e.g., a monoclonal antibody, such as a chimeric or humanized antibody, or an antigen-binding fragment thereof) is used in combination with another antibody that binds to an influenza B virus HA stem domain to treat an influenza virus infection and/or influenza virus disease. In another specific embodiment, one or more antibodies described herein (e.g., a monoclonal antibody, such as a chimeric or humanized antibody, or an antigen-binding fragment thereof) is used in combination with another antibody that binds to influenza B virus HA stem domain and another antibody that binds to influenza B virus HA globular head domain to prevent an influenza virus disease. In another specific embodiment, one or more antibodies described herein (e.g., a monoclonal antibody, such as a chimeric or humanized antibody, or an antigen-binding fragment thereof) is used in combination with another antibody that binds to influenza B virus HA stem domain and another antibody that binds to influenza B virus HA globular head domain to treat an influenza virus infection and/or influenza virus disease. In another specific embodiment, one or more antibodies described herein (e.g., 1F2, 1F4, 3G1, 4B2, or 4F11 described in Section 6, infra) is used in combination with another antibody that binds to influenza B virus HA stem domain (e.g., an antibody described in Section 7, infra) and another antibody that binds to influenza B virus HA globular head domain (e.g., an antibody described in Section 7, infra) to prevent an influenza virus disease. In another specific embodiment, one or more antibodies described herein (e.g., 1F2, 1F4, 3G1, 4B2, or 4F11 described in Section 6, infra) is used in combination with another antibody that binds to influenza B virus HA stem domain (e.g., an antibody described in Section 7, infra) and another antibody that binds to influenza B virus HA globular head domain (e.g., an antibody described in Section 7, infra) to treat an influenza virus infection and/or influenza virus disease. See, e.g., Shen et al., 2017, Science Translational Medicine, 9(412):eaam5752 and Dreyfus et al., 2012, Science, 337(6100):1343-1348, each of which is incorporated by reference in its entirety, for examples of anti-influenza B virus HA antibodies. One or more of such anti-influenza B virus HA antibodies may be administered in combination with an antibody described herein for the prevention of an influenza virus disease, or the treatment of an influenza virus infection or influenza virus disease.

In a specific embodiment, one or more antibodies described herein (e.g., a monoclonal antibody, such as a chimeric or humanized antibody, or an antigen-binding fragment thereof) is used in combination with another antibody (e.g., an anti-influenza virus monoclonal antibody) or a set of other antibodies (e.g., a set of anti-influenza virus monoclonal antibodies) in order to enhance the prophylactic and/or therapeutic effect of the other antibody or set of other antibodies.

In some embodiments, a combination therapy comprises the administration of one or more antibodies described herein. In some embodiments, a combination therapy comprises administration of two or more antibodies described herein. In a specific embodiment, a combination therapy comprises the administration of the 1F2, 1F4, 3G1, 4B2 or 4F11 antibody or a humanized or chimeric form thereof and one or more other therapies.

5.5.3 Patient Populations

As used herein, the terms "subject" and "patient" are used interchangeably to refer to an animal (e.g., birds, reptiles, and mammals). In one embodiment, a patient treated or prevented in accordance with the methods provided herein is a naïve subject, i.e., a subject that does not have a disease caused by influenza virus infection (e.g., an influenza B virus infection) or has not been and is not currently infected with an influenza virus infection (e.g., an influenza B virus infection). In another embodiment, a patient treated or prevented in accordance with the methods provided herein is a subject that is at risk of acquiring an influenza virus infection (e.g., an influenza B virus infection). In another embodiment, a patient treated or prevented in accordance with the methods provided herein is a naïve subject that is at risk of acquiring an influenza virus infection (e.g., an influenza B virus infection). In another embodiment, a patient treated or prevented in accordance with the methods provided herein is a patient suffering from or expected to suffer from an influenza virus disease (e.g., an influenza B virus disease). In another embodiment, a patient treated or prevented in accordance with the methods provided herein is a patient diagnosed with an influenza virus infection (e.g., an influenza B virus infection) or a disease associated therewith. In some embodiments, a patient treated or prevented in accordance with the methods provided herein is a patient infected with an influenza virus (e.g., an influenza B virus) that does not manifest any symptoms of influenza virus disease.

In a specific embodiment, a patient treated or prevented in accordance with the methods provided herein is a subject that is at risk of an infection with an influenza B virus. In another specific embodiment, a patient treated or prevented in accordance with the methods provided herein is a naïve subject that is at risk of an infection with an influenza B virus. In another specific embodiment, a patient treated or prevented in accordance with the methods provided herein is a patient suffering from or expected to suffer from an influenza virus disease caused by an influenza B virus. In another specific embodiment, a patient treated or prevented in accordance with the methods provided herein is a patient diagnosed with an influenza virus (e.g., an influenza B virus) infection or a disease associated therewith. In certain embodiments, a patient treated or prevented in accordance with the methods provided herein is a patient diagnosed with an influenza virus (e.g., an influenza B virus) infection or a disease associated therewith using a rapid influenza virus test, such as commercially available by Sekisi Diagnostics, Quidel QuickVue, Alere Binaxnow or Becton Dickinson. In some embodiments, a patient is administered an antibody described herein with 72 hours of diagnosis of an influenza virus (e.g., influenza B virus) infection or influenza virus disease. In certain embodiments, a patient is administered an antibody described herein 1 to 6 hours, 6 to 12 hours, 12 to 24 hours, 24 to 48 hours, 36 to 48 hours, 24 to 72 hours, 36 to 72 hours, or 48 to 72 hours after diagnosis of an influenza virus (e.g., influenza B virus) infection or influenza virus disease.

In another embodiment, a patient treated or prevented in accordance with the methods provided herein is a patient experiencing one or more symptoms of influenza virus disease. Symptoms of influenza virus disease include, but are not limited to, body aches (especially joints and throat), fever, nausea, headaches, irritated eyes, fatigue, sore throat, reddened eyes or skin, and abdominal pain. In another embodiment, a patient treated or prevented in accordance with the methods provided herein is a patient with influenza virus disease who does not manifest symptoms of the disease that are severe enough to require hospitalization. In a specific embodiment, a patient is administered an antibody described herein within 4 days of the onset of one, two or more symptoms of an influenza virus infection or an influenza virus disease. In another specific embodiment, a patient is administered an antibody described herein 1 to 6 hours, 6 to 12 hours, 12 to 24 hours, 24 to 48 hours, 36 to 48 hours, 24 to 72 hours, 36 to 72 hours, or 48 to 72 hours after the onset of one, two or more symptoms of an influenza virus infection (e.g., an influenza B virus infection) or an influenza virus disease (e.g., an influenza B virus disease). In another specific embodiment, a patient is administered an antibody described herein within 4 days of the onset of one, two or more symptoms of an influenza virus infection (e.g., an influenza B virus infection) or an influenza virus disease (e.g., an influenza B virus disease).

In another embodiment, a patient treated or prevented in accordance with the methods provided herein is a patient infected with an influenza B virus. In accordance with such embodiment, the patients that are infected with the virus may manifest symptoms of influenza virus disease.

In some embodiments, a patient treated or prevented in accordance with the methods provided herein is an animal. In certain embodiments, the animal is a bird. In certain embodiments, the animal is a mammal, e.g., a horse, canine, cow, feline, swine, mouse, or primate, preferably a human. In a specific embodiment, a subject is a bird. In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human).

In a specific embodiment, a patient treated or prevented in accordance with the methods provided herein is a human. In certain embodiments, a patient treated or prevented in accordance with the methods provided herein is a human infant. In some embodiments, a patient treated or prevented in accordance with the methods provided herein is a human toddler. In certain embodiments, a patient treated or prevented in accordance with the methods provided herein is a human child. In other embodiments, a patient treated or prevented in accordance with the methods provided herein is a human adult. In some embodiments, a patient treated or prevented in accordance with the methods provided herein is an elderly human.

As used herein, the term "human adult" refers to a human that is 18 years or older.

As used herein, the term "human child" refers to a human that is 1 year to 18 years old. As used herein, the term "human infant" refers to a newborn to 1 year old human. As used herein, the term "human toddler" refers to a human that is 1 years to 3 years old. In a specific embodiment, an elderly human is 65 years old or older.

In certain embodiments, a patient treated or prevented in accordance with the methods provided herein is patient that is pregnant. In another embodiment, a patient treated or prevented in accordance with the methods provided herein is a patient who may or will be pregnant during the influenza season (e.g., November to April in the Northern Hemisphere).

In some embodiments, a patient treated or prevented in accordance with the methods provided herein is any subject at increased risk of influenza virus infection or disease resulting from influenza virus infection (e.g., an immunocompromised or immunodeficient individual). In some embodiments, a patient treated or prevented in accordance with the methods provided herein is any subject in close contact with an individual with increased risk of influenza virus infection or disease resulting from influenza virus infection (e.g., immunocompromised or immunosuppressed individuals).

In some embodiments, a patient treated or prevented in accordance with the methods provided herein is a subject affected by any condition that increases susceptibility to influenza virus infection (e.g., an influenza B virus infection) or complications or disease resulting from influenza virus infection (e.g., an influenza B virus infection). In other embodiments, a patient treated or prevented in accordance with the methods provided herein is a subject in which an influenza virus infection has the potential to increase complications of another condition that the individual is affected by, or for which they are at risk. In particular embodiments, such conditions that increase susceptibility to influenza virus complications or for which influenza virus increases complications associated with the condition are, e.g., conditions that affect the lung, such as cystic fibrosis, asthma, chronic obstructive pulmonary disease, emphysema, or bacterial infections; cardiovascular disease; or diabetes. Other conditions that may increase influenza virus complications include kidney disorders; blood disorders (including anemia or sickle cell disease); or weakened immune systems (including immunosuppression caused by medications, malignancies such as cancer, organ transplant, or HIV infection).

In some embodiments, a patient treated or prevented in accordance with the methods provided herein is a subject that resides in a group home, such as a nursing home or orphanage. In some embodiments, a patient treated or prevented in accordance with the methods provided herein is subject that works in, or spends a significant amount of time in, a group home, e.g., a nursing home or orphanage. In some embodiments, a patient treated or prevented in accordance with the methods provided herein is a health care worker (e.g., a doctor or nurse). In some embodiments, a patient treated or prevented in accordance with the methods provided herein resides in a dormitory (e.g., a college dormitory). In some embodiments, a patient treated or prevented in accordance with the methods provided herein is a member of the military. In some embodiments, a patient treated or prevented in accordance with the methods provided herein is a child that attends school or daycare.

In some embodiments, a patient treated or prevented in accordance with the methods provided herein is a subject at increased risk of developing complications from influenza virus infection (e.g., an influenza B virus infection) including: any individual who can transmit influenza viruses to those at high risk for complications, such as, e.g., members of households with high-risk individuals, including households that will include infants younger than 6 months, individuals coming into contact with infants less than 6 months of age, or individuals who will come into contact with individuals who live in nursing homes or other long-term care facilities; individuals with long-term disorders of the lungs, heart, or circulation; individuals with metabolic diseases (e.g., diabetes); individuals with kidney disorders; individuals with blood disorders (including anemia or sickle cell disease); individuals with weakened immune systems (including immunosuppression caused by medications, malignancies such as cancer, organ transplant, or HIV infection); children who receive long-term aspirin therapy (and therefore have a higher chance of developing Reye syndrome if infected with influenza).

In other embodiments, a patient treated or prevented in accordance with the methods provided herein includes healthy individuals six months of age or older, who: plan to travel to foreign countries and areas where flu outbreaks may be occurring, such, e.g., as the tropics and the Southern Hemisphere from April through September; travel as a part of large organized tourist groups that may include persons from areas of the world where influenza viruses are circulating; attend school or college and reside in dormitories, or reside in institutional settings; or wish to reduce their risk of becoming ill with influenza virus disease.

In specific embodiments, a patient treated or prevented in accordance with the methods provided herein is an individual who is susceptible to adverse reactions to conventional therapies. In other embodiments, the patient may be a person who has proven refractory to therapies other than an antibody described herein (e.g., a monoclonal antibody, such as a chimeric or humanized antibody, or an antigen-binding fragment thereof) but are no longer on these therapies. In certain embodiments, a patient with an influenza virus disease is refractory to a therapy when the infection has not significantly been eradicated and/or the symptoms have not been significantly alleviated. The determination of whether a patient is refractory can be made either in vivo or in vitro by any method known in the art for assaying the effectiveness of a therapy for infections, using art-accepted meanings of "refractory" in such a context. In various embodiments, a patient with an influenza virus disease is refractory when viral replication has not decreased or has increased following therapy.

In certain embodiments, patients treated or prevented in accordance with the methods provided herein are patients already being treated with antibiotics, antivirals, antifungals, or other biological therapy/immunotherapy. Among these patients are refractory patients, patients who are too young for conventional therapies, and patients with reoccurring influenza virus disease or a symptom relating thereto despite treatment with existing therapies.

In specific embodiments, patients treated or prevented in accordance with the methods provided herein are patients refractory to treatment with an antiviral (e.g., an NA inhibitor, such as osteltmivir or zanamivir). In a particular embodiment, patients treated or prevented in accordance with the methods provided herein are patients refractory to treatment with osteltmivir. In another embodiment, patients treated or prevented in accordance with the methods provided herein are patients refractory to treatment with baloxavir marboxil.

5.6 Diagnostic Uses

The antibodies described herein (e.g., a monoclonal antibody, such as a chimeric or humanized antibody, or an antigen-binding fragment thereof) can be used for diagnostic purposes to detect an influenza virus as well as detect, diagnose, or monitor an influenza virus infection. In specific embodiments, the antibodies (e.g., a monoclonal antibody, such as a chimeric or humanized antibody, or an antigen-binding fragment thereof) can be used to determine whether a particular influenza virus is present, or a particular influenza virus subtype is present in a biological specimen (e.g., sputum, nasal drippings, other fluids, cells, or tissue samples).

Provided herein are methods for the detection of an influenza virus infection comprising: (a) assaying the expression of an influenza B virus NA in a biological specimen (e.g., sputum, nasal drippings, cells or tissue samples) from a subject using an antibody described herein (e.g., a monoclonal antibody, such as a chimeric or humanized antibody, or an antigen-binding fragment thereof); and (b) comparing the level of the influenza B virus NA with a control level, e.g., levels in a biological specimen from a subject not infected with influenza virus, wherein an increase in the assayed level of influenza B virus NA compared to the control level of the influenza B virus NA is indicative of an influenza virus infection.

Provided herein is a diagnostic assay for diagnosing an influenza virus infection comprising: (a) assaying for the level of an influenza B virus NA in a biological specimen from a subject using an antibody described herein (e.g., a monoclonal antibody, such as a chimeric or humanized antibody, or an antigen-binding fragment thereof); and (b) comparing the level of the influenza B virus NA with a control level, e.g., levels in a biological specimen from a subject not infected with influenza virus, wherein an increase in the assayed influenza B virus NA level compared to the control level of the influenza virus HA is indicative of an influenza B virus infection. A more definitive diagnosis of an influenza B virus infection may allow health professionals to employ preventative measures or aggressive treatment earlier thereby preventing the development or further progression of the influenza B virus infection.

In a specific embodiment, provided herein is a method for detecting an influenza B virus, comprising: (a) contacting a biological sample (e.g., cells, sputum, nasal swab, mucous, etc.) with the antibody described herein; (b) detecting the binding of the antibody to an NA of an influenza B virus, wherein influenza B virus is detected if the level of binding of the antibody to an NA of an influenza B virus is greater than the level of binding of the antibody to non-influenza virus infected cells or a biological sample not infected with an influenza virus. In a particular embodiment, the detection is done in vitro. In other embodiments, the detection is done in vivo. Techniques known to one of skill in the art may be used to detect the binding of the antibody to the NA of an influenza B virus.

Antibodies described herein (e.g., a monoclonal antibody, such as a chimeric or humanized antibody, or an antigen-binding fragment thereof) can be used to assay influenza B virus NA levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:3087-3096). Antibody-based methods useful for detecting protein expression include immunoassays, such as the enzyme linked immunosorbent assay (ELISA) and the radioimmunoassay (RIA). An antibody described herein or generated in accordance with the methods described herein may be labeled with a detectable label or a secondary antibody that binds to such an antibody may be labeled with a detectable label. Suitable antibody assay labels are known in the art and include enzyme labels, such as, glucose oxidase; radioisotopes, such as iodine ($^{125}$I, $^{121}$I), carbon (C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. See, Section 5.1.2, supra, for examples of antibody conjugates that might be useful in the detection and diagnosis of influenza B virus infection.

Also provided herein is the detection and diagnosis of an influenza B virus infection in a human. In one embodiment, diagnosis comprises: a) administering (for example, parenterally, intranasally, subcutaneously, or intraperitoneally) to a subject an effective amount of a labeled monoclonal antibody described herein (e.g., a monoclonal antibody, such as a chimeric or humanized antibody, or an antigen-binding fragment thereof); b) waiting for a time interval following the administering for permitting the labeled antibody to preferentially concentrate at sites in the subject (e.g., the nasal passages, lungs, mouth and ears) where the influenza virus antigen is expressed (and for unbound labeled molecule to be cleared to background level); c) determining background level; and d) detecting the labeled antibody in the subject, such that detection of labeled antibody above the background level indicates that the subject has an influenza virus infection or a symptom relating thereto. Background level can be determined by various methods, including comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled antibody to preferentially concentrate at sites in the subject and for unbound labeled antibody to be cleared to background level is 6 to 48 hours, or 6 to 24 hours or 6 to 12 hours. In another embodiment the time interval following administration is 5 to 20 days or 5 to 10 days.

In one embodiment, monitoring of an influenza B virus infection is carried out by repeating the method for diagnosing the influenza B virus infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods provided herein include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

5.7 Biological Assays

An antibody described herein (e.g., a monoclonal antibody, such as a chimeric or humanized antibody, or an antigen-binding fragment thereof) may be characterized using any assay known to one of skill in the art or described herein (e.g., as described in Section 5.1, 6, or 7 herein).

5.7.1 Assays for Testing Antibody Activity

An antibody may be characterized in a variety of ways known to one of skill in the art (e.g., ELISA, biolayer interferometry, surface plasmon resonance display (BIAcore kinetic), Western blot, immunofluorescence, immunostaining and/or microneutralization assays). In some embodiments, an antibody is assayed for its ability to bind to an influenza B virus NA, or an influenza B virus.

The specificity or selectivity of an antibody for an influenza B virus NA and cross-reactivity with other antigens can be assessed by any method known in the art. Immunoassays which can be used to analyze specific binding and cross-reactivity include, but are not limited to, competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety).

The binding affinity of an antibody to an influenza B virus NA and the off-rate of an antibody-antigen interaction can be determined by competitive binding assays. One example of a competitive binding assay is a radioimmunoassay comprising the incubation of labeled antigen (e.g., $^{3}H$ or $^{125}I$) with the antibody of interest in the presence of increasing amounts of unlabeled antigen, and the detection of the antibody bound to the labeled antigen. The affinity of the antibody for an influenza virus antigen or an influenza virus and the binding off-rates can be determined from the data by Scatchard plot analysis. Competition with a second antibody can also be determined using radioimmunoassays. In this case, an influenza virus antigen or an influenza virus is incubated with the test antibody conjugated to a detectable labeled (e.g., $^{3}H$ or $^{121}I$) in the presence of increasing amounts of an unlabeled second antibody.

In some embodiments, surface plasmon resonance (e.g., BIAcore kinetic) analysis is used to determine the binding on and off rates of an antibody to an influenza virus antigen (e.g., hemagglutinin polypeptide), or an influenza virus. BIAcore kinetic analysis typically comprises analyzing the binding and dissociation of influenza virus antigen from chips with immobilized antibodies to an influenza virus antigen on their surface. Briefly, a typical BIAcore kinetic study involves the injection of 250 μL of an antibody reagent (mAb, Fab) at varying concentration in HBS buffer containing 0.005% Tween-20 over a sensor chip surface, onto which has been immobilized the influenza virus hemagglutinin polypeptide. The flow rate is maintained constant at 75 μL/min. Dissociation data is collected for 15 min or longer as necessary. Following each injection/dissociation cycle, the bound antibody is removed from the influenza virus hemagglutinin polypeptide surface using brief, 1 min pulses of dilute acid, typically 10-100 mM HCl, though other regenerants are employed as the circumstances warrant. More specifically, for measurement of the rates of association, $k_{on}$, and dissociation, $k_{off}$, the polypeptide is directly immobilized onto the sensor chip surface through the use of standard amine coupling chemistries, namely the EDC/NHS method (EDC=N-diethylaminopropyl)-carbodiimide). Briefly, a 5-100 nM solution of the polypeptide in 10 mM NaOAc, pH 4 or pH 5 is prepared and passed over the EDC/NHS-activated surface until approximately 30-50 RU's worth of polypeptide are immobilized. Following this, the unreacted active esters are "capped" off with an injection of 1M Et-$NH_2$. A blank surface, containing no polypeptide, is prepared under identical immobilization conditions for reference purposes. Once an appropriate surface has been prepared, a suitable dilution series of each one of the antibody reagents is prepared in HBS/Tween-20, and passed over both the polypeptide and reference cell surfaces, which are connected in series. The range of antibody concentrations that are prepared varies, depending on what the equilibrium binding constant, $K_D$, is estimated to be. As described above, the bound antibody is removed after each injection/dissociation cycle using an appropriate regenerant.

In a specific embodiment, an antibody described herein may be tested for enzymatic activity using any technique known to one of skill in the art (e.g., ELLA or NA-star assays) or described herein (e.g., in Section 6 and/or Section 7, infra). In particular, an antibody described herein may be tested for its ability to inhibit NA's cleavage of terminal sialic acid residues that serve as receptors for hemagglutinin, promoting the release of the virus from host cells.

5.7.2 Cell Culture Assays

An antibody or a composition thereof can be assessed in vitro for activity. In one embodiment, an antibody or composition thereof is tested in vitro for its effect on growth of an influenza B virus. Growth of influenza B virus can be assessed by any method known in the art or described herein (e.g. in cell culture). In a specific embodiment, cells are infected at a MOI of 0.0005 and 0.001, 0.001 and 0.01, 0.01 and 0.1, 0.1 and 1, or 1 and 10, or a MOI of 0.0005, 0.001, 0.005, 0.01, 0.05, 0.1, 0.5, 1, 5 or 10 and incubated with serum free media supplemented a monoclonal antibody described herein (or an antigen-binding fragment thereof)

Viral titers are determined in the supernatant by hemagglutinin plaques or any other viral assay described herein. Cells in which viral titers can be assessed include, but are not limited to, MDCK cells, EFK-2 cells, Vero cells, primary human umbilical vein endothelial cells (HUVEC), H292 human epithelial cell line and HeLa cells. In vitro assays include those that measure altered viral replication (as determined, e.g., by plaque formation) or the production of viral proteins (as determined, e.g., by Western blot analysis) or viral RNAs (as determined, e.g., by RT-PCR or northern blot analysis) in cultured cells in vitro using methods that are well known in the art or described herein. In a specific embodiment, the antibody or a composition thereof reduces the size of plaques.

In one non-limiting example, a monolayer of the target mammalian cell line is infected with different amounts (e.g., multiplicity of 3 plaque forming units (pfu) or 5 pfu) of influenza virus and subsequently cultured at 37° C. in the presence or absence of various dilutions of a monoclonal antibody described herein (or an antigen-binding fragment thereof) (e.g., 0.1 g/ml, 1 μg/ml, 5 μg/ml, or 10 μg/ml). Cultures are overlaid with agar and harvested 48 hours or 72 hours post infection and titered by standard plaque assays known in the art on the appropriate target cell line (e.g., MDCK cells).

5.7.3 Cytotoxicity Assays

Many assays well-known in the art can be used to assess viability of cells (infected or uninfected) or cell lines following exposure to an antibody or composition thereof and, thus, determine the cytotoxicity of the antibody or composition thereof. For example, cell proliferation can be assayed by measuring Bromodeoxyuridine (BrdU) incorporation (See, e.g., Hoshino et al., 1986, Int. J. Cancer 38, 369; Campana et al., 1988, J. Immunol. Meth. 107:79), (3H) thymidine incorporation (See, e.g., Chen, J., 1996, Oncogene 13:1395-403; Jeoung, J., 1995, J. Biol. Chem. 270: 18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes may be given a designation of T (100% toxic), PVH (partially toxic-very heavy—80%), PH (partially toxic-heavy—60%), P (partially toxic—40%), Ps (partially toxic-slight—20%), or 0 (no toxicity—0%), conforming to the degree of cytotoxicity seen. A 50% cell inhibitory (cytotoxic) concentration ($IC_{50}$) is determined by regression analysis of these data.

In a specific embodiment, the cells used in the cytotoxicity assay are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocytic cells. In certain embodiments, cytotoxicity is assessed in one or more of the following cell lines: MDCK, MEF, Huh 7.5, Detroit, or human tracheobronchial epithelial (HTBE) cells.

An antibody or composition thereof can be tested for in vivo toxicity in animal models. For example, animal models, described herein and/or others known in the art, used to test the activities of an antibody or composition thereof can also be used to determine the in vivo toxicity of these antibodies. For example, animals are administered a range of concentrations of an antibody. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of an antibody or composition thereof can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An antibody or composition thereof that exhibits large therapeutic indices is preferred. While an antibody or composition thereof that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of an antibody or composition thereof for use in humans. The dosage of such antibodies lies preferably within a range of circulating concentrations that include the $ED_{50}$ with little or no toxicity. The dosage may vary within this range depending upon the dosage form employed and the route of administration utilized. For an antibody or composition thereof used in a method described herein, the effective dose can be estimated initially from cell culture assays. A dose may be formulated in animal models to achieve a circulating plasma concentration range that includes the $IC_{50}$ (i.e., the concentration of the antibody that achieves a half-maximal inhibition of symptoms) as determined in cell culture. Such information can be used to more accurately determine useful doses in humans. Levels in plasma may be measured, for example, by high-performance liquid chromatography. Additional information concerning dosage determination is provided herein.

Further, any assays known to those skilled in the art can be used to evaluate the prophylactic and/or therapeutic utility of an antibody or composition thereof, for example, by measuring viral infection or a condition or symptoms associated therewith.

5.7.4 In Vivo Assays

Antibodies and compositions thereof are preferably assayed in vivo for the desired therapeutic or prophylactic activity prior to use in humans. For example, in vivo assays can be used to determine whether it is preferable to administer an antibody or composition thereof and/or another therapy. For example, to assess the use of an antibody or composition thereof to prevent an influenza virus disease, the antibody or composition can be administered before the animal is infected with influenza virus. Alternatively, or in addition, an antibody or composition thereof can be administered to the animal at the same time that the animal is infected with influenza virus. To assess the use of an antibody or composition thereof to treat an influenza virus infection or disease associated therewith, the antibody or composition may be administered after infecting the animal with influenza virus. In a specific embodiment, an antibody or composition thereof is administered to the animal more than one time.

Antibodies and compositions thereof can be tested for antiviral activity in animal model systems including, but are not limited to, rats, mice, chicken, cows, monkeys, pigs, goats, sheep, dogs, rabbits, guinea pigs, etc. In a specific embodiment, an antibody or composition thereof is tested in a mouse model system. Such model systems are widely used and well-known to the skilled artisan. Non-limiting examples of animal models for influenza virus are provided in this section.

In general, animals are infected with influenza virus and concurrently or subsequently treated with an antibody or composition thereof, or placebo. Alternatively, animals are treated with an antibody or composition thereof or placebo and subsequently infected with influenza virus. Samples obtained from these animals (e.g., serum, urine, sputum, semen, saliva, plasma, or tissue sample) can be tested for viral replication via well known methods in the art, e.g., those that measure altered viral titers (as determined, e.g., by plaque formation), the production of viral proteins (as determined, e.g., by Western blot, ELISA, or flow cytometry analysis) or the production of viral nucleic acids (as determined, e.g., by RT-PCR or northern blot analysis). For quantitation of virus in tissue samples, tissue samples are homogenized in phosphate-buffered saline (PBS), and dilutions of clarified homogenates are adsorbed for a time period (e.g., 20 minutes or 1 hour) at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody.

The effect of an antibody or composition thereof on the infectious disease process or pathogenicity of a given virus can also be determined using in vivo assays in which the titer of the virus in an infected subject administered an antibody or composition thereof, the length of survival of an infected subject administered an antibody or composition thereof, the immune response in an infected subject administered an antibody or composition thereof, the number, duration and/or severity of the symptoms in an infected subject administered an antibody or composition thereof, and/or the time period before onset of one or more symptoms in an infected subject administered an antibody or composition thereof, is assessed. Techniques known to one of skill in the art can be used to measure such effects.

Influenza virus animal models, such as ferret, mouse, guinea pig, and chicken, developed for use to test antiviral agents against influenza virus have been described. See, e.g., Sidwell et al., Antiviral Res., 2000, 48:1-16; Lowen A. C. et al. PNAS., 2006, 103: 9988-92; and McCauley et al., Antiviral Res., 1995, 27:179-186. For mouse models of influenza, non-limiting examples of parameters that can be used to assay antiviral activity of antibodies administered to the influenza-infected mice include pneumonia-associated death, serum al-acid glycoprotein increase, animal weight, lung virus assayed by hemagglutinin, lung virus assayed by plaque assays, and histopathological change in the lung. Statistical analysis is carried out to calculate significance (e.g., a P value of 0.05 or less).

In yet other assays, histopathologic evaluations are performed after infection of an animal model subject. Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); 3+ (epithelial layer markedly disrupted and disorganized with necrotic cells visible in the lumen; some bronchioles attenuated and others in marked reactive proliferation).

The trachea may be graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+ (focal squamous metaplasia of the epithelial layer); 2+ (diffuse squamous metaplasia of much of the epithelial layer, cilia may be evident focally); 2.5+ (diffuse squamous metaplasia with very few cilia evident).

Virus immunohistochemistry may be performed using a viral-specific monoclonal antibody (e.g. NP-, N- or HN-specific monoclonal antibodies). Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

In one example, the ability to induce lung lesions and cause infection in an animal model of virus infection is compared using wild-type virus and mock virus. Lung lesions can be assessed as a percentage of lung lobes that are healthy by visual inspection. Animals are euthanized 5 days p.i. by intravenous administration of pentobarbital, and their lungs are removed in toto. The percentage of the surface of each pulmonary lobe that is affected by macroscopic lesions is estimated visually. The percentages are averaged to obtain a mean value for the 7 pulmonary lobes of each animal. In other assays, nasal swabs can be tested to determine virus burden or titer. Nasal swabs can be taken during necropsy to determine viral burden post-infection.

In one embodiment, virus is quantified in tissue samples. For example, tissue samples are homogenized in phosphate-buffered saline (PBS), and dilutions of clarified homogenates adsorbed for 1 h at 37° C. onto monolayers of cells (e.g., MDCK cells). Infected monolayers are then overlaid with a solution of minimal essential medium containing 0.1% bovine serum albumin (BSA), 0.01% DEAE-dextran, 0.1% $NaHCO_3$, and 1% agar. Plates are incubated 2 to 3 days until plaques could be visualized. Tissue culture infectious dose (TCID) assays to titrate virus from PR8-infected samples are carried out as follows. Confluent monolayers of cells (e.g., MDCK cells) in 96-well plates are incubated with log dilutions of clarified tissue homogenates in media. Two to three days after inoculation, 0.05-ml aliquots from each well are assessed for viral growth by hemagglutination assay (HA assay).

In a specific embodiment, the ability of an antibody or composition thereof to treat an influenza virus infection or disease associated therewith is assessed by determining the ability of the antibody to confer passive immunity to an influenza virus disease in a subject. The ability of an antibody described herein (e.g., a monoclonal antibody, such as a chimeric or humanized antibody, or an antigen-binding fragment thereof) to confer passive immunity to an influenza virus disease in a subject can be assessed using any methods known in the art or described herein (see, e.g., Section 6 and/or Section 7, infra).

5.7.5 Assays in Humans

In one embodiment, an antibody or composition thereof that modulates replication of an influenza virus is assessed in infected human subjects. In accordance with this embodiment, an antibody or composition thereof is administered to the human subject, and the effect of the antibody and/or composition on viral replication is determined by, e.g., analyzing the level of the virus or viral nucleic acids in a biological sample (e.g., serum or plasma). An antibody or composition thereof that alters virus replication can be identified by comparing the level of virus replication in a subject or group of subjects treated with a control antibody to that in a subject or group of subjects treated with an antibody or composition thereof. Alternatively, alterations in viral replication can be identified by comparing the level of the virus replication in a subject or group of subjects before and after the administration of an antibody or composition thereof. Techniques known to those of skill in the art can be used to obtain the biological sample and analyze the mRNA or protein expression.

In another embodiment, the effect of an antibody or composition thereof on the severity of one or more symptoms associated with an influenza virus infection/disease are assessed in an infected subject. In accordance with this embodiment, an antibody or composition thereof or a control antibody is administered to a human subject suffering from influenza virus infection and the effect of the antibody or composition on one or more symptoms of the virus infection is determined. An antibody or composition thereof that reduces one or more symptoms can be identified by comparing the subjects treated with a control antibody to the subjects treated with the antibody or composition. Techniques known to physicians familiar with infectious diseases can be used to determine whether an antibody or composition thereof reduces one or more symptoms associated with the influenza virus disease.

5.8 Kits

In another aspect, provided herein is a pharmaceutical pack or kit comprising one or more containers filled with one or more of the ingredients of a composition (e.g., a pharmaceutical compositions) described herein, such as one or more antibodies provided herein (e.g., a monoclonal antibody, such as a chimeric or humanized antibody, or an antigen-binding fragment thereof), one or more polynucleotides described herein, or one or more antibody conjugates described herein. Optionally associated with such container(s) can be a notice in the form prescribed by a governmental agency regulating the manufacture, use or sale of pharmaceuticals or biological products, which notice reflects approval by the agency of manufacture, use or sale for human administration.

The kits encompassed herein can be used in the above methods. In one embodiment, a kit comprises an antibody described herein, preferably an isolated antibody, in one or more containers. In a specific embodiment, the kits encompassed herein contain an isolated influenza virus antigen that the antibodies encompassed herein react with (e.g., the antibody binds to the antigen) as a control. In a specific embodiment, the kits provided herein further comprise a control antibody which does not react with an influenza B virus NA (e.g., the antibody does not bind to the influenza B virus NA, such as a control IgG). In another specific embodiment, the kits provided herein contain a means for detecting the binding of an antibody to an influenza B virus NA (e.g., the antibody may be conjugated to a detectable substrate such as a fluorescent compound, an enzymatic substrate, a radioactive compound, a luminescent compound, or another antibody that is conjugated to a detectable substrate (e.g., the antibody may be conjugated to a second antibody which recognizes/binds to the first antibody)). In certain embodiments, the kits comprise a second antibody which is labeled with a detectable substance and which binds to an antibody described herein. In specific embodiments, the kit may include a recombinantly produced or chemically synthesized influenza B virus NA (such as, e.g., described in Section 6 and/or Section 7, infra). The influenza B virus NA provided in the kit may also be attached to a solid support. In a more specific embodiment the detecting means of the above described kit includes a solid support to which an influenza virus antigen is attached. Such a kit may also include a non-attached reporter-labeled antibody. In this embodiment, binding of the antibody to the influenza B virus NA can be detected by binding of the said reporter-labeled antibody.

6. EXAMPLE: BROADLY PROTECTIVE MONOCLONAL ANTIBODIES AGAINST INFLUENZA B VIRUS TARGET HIGHLY CONSERVED NEURAMINIDASE EPITOPES

This example describes a panel of five murine anti-neuraminidase monoclonal antibodies which demonstrate broad binding, neuraminidase inhibition, in vitro antibody-dependent cell-mediated cytotoxicity, and in vivo protection against influenza B viruses belonging to both HA lineages and spanning over 70 years of antigenic drift. Electron microscopic analysis of two neuraminidase-antibody complexes shows that the conserved neuraminidase epitopes are located on the head of the molecule and that they are distinct from the enzymatic active site. In the mouse model, one therapeutic dose of antibody 1F2 was more protective than the current standard of treatment, oseltamivir, given twice daily for six days.

Also presented in this example are novel structures of recombinant IBV NA in complex with the fragment antigen-binding (Fab) portion of antibody, allowing for the direct comparison of structural binding footprints with critical binding residues (mapped using escape mutagenesis). Furthermore, such studies highlight the potential benefits of targeting the conserved regions of the NA when designing innovative influenza virus vaccines.

6.1 Materials and Methods

Cells, viruses, and proteins. As described previously (Wohlbold et al., J Virol 90, 851-861 (2015), Madin-Darby canine kidney (MDCK) cells (originated from MDCK (NBL-2; ATCC CCL-34) were grown in complete Dulbecco's modified Eagle medium (DMEM; Life Technologies) supplemented with antibiotics (100 U/ml penicillin-100 μg/ml streptomycin [Pen-Strep]; Gibco), 10% fetal bovine serum (FBS; HyClone), and 10 ml of 1 M HEPES (Life Technologies). Sf9 insect cells (originated from ATCC CRL-1711) were grown in TNM-FH insect medium (Gemini Bioproducts) supplemented with antibiotics (Pen-Strep) and 10% FBS, and High Five cells (BTI-TN-5B1-4 subclone; Vienna Institute of Biotechnology) (Krammer et al., Mol. Biotechnol. 45, 226-234 (2010)) were grown in serum-free SFX-insect cell medium (HyClone). SP2/0 mouse myeloma cells (originated from SP2/0-Agl4; ATCC CRL-1581) were passaged and maintained in complete DMEM supplemented with antibiotics (Pen-Step) prior to fusion with primary mouse splenocytes. Monoclonal, immortalized B cells (obtained from the hybridoma fusion) were initially grown in Clonacell-HY Medium E (Stemcell Technologies) and gradually switched to serum-free hybridoma medium (Hybridoma-SFM; Life Technologies) for high-volume production. All cell lines used tested negative for mycoplasma contamination using the MycoAlert™ Mycoplasma Detection Kit (Lonza).

The influenza viruses B/Lee/40, B/Victoria/2/87, B/Yamagata/16/88 B/Florida/04/06, B/Perth/211/2001 198D, B/Perth/211/2011 198E, B/Memphis/1B/2003, B/Malaysia/2506/04, B/Wisconsin/1/10, B/New Jersey/1/12, B/Massachusetts/2/12, B/Texas/2/13, and escape mutant viruses were grown in 8- to 10-day-old embryonated chicken eggs, and titers were determined on MDCK cells in the presence of TPCK (tosyl phenylalanyl chloromethyl ketone)-treated trypsin. To create purified virus preparations, allantoic fluid containing virus was harvested and subjected to low-speed centrifugation (at 3,000×g for 30 min at 4° C.) to remove cellular debris. Viruses were pelleted through a 30% sucrose cushion (30% sucrose in NTE buffer [100 mM NaCl, 10 mM Tris-HCl, 1 mM EDTA]; pH 7.4) by ultracentrifugation (Beckman L7-65 ultracentrifuge with SW-28 rotor at 25,000 rpm for 2 h). Once all of the supernatant was aspirated, virus pellets were resuspended in phosphate-buffered saline (PBS). B/Perth/211/2001 198D, B/Perth/211/2011 198E were kindly provided by Drs. Aeron Hurt and Elena Govorkova and are part of the 'Panel of Influenza A and B Viruses for Assessment of Neuraminidase Inhibitor Susceptibility' provided by the International Society for Influenza and other Respiratory Virus Diseases website.

The recombinant proteins used—B/Yamagata/16/88, B/Malaysia/2506/04, B/Florida/04/06, B/Brisbane/60/08, B/Wisconsin/1/10 NAs—were expressed in High Five cells and purified from cell culture supernatants as described previously (Krammer et al., PLoS One 7, e43603 (2012) and Margine et al., J. Vis. Exp., e51112 (2013)). In brief, cultures were infected with recombinant baculoviruses at a multiplicity of infection of 10. Supernatants were then harvested by low-speed centrifugation at 72 h post infection and purified by using Ni-nitrilotriacetic acid resin (Qiagen) according to a published protocol (Margine et al., J. Vis. Exp., e51112 (2013)).

Generation and screening of mAbs. Similarly to the protocol described previously (Wohlbold et al., J Virol 90, 851-861 (2015) and Wang et al., PLoS Pathog. 6, e1000796 (2010)), six- to eight-week-old female BALB/c mice were first immunized with 40 ug of DNA (in 40 uL distilled H2O) encoding the open reading frame of the HA from the parental strain B/Yamagata/16/88 in the PCAGGS vector (DNA was delivered via intramuscular electroporation in the medial thigh using a TriGrid Delviery System [Ichor Medical Systems]) followed 4 weeks later by a second immunization with the HA from the parental strain B/Victoria/2/87 (this vaccination regimen was initially designed to elicit both HA- and NA-directed mAbs). Four weeks after the second immunization, mice were intranasally infected with a sublethal dose ($10^4$ plaque-forming units [PFU] in 50 uL PBS) of B/Florida/4/06, followed 6 weeks later by intranasal infection with a sublethal dose ($10^4$ PFU in 50 uL PBS) of B/Malaysia/2506/04. Approximately 6 weeks after the second infection, one mouse was boosted with a unilateral, intraperitoneal injection of 100 ug of formalin-inactivated, purified B/Wisconsin/1/2010 virus adjuvanted with 10 ug of poly(I·C).

Three days post-boost, one mouse was sacrificed, and its spleen was sterilely removed. The spleen was flushed forcefully with serum-free DMEM (with antibiotics [Pen-Strep]) using a 10-ml syringe with a 20-gauge needle, followed by repeated mashing with flat-ending forceps. Splenocytes and SP2/0 myeloma cells (in log phase) were combined in a 5:1 ratio, and cell fusion was mediated via slow, drop-wise addition of 1 ml of polyethylene glycol (molecular weight, 4,000 g/mol). The splenocyte/SP2 mixture was resuspended in 25 ml of complete DMEM (supplemented with antibiotics [Pen-Strep], FBS, and HEPES) and left to incubate for 24 h. After this incubation, the cells were spun down, resuspended in 10 ml of complete DMEM, mixed with a proprietary bottle of 90 ml of semisolid Clonacell-HY Medium D (Stemcell Technologies), and dispensed onto tissue culture dishes (10 ml each) using a 10-ml syringe with a 15-gauge Luer Stub adapter (Becton Dickinson). Individual colonies were picked 10 days later and transferred into 96-well plates containing Clonacell-HY Medium E. Five days after transfer to 96-well plates, hybridoma supernatants were screened by ELISA for binding reactivity to B/Lee/40 (purified, whole virus), B/Yamagata/16/88 (rNA), and NI activity to B/Wisconsin/1/2010 virus. Positive clones were isotyped using a Pierce rapid antibody isotyping kit (Life Technologies); only the mAbs isotyped to the IgG heavy-chain subclasses were selected for further expansion and purification. All animal procedures were performed in accordance with the Icahn School of Medicine at Mount Sinai Institutional Animal Care and Use Committee (IACUC).

Expansion and purification of mAbs. Mabs were produced and purified as described previously (Wohlbold et al., J Virol 90, 851-861 (2015)). Fab fragments for mAbs 1F2 and 4F11 were generated by papain digestion by Southern Biotech (Birmingham, AL).

ELISA. ELISAs were performed as described previously (Wohlbold et al., J Virol 90, 851-861 (2015)). An endpoint titer was defined as the final concentration at which the antibody signal remained greater than 3 standard deviations above the average of the blank wells, as described in Wang et al., PLoS Pathog. 6, e1000796 (2010).

Enzyme-linked lectin assay. Enzyme-linked lectin assays (ELLAs), used to determine NA inhibition (NI) activity, were performed as described in detail in previous reports (Wohlbold et al., MBio 6, 1-13 (2015) and Wohlbold et al., J Virol 90, 851-861 (2015)).

NA-Star Assay. The NA-Star Influenza Neuraminidase Inhibitor Resistance Detection Kit (Applied Biosystems) was used to assess mAb (or Fab) inhibition of the neuraminidase's ability to cleave a small, soluble, chemiluminescent substrate (sodium (2-chloro-5-(4-methoxyspiro{1,2-dioxetane-3,2'-(5-chloro)tricyclo[3.3.1.13,7]decan}-4-yl-phenyl 5-acetamido-3,5-dideoxy-α-D-glycero-D-galacto-2-nonulopyranoside)onate).

To measure antibody-mediated inhibition, mAb (or Fab) was diluted 1:3 in NA-Star Assay Buffer (starting concentration, 100 ug/ml; final volume per well, 25 μl) in white, flat bottom, 96-well cell culture plates. Twenty-five μl of virus at the determined $3\times EC_{50}$ (half-maximum effective concentration), was added to each well and plates were shaken and incubated for 30 min at 37° C. The remainder of the assay was performed identically to the method described above beginning with the addition of NA-Star Substrate. Data points were expressed as percent inhibition of maximal NA enzymatic activity, which was determined by the activity of virus without the addition of antibody. Curves were plotted using Prism software (GraphPad).

Sequencing variable sequences of BNA antibodies. $5\times10^6$ cells from hybridoma cell lines were used to purify the total mRNA using a Direct-zol RNA Miniprep kit (Zymo Research) according to the manufacturer's instructions. Purified RNA was reverse transcribed using SuperScript™ III Reverse Transcriptase (Thermo Fisher) and the cDNA was stabilized in a Terminal Deoxynucleotidyl Transferase (TdT) tailing reaction (Invitrogen). The product of TdT tailing was used as a template in a PCR reaction using high fidelity Taq Platinum polymerase (Invitrogen) with a variable region specific 5' consensus anchor primer (5' GGCCACGCGTCGACTAGTACGGGNNGGGNNGGGNNG 3', wherein N is C, T, or A (SEQ ID NO: 91)) and a constant region specific reverse primer (5' CCTTGACCAGGCATCCTAGAGTC 3' (SEQ ID NO: 92) or 5' GGAGGTGTGCACACTGCTGGACAG 3' (SEQ ID NO: 93), for IgG2a and IgG2b respectively). PCR reaction products were sequenced, and the obtained sequences were entered into the IMGT/V-QUEST database tool (www.imgt.org/IMGT_vquest/share/textes/) to determine complete variable region sequence as well as individual germline genes. In cases where the quality of sequencing read was not sufficient, the PCR product was first cloned into Strataclone vectors (Agilent Technologies) which were then amplified in StrataClone competent cells, purified using QIAPrep Spin Miniprep Kit (Qiagen) and then sequenced before entering them into the IMGT/V-Quest.

Antibody/antigen biotinylation. Antibodies and rNA were biotinylated using an EZ-Link NHS-PEG4-Biotin kit (Thermo Fisher Scientific) according to the manufacturer's instructions.

$K_D$ determination using biolayer interferometry. Antibody dissociation constants ($K_D$ values) were determined by biolayer interferometry using an Octet Red96 instrument (ForteBio, Inc.), as described previously (Dunand et al., Cell Host Microbe. 2016; 19:800-813). Biosensors were loaded with rNA from B/Malaysia/2506/04.

Multiple sequence alignment. Sequences were obtained from the Global Initiative on Sharing All Influenza Data (GISAID) website with any laboratory-associated strains or truncated sequences removed from analysis. There were a total of 2409 sequences in the final file that was used for alignments. Sequence alignments were performed using MEGA 6.0 software (MUSCLE alignment).

Phylogenetic tree generation. A subsample of 280 sequences were chosen to form the phylogenic tree. For years in which 10 or less sequences were available, all sequences were used; for years with greater than 10 sequences, a random selection of 10 sequences was chosen to minimize the bias of more recent isolates. Sequences were aligned using MUSCLE and manually edited using the MEGA 6.0 software when applicable. Phylogenetic tree was assembled using Clustal Omega web server with a Neighbor-joining clustering method and default setting. The tree was cleaned and edited using FigTree.

Percent conservation calculation. Escape residues were isolated from the whole NA protein sequence alignment using sequence editing tools in MEGA 6.06. A subsample of 944 sequences was used for calculations. For years in which 50 or less sequences were available, all sequences were used; for years with greater than 50 sequences, a random selection of 50 sequences was chosen to minimize the bias of more recent isolates. To give the percentage of the number of sequences that contained a specific amino acid at each escape reside location, the amino acid phenotypes at the site were sorted and then divided by the total number of sequences.

Negative stain electron microscopy. Recombinant NA and Fabs were diluted with buffer (5 mM HEPES, 150 mM NaCl pH 7.3) to approximately 0.02 mg/mL and 0.04 mg/mL respectively. To prepare Fab bound samples, equal volumes of NA and Fabs 1F2 or 4F11 were mixed and incubated for 5-10 minutes. The samples were adsorbed to plasma cleaned (Solarus Model 950 cleaner, Gatan Inc., Pleasanton, CA) EM grids coated with continuous carbon film that were subsequently washed with buffer and stained with 0.75% uranyl formate. Images were collected using EPU software (FEI Company, Hillsboro, OR) on a Tecnai T12 electron microscope (FEI Company) fitted with a 4K CCD camera (Gatan Inc.) at an effective pixel size of 0.18 nm in the specimen plane. The software package RELION 1.4 (Scheres et al., J. Struct. Biol. 180, 519-530 (2012)) was used to obtain 3D reconstructions. The maps for unbound NA, and for the complexes with 1F2, and 4F11 were constructed using 47,592, 4,326, and 13,665 particles, respectively and visualized using UCSF Chimera software Pettersen et al., J. Comput. Chem. 25, 1605-1612 (2004).

Modeling Fab binding footprints. NA and Fab (Influenza B HA Fab CR8033) X-ray coordinates (PDB IDs: 4CPL and 4FQL, respectively) were fitted to density maps using UCSF Chimera software. To highlight the binding footprints of the Fabs, the regions of NA that most closely interacted with each Fab were identified by manual inspection.

Generation of IBV anti-NA mAb escape mutant viruses. MAb escape mutant variants of B/Malaysia/2506/04 virus were generated based on the methods described in Wan et al., J Virol 87, 9290-9300 (2013). MAb (250 μg) and virus ($10^6$ PFU) were combined (total volume, 800 ul), incubated for 1 h at RT, split evenly into thirds and injected into three 8-day old embryonated chicken eggs. After incubating for 72 hours at 33° C., allantoic fluid was harvested and plaqued in the presence of mAb (100 ug/ml in both inoculum and overlay). After incubating for 72 hours at 33° C., plaque assays were inspected for escape variants (as evidenced by large plaque size). Large plaques were picked and inoculated into 10-day old embryonated chicken eggs for amplification. All escape mutant variants, excluding that of mAb 4B2, were generated in this way. In the case of 4B2, B/Malaysia/2506/04 virus was serially passaged on an MDCK cell monolayer in the presence of increasing amounts of mAb, with a starting concentration of 0.25×IC50 (as calculated from the NI assay against B/Malaysia/2506/04 virus). Initially, MDCK cells in 1 well of a 6-well plate were infected with B/Malaysia/2506/04 virus at an MOI of 0.1 in the presence of 0.5×IC50 of mAb. After incubating for 72 hours at 33° C., 10 ul of supernatant was collected and used to directly inoculate a fresh monolayer of MDCK cells in the presence of increased mAb concentration. This process was repeated for 15 passages, until the final antibody concentration was ~1 mg/ml. Throughout serial passaging, successful infection was confirmed by the presence of cytopathic effect (CPE) or—if CPE was not clear—positive staining with polyclonal anti-IBV mouse serum (detailed immunostaining procedure is described below in the "evaluation of the prophylactic and therapeutic efficacy in mice" section). Both CPE and positive immunostaining were present in the last passage. Virus was additionally passaged in the presence of an irrelevant mouse mAb (3C12, anti-N8, IgG, characterized previously in Wohlbold et al., J Virol 90, 851-861 (2015) throughout all experiments to control for mutational variants obtained from passaging alone. Viruses were plaque purified once serial passaging was completed to create monoclonal stocks for deep sequencing and growth curve analysis.

Growth curve analysis. To compare viral fitness in the presence of mAb, growth curves were performed in MDCK cells. Cells were plated as a confluent monolayer in 12-well tissue culture plates (Sigma) and infected with virus at an MOI of 0.01 (final volume of 1 ml/well). The experiment was performed in triplicate for each time point and each antibody condition. MAb was added to infection media at a concentration of 10 μg/ml. Cells were incubated at 33° C., and supernatant was collected at 12, 24, 48, or 72 hpi. Collected supernatant was clarified by centrifugation (at a relative centrifugal force of 3,000 for 10 min at 4° C.) and immediately stored at −80° C. For simplicity, only titers at 72 hpi are reported here. Viral titers were assessed via hemagglutination assays, as described previously (Wohlbold et al., Vaccine 33, 1102-1106 (2015), Klausberger et al., Vaccine 32, 355-62 (2014), and Krammer et al., J. Virol. 88, 3976-85 (2014)).

Deep sequencing of escape mutant variants. RNA from the escape mutant variants was obtained using the Direct-zol RNA kit (Zymo Research). The samples were processed using the Illumina TruSeq RNA Sample Preparation Kit according to the manufacturers instructions and sequenced using a MiSeq Illumina instrument. Reads were consolidated and aligned to B/Malaysia/2506/04 using Bowtie2. The assembled genomes and minority variants were visualized with the Integrative Genomic Viewer (IGV) (Broad Institute).

Immunofluorescence. To screen for escape mutants, MDCK cells were plated in 96-well, sterile, flat-bottom tissue culture plates (Sigma) and subsequently infected with either wt B/Malaysia/2506/04 or mutant viruses at an MOI of 10. After incubating for 18 hours at 33° C. in MEM lacking TPCK-trypsin (to limit viral growth to 1 infectious cycle), media was removed, and cells were fixed with 3.7% formaldehyde for at least 1 h at 4° C. Next, the formaldehyde was discarded and the cell monolayer was blocked with 3% milk in PBS for at least 1 h. For the primary antibody step, plates were incubated with either the respective IBV anti-NA mAb (30 ug/ml), a positive infection control (a polyclonal cocktail of purified mouse mAb IgGs against the IBV HA [1:1000 dilution], or irrelevant negative control mouse mAb 8H9 in PBS, 1% milk (100 ul/well) for 1 h at RT, while shaking. Next, plates were washed 3 times with PBS and incubated with Alexa Fluor® 488 goat anti-mouse secondary antibody in PBS, 1% milk (100 ul/well) for 1 h at RT in the dark. Finally, after washing 3 additional times, cells were visualized via fluorescent microscopy.

3D mapping of escape mutations. Escape mutations were represented on a 3D structure of the NA of B/Brisbane/60/2008 (PDB ID: 4CPL) using PyMOL™ version 1.8.4.2 (Schrodinger, LLC).

Competition ELISAs. Microtiter 96-well plates (Immulon 4 HBX, Thermo Fisher Scientific) were coated with 2 μg/mL (50 μL/well) of rNA from B/Florida/04/2006 diluted in coating solution (KPL). The plates were incubated at 4° C. overnight. The next day, plates were washed three times with PBS containing 0.1% Tween-20 (PBS-T) and then incubated for 1 hour at 20° C. with 225 μL/well of blocking solution (PBS-T with 3% goat serum (Life Technologies, Inc.) and 0.5% milk powder)). After the blocking solution was removed, the competing monoclonal antibodies were diluted in blocking solution at 20 μg/ml and transferred to the plate. Blocking solution with no antibodies was used as a no-competition control. The final volume in each well after dilution was 100 μL. After a 2 hour incubation period at 20° C., the plates were washed three times with PBS-T. Following the wash, the biotinylated target antibodies were diluted in 1:3 steps with a starting concentration of 30 μg/ml in blocking solution and then incubated for 2 hours at 20° C. Subsequently, the plates were washed three times with PBS-T and then incubated with Streptavidin conjugated to HRP (1:3000, 50 μL/well, Thermo Fisher Scientific). After 1 hour at 20° C. the plates were washed four times with PBS-T and then developed with SigmaFast o-phenylenediamine dichloride (OPD, 100 μl/well) (Sigma) for 10 minutes. The reaction was stopped with the addition of 3 M hydrochloric acid (50 μl/well). The plates were immediately read using a Synergy H1 hybrid multimode microplate reader (BioTek) at an optical density of 490 nm.

Animals. All animal procedures were performed in accordance with the Icahn School of Medicine at Mount Sinai Institutional Animal Care and Use Committee (IACUC). Female mice (species: *Mus musculus*; strain: BALB/c) aged 4-6 weeks (The Jackson Laboratory) were used for all studies. Researchers performing animal experiments were not blinded. Mice were randomly assigned to infection and treatment groups without the use of a specific algorithm. A sample size of 3 mice per group was chosen for lung titer analyses and 5 mice per group for challenge studies according to the general practices in the influenza field. Sample sizes were not determined using power analyses.

Evaluation of the prophylactic and therapeutic efficacy in mice. Prophylactic and therapeutic protection studies and quantification of viral lung titers in mice were performed as described previously in (Wohlbold et al., MBio 6, 1-13 (2015) and Wohlbold et al., J Virol 90, 851-861 (2015)). All animal procedures were performed in accordance with the Icahn School of Medicine at Mount Sinai IACUC.

Oseltamivir treatment studies. Oseltamivir phosphate (Fischer Scientific, United States Pharmacopeia [USP] Reference Standard) was administered to mice via oral gavage twice daily (every 12 hours) at a dose of 20 mg/kg (in a total volume of 100 ul water for injection [Gibco]) for 6 days following treatment commencement. This dosing (40 mg/kg/day) was based off of recently published dosing regimens used in the BALB/c mouse model (Hai et al., Nat. Commun. 4, 1-16 (2013) and Marathe et al., Sci. Rep. 6, 1-14 (2016)) as well as the standard dosing recommended for therapeutic treatment in adult humans by the Advisory Committee on Immunization Practices (ACIP) (Fiore et al., MMWR. Recomm. Rep. 60, 1-24 (2011)).

Mouse ADCC assays. Assessment of the ability of mAbs to trigger ADCC was performed using a commercial ADCC kit (Promega) and according to the manufacturer's instructions. Briefly, MDCK cells were seeded into white, flat bottom, 96-well cell culture plates (Costar) at a density of $3.0\times10^4$ cells/well and incubated overnight at 37° C. and 5% $CO_2$. The following day, the cells were infected with B/Yamagata/16/88, B/Malaysia/2506/04 or B/Florida/04/06 virus at a multiplicity of infection of 3 and incubated at 33° C., 5% $CO_2$. Sixteen hours later, cell medium was exchanged for 3-fold serial dilutions of antibody in assay buffer, starting at 30 μg/mL. Effector cells were added and after another 6 hours of incubation (37° C., 5% $CO_2$), Bio-Glo™ luminescence reagent and substrate (Promega) were added and luminescence was measured on a Synergy H1 microplate reader (BioTek). Data were analyzed using Prism 6 software (GraphPad).

PRNAs. Plaque reduction neutralization assays (PRNAs) were performed according to the protocols described by Tan et al., J. Virol. 86, 6179-6188 (2012) and Wohlbold et al., J Virol 90, 851-861 (2015), with some modifications. In duplicate, six 5-fold dilutions of mAbs (highest concentration: 100 μg/ml; lowest concentration: $3.2\times10^{-1}$ μg/ml) were prepared in serum free, 1×MEM and each dilution was incubated with 100 PFU of virus for 1 h 30 min at RT, on a shaker. The inocula were then plaqued on MDCK cell monolayers in either 12 (B/Victoria/2/87, B/Yamagata/16/88, B/Victoria/2/87 viruses) or 6-well (B/Malaysia/2506/04 virus) plates, similar to the protocol used to plaque lung titers (described earlier). After 3 days of incubation at 33° C., the cells were fixed with 3.7% formaldehyde for at least 1 h at 4° C. and blocked with 3% milk in PBS for at least 1 h. For the primary antibody step, plates were then incubated with a cocktail of broadly-reactive, anti-IBV HA mouse mAbs (1:5000 dilution in PBS, 1% milk) for 1 h at RT, while shaking. Next, plates were washed with PBS and incubated with an anti-mouse secondary antibody conjugated to HRP (Sigma) for 30 min at 37° C. Finally, plates were washed and stained with True-Blue (KPL) so plaques could be visualized and counted. The plaques were counted in each mAb dilution, and the percent inhibition for each mAb at each dilution was calculated based on a no-antibody control. An irrelevant murine IgG (8H9) was used as a negative control. The data were analyzed by using Prism software (GraphPad). The decrease in plaque size upon incubation with antibody was also assessed. To analyze average plaque diameter, 10 plaques were randomly selected in each well using a technique described previously (Wohlbold et al., J Virol 90, 851-861 (2015)).

Statistical analysis. Statistical analysis was performed using Prism software (GraphPad). Lung virus titers were compared using a one-way ANOVA corrected for multiple comparisons. Differences in survival were analyzed using a Matel-Cox log rank test. Statistical significance is indicated where tested as follows: n.s. is $p>0.05$, * is $p\leq0.05$,  is $p\leq0.01$, * is $p\leq0.001$ and **** is $p\leq0.0001$.

6.2 Results

Using hybridoma technology, a panel of five broadly cross-reactive IBV NA-binding mAbs were identified from the spleen of a single female BALB/c mouse which was serially immunized with IBVs from both the Victoria (V) and Yamagata (Y) lineages. All IgG-producing hybridoma clones were initially screened for binding to the ancestral B/Lee/40 strain (purified, whole virus), binding to recombinant, baculovirus-expressed NA (rNA) from B/Yamagata/16/88, and inhibiting neuraminidase activity of B/Wisconsin/1/2010 (Y) virus. Five hybridomas—1F2 (IgG2a), 1F4 (IgG2a), 3G1 (IgG2a), 4B2 (IgG2a), and 4F11 (IgG2b)—were selected based on robust reactivity and were further tested for binding and neuraminidase inhibition (NI) activity to a wide array of IBVs covering both lineages and spanning 73 years of antigenic drift. The five mAbs were encoded by different light chain/heavy chain combinations with various degrees of mutations as compared to the germline sequences. All five mAbs displayed broad cross-reactivity to purified whole virus and rNA in enzyme-linked immunosorbent assays (ELISAs) and functionally inhibited NA enzymatic activity in enzyme-linked lectin assays (ELLAs) (FIGS. 1A and 1B). Most mAbs displayed minimal binding concentrations to rNA in the sub-micromolar range, with binding to certain rNA substrates reaching minimal binding concentrations in the nanomolar range (between 1.5-150 nM). These findings were corroborated by affinity measurements via biolayer interferometry where all but one mAb (4B2) reached sub-nanomolar binding affinities (see Table 6). Since whole virus was coated based on amount of total protein in the preparation, the minimal binding concentrations in these ELISAs tended to be greater, on average, than those in which rNA was used as a substrate; other differences in binding between whole virus and rNA may be attributed to variation in protein folding and epitope availability. Expectedly, if a mAb did not bind the NA from a particular strain at a concentration of 10 μg/mL, it did not display NI activity against that strain. However, for some mAb/NA combinations, binding was observed at higher antibody concentrations (>10 μg/ml). Binding and NI activity against the ancestral B/Lee/40 strain was weak, but still present, compared to the negative control. By displaying a subsample of IBV NA amino acid sequences as a phylogenetic tree, it was observed that the strains used in this study are representative of the amino acid sequence diversity of IBV NAs, strengthening the conclusion that these anti-NA mAbs are broadly cross-reactive (FIG. 1C).

TABLE 6

Summary of the measured Kd, $k_{on}$, $k_{diss}$ as well as curve fitting parameters.

| Antibody | Kd (M) | $k_{on}$ (1/Ms) | $k_{diss}$ (1/s) | $X^2$ | $R^2$ |
|---|---|---|---|---|---|
| mAb 1F2 | 3.64E−10 | 3.99E+05 | 1.45E−04 | 0.1661 | 0.9988 |
| mAb 1F4 | 8.19E−10 | 5.19E+04 | 4.25E−05 | 0.086 | 0.9941 |
| mAb 3G1 | 5.32E−10 | 4.78E+05 | 2.55E−04 | 0.1646 | 0.9949 |
| mAb 4B2 | 1.75E−09 | 2.09E+05 | 3.64E−04 | 0.1503 | 0.9959 |
| mAb 4F11 | 1.52E−10 | 2.48E+05 | 3.76E−05 | 0.2054 | 0.9982 |

Protective epitopes on the IBV NA have yet to be described. To map the relevant epitopes on the surface of the NA protein, electron microscopic analysis of the complex between rNA and the Fab portions of antibodies 1F2 and 4F11 was carried out. The analysis was focused on 4F11 (because it displayed the widest binding breadth and greatest binding affinities overall), and 1F2 (because it displayed the strongest binding affinity to the ancestral B/Lee/40 strain) Fab fragments. The resultant density maps (resolution ~25 Å) were interpreted (FIGS. 2A and 2B) using coordinates from the X-ray structures of NA from B/Brisbane/60/2008 (PDB ID: 4CPL) and a Fab that binds an IBV HA (PDB ID: 4FQL). Top and oblique views of the complex (FIGS. 2A and 2B), enable visualization of the locations of the bound antibodies at the periphery of the NA tetramer, indicating that 1F2 has an orientation that is tilted relative to the plane of the NA tetramer, while 4F11 binds in an orientation in which the Fab is in the same plane as that of the tetramer. Detailed inspection of the footprints of the bound Fab molecules shows that the structural footprints of 4F11 and 1F2 are adjacent to each other, but separate. The amino acid residues of the binding footprints are highly conserved across all IBVs, consistent with the broad binding profiles of mAbs 4F11 and 1F2 (FIG. 2E). Interestingly, the binding sites of both Fabs appear to not directly overlap the enzymatic active site of NA (FIG. 2C). Reconstructions thus show that antibodies that inhibit NA activity need not contact the catalytic site directly and instead may function by binding and sterically hindering access of the NA to substrate.

Figure 24A:
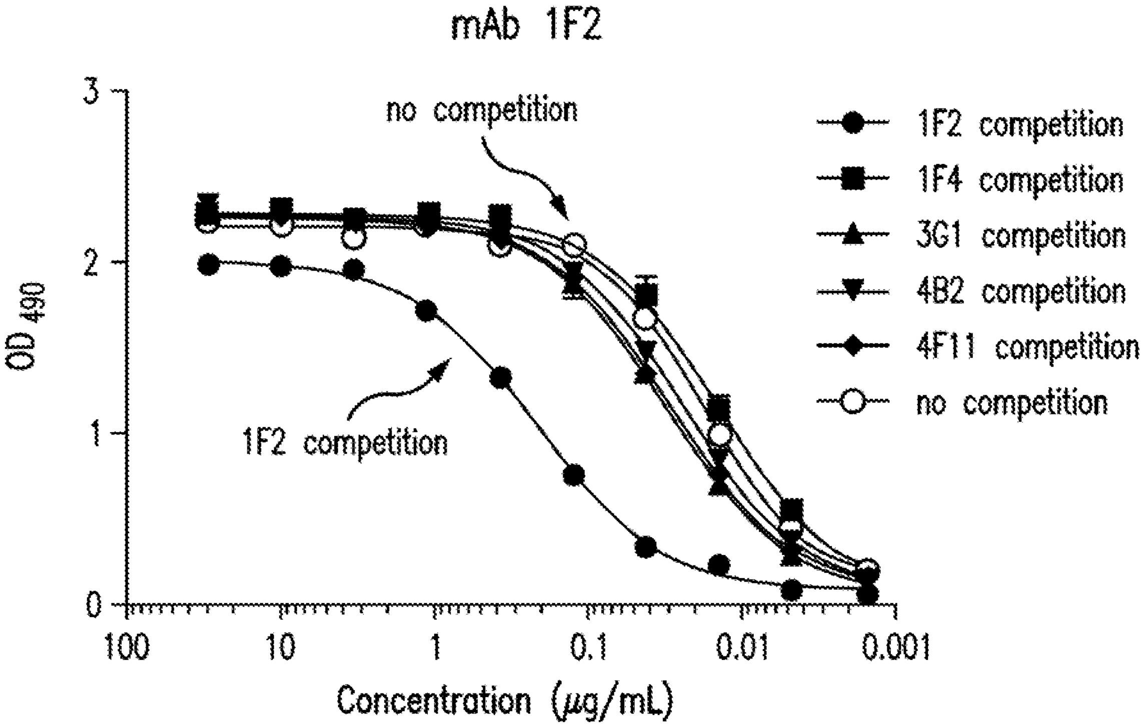
Figure 24B:
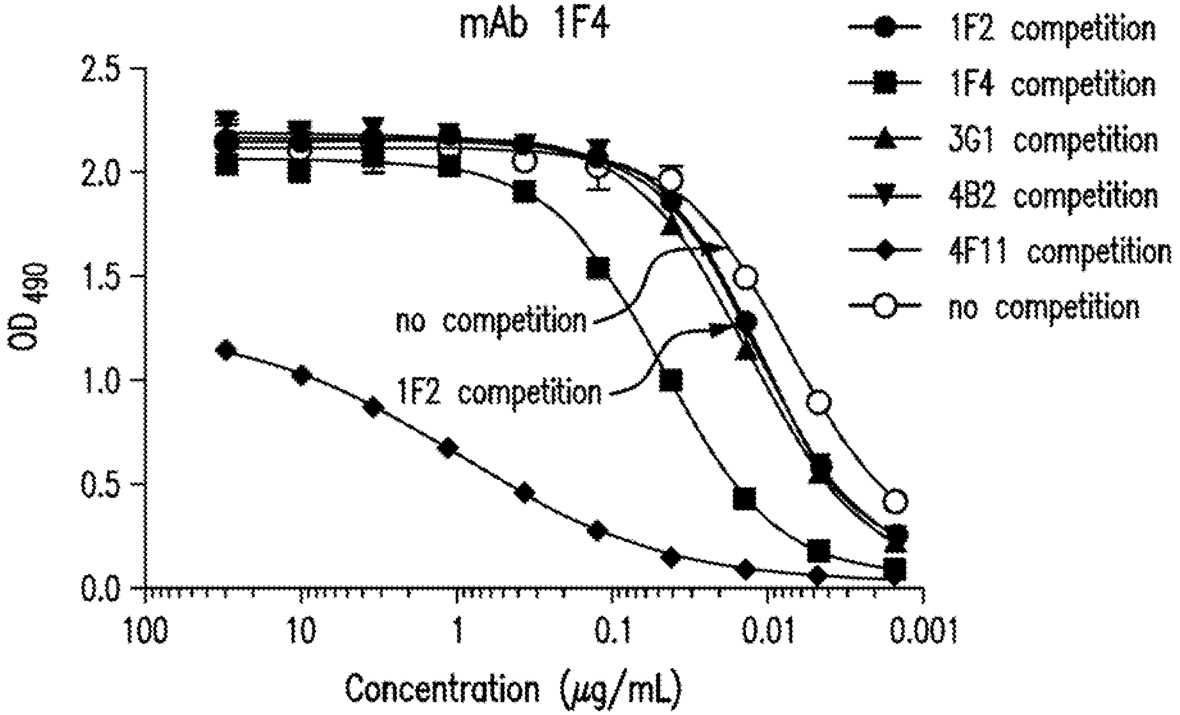
Figure 24C:
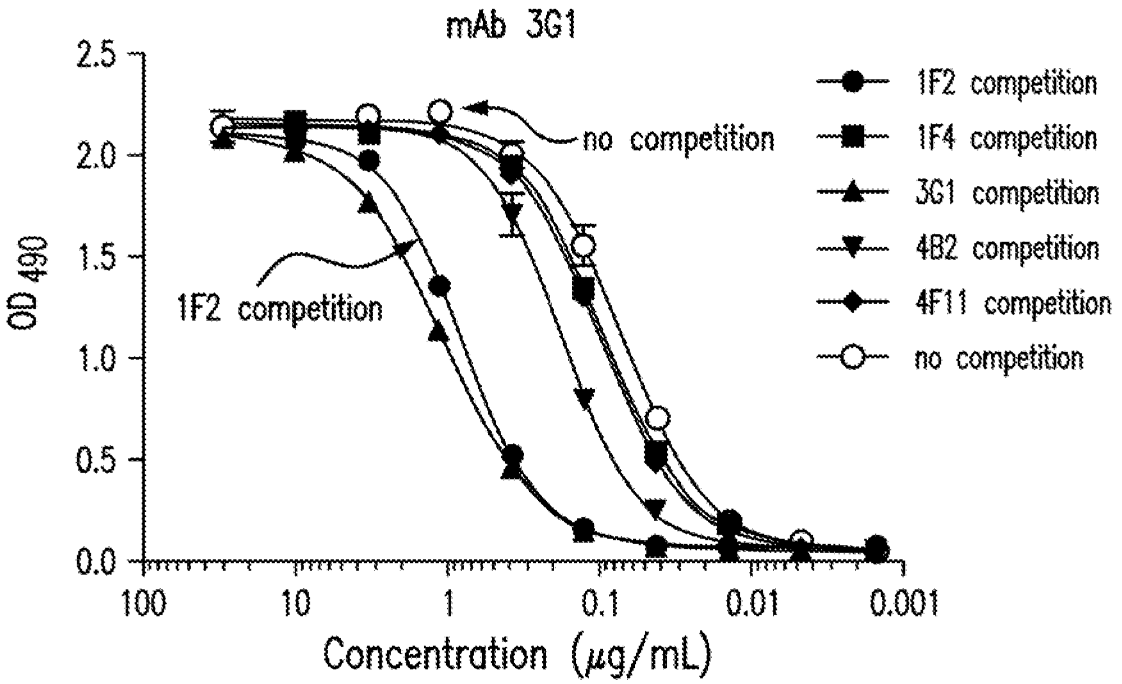
Figure 24D:
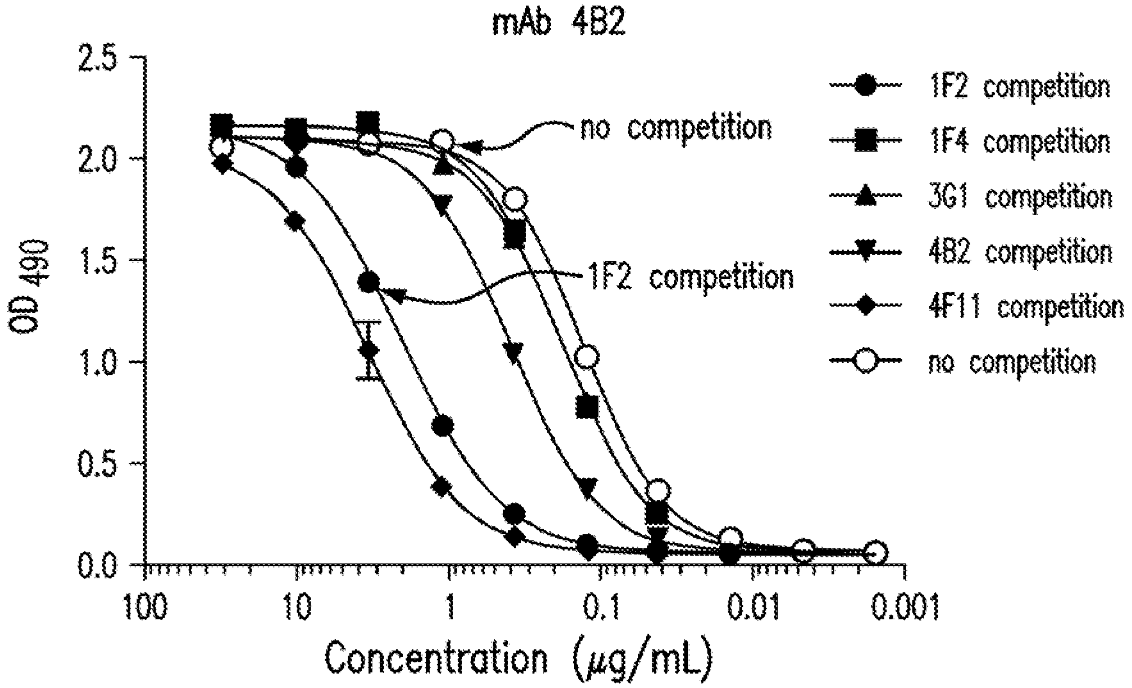
Figure 24E:
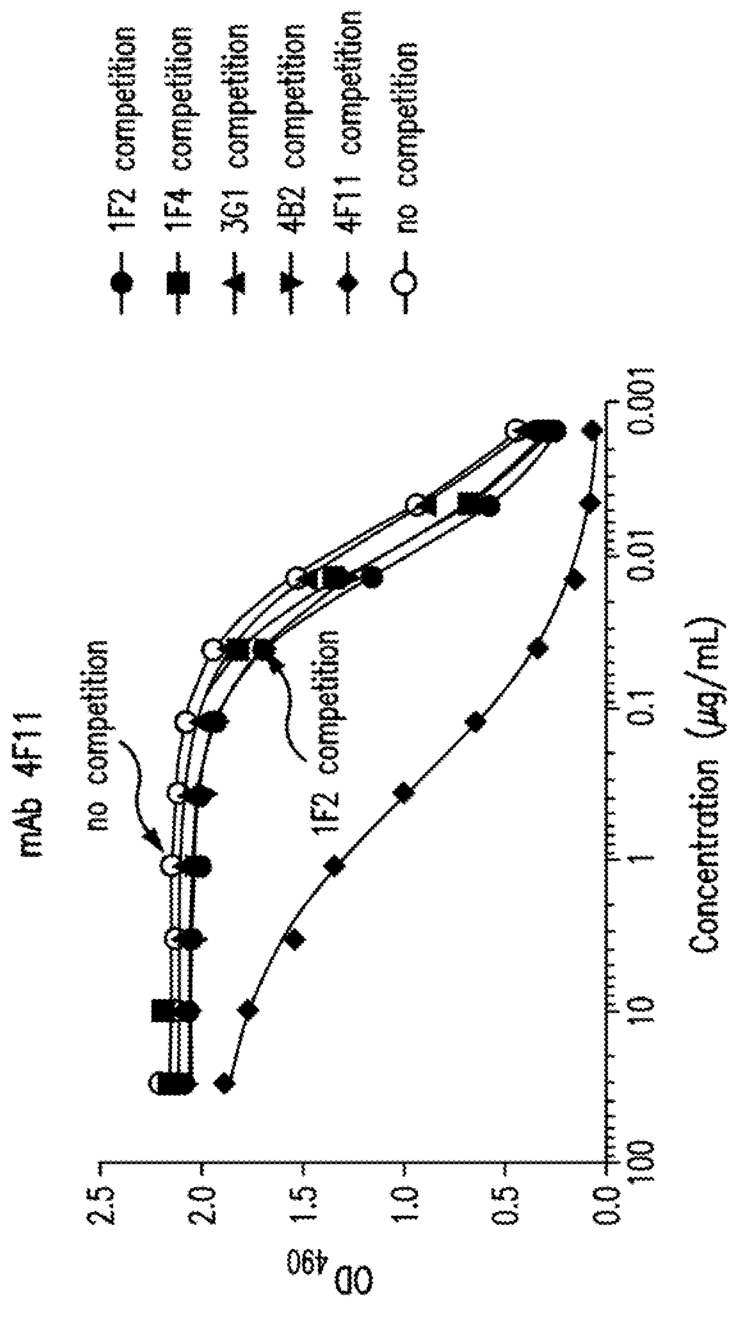
Figure 25B:
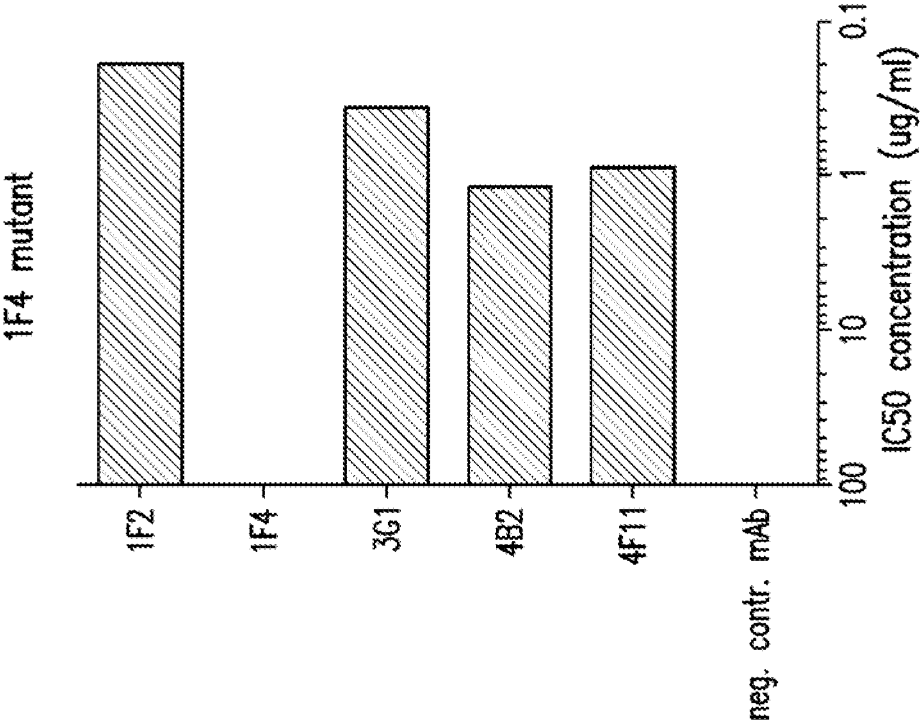
Figure 25A:
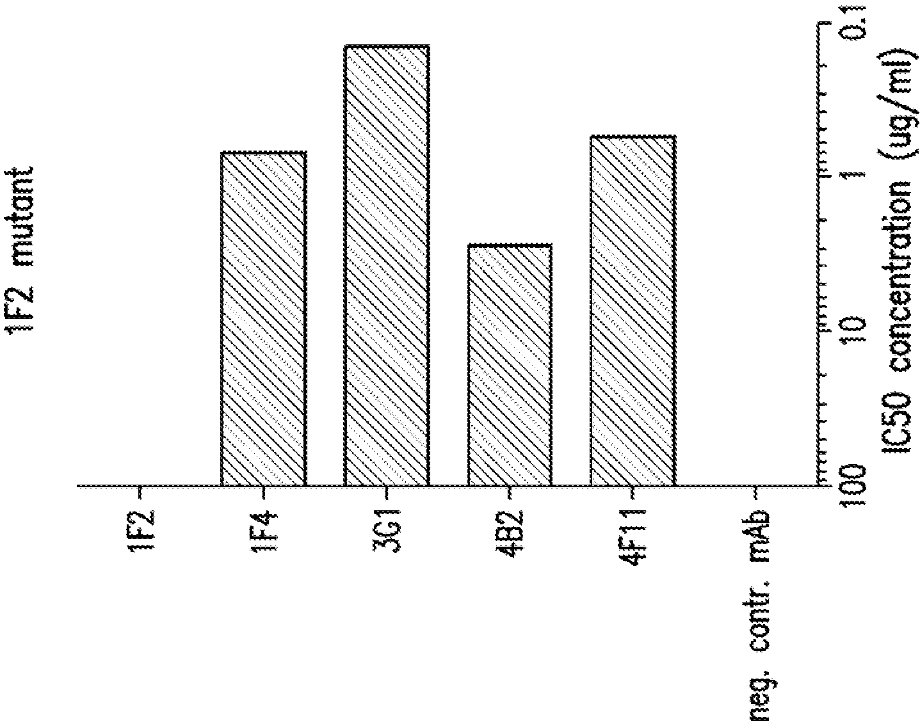
Figure 25C:
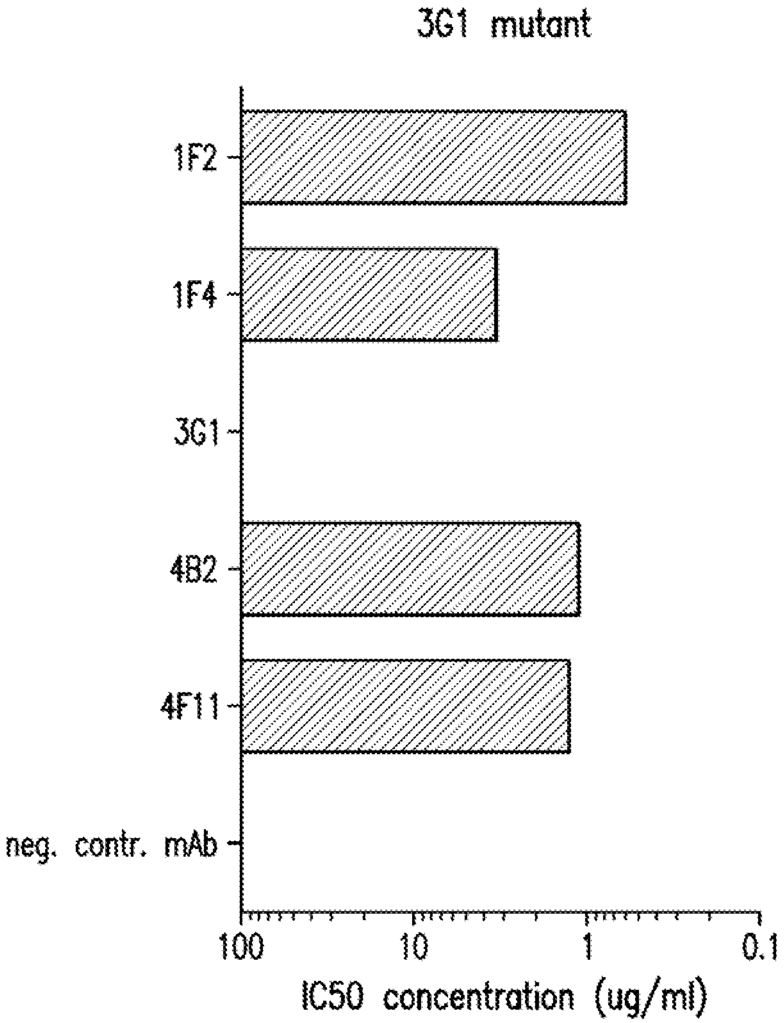
Figure 25D:
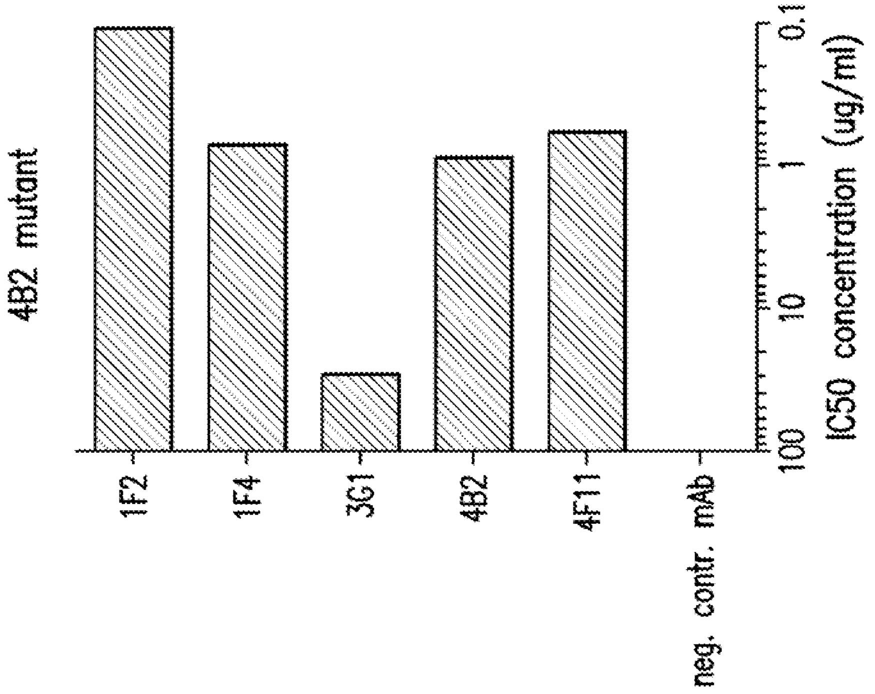
Figure 25E:
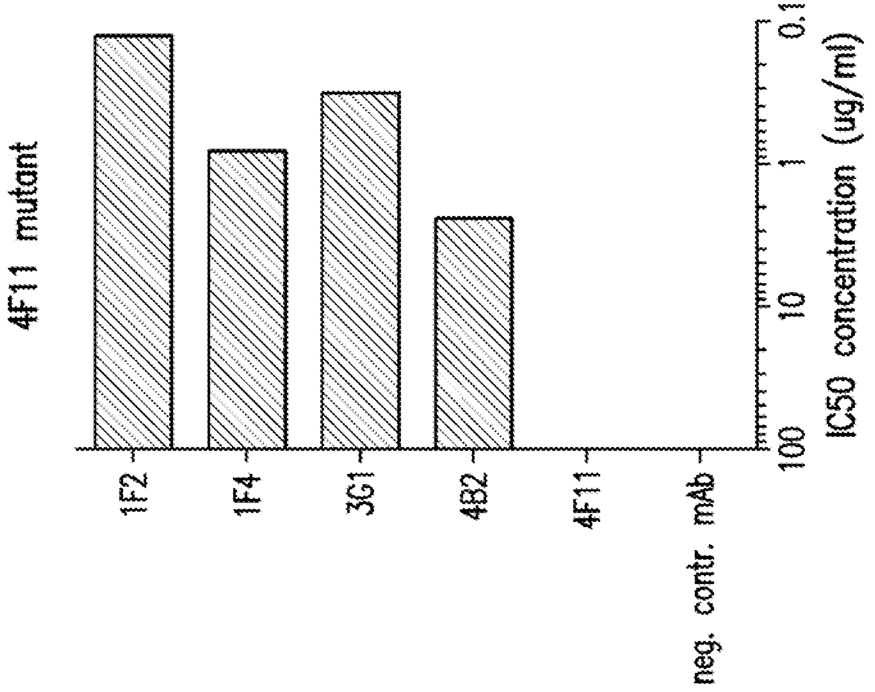

Residues critical for antibody binding were identified through the generation of escape mutant IBVs. Escape mutants generated against 4 out of the 5 mAbs showed drastic loss of binding to mAbs via immunofluorescence staining of infected Madin-Darby canine kidney (MDCK) cells (FIGS. 5A and 5B). Interestingly, the 4B2 escape mutant retained robust binding to antibody, but is nevertheless a true escape mutant, as demonstrated by its ability to grow to high titers compared to wild type (wt) virus in the presence of antibody (FIG. 5C). In this instance, mutations in other gene segments may have contributed to the ability of the mutant virus to escape antibody pressure. The critical residues identified in 1F2 and 4F11 escape mutants (E338K and G385R, respectively) are located either within or at the periphery of the binding footprints determined by electron microscopy (FIG. 5D). The critical residue identified in the 3G1 escape mutant (G346R) maps to a location close to the active site, consistent with the finding that this was the only one of the analyzed mAbs that could inhibit NA enzymatic activity to levels comparable to oseltamivir when using a small molecule substrate (FIG. 7F). Interestingly, mAb 1F2, which has a footprint adjacent to the 3G1 escape mutation, competed with mAb 3G1 in an ELISA assay (FIG. 24C). This was an asymmetric interaction since mAb 3G1 was unable to block 1F2 binding (FIG. 24A). The critical residue identified in the 1F4 escape mutant (Q453R) mapped close to the monomer-monomer interface of the NA tetramer. Of relevance, a quaternary, protective epitope spanning two monomers of the NA from pandemic H1N1 (A/California/07/2009) has been previously reported as the target of a human mAb (Wan et al., *Nat. Commun.* 6, 6114 (2015)). It is conceivable that 1F4 binds to IBV NA in a similar manner. mAb 1F4 asymmetrically competed with mAb 4F11 suggesting that it binds closer to the 4F11 footprint than to the 1F2 footprint (FIGS. 5 and 24). Finally, deep sequencing of the 4B2 escape mutant did indeed reveal a non-synonymous mutation in NA (G344E), although the mutation does not alter the binding of mAb 4B2 as assessed by immunofluorescence (FIG. 5D). Competition ELISA analysis corroborated these findings with asymmetric competition between 4B2 with both 1F2 and 4F11 (FIG. 24). The mutation found in the 4B2 escape mutant is located right above both the 1F2 and the 4F11 footprint. All generated escape mutants lost sensitivity to the respective mAbs in an NI assay with the exception of the 4B2 escape mutant, which was still inhibited by mAb 4B2 (FIGS. 25A-25E). However, this virus does not seem to escape by abolishing antibody binding to the NA as discussed above (FIG. 5C).

Figure 3B:
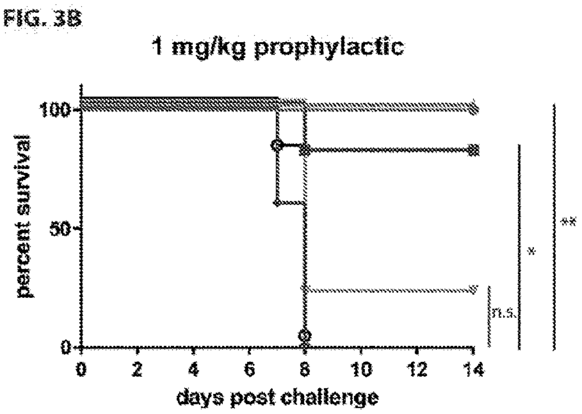
Figure 3E:
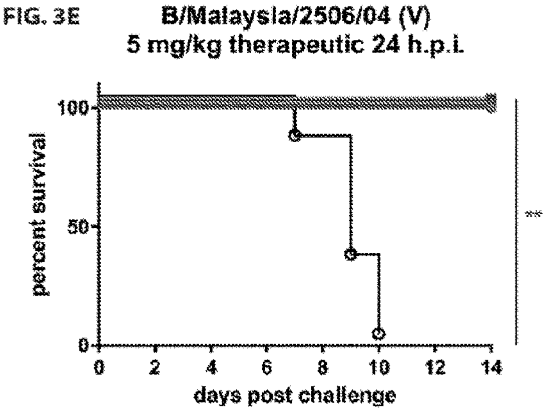
Figure 3C:
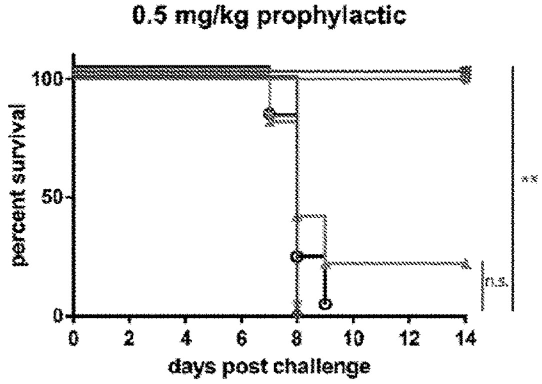
Figure 3F:
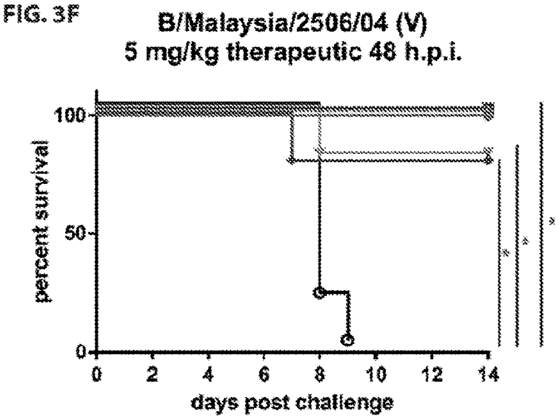
Figure 6E:
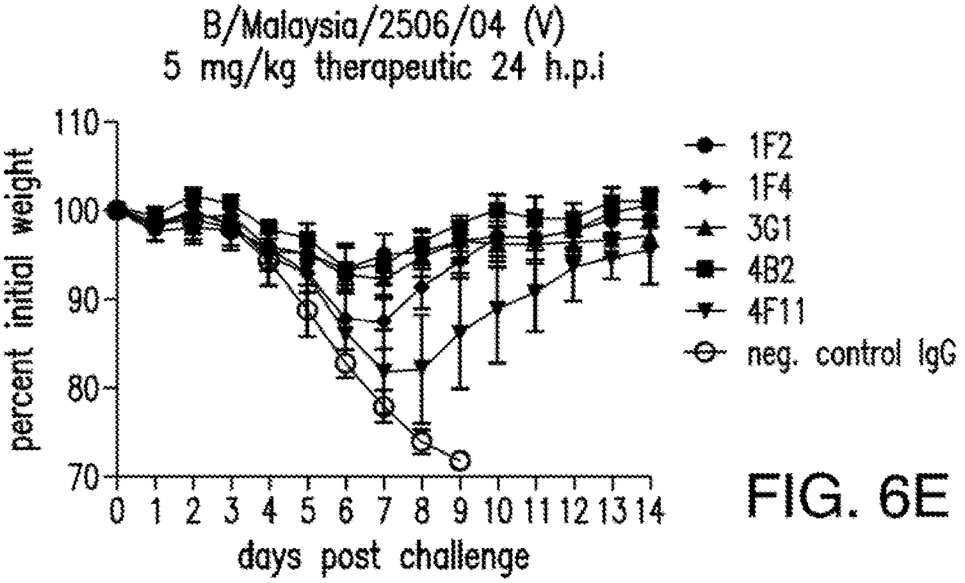
Figure 6F:
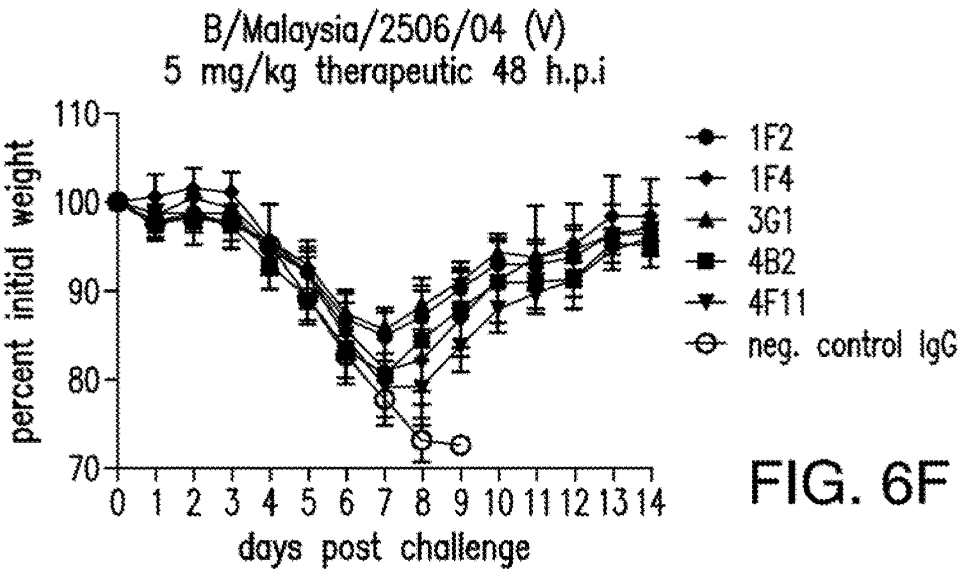

As previous reports have demonstrated the potential of influenza A virus NA-directed antibodies to protect in vivo (Wan et al., *J Virol* 87, 9290-9300 (2013) and Wohlbold et al., *J Virol* 90, 851-861 (2015)), it was decided to test the in vivo efficacy of the panel of mAbs in a well-established influenza virus challenge model, using female BALB/c mice. In the case of all five mAbs, mice were fully protected from morbidity (FIGS. 6A and 6D) and mortality (FIGS. 3A and 3D) when administered antibody prophylactically at the highest tested dose (5 mg/kg) and challenged with 5 murine lethal doses ($mLD_{50}$) of either B/Malaysia/2506/04 (Victoria lineage) or B/Florida/04/06 (Yamagata lineage) virus strains. At lower prophylactic doses of 1 mg/kg and 0.5 mg/kg, the mAbs did not prevent morbidity (FIGS. 6B and 6C), but nevertheless prevented mortality against B/Malaysia/2506/04 virus, with 1F2 demonstrating 100% protection at both of the lower doses tested (FIGS. 3B and 3C). All five mAbs were 100% protective when administered to mice 24 hours post infection (hpi) with $5mLD_{50}$ B/Malaysia/2506/04 virus, and 3 out of 5 were 100% protective when administered 48 hpi (FIGS. 3E and 3F; FIGS. 6E and 6F).

Figure 4A:
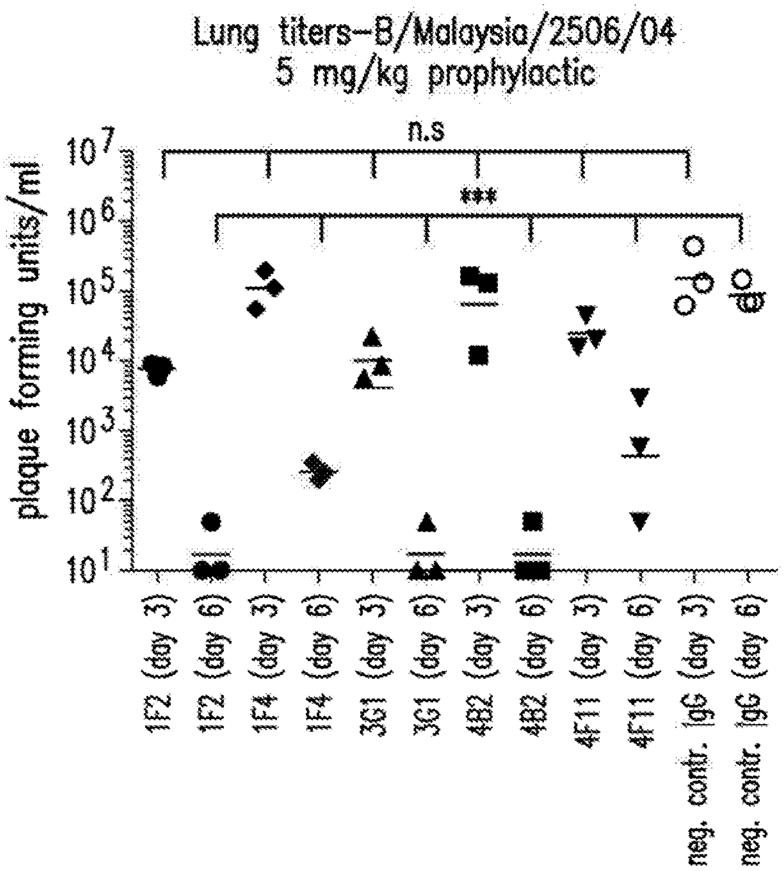

To investigate the in vivo protective breadth of the mAb panel, mice were prophylactically administered with antibodies as in FIG. 3, but were sacrificed on days 3 or 6 for lung titer analysis. When mice were challenged with B/Malaysia/2506/04 virus, lung titers were significantly reduced on day 6—but not 3—post infection relative to the negative control group ($P \leq 0.0001$), suggesting enhanced viral clearance as a possible mechanism of protection (FIG. 4A). This pattern was also seen when mice were challenged with B/Yamagata/16/88, B/Victoria/2/87, and B/Lee/40 viruses, respectively (FIGS. 7A, 7B, and 7C).

Figure 4B:
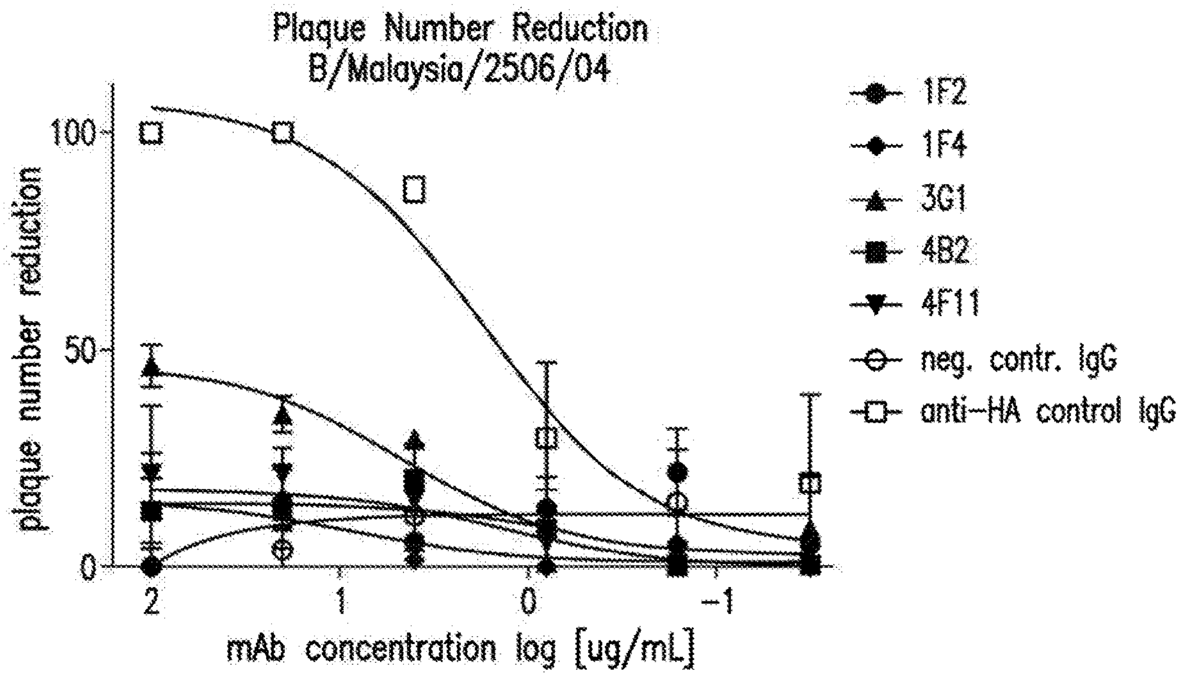
Figure 4C:
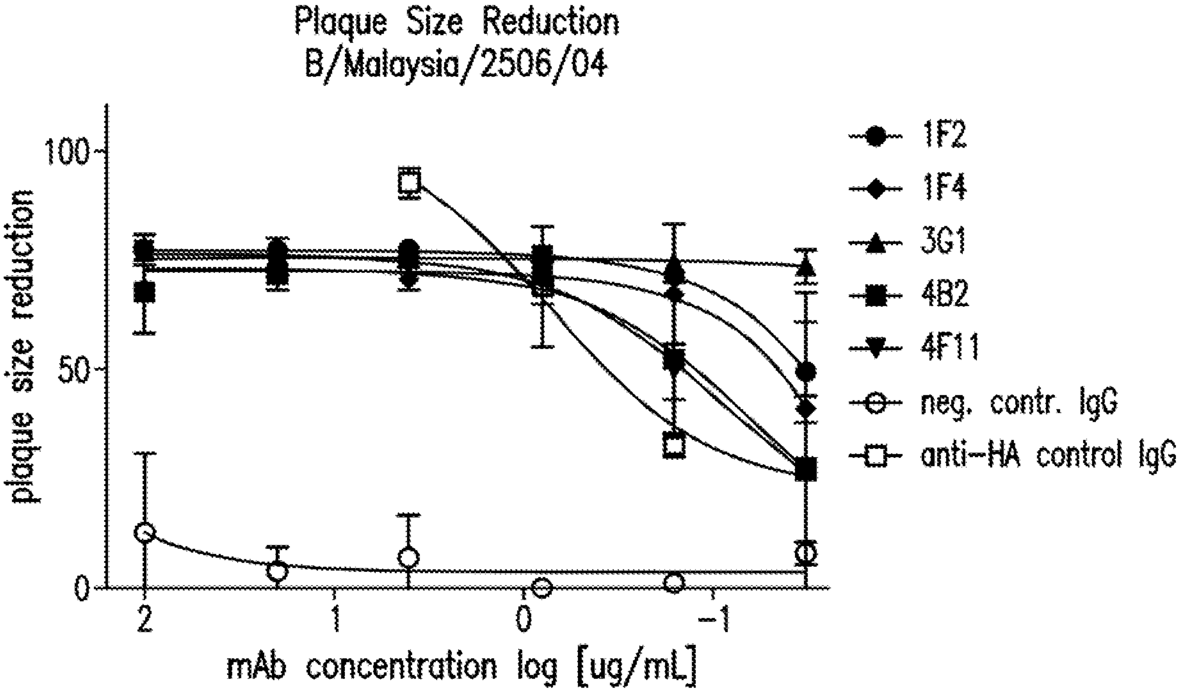
Figure 4D:
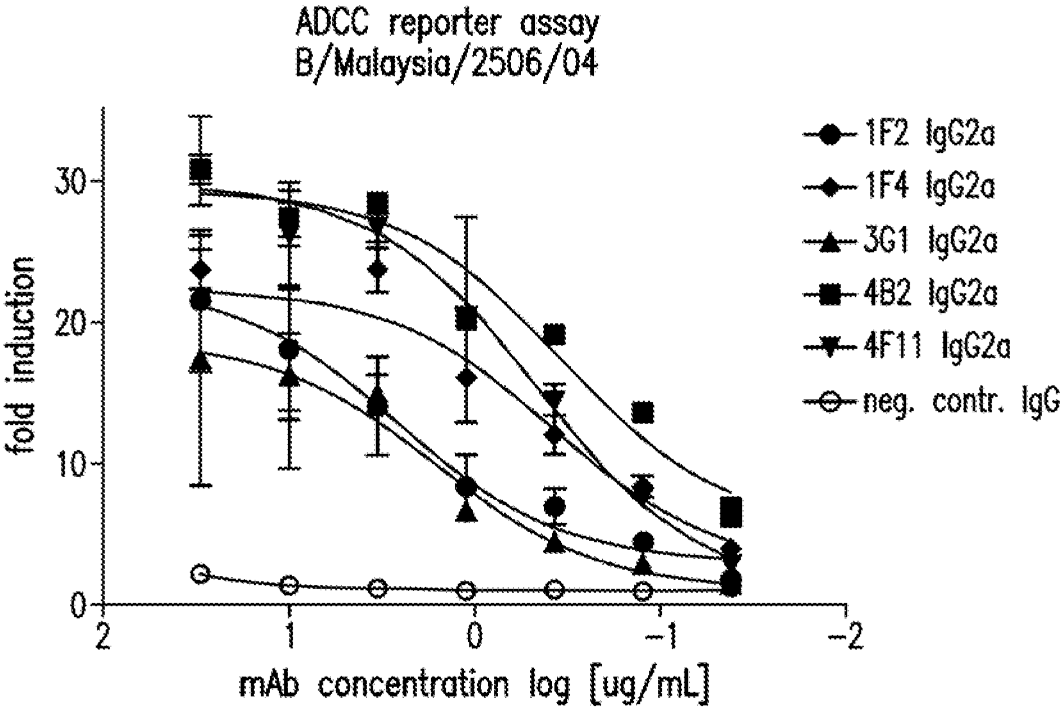

NA antibodies, which are typically considered non-neutralizing, have been shown to decrease plaque size—but not plaque number—in plaque reduction neutralization assays (PRNAs), an in vitro phenomenon that stems from their ability to inhibit viral egress (Wan et al., *J Virol* 87, 9290-9300 (2013), Wohlbold et al., *J Virol* 90, 851-861 (2015), Palese et al., *Virology* 61, 397-410 (1974), Wan et al., *Nat. Commun.* 6, 6114 (2015), Kilbourne et al., *J. Infect. Dis.* 134, 384-394 (1976), and Webster et al., *J Gen Virol* 3, 315-326 (1968)). The anti-NA mAbs displayed this phenotype in a PRNA when tested against B/Malaysia/2506/04 virus (FIGS. 4B and 4C). Additionally, recent findings have shown that Fc-FcY receptor interactions are necessary for broadly reactive HA head-, HA stalk-, and NA-directed antibodies to mediate protection in vivo (DiLillo et al., *Nat. Med.* 20, 143-51 (2014), DiLillo et al., *J. Clin. Invest.* 126, 605-610 (2016), and Dunand et al., *Cell Host Microbe* 19, 800-813 (2016)). In light of the increasingly recognized implications of Fc receptor-mediated effector functions, such as antibody-dependent cell-mediated (ADCC) and antibody-dependent cellular phagocytosis (ADCP), the ability of the IBV NA-directed mAbs to engage with and activate Fc receptors in vitro was tested. Using a commercially available ADCC Reporter Assay Core Kit (Promega), which utilizes Jurkat cells engineered to express firefly luciferase upon Fc receptor activation, it was confirmed that all five mAbs displayed ADCC activity when incubated with MDCK cells infected with B/Malaysia/2506/04 or B/Florida/04/06 virus, respectively (FIG. 4D; FIGS. 7D and 7E). Four of the five mAbs displayed ADCC activity when incubated with cells infected with B/Yamagata/16/88 virus, with the exception of 3G1, which is expected because 3G1 does not bind the NA of B/Yamagata/16/88 at low concentrations.

As mentioned, 3G1 was the only mAb that possessed a critical binding residue located directly adjacent to the enzymatic active site (FIG. 5D). Yet, all mAbs displayed robust NI activity by ELLA, an assay that utilizes fetuin as a substrate (FIG. 1C). The ability of antibodies that bind epitopes outside of the active site to inhibit NA enzymatic activity by ELLA has been documented in the case of N1- and N2-binding mAbs (Wan et al., *J Virol* 87, 9290-9300 (2013), Webster et al., *Virology* 135, 30-42 (1984), Air et al., *Virology* 145, 337-248 (1985), and Gulati et al., *J Virol.* 76, 12274-12280 (2002)). Fetuin, a glycoprotein (molecular weight=48.4 kDa), is immobilized to the 96-well plate during the ELLA coating process, so it is conceivable that antibodies that bind distal to the active site may inhibit access of the NA to fetuin by steric hindrance. To understand if this may account for the mechanism of inhibition in some of the other antibodies studied, the NI activity was assessed in an NA-Star assay, which uses a small, soluble chemiluminescent substrate (molecular weight=684.5 Da). All five mAbs inhibited NA activity in the NA-Star assay to some extent, but only 3G1 was able to achieve 100% inhibition with an $IC_{50}$ comparable to that of oseltamivir, a small molecule NA inhibitor (molecular weight=312.4 Da) (FIG. 7F). Such data additionally supports the hypothesis that the epitope of 3G1 overlaps—or is in immediate proximity to—the enzymatic active site. In separate studies, the role of steric hindrance was tested by removal of the Fc region of the antibodies. Inhibition studies showed that 4F11 Fab, but not 1F2 Fab lost NI activity in the NA-Star assay, suggesting steric hindrance plays a role in the NI of this antibody.

Figure 4E:
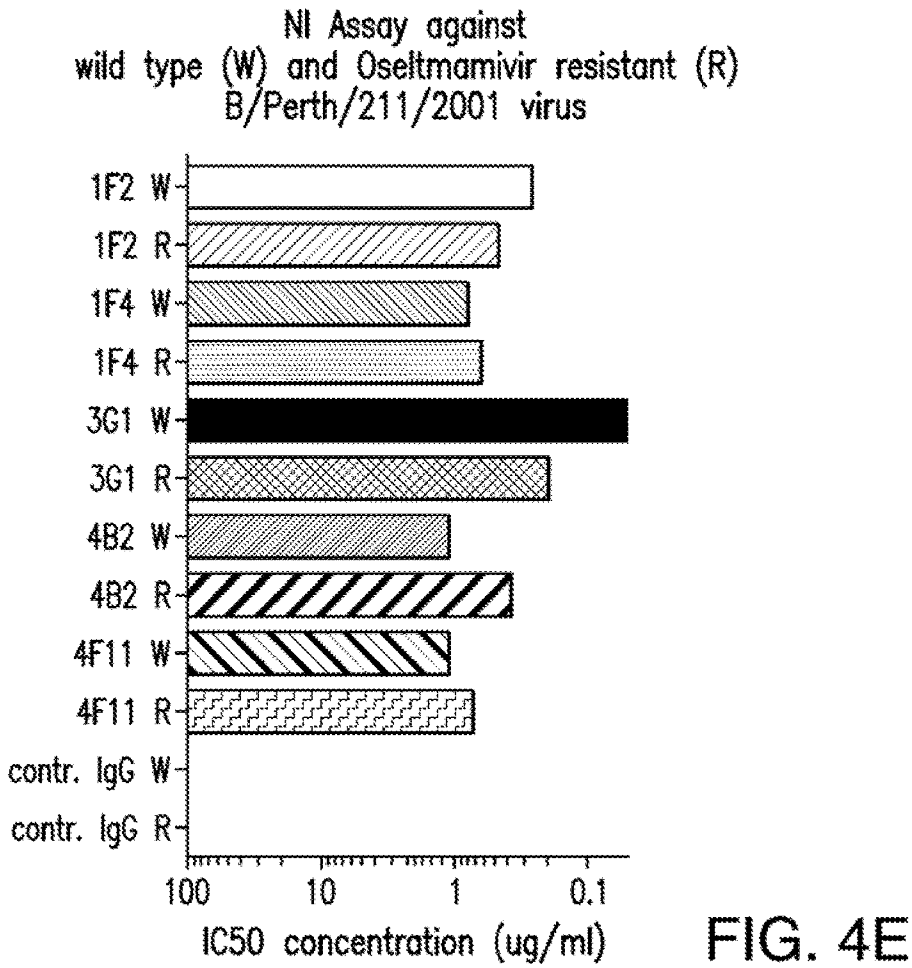
Figure 4F:
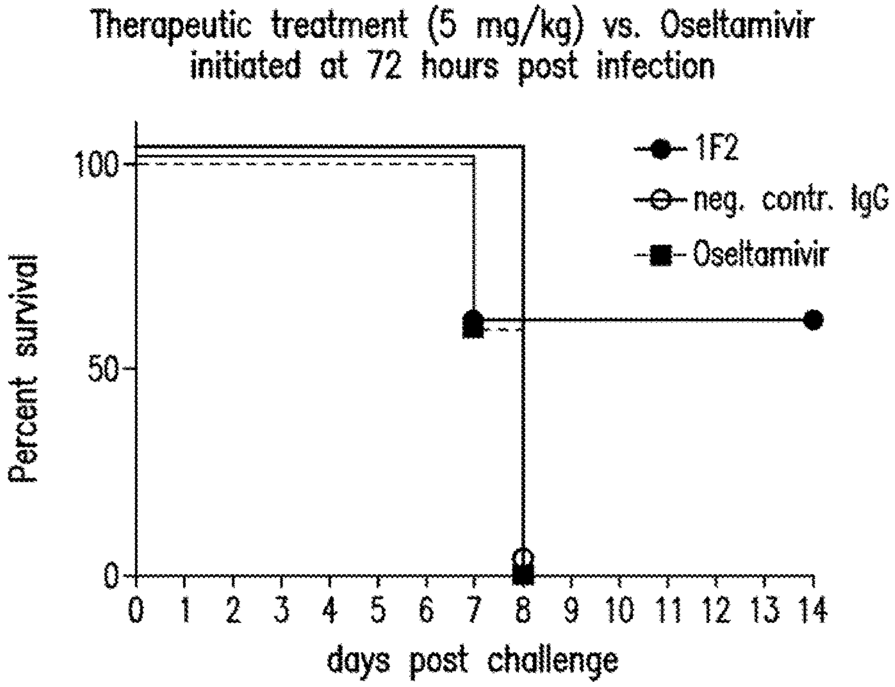

Importantly, influenza viruses may develop resistance to oseltamivir and other NA inhibitors. As most of the mAbs from this study likely bind distal to the NA active site, it was hypothesized they could still effectively inhibit the enzymatic activity of drug-resistant IBV strains. Indeed, when tested against an IBV strain (B/Perth/211/2001) containing a known oseltamivir-resistance mutation (D197E) all five mAbs—even 3G1—inhibited NA activity (FIG. 4E).

Finally, treatment with mAb was compared to treatment with oseltamivir in the mouse model. In the BALB/c mouse challenge model, a 20 mg/kg, twice-daily, 6-day long oral regimen of oseltamivir initiated 48 hpi with $5mLD_{50}$ B/Malaysia/2506/04 resulted in 100% survival (FIG. 26). However, timing of the onset of antiviral therapy with NA inhibitors is crucial, as the greatest reduction in morbidity has been observed when treatment is initiated 48 hours prior to symptom onset in both pediatric and adult cases of uncomplicated influenza (Nicholson et al., *Lancet* 355, 1845-1850 (2000), Heinonen et al., *Clin. Infect. Dis.* 51, 887-894 (2010), and Fiore et al., *MMWR. Recomm. Rep.* 60, 1-24 (2011)). Thus the therapeutic efficacy of mAb 1F2 was compared to that of oseltamivir as late as 72 hpi. When administered at this time-point, a single bolus of 1F2 (5 mg/kg) delivered Intraperitoneally (IP) performed superiorly to the twice-daily regimen of oseltamivir, initiated at the same time point and continued for six days (72 hpi). Sixty percent of mice treated with mAb 1F2 survived, compared to 0% in the oseltamivir treatment group (FIG. 4G). Corresponding weight loss curves are shown in FIG. 7G.

Here, for the first time, broadly reactive epitopes located on the influenza B virus NA, using both structural and escape mutant mapping of murine monoclonal antibodies were elucidated; the antibodies that were generated bound to both Victoria and Yamagata lineage IBVs spanning 73 years of antigenic drift. While NA antibodies may inhibit enzymatic activity by binding, they also possess Fc regions capable of binding to—and activating—effector cells; indeed, the ability of the mAbs to robustly activate effector cells in vitro was demonstrated. The critical importance of Fc effector functions—such as ADCP and ADCC—to the mechanism of protection of non-neutralizing antibodies against the influenza virus is becoming increasingly appreciated. Of particular note, mAb 1F2 exhibited superior efficacy to the standard of care, oseltamivir treatment, when administered 72 hpi in a mouse challenge model. Conceivably, the combined ability of an anti-NA antibody to interfere with NA enzymatic activity while engaging in effector functions that allow for enhanced, immune-mediated viral clearance may explain why mAb treatment is able to outperform treatment with NA inhibitor in vivo. These mAbs possess the potential to be developed into novel therapeutics for high-risk patient populations or against drug-resistant strains of IBV and highlight the benefits of targeting broadly protective NA epitopes in innovative influenza virus vaccine formulations.

7. EXAMPLE 2: INFLUENZA B NEURAMINIDASE-SPECIFIC MONOCLONAL ANTIBODIES

7.1 Materials and Methods

Production of recombinant antibodies: The variable regions of heavy and light chains (VH and VL, respectively) of all five monoclonal antibodies (mAbs) were obtained and the germline genes were determined with the help of IMGT/V-QUEST database. The vH and vL sequences were then cloned into a multiple cloning site on commercially available plasmids containing mouse heavy chain constant regions (IgG1, IgG2a, IgG2b, IgA and IgM) or mouse kappa-chain constant region. The nucleotide sequence of mouse J-chain was synthesized and cloned into MCS A on a pIRES plasmid (Clonetech). pIRES was then co-transfected with heavy and light chain containing plasmids to obtain polymeric IgA and IgM mAbs. Recombinant mAbs were produced by transient transfection of 293F cells in a serum-free medium. Supernatants from 293F cells transfected with above described plasmids were purified on AKTA purifier using either protein G column or IgM-capture select column (both from GE Healthcare).

Enzyme-linked immunosorbent assay (ELISA): 96-well ELISA plates were coated with recombinant neuraminidase (NA) at 2 μg/mL in coating buffer overnight and plates were stored at 4° C. On the next day, the plates were blocked 2 hours at room temperature (RT) with 5% milk in phosphate buffered saline with 0.1% Tween 20 (PBS-T) and antibody dilutions were applied. After an incubation for 90 minutes at RT with shaking, plates were washed, secondary anti-mouse kappa chain antibody conjugated to horse radish peroxidase (HRP) was applied and incubated for another 50-60 minutes. After the last washing step, o-phenylenediamine (OPD) was used as a substrate for HRP and the reaction was stopped using 3M HCl. The plates were read at 490 nm using a plate reader.

Biolayer interferometry: Binding affinity values were determined by biolayer interferometry using an Octet Red96 instrument (ForteBio, Inc.). B/Malaysia/2506/04 rNA protein was biotinylated using the EZ-Link NHS-PEG4-Biotin kit (Thermo-Scientific) at 1:1 protein to biotin ratio. Biotin was combined with B/Malaysia/2506/04 recombinant neuraminidase (rNA) and incubated at room temperature for 30 minutes. The sample was then purified using desalting ZEBA column 0.5 mL (Thermo Fisher). Biotinylated rNA was then diluted until the final concentration was 10 μg/mL. Recombinantly expressed 1F2 and 4F11 mAbs (IgG1, IgG2a, IgG2b, mIgA, pIgA, and IgM) and the original hybridoma derived 1F2 (IgG2a) and 4F11 (IgG2b) mAb were diluted to a concentration of 10 μg/ml in 500 μL volume and then serial diluted 1:2 in a 96-well plate, then moved into a fresh, black 96-well plate (final volume in each well was 200 μL). Eight streptavidin-coated biosensors per antibody were equilibrated in PBS (Gibco) and a baseline was measured for 180 seconds. Biotinylated rNA was loaded onto biosensors (ForteBio, Inc) in PBS for 300 seconds. A second baseline was measured for 180 seconds. To determine $k_{on}$, the eight sensors were submerged in different dilutions of antibodies for 300 seconds. To determine $k_{off}$, the dissociation was measured in PBS for 900 seconds. Analysis was performed on Octet Red96 operating software. All sensor reads were aligned to baseline with an inter-step correction and best global fit was performed. The ratio of $k_{off}$ to $k_{on}$ determines the $K_D$. $R^2$ values were calculated to express the reliability of calculated $K_D$ value.

Enzyme-linked lectin assay (ELLA)—Neuraminidase inhibition (NI) assay: Ninty-six-well plate Immunlon 4HBX flat bottom plates (ThermoFisher) were coated with 50 μL/mL fetuin in coating buffer (150 uL). Plates were incubated overnight at 4° C. The next day the fetuin was removed, and plates were washed three times with PBS-T using an Aqua Max 2000 (Molecular Devices) plate washer. Plates were blocked with 200 μL of 5% bovine serum albumin in PBS at room temperature for one hour, without shaking. While these plates incubated, 75 μL of diluted virus was added (B/Malaysia/2506/04) to a 96-well U-shaped plate. (Virus dilution was determined by preforming a modified NI assay to determine the IC50 of B/Malaysia/2506/04.) Once virus was added to a 96-well U-shaped plate, antibodies were plated on another set of 96-well plate with a starting concentration of 50 μg/mL and diluted 1:4 down the rows. Seventy-five μL of diluted antibody was moved to the plate containing the diluted virus. The virus/antibody mixture was incubated for 1.5 hours at room temperature. One hundred μL virus/antibody mixture was then transferred to the fetuin coated plate and incubated at 37° C. for 1.5 hours. During the incubation, peanut agglutinin conjugated with HRP (PNA-HRP) was thawed and diluted in 9 mL of PBS to a final concentration 5 μg/mL. The fetuin plate containing the virus/antibody mixture was then washed three times with PBS-T on a washer and 100 μL of PNA-RP was added and incubated at room temperature in the dark for two hours. The plates were washed again six times with PBS-T, and 100 μL of OPD substrate (Sigma) was added. The reaction was allowed to proceed for ten minutes, and then stopped with addition of 50 μL of 3M HCl. The plates were read on the plate reader (Biotek Synergy H1) at 490 nm wavelength.

In vivo experiments: For the in vivo experiments, 6-8 weeks old female BALB/c mice (Jackson laboratories) were used. Both studies recapitulated prophylactic settings. The antibodies were administered at indicated concentrations intraperitoneally 2 hours prior to IN challenge with 5×LD50 B/Malaysia/2506/04 virus. Mice were observed for weight loss daily. 75% percent of initial weight was established as the humane end point. All animal procedures were performed in accordance with the Icahn School of Medicine at Mount Sinai Institutional Animal Care and Use Committee (IACUC).

7.2 Results

Two out of five identified broadly reactive B/NA antibodies, mAbs 1F2 and 4F11, were class-switched into all antibody isotypes/subtypes potentially relevant for influenza infections to explore the effect of antibody constant region on antibody's in vivo protection potential. The recombinant isoforms expressed were IgG1, IgG2a, IgG2b, monomeric and polymeric IgA, and IgM. All recombinant antibodies were produced by transient transfection of 293F cells in a serum-free medium and subsequently purified using protein G or IgM-capture select protein columns (depending on isotype). Purified proteins were assessed for purity (PAGE gel) and binding of antigen (ELISA; FIGS. 19A-19B). NI activity was tested in both antibody sets (ELLA; FIGS. 20A-20B) as well as the binding affinity (BLI; Table 7) towards an antigen. The set of 1F2 antibody isotypes was examined in in vivo study, where all the IgG subtypes as well as polymeric IgA showed protection from mortality, however monomeric IgA and IgM did not have any effect (FIGS. 21A-21B). Without being bound by any particular theory, it is necessary to mention that the intraperitoneal route of administration might not be the most suitable for the larger molecules (IgM) which might become trapped in a tissue surrounding the place of injection and intravenous administration might be preferred in this case. An investigation of Fc-effector functions followed (ADCC; FIG. 22). Based on these results it can be concluded that the 1F2 IgG1 did not rely on ADCC for in vivo protection although the original, 1F2 IgG2a displayed ADCC activity. From the obtained antibody yields, data provided by biolayer interferometry (Table 7), and NI data, it was expected that some of the class-switched mAbs would display the decreased stability, which was further confirmed in thermal shift assay (data not shown). Without being bound by any particular theory, it is reasonable to assume this was caused by incompatibility of variable region with a "new" constant region that was used for a class-switch and most notable in case of 4F11 IgG2a. This issue can be solved by sequence optimization. Lastly, the in vivo performance was compared between anti-B/HA head specific mAb, anti-B/HA stalk specific mAb, anti-B/NA mAb 1F2, and the combination of three (FIGS. 23A-23B). The anti-B/HA stalk and head antibodies are both broadly reactive antibodies towards the B influenza HAs from Yamagata-like as well as Victoria-like lineage. One of the influenza B virus HA-specific mAbs behaves like a typical head-specific antibody exhibiting neutralization and hemagglutinin inhibition activity. The other influenza B virus HA-specific mAb is a typical stalk-reactive antibody heavily relying on its Fc-effector functions. FIGS. 23A-23B demonstrate the smaller weight loss in a mouse group receiving the combination of all three of these antibodies compared to groups which received the above mentioned antibodies individually.

TABLE 7

Binding affinity of 1F2 and 4F11 isotypes to an antigen was calculated using biolayer interferometry. Streptavidin sensors were bound to biotinylated recombinant NA (B/Malaysia/2506/04) and subsequently dipped into 2-fold dilution series of monoclonal antibodies. $K_D$ values were calculated and are provided in Table 7. $R^2$ values were calculated to provide the reliability of the $K_D$ values. 4F11 IgGl, IgG2a and mIgA did not reach the $R^2$ value of 0.9 implying the calculated value might not be true. MW for IgM was assuming a monomer.

| | 1F2 $K_D$ (M) | 4F11 $K_D$ (M) |
|---|---|---|
| IgG1 | 1.05E−09 | 8.91E−12 |
| | 1F2 $K_D$ (M) | 4F11 $K_D$ (M) |
| IgG2a | 6.8E−10 | 3.36E−12 |
| IgG2b | 1.16E−09 | 2.98E−12 |
| mIgA | 9.58E−10 | 4.72E−12 |
| pIgA | 2.80E−10 | 2.42E−12 |
| IgM | 6.50E−10 | 5.11E−12 |
| Hybridoma | 3.64E−10 | 6.53E−12 |

8. EXAMPLE 3: BINDING STUDIES WITH HUMANIZED ANTIBODIES

This example relates to binding studies using humanized variants of the 1F2 antibody.

Methods: IgG antibodies were immobilized onto biosensors using suitable capture surfaces (anti-human Fc) and binding of soluble antigen to immobilized antibodies was monitored using BLI (Octet). Data was generated for both antigen binding response and stability. Results from these experiments are detailed below.

Antigens:

| Antigen | MW (kDa) |
|---|---|
| B/Brisbane NA | 240 |
| B/Yamagata NA | 240 |
| B/Wisconsin NA | 240 |
| B/Malaysia NA | 240 |

Details of Antibodies Tested:

| Antibody identifier | Species | Capture method |
|---|---|---|
| HCX LCX | Humanised | Anti-human IgG Fc (AHC) |

Binding Stability Analysis: Experimental Parameters

Binding stability assays were performed by first capturing IgG using anti-human Octet biosensors (ForteBio part no. 18-5060) followed by a baseline step of 2 minutes in HBS-P+ buffer (10 mM HEPES, 150 mM NaCl, 1 mg/ml BSA, and 0.05% Tween-20, pH 7.4). The mAb capture biosensors were then submerged in wells containing 25 nM of antigen for 900 seconds (association step), followed by a 1200 second dissociation step in running buffer. To allow for reference correction, blank sensors were dipped into wells containing the analyte concentration and Ab HC0 LC0 (SEQ ID Nos:185 and 194) was included in all runs. This referencing provides a means of compensating for non-specific binding of the antigen to the sensor surface. All steps were performed at 25° C. in kinetics buffer at a constant flow-rate of 1000 rpm. New sensors were used for each sample. All consumables used were those recommended by ForteBio. Data was analysed using the ForteBio Data Analysis software.

Results: Binding Stability Ranking

A panel of 25+1 Ab 1F2 variants were screened for binding to four different antigens using biolayer interferometry. FIG. 27 shows a scatterplot of the report points stability_early plotted against stability_late for all four antigens tested. The best binders, with a high binding stability and slow dissociation, are highlighted with a circle. The data used to generate these plots are shown in the table in FIG. 28. The sequences of HC0 to HC8 are found in Section 4.1 (SEQ ID Nos: 185, 186, 187, 188, 189, 190, 191, 192, and 193, respectively), and the sequences of LC0 to LC8 are found in Section 4.1 (SEQ ID Nos: 194, 195, 196, 197, 198, 199, 200, 201, and 202).

The top five antibodies showing both a high antigen binding response and the most stability are as follows: HC2 LC2 (SEQ ID Nos: 187 and 196), HC2 LC3 (SEQ ID Nos: 187 and 197), HC3 LC2 (SEQ ID Nos: 188 and 196), HC4 LC2 (SEQ ID Nos: 189 and 196), HC4 LC3 (SEQ ID Nos: 189 and 197).

9. EXAMPLE 4: NEURAMINIDASE INHIBITION OF 1F2 HUMANIZED MONOCLONAL ANTIBODY VARIANTS

All influenza B viruses (B/Wisconsin/1/2010, B/Lee/40, B/Brisbane/60/2008, B/Malaysia/2506/04, B/Yamagata/16/88, B/New York/PV000094/2017 and B/New York/PV01181/2018) were grown in embryonated, 8-10 days old chicken eggs for 72 hours at 33° C. before the allantoic fluid was harvested, centrifuged, aliquoted into cryovials and frozen at −80° C.

The 96-well microtiter plates (Thermo Fisher Scientific) were coated in advance using 25 ug/mL fetuin (EMD Millipore) diluted in coating buffer (PBS, Gibco), 100 uL/well. Each plate was covered with a plastic plate seal (Excel Scientific) and stored in a fridge (at 2-8° C.) for at least 18 hours. The plates coated in advance can be stored this way for up to two months protected from light.

To determine the standard amount of virus to use in neuraminidase inhibition experiments (virus amount calibration), 1:2 serial dilutions of each virus were prepared in a dilution buffer (PBS+0.9 mM CaCl2)+0.5 mM MgCl2+1% BSA (Fisher Scientific)+0.5% Tween 20 (Fisher BioReagents)) in dilution plates. Fetuin coated plates were washed 3× with PBS-T. Sample dilution buffer (50 uL) was added into each well. 50 uL of pre-diluted virus from the dilution plates was transferred into fetuin-coated plates. Space for no virus control wells was reserved and an additional 50 uL of sample dilution buffer was added into these wells. Plates were sealed again with the plastic seal and placed into a humidified 37° C. cell culture incubator for 16-18 hours.

Next day, the plate seals were discarded, and plates were washed 6× with PBS-T (PBS+Tween 20). Peanut agglutinin conjugated to horse radish peroxidase (PNA-HRP, Bio-World) was added into each well at the concentration 1 μg/mL (100 μL/well). Plates were incubated for 2 hours at room temperature (RT) then washed 3× with PBS-T. 100 μL of o-Phenylenediamine dihydrochloride (OPD, Sigma) peroxidase substrate was added into each well and plates were incubated for 10 minutes at RT. The reaction was stopped by addition of 50 μL of 3M hydrochloric acid (HCl) and plates were read using a Synergy microplate reader (BioTek) at 490 nm.

The dilution curves were plotted and analyzed and the EC50 values for each virus were generated using GraphPad Prism 7.0 software.

Once the optimal dilution for each virus was calculated, the testing of humanized antibody variants commenced. The experimental set up followed steps described above with a small change. Briefly, 1:3 serial dilutions of tested antibody variants starting at 30 μg/mL were prepared in the sample dilution buffer in dilution plates. 50 μL of antibody dilutions was then moved to fetuin coated plates, followed by an addition of a single dilution of a virus, calculated based on the EC50 from the calibration runs. The antibody-virus mixture in fetuin coated plates was then sealed using plastic seals and incubated at 37° C. for 16-18 hours followed by final steps the next day. Each plate had no mAb, and no mAb no virus controls, representing 0% and 100% inhibition, respectively.

Following the acquisition of raw data for each plate using a microplate reader, the IC50 values for individual mAb variants were obtained using GraphPad Prism 7.0 software.

The results for the humanized antibodies comprising the variable regions set forth in Table 8 are provided in FIG. 29. The sequences of VH0 to VH8 are found in Section 4.1 (SEQ ID Nos:1, 168, 169, 170, 171, 172, 173, 174 or 175, respectively), and the sequences of VL0 to VL8 are found in Section 4.1 (SEQ ID Nos: 2, 177, 178, 179, 180, 181, 182, 183, or 184). Also provided in FIG. 29 are the results for a chimeric antibody comprising the sequences of VH0 and VL0.

TABLE 8

| Number in FIG. 29 | Antibody |
|---|---|
| 1 | Chimeric VH0:VL0 |
| 2 | VH1:VL1 |
| 3 | VH1:VL2 |
| 4 | VH1:VL3 |
| 5 | VH1:VL4 |
| 6 | VH1:VH5 |
| 7 | VH2:VL1 |
| 8 | VH2:VL2 |
| 9 | VH2:VL3 |
| 10 | VH2:VL4 |
| 11 | VH2:VH5 |
| 12 | VH3:VL1 |
| 13 | VH3:VL2 |
| 14 | VH3:VL3 |
| 15 | VH3:VL4 |
| 16 | VH3:VL5 |
| 17 | VH4:VL1 |
| 18 | VH4:VL2 |
| 19 | VH4:VL3 |
| 20 | VH4:VL4 |
| 21 | VH4:VL5 |

TABLE 8-continued

| Number in FIG. 29 | Antibody |
|---|---|
| 22 | VH5:VL1 |
| 23 | VH5:VL2 |
| 24 | VH5:VL3 |
| 25 | VH5:VL4 |
| 26 | VH5:VL5 |

The foregoing is not to be limited in scope by the specific embodiments described herein. Indeed, various modifications of the antibodies and methods provided herein and their equivalents, in addition to those described herein will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

We claim:

1. An isolated antibody that binds to an influenza B virus neuraminidase (NA), wherein the antibody comprises:

a. (i) a variable heavy chain region complementarity determining region 1 (VHCDR1) comprising the amino acid sequence of SEQ ID NO: 3, (ii) a variable heavy chain region CDR2 (VHCDR2) comprising the amino acid sequence of SEQ ID NO: 4, (iii) a variable heavy chain region CDR3 (VHCDR3) comprising the amino acid sequence of SEQ ID NO: 5, (iv) a variable light chain region CDR1 (VLCDR1) comprising the amino acid sequence of SEQ ID NO: 6, (v) a variable light chain region CDR2 (VLCDR2) comprising the amino acid sequence of SEQ ID NO: 7, and (vi) a variable light chain region CDR3 (VLCDR3) comprising the amino acid sequence of SEQ ID NO: 8;

b. (i) a variable heavy chain region that is at least 95% identical to the amino acid sequence of SEQ ID NO: 1, wherein the variable heavy chain region comprises a variable heavy chain region complementarity determining region (CDR1) comprising the amino acid sequence of SEQ ID NO: 3, a variable heavy chain region CDR2 comprising the amino acid sequence of SEQ ID NO: 4, and a variable heavy chain region CDR3 comprising the amino acid sequence of SEQ ID NO: 5; and (ii) a variable light chain region that is at least 95% identical to the amino acid sequence of SEQ ID NO: 2, wherein the variable light chain region comprises a variable light chain region CDR1 comprising the amino acid sequence of SEQ ID NO: 6, a variable light chain region CDR2 comprising the amino acid sequence of SEQ ID NO: 7, and a variable light chain region CDR3 comprising the amino acid sequence of SEQ ID NO: 8;

c. (i) a VHCDR1 comprising the amino acid sequence of SEQ ID NO: 94, (ii) a VHCDR2 comprising the amino acid sequence of SEQ ID NO: 95, (iii) a VHCDR3 comprising the amino acid sequence of SEQ ID NO: 96, (iv) a VLCDR1 comprising the amino acid sequence of SEQ ID NO: 97, (v) a VLCDR2 comprising the amino acid sequence of SEQ ID NO: 98, and (vi) a VLCDR3 comprising the amino acid sequence of SEQ ID NO: 99;

d. (i) a VHCDR1 comprising the amino acid sequence of SEQ ID NO: 100, (ii) a VHCDR2 comprising the amino acid sequence of SEQ ID NO: 101, (iii) a VHCDR3 comprising the amino acid sequence of SEQ ID NO: 102, (iv) a VLCDR1 comprising the amino acid sequence of SEQ ID NO: 103, (v) a VLCDR2 comprising the amino acid sequence of SEQ ID NO: 104, and (vi) a VLCDR3 comprising the amino acid sequence of SEQ ID NO: 105;

e. (i) a VHCDR1 comprising the amino acid sequence of SEQ ID NO: 106, (ii) a VHCDR2 comprising the amino acid sequence of SEQ ID NO: 107, (iii) a VHCDR3 comprising the amino acid sequence of SEQ ID NO: 108, (iv) a VLCDR1 comprising the amino acid sequence of SEQ ID NO: 109, (v) a VLCDR2 comprising the amino acid sequence of SEQ ID NO: 110, and (vi) a VLCDR3 comprising the amino acid sequence of SEQ ID NO: 111;

f. a variable heavy chain region comprising the amino acid sequence of SEQ ID NO: 1, and a variable light chain region comprising the amino acid sequence of SEQ ID NO: 2;

g. (i) a variable heavy chain region comprising the amino acid sequence of SEQ ID NO: 168, 169, 170, 171, 172, 173, 174 or 175, and (ii) a variable light chain region comprising the amino acid sequence of SEQ ID NO: 178, 179, 177, 180, 181, 182, 183, or 184;

h. (i) a variable heavy chain region comprising the amino acid sequence of SEQ ID NO: 168 and a variable light chain region comprising the amino acid sequence of SEQ ID NO: 178; (ii) a variable heavy chain region comprising the amino acid sequence of SEQ ID NO: 168 and a variable light chain region comprising the amino acid sequence of SEQ ID NO: 179; (iii) a variable heavy chain region comprising the amino acid sequence of SEQ ID NO: 168 and a variable light chain region comprising the amino acid sequence of SEQ ID NO: 177; (iv) a variable heavy chain region comprising the amino acid sequence of SEQ ID NO: 168 and a variable light chain region comprising the amino acid sequence of SEQ ID NO: 180; (v) a variable heavy chain region comprising the amino acid sequence of SEQ ID NO: 169 and a variable light chain region comprising the amino acid sequence of SEQ ID NO: 178; (vi) a variable heavy chain region comprising the amino acid sequence of SEQ ID NO: 169 and a variable light chain region comprising the amino acid sequence of SEQ ID NO: 179; (vii) a variable heavy chain region comprising the amino acid sequence of SEQ ID NO: 169 and a variable light chain region comprising the amino acid sequence of SEQ ID NO: 180; (viii) a variable heavy chain region comprising the amino acid sequence of SEQ ID NO: 170 and a variable light chain region comprising the amino acid sequence of SEQ ID NO: 178; (ix) a variable heavy chain region comprising the amino acid sequence of SEQ ID NO: 170 and a variable light chain region comprising the amino acid sequence of SEQ ID NO: 180; (x) a variable heavy chain region comprising the amino acid sequence of SEQ ID NO: 171 and a variable light chain region comprising the amino acid sequence of SEQ ID NO: 178; (xi) a variable heavy chain region comprising the amino acid sequence of SEQ ID NO: 171 and a variable light chain region comprising the amino acid sequence of SEQ ID NO: 179; (xii) a variable heavy chain region comprising the amino acid sequence of SEQ ID NO: 171 and a variable light chain region comprising the amino acid sequence of SEQ ID NO: 180; (xiii) a variable heavy chain region comprising the amino acid sequence of SEQ ID NO: 172 and a variable light chain region comprising the amino acid sequence of SEQ ID NO: 180; (xiv) a variable heavy chain region comprising the amino acid sequence of SEQ ID NO: 172 and a variable light chain region comprising the amino acid sequence of SEQ ID NO: 181; (xv) a variable heavy chain region comprising the amino acid sequence of SEQ ID NO: 168 and a variable light chain region comprising the amino acid sequence of SEQ ID NO: 181; (xvi) a variable heavy chain region comprising the amino acid sequence of SEQ ID NO: 168 and a variable light chain region comprising the amino acid sequence of SEQ ID NO: 182; (xvii) a variable heavy chain region comprising the amino acid sequence of SEQ ID NO: 168 and a variable light chain region comprising the amino acid sequence of SEQ ID NO: 183; (xviii) a variable heavy chain region comprising the amino acid sequence of SEQ ID NO: 168 and a variable light chain region comprising the amino acid sequence of SEQ ID NO: 184; (xix) a variable heavy chain region comprising the amino acid sequence of SEQ ID NO: 169 and a variable light chain region comprising the amino acid sequence of SEQ ID NO: 177; (xx) a variable heavy chain region comprising the amino acid sequence of SEQ ID NO: 169 and a variable light chain region comprising the amino acid sequence of SEQ ID NO: 181; (xxi) a variable heavy chain region comprising the amino acid sequence of SEQ ID NO: 169 and a variable light chain region comprising the amino acid sequence of SEQ ID NO: 182; (xxii) a variable heavy chain region comprising the amino acid sequence of SEQ ID NO: 169 and a variable light chain region comprising the amino acid sequence of SEQ ID NO: 183; (xxiii) a variable heavy chain region comprising the amino acid sequence of SEQ ID NO: 169 and a variable light chain region comprising the amino acid sequence of SEQ ID NO: 184; (xxiv) a variable heavy chain region comprising the amino acid sequence of SEQ ID NO: 170 and a variable light chain region comprising the amino acid sequence of SEQ ID NO: 177; (xxv) a variable heavy chain region comprising the amino acid sequence of SEQ ID NO: 170 and a variable light chain region comprising the amino acid sequence of SEQ ID NO: 179; (xxvi) a variable heavy chain region comprising the amino acid sequence of SEQ ID NO: 170 and a variable light chain region comprising the amino acid sequence of SEQ ID NO: 181; (xxvii) a variable heavy chain region comprising the amino acid sequence of SEQ ID NO: 170 and a variable light chain region comprising the amino acid sequence of SEQ ID NO: 182; (xxviii) a variable heavy chain region comprising the amino acid sequence of SEQ ID NO: 170 and a variable light chain region comprising the amino acid sequence of SEQ ID NO: 183; (xxix) a variable heavy chain region comprising the amino acid sequence of SEQ ID NO: 170 and a variable light chain region comprising the amino acid sequence of SEQ ID NO: 184; (xxx) a variable heavy chain region comprising the amino acid sequence of SEQ ID NO: 171 and a variable light chain region comprising the amino acid sequence of SEQ ID NO: 177; (xxxi) a variable heavy chain region comprising the amino acid sequence of SEQ ID NO: 171 and a variable light chain region comprising the amino acid sequence of SEQ ID NO: 181; (xxxii) a variable heavy chain region comprising the amino acid sequence of SEQ ID NO: 171 and a variable light chain region comprising the amino acid sequence of SEQ ID NO: 182; (xxxiii) a variable heavy chain region comprising the amino acid sequence of SEQ ID NO: 171 and a variable light chain region comprising the amino acid sequence of SEQ ID NO: 183; (xxxiv) a variable heavy chain region comprising the amino acid sequence of SEQ ID NO: 171 and a variable light chain region comprising the amino acid sequence of SEQ ID NO: 184; (xxxv) a variable heavy chain region comprising the amino acid sequence of SEQ ID NO: 172 and a variable light chain region comprising the amino acid sequence of SEQ ID NO: 177; (xxxvi) a variable heavy chain region comprising the amino acid sequence of SEQ ID NO: 172 and a variable light chain region comprising the amino acid sequence of SEQ ID NO: 178; (xxxvii) a variable heavy chain region comprising the amino acid sequence of SEQ ID NO: 172 and a variable light chain region comprising the amino acid sequence of SEQ ID NO: 179; (xxxviii) a variable heavy chain region comprising the amino acid sequence of SEQ ID NO: 172 and a variable light chain region comprising the amino acid sequence of SEQ ID NO: 182; (xxxix) a variable heavy chain region comprising the amino acid sequence of SEQ ID NO: 172 and a variable light chain region comprising the amino acid sequence of SEQ ID NO: 183; (xl) a variable heavy chain region comprising the amino acid sequence of SEQ ID NO: 172 and a variable light chain region comprising the amino acid sequence of SEQ ID NO: 184; (xli) a variable heavy chain region comprising the amino acid sequence of SEQ ID NO: 173 and a variable light chain region comprising the amino acid sequence of SEQ ID NO: 177; (xlii) a variable heavy chain region comprising the amino acid sequence of SEQ ID NO: 173 and a variable light chain region comprising the amino acid sequence of SEQ ID NO: 178; (xliii) a variable heavy chain region comprising the amino acid sequence of SEQ ID NO: 173 and a variable light chain region comprising the amino acid sequence of SEQ ID NO: 179; (xliv) a variable heavy chain region comprising the amino acid sequence of SEQ ID NO: 173 and a variable light chain region comprising the amino acid sequence of SEQ ID NO: 180; (xlv) a variable heavy chain region comprising the amino acid sequence of SEQ ID NO: 173 and a variable light chain region comprising the amino acid sequence of SEQ ID NO: 181; (xlvi) a variable heavy chain region comprising the amino acid sequence of SEQ ID NO: 173 and a variable light chain region comprising the amino acid sequence of SEQ ID NO: 182; (xlvii) a variable heavy chain region comprising the amino acid sequence of SEQ ID NO: 173 and a variable light chain region comprising the amino acid sequence of SEQ ID NO: 183; (xlviii) a variable heavy chain region comprising the amino acid sequence of SEQ ID NO: 173 and a variable light chain region comprising the amino acid sequence of SEQ ID NO: 184; (xlix) a variable heavy chain region comprising the amino acid sequence of SEQ ID NO: 174 and a variable light chain region comprising the amino acid sequence of SEQ ID NO: 177; (l) a variable heavy chain region comprising the amino acid sequence of SEQ ID NO: 174 and a variable light chain region comprising the amino acid sequence of SEQ ID NO: 178; (li) a variable heavy chain region comprising the amino acid sequence of SEQ ID NO: 174 and a variable light chain region comprising the amino acid sequence of SEQ ID NO: 179; (lii) a variable heavy chain region comprising the amino acid sequence of SEQ ID NO: 174 and a variable light chain region comprising the amino acid sequence of SEQ ID NO: 180; (liii) a variable heavy chain region comprising the amino acid sequence of SEQ ID NO: 174 and a variable light chain region comprising the amino acid sequence of SEQ ID NO: 181; (liv) a variable heavy chain region comprising the amino acid sequence of SEQ ID NO: 174 and a variable light chain region comprising the amino acid sequence of SEQ ID NO: 182; (lv) a variable heavy chain region comprising the amino acid sequence of SEQ ID NO: 174 and a variable light chain region comprising the amino acid sequence of SEQ ID NO: 183; (lvi) a variable heavy chain region comprising the amino acid sequence of SEQ ID NO: 174 and a variable light chain region comprising the amino acid sequence of SEQ ID NO: 184; (lvii) a variable heavy chain region comprising the amino acid sequence of SEQ ID NO: 175 and a variable light chain region comprising the amino acid sequence of SEQ ID NO: 177; (lviii) a variable heavy chain region comprising the amino acid sequence of SEQ ID NO: 175 and a variable light chain region comprising the amino acid sequence of SEQ ID NO: 178; (lix) a variable heavy chain region comprising the amino acid sequence of SEQ ID NO: 175 and a variable light chain region comprising the amino acid sequence of SEQ ID NO: 179; (lx) a variable heavy chain region comprising the amino acid sequence of SEQ ID NO: 175 and a variable light chain region comprising the amino acid sequence of SEQ ID NO: 180; (lxi) a variable heavy chain region comprising the amino acid sequence of SEQ ID NO: 175 and a variable light chain region comprising the amino acid sequence of SEQ ID NO: 181; (lxii) a variable heavy chain region comprising the amino acid sequence of SEQ ID NO: 175 and a variable light chain region comprising the amino acid sequence of SEQ ID NO: 182; (lxiii) a variable heavy chain region comprising the amino acid sequence of SEQ ID NO: 175 and a variable light chain region comprising the amino acid sequence of SEQ ID NO: 183; or (lxiv) a variable heavy chain region comprising the amino acid sequence of SEQ ID NO: 175 and a variable light chain region comprising the amino acid sequence of SEQ ID NO: 184;

i. (i) a heavy chain comprising the amino acid sequence of SEQ ID NO: 185, 186, 187, 188, 189, 190, 191, 192, or 193, and (ii) a light chain comprising the amino acid sequence of SEQ ID NO: 194, 195, 196, 197, 198, 199, 200, 201, or 202;

j. (i) VHCDR1 comprising the amino acid sequence of SEQ ID NO: 19, (ii) a VHCDR2 comprising the amino acid sequence of SEQ ID NO: 20, (iii) a VHCDR3 comprising the amino acid sequence of SEQ ID NO: 21, (iv) a VLCDR1 comprising the amino acid sequence of SEQ ID NO: 22, (v) a VLCDR2 comprising the amino acid sequence of SEQ ID NO: 23, and (vi) a VLCDR3 comprising the amino acid sequence of SEQ ID NO: 24;

k. (i) a VHCDR1 comprising the amino acid sequence of SEQ ID NO: 112, (ii) a VHCDR2 comprising the amino acid sequence of SEQ ID NO: 113, (iii) a VHCDR3 comprising the amino acid sequence of SEQ ID NO: 114, (iv) a VLCDR1 comprising the amino acid sequence of SEQ ID NO: 115, (v) a VLCDR2 comprising the amino acid sequence of SEQ ID NO: 116, and (vi) a VLCDR3 comprising the amino acid sequence of SEQ ID NO: 117;

l. (i) a VHCDR1 comprising the amino acid sequence of SEQ ID NO: 118, (ii) a VHCDR2 comprising the amino acid sequence of SEQ ID NO: 119, (iii) a VHCDR3 comprising the amino acid sequence of SEQ ID NO: 120, (iv) a VLCDR1 comprising the amino acid sequence of SEQ ID NO: 121, (v) a VLCDR2 comprising the amino acid sequence of SEQ ID NO: 122, and (vi) a VLCDR3 comprising the amino acid sequence of SEQ ID NO: 123;

m. (i) a VHCDR1 comprising the amino acid sequence of SEQ ID NO: 124, (ii) a VHCDR2 comprising the amino acid sequence of SEQ ID NO: 125, (iii) a VHCDR3 comprising the amino acid sequence of SEQ ID NO: 126, (iv) a VLCDR1 comprising the amino acid sequence of SEQ ID NO: 127, (v) a VLCDR2 comprising the amino acid sequence of SEQ ID NO: 128, and (vi) a VLCDR3 comprising the amino acid sequence of SEQ ID NO: 129;

n. (i) a variable heavy chain region that is at least 95% identical to the amino acid sequence of SEQ ID NO: 17, wherein the variable heavy chain region comprises a variable heavy chain region CDR1 comprising the amino acid sequence of SEQ ID NO: 19, a variable heavy chain region CDR2 comprising the amino acid sequence of SEQ ID NO: 20, and a variable heavy chain region CDR3 comprising the amino acid sequence of SEQ ID NO: 21; and (ii) a variable light chain region that is at least 95% identical to the amino acid sequence of SEQ ID NO: 18, wherein the variable light chain region comprises a variable light chain region CDR1 comprising the amino acid sequence of SEQ ID NO: 22, a variable light chain region CDR2 comprising the amino acid sequence of SEQ ID NO: 23, and a variable light chain region CDR3 comprising the amino acid sequence of SEQ ID NO: 24;

o. a variable heavy chain region comprising the amino acid sequence of SEQ ID NO: 17, and a variable light chain region comprising the amino acid sequence of SEQ ID NO: 18;

p. (i) a VHCDR1 comprising the amino acid sequence of SEQ ID NO: 51, (ii) a VHCDR2 comprising the amino acid sequence of SEQ ID NO: 52, (iii) a VHCDR3 comprising the amino acid sequence of SEQ ID NO: 53, (iv) a VLCDR1 comprising the amino acid sequence of SEQ ID NO: 54, (v) a VLCDR2 comprising the amino acid sequence of SEQ ID NO: 55, and (vi) a VLCDR3 comprising the amino acid sequence of SEQ ID NO: 56;

q. (i) a variable heavy chain region that is at least 95% identical to the amino acid sequence of SEQ ID NO: 49, wherein the variable heavy chain region comprises a variable heavy chain region CDR1 comprising the amino acid sequence of SEQ ID NO: 51, a variable heavy chain region CDR2 comprising the amino acid sequence of SEQ ID NO: 52, and a variable heavy chain region CDR3 comprising the amino acid sequence of SEQ ID NO: 53; and (ii) a variable light chain region that is at least 95% identical to the amino acid sequence of SEQ ID NO: 50, wherein the variable light chain region comprises a variable light chain region CDR1 comprising the amino acid sequence of SEQ ID NO: 54, a variable light chain region CDR2 comprising the amino acid sequence of SEQ ID NO: 55, and a variable light chain region CDR3 comprising the amino acid sequence of SEQ ID NO: 56; or r. a variable heavy chain region comprising the amino acid sequence of SEQ ID NO: 49, and a variable light chain region comprising the amino acid sequence of SEQ ID NO: 50.

2. The antibody of claim 1, wherein the antibody is a monoclonal antibody or antigen binding fragment thereof.

3. The antibody of claim 1, wherein the antibody is a chimeric antibody, or a humanized antibody.

4. The antibody of claim 1, wherein the antibody is conjugated to a detectable agent or a therapeutic agent.

5. An isolated polynucleotide sequence comprising a nucleotide sequence encoding an antibody of claim 1.

6. An expression vector comprising the polynucleotide sequence of claim 5.

7. A host cell comprising the polynucleotide sequence of claim 5.

8. A host cell engineered to express the antibody of claim 1.

9. A method for expressing the antibody of claim 1, comprising:

a. culturing the host cell of claim 7, and b. isolating the antibody from the host cell or cell culture.

10. A method for detecting an influenza B virus, comprising:

a. contacting cells or a biological sample with the antibody of claim 1; and b. detecting the binding of the antibody to an NA of an influenza B virus, wherein influenza B virus is detected if the level of binding of the antibody to an NA of an influenza B virus is greater than the level of binding of the antibody to non-influenza virus infected cells or a biological sample not infected with an influenza virus.

11. A pharmaceutical composition comprising the antibody of claim 1, and pharmaceutically acceptable carrier.

12. The pharmaceutical composition of claim 11, which is formulated for intranasal or parenteral administration to a subject.

13. A method for treating an influenza B virus infection or a disease caused by an influenza B virus in a subject, comprising administering to the subject an effective amount of the antibody of claim 1.

14. The method of claim 13, wherein the antibody is administered to the subject within 72 hours of the onset of symptoms of an influenza virus infection or an influenza virus disease.

15. The method of claim 13, wherein the subject is refractory to treatment with an antiviral agent.

16. A method for inhibiting or reducing onset, development and/or severity of one or more symptoms of a disease caused by an influenza B virus in a subject, comprising administering to the subject to the subject an effective amount of the antibody of claim 1.

17. The method of claim 16, wherein the method further comprises administering to the subject one or more antibodies that bind to a hemagglutinin (HA) of an influenza virus.

18. The method of claim 16, wherein the method further comprises administering to the subject an antibody that binds to an NA of an influenza A virus strain or an anti-viral agent.

19. The method of claim 13, wherein the subject is a human.

20. A kit comprising the antibody of claim 1, and instructions for use of the antibody in the treatment of an influenza virus infection or an influenza virus disease, or the inhibition or reduction of the onset, development and/or severity of one or more symptoms of an influenza virus disease or in the detection of an influenza B virus.

21. The antibody of claim 1, wherein the antibody comprises:

a. (i) a VHCDR1 comprising the amino acid sequence of SEQ ID NO: 3, (ii) a VHCDR2 comprising the amino acid sequence of SEQ ID NO: 4, (iii) a VHCDR3 comprising the amino acid sequence of SEQ ID NO: 5, (iv) a VLCDR1 comprising the amino acid sequence of SEQ ID NO: 6, (v) a VLCDR2 comprising the amino acid sequence of SEQ ID NO: 7, and (vi) a VLCDR3 comprising the amino acid sequence of SEQ ID NO: 8;

b. (i) a VHCDR1 comprising the amino acid sequence of SEQ ID NO: 94, (ii) a VHCDR2 comprising the amino acid sequence of SEQ ID NO: 95, (iii) a VHCDR3 comprising the amino acid sequence of SEQ ID NO: 96, (iv) a VLCDR1 comprising the amino acid sequence of SEQ ID NO: 97, (v) a VLCDR2 comprising the amino acid sequence of SEQ ID NO: 98, and (vi) a VLCDR3 comprising the amino acid sequence of SEQ ID NO: 99;

c. (i) a VHCDR1 comprising the amino acid sequence of SEQ ID NO: 100, (ii) a VHCDR2 comprising the amino acid sequence of SEQ ID NO: 101, (iii) a VHCDR3 comprising the amino acid sequence of SEQ ID NO: 102, (iv) a VLCDR1 comprising the amino acid sequence of SEQ ID NO: 103, (v) a VLCDR2 comprising the amino acid sequence of SEQ ID NO: 104, and (vi) a VLCDR3 comprising the amino acid sequence of SEQ ID NO: 105; or d. (i) a VHCDR1 comprising the amino acid sequence of SEQ ID NO: 106, (ii) a VHCDR2 comprising the amino acid sequence of SEQ ID NO: 107, (iii) a VHCDR3 comprising the amino acid sequence of SEQ ID NO: 108, (iv) a VLCDR1 comprising the amino acid sequence of SEQ ID NO: 109, (v) a VLCDR2 comprising the amino acid sequence of SEQ ID NO: 110, and (vi) a VLCDR3 comprising the amino acid sequence of SEQ ID NO: 111.

22. The antibody of claim 1, wherein the antibody comprises:

a. (i) VHCDR1 comprising the amino acid sequence of SEQ ID NO: 19, (ii) a VHCDR2 comprising the amino acid sequence of SEQ ID NO: 20, (iii) a VHCDR3 comprising the amino acid sequence of SEQ ID NO: 21, (iv) a VLCDR1 comprising the amino acid sequence of SEQ ID NO: 22, (v) a VLCDR2 comprising the amino acid sequence of SEQ ID NO: 23, and (vi) a VLCDR3 comprising the amino acid sequence of SEQ ID NO: 24;

b. (i) a VHCDR1 comprising the amino acid sequence of SEQ ID NO: 112, (ii) a VHCDR2 comprising the amino acid sequence of SEQ ID NO: 113, (iii) a VHCDR3 comprising the amino acid sequence of SEQ ID NO: 114, (iv) a VLCDR1 comprising the amino acid sequence of SEQ ID NO: 115, (v) a VLCDR2 comprising the amino acid sequence of SEQ ID NO: 116, and (vi) a VLCDR3 comprising the amino acid sequence of SEQ ID NO: 117;

c. (i) a VHCDR1 comprising the amino acid sequence of SEQ ID NO: 118, (ii) a VHCDR2 comprising the amino acid sequence of SEQ ID NO: 119, (iii) a VHCDR3 comprising the amino acid sequence of SEQ ID NO: 120, (iv) a VLCDR1 comprising the amino acid sequence of SEQ ID NO: 121, (v) a VLCDR2 comprising the amino acid sequence of SEQ ID NO: 122, and (vi) a VLCDR3 comprising the amino acid sequence of SEQ ID NO: 123; or d. (i) a VHCDR1 comprising the amino acid sequence of SEQ ID NO: 124, (ii) a VHCDR2 comprising the amino acid sequence of SEQ ID NO: 125, (iii) a VHCDR3 comprising the amino acid sequence of SEQ ID NO: 126, (iv) a VLCDR1 comprising the amino acid sequence of SEQ ID NO: 127, (v) a VLCDR2 comprising the amino acid sequence of SEQ ID NO: 128, and (vi) a VLCDR3 comprising the amino acid sequence of SEQ ID NO: 129.

23. The antibody of claim 1, wherein the antibody comprises: (i) a VHCDR1 comprising the amino acid sequence of SEQ ID NO: 51, (ii) a VHCDR2 comprising the amino acid sequence of SEQ ID NO: 52, (iii) a VHCDR3 comprising the amino acid sequence of SEQ ID NO: 53, (iv) a VLCDR1 comprising the amino acid sequence of SEQ ID NO: 54, (v) a VLCDR2 comprising the amino acid sequence of SEQ ID NO: 55, and (vi) a VLCDR3 comprising the amino acid sequence of SEQ ID NO: 56.

24. The method of claim 15, wherein the antiviral agent is an NA inhibitor.

25. The method of claim 18, the antiviral agent is an NA inhibitor or baloxavir marboxil.

26. The method of claim 14, wherein the subject is human.

27. The method of claim 16, wherein the subject is human.

* * * * *